US007589069B1

(12) United States Patent
Wold et al.

(10) Patent No.: US 7,589,069 B1
(45) **Date of Patent: *Sep. 15, 2009**

(54) REPLICATION-COMPETENT ANTI-CANCER VECTORS

(75) Inventors: William S. M. Wold, Chesterfield, MO (US); Karoly Toth, St. Louis, MO (US); Konstantin Doronin, St. Louis, MO (US); Ann E. Tollefson, St. Louis, MO (US)

(73) Assignee: Saint Louis University, St. Louis, MO (US)

( * ) Notice: Subject to any disclaimer, the term of this patent is extended or adjusted under 35 U.S.C. 154(b) by 1425 days.

This patent is subject to a terminal disclaimer.

(21) Appl. No.: 09/351,778

(22) Filed: Jul. 12, 1999

(51) Int. Cl.
*A61K 48/00* (2006.01)
*A61K 39/235* (2006.01)

(52) U.S. Cl. .................. 514/44; 424/199.1; 424/205.1; 424/233.1

(58) Field of Classification Search .................. 514/44; 424/93.2, 199.1, 205.1, 233.1, 320.1, 455; 435/320.1, 455
See application file for complete search history.

(56) References Cited

U.S. PATENT DOCUMENTS

| | | | | |
|---|---|---|---|---|
| 5,677,178 A | 10/1997 | McCormick | | |
| 5,846,945 A | 12/1998 | McCormick | | |
| 6,197,293 B1 * | 3/2001 | Henderson et al. | 424/93.2 |
| 6,254,862 B1 * | 7/2001 | Little et al. | 424/93.2 |
| 6,627,190 B2 * | 9/2003 | Wold et al. | 424/93.2 |

FOREIGN PATENT DOCUMENTS

| | | |
|---|---|---|
| WO | 98/39465 | 9/1998 |

OTHER PUBLICATIONS

Anderson; Human gene therapy, 1998, Nature vol. 392: 25-30.*
Verma et. al.; Gene therapy- promises, problems and prospects, 1997, Nature vol. 389: 239-242.*
Curiel ; Strategies to Adapt Adenovirl Vectors for Targeted Delivery, Curiel: Gene Therapy Strategies: 158-171.*
Gomez-Navarro et. al.; Gene Therapy for Cancer, 1999, european Journal of Cancer vol. 35, No. 6: 867-885.*
Li et. al.; Loss of Adenoviral Receptor Expression in Human Bladder Cancer Cells: A Potential Impact on the Efficacy of Gene Therapy, 1999, Cancer Research 59: 325-330.*
Geertsen et. al.; The Presence of Human Coxsackievirus and Adenovirus Receptor Is Associated with Efficient Adenkovirus-Mediated Transgene Expression in Human Melanoma Cell Cultures, 1998; Human Gene Therapy 9: 2363-2373.*
Li. et. al.; Variability of Adenovirus Receptor Density Influences Gene Transfer Efficiency and Therapeutic Response in Head and Neck Cancer, 1999, Clinical Cancer Research vol. 5: 4175-4181.*
Jain; Delivery of molecular and cellular medicine to solid tumors, 1998, Journal of Controlled Release 53: 49-67.*
Hobbs et. al.; Regulation of transport pathways in tumor vessels: Role of tumor type and microenvironment , 1998, Proc. Natl., Acad. Sci., vol. 95: 4607-4612.*
Elshami et. al.; Treatment of Pleural Mesothelioma in an Immunocompetent Rat Model Utilizing Adenoviral Transfer of the Herpes Simplex Virus Thymidine Kinase Gene; 1996, Human Gene Therapy 7: 141-148.*
Niiler; FDA, researchers consider first transgenic fish, 2000, Nature Biotechnology vol. 18: 143-144.*
Rudinger; Characteristics of the amino acids as components of a peptide hormone sequence, 1976, Peptide Hormones, 1-7.*
Tollefson et. al.; The Adenovirus Death Protein (E3-11.6K) Is Required at Very late Stages of Infection for Efficient Cell Lysis and Release of Adenovirus from Infected Cells, 1996, Journal of Virology: 2296-2306.*
Freytag et. al.; A Novel Three Pronged Approach to Kill Cancer Cells Selectively: Concomitant Viral , Double Suicide Gene , and Radiotherapy, 1998, Human Gene Therapy 9: 1323-1333.*
Bett et al., "An efficient and flexible system for construction of adenovirus vecotrs with insertions or deletions in early regions 1 and 3," Proc. Natl. Acad. Sci. USA 91: 8802-8806, Sep. 1994.*
Anderson et al., Adenovirus-mediated tissue-targeted expression of the HSVtk gene for the treatment of breast cancer, *Gene Therapy 6*:854-864 (1999).
Arai et al., Gene transfer of Fas ligand induces tumor regression in vivo, *Proc. Natl. Acad. Sci. USA 94*:13862-13867 (1997).
Bischoff et al., An Adenovirus Mutant that Replicates Selectively in p53-Deficient Human Tumor Cells, *Science 274*:373-376 (1996).
Chakravarti et al., A Viral Mechanism for Inhibition of p300 and PCAF Acetyltransferase Activity, *Cell 96*:393-403 (1999).
De-Chao et al., The addition of Adenovirus Type 5 Region E3 Enables Calydon Virus 787 to Eliminate Distant Prostate Tumor Xenografts, *Cancer Research 59*:4200-4203 (1999).
Felzmann et al., Characterization of the antitumor immune response generated by treatment of murine tumors with recombinant adenoviruses expressing HSVtk, IL-2, IL-6 or B7-1, *Gene Ther. 4*: 1322-1329 (1997).
Greenberg et al., Liver-specific expression of the human factor VII gene, *Proc. Natl. Acad. Sci. USA 92*:12347-12351 (1995).
Hallenbeck et al., A Novel Tumor-Specific Replication-Restricted Adenoviral Vector for Gene Therapy of Hepatocellular Carcinoma, *Human Gene Therapy 10*:1721-1733 (1999).
Hamamori et al., Regulation of Histone Acetyltransferases p300 and PCAF by thge bHLH Protein Twist and Adenoviral Oncoprotein E1A, *Cell 96*:405-413 (1999).
Harada et al., p53-Independent and -Dependent Requirements for E1B-55K in Adenovirus Type 5 Replication, *J. Virol 73*:5333-5344 (1999).
Harrod et al., Lung-Specific Expression of Adenovirus E3-14.7K in Transgenic Mice Attenuates Adenoviral Vector-Mediated Lung Inflammation and Enhances Transgene Expression, *Human Gene Therapy 9*:1885-1898 (1998).

(Continued)

*Primary Examiner*—Anne Marie S Wehbe
(74) *Attorney, Agent, or Firm*—Fulbright & Jaworski L.L.P.

(57) ABSTRACT

Novel vectors which are replication competent in neoplastic cells and which overexpress an adenovirus death protein are disclosed. Some of the disclosed vectors are replication-restricted to neoplastic cells or to neoplastic alveolar type II cells. Compositions and methods for promoting the death of neoplastic cells using these replication-competent vectors are also disclosed.

61 Claims, 55 Drawing Sheets

OTHER PUBLICATIONS

Heise et al., ONYX-015, an E1B gene-attenuated adenovirus, causes tumor-specific cytolysis and antitumoral efficacy that can be augmented by standard chemotherapeutic agents, *Nature Med. 3*:639-645 (1997).

Howe et al., Retinoblastoma growth suppressor and 300-kDa protein appear to regulate cellular DNA synthesis, *Proc. Natl. Acad. Sci. 87*:5883-5887 (1990).

Jones et al., Isolation of Adenovirus Type 5 Host Range Deletion Mutants Defective for transformation of Rat Embryo Cells, *Cell 17*:683-689 (1979).

Lazzaro et al., The transcription factor TTF-1 is expressed at the onset of thyroid and lunc morphogenesis and in restricted regions of the foetal brain, *Development 113*:1093-1104 (1991).

Li et al., Control of apoptosis and mitotic spindle checkpoint by survivin, *Nature 396*:580-584 (1998).

Lubeck et al., Immunogenicity of Recombinant Adenovirus-Human Immunodeficiency Virus Vaccines in Chimpanzees Following Intranasal Administration, *AIDS Res. Hum. Retroviruses 10*:1443-1449 (1994).

Massie et al., Inducible Overexpression of a Toxic Protein by an Adenovirus Vector with a Tetracycline-Rugulatable Expression Cassett, *J. of Virol. 72*:2289-2296 (1998).

Miller et al., Progress in Transcriptionally Targeted and Regulatable Vectors for Geneetic Therapy, *Human Gene Therapy 8*:803-815 (1997).

Putzer et al., Interleukin 12 and B7-1 costimulatory molecule expressed by an adenovirus vector act synergistically to facilitate tumor regression, *Proc. Natl. Acad. Sci. USA 94*:10889-10894 (1997).

Rodriguez et al., Prostate Attenuated Replication Competent Adenovirus (ARCA) CN706: A Selective Cytotoxic for Prostate-specific Antigen-positive Prostate Cancer Cells, *Cancer Res. 57*:2559-2563 (1997).

Scaria et al., The E3-11.6K Protein of Adenovirus in an Asn-Glycosylated Integral Membrane Protein That Localizes to the Nuclear Membrane, *Virology 191*:743-753 (1992).

Sparer et al., The Role of Human Adenovirus Early Region 3 Proteins (gp19K, 10.4K, 14.5K, and 14.7K) in a Murine Pneumonia Model, *J. Virol. 70*:2431-2439 (1996).

Tollefson et al., Forced degradation of Fas inhibits apoptosis in adenovirus-infected cells, *Nature 392*:726-730 (1998).

Tollefson et al., The E3-11.6-kDa Adenovirus Death Protein (AdP) Is Required for Efficient Cell Death: Characterization of Cells Infected with *adp* Mutants, *Virol. 220*:152-162 (1996).

Tollefson et al., The Adenovirus Death Protein (E3-11.6K) Is Required at Very Late Stages of Infection for Efficient Cell Lysis and Release of Adenovirus from Infected Cells, *J. Virol. 70*:2296-2306 (1996).

Topf et al., Regional 'pro-drug' gene therapy: intravenous administration of an adenoviral vector expressing the *E. coli* cytosine deaminase gene and systemic administration of 5-fluorocytosine suppresses growth of hepatic metastasis of colon carcinoma, *Gene Ther. 5*:507-513 (1998).

Wildner et al., Therapy of Colon Cancer with Oncolytic Adenovirus Is Enhanced by the Addition of Herpes Simplex Virus-*thymidine kinase, Cancer Res*. 59:410-413 (1999).

Wildner et al., Adenoviral vectors capable of replication improve the efficacy of HSVtk/GCV suicide gene therapy of cancer, *Gene Therapy 6*:57-62 (1999).

Wold et al., Adenovirus E3 Proteins: 14.7K, RID, and gp19K Inhibit Immune-Induced Cell Death; Adenovirus Death Protein Promotes Cell Death, *Semin. Virol. 8*:515-523 (1998).

Wold et al., Evidence that AGUAUAUGA and CCAAGAUGA Initiate Translation in the Same mRNA in Region E3 of Adenovirus, *Virology 148*:168-180 (1986).

Yan et al., Upstream Enhancer Activity in the Human Surfactant Protein B Gene Is Mediated by Thyroid Transcription Factor 1, *J. Biol. Chem. 270*:24852-24857 (1995).

Doronin et al., Journal of Virology vol. 74, No. 13, XP-002162706, Tumor-Specific, Replication-Competent Adenovirus Vectors Overexpressing the Adenovirus Death Protein, pp. 6147-6155, Jul. 2000.

Hausmann et al., Virology, vol. 244, XP-0021162709, Adenovirus Death Protein, a Transmembrane Protein Encoded in the E3 Region, Is Palmitoylated at the Cytoplasmic Tail, pp. 343-351, 1998.

Wold, William S., Adenovirus replication competent anticancer vector, Abstract to NIH Grant No. 1R41CA081829-01; Sep. 1, 1999.

Wold, William S., Adenovirus death protein, Abstract to NIH Grant No. 5R01CA071704-05; Aug. 1, 1996.

Wold, William S., Adenovirus death protein, Abstract to NIH Grant No. 5R01CA071704-03; Aug. 1, 1996.

Wold, William S., Adenovirus death protein, Abstract to NIH Grant No. 5R01CA071704-04; Aug. 1, 1996.

Wold, William S., Adenovirus death protein, Abstract to NIH Grant No. 5R01CA071704-02; Aug. 1, 1996.

Toth et al., Adenovirus Replication-competent vectors to treat cancer-preclinical studies; Abstract presented at the Imperial Cancer Research Fund Tumour Virus Meeting, Jul. 13, 1999.

Kuppuswamy et al., Adenovirus death protein-expressing replication-competent vectors to treat cancer-preclinical studies, Abstract to the 1999 meeting on programmed cell death at Cold Spring Harbor Laboratory, Sep. 29, 1999.

Kim et al., Synergistic effects of specially designed replication competent adenovirus vector and radiotherapy, Abstract in Proceedings of the American Society for Therapeutic Radiology and Oncology $42^{nd}$ Annual Meeting, Oct. 22, 2000.

Toth et al., Adenovirus replication-competent anti-cancer vector with the E4 promoter replaced by a tissue-specific promoter, Abstract of the 2000 Molecular Biology of DNA Tumor Viruses Conference, Jul. 8, 2000.

Kim et al., Replication-competent adenovirus anticancer vectors-radiotherapy synergy experiment in tissue culture phase, Abstract presented at 1999 ASTRO conference, Oct. 1999.

Doronin et al., Adenovirus replication-competent, tumor-specific vectors that overexpress ADP, Abstract for American Society of Gene Therapy Meeting, *Molecular Therapy* May 2000.

Machemer et al., Efficacy of a replicating adenovirus (K9TB) in human tumor xenograft mouse models, American Society of Gene Therapy Meeting Abstract, Jun. 2001.

Ramachandra et al., Reengineering adenovirus regulatory pathways to enhance oncolytic specificity and efficacy, American Society of Gene Therapy Meeting Abstract, Jun. 2002.

Zou et al., Analysis of cell death induced by adenovirus E3-11.6K protein, American Society of Gene Therapy Meeting Abstract, Jun. 2001.

Suzuki et al., The presence of the adenoviral E3 gene improves the oncolytic ptency of a conditionally replicative adenovirus, American Society of Gene Therapy Meeting Abstract, Jun. 2001.

Ramachandra et al., Re-engineering adenovirus regulatory pathways to enhance oncolytic specificity and efficacy, *Nature Biotechnology* 19:1035-1041, Nov. 2001.

Ghosh and Ghosh, Role of the membrane anchoring and cytoplasmic domains in intracellular transport and localization of viral glycoproteins, *Biochem Cell Biol*. 77:165-178, Jun. 1999.

Wold et al., Mapping a new gene that encodes an 11,600-molecular-weight protein the the E3 transcription unit of adenovirus 2, *J. Virol*. 52:307-313, Nov. 1984.

The 11,600-$M_w$ protein encoded by region E3 of adenovirus is expressed early but is greatly amplified at late stages of infection, *J. Virol* 66:3633-3642, Jun. 1992.

Doronin et al., Tissue-specific, tumor-selective, replication-competent adenovirus vector for cancer gene therapy, *J. Virol*. 75:3314-3324, Apr. 2001.

Gastroenterology, vol. 18, No. 1, *Inhibition of hepatic metastases of human colon cancer in nude mice by a chimeric SF-25 monoclonal antibody*, abstract, Jan. 1995.

Alberts et al., Molecular Biology of the Cell, 3rd Edition, Chapter 24: Cancer, *Cancers Differ According to the Cell Type from Which They Derive*, pp. 1256, 1994.

Abbas et al., Cellular and Molecular Immunology, 2nd Edition, Section III: Effector Mechanisms of Immune Responses, pp. 294-295, 1994.
Japanese Office Action, issued in Japanese Patent Application No. 2001-509486, dated Dec. 18, 2007.
Strayer et al., "Targeting type II and Clara cells for adenovirus-mediated gene transfer using the surfactant protein B promoter," *Am. J. Respir. Cell Mol. Biol.*, 18:1-11, 1998.

* cited by examiner

ADP Is Expressed Earlier in Infection
By KD1, KD3, GZ1, and GZ3

The E1A 01/07 Mutation
Retards Late Gene Expression

KD1-SPB With the SPB Promoter in Place of the E4 Promoter Grows on H44a Lung Cancer Cells with the TTF1 Transcription Factor

Ad2 Adenovirus Death Protein

*Lumenal Domain*

M T G S T I A P T T D Y R N T T A T G L T S A L N L P Q V H A F V N D 35

*O - glycosylation* *N - glycosylation*

W A S L D M W W F S I A L M F V C L I I M W L I C C L K R R R A R P P 70

*Transmembrane (Signal - Anchor)* *Basic - Proline*

I Y R P I I V L N P H N E K I H R L D G L K P C S L L L Q Y D 101

*Cytoplasmic - Nucleoplasmic Domain*

FIGURE 18A

Seq ID No.

| | | 10 | 20 | 30 | 40 | 50 |
|---|---|---|---|---|---|---|
| 5 | Ad1 | ------MVDT | VNSYNTATGL | TSALNLPQVS | TFVNNWANLG | MWWFSIALMF |
| 6 | Ad2 | MTGSTIAPTT | DYRNTTATGL | TSALNLPQVH | AFVNDWASLD | MWWFSIALMF |
| 7 | Ad5 | -------MTN | TTNAAAATGL | TSTTNTPQVS | AFVNNWDNLG | MWWFSIALMF |
| 8 | Ad6 | ------MVDT | VNSYNTATGL | KSALNLPQVH | AFVNDWASLG | MWWFSIALMF |
| 9 | dl716 | MTGSTIAPTT | DYRNTTATGL | TSALNLPQVH | AFVNDWASLD | MWWFSIALMF |
| 10 | dl715 | MTGSTIAPTT | DYRNTTATGL | TSALNLPQVH | AFVNDWASLD | MWWFSIALMF |
| 11 | dl714 | MTGSTIAPTT | DYRNTTATGL | TSALNLPQVH | AFVNDWASLD | MWWFSIALMF |
| 12 | dl737 | MTGSTIAPTT | DYRNTTATGL | TSALNLPQ-- | ---------- | -----IALMF |

| | | 60 | 70 | 80 | 90 | 100 | |
|---|---|---|---|---|---|---|---|
| 5 | Ad1 | VCLIIMWLSC | CLKRKRARPP | IYKPIIVLNP | NNDGIHRLDG | LNTCSFSFAV | - |
| 6 | Ad2 | VCLIIMWLIC | CLKRRRARPP | IYRPIIVLNP | HNEKIHRLDG | LKPCSLLLQY | D |
| 7 | Ad5 | VCLIIMWLIC | CLKRKRARPP | IYSPIIVLHP | NNDGIHRLDG | LKHMFFSLTV | - |
| 8 | Ad6 | VCLIIMWLIC | CLKRRRARPP | IYRPIIVLNP | HNEKIHRLDG | LKPCSLLLQY | D |
| 9 | dl716 | VCLIIMWLIC | CLKRRRARPP | IYRPIIVL-- | ---------- | ---------- | - |
| 10 | dl715 | VCLIIMWLIC | CLKRRRARPP | IYRPI----- | ---------G | LKPCSLLLQY | D |
| 11 | dl714 | VCLIIMWLIC | CLKRRRARPP | ---------- | ---------- | ----SLLLQY | D |
| 12 | dl737 | VCLIIMWLIC | CLKRRRARPP | IYRPIIVLNP | HNEKIHRLDG | LKPCSLLLQY | D |

Seq. ID No.

| | | |
|---|---|---|
| 17 | aa 1-40 of Ad2 ADP | MTGSTIAPTT DYRNTTATGL TSALNLPQVH AFVNDWASLD |
| 18 | aa 41-59 of Ad2 ADP | MWWFSIALMF VCLIIMWLI |
| 19 | aa 63-70 of Ad2 ADP | KRRRARPP |
| 20 | aa 60-101 of Ad2 ADP | C CLKRRRARPP IYRPIIVLNP HNEKIHRLDG LKPCSLLLQY D |

FIGURE 20

```
LOCUS       ad5 comple  35935 bp    DNA             SYN        06-FEB-1999
DEFINITION  ad5 complete genome
ACCESSION   ad5 comple
KEYWORDS    .
SOURCE      Unknown.
  ORGANISM  Unknown
            Unclassified.
REFERENCE   1  (bases 1 to 35935)
  AUTHORS   Self
  JOURNAL   Unpublished.
BASE COUNT     8367 a  10073 c    9761 g   7734 t
ORIGIN
        1 CATCATCAAT AATATACCTT ATTTTGGATT GAAGCCAATA TGATAATGAG GGGGTGGAGT
       61 TTGTGACGTG GCGCGGGGCG TGGGAACGGG GCGGGTGACG TAGTAGTGTG GCGGAAGTGT
      121 GATGTTGCAA GTGTGGCGGA ACACATGTAA GCGACGGATG TGGCAAAAGT GACGTTTTTG
      181 GTGTGCGCCG GTGTACACAG GAAGTGACAA TTTTCGCGCG GTTTTAGGCG GATGTTGTAG
      241 TAAATTTGGG CGTAACCGAG TAAGATTTGG CCATTTTCGC GGGAAAACTG AATAAGAGGA
      301 AGTGAAATCT GAATAATTTT GTGTTACTCA TAGCGCGTAA TATTTGTCTA GGGCCGCGGG
      361 GACTTTGACC GTTTACGTGG AGACTCGCCC AGGTGTTTTT CTCAGGTGTT TTCCGCGTTC
      421 CGGGTCAAAG TTGGCGTTTT ATTATTATAG TCAGCTGACG TGTAGTGTAT TTATACCCGG
      481 TGAGTTCCTC AAGAGGCCAC TCTTGAGTGC CAGCGAGTAG AGTTTTCTCC TCCGAGCCGC
      541 TCCGACACCG GGACTGAAAA TGAGACATAT TATCTGCCAC GGAGGTGTTA TTACCGAAGA
      601 AATGGCCGCC AGTCTTTTGG ACCAGCTGAT CGAAGAGGTA CTGGCTGATA ATCTTCCACC
      661 TCCTAGCCAT TTTGAACCAC CTACCCTTCA CGAACTGTAT GATTTAGACG TGACGGCCCC
      721 CGAAGATCCC AACGAGGAGG CGGTTTCGCA GATTTTTCCC GACTCTGTAA TGTTGGCGGT
      781 GCAGGAAGGG ATTGACTTAC TCACTTTTCC GCCGGCGCCC GGTTCTCCGG AGCCGCCTCA
      841 CCTTTCCCGG CAGCCCGAGC AGCCGGAGCA GAGAGCCTTG GGTCCGGTTT CTATGCCAAA
      901 CCTTGTACCG GAGGTGATCG ATCTTACCTG CCACGAGGCT GGCTTTCCAC CCAGTGACGA
      961 CGAGGATGAA GAGGGTGAGG AGTTTGTGTT AGATTATGTG GAGCACCCCG GGCACGGTTG
     1021 CAGGTCTTGT CATTATCACC GGAGGAATAC GGGGGACCCA GATATTATGT GTTCGCTTTG
     1081 CTATATGAGG ACCTGTGGCA TGTTTGTCTA CAGTAAGTGA AAATTATGGG CAGTGGGTGA
     1141 TAGAGTGGTG GGTTTGGTGT GGTAATTTTT TTTTTAATTT TTACAGTTTT GTGGTTTAAA
     1201 GAATTTTGTA TTGTGATTTT TTTAAAAGGT CCTGTGTCTG AACCTGAGCC TGAGCCCGAG
     1261 CCAGAACCGG AGCCTGCAAG ACCTACCCGC CGTCCTAAAA TGGCGCCTGC TATCCTGAGA
     1321 CGCCCGACAT CACCTGTGTC TAGAGAATGC AATAGTAGTA CGGATAGCTG TGACTCCGGT
     1381 CCTTCTAACA CACCTCCTGA GATACACCCG GTGGTCCCGC TGTGCCCCAT TAAACCAGTT
     1441 GCCGTGAGAG TTGGTGGGCG TCGCCAGGCT GTGGAATGTA TCGAGGACTT GCTTAACGAG
     1501 CCTGGGCAAC CTTTGGACTT GAGCTGTAAA CGCCCCAGGC CATAAGGTGT AAACCTGTGA
     1561 TTGCGTGTGT GGTTAACGCC TTTGTTTGCT GAATGAGTTG ATGTAAGTTT AATAAAGGGT
     1621 GAGATAATGT TTAACTTGCA TGGCGTGTTA AATGGGGCGG GGCTTAAAGG GTATATAATG
     1681 CGCCGTGGGC TAATCTTGGT TACATCTGAC CTCATGGAGG CTTGGGAGTG TTTGGAAGAT
     1741 TTTTCTGCTG TGCGTAACTT GCTGGAACAG AGCTCTAACA GTACCTCTTG GTTTTGGAGG
     1801 TTTCTGTGGG GCTCATCCCA GGCAAAGTTA GTCTGCAGAA TTAAGGAGGA TTACAAGTGG
     1861 GAATTTGAAG AGCTTTTGAA ATCCTGTGGT GAGCTGTTTG ATTCTTTGAA TCTGGGTCAC
     1921 CAGGCGCTTT TCCAAGAGAA GGTCATCAAG ACTTTGGATT TTTCCACACC GGGGCGCGCT
     1981 GCGGCTGCTG TTGCTTTTTT GAGTTTTATA AAGGATAAAT GGAGCGAAGA AACCCATCTG
     2041 AGCGGGGGGT ACCTGCTGGA TTTTCTGGCC ATGCATCTGT GGAGAGCGGT TGTGAGACAC
     2101 AAGAATCGCC TGCTACTGTT GTCTTCCGTC CGCCCGGCGA TAATACCGAC GGAGGAGCAG
     2161 CAGCAGCAGC AGGAGGAAGC CAGGCGGCGG CGGCAGGAGC AGAGCCCATG GAACCCGAGA
     2221 GCCGGCCTGG ACCCTCGGGA ATGAATGTTG TACAGGTGGC TGAACTGTAT CCAGAACTGA
     2281 GACGCATTTT GACAATTACA GAGGATGGGC AGGGGCTAAA GGGGGTAAAG AGGGAGCGGG
     2341 GGGCTTGTGA GGCTACAGAG GAGGCTAGGA ATCTAGCTTT TAGCTTAATG ACCAGACACC
     2401 GTCCTGAGTG TATTACTTTT CAACAGATCA AGGATAATTG CGCTAATGAG CTTGATCTGC
     2461 TGGCGCAGAA GTATTCCATA GAGCAGCTGA CCACTTACTG GCTGCAGCCA GGGGATGATT
     2521 TTGAGGAGGC TATTAGGGTA TATGCAAAGG TGGCACTTAG GCCAGATTGC AAGTACAAGA
     2581 TCAGCAAACT TGTAAATATC AGGAATTGTT GCTACATTTC TGGGAACGGG GCCGAGGTGG
     2641 AGATAGATAC GGAGGATAGG GTGGCCTTTA GATGTAGCAT GATAAATATG TGGCCGGGGG
```

FIGURE 21
(SHEET 1)

2701 TGCTTGGCAT GGACGGGGTG GTTATTATGA ATGTAAGGTT TACTGGCCCC AATTTTAGCG
2761 GTACGGTTTT CCTGGCCAAT ACCAACCTTA TCCTACACGG TGTAAGCTTC TATGGGTTTA
2821 ACAATACCTG TGTGGAAGCC TGGACCGATG TAAGGGTTCG GGGCTGTGCC TTTTACTGCT
2881 GCTGGAAGGG GGTGGTGTGT CGCCCCAAAA GCAGGGCTTC AATTAAGAAA TGCCTCTTTG
2941 AAAGGTGTAC CTTGGGTATC CTGTCTGAGG GTAACTCCAG GGTGCGCCAC AATGTGGCCT
3001 CCGACTGTGG TTGCTTCATG CTAGTGAAAA GCGTGGCTGT GATTAAGCAT AACATGGTAT
3061 GTGGCAACTG CGAGGACAGG GCCTCTCAGA TGCTGACCTG CTCGGACGGC AACTGTCACC
3121 TGCTGAAGAC CATTCACGTA GCCAGCCACT CTCGCAAGGC CTGGCCAGTG TTTGAGCATA
3181 ACATACTGAC CCGCTGTTCC TTGCATTTGG GTAACAGGAG GGGGGTGTTC CTACCTTACC
3241 AATGCAATTT GAGTCACACT AAGATATTGC TTGAGCCCGA GAGCATGTCC AAGGTGAACC
3301 TGAACGGGGT GTTTGACATG ACCATGAAGA TCTGGAAGGT GCTGAGGTAC GATGAGACCC
3361 GCACCAGGTG CAGACCCTGC GAGTGTGGCG GTAAACATAT TAGGAACCAG CCTGTGATGC
3421 TGGATGTGAC CGAGGAGCTG AGGCCCGATC ACTTGGTGCT GGCCTGCACC CGCGCTGAGT
3481 TTGGCTCTAG CGATGAAGAT ACAGATTGAG GTACTGAAAT GTGTGGGCGT GGCTTAAGGG
3541 TGGGAAAGAA TATATAAGGT GGGGGTCTTA TGTAGTTTTG TATCTGTTTT GCAGCAGCCG
3601 CCGCCGCCAT GAGCACCAAC TCGTTTGATG GAAGCATTGT GAGCTCATAT TTGACAACGC
3661 GCATGCCCCC ATGGGCCGGG GTGCGTCAGA ATGTGATGGG CTCCAGCATT GATGGTCGCC
3721 CCGTCCTGCC CGCAAACTCT ACTACCTTGA CCTACGAGAC CGTGTCTGGA ACGCCGTTGG
3781 AGACTGCAGC CTCCGCCGCC GCTTCAGCCG CTGCAGCCAC CGCCCGCGGG ATTGTGACTG
3841 ACTTTGCTTT CCTGAGCCCG CTTGCAAGCA GTGCAGCTTC CCGTTCATCC GCCCGCGATG
3901 ACAAGTTGAC GGCTCTTTTG GCACAATTGG ATTCTTTGAC CCGGGAACTT AATGTCGTTT
3961 CTCAGCAGCT GTTGGATCTG CGCCAGCAGG TTTCTGCCCT GAAGGCTTCC TCCCCTCCCA
4021 ATGCGGTTTA AAACATAAAT AAAAAACCAG ACTCTGTTTG GATTTGGATC AAGCAAGTGT
4081 CTTGCTGTCT TTATTTAGGG GTTTTGCGCG CGCGGTAGGC CCGGGACCAG CGGTCTCGGT
4141 CGTTGAGGGT CCTGTGTATT TTTTCCAGGA CGTGGTAAAG GTGACTCTGG ATGTTCAGAT
4201 ACATGGGCAT AAGCCCGTCT CTGGGGTGGA GGTAGCACCA CTGCAGAGCT TCATGCTGCG
4261 GGGTGGTGTT GTAGATGATC CAGTCGTAGC AGGAGCGCTG GGCGTGGTGC CTAAAAATGT
4321 CTTTCAGTAG CAAGCTGATT GCCAGGGGCA GGCCCTTGGT GTAAGTGTTT ACAAAGCGGT
4381 TAAGCTGGGA TGGGTGCATA CGTGGGGATA TGAGATGCAT CTTGGACTGT ATTTTTAGGT
4441 TGGCTATGTT CCCAGCCATA TCCCTCCGGG GATTCATGTT GTGCAGAACC ACCAGCACAG
4501 TGTATCCGGT GCACTTGGGA AATTTGTCAT GTAGCTTAGA AGGAAATGCG TGGAAGAACT
4561 TGGAGACGCC CTTGTGACCT CCAAGATTTT CCATGCATTC GTCCATAATG ATGGCAATGG
4621 GCCCACGGGC GGCGGCCTGG GCGAAGATAT TTCTGGGATC ACTAACGTCA TAGTTGTGTT
4681 CCAGGATGAG ATCGTCATAG GCCATTTTTA CAAAGCGCGG GCGGAGGGTG CCAGACTGCG
4741 GTATAATGGT TCCATCCGGC CCAGGGGCGT AGTTACCCTC ACAGATTTGC ATTTCCCACG
4801 CTTTGAGTTC AGATGGGGGG ATCATGTCTA CCTGCGGGGC GATGAAGAAA ACGGTTTCCG
4861 GGGTAGGGGA GATCAGCTGG GAAGAAAGCA GGTTCCTGAG CAGCTGCGAC TTACCGCAGC
4921 CGGTGGGCCC GTAAATCACA CCTATTACCG GGTGCAACTG GTAGTTAAGA GAGCTGCAGC
4981 TGCCGTCATC CCTGAGCAGG GGGGCCACTT CGTTAAGCAT GTCCCTGACT CGCATGTTTT
5041 CCCTGACCAA ATCCGCCAGA AGGCGCTCGC CGCCCAGCGA TAGCAGTTCT TGCAAGGAAG
5101 CAAAGTTTTT CAACGGTTTG AGACCGTCCG CCGTAGGCAT GCTTTTGAGC GTTTGACCAA
5161 GCAGTTCCAG GCGGTCCCAC AGCTCGGTCA CCTGCTCTAC GGCATCTCGA TCCAGCATAT
5221 CTCCTCGTTT CGCGGGTTGG GGCGGCTTTC GCTGTACGGC AGTAGTCGGT GCTCGTCCAG
5281 ACGGGCCAGG GTCATGTCTT TCCACGGGCG CAGGGTCCTC GTCAGCGTAG TCTGGGTCAC
5341 GGTGAAGGGG TGCGCTCCGG GCTGCGCGCT GGCCAGGGTG CGCTTGAGGC TGGTCCTGCT
5401 GGTGCTGAAG CGCTGCCGGT CTTCGCCCTG CGCGTCGGCC AGGTAGCATT TGACCATGGT
5461 GTCATAGTCC AGCCCCTCCG CGGCGTGGCC CTTGGCGCGC AGCTTGCCCT TGGAGGAGGC
5521 GCCGCACGAG GGGCAGTGCA GACTTTTGAG GGCGTAGAGC TTGGGCGCGA GAAATACCGA
5581 TTCCGGGGAG TAGGCATCCG CGCCGCAGGC CCCGCAGACG GTCTCGCATT CCACGAGCCA
5641 GGTGAGCTCT GGCCGTTCGG GGTCAAAAAC CAGGTTTCCC CCATGCTTTT TGATGCGTTT
5701 CTTACCTCTG GTTTCCATGA GCCGGTGTCC ACGCTCGGTG ACGAAAAGGC TGTCCGTGTC
5761 CCCGTATACA GACTTGAGAG GCCTGTCCTC GAGCGGTGTT CCGCGGTCCT CCTCGTATAG
5821 AAACTCGGAC CACTCTGAGA CAAAGGCTCG CGTCCAGGCC AGCACGAAGG AGGCTAAGTG
5881 GGAGGGGTAG CGGTCGTTGT CCACTAGGGG GTCCACTCGC TCCAGGGTGT GAAGACACAT
5941 GTCGCCCTCT TCGGCATCAA GGAAGGTGAT TGGTTTGTAG GTGTAGGCCA CGTGACCGGG
6001 TGTTCCTGAA GGGGGGCTAT AAAAGGGGGT GGGGGCGCGT TCGTCCTCAC TCTCTTCCGC
6061 ATCGCTGTCT GCGAGGGCCA GCTGTTGGGG TGAGTACTCC CTCTGAAAAG CGGGCATGAC

FIGURE 21
(SHEET 2)

```
6121 TTCTGCGCTA AGATTGTCAG TTTCCAAAAA CGAGGAGGAT TTGATATTCA CCTGGCCCGC
6181 GGTGATGCCT TTGAGGGTGG CCGCATCCAT CTGGTCAGAA AAGACAATCT TTTTGTTGTC
6241 AAGCTTGGTG GCAAACGACC CGTAGAGGGC GTTGGACAGC AACTTGGCGA TGGAGCGCAG
6301 GGTTTGGTTT TTGTCGCGAT CGGCGCGCTC CTTGGCCGCG ATGTTTAGCT GCACGTATTC
6361 GCGCGCAACG CACCGCCATT CGGGAAAGAC GGTGGTGCGC TCGTCGGGCA CCAGGTGCAC
6421 GCGCCAACCG CGGTTGTGCA GGGTGACAAG GTCAACGCTG GTGGCTACCT CTCCGCGTAG
6481 GCGCTCGTTG GTCCAGCAGA GGCGGCCGCC CTTGCGCGAG CAGAATGGCG GTAGGGGGTC
6541 TAGCTGCGTC TCGTCCGGGG GGTCTGCGTC CACGGTAAAG ACCCCGGGCA GCAGGCGCGC
6601 GTCGAAGTAG TCTATCTTGC ATCCTTGCAA GTCTAGCGCC TGCTGCCATG CGCGGGCGGC
6661 AAGCGCGCGC TCGTATGGGT TGAGTGGGGG ACCCCATGGC ATGGGGTGGG TGAGCGCGGA
6721 GGCGTACATG CCGCAAATGT CGTAAACGTA GAGGGGCTCT CTGAGTATTC CAAGATATGT
6781 AGGGTAGCAT CTTCCACCGC GGATGCTGGC GCGCACGTAA TCGTATAGTT CGTGCGAGGG
6841 AGCGAGGAGG TCGGGACCGA GGTTGCTACG GGCGGGCTGC TCTGCTCGGA AGACTATCTG
6901 CCTGAAGATG GCATGTGAGT TGGATGATAT GGTTGGACGC TGGAAGACGT TGAAGCTGGC
6961 GTCTGTGAGA CCTACCGCGT CACGCACGAA GGAGGCGTAG GAGTCGCGCA GCTTGTTGAC
7021 CAGCTCGGCG GTGACCTGCA CGTCTAGGGC GCAGTAGTCC AGGGTTTCCT TGATGATGTC
7081 ATACTTATCC TGTCCCTTTT TTTTCCACAG CTCGCGGTTG AGGACAAACT CTTCGCGGTC
7141 TTTCCAGTAC TCTTGGATCG GAAACCCGTC GGCCTCCGAA CGGTAAGAGC CTAGCATGTA
7201 GAACTGGTTG ACGGCCTGGT AGGCGCAGCA TCCCTTTTCT ACGGGTAGCG CGTATGCCTG
7261 CGCGGCCTTC CGGAGCGAGG TGTGGGTGAG CGCAAAGGTG TCCCTGACCA TGACTTTGAG
7321 GTACTGGTAT TTGAAGTCAG TGTCGTCGCA TCCGCCCTGC TCCCAGAGCA AAAAGTCCGT
7381 GCGCTTTTTG GAACGCGGAT TTGGCAGGGC GAAGGTGACA TCGTTGAAGA GTATCTTTCC
7441 CGCGCGAGGC ATAAAGTTGC GTGTGATGCG GAAGGGTCCC GGCACCTCGG AACGGTTGTT
7501 AATTACCTGG GCGGCGAGCA CGATCTCGTC AAAGCCGTTG ATGTTGTGGC CCACAATGTA
7561 AAGTTCCAAG AAGCGCGGGA TGCCCTTGAT GGAAGGCAAT TTTTTAAGTT CCTCGTAGGT
7621 GAGCTCTTCA GGGGAGCTGA GCCCGTGCTC TGAAAGGGCC CAGTCTGCAA GATGAGGGTT
7681 GGAAGCGACG AATGAGCTCC ACAGGTCACG GGCCATTAGC ATTTGCAGGT GGTCGCGAAA
7741 GGTCCTAAAC TGGCGACCTA TGGCCATTTT TTCTGGGGTG ATGCAGTAGA AGGTAAGCGG
7801 GTCTTGTTCC CAGCGGTCCC ATCCAAGGTT CGCGGCTAGG TCTCGCGCGG CAGTCACTAG
7861 AGGCTCATCT CCGCCGAACT TCATGACCAG CATGAAGGGC ACGAGCTGCT TCCCAAAGGC
7921 CCCCATCCAA GTATAGGTCT CTACATCGTA GGTGACAAAG AGACGCTCGG TGCGAGGATG
7981 CGAGCCGATC GGGAAGAACT GGATCTCCCG CCACCAATTG GAGGAGTGGC TATTGATGTG
8041 GTGAAAGTAG AAGTCCCTGC GACGGGCCGA ACACTCGTGC TGGCTTTTGT AAAAACGTGC
8101 GCAGTACTGG CAGCGGTGCA CGGGCTGTAC ATCCTGCACG AGGTTGACCT GACGACCGCG
8161 CACAAGGAAG CAGAGTGGGA ATTTGAGCCC CTCGCCTGGC GGGTTTGGCT GGTGGTCTTC
8221 TACTTCGGCT GCTTGTCCTT GACCGTCTGG CTGCTCGAGG GGAGTTACGG TGGATCGGAC
8281 CACCACGCCG CGCGAGCCCA AAGTCCAGAT GTCCGCGCGC GGCGGTCGGA GCTTGATGAC
8341 AACATCGCGC AGATGGGAGC TGTCCATGGT CTGGAGCTCC CGCGGCGTCA GGTCAGGCGG
8401 GAGCTCCTGC AGGTTTACCT CGCATAGACG GGTCAGGGCG CGGGCTAGAT CCAGGTGATA
8461 CCTAATTTCC AGGGGCTGGT TGGTGGCGGC GTCGATGGCT TGCAAGAGGC CGCATCCCCG
8521 CGGCGCGACT ACGGTACCGC GCGGCGGGCG GTGGGCCGCG GGGGTGTCCT TGGATGATGC
8581 ATCTAAAAGC GGTGACGCGG GCGAGCCCCC GGAGGTAGGG GGGGCTCCGG ACCCGCCGGG
8641 AGAGGGGGCA GGGGCACGTC GGCGCCGCGC GCGGGCAGGA GCTGGTGCTG CGCGCGTAGG
8701 TTGCTGGCGA ACGCGACGAC GCGGCGGTTG ATCTCCTGAA TCTGGCGCCT CTGCGTGAAG
8761 ACGACGGGCC CGGTGAGCTT GAGCCTGAAA GAGAGTTCGA CAGAATCAAT TTCGGTGTCG
8821 TTGACGGCGG CCTGGCGCAA AATCTCCTGC ACGTCTCCTG AGTTGTCTTG ATAGGCGATC
8881 TCGGCCATGA ACTGCTCGAT CTCTTCCTCC TGGAGATCTC CGCGTCCGGC TCGCTCCACG
8941 GTGGCGGCGA GGTCGTTGGA AATGCGGGCC ATGAGCTGCG AGAAGGCGTT GAGGCCTCCC
9001 TCGTTCCAGA CGCGGCTGTA GACCACGCCC CCTTCGGCAT CGCGGGCGCG CATGACCACC
9061 TGCGCGAGAT TGAGCTCCAC GTGCCGGGCG AAGACGGCGT AGTTTCGCAG GCGCTGAAAG
9121 AGGTAGTTGA GGGTGGTGGC GGTGTGTTCT GCCACGAAGA AGTACATAAC CCAGCGTCGC
9181 AACGTGGATT CGTTGATATC CCCCAAGGCC TCAAGGCGCT CCATGGCCTC GTAGAAGTCC
9241 ACGGCGAAGT TGAAAAACTG GGAGTTGCGC GCCGACACGG TTAACTCCTC CTCCAGAAGA
9301 CGGATGAGCT CGGCGACAGT GTCGCGCACC TCGCGCTCAA AGGCTACAGG GGCCTCTTCT
9361 TCTTCTTCAA TCTCCTCTTC CATAAGGGCC TCCCCTTCTT CTTCTTCTGG CGGCGGTGGG
9421 GGAGGGGGGA CACGGCGGCG ACGACGGCGC ACCGGGAGGC GGTCGACAAA GCGCTCGATC
9481 ATCTCCCCGC GGCGACGGCG CATGGTCTCG GTGACGGCGC GGCCGTTCTC GCGGGGGCGC
```

FIGURE 21
(SHEET 3)

9541 AGTTGGAAGA CGCCGCCCGT CATGTCCCGG TTATGGGTTG GCGGGGGGCT GCCATGCGGC
9601 AGGGATACGG CGCTAACGAT GCATCTCAAC AATTGTTGTG TAGGTACTCC GCCGCCGAGG
9661 GACCTGAGCG AGTCCGCATC GACCGGATCG GAAAACCTCT CGAGAAAGGC GTCTAACCAG
9721 TCACAGTCGC AAGGTAGGCT GAGCACCGTG GCGGGCGGCA GCGGGCGGCG GTCGGGGTTG
9781 TTTCTGGCGG AGGTGCTGCT GATGATGTAA TTAAAGTAGG CGGTCTTGAG ACGGCGGATG
9841 GTCGACAGAA GCACCATGTC CTTGGGTCCG GCCTGCTGAA TGCGCAGGCG GTCGGCCATG
9901 CCCCAGGCTT CGTTTTGACA TCGGCGCAGG TCTTTGTAGT AGTCTTGCAT GAGCCTTTCT
9961 ACCGGCACTT CTTCTTCTCC TTCCTCTTGT CCTGCATCTC TTGCATCTAT CGCTGCGGCG
10021 GCGGCGGAGT TTGGCCGTAG GTGGCGCCCT CTTCCTCCCA TGCGTGTGAC CCCGAAGCCC
10081 CTCATCGGCT GAAGCAGGGC TAGGTCGGCG ACAACGCGCT CGGCTAATAT GGCCTGCTGC
10141 ACCTGCGTGA GGGTAGACTG GAAGTCATCC ATGTCCACAA AGCGGTGGTA TGCGCCCGTG
10201 TTGATGGTGT AAGTGCAGTT GGCCATAACG GACCAGTTAA CGGTCTGGTG ACCCGGCTGC
10261 GAGAGCTCGG TGTACCTGAG ACGCGAGTAA GCCCTCGAGT CAAATACGTA GTCGTTGCAA
10321 GTCCGCACCA GGTACTGGTA TCCCACCAAA AAGTGCGGCG GCGGCTGGCG GTAGAGGGGC
10381 CAGCGTAGGG TGGCCGGGGC TCCGGGGGCG AGATCTTCCA ACATAAGGCG ATGATATCCG
10441 TAGATGTACC TGGACATCCA GGTGATGCCG GCGGCGGTGG TGGAGGCGCG CGGAAAGTCG
10501 CGGACGCGGT TCCAGATGTT GCGCAGCGGC AAAAAGTGCT CCATGGTCGG GACGCTCTGG
10561 CCGGTCAGGC GCGCGCAATC GTTGACGCTC TAGACCGTGC AAAAGGAGAG CCTGTAAGCG
10621 GGCACTCTTC CGTGGTCTGG TGGATAAATT CGCAAGGGTA TCATGGCGGA CGACCGGGGT
10681 TCGAGCCCCG TATCCGGCCG TCCGCCGTGA TCCATGCGGT TACCGCCCGC GTGTCGAACC
10741 CAGGTGTGCG ACGTCAGACA ACGGGGGAGT GCTCCTTTTG GCTTCCTTCC AGGCGCGGCG
10801 GCTGCTGCGC TAGCTTTTTT GGCCACTGGC CGCGCGCAGC GTAAGCGGTT AGGCTGGAAA
10861 GCGAAAGCAT TAAGTGGCTC GCTCCCTGTA GCCGGAGGGT TATTTTCCAA GGGTTGAGTC
10921 GCGGGACCCC CGGTTCGAGT CTCGGACCGG CCGGACTGCG GCGAACGGGG GTTTGCCTCC
10981 CCGTCATGCA AGACCCCGCT TGCAAATTCC TCCGGAAACA GGGACGAGCC CCTTTTTTGC
11041 TTTTCCCAGA TGCATCCGGT GCTGCGGCAG ATGCGCCCCC CTCCTCAGCA GCGGCAAGAG
11101 CAAGAGCAGC GGCAGACATG CAGGGCACCC TCCCCTCCTC CTACCGCGTC AGGAGGGGCG
11161 ACATCCGCGG TTGACGCGGC AGCAGATGGT GATTACGAAC CCCCGCGGCG CCGGGCCCGG
11221 CACTACCTGG ACTTGGAGGA GGGCGAGGGC CTGGCGCGGC TAGGAGCGCC CTCTCCTGAG
11281 CGGTACCCAA GGGTGCAGCT GAAGCGTGAT ACGCGTGAGG CGTACGTGCC GCGGCAGAAC
11341 CTGTTTCGCG ACCGCGAGGG AGAGGAGCCC GAGGAGATGC GGGATCGAAA GTTCCACGCA
11401 GGGCGCGAGC TGCGGCATGG CCTGAATCGC GAGCGGTTGC TGCGCGAGGA GGACTTTGAG
11461 CCCGACGCGC GAACCGGGAT TAGTCCCGCG CGCGCACACG TGGCGGCCGC CGACCTGGTA
11521 ACCGCATACG AGCAGACGGT GAACCAGGAG ATTAACTTTC AAAAAAGCTT TAACAACCAC
11581 GTGCGTACGC TTGTGGCGCG CGAGGAGGTG GCTATAGGAC TGATGCATCT GTGGGACTTT
11641 GTAAGCGCGC TGGAGCAAAA CCCAAATAGC AAGCCGCTCA TGGCGCAGCT GTTCCTTATA
11701 GTGCAGCACA GCAGGGACAA CGAGGCATTC AGGGATGCGC TGCTAAACAT AGTAGAGCCC
11761 GAGGGCCGCT GGCTGCTCGA TTTGATAAAC ATCCTGCAGA GCATAGTGGT GCAGGAGCGC
11821 AGCTTGAGCC TGGCTGACAA GGTGGCCGCC ATCAACTATT CCATGCTTAG CCTGGGCAAG
11881 TTTTACGCCC GCAAGATATA CCATACCCCT TACGTTCCCA TAGACAAGGA GGTAAAGATC
11941 GAGGGGTTCT ACATGCGCAT GGCGCTGAAG GTGCTTACCT TGAGCGACGA CCTGGGCGTT
12001 TATCGCAACG AGCGCATCCA CAAGGCCGTG AGCGTGAGCC GGCGGCGCGA GCTCAGCGAC
12061 CGCGAGCTGA TGCACAGCCT GCAAAGGGCC CTGGCTGGCA CGGGCAGCGG CGATAGAGAG
12121 GCCGAGTCCT ACTTTGACGC GGGCGCTGAC CTGCGCTGGG CCCCAAGCCG ACGCGCCCTG
12181 GAGGCAGCTG GGGCCGGACC TGGGCTGGCG GTGGCACCCG CGCGCGCTGG CAACGTCGGC
12241 GGCGTGGAGG AATATGACGA GGACGATGAG TACGAGCCAG AGGACGGCGA GTACTAAGCG
12301 GTGATGTTTC TGATCAGATG ATGCAAGACG CAACGGACCC GGCGGTGCGG GCGGCGCTGC
12361 AGAGCCAGCC GTCCGGCCTT AACTCCACGG ACGACTGGCG CCAGGTCATG GACCGCATCA
12421 TGTCGCTGAC TGCGCGCAAT CCTGACGCGT TCCGGCAGCA GCCGCAGGCC AACCGGCTCT
12481 CCGCAATTCT GGAAGCGGTG GTCCCGGCGC GCGCAAACCC CACGCACGAG AAGGTGCTGG
12541 CGATCGTAAA CGCGCTGGCC GAAAACAGGG CCATCCGGCC CGACGAGGCC GGCCTGGTCT
12601 ACGACGCGCT GCTTCAGCGC GTGGCTCGTT ACAACAGCGG CAACGTGCAG ACCAACCTGG
12661 ACCGGCTGGT GGGGGATGTG CGCGAGGCCG TGGCGCAGCG TGAGCGCGCG CAGCAGCAGG
12721 GCAACCTGGG CTCCATGGTT GCACTAAACG CCTTCCTGAG TACACAGCCC GCCAACGTGC
12781 CGCGGGGACA GGAGGACTAC ACCAACTTTG TGAGCGCACT GCGGCTAATG GTGACTGAGA
12841 CACCGCAAAG TGAGGTGTAC CAGTCTGGGC CAGACTATTT TTTCCAGACC AGTAGACAAG
12901 GCCTGCAGAC CGTAAACCTG AGCCAGGCTT TCAAAAACTT GCAGGGGCTG TGGGGGGTGC

FIGURE 21
(SHEET 4)

12961 GGGCTCCCAC AGGCGACCGC GCGACCGTGT CTAGCTTGCT GACGCCCAAC TCGCGCCTGT
13021 TGCTGCTGCT AATAGCGCCC TTCACGGACA GTGGCAGCGT GTCCCGGGAC ACATACCTAG
13081 GTCACTTGCT GACACTGTAC CGCGAGGCCA TAGGTCAGGC GCATGTGGAC GAGCATACTT
13141 TCCAGGAGAT TACAAGTGTC AGCCGCGCGC TGGGGCAGGA GGACACGGGC AGCCTGGAGG
13201 CAACCCTAAA CTACCTGCTG ACCAACCGGC GGCAGAAGAT CCCCTCGTTG CACAGTTTAA
13261 ACAGCGAGGA GGAGCGCATT TTGCGCTACG TGCAGCAGAG CGTGAGCCTT AACCTGATGC
13321 GCGACGGGGT AACGCCCAGC GTGGCGCTGG ACATGACCGC GCGCAACATG GAACCGGGCA
13381 TGTATGCCTC AAACCGGCCG TTTATCAACC GCCTAATGGA CTACTTGCAT CGCGCGGCCG
13441 CCGTGAACCC CGAGTATTTC ACCAATGCCA TCTTGAACCC GCACTGGCTA CCGCCCCCTG
13501 GTTTCTACAC CGGGGGATTC GAGGTGCCCG AGGGTAACGA TGGATTCCTC TGGGACGACA
13561 TAGACGACAG CGTGTTTTCC CCGCAACCGC AGACCCTGCT AGAGTTGCAA CAGCGCGAGC
13621 AGGCAGAGGC GGCGCTGCGA AAGGAAAGCT TCCGCAGGCC AAGCAGCTTG TCCGATCTAG
13681 GCGCTGCGGC CCCGCGGTCA GATGCTAGTA GCCCATTTCC AAGCTTGATA GGGTCTCTTA
13741 CCAGCACTCG CACCACCCGC CCGCGCCTGC TGGGCGAGGA GGAGTACCTA AACAACTCGC
13801 TGCTGCAGCC GCAGCGCGAA AAAAACCTGC CTCCGGCATT TCCCAACAAC GGGATAGAGA
13861 GCCTAGTGGA CAAGATGAGT AGATGGAAGA CGTACGCGCA GGAGCACAGG GACGTGCCAG
13921 GCCCGCGCCC GCCCACCCGT CGTCAAAGGC ACGACCGTCA GCGGGGTCTG GTGTGGGAGG
13981 ACGATGACTC GGCAGACGAC AGCAGCGTCC TGGATTTGGG AGGGAGTGGC AACCCGTTTG
14041 CGCACCTTCG CCCCAGGCTG GGGAGAATGT TTTAAAAAAA AAAAAGCATG ATGCAAAATA
14101 AAAAACTCAC CAAGGCCATG GCACCGAGCG TTGGTTTTCT TGTATTCCCC TTAGTATGCG
14161 GCGCGCGGCG ATGTATGAGG AAGGTCCTCC TCCCTCCTAC GAGAGTGTGG TGAGCGCGGC
14221 GCCAGTGGCG GCGGCGCTGG GTTCTCCCTT CGATGCTCCC CTGGACCCGC CGTTTGTGCC
14281 TCCGCGGTAC CTGCGGCCTA CCGGGGGGAG AAACAGCATC CGTTACTCTG AGTTGGCACC
14341 CCTATTCGAC ACCACCCGTG TGTACCTGGT GGACAACAAG TCAACGGATG TGGCATCCCT
14401 GAACTACCAG AACGACCACA GCAACTTTCT GACCACGGTC ATTCAAAACA ATGACTACAG
14461 CCCGGGGGAG GCAAGCACAC AGACCATCAA TCTTGACGAC CGGTCGCACT GGGGCGGCGA
14521 CCTGAAAACC ATCCTGCATA CCAACATGCC AAATGTGAAC GAGTTCATGT TTACCAATAA
14581 GTTTAAGGCG CGGGTGATGG TGTCGCGCTT GCCTACTAAG GACAATCAGG TGGAGCTGAA
14641 ATACGAGTGG GTGGAGTTCA CGCTGCCCGA GGGCAACTAC TCCGAGACCA TGACCATAGA
14701 CCTTATGAAC AACGCGATCG TGGAGCACTA CTTGAAAGTG GGCAGACAGA ACGGGGTTCT
14761 GGAAAGCGAC ATCGGGGTAA AGTTTGACAC CCGCAACTTC AGACTGGGGT TTGACCCCGT
14821 CACTGGTCTT GTCATGCCTG GGGTATATAC AAACGAAGCC TTCCATCCAG ACATCATTTT
14881 GCTGCCAGGA TGCGGGGTGG ACTTCACCCA CAGCCGCCTG AGCAACTTGT TGGGCATCCG
14941 CAAGCGGCAA CCCTTCCAGG AGGGCTTTAG GATCACCTAC GATGATCTGG AGGGTGGTAA
15001 CATTCCCGCA CTGTTGGATG TGGACGCCTA CCAGGCGAGC TTGAAAGATG ACACCGAACA
15061 GGGCGGGGGT GGCGCAGGCG GCAGCAACAG CAGTGGCAGC GGCGCGGAAG AGAACTCCAA
15121 CGCGGCAGCC GCGGCAATGC AGCCGGTGGA GGACATGAAC GATCATGCCA TTCGCGGCGA
15181 CACCTTTGCC ACACGGGCTG AGGAGAAGCG CGCTGAGGCC GAAGCAGCGG CCGAAGCTGC
15241 CGCCCCCGCT GCGCAACCCG AGGTCGAGAA GCCTCAGAAG AAACCGGTGA TCAAACCCCT
15301 GACAGAGGAC AGCAAGAAAC GCAGTTACAA CCTAATAAGC AATGACAGCA CCTTCACCCA
15361 GTACCGCAGC TGGTACCTTG CATACAACTA CGGCGACCCT CAGACCGGAA TCCGCTCATG
15421 GACCCTGCTT TGCACTCCTG ACGTAACCTG CGGCTCGGAG CAGGTCTACT GGTCGTTGCC
15481 AGACATGATG CAAGACCCCG TGACCTTCCG CTCCACGCGC CAGATCAGCA ACTTTCCGGT
15541 GGTGGGCGCC GAGCTGTTGC CCGTGCACTC CAAGAGCTTC TACAACGACC AGGCCGTCTA
15601 CTCCCAACTC ATCCGCCAGT TTACCTCTCT GACCCACGTG TTCAATCGCT TTCCCGAGAA
15661 CCAGATTTTG GCGCGCCCGC CAGCCCCCAC CATCACCACC GTCAGTGAAA ACGTTCCTGC
15721 TCTCACAGAT CACGGGACGC TACCGCTGCG CAACAGCATC GGAGGAGTCC AGCGAGTGAC
15781 CATTACTGAC GCCAGACGCC GCACCTGCCC CTACGTTTAC AAGGCCCTGG GCATAGTCTC
15841 GCCGCGCGTC CTATCGAGCC GCACTTTTTG AGCAAGCATG TCCATCCTTA TATCGCCCAG
15901 CAATAACACA GGCTGGGGCC TGCGCTTCCC AAGCAAGATG TTTGGCGGGG CCAAGAAGCG
15961 CTCCGACCAA CACCCAGTGC GCGTGCGCGG GCACTACCGC GCGCCCTGGG GCGCGCACAA
16021 ACGCGGCCGC ACTGGGCGCA CCACCGTCGA TGACGCCATC GACGCGGTGG TGGAGGAGGC
16081 GCGCAACTAC ACGCCCACGC CGCCACCAGT GTCCACAGTG GACGCGGCCA TTCAGACCGT
16141 GGTGCGCGGA GCCCGGCGCT ATGCTAAAAT GAAGAGACGG CGGAGGCGCG TAGCACGTCG
16201 CCACCGCCGC CGACCCGGCA CTGCCGCCCA ACGCGCGGCG GCGGCCCTGC TTAACCGCGC
16261 ACGTCGCACC GGCCGACGGG CGGCCATGCG GGCCGCTCGA AGGCTGGCCG CGGGTATTGT
16321 CACTGTGCCC CCCAGGTCCA GGCGACGAGC GGCCGCCGCA GCAGCCGCGG CCATTAGTGC

FIGURE 21
(SHEET 5)

16381 TATGACTCAG GGTCGCAGGG GCAACGTGTA TTGGGTGCGC GACTCGGTTA GCGGCCTGCG
16441 CGTGCCCGTG CGCACCCGCC CCCCGCGCAA CTAGATTGCA AGAAAAAACT ACTTAGACTC
16501 GTACTGTTGT ATGTATCCAG CGGCGGCGGC GCGCAACGAA GCTATGTCCA AGCGCAAAAT
16561 CAAAGAAGAG ATGCTCCAGG TCATCGCGCC GGAGATCTAT GGCCCCCCGA AGAAGGAAGA
16621 GCAGGATTAC AAGCCCCGAA AGCTAAAGCG GGTCAAAAAG AAAAAGAAAG ATGATGATGA
16681 TGAACTTGAC GACGAGGTGG AACTGCTGCA CGCTACCGCG CCCAGGCGAC GGGTACAGTG
16741 GAAAGGTCGA CGCGTAAAAC GTGTTTTGCG ACCCGGCACC ACCGTAGTCT TTACGCCCGG
16801 TGAGCGCTCC ACCCGCACCT ACAAGCGCGT GTATGATGAG GTGTACGGCG ACGAGGACCT
16861 GCTTGAGCAG GCCAACGAGC GCCTCGGGGA GTTTGCCTAC GGAAAGCGGC ATAAGGACAT
16921 GCTGGCGTTG CCGCTGGACG AGGGCAACCC AACACCTAGC CTAAAGCCCG TAACACTGCA
16981 GCAGGTGCTG CCCGCGCTTG CACCGTCCGA AGAAAAGCGC GGCCTAAAGC GCGAGTCTGG
17041 TGACTTGGCA CCCACCGTGC AGCTGATGGT ACCCAAGCGC CAGCGACTGG AAGATGTCTT
17101 GGAAAAAATG ACCGTGGAAC CTGGGCTGGA GCCCGAGGTC CGCGTGCGGC CAATCAAGCA
17161 GGTGGCGCCG GGACTGGGCG TGCAGACCGT GGACGTTCAG ATACCCACTA CCAGTAGCAC
17221 CAGTATTGCC ACCGCCACAG AGGGCATGGA GACACAAACG TCCCCGGTTG CCTCAGCGGT
17281 GGCGGATGCC GCGGTGCAGG CGGTCGCTGC GGCCGCGTCC AAGACCTCTA CGGAGGTGCA
17341 AACGGACCCG TGGATGTTTC GCGTTTCAGC CCCCCGGCGC CCGCGCGGTT CGAGGAAGTA
17401 CGGCGCCGCC AGCGCGCTAC TGCCCGAATA TGCCCTACAT CCTTCCATTG CGCCTACCCC
17461 CGGCTATCGT GGCTACACCT ACCGCCCCAG AAGACGAGCA ACTACCCGAC GCCGAACCAC
17521 CACTGGAACC CGCCGCCGCC GTCGCCGTCG CCAGCCCGTG CTGGCCCCGA TTTCCGTGCG
17581 CAGGGTGGCT CGCGAAGGAG GCAGGACCCT GGTGCTGCCA ACAGCGCGCT ACCACCCCAG
17641 CATCGTTTAA AAGCCGGTCT TTGTGGTTCT TGCAGATATG GCCCTCACCT GCCGCCTCCG
17701 TTTCCCGGTG CCGGGATTCC GAGGAAGAAT GCACCGTAGG AGGGGCATGG CCGGCCACGG
17761 CCTGACGGGC GGCATGCGTC GTGCGCACCA CCGGCGGCGG CGCGCGTCGC ACCGTCGCAT
17821 GCGCGGCGGT ATCCTGCCCC TCCTTATTCC ACTGATCGCC GCGGCGATTG GCGCCGTGCC
17881 CGGAATTGCA TCCGTGGCCT TGCAGGCGCA GAGACACTGA TTAAAAACAA GTTGCATGTG
17941 GAAAAATCAA AATAAAAAGT CTGGACTCTC ACGCTCGCTT GGTCCTGTAA CTATTTTGTA
18001 GAATGGAAGA CATCAACTTT GCGTCTCTGG CCCCGCGACA CGGCTCGCGC CCGTTCATGG
18061 GAAACTGGCA AGATATCGGC ACCAGCAATA TGAGCGGTGG CGCCTTCAGC TGGGGCTCGC
18121 TGTGGAGCGG CATTAAAAAT TTCGGTTCCA CCGTTAAGAA CTATGGCAGC AAGGCCTGGA
18181 ACAGCAGCAC AGGCCAGATG CTGAGGGATA AGTTGAAAGA GCAAAATTTC CAACAAAAGG
18241 TGGTAGATGG CCTGGCCTCT GGCATTAGCG GGGTGGTGGA CCTGGCCAAC CAGGCAGTGC
18301 AAAATAAGAT TAACAGTAAG CTTGATCCCC GCCCTCCCGT AGAGGAGCCT CCACCGGCCG
18361 TGGAGACAGT GTCTCCAGAG GGGCGTGGCG AAAAGCGTCC GCGCCCCGAC AGGGAAGAAA
18421 CTCTGGTGAC GCAAATAGAC GAGCCTCCCT CGTACGAGGA GGCACTAAAG CAAGGCCTGC
18481 CCACCACCCG TCCCATCGCG CCCATGGCTA CCGGAGTGCT GGGCCAGCAC ACACCCGTAA
18541 CGCTGGACCT GCCTCCCCCC GCCGACACCC AGCAGAAACC TGTGCTGCCA GGCCCGACCG
18601 CCGTTGTTGT AACCCGTCCT AGCCGCGCGT CCCTGCGCCG CGCCGCCAGC GGTCCGCGAT
18661 CGTTGCGGCC CGTAGCCAGT GGCAACTGGC AAAGCACACT GAACAGCATC GTGGGTCTGG
18721 GGGTGCAATC CCTGAAGCGC CGACGATGCT TCTGAATAGC TAACGTGTCG TATGTGTGTC
18781 ATGTATGCGT CCATGTCGCC GCCAGAGGAG CTGCTGAGCC GCCGCGCGCC CGCTTTCCAA
18841 GATGGCTACC CCTTCGATGA TGCCGCAGTG GTCTTACATG CACATCTCGG GCCAGGACGC
18901 CTCGGAGTAC CTGAGCCCCG GGCTGGTGCA GTTTGCCCGC GCCACCGAGA CGTACTTCAG
18961 CCTGAATAAC AAGTTTAGAA ACCCCACGGT GGCGCCTACG CACGACGTGA CCACAGACCG
19021 GTCCCAGCGT TTGACGCTGC GGTTCATCCC TGTGGACCGT GAGGATACTG CGTACTCGTA
19081 CAAGGCGCGG TTCACCCTAG CTGTGGGTGA TAACCGTGTG CTGGACATGG CTTCCACGTA
19141 CTTTGACATC CGCGGCGTGC TGGACAGGGG CCCTACTTTT AAGCCCTACT CTGGCACTGC
19201 CTACAACGCC CTGGCTCCCA AGGGTGCCCC AAATCCTTGC GAATGGGATG AAGCTGCTAC
19261 TGCTCTTGAA ATAAACCTAG AAGAAGAGGA CGATGACAAC GAAGACGAAG TAGACGAGCA
19321 AGCTGAGCAG CAAAAAACTC ACGTATTTGG GCAGGCGCCT TATTCTGGTA TAAATATTAC
19381 AAAGGAGGGT ATTCAAATAG GTGTCGAAGG TCAAACACCT AAATATGCCG ATAAAACATT
19441 TCAACCTGAA CCTCAAATAG GAGAATCTCA GTGGTACGAA ACTGAAATTA ATCATGCAGC
19501 TGGGAGAGTC CTTAAAAAGA CTACCCCAAT GAAACCATGT TACGGTTCAT ATGCAAAACC
19561 CACAAATGAA AATGGAGGGC AAGGCATTCT TGTAAAGCAA CAAAATGGAA AGCTAGAAAG
19621 TCAAGTGGAA ATGCAATTTT TCTCAACTAC TGAGGCGACC GCAGGCAATG GTGATAACTT
19681 GACTCCTAAA GTGGTATTGT ACAGTGAAGA TGTAGATATA GAAACCCCAG ACACTCATAT
19741 TTCTTACATG CCCACTATTA AGGAAGGTAA CTCACGAGAA CTAATGGGCC AACAATCTAT

FIGURE 21
(SHEET 6)

19801 GCCCAACAGG CCTAATTACA TTGCTTTTAG GGACAATTTT ATTGGTCTAA TGTATTACAA
19861 CAGCACGGGT AATATGGGTG TTCTGGCGGG CCAAGCATCG CAGTTGAATG CTGTTGTAGA
19921 TTTGCAAGAC AGAAACACAG AGCTTTCATA CCAGCTTTTG CTTGATTCCA TTGGTGATAG
19981 AACCAGGTAC TTTTCTATGT GGAATCAGGC TGTTGACAGC TATGATCCAG ATGTTAGAAT
20041 TATTGAAAAT CATGGAACTG AAGATGAACT TCCAAATTAC TGCTTTCCAC TGGGAGGTGT
20101 GATTAATACA GAGACTCTTA CCAAGGTAAA ACCTAAAACA GGTCAGGAAA ATGGATGGGA
20161 AAAAGATGCT ACAGAATTTT CAGATAAAAA TGAAATAAGA GTTGGAAATA ATTTTGCCAT
20221 GGAAATCAAT CTAAATGCCA ACCTGTGGAG AAATTTCCTG TACTCCAACA TAGCGCTGTA
20281 TTTGCCCGAC AAGCTAAAGT ACAGTCCTTC CAACGTAAAA ATTTCTGATA ACCCAAACAC
20341 CTACGACTAC ATGAACAAGC GAGTGGTGGC TCCCGGGTTA GTGGACTGCT ACATTAACCT
20401 TGGAGCACGC TGGTCCCTTG ACTATATGGA CAACGTCAAC CCATTTAACC ACCACCGCAA
20461 TGCTGGCCTG CGCTACCGCT CAATGTTGCT GGGCAATGGT CGCTATGTGC CCTTCCACAT
20521 CCAGGTGCCT CAGAAGTTCT TTGCCATTAA AAACCTCCTT CTCCTGCCGG GCTCATACAC
20581 CTACGAGTGG AACTTCAGGA AGGATGTTAA CATGGTTCTG CAGAGCTCCC TAGGAAATGA
20641 CCTAAGGGTT GACGGAGCCA GCATTAAGTT TGATAGCATT TGCCTTTACG CCACCTTCTT
20701 CCCCATGGCC CACAACACCG CCTCCACGCT TGAGGCCATG CTTAGAAACG ACACCAACGA
20761 CCAGTCCTTT AACGACTATC TCTCCGCCGC CAACATGCTC TACCCTATAC CCGCCAACGC
20821 TACCAACGTG CCCATATCCA TCCCCTCCCG CAACTGGGCG GCTTTCCGCG GCTGGGCCTT
20881 CACGCGCCTT AAGACTAAGG AAACCCCATC ACTGGGCTCG GGCTACGACC CTTATTACAC
20941 CTACTCTGGC TCTATACCCT ACCTAGATGG AACCTTTTAC CTCAACCACA CCTTTAAGAA
21001 GGTGGCCATT ACCTTTGACT CTTCTGTCAG CTGGCCTGGC AATGACCGCC TGCTTACCCC
21061 CAACGAGTTT GAAATTAAGC GCTCAGTTGA CGGGGAGGGT TACAACGTTG CCCAGTGTAA
21121 CATGACCAAA GACTGGTTCC TGGTACAAAT GCTAGCTAAC TACAACATTG GCTACCAGGG
21181 CTTCTATATC CCAGAGAGCT ACAAGGACCG CATGTACTCC TTCTTTAGAA ACTTCCAGCC
21241 CATGAGCCGT CAGGTGGTGG ATGATACTAA ATACAAGGAC TACCAACAGG TGGGCATCCT
21301 ACACCAACAC AACAACTCTG GATTTGTTGG CTACCTTGCC CCCACCATGC GCGAAGGACA
21361 GGCCTACCCT GCTAACTTCC CCTATCCGCT TATAGGCAAG ACCGCAGTTG ACAGCATTAC
21421 CCAGAAAAAG TTTCTTTGCG ATCGCACCCT TTGGCGCATC CCATTCTCCA GTAACTTTAT
21481 GTCCATGGGC GCACTCACAG ACCTGGGCCA AAACCTTCTC TACGCCAACT CCGCCCACGC
21541 GCTAGACATG ACTTTTGAGG TGGATCCCAT GGACGAGCCC ACCCTTCTTT ATGTTTTGTT
21601 TGAAGTCTTT GACGTGGTCC GTGTGCACCG GCCGCACCGC GGCGTCATCG AAACCGTGTA
21661 CCTGCGCACG CCCTTCTCGG CCGGCAACGC CACAACATAA AGAAGCAAGC AACATCAACA
21721 ACAGCTGCCG CCATGGGCTC CAGTGAGCAG GAACTGAAAG CCATTGTCAA AGATCTTGGT
21781 TGTGGGCCAT ATTTTTTGGG CACCTATGAC AAGCGCTTTC CAGGCTTTGT TTCTCCACAC
21841 AAGCTCGCCT GCGCCATAGT CAATACGGCC GGTCGCGAGA CTGGGGGCGT ACACTGGATG
21901 GCCTTTGCCT GGAACCCGCA CTCAAAAACA TGCTACCTCT TTGAGCCCTT TGGCTTTTCT
21961 GACCAGCGAC TCAAGCAGGT TTACCAGTTT GAGTACGAGT CACTCCTGCG CCGTAGCGCC
22021 ATTGCTTCTT CCCCCGACCG CTGTATAACG CTGGAAAAGT CCACCCAAAG CGTACAGGGG
22081 CCCAACTCGG CCGCCTGTGG ACTATTCTGC TGCATGTTTC TCCACGCCTT TGCCAACTGG
22141 CCCCAAACTC CCATGGATCA CAACCCCACC ATGAACCTTA TTACCGGGGT ACCCAACTCC
22201 ATGCTCAACA GTCCCCAGGT ACAGCCCACC CTGCGTCGCA ACCAGGAACA GCTCTACAGC
22261 TTCCTGGAGC GCCACTCGCC CTACTTCCGC AGCCACAGTG CGCAGATTAG GAGCGCCACT
22321 TCTTTTTGTC ACTTGAAAAA CATGTAAAAA TAATGTACTA GAGACACTTT CAATAAAGGC
22381 AAATGCTTTT ATTTGTACAC TCTCGGGTGA TTATTTACCC CCACCCTTGC CGTCTGCGCC
22441 GTTTAAAAAT CAAAGGGGTT CTGCCGCGCA TCGCTATGCG CCACTGGCAG GGACACGTTG
22501 CGATACTGGT GTTTAGTGCT CCACTTAAAC TCAGGCACAA CCATCCGCGG CAGCTCGGTG
22561 AAGTTTTCAC TCCACAGGCT GCGCACCATC ACCAACGCGT TTAGCAGGTC GGGCGCCGAT
22621 ATCTTGAAGT CGCAGTTGGG GCCTCCGCCC TGCGCGCGCG AGTTGCGATA CACAGGGTTG
22681 CAGCACTGGA ACACTATCAG CGCCGGGTGG TGCACGCTGG CCAGCACGCT CTTGTCGGAG
22741 ATCAGATCCG CGTCCAGGTC CTCCGCGTTG CTCAGGGCGA ACGGAGTCAA CTTTGGTAGC
22801 TGCCTTCCCA AAAAGGGCGC GTGCCCAGGC TTTGAGTTGC ACTCGCACCG TAGTGGCATC
22861 AAAAGGTGAC CGTGCCCGGT CTGGGCGTTA GGATACAGCG CCTGCATAAA AGCCTTGATC
22921 TGCTTAAAAG CCACCTGAGC CTTTGCGCCT TCAGAGAAGA ACATGCCGCA AGACTTGCCG
22981 GAAAACTGAT TGGCCGGACA GGCCGCGTCG TGCACGCAGC ACCTTGCGTC GGTGTTGGAG
23041 ATCTGCACCA CATTTCGGCC CCACCGGTTC TTCACGATCT TGGCCTTGCT AGACTGCTCC
23101 TTCAGCGCGC GCTGCCCGTT TTCGCTCGTC ACATCCATTT CAATCACGTG CTCCTTATTT
23161 ATCATAATGC TTCCGTGTAG ACACTTAAGC TCGCCTTCGA TCTCAGCGCA GCGGTGCAGC

FIGURE 21
(SHEET 7)

23221 CACAACGCGC AGCCCGTGGG CTCGTGATGC TTGTAGGTCA CCTCTGCAAA CGACTGCAGG
23281 TACGCCTGCA GGAATCGCCC CATCATCGTC ACAAAGGTCT TGTTGCTGGT GAAGGTCAGC
23341 TGCAACCCGC GGTGCTCCTC GTTCAGCCAG GTCTTGCATA CGGCCGCCAG AGCTTCCACT
23401 TGGTCAGGCA GTAGTTTGAA GTTCGCCTTT AGATCGTTAT CCACGTGGTA CTTGTCCATC
23461 AGCGCGCGCG CAGCCTCCAT GCCCTTCTCC CACGCAGACA CGATCGGCAC ACTCAGCGGG
23521 TTCATCACCG TAATTTCACT TTCCGCTTCG CTGGGCTCTT CCTCTTCCTC TTGCGTCCGC
23581 ATACCACGCG CCACTGGGTC GTCTTCATTC AGCCGCCGCA CTGTGCGCTT ACCTCCTTTG
23641 CCATGCTTGA TTAGCACCGG TGGGTTGCTG AAACCCACCA TTTGTAGCGC CACATCTTCT
23701 CTTTCTTCCT CGCTGTCCAC GATTACCTCT GGTGATGGCG GGCGCTCGGG CTTGGGAGAA
23761 GGGCGCTTCT TTTTCTTCTT GGGCGCAATG GCCAAATCCG CCGCCGAGGT CGATGGCCGC
23821 GGGCTGGGTG TGCGCGGCAC CAGCGCGTCT TGTGATGAGT CTTCCTCGTC CTCGGACTCG
23881 ATACGCCGCC TCATCCGCTT TTTTGGGGGC GCCCGGGGAG GCGGCGGCGA CGGGGACGGG
23941 GACGACACGT CCTCCATGGT TGGGGGACGT CGCGCCGCAC CGCGTCCGCG CTCGGGGGTG
24001 GTTTCGCGCT GCTCCTCTTC CCGACTGGCC ATTTCCTTCT CCTATAGGCA GAAAAAGATC
24061 ATGGAGTCAG TCGAGAAGAA GGACAGCCTA ACCGCCCCCT CTGAGTTCGC CACCACCGCC
24121 TCCACCGATG CCGCCAACGC GCCTACCACC TTCCCCGTCG AGGCACCCCC GCTTGAGGAG
24181 GAGGAAGTGA TTATCGAGCA GGACCCAGGT TTTGTAAGCG AAGACGACGA GGACCGCTCA
24241 GTACCAACAG AGGATAAAAA GCAAGACCAG GACAACGCAG AGGCAAACGA GGAACAAGTC
24301 GGGCGGGGGG ACGAAAGGCA TGGCGACTAC CTAGATGTGG GAGACGACGT GCTGTTGAAG
24361 CATCTGCAGC GCCAGTGCGC CATTATCTGC GACGCGTTGC AAGAGCGCAG CGATGTGCCC
24421 CTCGCCATAG CGGATGTCAG CCTTGCCTAC GAACGCCACC TATTCTCACC GCGCGTACCC
24481 CCCAAACGCC AAGAAAACGG CACATGCGAG CCCAACCCGC GCCTCAACTT CTACCCCGTA
24541 TTTGCCGTGC CAGAGGTGCT TGCCACCTAT CACATCTTTT TCCAAAACTG CAAGATACCC
24601 CTATCCTGCC GTGCCAACCG CAGCCGAGCG GACAAGCAGC TGGCCTTGCG GCAGGGCGCT
24661 GTCATACCTG ATATCGCCTC GCTCAACGAA GTGCCAAAAA TCTTTGAGGG TCTTGGACGC
24721 GACGAGAAGC GCGCGGCAAA CGCTCTGCAA CAGGAAAACA GCGAAAATGA AAGTCACTCT
24781 GGAGTGTTGG TGGAACTCGA GGGTGACAAC GCGCGCCTAG CCGTACTAAA ACGCAGCATC
24841 GAGGTCACCC ACTTTGCCTA CCCGGCACTT AACCTACCCC CCAAGGTCAT GAGCACAGTC
24901 ATGAGTGAGC TGATCGTGCG CCGTGCGCAG CCCCTGGAGA GGGATGCAAA TTTGCAAGAA
24961 CAAACAGAGG AGGGCCTACC CGCAGTTGGC GACGAGCAGC TAGCGCGCTG GCTTCAAACG
25021 CGCGAGCCTG CCGACTTGGA GGAGCGACGC AAACTAATGA TGGCCGCAGT GCTCGTTACC
25081 GTGGAGCTTG AGTGCATGCA GCGGTTCTTT GCTGACCCGG AGATGCAGCG CAAGCTAGAG
25141 GAAACATTGC ACTACACCTT TCGACAGGGC TACGTACGCC AGGCCTGCAA GATCTCCAAC
25201 GTGGAGCTCT GCAACCTGGT CTCCTACCTT GGAATTTTGC ACGAAAACCG CCTTGGGCAA
25261 AACGTGCTTC ATTCCACGCT CAAGGGCGAG GCGCGCCGCG ACTACGTCCG CGACTGCGTT
25321 TACTTATTTC TATGCTACAC CTGGCAGACG GCCATGGGCG TTTGGCAGCA GTGCTTGGAG
25381 GAGTGCAACC TCAAGGAGCT GCAGAAACTG CTAAAGCAAA ACTTGAAGGA CCTATGGACG
25441 GCCTTCAACG AGCGCTCCGT GGCCGCGCAC CTGGCGGACA TCATTTTCCC CGAACGCCTG
25501 CTTAAAACCC TGCAACAGGG TCTGCCAGAC TTCACCAGTC AAAGCATGTT GCAGAACTTT
25561 AGGAACTTTA TCCTAGAGCG CTCAGGAATC TTGCCCGCCA CCTGCTGTGC ACTTCCTAGC
25621 GACTTTGTGC CCATTAAGTA CCGCGAATGC CCTCCGCCGC TTTGGGGCCA CTGCTACCTT
25681 CTGCAGCTAG CCAACTACCT TGCCTACCAC TCTGACATAA TGGAAGACGT GAGCGGTGAC
25741 GGTCTACTGG AGTGTCACTG TCGCTGCAAC CTATGCACCC CGCACCGCTC CCTGGTTTGC
25801 AATTCGCAGC TGCTTAACGA AAGTCAAATT ATCGGTACCT TTGAGCTGCA GGGTCCCTCG
25861 CCTGACGAAA AGTCCGCGGC TCCGGGGTTG AAACTCACTC CGGGGCTGTG GACGTCGGCT
25921 TACCTTCGCA AATTTGTACC TGAGGACTAC CACGCCCACG AGATTAGGTT CTACGAAGAC
25981 CAATCCCGCC CGCCAAATGC GGAGCTTACC GCCTGCGTCA TTACCCAGGG CCACATTCTT
26041 GGCCAATTGC AAGCCATCAA CAAAGCCCGC CAAGAGTTTC TGCTACGAAA GGGACGGGGG
26101 GTTTACTTGG ACCCCCAGTC CGGCGAGGAG CTCAACCCAA TCCCCCCGCC GCCGCAGCCC
26161 TATCAGCAGC AGCCGCGGGC CCTTGCTTCC CAGGATGGCA CCCAAAAAGA AGCTGCAGCT
26221 GCCGCCGCCA CCCACGGACG AGGAGGAATA CTGGGACAGT CAGGCAGAGG AGGTTTTGGA
26281 CGAGGAGGAG GAGGACATGA TGGAAGACTG GGAGAGCCTA GACGAGGAAG CTTCCGAGGT
26341 CGAAGAGGTG TCAGACGAAA CACCGTCACC CTCGGTCGCA TTCCCCTCGC CGGCGCCCCA
26401 GAAATCGGCA ACCGGTTCCA GCATGGCTAC AACCTCCGCT CCTCAGGCGC CGCCGGCACT
26461 GCCCGTTCGC CGACCCAACC GTAGATGGGA CACCACTGGA ACCAGGGCCG GTAAGTCCAA
26521 GCAGCCGCCG CCGTTAGCCC AAGAGCAACA ACAGCGCCAA GGCTACCGCT CATGGCGCGG
26581 GCACAAGAAC GCCATAGTTG CTTGCTTGCA AGACTGTGGG GGCAACATCT CCTTCGCCCG

FIGURE 21
(SHEET 8)

26641 CCGCTTTCTT CTCTACCATC ACGGCGTGGC CTTCCCCCGT AACATCCTGC ATTACTACCG
26701 TCATCTCTAC AGCCCATACT GCACCGGCGG CAGCGGCAGC GGCAGCAACA GCAGCGGCCA
26761 CACAGAAGCA AAGGCGACCG GATAGCAAGA CTCTGACAAA GCCCAAGAAA TCCACAGCGG
26821 CGGCAGCAGC AGGAGGAGGA GCGCTGCGTC TGGCGCCCAA CGAACCCGTA TCGACCCGCG
26881 AGCTTAGAAA CAGGATTTTT CCCACTCTGT ATGCTATATT TCAACAGAGC AGGGGCCAAG
26941 AACAAGAGCT GAAAATAAAA AACAGGTCTC TGCGATCCCT CACCCGCAGC TGCCTGTATC
27001 ACAAAAGCGA AGATCAGCTT CGGCGCACGC TGGAAGACGC GGAGGCTCTC TTCAGTAAAT
27061 ACTGCGCGCT GACTCTTAAG GACTAGTTTC GCGCCCTTTC TCAAATTTAA GCGCGAAAAC
27121 TACGTCATCT CCAGCGGCCA CACCCGGCGC CAGCACCTGT CGTCAGCGCC ATTATGAGCA
27181 AGGAAATTCC CACGCCCTAC ATGTGGAGTT ACCAGCCACA AATGGGACTT GCGGCTGGAG
27241 CTGCCCAAGA CTACTCAACC CGAATAAACT ACATGAGCGC GGGACCCCAC ATGATATCCC
27301 GGGTCAACGG AATCCGCGCC CACCGAAACC GAATTCTCTT GGAACAGGCG GCTATTACCA
27361 CCACACCTCG TAATAACCTT AATCCCCGTA GTTGGCCCGC TGCCCTGGTG TACCAGGAAA
27421 GTCCCGCTCC CACCACTGTG GTACTTCCCA GAGACGCCCA GGCCGAAGTT CAGATGACTA
27481 ACTCAGGGGC GCAGCTTGCG GGCGGCTTTC GTCACAGGGT GCGGTCGCCC GGGCAGGGTA
27541 TAACTCACCT GACAATCAGA GGGCGAGGTA TTCAGCTCAA CGACGAGTCG GTGAGCTCCT
27601 CGCTTGGTCT CCGTCCGGAC GGGACATTTC AGATCGGCGG CGCCGGCCGT CCTTCATTCA
27661 CGCCTCGTCA GGCAATCCTA ACTCTGCAGA CCTCGTCCTC TGAGCCGCGC TCTGGAGGCA
27721 TTGGAACTCT GCAATTTATT GAGGAGTTTG TGCCATCGGT CTACTTTAAC CCCTTCTCGG
27781 GACCTCCCGG CCACTATCCG GATCAATTTA TTCCTAACTT TGACGCGGTA AAGGACTCGG
27841 CGGACGGCTA CGACTGAATG TTAAGTGGAG AGGCAGAGCA ACTGCGCCTG AAACACCTGG
27901 TCCACTGTCG CCGCCACAAG TGCTTTGCCC GCGACTCCGG TGAGTTTTGC TACTTTGAAT
27961 TGCCCGAGGA TCATATCGAG GGCCCGGCGC ACGGCGTCCG GCTTACCGCC CAGGGAGAGC
28021 TTGCCCGTAG CCTGATTCGG GAGTTTACCC AGCGCCCCCT GCTAGTTGAG CGGGACAGGG
28081 GACCCTGTGT TCTCACTGTG ATTTGCAACT GTCCTAACCT TGGATTACAT CAAGATCTTT
28141 GTTGCCATCT CTGTGCTGAG TATAATAAAT ACAGAAATTA AAATATACTG GGGCTCCTAT
28201 CGCCATCCTG TAAACGCCAC CGTCTTCACC CGCCCAAGCA AACCAAGGCG AACCTTACCT
28261 GGTACTTTTA ACATCTCTCC CTCTGTGATT TACAACAGTT TCAACCCAGA CGGAGTGAGT
28321 CTACGAGAGA ACCTCTCCGA GCTCAGCTAC TCCATCAGAA AAAACACCAC CCTCCTTACC
28381 TGCCGGGAAC GTACGAGTGC GTCACCGGCC GCTGCACCAC ACCTACCGCC TGACCGTAAA
28441 CCAGACTTTT TCCGGACAGA CCTCAATAAC TCTGTTTACC AGAACAGGAG GTGAGCTTAG
28501 AAAACCCTTA GGGTATTAGG CCAAAGGCGC AGCTACTGTG GGGTTTATGA ACAATTCAAG
28561 CAACTCTACG GGCTATTCTA ATTCAGGTTT CTCTAGAATC GGGGTTGGGG TTATTCTCTG
28621 TCTTGTGATT CTCTTTATTC TTATACTAAC GCTTCTCTGC CTAAGGCTCG CCGCCTGCTG
28681 TGTGCACATT TGCATTTATT GTCAGCTTTT TAAACGCTGG GGTCGCCACC CAAGATGATT
28741 AGGTACATAA TCCTAGGTTT ACTCACCCTT GCGTCAGCCC ACGGTACCAC CCAAAAGGTG
28801 GATTTTAAGG AGCCAGCCTG TAATGTTACA TTCGCAGCTG AAGCTAATGA GTGCACCACT
28861 CTTATAAAAT GCACCACAGA ACATGAAAAG CTGCTTATTC GCCACAAAAA CAAAATTGGC
28921 AAGTATGCTG TTTATGCTAT TTGGCAGCCA GGTGACACTA CAGAGTATAA TGTTACAGTT
28981 TTCCAGGGTA AAAGTCATAA AACTTTTATG TATACTTTTC CATTTTATGA AATGTGCGAC
29041 ATTACCATGT ACATGAGCAA ACAGTATAAG TTGTGGCCCC CACAAAATTG TGTGGAAAAC
29101 ACTGGCACTT TCTGCTGCAC TGCTATGCTA ATTACAGTGC TCGCTTTGGT CTGTACCCTA
29161 CTCTATATTA AATACAAAAG CAGACGCAGC TTTATTGAGG AAAAGAAAAT GCCTTAATTT
29221 ACTAAGTTAC AAAGCTAATG TCACCACTAA CTGCTTTACT CGCTGCTTGC AAAACAAATT
29281 CAAAAAGTTA GCATTATAAT TAGAATAGGA TTTAAACCCC CCGGTCATTT CCTGCTCAAT
29341 ACCATTCCCC TGAACAATTG ACTCTATGTG GGATATGCTC CAGCGCTACA ACCTTGAAGT
29401 CAGGCTTCCT GGATGTCAGC ATCTGACTTT GGCCAGCACC TGTCCCGCGG ATTTGTTCCA
29461 GTCCAACTAC AGCGACCCAC CCTAACAGAG ATGACCAACA CAACCAACGC GGCCGCCGCT
29521 ACCGGACTTA CATCTACCAC AAATACACCC CAAGTTTCTG CCTTTGTCAA TAACTGGGAT
29581 AACTTGGGCA TGTGGTGGTT CTCCATAGCG CTTATGTTTG TATGCCTTAT TATTATGTGG
29641 CTCATCTGCT GCCTAAAGCG CAAACGCGCC CGACCACCCA TCTATAGTCC CATCATTGTG
29701 CTACACCCAA ACAATGATGG AATCCATAGA TTGGACGGAC TGAAACACAT GTTCTTTTCT
29761 CTTACAGTAT GATTAAATGA GACATGATTC CTCGAGTTTT TATATTACTG ACCCTTGTTG
29821 CGCTTTTTTG TGCGTGCTCC ACATTGGCTG CGGTTTCTCA CATCGAAGTA GACTGCATTC
29881 CAGCCTTCAC AGTCTATTTG CTTTACGGAT TTGTCACCCT CACGCTCATC TGCAGCCTCA
29941 TCACTGTGGT CATCGCCTTT ATCCAGTGCA TTGACTGGGT CTGTGTGCGC TTTGCATATC
30001 TCAGACACCA TCCCCAGTAC AGGGACAGGA CTATAGCTGA GCTTCTTAGA ATTCTTTAAT

FIGURE 21
(SHEET 9)

30061 TATGAAATTT ACTGTGACTT TTCTGCTGAT TATTTGCACC CTATCTGCGT TTTGTTCCCC
30121 GACCTCCAAG CCTCAAAGAC ATATATCATG CAGATTCACT CGTATATGGA ATATTCCAAG
30181 TTGCTACAAT GAAAAAAGCG ATCTTTCCGA AGCCTGGTTA TATGCAATCA TCTCTGTTAT
30241 GGTGTTCTGC AGTACCATCT TAGCCCTAGC TATATATCCC TACCTTGACA TTGGCTGGAA
30301 ACGAATAGAT GCCATGAACC ACCCAACTTT CCCCGCGCCC GCTATGCTTC CACTGCAACA
30361 AGTTGTTGCC GGCGGCTTTG TCCCAGCCAA TCAGCCTCGC CCCACTTCTC CCACCCCCAC
30421 TGAAATCAGC TACTTTAATC TAACAGGAGG AGATGACTGA CACCCTAGAT CTAGAAATGG
30481 ACGGAATTAT TACAGAGCAG CGCCTGCTAG AAAGACGCAG GGCAGCGGCC GAGCAACAGC
30541 GCATGAATCA AGAGCTCCAA GACATGGTTA ACTTGCACCA GTGCAAAAGG GGTATCTTTT
30601 GTCTGGTAAA GCAGGCCAAA GTCACCTACG ACAGTAATAC CACCGGACAC CGCCTTAGCT
30661 ACAAGTTGCC AACCAAGCGT CAGAAATTGG TGGTCATGGT GGGAGAAAAG CCCATTACCA
30721 TAACTCAGCA CTCGGTAGAA ACCGAAGGCT GCATTCACTC ACCTTGTCAA GGACCTGAGG
30781 ATCTCTGCAC CCTTATTAAG ACCCTGTGCG GTCTCAAAGA TCTTATTCCC TTTAACTAAT
30841 AAAAAAAAAT AATAAAGCAT CACTTACTTA AAATCAGTTA GCAAATTTCT GTCCAGTTTA
30901 TTCAGCAGCA CCTCCTTGCC CTCCTCCCAG CTCTGGTATT GCAGCTTCCT CCTGGCTGCA
30961 AACTTTCTCC ACAATCTAAA TGGAATGTCA GTTTCCTCCT GTTCCTGTCC ATCCGCACCC
31021 ACTATCTTCA TGTTGTTGCA GATGAAGCGC GCAAGACCGT CTGAAGATAC CTTCAACCCC
31081 GTGTATCCAT ATGACACGGA AACCGGTCCT CCAACTGTGC CTTTTCTTAC TCCTCCCTTT
31141 GTATCCCCCA ATGGGTTTCA AGAGAGTCCC CCTGGGGTAC TCTCTTTGCG CCTATCCGAA
31201 CCTCTAGTTA CCTCCAATGG CATGCTTGCG CTCAAAATGG GCAACGGCCT CTCTCTGGAC
31261 GAGGCCGGCA ACCTTACCTC CCAAAATGTA ACCACTGTGA GCCCACCTCT CAAAAAAACC
31321 AAGTCAAACA TAAACCTGGA AATATCTGCA CCCCTCACAG TTACCTCAGA AGCCCTAACT
31381 GTGGCTGCCG CCGCACCTCT AATGGTCGCG GGCAACACAC TCACCATGCA ATCACAGGCC
31441 CCGCTAACCG TGCACGACTC CAAACTTAGC ATTGCCACCC AAGGACCCCT CACAGTGTCA
31501 GAAGGAAAGC TAGCCCTGCA AACATCAGGC CCCCTCACCA CCACCGATAG CAGTACCCTT
31561 ACTATCACTG CCTCACCCCC TCTAACTACT GCCACTGGTA GCTTGGGCAT TGACTTGAAA
31621 GAGCCCATTT ATACACAAAA TGGAAAACTA GGACTAAAGT ACGGGGCTCC TTTGCATGTA
31681 ACAGACGACC TAAACACTTT GACCGTAGCA ACTGGTCCAG GTGTGACTAT TAATAATACT
31741 TCCTTGCAAA CTAAAGTTAC TGGAGCCTTG GGTTTTGATT CACAAGGCAA TATGCAACTT
31801 AATGTAGCAG GAGGACTAAG GATTGATTCT CAAAACAGAC GCCTTATACT TGATGTTAGT
31861 TATCCGTTTG ATGCTCAAAA CCAACTAAAT CTAAGACTAG GACAGGGCCC TCTTTTTATA
31921 AACTCAGCCC ACAACTTGGA TATTAACTAC AACAAAGGCC TTTACTTGTT TACAGCTTCA
31981 AACAATTCCA AAAAGCTTGA GGTTAACCTA AGCACTGCCA AGGGGTTGAT GTTTGACGCT
32041 ACAGCCATAG CCATTAATGC AGGAGATGGG CTTGAATTTG GTTCACCTAA TGCACCAAAC
32101 ACAAATCCCC TCAAAACAAA AATTGGCCAT GGCCTAGAAT TTGATTCAAA CAAGGCTATG
32161 GTTCCTAAAC TAGGAACTGG CCTTAGTTTT GACAGCACAG GTGCCATTAC AGTAGGAAAC
32221 AAAAATAATG ATAAGCTAAC TTTGTGGACC ACACCAGCTC CATCTCCTAA CTGTAGACTA
32281 AATGCAGAGA AAGATGCTAA ACTCACTTTG GTCTTAACAA AATGTGGCAG TCAAATACTT
32341 GCTACAGTTT CAGTTTTGGC TGTTAAAGGC AGTTTGGCTC CAATATCTGG AACAGTTCAA
32401 AGTGCTCATC TTATTATAAG ATTTGACGAA AATGGAGTGC TACTAAACAA TTCCTTCCTG
32461 GACCCAGAAT ATTGGAACTT TAGAAATGGA GATCTTACTG AAGGCACAGC CTATACAAAC
32521 GCTGTTGGAT TTATGCCTAA CCTATCAGCT TATCCAAAAT CTCACGGTAA AACTGCCAAA
32581 AGTAACATTG TCAGTCAAGT TTACTTAAAC GGAGACAAAA CTAAACCTGT AACACTAACC
32641 ATTACACTAA ACGGTACACA GGAAACAGGA GACACAACTC CAAGTGCATA CTCTATGTCA
32701 TTTTCATGGG ACTGGTCTGG CCACAACTAC ATTAATGAAA TATTTGCCAC ATCCTCTTAC
32761 ACTTTTTCAT ACATTGCCCA AGAATAAAGA ATCGTTTGTG TTATGTTTCA ACGTGTTTAT
32821 TTTTCAATTG CAGAAAATTT CAAGTCATTT TTCATTCAGT AGTATAGCCC CACCACCACA
32881 TAGCTTATAC AGATCACCGT ACCTTAATCA AACTCACAGA ACCCTAGTAT TCAACCTGCC
32941 ACCTCCCTCC CAACACACAG AGTACACAGT CCTTTCTCCC CGGCTGGCCT TAAAAAGCAT
33001 CATATCATGG GTAACAGACA TATTCTTAGG TGTTATATTC CACACGGTTT CCTGTCGAGC
33061 CAAACGCTCA TCAGTGATAT TAATAAACTC CCCGGGCAGC TCACTTAAGT TCATGTCGCT
33121 GTCCAGCTGC TGAGCCACAG GCTGCTGTCC AACTTGCGGT TGCTTAACGG GCGGCGAAGG
33181 AGAAGTCCAC GCCTACATGG GGGTAGAGTC ATAATCGTGC ATCAGGATAG GGCGGTGGTG
33241 CTGCAGCAGC GCGCGAATAA ACTGCTGCCG CCGCCGCTCC GTCCTGCAGG AATACAACAT
33301 GGCAGTGGTC TCCTCAGCGA TGATTCGCAC CGCCCGCAGC ATAAGGCGCC TTGTCCTCCG
33361 GGCACAGCAG CGCACCCTGA TCTCACTTAA ATCAGCACAG TAACTGCAGC ACAGCACCAC
33421 AATATTGTTC AAAATCCCAC AGTGCAAGGC GCTGTATCCA AAGCTCATGG CGGGGACCAC

FIGURE 21
(SHEET 10)

33481 AGAACCCACG TGGCCATCAT ACCACAAGCG CAGGTAGATT AAGTGGCGAC CCCTCATAAA
33541 CACGCTGGAC ATAAACATTA CCTCTTTTGG CATGTTGTAA TTCACCACCT CCCGGTACCA
33601 TATAAACCTC TGATTAAACA TGGCGCCATC CACCACCATC CTAAACCAGC TGGCCAAAAC
33661 CTGCCCGCCG GCTATACACT GCAGGGAACC GGGACTGGAA CAATGACAGT GGAGAGCCCA
33721 GGACTCGTAA CCATGGATCA TCATGCTCGT CATGATATCA ATGTTGGCAC AACACAGGCA
33781 CACGTGCATA CACTTCCTCA GGATTACAAG CTCCTCCCGC GTTAGAACCA TATCCCAGGG
33841 AACAACCCAT TCCTGAATCA GCGTAAATCC CACACTGCAG GGAAGACCTC GCACGTAACT
33901 CACGTTGTGC ATTGTCAAAG TGTTACATTC GGGCAGCAGC GGATGATCCT CCAGTATGGT
33961 AGCGCGGGTT TCTGTCTCAA AAGGAGGTAG ACGATCCCTA CTGTACGGAG TGCGCCGAGA
34021 CAACCGAGAT CGTGTTGGTC GTAGTGTCAT GCCAAATGGA ACGCCGGACG TAGTCATATT
34081 TCCTGAAGCA AAACCAGGTG CGGGCGTGAC AAACAGATCT GCGTCTCCGG TCTCGCCGCT
34141 TAGATCGCTC TGTGTAGTAG TTGTAGTATA TCCACTCTCT CAAAGCATCC AGGCGCCCCC
34201 TGGCTTCGGG TTCTATGTAA ACTCCTTCAT GCGCCGCTGC CCTGATAACA TCCACCACCG
34261 CAGAATAAGC CACACCCAGC CAACCTACAC ATTCGTTCTG CGAGTCACAC ACGGGAGGAG
34321 CGGGAAGAGC TGGAAGAACC ATGTTTTTTT TTTTATTCCA AAAGATTATC CAAAACCTCA
34381 AAATGAAGAT CTATTAAGTG AACGCGCTCC CCTCCGGTGG CGTGGTCAAA CTCTACAGCC
34441 AAAGAACAGA TAATGGCATT TGTAAGATGT TGCACAATGG CTTCCAAAAG GCAAACGGCC
34501 CTCACGTCCA AGTGGACGTA AAGGCTAAAC CCTTCAGGGT GAATCTCCTC TATAAACATT
34561 CCAGCACCTT CAACCATGCC CAAATAATTC TCATCTCGCC ACCTTCTCAA TATATCTCTA
34621 AGCAAATCCC GAATATTAAG TCCGGCCATT GTAAAAATCT GCTCCAGAGC GCCCTCCACC
34681 TTCAGCCTCA AGCAGCGAAT CATGATTGCA AAAATTCAGG TTCCTCACAG ACCTGTATAA
34741 GATTCAAAAG CGGAACATTA ACAAAAATAC CGCGATCCCG TAGGTCCCTT CGCAGGGCCA
34801 GCTGAACATA ATCGTGCAGG TCTGCACGGA CCAGCGCGGC CACTTCCCCG CCAGGAACCT
34861 TGACAAAAGA ACCCACACTG ATTATGACAC GCATACTCGG AGCTATGCTA ACCAGCGTAG
34921 CCCCGATGTA AGCTTTGTTG CATGGGCGGC GATATAAAAT GCAAGGTGCT GCTCAAAAAA
34981 TCAGGCAAAG CCTCGCGCAA AAAAGAAAGC ACATCGTAGT CATGCTCATG CAGATAAAGG
35041 CAGGTAAGCT CCGGAACCAC CACAGAAAAA GACACCATTT TTCTCTCAAA CATGTCTGCG
35101 GGTTTCTGCA TAAACACAAA ATAAAATAAC AAAAAAACAT TTAAACATTA GAAGCCTGTC
35161 TTACAACAGG AAAAACAACC CTTATAAGCA TAAGACGGAC TACGGCCATG CCGGCGTGAC
35221 CGTAAAAAAA CTGGTCACCG TGATTAAAAA GCACCACCGA CAGCTCCTCG GTCATGTCCG
35281 GAGTCATAAT GTAAGACTCG GTAAACACAT CAGGTTGATT CATCGGTCAG TGCTAAAAAG
35341 CGACCGAAAT AGCCCGGGGG AATACATACC CGCAGGCGTA GAGACAACAT TACAGCCCCC
35401 ATAGGAGGTA TAACAAAATT AATAGGAGAG AAAAACACAT AAACACCTGA AAAACCCTCC
35461 TGCCTAGGCA AAATAGCACC CTCCCGCTCC AGAACAACAT ACAGCGCTTC ACAGCGGCAG
35521 CCTAACAGTC AGCCTTACCA GTAAAAAAGA AAACCTATTA AAAAAACACC ACTCGACACG
35581 GCACCAGCTC AATCAGTCAC AGTGTAAAAA AGGGCCAAGT GCAGAGCGAG TATATATAGG
35641 ACTAAAAAAT GACGTAACGG TTAAAGTCCA CAAAAAACAC CCAGAAAACC GCACGCGAAC
35701 CTACGCCCAG AAACGAAAGC CAAAAAACCC ACAACTTCCT CAAATCGTCA CTTCCGTTTT
35761 CCCACGTTAC GTAACTTCCC ATTTTAAGAA AACTACAATT CCCAACACAT ACAAGTTACT
35821 CCGCCCTAAA ACCTACGTCA CCCGCCCCGT TCCCACGCCC CGCGCCACGT CACAAACTCC
35881 ACCCCCTCAT TATCATATTG GCTTCAATCC AAAATAAGGT ATATTATTGA TGATG

FIGURE 21
(SHEET 11)

```
LOCUS       KD1         33592 bp    DNA             SYN        28-APR-1999
DEFINITION  KD1
ACCESSION   KD1
KEYWORDS
SOURCE      Unknown.
  ORGANISM  Unknown
            Unclassified.
REFERENCE   1  (bases 1 to 33592)
  AUTHORS   Self
  JOURNAL   Unpublished.
FEATURES             Location/Qualifiers
     CDS             1..33592
                     /gene="KD1"
                     /product="KD1"
BASE COUNT     7744 a   9470 c   9285 g   7093 t
ORIGIN
        1 CATCATCAAT AATATACCTT ATTTTGGATT GAAGCCAATA TGATAATGAG GGGGTGGAGT
       61 TTGTGACGTG GCGCGGGGCG TGGGAACGGG GCGGGTGACG TAGTAGTGTG GCGGAAGTGT
      121 GATGTTGCAA GTGTGGCGGA ACACATGTAA GCGACGGATG TGGCAAAAGT GACGTTTTTG
      181 GTGTGCGCCG GTGTACACAG GAAGTGACAA TTTTCGCGCG GTTTTAGGCG GATGTTGTAG
      241 TAAATTTGGG CGTAACCGAG TAAGATTTGG CCATTTTCGC GGGAAAACTG AATAAGAGGA
      301 AGTGAAATCT GAATAATTTT GTGTTACTCA TAGCGCGTAA TATTTGTCTA GGGCCGCGGG
      361 GACTTTGACC GTTTACGTGG AGACTCGCCC AGGTGTTTTT CTCAGGTGTT TTCCGCGTTC
      421 CGGGTCAAAG TTGGCGTTTT ATTATTATAG TCAGCTGACG TGTAGTGTAT TTATACCCGG
      481 TGAGTTCCTC AAGAGGCCAC TCTTGAGTGC CAGCGAGTAG AGTTTTCTCC TCCGAGCCGC
      541 TCCGACACCG GGACTGAAAA TGAGACATGA GGTACTGGCT GATAATCTTC CACCTCCTAG
      601 CCATTTTGAA CCACCTACCC TTCACGAACT GTATGATTTA GACGTGACGG CCCCCGAAGA
      661 TCCCAACGAG GAGGCGGTTT CGCAGATTTT TCCCGACTCT GTAATGTTGG CGGTGCAGGA
      721 AGGGATTGAC TTACTCACTT TTCCGCCGGC GCCCGGTTCT CCGGAGCCGC CTCACCTTTC
      781 CCGGCAGCCC GAGCAGCCGG AGCAGAGAGC CTTGGGTCCG GTTTGCCACG AGGCTGGCTT
      841 TCCACCCAGT GACGACGAGG ATGAAGAGGG TGAGGAGTTT GTGTTAGATT ATGTGGAGCA
      901 CCCCGGGCAC GGTTGCAGGT CTTGTCATTA TCACCGGAGG AATACGGGGG ACCCAGATAT
      961 TATGTGTTCG CTTTGCTATA TGAGGACCTG TGGCATGTTT GTCTACAGTA AGTGAAAATT
     1021 ATGGGCAGTG GGTGATAGAG TGGTGGGTTT GGTGTGGTAA TTTTTTTTTT AATTTTTACA
     1081 GTTTTGTGGT TTAAAGAATT TTGTATTGTG ATTTTTTTAA AAGGTCCTGT GTCTGAACCT
     1141 GAGCCTGAGC CCGAGCCAGA ACCGGAGCCT GCAAGACCTA CCCGCCGTCC TAAAATGGCG
     1201 CCTGCTATCC TGAGACGCCC GACATCACCT GTGTCTAGAG AATGCAATAG TAGTACGGAT
     1261 AGCTGTGACT CCGGTCCTTC TAACACACCT CCTGAGATAC ACCCGGTGGT CCCGCTGTGC
     1321 CCCATTAAAC CAGTTGCCGT GAGAGTTGGT GGGCGTCGCC AGGCTGTGGA ATGTATCGAG
     1381 GACTTGCTTA ACGAGCCTGG GCAACCTTTG GACTTGAGCT GTAAACGCCC CAGGCCATAA
     1441 GGTGTAAACC TGTGATTGCG TGTGTGGTTA ACGCCTTTGT TTGCTGAATG AGTTGATGTA
     1501 AGTTTAATAA AGGGTGAGAT AATGTTTAAC TTGCATGGCG TGTTAAATGG GGCGGGGCTT
     1561 AAAGGGTATA TAATGCGCCG TGGGCTAATC TTGGTTACAT CTGACCTCAT GGAGGCTTGG
     1621 GAGTGTTTGG AAGATTTTTC TGCTGTGCGT AACTTGCTGG AACAGAGCTC TAACAGTACC
     1681 TCTTGGTTTT GGAGGTTTCT GTGGGGCTCA TCCCAGGCAA AGTTAGTCTG CAGAATTAAG
     1741 GAGGATTACA AGTGGGAATT TGAAGAGCTT TTGAAATCCT GTGGTGAGCT GTTTGATTCT
     1801 TTGAATCTGG GTCACCAGGC GCTTTTCCAA GAGAAGGTCA TCAAGACTTT GGATTTTTCC
     1861 ACACCGGGGC GCGCTGCGGC TGCTGTTGCT TTTTTGAGTT TTATAAAGGA TAAATGGAGC
     1921 GAAGAAACCC ATCTGAGCGG GGGGTACCTG CTGGATTTTC TGGCCATGCA TCTGTGGAGA
     1981 GCGGTTGTGA GACACAAGAA TCGCCTGCTA CTGTTGTCTT CCGTCCGCCC GGCGATAATA
     2041 CCGACGGAGG AGCAGCAGCA GCAGCAGGAG GAAGCCAGGC GGCGGCGGCA GGAGCAGAGC
     2101 CCATGGAACC CGAGAGCCGG CCTGGACCCT CGGGAATGAA TGTTGTACAG GTGGCTGAAC
     2161 TGTATCCAGA ACTGAGACGC ATTTTGACAA TTACAGAGGA TGGGCAGGGG CTAAAGGGGG
     2221 TAAAGAGGGA GCGGGGGGCT TGTGAGGCTA CAGAGGAGGC TAGGAATCTA GCTTTTAGCT
     2281 TAATGACCAG ACACCGTCCT GAGTGTATTA CTTTTCAACA GATCAAGGAT AATTGCGCTA
     2341 ATGAGCTTGA TCTGCTGGCG CAGAAGTATT CCATAGAGCA GCTGACCACT TACTGGCTGC
     2401 AGCCAGGGGA TGATTTTGAG GAGGCTATTA GGGTATATGC AAAGGTGGCA CTTAGGCCAG
```

FIGURE 22
(SHEET 1)

2461 ATTGCAAGTA CAAGATCAGC AAACTTGTAA ATATCAGGAA TTGTTGCTAC ATTTCTGGGA
2521 ACGGGGCCGA GGTGGAGATA GATACGGAGG ATAGGGTGGC CTTTAGATGT AGCATGATAA
2581 ATATGTGGCC GGGGGTGCTT GGCATGGACG GGGTGGTTAT TATGAATGTA AGGTTTACTG
2641 GCCCCAATTT TAGCGGTACG GTTTTCCTGG CCAATACCAA CCTTATCCTA CACGGTGTAA
2701 GCTTCTATGG GTTTAACAAT ACCTGTGTGG AAGCCTGGAC CGATGTAAGG GTTCGGGGCT
2761 GTGCCTTTTA CTGCTGCTGG AAGGGGGTGG TGTGTCGCCC CAAAAGCAGG GCTTCAATTA
2821 AGAAATGCCT CTTTGAAAGG TGTACCTTGG GTATCCTGTC TGAGGGTAAC TCCAGGGTGC
2881 GCCACAATGT GGCCTCCGAC TGTGGTTGCT TCATGCTAGT GAAAAGCGTG GCTGTGATTA
2941 AGCATAACAT GGTATGTGGC AACTGCGAGG ACAGGGCCTC TCAGATGCTG ACCTGCTCGG
3001 ACGGCAACTG TCACCTGCTG AAGACCATTC ACGTAGCCAG CCACTCTCGC AAGGCCTGGC
3061 CAGTGTTTGA GCATAACATA CTGACCCGCT GTTCCTTGCA TTTGGGTAAC AGGAGGGGGG
3121 TGTTCCTACC TTACCAATGC AATTTGAGTC ACACTAAGAT ATTGCTTGAG CCCGAGAGCA
3181 TGTCCAAGGT GAACCTGAAC GGGGTGTTTG ACATGACCAT GAAGATCTGG AAGGTGCTGA
3241 GGTACGATGA GACCCGCACC AGGTGCAGAC CCTGCGAGTG TGGCGGTAAA CATATTAGGA
3301 ACCAGCCTGT GATGCTGGAT GTGACCGAGG AGCTGAGGCC CGATCACTTG GTGCTGGCCT
3361 GCACCCGCGC TGAGTTTGGC TCTAGCGATG AAGATACAGA TTGAGGTACT GAAATGTGTG
3421 GGCGTGGCTT AAGGGTGGGA AAGAATATAT AAGGTGGGGG TCTTATGTAG TTTTGTATCT
3481 GTTTTGCAGC AGCCGCCGCC GCCATGAGCA CCAACTCGTT TGATGGAAGC ATTGTGAGCT
3541 CATATTTGAC AACGCGCATG CCCCCATGGG CCGGGGTGCG TCAGAATGTG ATGGGCTCCA
3601 GCATTGATGG TCGCCCCGTC CTGCCCGCAA ACTCTACTAC CTTGACCTAC GAGACCGTGT
3661 CTGGAACGCC GTTGGAGACT GCAGCCTCCG CCGCCGCTTC AGCCGCTGCA GCCACCGCCC
3721 GCGGGATTGT GACTGACTTT GCTTTCCTGA GCCCGCTTGC AAGCAGTGCA GCTTCCCGTT
3781 CATCCGCCCG CGATGACAAG TTGACGGCTC TTTTGGCACA ATTGGATTCT TTGACCCGGG
3841 AACTTAATGT CGTTTCTCAG CAGCTGTTGG ATCTGCGCCA GCAGGTTTCT GCCCTGAAGG
3901 CTTCCTCCCC TCCCAATGCG GTTTAAAACA TAAATAAAAA ACCAGACTCT GTTTGGATTT
3961 GGATCAAGCA AGTGTCTTGC TGTCTTTATT TAGGGGTTTT GCGCGCGCGG TAGGCCCGGG
4021 ACCAGCGGTC TCGGTCGTTG AGGGTCCTGT GTATTTTTTC CAGGACGTGG TAAAGGTGAC
4081 TCTGGATGTT CAGATACATG GGCATAAGCC CGTCTCTGGG GTGGAGGTAG CACCACTGCA
4141 GAGCTTCATG CTGCGGGGTG GTGTTGTAGA TGATCCAGTC GTAGCAGGAG CGCTGGGCGT
4201 GGTGCCTAAA AATGTCTTTC AGTAGCAAGC TGATTGCCAG GGGCAGGCCC TTGGTGTAAG
4261 TGTTTACAAA GCGGTTAAGC TGGGATGGGT GCATACGTGG GGATATGAGA TGCATCTTGG
4321 ACTGTATTTT TAGGTTGGCT ATGTTCCCAG CCATATCCCT CCGGGGATTC ATGTTGTGCA
4381 GAACCACCAG CACAGTGTAT CCGGTGCACT TGGGAAATTT GTCATGTAGC TTAGAAGGAA
4441 ATGCGTGGAA GAACTTGGAG ACGCCCTTGT GACCTCCAAG ATTTTCCATG CATTCGTCCA
4501 TAATGATGGC AATGGGCCCA CGGGCGGCGG CCTGGGCGAA GATATTTCTG GGATCACTAA
4561 CGTCATAGTT GTGTTCCAGG ATGAGATCGT CATAGGCCAT TTTTACAAAG CGCGGGCGGA
4621 GGGTGCCAGA CTGCGGTATA ATGGTTCCAT CCGGCCCAGG GGCGTAGTTA CCCTCACAGA
4681 TTTGCATTTC CCACGCTTTG AGTTCAGATG GGGGGATCAT GTCTACCTGC GGGGCGATGA
4741 AGAAAACGGT TTCCGGGGTA GGGGAGATCA GCTGGGAAGA AAGCAGGTTC CTGAGCAGCT
4801 GCGACTTACC GCAGCCGGTG GGCCCGTAAA TCACACCTAT TACCGGGTGC AACTGGTAGT
4861 TAAGAGAGCT GCAGCTGCCG TCATCCCTGA GCAGGGGGGC CACTTCGTTA AGCATGTCCC
4921 TGACTCGCAT GTTTTCCCTG ACCAAATCCG CCAGAAGGCG CTCGCCGCCC AGCGATAGCA
4981 GTTCTTGCAA GGAAGCAAAG TTTTTCAACG GTTTGAGACC GTCCGCCGTA GGCATGCTTT
5041 TGAGCGTTTG ACCAAGCAGT TCCAGGCGGT CCCACAGCTC GGTCACCTGC TCTACGGCAT
5101 CTCGATCCAG CATATCTCCT CGTTTCGCGG GTTGGGGCGG CTTTCGCTGT ACGGCAGTAG
5161 TCGGTGCTCG TCCAGACGGG CCAGGGTCAT GTCTTTCCAC GGGCGCAGGG TCCTCGTCAG
5221 CGTAGTCTGG GTCACGGTGA AGGGGTGCGC TCCGGGCTGC GCGCTGGCCA GGGTGCGCTT
5281 GAGGCTGGTC CTGCTGGTGC TGAAGCGCTG CCGGTCTTCG CCCTGCGCGT CGGCCAGGTA
5341 GCATTTGACC ATGGTGTCAT AGTCCAGCCC CTCCGCGGCG TGGCCCTTGG CGCGCAGCTT
5401 GCCCTTGGAG GAGGCGCCGC ACGAGGGGCA GTGCAGACTT TTGAGGGCGT AGAGCTTGGG
5461 CGCGAGAAAT ACCGATTCCG GGGAGTAGGC ATCCGCGCCG CAGGCCCCGC AGACGGTCTC
5521 GCATTCCACG AGCCAGGTGA GCTCTGGCCG TTCGGGGTCA AAAACCAGGT TTCCCCCATG
5581 CTTTTTGATG CGTTTCTTAC CTCTGGTTTC CATGAGCCGG TGTCCACGCT CGGTGACGAA
5641 AAGGCTGTCC GTGTCCCCGT ATACAGACTT GAGAGGCCTG TCCTCGAGCG GTGTTCCGCG
5701 GTCCTCCTCG TATAGAAACT CGGACCACTC TGAGACAAAG GCTCGCGTCC AGGCCAGCAC
5761 GAAGGAGGCT AAGTGGGAGG GGTAGCGGTC GTTGTCCACT AGGGGGTCCA CTCGCTCCAG
5821 GGTGTGAAGA CACATGTCGC CCTCTTCGGC ATCAAGGAAG GTGATTGGTT TGTAGGTGTA

FIGURE 22
(SHEET 2)

5881 GGCCACGTGA CCGGGTGTTC CTGAAGGGGG GCTATAAAAG GGGGTGGGGG CGCGTTCGTC
5941 CTCACTCTCT TCCGCATCGC TGTCTGCGAG GGCCAGCTGT TGGGGTGAGT ACTCCCTCTG
6001 AAAAGCGGGC ATGACTTCTG CGCTAAGATT GTCAGTTTCC AAAAACGAGG AGGATTTGAT
6061 ATTCACCTGG CCCGCGGTGA TGCCTTTGAG GGTGGCCGCA TCCATCTGGT CAGAAAAGAC
6121 AATCTTTTTG TTGTCAAGCT TGGTGGCAAA CGACCCGTAG AGGGCGTTGG ACAGCAACTT
6181 GGCGATGGAG CGCAGGGTTT GGTTTTTGTC GCGATCGGCG CGCTCCTTGG CCGCGATGTT
6241 TAGCTGCACG TATTCGCGCG CAACGCACCG CCATTCGGGA AAGACGGTGG TGCGCTCGTC
6301 GGGCACCAGG TGCACGCGCC AACCGCGGTT GTGCAGGGTG ACAAGGTCAA CGCTGGTGGC
6361 TACCTCTCCG CGTAGGCGCT CGTTGGTCCA GCAGAGGCGG CCGCCCTTGC GCGAGCAGAA
6421 TGGCGGTAGG GGGTCTAGCT GCGTCTCGTC CGGGGGGTCT GCGTCCACGG TAAAGACCCC
6481 GGGCAGCAGG CGCGCGTCGA AGTAGTCTAT CTTGCATCCT TGCAAGTCTA GCGCCTGCTG
6541 CCATGCGCGG GCGGCAAGCG CGCGCTCGTA TGGGTTGAGT GGGGGACCCC ATGGCATGGG
6601 GTGGGTGAGC GCGGAGGCGT ACATGCCGCA AATGTCGTAA ACGTAGAGGG GCTCTCTGAG
6661 TATTCCAAGA TATGTAGGGT AGCATCTTCC ACCGCGGATG CTGGCGCGCA CGTAATCGTA
6721 TAGTTCGTGC GAGGGAGCGA GGAGGTCGGG ACCGAGGTTG CTACGGGCGG GCTGCTCTGC
6781 TCGGAAGACT ATCTGCCTGA AGATGGCATG TGAGTTGGAT GATATGGTTG GACGCTGGAA
6841 GACGTTGAAG CTGGCGTCTG TGAGACCTAC CGCGTCACGC ACGAAGGAGG CGTAGGAGTC
6901 GCGCAGCTTG TTGACCAGCT CGGCGGTGAC CTGCACGTCT AGGGCGCAGT AGTCCAGGGT
6961 TTCCTTGATG ATGTCATACT TATCCTGTCC CTTTTTTTTC CACAGCTCGC GGTTGAGGAC
7021 AAACTCTTCG CGGTCTTTCC AGTACTCTTG GATCGGAAAC CCGTCGGCCT CCGAACGGTA
7081 AGAGCCTAGC ATGTAGAACT GGTTGACGGC CTGGTAGGCG CAGCATCCCT TTTCTACGGG
7141 TAGCGCGTAT GCCTGCGCGG CCTTCCGGAG CGAGGTGTGG GTGAGCGCAA AGGTGTCCCT
7201 GACCATGACT TTGAGGTACT GGTATTTGAA GTCAGTGTCG TCGCATCCGC CCTGCTCCCA
7261 GAGCAAAAAG TCCGTGCGCT TTTTGGAACG CGGATTTGGC AGGGCGAAGG TGACATCGTT
7321 GAAGAGTATC TTTCCCGCGC GAGGCATAAA GTTGCGTGTG ATGCGGAAGG GTCCCGGCAC
7381 CTCGGAACGG TTGTTAATTA CCTGGGCGGC GAGCACGATC TCGTCAAAGC CGTTGATGTT
7441 GTGGCCCACA ATGTAAAGTT CCAAGAAGCG CGGGATGCCC TTGATGGAAG GCAATTTTTT
7501 AAGTTCCTCG TAGGTGAGCT CTTCAGGGGA GCTGAGCCCG TGCTCTGAAA GGGCCCAGTC
7561 TGCAAGATGA GGGTTGGAAG CGACGAATGA GCTCCACAGG TCACGGGCCA TTAGCATTTG
7621 CAGGTGGTCG CGAAAGGTCC TAAACTGGCG ACCTATGGCC ATTTTTTCTG GGGTGATGCA
7681 GTAGAAGGTA AGCGGGTCTT GTTCCCAGCG GTCCCATCCA AGGTTCGCGG CTAGGTCTCG
7741 CGCGGCAGTC ACTAGAGGCT CATCTCCGCC GAACTTCATG ACCAGCATGA AGGGCACGAG
7801 CTGCTTCCCA AAGGCCCCCA TCCAAGTATA GGTCTCTACA TCGTAGGTGA CAAAGAGACG
7861 CTCGGTGCGA GGATGCGAGC CGATCGGGAA GAACTGGATC TCCCGCCACC AATTGGAGGA
7921 GTGGCTATTG ATGTGGTGAA AGTAGAAGTC CCTGCGACGG GCCGAACACT CGTGCTGGCT
7981 TTTGTAAAAA CGTGCGCAGT ACTGGCAGCG GTGCACGGGC TGTACATCCT GCACGAGGTT
8041 GACCTGACGA CCGCGCACAA GGAAGCAGAG TGGGAATTTG AGCCCCTCGC CTGGCGGGTT
8101 TGGCTGGTGG TCTTCTACTT CGGCTGCTTG TCCTTGACCG TCTGGCTGCT CGAGGGGAGT
8161 TACGGTGGAT CGGACCACCA CGCCGCGCGA GCCCAAAGTC CAGATGTCCG CGCGCGGCGG
8221 TCGGAGCTTG ATGACAACAT CGCGCAGATG GGAGCTGTCC ATGGTCTGGA GCTCCCGCGG
8281 CGTCAGGTCA GGCGGGAGCT CCTGCAGGTT TACCTCGCAT AGACGGGTCA GGGCGCGGGC
8341 TAGATCCAGG TGATACCTAA TTTCCAGGGG CTGGTTGGTG GCGGCGTCGA TGGCTTGCAA
8401 GAGGCCGCAT CCCCGCGGCG CGACTACGGT ACCGCGCGGC GGGCGGTGGG CCGCGGGGGT
8461 GTCCTTGGAT GATGCATCTA AAAGCGGTGA CGCGGGCGAG CCCCCGGAGG TAGGGGGGGC
8521 TCCGGACCCG CCGGGAGAGG GGGCAGGGGC ACGTCGGCGC CGCGCGCGGG CAGGAGCTGG
8581 TGCTGCGCGC GTAGGTTGCT GGCGAACGCG ACGACGCGGC GGTTGATCTC CTGAATCTGG
8641 CGCCTCTGCG TGAAGACGAC GGGCCCGGTG AGCTTGAGCC TGAAAGAGAG TTCGACAGAA
8701 TCAATTTCGG TGTCGTTGAC GGCGGCCTGG CGCAAAATCT CCTGCACGTC TCCTGAGTTG
8761 TCTTGATAGG CGATCTCGGC CATGAACTGC TCGATCTCTT CCTCCTGGAG ATCTCCGCGT
8821 CCGGCTCGCT CCACGGTGGC GGCGAGGTCG TTGGAAATGC GGGCCATGAG CTGCGAGAAG
8881 GCGTTGAGGC CTCCCTCGTT CCAGACGCGG CTGTAGACCA CGCCCCCTTC GGCATCGCGG
8941 GCGCGCATGA CCACCTGCGC GAGATTGAGC TCCACGTGCC GGGCGAAGAC GGCGTAGTTT
9001 CGCAGGCGCT GAAAGAGGTA GTTGAGGGTG GTGGCGGTGT GTTCTGCCAC GAAGAAGTAC
9061 ATAACCCAGC GTCGCAACGT GGATTCGTTG ATATCCCCCA AGGCCTCAAG GCGCTCCATG
9121 GCCTCGTAGA AGTCCACGGC GAAGTTGAAA AACTGGGAGT TGCGCGCCGA CACGGTTAAC
9181 TCCTCCTCCA GAAGACGGAT GAGCTCGGCG ACAGTGTCGC GCACCTCGCG CTCAAAGGCT
9241 ACAGGGGCCT CTTCTTCTTC TTCAATCTCC TCTTCCATAA GGGCCTCCCC TTCTTCTTCT

FIGURE 22
(SHEET 3)

9301 TCTGGCGGCG GTGGGGGAGG GGGGACACGG CGGCGACGAC GGCGCACCGG GAGGCGGTCG
9361 ACAAAGCGCT CGATCATCTC CCCGCGGCGA CGGCGCATGG TCTCGGTGAC GGCGCGGCCG
9421 TTCTCGCGGG GGCGCAGTTG GAAGACGCCG CCCGTCATGT CCCGGTTATG GGTTGGCGGG
9481 GGGCTGCCAT GCGGCAGGGA TACGGCGCTA ACGATGCATC TCAACAATTG TTGTGTAGGT
9541 ACTCCGCCGC CGAGGGACCT GAGCGAGTCC GCATCGACCG GATCGGAAAA CCTCTCGAGA
9601 AAGGCGTCTA ACCAGTCACA GTCGCAAGGT AGGCTGAGCA CCGTGGCGGG CGGCAGCGGG
9661 CGGCGGTCGG GGTTGTTTCT GGCGGAGGTG CTGCTGATGA TGTAATTAAA GTAGGCGGTC
9721 TTGAGACGGC GGATGGTCGA CAGAAGCACC ATGTCCTTGG GTCCGGCCTG CTGAATGCGC
9781 AGGCGGTCGG CCATGCCCCA GGCTTCGTTT TGACATCGGC GCAGGTCTTT GTAGTAGTCT
9841 TGCATGAGCC TTTCTACCGG CACTTCTTCT TCTCCTTCCT CTTGTCCTGC ATCTCTTGCA
9901 TCTATCGCTG CGGCGGCGGC GGAGTTTGGC CGTAGGTGGC GCCCTCTTCC TCCCATGCGT
9961 GTGACCCCGA AGCCCCTCAT CGGCTGAAGC AGGGCTAGGT CGGCGACAAC GCGCTCGGCT
10021 AATATGGCCT GCTGCACCTG CGTGAGGGTA GACTGGAAGT CATCCATGTC CACAAAGCGG
10081 TGGTATGCGC CCGTGTTGAT GGTGTAAGTG CAGTTGGCCA TAACGGACCA GTTAACGGTC
10141 TGGTGACCCG GCTGCGAGAG CTCGGTGTAC CTGAGACGCG AGTAAGCCCT CGAGTCAAAT
10201 ACGTAGTCGT TGCAAGTCCG CACCAGGTAC TGGTATCCCA CCAAAAAGTG CGGCGGCGGC
10261 TGGCGGTAGA GGGGCCAGCG TAGGGTGGCC GGGGCTCCGG GGGCGAGATC TTCCAACATA
10321 AGGCGATGAT ATCCGTAGAT GTACCTGGAC ATCCAGGTGA TGCCGGCGGC GGTGGTGGAG
10381 GCGCGCGGAA AGTCGCGGAC GCGGTTCCAG ATGTTGCGCA GCGGCAAAAA GTGCTCCATG
10441 GTCGGGACGC TCTGGCCGGT CAGGCGCGCG CAATCGTTGA CGCTCTAGCG TGCAAAAGGA
10501 GAGCCTGTAA GCGGGCACTC TTCCGTGGTC TGGTGGATAA ATTCGCAAGG GTATCATGGC
10561 GGACGACCGG GGTTCGAGCC CCGTATCCGG CCGTCCGCCG TGATCCATGC GGTTACCGCC
10621 CGCGTGTCGA ACCCAGGTGT GCGACGTCAG ACAACGGGGG AGTGCTCCTT TTGGCTTCCT
10681 TCCAGGCGCG GCGGCTGCTG CGCTAGCTTT TTTGGCCACT GGCCGCGCGC AGCGTAAGCG
10741 GTTAGGCTGG AAAGCGAAAG CATTAAGTGG CTCGCTCCCT GTAGCCGGAG GGTTATTTTC
10801 CAAGGGTTGA GTCGCGGGAC CCCCGGTTCG AGTCTCGGAC CGGCCGGACT GCGGCGAACG
10861 GGGGTTTGCC TCCCCGTCAT GCAAGACCCC GCTTGCAAAT TCCTCCGGAA ACAGGGACGA
10921 GCCCCTTTTT TGCTTTTCCC AGATGCATCC GGTGCTGCGG CAGATGCGCC CCCCTCCTCA
10981 GCAGCGGCAA GAGCAAGAGC AGCGGCAGAC ATGCAGGGCA CCCTCCCCTC CTCCTACCGC
11041 GTCAGGAGGG GCGACATCCG CGGTTGACGC GGCAGCAGAT GGTGATTACG AACCCCCGCG
11101 GCGCCGGGCC CGGCACTACC TGGACTTGGA GGAGGGCGAG GGCCTGGCGC GGCTAGGAGC
11161 GCCCTCTCCT GAGCGGTACC CAAGGGTGCA GCTGAAGCGT GATACGCGTG AGGCGTACGT
11221 GCCGCGGCAG AACCTGTTTC GCGACCGCGA GGGAGAGGAG CCCGAGGAGA TGCGGGATCG
11281 AAAGTTCCAC GCAGGGCGCG AGCTGCGGCA TGGCCTGAAT CGCGAGCGGT TGCTGCGCGA
11341 GGAGGACTTT GAGCCCGACG CGCGAACCGG GATTAGTCCC GCGCGCGCAC ACGTGGCGGC
11401 CGCCGACCTG GTAACCGCAT ACGAGCAGAC GGTGAACCAG GAGATTAACT TTCAAAAAAG
11461 CTTTAACAAC CACGTGCGTA CGCTTGTGGC GCGCGAGGAG GTGGCTATAG GACTGATGCA
11521 TCTGTGGGAC TTTGTAAGCG CGCTGGAGCA AAACCCAAAT AGCAAGCCGC TCATGGCGCA
11581 GCTGTTCCTT ATAGTGCAGC ACAGCAGGGA CAACGAGGCA TTCAGGGATG CGCTGCTAAA
11641 CATAGTAGAG CCCGAGGGCC GCTGGCTGCT CGATTTGATA AACATCCTGC AGAGCATAGT
11701 GGTGCAGGAG CGCAGCTTGA GCCTGGCTGA CAAGGTGGCC GCCATCAACT ATTCCATGCT
11761 TAGCCTGGGC AAGTTTTACG CCCGCAAGAT ATACCATACC CCTTACGTTC CCATAGACAA
11821 GGAGGTAAAG ATCGAGGGGT TCTACATGCG CATGGCGCTG AAGGTGCTTA CCTTGAGCGA
11881 CGACCTGGGC GTTTATCGCA ACGAGCGCAT CCACAAGGCC GTGAGCGTGA GCCGGCGGCG
11941 CGAGCTCAGC GACCGCGAGC TGATGCACAG CCTGCAAAGG GCCCTGGCTG GCACGGGCAG
12001 CGGCGATAGA GAGGCCGAGT CCTACTTTGA CGCGGGCGCT GACCTGCGCT GGGCCCCAAG
12061 CCGACGCGCC CTGGAGGCAG CTGGGGCCGG ACCTGGGCTG GCGGTGGCAC CCGCGCGCGC
12121 TGGCAACGTC GGCGGCGTGG AGGAATATGA CGAGGACGAT GAGTACGAGC CAGAGGACGG
12181 CGAGTACTAA GCGGTGATGT TTCTGATCAG ATGATGCAAG ACGCAACGGA CCCGGCGGTG
12241 CGGGCGGCGC TGCAGAGCCA GCCGTCCGGC CTTAACTCCA CGGACGACTG GCGCCAGGTC
12301 ATGGACCGCA TCATGTCGCT GACTGCGCGC AATCCTGACG CGTTCCGGCA GCAGCCGCAG
12361 GCCAACCGGC TCTCCGCAAT TCTGGAAGCG GTGGTCCCGG CGCGCGCAAA CCCCACGCAC
12421 GAGAAGGTGC TGGCGATCGT AAACGCGCTG GCCGAAAACA GGGCCATCCG GCCCGACGAG
12481 GCCGGCCTGG TCTACGACGC GCTGCTTCAG CGCGTGGCTC GTTACAACAG CGGCAACGTG
12541 CAGACCAACC TGGACCGGCT GGTGGGGGAT GTGCGCGAGG CCGTGGCGCA GCGTGAGCGC
12601 GCGCAGCAGC AGGGCAACCT GGGCTCCATG GTTGCACTAA ACGCCTTCCT GAGTACACAG
12661 CCCGCCAACG TGCCGCGGGG ACAGGAGGAC TACACCAACT TTGTGAGCGC ACTGCGGCTA

FIGURE 22
(SHEET 4)

12721 ATGGTGACTG AGACACCGCA AAGTGAGGTG TACCAGTCTG GGCCAGACTA TTTTTTCCAG
12781 ACCAGTAGAC AAGGCCTGCA GACCGTAAAC CTGAGCCAGG CTTTCAAAAA CTTGCAGGGG
12841 CTGTGGGGGG TGCGGGCTCC CACAGGCGAC CGCGCGACCG TGTCTAGCTT GCTGACGCCC
12901 AACTCGCGCC TGTTGCTGCT GCTAATAGCG CCCTTCACGG ACAGTGGCAG CGTGTCCCGG
12961 GACACATACC TAGGTCACTT GCTGACACTG TACCGCGAGG CCATAGGTCA GGCGCATGTG
13021 GACGAGCATA CTTTCCAGGA GATTACAAGT GTCAGCCGCG CGCTGGGGCA GGAGGACACG
13081 GGCAGCCTGG AGGCAACCCT AAACTACCTG CTGACCAACC GGCGGCAGAA GATCCCCTCG
13141 TTGCACAGTT TAAACAGCGA GGAGGAGCGC ATTTTGCGCT ACGTGCAGCA GAGCGTGAGC
13201 CTTAACCTGA TGCGCGACGG GGTAACGCCC AGCGTGGCGC TGGACATGAC CGCGCGCAAC
13261 ATGGAACCGG GCATGTATGC CTCAAACCGG CCGTTTATCA ACCGCCTAAT GGACTACTTG
13321 CATCGCGCGG CCGCCGTGAA CCCCGAGTAT TTCACCAATG CCATCTTGAA CCCGCACTGG
13381 CTACCGCCCC CTGGTTTCTA CACCGGGGGA TTCGAGGTGC CCGAGGGTAA CGATGGATTC
13441 CTCTGGGACG ACATAGACGA CAGCGTGTTT TCCCCGCAAC CGCAGACCCT GCTAGAGTTG
13501 CAACAGCGCG AGCAGGCAGA GGCGGCGCTG CGAAAGGAAA GCTTCCGCAG GCCAAGCAGC
13561 TTGTCCGATC TAGGCGCTGC GGCCCCGCGG TCAGATGCTA GTAGCCCATT TCCAAGCTTG
13621 ATAGGGTCTC TTACCAGCAC TCGCACCACC CGCCCGCGCC TGCTGGGCGA GGAGGAGTAC
13681 CTAAACAACT CGCTGCTGCA GCCGCAGCGC GAAAAAAACC TGCCTCCGGC ATTTCCCAAC
13741 AACGGGATAG AGAGCCTAGT GGACAAGATG AGTAGATGGA AGACGTACGC GCAGGAGCAC
13801 AGGGACGTGC CAGGCCCGCG CCCGCCCACC CGTCGTCAAA GGCACGACCG TCAGCGGGGT
13861 CTGGTGTGGG AGGACGATGA CTCGGCAGAC GACAGCAGCG TCCTGGATTT GGGAGGGAGT
13921 GGCAACCCGT TTGCGCACCT TCGCCCCAGG CTGGGGAGAA TGTTTTAAAA AAAAAAAAGC
13981 ATGATGCAAA ATAAAAAACT CACCAAGGCC ATGGCACCGA GCGTTGGTTT TCTTGTATTC
14041 CCCTTAGTAT GCGGCGCGCG GCGATGTATG AGGAAGGTCC TCCTCCCTCC TACGAGAGTG
14101 TGGTGAGCGC GGCGCCAGTG GCGGCGGCGC TGGGTTCTCC CTTCGATGCT CCCCTGGACC
14161 CGCCGTTTGT GCCTCCGCGG TACCTGCGGC CTACCGGGGG GAGAAACAGC ATCCGTTACT
14221 CTGAGTTGGC ACCCCTATTC GACACCACCC GTGTGTACCT GGTGGACAAC AAGTCAACGG
14281 ATGTGGCATC CCTGAACTAC CAGAACGACC ACAGCAACTT TCTGACCACG GTCATTCAAA
14341 ACAATGACTA CAGCCCGGGG GAGGCAAGCA CACAGACCAT CAATCTTGAC GACCGGTCGC
14401 ACTGGGGCGG CGACCTGAAA ACCATCCTGC ATACCAACAT GCCAAATGTG AACGAGTTCA
14461 TGTTTACCAA TAAGTTTAAG GCGCGGGTGA TGGTGTCGCG CTTGCCTACT AAGGACAATC
14521 AGGTGGAGCT GAAATACGAG TGGGTGGAGT TCACGCTGCC CGAGGGCAAC TACTCCGAGA
14581 CCATGACCAT AGACCTTATG AACAACGCGA TCGTGGAGCA CTACTTGAAA GTGGGCAGAC
14641 AGAACGGGGT TCTGGAAAGC GACATCGGGG TAAAGTTTGA CACCCGCAAC TTCAGACTGG
14701 GGTTTGACCC CGTCACTGGT CTTGTCATGC CTGGGGTATA TACAAACGAA GCCTTCCATC
14761 CAGACATCAT TTTGCTGCCA GGATGCGGGG TGGACTTCAC CCACAGCCGC CTGAGCAACT
14821 TGTTGGGCAT CCGCAAGCGG CAACCCTTCC AGGAGGGCTT TAGGATCACC TACGATGATC
14881 TGGAGGGTGG TAACATTCCC GCACTGTTGG ATGTGGACGC CTACCAGGCG AGCTTGAAAG
14941 ATGACACCGA ACAGGGCGGG GGTGGCGCAG GCGGCAGCAA CAGCAGTGGC AGCGGCGCGG
15001 AAGAGAACTC CAACGCGGCA GCCGCGGCAA TGCAGCCGGT GGAGGACATG AACGATCATG
15061 CCATTCGCGG CGACACCTTT GCCACACGGG CTGAGGAGAA GCGCGCTGAG GCCGAAGCAG
15121 CGGCCGAAGC TGCCGCCCCC GCTGCGCAAC CCGAGGTCGA GAAGCCTCAG AAGAAACCGG
15181 TGATCAAACC CCTGACAGAG GACAGCAAGA AACGCAGTTA CAACCTAATA AGCAATGACA
15241 GCACCTTCAC CCAGTACCGC AGCTGGTACC TTGCATACAA CTACGGCGAC CCTCAGACCG
15301 GAATCCGCTC ATGGACCCTG CTTTGCACTC CTGACGTAAC CTGCGGCTCG GAGCAGGTCT
15361 ACTGGTCGTT GCCAGACATG ATGCAAGACC CCGTGACCTT CCGCTCCACG CGCCAGATCA
15421 GCAACTTTCC GGTGGTGGGC GCCGAGCTGT TGCCCGTGCA CTCCAAGAGC TTCTACAACG
15481 ACCAGGCCGT CTACTCCCAA CTCATCCGCC AGTTTACCTC TCTGACCCAC GTGTTCAATC
15541 GCTTTCCCGA GAACCAGATT TTGGCGCGCC CGCCAGCCCC CACCATCACC ACCGTCAGTG
15601 AAAACGTTCC TGCTCTCACA GATCACGGGA CGCTACCGCT GCGCAACAGC ATCGGAGGAG
15661 TCCAGCGAGT GACCATTACT GACGCCAGAC GCCGCACCTG CCCCTACGTT TACAAGGCCC
15721 TGGGCATAGT CTCGCCGCGC GTCCTATCGA GCCGCACTTT TTGAGCAAGC ATGTCCATCC
15781 TTATATCGCC CAGCAATAAC ACAGGCTGGG GCCTGCGCTT CCCAAGCAAG ATGTTTGGCG
15841 GGGCCAAGAA GCGCTCCGAC CAACACCCAG TGCGCGTGCG CGGGCACTAC CGCGCGCCCT
15901 GGGGCGCGCA CAAACGCGGC CGCACTGGGC GCACCACCGT CGATGACGCC ATCGACGCGG
15961 TGGTGGAGGA GGCGCGCAAC TACACGCCCA CGCCGCCACC AGTGTCCACA GTGGACGCGG
16021 CCATTCAGAC CGTGGTGCGC GGAGCCCGGC GCTATGCTAA AATGAAGAGA CGGCGGAGGC
16081 GCGTAGCACG TCGCCACCGC CGCCGACCCG GCACTGCCGC CCAACGCGCG GCGGCGGCCC

FIGURE 22
(SHEET 5)

```
16141 TGCTTAACCG CGCACGTCGC ACCGGCCGAC GGGCGGCCAT GCGGGCCGCT CGAAGGCTGG
16201 CCGCGGGTAT TGTCACTGTG CCCCCCAGGT CCAGGCGACG AGCGGCCGCC GCAGCAGCCG
16261 CGGCCATTAG TGCTATGACT CAGGGTCGCA GGGGCAACGT GTATTGGGTG CGCGACTCGG
16321 TTAGCGGCCT GCGCGTGCCC GTGCGCACCC GCCCCCCGCG CAACTAGATT GCAAGAAAAA
16381 ACTACTTAGA CTCGTACTGT TGTATGTATC CAGCGGCGGC GGCGCGCAAC GAAGCTATGT
16441 CCAAGCGCAA AATCAAAGAA GAGATGCTCC AGGTCATCGC GCCGGAGATC TATGGCCCCC
16501 CGAAGAAGGA AGAGCAGGAT TACAAGCCCC GAAAGCTAAA GCGGGTCAAA AAGAAAAAGA
16561 AAGATGATGA TGATGAACTT GACGACGAGG TGGAACTGCT GCACGCTACC GCGCCCAGGC
16621 GACGGGTACA GTGGAAAGGT CGACGCGTAA AACGTGTTTT GCGACCCGGC ACCACCGTAG
16681 TCTTTACGCC CGGTGAGCGC TCCACCCGCA CCTACAAGCG CGTGTATGAT GAGGTGTACG
16741 GCGACGAGGA CCTGCTTGAG CAGGCCAACG AGCGCCTCGG GGAGTTTGCC TACGGAAAGC
16801 GGCATAAGGA CATGCTGGCG TTGCCGCTGG ACGAGGGCAA CCCAACACCT AGCCTAAAGC
16861 CCGTAACACT GCAGCAGGTG CTGCCCGCGC TTGCACCGTC CGAAGAAAAG CGCGGCCTAA
16921 AGCGCGAGTC TGGTGACTTG GCACCCACCG TGCAGCTGAT GGTACCCAAG CGCCAGCGAC
16981 TGGAAGATGT CTTGGAAAAA ATGACCGTGG AACCTGGGCT GGAGCCCGAG GTCCGCGTGC
17041 GGCCAATCAA GCAGGTGGCG CCGGGACTGG GCGTGCAGAC CGTGGACGTT CAGATACCCA
17101 CTACCAGTAG CACCAGTATT GCCACCGCCA CAGAGGGCAT GGAGACACAA ACGTCCCCGG
17161 TTGCCTCAGC GGTGGCGGAT GCCGCGGTGC AGGCGGTCGC TGCGGCCGCG TCCAAGACCT
17221 CTACGGAGGT GCAAACGGAC CCGTGGATGT TTCGCGTTTC AGCCCCCCGG CGCCCGCGCG
17281 GTTCGAGGAA GTACGGCGCC GCCAGCGCGC TACTGCCCGA ATATGCCCTA CATCCTTCCA
17341 TTGCGCCTAC CCCCGGCTAT CGTGGCTACA CCTACCGCCC CAGAAGACGA GCAACTACCC
17401 GACGCCGAAC CACCACTGGA ACCCGCCGCC GCCGTCGCCG TCGCCAGCCC GTGCTGGCCC
17461 CGATTTCCGT GCGCAGGGTG GCTCGCGAAG GAGGCAGGAC CCTGGTGCTG CCAACAGCGC
17521 GCTACCACCC CAGCATCGTT TAAAAGCCGG TCTTTGTGGT TCTTGCAGAT ATGGCCCTCA
17581 CCTGCCGCCT CCGTTTCCCG GTGCCGGGAT TCCGAGGAAG AATGCACCGT AGGAGGGGCA
17641 TGGCCGGCCA CGGCCTGACG GGCGGCATGC GTCGTGCGCA CCACCGGCGG CGGCGCGCGT
17701 CGCACCGTCG CATGCGCGGC GGTATCCTGC CCCTCCTTAT TCCACTGATC GCCGCGGCGA
17761 TTGGCGCCGT GCCCGGAATT GCATCCGTGG CCTTGCAGGC GCAGAGACAC TGATTAAAAA
17821 CAAGTTGCAT GTGGAAAAAT CAAAATAAAA AGTCTGGACT CTCACGCTCG CTTGGTCCTG
17881 TAACTATTTT GTAGAATGGA AGACATCAAC TTTGCGTCTC TGGCCCCGCG ACACGGCTCG
17941 CGCCCGTTCA TGGGAAACTG GCAAGATATC GGCACCAGCA ATATGAGCGG TGGCGCCTTC
18001 AGCTGGGGCT CGCTGTGGAG CGGCATTAAA AATTTCGGTT CCACCGTTAA GAACTATGGC
18061 AGCAAGGCCT GGAACAGCAG CACAGGCCAG ATGCTGAGGG ATAAGTTGAA AGAGCAAAAT
18121 TTCCAACAAA AGGTGGTAGA TGGCCTGGCC TCTGGCATTA GCGGGGTGGT GGACCTGGCC
18181 AACCAGGCAG TGCAAAATAA GATTAACAGT AAGCTTGATC CCCGCCCTCC CGTAGAGGAG
18241 CCTCCACCGG CCGTGGAGAC AGTGTCTCCA GAGGGGCGTG GCGAAAAGCG TCCGCGCCCC
18301 GACAGGGAAG AAACTCTGGT GACGCAAATA GACGAGCCTC CCTCGTACGA GGAGGCACTA
18361 AAGCAAGGCC TGCCCACCAC CCGTCCCATC GCGCCCATGG CTACCGGAGT GCTGGGCCAG
18421 CACACACCCG TAACGCTGGA CCTGCCTCCC CCCGCCGACA CCCAGCAGAA ACCTGTGCTG
18481 CCAGGCCCGA CCGCCGTTGT TGTAACCCGT CCTAGCCGCG CGTCCCTGCG CCGCGCCGCC
18541 AGCGGTCCGC GATCGTTGCG GCCCGTAGCC AGTGGCAACT GGCAAAGCAC ACTGAACAGC
18601 ATCGTGGGTC TGGGGGTGCA ATCCCTGAAG CGCCGACGAT GCTTCTGAAT AGCTAACGTG
18661 TCGTATGTGT GTCATGTATG CGTCCATGTC GCCGCCAGAG GAGCTGCTGA GCCGCCGCGC
18721 GCCCGCTTTC CAAGATGGCT ACCCCTTCGA TGATGCCGCA GTGGTCTTAC ATGCACATCT
18781 CGGGCCAGGA CGCCTCGGAG TACCTGAGCC CCGGGCTGGT GCAGTTTGCC CGCGCCACCG
18841 AGACGTACTT CAGCCTGAAT AACAAGTTTA GAAACCCCAC GGTGGCGCCT ACGCACGACG
18901 TGACCACAGA CCGGTCCCAG CGTTTGACGC TGCGGTTCAT CCCTGTGGAC CGTGAGGATA
18961 CTGCGTACTC GTACAAGGCG CGGTTCACCC TAGCTGTGGG TGATAACCGT GTGCTGGACA
19021 TGGCTTCCAC GTACTTTGAC ATCCGCGGCG TGCTGGACAG GGGCCCTACT TTTAAGCCCT
19081 ACTCTGGCAC TGCCTACAAC GCCCTGGCTC CCAAGGGTGC CCCAAATCCT TGCGAATGGG
19141 ATGAAGCTGC TACTGCTCTT GAAATAAACC TAGAAGAAGA GGACGATGAC AACGAAGACG
19201 AAGTAGACGA GCAAGCTGAG CAGCAAAAAA CTCACGTATT TGGGCAGGCG CCTTATTCTG
19261 GTATAAATAT TACAAAGGAG GGTATTCAAA TAGGTGTCGA AGGTCAAACA CCTAAATATG
19321 CCGATAAAAC ATTTCAACCT GAACCTCAAA TAGGAGAATC TCAGTGGTAC GAAACTGAAA
19381 TTAATCATGC AGCTGGGAGA GTCCTTAAAA AGACTACCCC AATGAAACCA TGTTACGGTT
19441 CATATGCAAA ACCCACAAAT GAAAATGGAG GGCAAGGCAT TCTTGTAAAG CAACAAAATG
19501 GAAAGCTAGA AAGTCAAGTG GAAATGCAAT TTTTCTCAAC TACTGAGGCG ACCGCAGGCA
```

FIGURE 22
(SHEET 6)

```
19561 ATGGTGATAA CTTGACTCCT AAAGTGGTAT TGTACAGTGA AGATGTAGAT ATAGAAACCC
19621 CAGACACTCA TATTTCTTAC ATGCCCACTA TTAAGGAAGG TAACTCACGA GAACTAATGG
19681 GCCAACAATC TATGCCCAAC AGGCCTAATT ACATTGCTTT TAGGGACAAT TTTATTGGTC
19741 TAATGTATTA CAACAGCACG GGTAATATGG GTGTTCTGGC GGGCCAAGCA TCGCAGTTGA
19801 ATGCTGTTGT AGATTTGCAA GACAGAAACA CAGAGCTTTC ATACCAGCTT TTGCTTGATT
19861 CCATTGGTGA TAGAACCAGG TACTTTTCTA TGTGGAATCA GGCTGTTGAC AGCTATGATC
19921 CAGATGTTAG AATTATTGAA AATCATGGAA CTGAAGATGA ACTTCCAAAT TACTGCTTTC
19981 CACTGGGAGG TGTGATTAAT ACAGAGACTC TTACCAAGGT AAAACCTAAA ACAGGTCAGG
20041 AAAATGGATG GGAAAAAGAT GCTACAGAAT TTTCAGATAA AAATGAAATA AGAGTTGGAA
20101 ATAATTTTGC CATGGAAATC AATCTAAATG CCAACCTGTG GAGAAATTTC CTGTACTCCA
20161 ACATAGCGCT GTATTTGCCC GACAAGCTAA AGTACAGTCC TTCCAACGTA AAAATTTCTG
20221 ATAACCCAAA CACCTACGAC TACATGAACA AGCGAGTGGT GGCTCCCGGG TTAGTGGACT
20281 GCTACATTAA CCTTGGAGCA CGCTGGTCCC TTGACTATAT GGACAACGTC AACCCATTTA
20341 ACCACCACCG CAATGCTGGC CTGCGCTACC GCTCAATGTT GCTGGGCAAT GGTCGCTATG
20401 TGCCCTTCCA CATCCAGGTG CCTCAGAAGT TCTTTGCCAT TAAAAACCTC CTTCTCCTGC
20461 CGGGCTCATA CACCTACGAG TGGAACTTCA GGAAGGATGT TAACATGGTT CTGCAGAGCT
20521 CCCTAGGAAA TGACCTAAGG GTTGACGGAG CCAGCATTAA GTTTGATAGC ATTTGCCTTT
20581 ACGCCACCTT CTTCCCCATG GCCCACAACA CCGCCTCCAC GCTTGAGGCC ATGCTTAGAA
20641 ACGACACCAA CGACCAGTCC TTTAACGACT ATCTCTCCGC CGCCAACATG CTCTACCCTA
20701 TACCCGCCAA CGCTACCAAC GTGCCCATAT CCATCCCCTC CCGCAACTGG GCGGCTTTCC
20761 GCGGCTGGGC CTTCACGCGC CTTAAGACTA AGGAAACCCC ATCACTGGGC TCGGGCTACG
20821 ACCCTTATTA CACCTACTCT GGCTCTATAC CCTACCTAGA TGGAACCTTT TACCTCAACC
20881 ACACCTTTAA GAAGGTGGCC ATTACCTTTG ACTCTTCTGT CAGCTGGCCT GGCAATGACC
20941 GCCTGCTTAC CCCCAACGAG TTTGAAATTA AGCGCTCAGT TGACGGGGAG GGTTACAACG
21001 TTGCCCAGTG TAACATGACC AAAGACTGGT TCCTGGTACA AATGCTAGCT AACTACAACA
21061 TTGGCTACCA GGGCTTCTAT ATCCCAGAGA GCTACAAGGA CCGCATGTAC TCCTTCTTTA
21121 GAAACTTCCA GCCCATGAGC CGTCAGGTGG TGGATGATAC TAAATACAAG GACTACCAAC
21181 AGGTGGGCAT CCTACACCAA CACAACAACT CTGGATTTGT TGGCTACCTT GCCCCCACCA
21241 TGCGCGAAGG ACAGGCCTAC CCTGCTAACT TCCCCTATCC GCTTATAGGC AAGACCGCAG
21301 TTGACAGCAT TACCCAGAAA AAGTTTCTTT GCGATCGCAC CCTTTGGCGC ATCCCATTCT
21361 CCAGTAACTT TATGTCCATG GGCGCACTCA CAGACCTGGG CCAAAACCTT CTCTACGCCA
21421 ACTCCGCCCA CGCGCTAGAC ATGACTTTTG AGGTGGATCC CATGGACGAG CCCACCCTTC
21481 TTTATGTTTT GTTTGAAGTC TTTGACGTGG TCCGTGTGCA CCGGCCGCAC CGCGGCGTCA
21541 TCGAAACCGT GTACCTGCGC ACGCCCTTCT CGGCCGGCAA CGCCACAACA TAAAGAAGCA
21601 AGCAACATCA ACAACAGCTG CCGCCATGGG CTCCAGTGAG CAGGAACTGA AAGCCATTGT
21661 CAAAGATCTT GGTTGTGGGC CATATTTTTT GGGCACCTAT GACAAGCGCT TTCCAGGCTT
21721 TGTTTCTCCA CACAAGCTCG CCTGCGCCAT AGTCAATACG GCCGGTCGCG AGACTGGGGG
21781 CGTACACTGG ATGGCCTTTG CCTGGAACCC GCACTCAAAA ACATGCTACC TCTTTGAGCC
21841 CTTTGGCTTT TCTGACCAGC GACTCAAGCA GGTTTACCAG TTTGAGTACG AGTCACTCCT
21901 GCGCCGTAGC GCCATTGCTT CTTCCCCCGA CCGCTGTATA ACGCTGGAAA AGTCCACCCA
21961 AAGCGTACAG GGGCCCAACT CGGCCGCCTG TGGACTATTC TGCTGCATGT TTCTCCACGC
22021 CTTTGCCAAC TGGCCCCAAA CTCCCATGGA TCACAACCCC ACCATGAACC TTATTACCGG
22081 GGTACCCAAC TCCATGCTCA ACAGTCCCCA GGTACAGCCC ACCCTGCGTC GCAACCAGGA
22141 ACAGCTCTAC AGCTTCCTGG AGCGCCACTC GCCCTACTTC CGCAGCCACA GTGCGCAGAT
22201 TAGGAGCGCC ACTTCTTTTT GTCACTTGAA AAACATGTAA AAATAATGTA CTAGAGACAC
22261 TTTCAATAAA GGCAAATGCT TTTATTTGTA CACTCTCGGG TGATTATTTA CCCCCACCCT
22321 TGCCGTCTGC GCCGTTTAAA AATCAAAGGG GTTCTGCCGC GCATCGCTAT GCGCCACTGG
22381 CAGGGACACG TTGCGATACT GGTGTTTAGT GCTCCACTTA AACTCAGGCA CAACCATCCG
22441 CGGCAGCTCG GTGAAGTTTT CACTCCACAG GCTGCGCACC ATCACCAACG CGTTTAGCAG
22501 GTCGGGCGCC GATATCTTGA AGTCGCAGTT GGGGCCTCCG CCCTGCGCGC GCGAGTTGCG
22561 ATACACAGGG TTGCAGCACT GGAACACTAT CAGCGCCGGG TGGTGCACGC TGGCCAGCAC
22621 GCTCTTGTCG GAGATCAGAT CCGCGTCCAG GTCCTCCGCG TTGCTCAGGG CGAACGGAGT
22681 CAACTTTGGT AGCTGCCTTC CCAAAAAGGG CGCGTGCCCA GGCTTTGAGT TGCACTCGCA
22741 CCGTAGTGGC ATCAAAAGGT GACCGTGCCC GGTCTGGGCG TTAGGATACA GCGCCTGCAT
22801 AAAAGCCTTG ATCTGCTTAA AAGCCACCTG AGCCTTTGCG CCTTCAGAGA AGAACATGCC
22861 GCAAGACTTG CCGGAAAACT GATTGGCCGG ACAGGCCGCG TCGTGCACGC AGCACCTTGC
22921 GTCGGTGTTG GAGATCTGCA CCACATTTCG GCCCCACCGG TTCTTCACGA TCTTGGCCTT
```

FIGURE 22
(SHEET 7)

22981 GCTAGACTGC TCCTTCAGCG CGCGCTGCCC GTTTTCGCTC GTCACATCCA TTTCAATCAC
23041 GTGCTCCTTA TTTATCATAA TGCTTCCGTG TAGACACTTA AGCTCGCCTT CGATCTCAGC
23101 GCAGCGGTGC AGCCACAACG CGCAGCCCGT GGGCTCGTGA TGCTTGTAGG TCACCTCTGC
23161 AAACGACTGC AGGTACGCCT GCAGGAATCG CCCCATCATC GTCACAAAGG TCTTGTTGCT
23221 GGTGAAGGTC AGCTGCAACC CGCGGTGCTC CTCGTTCAGC CAGGTCTTGC ATACGGCCGC
23281 CAGAGCTTCC ACTTGGTCAG GCAGTAGTTT GAAGTTCGCC TTTAGATCGT TATCCACGTG
23341 GTACTTGTCC ATCAGCGCGC GCGCAGCCTC CATGCCCTTC TCCCACGCAG ACACGATCGG
23401 CACACTCAGC GGGTTCATCA CCGTAATTTC ACTTTCCGCT TCGCTGGGCT CTTCCTCTTC
23461 CTCTTGCGTC CGCATACCAC GCGCCACTGG GTCGTCTTCA TTCAGCCGCC GCACTGTGCG
23521 CTTACCTCCT TTGCCATGCT TGATTAGCAC CGGTGGGTTG CTGAAACCCA CCATTTGTAG
23581 CGCCACATCT TCTCTTTCTT CCTCGCTGTC CACGATTACC TCTGGTGATG GCGGGCGCTC
23641 GGGCTTGGGA GAAGGGCGCT TCTTTTTCTT CTTGGGCGCA ATGGCCAAAT CCGCCGCCGA
23701 GGTCGATGGC CGCGGGCTGG GTGTGCGCGG CACCAGCGCG TCTTGTGATG AGTCTTCCTC
23761 GTCCTCGGAC TCGATACGCC GCCTCATCCG CTTTTTTGGG GGCGCCCGGG GAGGCGGCGG
23821 CGACGGGGAC GGGGACGACA CGTCCTCCAT GGTTGGGGGA CGTCGCGCCG CACCGCGTCC
23881 GCGCTCGGGG GTGGTTTCGC GCTGCTCCTC TTCCCGACTG GCCATTTCCT TCTCCTATAG
23941 GCAGAAAAAG ATCATGGAGT CAGTCGAGAA GAAGGACAGC CTAACCGCCC CCTCTGAGTT
24001 CGCCACCACC GCCTCCACCG ATGCCGCCAA CGCGCCTACC ACCTTCCCCG TCGAGGCACC
24061 CCCGCTTGAG GAGGAGGAAG TGATTATCGA GCAGGACCCA GGTTTTGTAA GCGAAGACGA
24121 CGAGGACCGC TCAGTACCAA CAGAGGATAA AAAGCAAGAC CAGGACAACG CAGAGGCAAA
24181 CGAGGAACAA GTCGGGCGGG GGACGAAAG GCATGGCGAC TACCTAGATG TGGGAGACGA
24241 CGTGCTGTTG AAGCATCTGC AGCGCCAGTG CGCCATTATC TGCGACGCGT TGCAAGAGCG
24301 CAGCGATGTG CCCCTCGCCA TAGCGGATGT CAGCCTTGCC TACGAACGCC ACCTATTCTC
24361 ACCGCGCGTA CCCCCCAAAC GCCAAGAAAA CGGCACATGC GAGCCCAACC CGCGCCTCAA
24421 CTTCTACCCC GTATTTGCCG TGCCAGAGGT GCTTGCCACC TATCACATCT TTTTCCAAAA
24481 CTGCAAGATA CCCCTATCCT GCCGTGCCAA CCGCAGCCGA GCGGACAAGC AGCTGGCCTT
24541 GCGGCAGGGC GCTGTCATAC CTGATATCGC CTCGCTCAAC GAAGTGCCAA AAATCTTTGA
24601 GGGTCTTGGA CGCGACGAGA AGCGCGCGGC AAACGCTCTG CAACAGGAAA ACAGCGAAAA
24661 TGAAAGTCAC TCTGGAGTGT TGGTGGAACT CGAGGGTGAC AACGCGCGCC TAGCCGTACT
24721 AAAACGCAGC ATCGAGGTCA CCCACTTTGC CTACCCGGCA CTTAACCTAC CCCCCAAGGT
24781 CATGAGCACA GTCATGAGTG AGCTGATCGT GCGCCGTGCG CAGCCCCTGG AGAGGGATGC
24841 AAATTTGCAA GAACAAACAG AGGAGGGCCT ACCCGCAGTT GGCGACGAGC AGCTAGCGCG
24901 CTGGCTTCAA ACGCGCGAGC CTGCCGACTT GGAGGAGCGA CGCAAACTAA TGATGGCCGC
24961 AGTGCTCGTT ACCGTGGAGC TTGAGTGCAT GCAGCGGTTC TTTGCTGACC CGGAGATGCA
25021 GCGCAAGCTA GAGGAAACAT TGCACTACAC CTTTCGACAG GGCTACGTAC GCCAGGCCTG
25081 CAAGATCTCC AACGTGGAGC TCTGCAACCT GGTCTCCTAC CTTGGAATTT TGCACGAAAA
25141 CCGCCTTGGG CAAAACGTGC TTCATTCCAC GCTCAAGGGC GAGGCGCGCC GCGACTACGT
25201 CCGCGACTGC GTTTACTTAT TTCTATGCTA CACCTGGCAG ACGGCCATGG GCGTTTGGCA
25261 GCAGTGCTTG GAGGAGTGCA ACCTCAAGGA GCTGCAGAAA CTGCTAAAGC AAAACTTGAA
25321 GGACCTATGG ACGGCCTTCA ACGAGCGCTC CGTGGCCGCG CACCTGGCGG ACATCATTTT
25381 CCCCGAACGC CTGCTTAAAA CCCTGCAACA GGGTCTGCCA GACTTCACCA GTCAAAGCAT
25441 GTTGCAGAAC TTTAGGAACT TTATCCTAGA GCGCTCAGGA ATCTTGCCCG CCACCTGCTG
25501 TGCACTTCCT AGCGACTTTG TGCCCATTAA GTACCGCGAA TGCCCTCCGC CGCTTTGGGG
25561 CCACTGCTAC CTTCTGCAGC TAGCCAACTA CCTTGCCTAC CACTCTGACA TAATGGAAGA
25621 CGTGAGCGGT GACGGTCTAC TGGAGTGTCA CTGTCGCTGC AACCTATGCA CCCCGCACCG
25681 CTCCCTGGTT TGCAATTCGC AGCTGCTTAA CGAAAGTCAA ATTATCGGTA CCTTTGAGCT
25741 GCAGGGTCCC TCGCCTGACG AAAAGTCCGC GGCTCCGGGG TTGAAACTCA CTCCGGGGCT
25801 GTGGACGTCG GCTTACCTTC GCAAATTTGT ACCTGAGGAC TACCACGCCC ACGAGATTAG
25861 GTTCTACGAA GACCAATCCC GCCCGCCAAA TGCGGAGCTT ACCGCCTGCG TCATTACCCA
25921 GGGCCACATT CTTGGCCAAT TGCAAGCCAT CAACAAAGCC CGCCAAGAGT TTCTGCTACG
25981 AAAGGGACGG GGGGTTTACT TGGACCCCCA GTCCGGCGAG GAGCTCAACC CAATCCCCCC
26041 GCCGCCGCAG CCCTATCAGC AGCAGCCGCG GGCCCTTGCT TCCCAGGATG GCACCCAAAA
26101 AGAAGCTGCA GCTGCCGCCG CCACCCACGG ACGAGGAGGA ATACTGGGAC AGTCAGGCAG
26161 AGGAGGTTTT GGACGAGGAG GAGGAGGACA TGATGGAAGA CTGGGAGAGC CTAGACGAGG
26221 AAGCTTCCGA GGTCGAAGAG GTGTCAGACG AAACACCGTC ACCCTCGGTC GCATTCCCCT
26281 CGCCGGCGCC CCAGAAATCG GCAACCGGTT CCAGCATGGC TACAACCTCC GCTCCTCAGG
26341 CGCCGCCGGC ACTGCCCGTT CGCCGACCCA ACCGTAGATG GGACACCACT GGAACCAGGG

FIGURE 22
(SHEET 8)

26401 CCGGTAAGTC CAAGCAGCCG CCGCCGTTAG CCCAAGAGCA ACAACAGCGC CAAGGCTACC
26461 GCTCATGGCG CGGGCACAAG AACGCCATAG TTGCTTGCTT GCAAGACTGT GGGGGCAACA
26521 TCTCCTTCGC CCGCCGCTTT CTTCTCTACC ATCACGGCGT GGCCTTCCCC CGTAACATCC
26581 TGCATTACTA CCGTCATCTC TACAGCCCAT ACTGCACCGG CGGCAGCGGC AGCGGCAGCA
26641 ACAGCAGCGG CCACACAGAA GCAAAGGCGA CCGGATAGCA AGACTCTGAC AAAGCCCAAG
26701 AAATCCACAG CGGCGGCAGC AGCAGGAGGA GGAGCGCTGC GTCTGGCGCC CAACGAACCC
26761 GTATCGACCC GCGAGCTTAG AAACAGGATT TTTCCCACTC TGTATGCTAT ATTTCAACAG
26821 AGCAGGGGCC AAGAACAAGA GCTGAAAATA AAAAACAGGT CTCTGCGATC CCTCACCCGC
26881 AGCTGCCTGT ATCACAAAAG CGAAGATCAG CTTCGGCGCA CGCTGGAAGA CGCGGAGGCT
26941 CTCTTCAGTA AATACTGCGC GCTGACTCTT AAGGACTAGT TTCGCGCCCT TTCTCAAATT
27001 TAAGCGCGAA AACTACGTCA TCTCCAGCGG CCACACCCGG CGCCAGCACC TGTCGTCAGC
27061 GCCATTATGA GCAAGGAAAT TCCCACGCCC TACATGTGGA GTTACCAGCC ACAAATGGGA
27121 CTTGCGGCTG GAGCTGCCCA AGACTACTCA ACCCGAATAA ACTACATGAG CGCGGGACCC
27181 CACATGATAT CCCGGGTCAA CGGAATCCGC GCCCACCGAA ACCGAATTCT CTTGGAACAG
27241 GCGGCTATTA CCACCACACC TCGTAATAAC CTTAATCCCC GTAGTTGGCC CGCTGCCCTG
27301 GTGTACCAGG AAAGTCCCGC TCCCACCACT GTGGTACTTC CCAGAGACGC CCAGGCCGAA
27361 GTTCAGATGA CTAACTCAGG GGCGCAGCTT GCGGGCGGCT TTCGTCACAG GGTGCGGTCG
27421 CCCGGGCAGG GTATAACTCA CCTGACAATC AGAGGGCGAG GTATTCAGCT CAACGACGAG
27481 TCGGTGAGCT CCTCGCTTGG TCTCCGTCCG GACGGGACAT TTCAGATCGG CGGCGCCGGC
27541 CGTCCTTCAT TCACGCCTCG TCAGGCAATC CTAACTCTGC AGACCTCGTC CTCTGAGCCG
27601 CGCTCTGGAG GCATTGGAAC TCTGCAATTT ATTGAGGAGT TTGTGCCATC GGTCTACTTT
27661 AACCCCTTCT CGGGACCTCC CGGCCACTAT CCGGATCAAT TTATTCCTAA CTTTGACGCG
27721 GTAAAGGACT CGGCGGACGG CTACGACTGA TAATTAAGTG GAGAGGCAGA GCAACTGCGC
27781 CTGAAACACC TGGTCCACTG TCGCCGCCAC AAGTGCTTTG CCCGCGACTC CGGTGAGTTT
27841 TGCTACTTTG AATTGCCCGA GGATCATATC GAGGATCTTT GTTGCCATCT CTGTGCTGAG
27901 TATAATAAAT ACAGAAATTA AAATATACTG GGGCTCCTAT CGCCATCCTG TAAACGCCAC
27961 CGTCTTCACC CGCCCAAGCA AACCAAGGCG AACCTTACCT GGTACTTTTA ACATCTCTCC
28021 CTCTGTGATT TACAACAGTT TCAACCCAGA CGGAGTGAGT CTACGAGAGA ACCTCTCCGA
28081 GCTCAGCTAC TCCATCAGAA AAAACACCAC CCTCCTTACC TGCCGGGAAC GTACCCTTAA
28141 TTAAAAGTCA GGCTTCCTGG ATGTCAGCAT CTGACTTTGG CCAGCACCTG TCCCGCGGAT
28201 TTGTTCCAGT CCAACTACAG CGACCCACCC TAACAGAGAT GACCAACACA ACCAACGCGG
28261 CCGCCGCTAC CGGACTTACA TCTACCACAA ATACACCCCA AGTTTCTGCC TTTGTCAATA
28321 ACTGGGATAA CTTGGGCATG TGGTGGTTCT CCATAGCGCT TATGTTTGTA TGCCTTATTA
28381 TTATGTGGCT CATCTGCTGC CTAAAGCGCA AACGCGCCCG ACCACCCATC TATAGTCCCA
28441 TCATTGTGCT ACACCCAAAC AATGATGGAA TCCATAGATT GGACGGACTG AAACACATGT
28501 TCTTTTCTCT TACAGTATGA TTAAATGAGA TTAATTAAGG AATTTCTGTC CAGTTTATTC
28561 AGCAGCACCT CCTTGCCCTC CTCCCAGCTC TGGTATTGCA GCTTCCTCCT GGCTGCAAAC
28621 TTTCTCCACA ATCTAAATGG AATGTCAGTT TCCTCCTGTT CCTGTCCATC CGCACCCACT
28681 ATCTTCATGT TGTTGCAGAT GAAGCGCGCA AGACCGTCTG AAGATACCTT CAACCCCGTG
28741 TATCCATATG ACACGGAAAC CGGTCCTCCA ACTGTGCCTT TTCTTACTCC TCCCTTTGTA
28801 TCCCCCAATG GGTTTCAAGA GAGTCCCCCT GGGGTACTCT CTTTGCGCCT ATCCGAACCT
28861 CTAGTTACCT CCAATGGCAT GCTTGCGCTC AAAATGGGCA ACGGCCTCTC TCTGGACGAG
28921 GCCGGCAACC TTACCTCCCA AAATGTAACC ACTGTGAGCC CACCTCTCAA AAAAACCAAG
28981 TCAAACATAA ACCTGGAAAT ATCTGCACCC CTCACAGTTA CCTCAGAAGC CCTAACTGTG
29041 GCTGCCGCCG CACCTCTAAT GGTCGCGGGC AACACACTCA CCATGCAATC ACAGGCCCCG
29101 CTAACCGTGC ACGACTCCAA ACTTAGCATT GCCACCCAAG GACCCCTCAC AGTGTCAGAA
29161 GGAAAGCTAG CCCTGCAAAC ATCAGGCCCC CTCACCACCA CCGATAGCAG TACCCTTACT
29221 ATCACTGCCT CACCCCCTCT AACTACTGCC ACTGGTAGCT TGGGCATTGA CTTGAAAGAG
29281 CCCATTTATA CACAAAATGG AAAACTAGGA CTAAAGTACG GGGCTCCTTT GCATGTAACA
29341 GACGACCTAA ACACTTTGAC CGTAGCAACT GGTCCAGGTG TGACTATTAA TAATACTTCC
29401 TTGCAAACTA AAGTTACTGG AGCCTTGGGT TTTGATTCAC AAGGCAATAT GCAACTTAAT
29461 GTAGCAGGAG GACTAAGGAT TGATTCTCAA AACAGACGCC TTATACTTGA TGTTAGTTAT
29521 CCGTTTGATG CTCAAAACCA ACTAAATCTA AGACTAGGAC AGGGCCCTCT TTTTATAAAC
29581 TCAGCCCACA ACTTGGATAT TAACTACAAC AAAGGCCTTT ACTTGTTTAC AGCTTCAAAC
29641 AATTCCAAAA AGCTTGAGGT TAACCTAAGC ACTGCCAAGG GGTTGATGTT TGACGCTACA
29701 GCCATAGCCA TTAATGCAGG AGATGGGCTT GAATTTGGTT CACCTAATGC ACCAAACACA
29761 AATCCCCTCA AAACAAAAAT TGGCCATGGC CTAGAATTTG ATTCAAACAA GGCTATGGTT

FIGURE 22
(SHEET 9)

29821 CCTAAACTAG GAACTGGCCT TAGTTTTGAC AGCACAGGTG CCATTACAGT AGGAAACAAA
29881 AATAATGATA AGCTAACTTT GTGGACCACA CCAGCTCCAT CTCCTAACTG TAGACTAAAT
29941 GCAGAGAAAG ATGCTAAACT CACTTTGGTC TTAACAAAAT GTGGCAGTCA AATACTTGCT
30001 ACAGTTTCAG TTTTGGCTGT TAAAGGCAGT TTGGCTCCAA TATCTGGAAC AGTTCAAAGT
30061 GCTCATCTTA TTATAAGATT TGACGAAAAT GGAGTGCTAC TAAACAATTC CTTCCTGGAC
30121 CCAGAATATT GGAACTTTAG AAATGGAGAT CTTACTGAAG GCACAGCCTA TACAAACGCT
30181 GTTGGATTTA TGCCTAACCT ATCAGCTTAT CCAAAATCTC ACGGTAAAAC TGCCAAAAGT
30241 AACATTGTCA GTCAAGTTTA CTTAAACGGA GACAAAACTA AACCTGTAAC ACTAACCATT
30301 ACACTAAACG GTACACAGGA AACAGGAGAC ACAACTCCAA GTGCATACTC TATGTCATTT
30361 TCATGGGACT GGTCTGGCCA CAACTACATT AATGAAATAT TTGCCACATC CTCTTACACT
30421 TTTTCATACA TTGCCCAAGA ATAAAGAATC GTTTGTGTTA TGTTTCAACG TGTTTATTTT
30481 TCAATTGCAG AAAATTTCAA GTCATTTTTC ATTCAGTAGT ATAGCCCCAC CACCACATAG
30541 CTTATACAGA TCACCGTACC TTAATCAAAC TCACAGAACC CTAGTATTCA ACCTGCCACC
30601 TCCCTCCCAA CACACAGAGT ACACAGTCCT TTCTCCCCGG CTGGCCTTAA AAAGCATCAT
30661 ATCATGGGTA ACAGACATAT TCTTAGGTGT TATATTCCAC ACGGTTTCCT GTCGAGCCAA
30721 ACGCTCATCA GTGATATTAA TAAACTCCCC GGGCAGCTCA CTTAAGTTCA TGTCGCTGTC
30781 CAGCTGCTGA GCCACAGGCT GCTGTCCAAC TTGCGGTTGC TTAACGGGCG GCGAAGGAGA
30841 AGTCCACGCC TACATGGGGG TAGAGTCATA ATCGTGCATC AGGATAGGGC GGTGGTGCTG
30901 CAGCAGCGCG CGAATAAACT GCTGCCGCCG CCGCTCCGTC CTGCAGGAAT ACAACATGGC
30961 AGTGGTCTCC TCAGCGATGA TTCGCACCGC CCGCAGCATA AGGCGCCTTG TCCTCCGGGC
31021 ACAGCAGCGC ACCCTGATCT CACTTAAATC AGCACAGTAA CTGCAGCACA GCACCACAAT
31081 ATTGTTCAAA ATCCCACAGT GCAAGGCGCT GTATCCAAAG CTCATGGCGG GGACCACAGA
31141 ACCCACGTGG CCATCATACC ACAAGCGCAG GTAGATTAAG TGGCGACCCC TCATAAACAC
31201 GCTGGACATA AACATTACCT CTTTTGGCAT GTTGTAATTC ACCACCTCCC GGTACCATAT
31261 AAACCTCTGA TTAAACATGG CGCCATCCAC CACCATCCTA AACCAGCTGG CCAAAACCTG
31321 CCCGCCGGCT ATACACTGCA GGGAACCGGG ACTGGAACAA TGACAGTGGA GAGCCCAGGA
31381 CTCGTAACCA TGGATCATCA TGCTCGTCAT GATATCAATG TTGGCACAAC ACAGGCACAC
31441 GTGCATACAC TTCCTCAGGA TTACAAGCTC CTCCCGCGTT AGAACCATAT CCCAGGGAAC
31501 AACCCATTCC TGAATCAGCG TAAATCCCAC ACTGCAGGGA AGACCTCGCA CGTAACTCAC
31561 GTTGTGCATT GTCAAAGTGT TACATTCGGG CAGCAGCGGA TGATCCTCCA GTATGGTAGC
31621 GCGGGTTTCT GTCTCAAAAG GAGGTAGACG ATCCCTACTG TACGGAGTGC GCCGAGACAA
31681 CCGAGATCGT GTTGGTCGTA GTGTCATGCC AAATGGAACG CCGGACGTAG TCATATTTCC
31741 TGAAGCAAAA CCAGGTGCGG GCGTGACAAA CAGATCTGCG TCTCCGGTCT CGCCGCTTAG
31801 ATCGCTCTGT GTAGTAGTTG TAGTATATCC ACTCTCTCAA AGCATCCAGG CGCCCCCTGG
31861 CTTCGGGTTC TATGTAAACT CCTTCATGCG CCGCTGCCCT GATAACATCC ACCACCGCAG
31921 AATAAGCCAC ACCCAGCCAA CCTACACATT CGTTCTGCGA GTCACACACG GGAGGAGCGG
31981 GAAGAGCTGG AAGAACCATG TTTTTTTTTT TATTCCAAAA GATTATCCAA AACCTCAAAA
32041 TGAAGATCTA TTAAGTGAAC GCGCTCCCCT CCGGTGGCGT GGTCAAACTC TACAGCCAAA
32101 GAACAGATAA TGGCATTTGT AAGATGTTGC ACAATGGCTT CCAAAAGGCA AACGGCCCTC
32161 ACGTCCAAGT GGACGTAAAG GCTAAACCCT TCAGGGTGAA TCTCCTCTAT AAACATTCCA
32221 GCACCTTCAA CCATGCCCAA ATAATTCTCA TCTCGCCACC TTCTCAATAT ATCTCTAAGC
32281 AAATCCCGAA TATTAAGTCC GGCCATTGTA AAAATCTGCT CCAGAGCGCC CTCCACCTTC
32341 AGCCTCAAGC AGCGAATCAT GATTGCAAAA ATTCAGGTTC CTCACAGACC TGTATAAGAT
32401 TCAAAAGCGG AACATTAACA AAAATACCGC GATCCCGTAG GTCCCTTCGC AGGGCCAGCT
32461 GAACATAATC GTGCAGGTCT GCACGGACCA GCGCGGCCAC TTCCCCGCCA GGAACCTTGA
32521 CAAAAGAACC CACACTGATT ATGACACGCA TACTCGGAGC TATGCTAACC AGCGTAGCCC
32581 CGATGTAAGC TTTGTTGCAT GGGCGGCGAT ATAAAATGCA AGGTGCTGCT CAAAAAATCA
32641 GGCAAAGCCT CGCGCAAAAA AGAAAGCACA TCGTAGTCAT GCTCATGCAG ATAAAGGCAG
32701 GTAAGCTCCG GAACCACCAC AGAAAAAGAC ACCATTTTTC TCTCAAACAT GTCTGCGGGT
32761 TTCTGCATAA ACACAAAATA AAATAACAAA AAAACATTTA AACATTAGAA GCCTGTCTTA
32821 CAACAGGAAA AACAACCCTT ATAAGCATAA GACGGACTAC GGCCATGCCG GCGTGACCGT
32881 AAAAAAACTG GTCACCGTGA TTAAAAAGCA CCACCGACAG CTCCTCGGTC ATGTCCGGAG
32941 TCATAATGTA AGACTCGGTA AACACATCAG GTTGATTCAT CGGTCAGTGC TAAAAAGCGA
33001 CCGAAATAGC CCGGGGGAAT ACATACCCGC AGGCGTAGAG ACAACATTAC AGCCCCCATA
33061 GGAGGTATAA CAAAATTAAT AGGAGAGAAA AACACATAAA CACCTGAAAA ACCCTCCTGC
33121 CTAGGCAAAA TAGCACCCTC CCGCTCCAGA ACAACATACA GCGCTTCACA GCGGCAGCCT
33181 AACAGTCAGC CTTACCAGTA AAAAAGAAAA CCTATTAAAA AAACACCACT CGACACGGCA

FIGURE 22
(SHEET 10)

```
33241 CCAGCTCAAT CAGTCACAGT GTAAAAAAGG GCCAAGTGCA GAGCGAGTAT ATATAGGACT
33301 AAAAAATGAC GTAACGGTTA AAGTCCACAA AAAACACCCA GAAAACCGCA CGCGAACCTA
33361 CGCCCAGAAA CGAAAGCCAA AAAACCCACA ACTTCCTCAA ATCGTCACTT CCGTTTTCCC
33421 ACGTTACGTA ACTTCCCATT TTAAGAAAAC TACAATTCCC AACACATACA AGTTACTCCG
33481 CCCTAAAACC TACGTCACCC GCCCCGTTCC CACGCCCCGC GCCACGTCAC AAACTCCACC
33541 CCCTCATTAT CATATTGGCT TCAATCCAAA ATAAGGTATA TTATTGATGA TG
```

FIGURE 22
(SHEET 11)

```
LOCUS       KD3         34341 bp    DNA              SYN       06-FEB-1999
DEFINITION  KD3
ACCESSION   KD3
KEYWORDS
SOURCE      Unknown.
  ORGANISM  Unknown
            Unclassified.
REFERENCE   1  (bases 1 to 34341)
  AUTHORS   Self
  JOURNAL   Unpublished.
FEATURES             Location/Qualifiers
     CDS             1..34341
                     /gene="KD3"
                     /product="KD3"
BASE COUNT     7951 a   9671 c   9464 g   7255 t
ORIGIN
        1 CATCATCAAT AATATACCTT ATTTTGGATT GAAGCCAATA TGATAATGAG GGGGTGGAGT
       61 TTGTGACGTG GCGCGGGGCG TGGGAACGGG GCGGGTGACG TAGTAGTGTG GCGGAAGTGT
      121 GATGTTGCAA GTGTGGCGGA ACACATGTAA GCGACGGATG TGGCAAAAGT GACGTTTTTG
      181 GTGTGCGCCG GTGTACACAG GAAGTGACAA TTTTCGCGCG GTTTTAGGCG GATGTTGTAG
      241 TAAATTTGGG CGTAACCGAG TAAGATTTGG CCATTTTCGC GGGAAAACTG AATAAGAGGA
      301 AGTGAAATCT GAATAATTTT GTGTTACTCA TAGCGCGTAA TATTTGTCTA GGGCCGCGGG
      361 GACTTTGACC GTTTACGTGG AGACTCGCCC AGGTGTTTTT CTCAGGTGTT TTCCGCGTTC
      421 CGGGTCAAAG TTGGCGTTTT ATTATTATAG TCAGCTGACG TGTAGTGTAT TTATACCCGG
      481 TGAGTTCCTC AAGAGGCCAC TCTTGAGTGC CAGCGAGTAG AGTTTTCTCC TCCGAGCCGC
      541 TCCGACACCG GGACTGAAAA TGAGACATGA GGTACTGGCT GATAATCTTC CACCTCCTAG
      601 CCATTTTGAA CCACCTACCC TTCACGAACT GTATGATTTA GACGTGACGG CCCCCGAAGA
      661 TCCCAACGAG GAGGCGGTTT CGCAGATTTT TCCCGACTCT GTAATGTTGG CGGTGCAGGA
      721 AGGGATTGAC TTACTCACTT TTCCGCCGGC GCCCGGTTCT CCGGAGCCGC CTCACCTTTC
      781 CCGGCAGCCC GAGCAGCCGG AGCAGAGAGC CTTGGGTCCG GTTTGCCACG AGGCTGGCTT
      841 TCCACCCAGT GACGACGAGG ATGAAGAGGG TGAGGAGTTT GTGTTAGATT ATGTGGAGCA
      901 CCCCGGGCAC GGTTGCAGGT CTTGTCATTA TCACCGGAGG AATACGGGGG ACCCAGATAT
      961 TATGTGTTCG CTTTGCTATA TGAGGACCTG TGGCATGTTT GTCTACAGTA AGTGAAAATT
     1021 ATGGGCAGTG GGTGATAGAG TGGTGGGTTT GGTGTGGTAA TTTTTTTTTT AATTTTTACA
     1081 GTTTTGTGGT TTAAAGAATT TTGTATTGTG ATTTTTTTAA AAGGTCCTGT GTCTGAACCT
     1141 GAGCCTGAGC CCGAGCCAGA ACCGGAGCCT GCAAGACCTA CCCGCCGTCC TAAAATGGCG
     1201 CCTGCTATCC TGAGACGCCC GACATCACCT GTGTCTAGAG AATGCAATAG TAGTACGGAT
     1261 AGCTGTGACT CCGGTCCTTC TAACACACCT CCTGAGATAC ACCCGGTGGT CCCGCTGTGC
     1321 CCCATTAAAC CAGTTGCCGT GAGAGTTGGT GGGCGTCGCC AGGCTGTGGA ATGTATCGAG
     1381 GACTTGCTTA ACGAGCCTGG GCAACCTTTG GACTTGAGCT GTAAACGCCC CAGGCCATAA
     1441 GGTGTAAACC TGTGATTGCG TGTGTGGTTA ACGCCTTTGT TTGCTGAATG AGTTGATGTA
     1501 AGTTTAATAA AGGGTGAGAT AATGTTTAAC TTGCATGGCG TGTTAAATGG GGCGGGGCTT
     1561 AAAGGGTATA TAATGCGCCG TGGGCTAATC TTGGTTACAT CTGACCTCAT GGAGGCTTGG
     1621 GAGTGTTTGG AAGATTTTTC TGCTGTGCGT AACTTGCTGG AACAGAGCTC TAACAGTACC
     1681 TCTTGGTTTT GGAGGTTTCT GTGGGGCTCA TCCCAGGCAA AGTTAGTCTG CAGAATTAAG
     1741 GAGGATTACA AGTGGGAATT TGAAGAGCTT TTGAAATCCT GTGGTGAGCT GTTTGATTCT
     1801 TTGAATCTGG GTCACCAGGC GCTTTTCCAA GAGAAGGTCA TCAAGACTTT GGATTTTTCC
     1861 ACACCGGGGC GCGCTGCGGC TGCTGTTGCT TTTTTGAGTT TTATAAAGGA TAAATGGAGC
     1921 GAAGAAACCC ATCTGAGCGG GGGGTACCTG CTGGATTTTC TGGCCATGCA TCTGTGGAGA
     1981 GCGGTTGTGA GACACAAGAA TCGCCTGCTA CTGTTGTCTT CCGTCCGCCC GGCGATAATA
     2041 CCGACGGAGG AGCAGCAGCA GCAGCAGGAG GAAGCCAGGC GGCGGCGGCA GGAGCAGAGC
     2101 CCATGGAACC CGAGAGCCGG CCTGGACCCT CGGGAATGAA TGTTGTACAG GTGGCTGAAC
     2161 TGTATCCAGA ACTGAGACGC ATTTTGACAA TTACAGAGGA TGGGCAGGGG CTAAAGGGGG
     2221 TAAAGAGGGA GCGGGGGGCT TGTGAGGCTA CAGAGGAGGC TAGGAATCTA GCTTTTAGCT
     2281 TAATGACCAG ACACCGTCCT GAGTGTATTA CTTTTCAACA GATCAAGGAT AATTGCGCTA
     2341 ATGAGCTTGA TCTGCTGGCG CAGAAGTATT CCATAGAGCA GCTGACCACT TACTGGCTGC
     2401 AGCCAGGGGA TGATTTTGAG GAGGCTATTA GGGTATATGC AAAGGTGGCA CTTAGGCCAG
```

FIGURE 23
(SHEET 1)

```
2461 ATTGCAAGTA CAAGATCAGC AAACTTGTAA ATATCAGGAA TTGTTGCTAC ATTTCTGGGA
2521 ACGGGGCCGA GGTGGAGATA GATACGGAGG ATAGGGTGGC CTTTAGATGT AGCATGATAA
2581 ATATGTGGCC GGGGGTGCTT GGCATGGACG GGGTGGTTAT TATGAATGTA AGGTTTACTG
2641 GCCCCAATTT TAGCGGTACG GTTTTCCTGG CCAATACCAA CCTTATCCTA CACGGTGTAA
2701 GCTTCTATGG GTTTAACAAT ACCTGTGTGG AAGCCTGGAC CGATGTAAGG GTTCGGGGCT
2761 GTGCCTTTTA CTGCTGCTGG AAGGGGGTGG TGTGTCGCCC CAAAAGCAGG GCTTCAATTA
2821 AGAAATGCCT CTTTGAAAGG TGTACCTTGG GTATCCTGTC TGAGGGTAAC TCCAGGGTGC
2881 GCCACAATGT GGCCTCCGAC TGTGGTTGCT TCATGCTAGT GAAAAGCGTG GCTGTGATTA
2941 AGCATAACAT GGTATGTGGC AACTGCGAGG ACAGGGCCTC TCAGATGCTG ACCTGCTCGG
3001 ACGGCAACTG TCACCTGCTG AAGACCATTC ACGTAGCCAG CCACTCTCGC AAGGCCTGGC
3061 CAGTGTTTGA GCATAACATA CTGACCCGCT GTTCCTTGCA TTTGGGTAAC AGGAGGGGGG
3121 TGTTCCTACC TTACCAATGC AATTTGAGTC ACACTAAGAT ATTGCTTGAG CCCGAGAGCA
3181 TGTCCAAGGT GAACCTGAAC GGGGTGTTTG ACATGACCAT GAAGATCTGG AAGGTGCTGA
3241 GGTACGATGA GACCCGCACC AGGTGCAGAC CCTGCGAGTG TGGCGGTAAA CATATTAGGA
3301 ACCAGCCTGT GATGCTGGAT GTGACCGAGG AGCTGAGGCC CGATCACTTG GTGCTGGCCT
3361 GCACCCGCGC TGAGTTTGGC TCTAGCGATG AAGATACAGA TTGAGGTACT GAAATGTGTG
3421 GGCGTGGCTT AAGGGTGGGA AAGAATATAT AAGGTGGGGG TCTTATGTAG TTTTGTATCT
3481 GTTTTGCAGC AGCCGCCGCC GCCATGAGCA CCAACTCGTT TGATGGAAGC ATTGTGAGCT
3541 CATATTTGAC AACGCGCATG CCCCCATGGG CCGGGGTGCG TCAGAATGTG ATGGGCTCCA
3601 GCATTGATGG TCGCCCCGTC CTGCCCGCAA ACTCTACTAC CTTGACCTAC GAGACCGTGT
3661 CTGGAACGCC GTTGGAGACT GCAGCCTCCG CCGCCGCTTC AGCCGCTGCA GCCACCGCCC
3721 GCGGGATTGT GACTGACTTT GCTTTCCTGA GCCCGCTTGC AAGCAGTGCA GCTTCCCGTT
3781 CATCCGCCCG CGATGACAAG TTGACGGCTC TTTTGGCACA ATTGGATTCT TTGACCCGGG
3841 AACTTAATGT CGTTTCTCAG CAGCTGTTGG ATCTGCGCCA GCAGGTTTCT GCCCTGAAGG
3901 CTTCCTCCCC TCCCAATGCG GTTTAAAACA TAAATAAAAA ACCAGACTCT GTTTGGATTT
3961 GGATCAAGCA AGTGTCTTGC TGTCTTTATT TAGGGGTTTT GCGCGCGCGG TAGGCCCGGG
4021 ACCAGCGGTC TCGGTCGTTG AGGGTCCTGT GTATTTTTTC CAGGACGTGG TAAAGGTGAC
4081 TCTGGATGTT CAGATACATG GGCATAAGCC CGTCTCTGGG GTGGAGGTAG CACCACTGCA
4141 GAGCTTCATG CTGCGGGGTG GTGTTGTAGA TGATCCAGTC GTAGCAGGAG CGCTGGGCGT
4201 GGTGCCTAAA AATGTCTTTC AGTAGCAAGC TGATTGCCAG GGGCAGGCCC TTGGTGTAAG
4261 TGTTTACAAA GCGGTTAAGC TGGGATGGGT GCATACGTGG GGATATGAGA TGCATCTTGG
4321 ACTGTATTTT TAGGTTGGCT ATGTTCCCAG CCATATCCCT CCGGGGATTC ATGTTGTGCA
4381 GAACCACCAG CACAGTGTAT CCGGTGCACT TGGGAAATTT GTCATGTAGC TTAGAAGGAA
4441 ATGCGTGGAA GAACTTGGAG ACGCCCTTGT GACCTCCAAG ATTTTCCATG CATTCGTCCA
4501 TAATGATGGC AATGGGCCCA CGGGCGGCGG CCTGGGCGAA GATATTTCTG GGATCACTAA
4561 CGTCATAGTT GTGTTCCAGG ATGAGATCGT CATAGGCCAT TTTTACAAAG CGCGGGCGGA
4621 GGGTGCCAGA CTGCGGTATA ATGGTTCCAT CCGGCCCAGG GGCGTAGTTA CCCTCACAGA
4681 TTTGCATTTC CCACGCTTTG AGTTCAGATG GGGGGATCAT GTCTACCTGC GGGGCGATGA
4741 AGAAAACGGT TTCCGGGGTA GGGGAGATCA GCTGGGAAGA AAGCAGGTTC CTGAGCAGCT
4801 GCGACTTACC GCAGCCGGTG GGCCCGTAAA TCACACCTAT TACCGGGTGC AACTGGTAGT
4861 TAAGAGAGCT GCAGCTGCCG TCATCCCTGA GCAGGGGGGC CACTTCGTTA AGCATGTCCC
4921 TGACTCGCAT GTTTTCCCTG ACCAAATCCG CCAGAAGGCG CTCGCCGCCC AGCGATAGCA
4981 GTTCTTGCAA GGAAGCAAAG TTTTTCAACG GTTTGAGACC GTCCGCCGTA GGCATGCTTT
5041 TGAGCGTTTG ACCAAGCAGT TCCAGGCGGT CCCACAGCTC GGTCACCTGC TCTACGGCAT
5101 CTCGATCCAG CATATCTCCT CGTTTCGCGG GTTGGGGCGG CTTTCGCTGT ACGGCAGTAG
5161 TCGGTGCTCG TCCAGACGGG CCAGGGTCAT GTCTTTCCAC GGGCGCAGGG TCCTCGTCAG
5221 CGTAGTCTGG GTCACGGTGA AGGGGTGCGC TCCGGGCTGC GCGCTGGCCA GGGTGCGCTT
5281 GAGGCTGGTC CTGCTGGTGC TGAAGCGCTG CCGGTCTTCG CCCTGCGCGT CGGCCAGGTA
5341 GCATTTGACC ATGGTGTCAT AGTCCAGCCC CTCCGCGGCG TGGCCCTTGG CGCGCAGCTT
5401 GCCCTTGGAG GAGGCGCCGC ACGAGGGGCA GTGCAGACTT TTGAGGGCGT AGAGCTTGGG
5461 CGCGAGAAAT ACCGATTCCG GGGAGTAGGC ATCCGCGCCG CAGGCCCCGC AGACGGTCTC
5521 GCATTCCACG AGCCAGGTGA GCTCTGGCCG TTCGGGGTCA AAAACCAGGT TTCCCCCATG
5581 CTTTTTGATG CGTTTCTTAC CTCTGGTTTC CATGAGCCGG TGTCCACGCT CGGTGACGAA
5641 AAGGCTGTCC GTGTCCCCGT ATACAGACTT GAGAGGCCTG TCCTCGAGCG GTGTTCCGCG
5701 GTCCTCCTCG TATAGAAACT CGGACCACTC TGAGACAAAG GCTCGCGTCC AGGCCAGCAC
5761 GAAGGAGGCT AAGTGGGAGG GGTAGCGGTC GTTGTCCACT AGGGGGTCCA CTCGCTCCAG
5821 GGTGTGAAGA CACATGTCGC CCTCTTCGGC ATCAAGGAAG GTGATTGGTT TGTAGGTGTA
```

FIGURE 23
(SHEET 2)

```
5881 GGCCACGTGA CCGGGTGTTC CTGAAGGGGG GCTATAAAAG GGGGTGGGGG CGCGTTCGTC
5941 CTCACTCTCT TCCGCATCGC TGTCTGCGAG GGCCAGCTGT TGGGGTGAGT ACTCCCTCTG
6001 AAAAGCGGGC ATGACTTCTG CGCTAAGATT GTCAGTTTCC AAAAACGAGG AGGATTTGAT
6061 ATTCACCTGG CCCGCGGTGA TGCCTTTGAG GGTGGCCGCA TCCATCTGGT CAGAAAAGAC
6121 AATCTTTTTG TTGTCAAGCT TGGTGGCAAA CGACCCGTAG AGGGCGTTGG ACAGCAACTT
6181 GGCGATGGAG CGCAGGGTTT GGTTTTTGTC GCGATCGGCG CGCTCCTTGG CCGCGATGTT
6241 TAGCTGCACG TATTCGCGCG CAACGCACCG CCATTCGGGA AAGACGGTGG TGCGCTCGTC
6301 GGGCACCAGG TGCACGCGCC AACCGCGGTT GTGCAGGGTG ACAAGGTCAA CGCTGGTGGC
6361 TACCTCTCCG CGTAGGCGCT CGTTGGTCCA GCAGAGGCGG CCGCCCTTGC GCGAGCAGAA
6421 TGGCGGTAGG GGGTCTAGCT GCGTCTCGTC CGGGGGGTCT GCGTCCACGG TAAAGACCCC
6481 GGGCAGCAGG CGCGCGTCGA AGTAGTCTAT CTTGCATCCT TGCAAGTCTA GCGCCTGCTG
6541 CCATGCGCGG GCGGCAAGCG CGCGCTCGTA TGGGTTGAGT GGGGGACCCC ATGGCATGGG
6601 GTGGGTGAGC GCGGAGGCGT ACATGCCGCA AATGTCGTAA ACGTAGAGGG GCTCTCTGAG
6661 TATTCCAAGA TATGTAGGGT AGCATCTTCC ACCGCGGATG CTGGCGCGCA CGTAATCGTA
6721 TAGTTCGTGC GAGGGAGCGA GGAGGTCGGG ACCGAGGTTG CTACGGGCGG GCTGCTCTGC
6781 TCGGAAGACT ATCTGCCTGA AGATGGCATG TGAGTTGGAT GATATGGTTG GACGCTGGAA
6841 GACGTTGAAG CTGGCGTCTG TGAGACCTAC CGCGTCACGC ACGAAGGAGG CGTAGGAGTC
6901 GCGCAGCTTG TTGACCAGCT CGGCGGTGAC CTGCACGTCT AGGGCGCAGT AGTCCAGGGT
6961 TTCCTTGATG ATGTCATACT TATCCTGTCC CTTTTTTTTC CACAGCTCGC GGTTGAGGAC
7021 AAACTCTTCG CGGTCTTTCC AGTACTCTTG GATCGGAAAC CCGTCGGCCT CCGAACGGTA
7081 AGAGCCTAGC ATGTAGAACT GGTTGACGGC CTGGTAGGCG CAGCATCCCT TTTCTACGGG
7141 TAGCGCGTAT GCCTGCGCGG CCTTCCGGAG CGAGGTGTGG GTGAGCGCAA AGGTGTCCCT
7201 GACCATGACT TTGAGGTACT GGTATTTGAA GTCAGTGTCG TCGCATCCGC CCTGCTCCCA
7261 GAGCAAAAAG TCCGTGCGCT TTTTGGAACG CGGATTTGGC AGGGCGAAGG TGACATCGTT
7321 GAAGAGTATC TTTCCCGCGC GAGGCATAAA GTTGCGTGTG ATGCGGAAGG GTCCCGGCAC
7381 CTCGGAACGG TTGTTAATTA CCTGGGCGGC GAGCACGATC TCGTCAAAGC CGTTGATGTT
7441 GTGGCCCACA ATGTAAAGTT CCAAGAAGCG CGGGATGCCC TTGATGGAAG GCAATTTTTT
7501 AAGTTCCTCG TAGGTGAGCT CTTCAGGGGA GCTGAGCCCG TGCTCTGAAA GGGCCCAGTC
7561 TGCAAGATGA GGGTTGGAAG CGACGAATGA GCTCCACAGG TCACGGGCCA TTAGCATTTG
7621 CAGGTGGTCG CGAAAGGTCC TAAACTGGCG ACCTATGGCC ATTTTTTCTG GGGTGATGCA
7681 GTAGAAGGTA AGCGGGTCTT GTTCCCAGCG GTCCCATCCA AGGTTCGCGG CTAGGTCTCG
7741 CGCGGCAGTC ACTAGAGGCT CATCTCCGCC GAACTTCATG ACCAGCATGA AGGGCACGAG
7801 CTGCTTCCCA AAGGCCCCCA TCCAAGTATA GGTCTCTACA TCGTAGGTGA CAAAGAGACG
7861 CTCGGTGCGA GGATGCGAGC CGATCGGGAA GAACTGGATC TCCCGCCACC AATTGGAGGA
7921 GTGGCTATTG ATGTGGTGAA AGTAGAAGTC CCTGCGACGG GCCGAACACT CGTGCTGGCT
7981 TTTGTAAAAA CGTGCGCAGT ACTGGCAGCG GTGCACGGGC TGTACATCCT GCACGAGGTT
8041 GACCTGACGA CCGCGCACAA GGAAGCAGAG TGGGAATTTG AGCCCCTCGC CTGGCGGGTT
8101 TGGCTGGTGG TCTTCTACTT CGGCTGCTTG TCCTTGACCG TCTGGCTGCT CGAGGGGAGT
8161 TACGGTGGAT CGGACCACCA CGCCGCGCGA GCCCAAAGTC CAGATGTCCG CGCGCGGCGG
8221 TCGGAGCTTG ATGACAACAT CGCGCAGATG GGAGCTGTCC ATGGTCTGGA GCTCCCGCGG
8281 CGTCAGGTCA GGCGGGAGCT CCTGCAGGTT TACCTCGCAT AGACGGGTCA GGGCGCGGGC
8341 TAGATCCAGG TGATACCTAA TTTCCAGGGG CTGGTTGGTG GCGGCGTCGA TGGCTTGCAA
8401 GAGGCCGCAT CCCCGCGGCG CGACTACGGT ACCGCGCGGC GGGCGGTGGG CCGCGGGGGT
8461 GTCCTTGGAT GATGCATCTA AAAGCGGTGA CGCGGGCGAG CCCCCGGAGG TAGGGGGGGC
8521 TCCGGACCCG CCGGGAGAGG GGGCAGGGGC ACGTCGGCGC CGCGCGCGGG CAGGAGCTGG
8581 TGCTGCGCGC GTAGGTTGCT GGCGAACGCG ACGACGCGGC GGTTGATCTC CTGAATCTGG
8641 CGCCTCTGCG TGAAGACGAC GGGCCCGGTG AGCTTGAGCC TGAAAGAGAG TTCGACAGAA
8701 TCAATTTCGG TGTCGTTGAC GGCGGCCTGG CGCAAAATCT CCTGCACGTC TCCTGAGTTG
8761 TCTTGATAGG CGATCTCGGC CATGAACTGC TCGATCTCTT CCTCCTGGAG ATCTCCGCGT
8821 CCGGCTCGCT CCACGGTGGC GGCGAGGTCG TTGGAAATGC GGGCCATGAG CTGCGAGAAG
8881 GCGTTGAGGC CTCCCTCGTT CCAGACGCGG CTGTAGACCA CGCCCCCTTC GGCATCGCGG
8941 GCGCGCATGA CCACCTGCGC GAGATTGAGC TCCACGTGCC GGGCGAAGAC GGCGTAGTTT
9001 CGCAGGCGCT GAAAGAGGTA GTTGAGGGTG GTGGCGGTGT GTTCTGCCAC GAAGAAGTAC
9061 ATAACCCAGC GTCGCAACGT GGATTCGTTG ATATCCCCCA AGGCCTCAAG GCGCTCCATG
9121 GCCTCGTAGA AGTCCACGGC GAAGTTGAAA AACTGGGAGT TGCGCGCCGA CACGGTTAAC
9181 TCCTCCTCCA GAAGACGGAT GAGCTCGGCG ACAGTGTCGC GCACCTCGCG CTCAAAGGCT
9241 ACAGGGGCCT CTTCTTCTTC TTCAATCTCC TCTTCCATAA GGGCCTCCCC TTCTTCTTCT
```

FIGURE 23
(SHEET 3)

```
9301 TCTGGCGGCG GTGGGGGAGG GGGGACACGG CGGCGACGAC GGCGCACCGG GAGGCGGTCG
9361 ACAAAGCGCT CGATCATCTC CCCGCGGCGA CGGCGCATGG TCTCGGTGAC GGCGCGGCCG
9421 TTCTCGCGGG GGCGCAGTTG GAAGACGCCG CCCGTCATGT CCCGGTTATG GGTTGGCGGG
9481 GGGCTGCCAT GCGGCAGGGA TACGGCGCTA ACGATGCATC TCAACAATTG TTGTGTAGGT
9541 ACTCCGCCGC CGAGGGACCT GAGCGAGTCC GCATCGACCG GATCGGAAAA CCTCTCGAGA
9601 AAGGCGTCTA ACCAGTCACA GTCGCAAGGT AGGCTGAGCA CCGTGGCGGG CGGCAGCGGG
9661 CGGCGGTCGG GGTTGTTTCT GGCGGAGGTG CTGCTGATGA TGTAATTAAA GTAGGCGGTC
9721 TTGAGACGGC GGATGGTCGA CAGAAGCACC ATGTCCTTGG GTCCGGCCTG CTGAATGCGC
9781 AGGCGGTCGG CCATGCCCCA GGCTTCGTTT TGACATCGGC GCAGGTCTTT GTAGTAGTCT
9841 TGCATGAGCC TTTCTACCGG CACTTCTTCT TCTCCTTCCT CTTGTCCTGC ATCTCTTGCA
9901 TCTATCGCTG CGGCGGCGGC GGAGTTTGGC CGTAGGTGGC GCCCTCTTCC TCCCATGCGT
9961 GTGACCCCGA AGCCCCTCAT CGGCTGAAGC AGGGCTAGGT CGGCGACAAC GCGCTCGGCT
10021 AATATGGCCT GCTGCACCTG CGTGAGGGTA GACTGGAAGT CATCCATGTC CACAAAGCGG
10081 TGGTATGCGC CCGTGTTGAT GGTGTAAGTG CAGTTGGCCA TAACGGACCA GTTAACGGTC
10141 TGGTGACCCG GCTGCGAGAG CTCGGTGTAC CTGAGACGCG AGTAAGCCCT CGAGTCAAAT
10201 ACGTAGTCGT TGCAAGTCCG CACCAGGTAC TGGTATCCCA CCAAAAAGTG CGGCGGCGGC
10261 TGGCGGTAGA GGGGCCAGCG TAGGGTGGCC GGGGCTCCGG GGGCGAGATC TTCCAACATA
10321 AGGCGATGAT ATCCGTAGAT GTACCTGGAC ATCCAGGTGA TGCCGGCGGC GGTGGTGGAG
10381 GCGCGCGGAA AGTCGCGGAC GCGGTTCCAG ATGTTGCGCA GCGGCAAAAA GTGCTCCATG
10441 GTCGGGACGC TCTGGCCGGT CAGGCGCGCG CAATCGTTGA CGCTCTAGCG TGCAAAAGGA
10501 GAGCCTGTAA GCGGGCACTC TTCCGTGGTC TGGTGGATAA ATTCGCAAGG GTATCATGGC
10561 GGACGACCGG GGTTCGAGCC CCGTATCCGG CCGTCCGCCG TGATCCATGC GGTTACCGCC
10621 CGCGTGTCGA ACCCAGGTGT GCGACGTCAG ACAACGGGGG AGTGCTCCTT TTGGCTTCCT
10681 TCCAGGCGCG GCGGCTGCTG CGCTAGCTTT TTTGGCCACT GGCCGCGCGC AGCGTAAGCG
10741 GTTAGGCTGG AAAGCGAAAG CATTAAGTGG CTCGCTCCCT GTAGCCGGAG GGTTATTTTC
10801 CAAGGGTTGA GTCGCGGGAC CCCCGGTTCG AGTCTCGGAC CGGCCGGACT GCGGCGAACG
10861 GGGGTTTGCC TCCCCGTCAT GCAAGACCCC GCTTGCAAAT TCCTCCGGAA ACAGGGACGA
10921 GCCCCTTTTT TGCTTTTCCC AGATGCATCC GGTGCTGCGG CAGATGCGCC CCCCTCCTCA
10981 GCAGCGGCAA GAGCAAGAGC AGCGGCAGAC ATGCAGGGCA CCCTCCCCTC CTCCTACCGC
11041 GTCAGGAGGG GCGACATCCG CGGTTGACGC GGCAGCAGAT GGTGATTACG AACCCCCGCG
11101 GCGCCGGGCC CGGCACTACC TGGACTTGGA GGAGGGCGAG GGCCTGGCGC GGCTAGGAGC
11161 GCCCTCTCCT GAGCGGTACC CAAGGGTGCA GCTGAAGCGT GATACGCGTG AGGCGTACGT
11221 GCCGCGGCAG AACCTGTTTC GCGACCGCGA GGGAGAGGAG CCCGAGGAGA TGCGGGATCG
11281 AAAGTTCCAC GCAGGGCGCG AGCTGCGGCA TGGCCTGAAT CGCGAGCGGT TGCTGCGCGA
11341 GGAGGACTTT GAGCCCGACG CGCGAACCGG GATTAGTCCC GCGCGCGCAC ACGTGGCGGC
11401 CGCCGACCTG GTAACCGCAT ACGAGCAGAC GGTGAACCAG GAGATTAACT TTCAAAAAAG
11461 CTTTAACAAC CACGTGCGTA CGCTTGTGGC GCGCGAGGAG GTGGCTATAG GACTGATGCA
11521 TCTGTGGGAC TTTGTAAGCG CGCTGGAGCA AAACCCAAAT AGCAAGCCGC TCATGGCGCA
11581 GCTGTTCCTT ATAGTGCAGC ACAGCAGGGA CAACGAGGCA TTCAGGGATG CGCTGCTAAA
11641 CATAGTAGAG CCCGAGGGCC GCTGGCTGCT CGATTTGATA AACATCCTGC AGAGCATAGT
11701 GGTGCAGGAG CGCAGCTTGA GCCTGGCTGA CAAGGTGGCC GCCATCAACT ATTCCATGCT
11761 TAGCCTGGGC AAGTTTTACG CCCGCAAGAT ATACCATACC CCTTACGTTC CCATAGACAA
11821 GGAGGTAAAG ATCGAGGGGT TCTACATGCG CATGGCGCTG AAGGTGCTTA CCTTGAGCGA
11881 CGACCTGGGC GTTTATCGCA ACGAGCGCAT CCACAAGGCC GTGAGCGTGA GCCGGCGGCG
11941 CGAGCTCAGC GACCGCGAGC TGATGCACAG CCTGCAAAGG GCCCTGGCTG GCACGGGCAG
12001 CGGCGATAGA GAGGCCGAGT CCTACTTTGA CGCGGGCGCT GACCTGCGCT GGGCCCCAAG
12061 CCGACGCGCC CTGGAGGCAG CTGGGGCCGG ACCTGGGCTG GCGGTGGCAC CCGCGCGCGC
12121 TGGCAACGTC GGCGGCGTGG AGGAATATGA CGAGGACGAT GAGTACGAGC CAGAGGACGG
12181 CGAGTACTAA GCGGTGATGT TTCTGATCAG ATGATGCAAG ACGCAACGGA CCCGGCGGTG
12241 CGGGCGGCGC TGCAGAGCCA GCCGTCCGGC CTTAACTCCA CGGACGACTG GCGCCAGGTC
12301 ATGGACCGCA TCATGTCGCT GACTGCGCGC AATCCTGACG CGTTCCGGCA GCAGCCGCAG
12361 GCCAACCGGC TCTCCGCAAT TCTGGAAGCG GTGGTCCCGG CGCGCGCAAA CCCCACGCAC
12421 GAGAAGGTGC TGGCGATCGT AAACGCGCTG GCCGAAAACA GGGCCATCCG GCCCGACGAG
12481 GCCGGCCTGG TCTACGACGC GCTGCTTCAG CGCGTGGCTC GTTACAACAG CGGCAACGTG
12541 CAGACCAACC TGGACCGGCT GGTGGGGGAT GTGCGCGAGG CCGTGGCGCA GCGTGAGCGC
12601 GCGCAGCAGC AGGGCAACCT GGGCTCCATG GTTGCACTAA ACGCCTTCCT GAGTACACAG
12661 CCCGCCAACG TGCCGCGGGG ACAGGAGGAC TACACCAACT TTGTGAGCGC ACTGCGGCTA
```

FIGURE 23
(SHEET 4)

```
12721 ATGGTGACTG AGACACCGCA AAGTGAGGTG TACCAGTCTG GGCCAGACTA TTTTTTCCAG
12781 ACCAGTAGAC AAGGCCTGCA GACCGTAAAC CTGAGCCAGG CTTTCAAAAA CTTGCAGGGG
12841 CTGTGGGGGG TGCGGGCTCC CACAGGCGAC CGCGCGACCG TGTCTAGCTT GCTGACGCCC
12901 AACTCGCGCC TGTTGCTGCT GCTAATAGCG CCCTTCACGG ACAGTGGCAG CGTGTCCCGG
12961 GACACATACC TAGGTCACTT GCTGACACTG TACCGCGAGG CCATAGGTCA GGCGCATGTG
13021 GACGAGCATA CTTTCCAGGA GATTACAAGT GTCAGCCGCG CGCTGGGGCA GGAGGACACG
13081 GGCAGCCTGG AGGCAACCCT AAACTACCTG CTGACCAACC GGCGGCAGAA GATCCCCTCG
13141 TTGCACAGTT TAAACAGCGA GGAGGAGCGC ATTTTGCGCT ACGTGCAGCA GAGCGTGAGC
13201 CTTAACCTGA TGCGCGACGG GGTAACGCCC AGCGTGGCGC TGGACATGAC CGCGCGCAAC
13261 ATGGAACCGG GCATGTATGC CTCAAACCGG CCGTTTATCA ACCGCCTAAT GGACTACTTG
13321 CATCGCGCGG CCGCCGTGAA CCCCGAGTAT TTCACCAATG CCATCTTGAA CCCGCACTGG
13381 CTACCGCCCC CTGGTTTCTA CACCGGGGGA TTCGAGGTGC CCGAGGGTAA CGATGGATTC
13441 CTCTGGGACG ACATAGACGA CAGCGTGTTT TCCCCGCAAC CGCAGACCCT GCTAGAGTTG
13501 CAACAGCGCG AGCAGGCAGA GGCGGCGCTG CGAAAGGAAA GCTTCCGCAG GCCAAGCAGC
13561 TTGTCCGATC TAGGCGCTGC GGCCCCGCGG TCAGATGCTA GTAGCCCATT TCCAAGCTTG
13621 ATAGGGTCTC TTACCAGCAC TCGCACCACC CGCCCGCGCC TGCTGGGCGA GGAGGAGTAC
13681 CTAAACAACT CGCTGCTGCA GCCGCAGCGC GAAAAAAACC TGCCTCCGGC ATTTCCCAAC
13741 AACGGGATAG AGAGCCTAGT GGACAAGATG AGTAGATGGA AGACGTACGC GCAGGAGCAC
13801 AGGGACGTGC CAGGCCCGCG CCCGCCCACC CGTCGTCAAA GGCACGACCG TCAGCGGGGT
13861 CTGGTGTGGG AGGACGATGA CTCGGCAGAC GACAGCAGCG TCCTGGATTT GGGAGGGAGT
13921 GGCAACCCGT TTGCGCACCT TCGCCCCAGG CTGGGGAGAA TGTTTTAAAA AAAAAAAAGC
13981 ATGATGCAAA ATAAAAAACT CACCAAGGCC ATGGCACCGA GCGTTGGTTT TCTTGTATTC
14041 CCCTTAGTAT GCGGCGCGCG GCGATGTATG AGGAAGGTCC TCCTCCCTCC TACGAGAGTG
14101 TGGTGAGCGC GGCGCCAGTG GCGGCGGCGC TGGGTTCTCC CTTCGATGCT CCCCTGGACC
14161 CGCCGTTTGT GCCTCCGCGG TACCTGCGGC CTACCGGGGG GAGAAACAGC ATCCGTTACT
14221 CTGAGTTGGC ACCCCTATTC GACACCACCC GTGTGTACCT GGTGGACAAC AAGTCAACGG
14281 ATGTGGCATC CCTGAACTAC CAGAACGACC ACAGCAACTT TCTGACCACG GTCATTCAAA
14341 ACAATGACTA CAGCCCGGGG GAGGCAAGCA CACAGACCAT CAATCTTGAC GACCGGTCGC
14401 ACTGGGGCGG CGACCTGAAA ACCATCCTGC ATACCAACAT GCCAAATGTG AACGAGTTCA
14461 TGTTTACCAA TAAGTTTAAG GCGCGGGTGA TGGTGTCGCG CTTGCCTACT AAGGACAATC
14521 AGGTGGAGCT GAAATACGAG TGGGTGGAGT TCACGCTGCC CGAGGGCAAC TACTCCGAGA
14581 CCATGACCAT AGACCTTATG AACAACGCGA TCGTGGAGCA CTACTTGAAA GTGGGCAGAC
14641 AGAACGGGGT TCTGGAAAGC GACATCGGGG TAAAGTTTGA CACCCGCAAC TTCAGACTGG
14701 GGTTTGACCC CGTCACTGGT CTTGTCATGC CTGGGGTATA TACAAACGAA GCCTTCCATC
14761 CAGACATCAT TTTGCTGCCA GGATGCGGGG TGGACTTCAC CCACAGCCGC CTGAGCAACT
14821 TGTTGGGCAT CCGCAAGCGG CAACCCTTCC AGGAGGGCTT TAGGATCACC TACGATGATC
14881 TGGAGGGTGG TAACATTCCC GCACTGTTGG ATGTGGACGC CTACCAGGCG AGCTTGAAAG
14941 ATGACACCGA ACAGGGCGGG GGTGGCGCAG GCGGCAGCAA CAGCAGTGGC AGCGGCGCGG
15001 AAGAGAACTC CAACGCGGCA GCCGCGGCAA TGCAGCCGGT GGAGGACATG AACGATCATG
15061 CCATTCGCGG CGACACCTTT GCCACACGGG CTGAGGAGAA GCGCGCTGAG GCCGAAGCAG
15121 CGGCCGAAGC TGCCGCCCCC GCTGCGCAAC CCGAGGTCGA GAAGCCTCAG AAGAAACCGG
15181 TGATCAAACC CCTGACAGAG GACAGCAAGA AACGCAGTTA CAACCTAATA AGCAATGACA
15241 GCACCTTCAC CCAGTACCGC AGCTGGTACC TTGCATACAA CTACGGCGAC CCTCAGACCG
15301 GAATCCGCTC ATGGACCCTG CTTTGCACTC CTGACGTAAC CTGCGGCTCG GAGCAGGTCT
15361 ACTGGTCGTT GCCAGACATG ATGCAAGACC CCGTGACCTT CCGCTCCACG CGCCAGATCA
15421 GCAACTTTCC GGTGGTGGGC GCCGAGCTGT TGCCCGTGCA CTCCAAGAGC TTCTACAACG
15481 ACCAGGCCGT CTACTCCCAA CTCATCCGCC AGTTTACCTC TCTGACCCAC GTGTTCAATC
15541 GCTTTCCCGA GAACCAGATT TTGGCGCGCC CGCCAGCCCC CACCATCACC ACCGTCAGTG
15601 AAAACGTTCC TGCTCTCACA GATCACGGGA CGCTACCGCT GCGCAACAGC ATCGGAGGAG
15661 TCCAGCGAGT GACCATTACT GACGCCAGAC GCCGCACCTG CCCCTACGTT TACAAGGCCC
15721 TGGGCATAGT CTCGCCGCGC GTCCTATCGA GCCGCACTTT TTGAGCAAGC ATGTCCATCC
15781 TTATATCGCC CAGCAATAAC ACAGGCTGGG GCCTGCGCTT CCCAAGCAAG ATGTTTGGCG
15841 GGGCCAAGAA GCGCTCCGAC CAACACCCAG TGCGCGTGCG CGGGCACTAC CGCGCGCCCT
15901 GGGGCGCGCA CAAACGCGGC CGCACTGGGC GCACCACCGT CGATGACGCC ATCGACGCGG
15961 TGGTGGAGGA GGCGCGCAAC TACACGCCCA CGCCGCCACC AGTGTCCACA GTGGACGCGG
16021 CCATTCAGAC CGTGGTGCGC GGAGCCCGGC GCTATGCTAA AATGAAGAGA CGGCGGAGGC
16081 GCGTAGCACG TCGCCACCGC CGCCGACCCG GCACTGCCGC CCAACGCGCG GCGGCGGCCC
```

FIGURE 23
(SHEET 5)

```
16141 TGCTTAACCG CGCACGTCGC ACCGGCCGAC GGGCGGCCAT GCGGGCCGCT CGAAGGCTGG
16201 CCGCGGGTAT TGTCACTGTG CCCCCCAGGT CCAGGCGACG AGCGGCCGCC GCAGCAGCCG
16261 CGGCCATTAG TGCTATGACT CAGGGTCGCA GGGGCAACGT GTATTGGGTG CGCGACTCGG
16321 TTAGCGGCCT GCGCGTGCCC GTGCGCACCC GCCCCCCGCG CAACTAGATT GCAAGAAAAA
16381 ACTACTTAGA CTCGTACTGT TGTATGTATC CAGCGGCGGC GGCGCGCAAC GAAGCTATGT
16441 CCAAGCGCAA AATCAAAGAA GAGATGCTCC AGGTCATCGC GCCGGAGATC TATGGCCCCC
16501 CGAAGAAGGA AGAGCAGGAT TACAAGCCCC GAAAGCTAAA GCGGGTCAAA AAGAAAAAGA
16561 AAGATGATGA TGATGAACTT GACGACGAGG TGGAACTGCT GCACGCTACC GCGCCCAGGC
16621 GACGGGTACA GTGGAAAGGT CGACGCGTAA AACGTGTTTT GCGACCCGGC ACCACCGTAG
16681 TCTTTACGCC CGGTGAGCGC TCCACCCGCA CCTACAAGCG CGTGTATGAT GAGGTGTACG
16741 GCGACGAGGA CCTGCTTGAG CAGGCCAACG AGCGCCTCGG GGAGTTTGCC TACGGAAAGC
16801 GGCATAAGGA CATGCTGGCG TTGCCGCTGG ACGAGGGCAA CCCAACACCT AGCCTAAAGC
16861 CCGTAACACT GCAGCAGGTG CTGCCCGCGC TTGCACCGTC CGAAGAAAAG CGCGGCCTAA
16921 AGCGCGAGTC TGGTGACTTG GCACCCACCG TGCAGCTGAT GGTACCCAAG CGCCAGCGAC
16981 TGGAAGATGT CTTGGAAAAA ATGACCGTGG AACCTGGGCT GGAGCCCGAG GTCCGCGTGC
17041 GGCCAATCAA GCAGGTGGCG CCGGGACTGG GCGTGCAGAC CGTGGACGTT CAGATACCCA
17101 CTACCAGTAG CACCAGTATT GCCACCGCCA CAGAGGGCAT GGAGACACAA ACGTCCCCGG
17161 TTGCCTCAGC GGTGGCGGAT GCCGCGGTGC AGGCGGTCGC TGCGGCCGCG TCCAAGACCT
17221 CTACGGAGGT GCAAACGGAC CCGTGGATGT TTCGCGTTTC AGCCCCCCGG CGCCCGCGCG
17281 GTTCGAGGAA GTACGGCGCC GCCAGCGCGC TACTGCCCGA ATATGCCCTA CATCCTTCCA
17341 TTGCGCCTAC CCCCGGCTAT CGTGGCTACA CCTACCGCCC CAGAAGACGA GCAACTACCC
17401 GACGCCGAAC CACCACTGGA ACCCGCCGCC GCCGTCGCCG TCGCCAGCCC GTGCTGGCCC
17461 CGATTTCCGT GCGCAGGGTG GCTCGCGAAG GAGGCAGGAC CCTGGTGCTG CCAACAGCGC
17521 GCTACCACCC CAGCATCGTT TAAAAGCCGG TCTTTGTGGT TCTTGCAGAT ATGGCCCTCA
17581 CCTGCCGCCT CCGTTTCCCG GTGCCGGGAT TCCGAGGAAG AATGCACCGT AGGAGGGGCA
17641 TGGCCGGCCA CGGCCTGACG GGCGGCATGC GTCGTGCGCA CCACCGGCGG CGGCGCGCGT
17701 CGCACCGTCG CATGCGCGGC GGTATCCTGC CCCTCCTTAT TCCACTGATC GCCGCGGCGA
17761 TTGGCGCCGT GCCCGGAATT GCATCCGTGG CCTTGCAGGC GCAGAGACAC TGATTAAAAA
17821 CAAGTTGCAT GTGGAAAAAT CAAAATAAAA AGTCTGGACT CTCACGCTCG CTTGGTCCTG
17881 TAACTATTTT GTAGAATGGA AGACATCAAC TTTGCGTCTC TGGCCCCGCG ACACGGCTCG
17941 CGCCCGTTCA TGGGAAACTG GCAAGATATC GGCACCAGCA ATATGAGCGG TGGCGCCTTC
18001 AGCTGGGGCT CGCTGTGGAG CGGCATTAAA AATTTCGGTT CCACCGTTAA GAACTATGGC
18061 AGCAAGGCCT GGAACAGCAG CACAGGCCAG ATGCTGAGGG ATAAGTTGAA AGAGCAAAAT
18121 TTCCAACAAA AGGTGGTAGA TGGCCTGGCC TCTGGCATTA GCGGGGTGGT GGACCTGGCC
18181 AACCAGGCAG TGCAAAATAA GATTAACAGT AAGCTTGATC CCCGCCCTCC CGTAGAGGAG
18241 CCTCCACCGG CCGTGGAGAC AGTGTCTCCA GAGGGGCGTG GCGAAAAGCG TCCGCGCCCC
18301 GACAGGGAAG AAACTCTGGT GACGCAAATA GACGAGCCTC CCTCGTACGA GGAGGCACTA
18361 AAGCAAGGCC TGCCCACCAC CCGTCCCATC GCGCCCATGG CTACCGGAGT GCTGGGCCAG
18421 CACACACCCG TAACGCTGGA CCTGCCTCCC CCCGCCGACA CCCAGCAGAA ACCTGTGCTG
18481 CCAGGCCCGA CCGCCGTTGT TGTAACCCGT CCTAGCCGCG CGTCCCTGCG CCGCGCCGCC
18541 AGCGGTCCGC GATCGTTGCG GCCCGTAGCC AGTGGCAACT GGCAAAGCAC ACTGAACAGC
18601 ATCGTGGGTC TGGGGGTGCA ATCCCTGAAG CGCCGACGAT GCTTCTGAAT AGCTAACGTG
18661 TCGTATGTGT GTCATGTATG CGTCCATGTC GCCGCCAGAG GAGCTGCTGA GCCGCCGCGC
18721 GCCCGCTTTC CAAGATGGCT ACCCCTTCGA TGATGCCGCA GTGGTCTTAC ATGCACATCT
18781 CGGGCCAGGA CGCCTCGGAG TACCTGAGCC CCGGGCTGGT GCAGTTTGCC CGCGCCACCG
18841 AGACGTACTT CAGCCTGAAT AACAAGTTTA GAAACCCCAC GGTGGCGCCT ACGCACGACG
18901 TGACCACAGA CCGGTCCCAG CGTTTGACGC TGCGGTTCAT CCCTGTGGAC CGTGAGGATA
18961 CTGCGTACTC GTACAAGGCG CGGTTCACCC TAGCTGTGGG TGATAACCGT GTGCTGGACA
19021 TGGCTTCCAC GTACTTTGAC ATCCGCGGCG TGCTGGACAG GGGCCCTACT TTTAAGCCCT
19081 ACTCTGGCAC TGCCTACAAC GCCCTGGCTC CCAAGGGTGC CCCAAATCCT TGCGAATGGG
19141 ATGAAGCTGC TACTGCTCTT GAAATAAACC TAGAAGAAGA GGACGATGAC AACGAAGACG
19201 AAGTAGACGA GCAAGCTGAG CAGCAAAAAA CTCACGTATT TGGGCAGGCG CCTTATTCTG
19261 GTATAAATAT TACAAAGGAG GGTATTCAAA TAGGTGTCGA AGGTCAAACA CCTAAATATG
19321 CCGATAAAAC ATTTCAACCT GAACCTCAAA TAGGAGAATC TCAGTGGTAC GAAACTGAAA
19381 TTAATCATGC AGCTGGGAGA GTCCTTAAAA AGACTACCCC AATGAAACCA TGTTACGGTT
19441 CATATGCAAA ACCCACAAAT GAAAATGGAG GGCAAGGCAT TCTTGTAAAG CAACAAAATG
19501 GAAAGCTAGA AAGTCAAGTG GAAATGCAAT TTTTCTCAAC TACTGAGGCG ACCGCAGGCA
```

FIGURE 23
(SHEET 6)

19561 ATGGTGATAA CTTGACTCCT AAAGTGGTAT TGTACAGTGA AGATGTAGAT ATAGAAACCC
19621 CAGACACTCA TATTTCTTAC ATGCCCACTA TTAAGGAAGG TAACTCACGA GAACTAATGG
19681 GCCAACAATC TATGCCCAAC AGGCCTAATT ACATTGCTTT TAGGGACAAT TTTATTGGTC
19741 TAATGTATTA CAACAGCACG GGTAATATGG GTGTTCTGGC GGGCCAAGCA TCGCAGTTGA
19801 ATGCTGTTGT AGATTTGCAA GACAGAAACA CAGAGCTTTC ATACCAGCTT TTGCTTGATT
19861 CCATTGGTGA TAGAACCAGG TACTTTTCTA TGTGGAATCA GGCTGTTGAC AGCTATGATC
19921 CAGATGTTAG AATTATTGAA AATCATGGAA CTGAAGATGA ACTTCCAAAT TACTGCTTTC
19981 CACTGGGAGG TGTGATTAAT ACAGAGACTC TTACCAAGGT AAAACCTAAA ACAGGTCAGG
20041 AAAATGGATG GGAAAAAGAT GCTACAGAAT TTTCAGATAA AAATGAAATA AGAGTTGGAA
20101 ATAATTTTGC CATGGAAATC AATCTAAATG CCAACCTGTG GAGAAATTTC CTGTACTCCA
20161 ACATAGCGCT GTATTTGCCC GACAAGCTAA AGTACAGTCC TTCCAACGTA AAAATTTCTG
20221 ATAACCCAAA CACCTACGAC TACATGAACA AGCGAGTGGT GGCTCCCGGG TTAGTGGACT
20281 GCTACATTAA CCTTGGAGCA CGCTGGTCCC TTGACTATAT GGACAACGTC AACCCATTTA
20341 ACCACCACCG CAATGCTGGC CTGCGCTACC GCTCAATGTT GCTGGGCAAT GGTCGCTATG
20401 TGCCCTTCCA CATCCAGGTG CCTCAGAAGT TCTTTGCCAT TAAAAACCTC CTTCTCCTGC
20461 CGGGCTCATA CACCTACGAG TGGAACTTCA GGAAGGATGT TAACATGGTT CTGCAGAGCT
20521 CCCTAGGAAA TGACCTAAGG GTTGACGGAG CCAGCATTAA GTTTGATAGC ATTTGCCTTT
20581 ACGCCACCTT CTTCCCCATG GCCCACAACA CCGCCTCCAC GCTTGAGGCC ATGCTTAGAA
20641 ACGACACCAA CGACCAGTCC TTTAACGACT ATCTCTCCGC CGCCAACATG CTCTACCCTA
20701 TACCCGCCAA CGCTACCAAC GTGCCCATAT CCATCCCCTC CCGCAACTGG GCGGCTTTCC
20761 GCGGCTGGGC CTTCACGCGC CTTAAGACTA AGGAAACCCC ATCACTGGGC TCGGGCTACG
20821 ACCCTTATTA CACCTACTCT GGCTCTATAC CCTACCTAGA TGGAACCTTT TACCTCAACC
20881 ACACCTTTAA GAAGGTGGCC ATTACCTTTG ACTCTTCTGT CAGCTGGCCT GGCAATGACC
20941 GCCTGCTTAC CCCCAACGAG TTTGAAATTA AGCGCTCAGT TGACGGGGAG GGTTACAACG
21001 TTGCCCAGTG TAACATGACC AAAGACTGGT TCCTGGTACA AATGCTAGCT AACTACAACA
21061 TTGGCTACCA GGGCTTCTAT ATCCCAGAGA GCTACAAGGA CCGCATGTAC TCCTTCTTTA
21121 GAAACTTCCA GCCCATGAGC CGTCAGGTGG TGGATGATAC TAAATACAAG GACTACCAAC
21181 AGGTGGGCAT CCTACACCAA CACAACAACT CTGGATTTGT TGGCTACCTT GCCCCCACCA
21241 TGCGCGAAGG ACAGGCCTAC CCTGCTAACT TCCCCTATCC GCTTATAGGC AAGACCGCAG
21301 TTGACAGCAT TACCCAGAAA AAGTTTCTTT GCGATCGCAC CCTTTGGCGC ATCCCATTCT
21361 CCAGTAACTT TATGTCCATG GGCGCACTCA CAGACCTGGG CCAAAACCTT CTCTACGCCA
21421 ACTCCGCCCA CGCGCTAGAC ATGACTTTTG AGGTGGATCC CATGGACGAG CCCACCCTTC
21481 TTTATGTTTT GTTTGAAGTC TTTGACGTGG TCCGTGTGCA CCGGCCGCAC CGCGGCGTCA
21541 TCGAAACCGT GTACCTGCGC ACGCCCTTCT CGGCCGGCAA CGCCACAACA TAAAGAAGCA
21601 AGCAACATCA ACAACAGCTG CCGCCATGGG CTCCAGTGAG CAGGAACTGA AAGCCATTGT
21661 CAAAGATCTT GGTTGTGGGC CATATTTTTT GGGCACCTAT GACAAGCGCT TTCCAGGCTT
21721 TGTTTCTCCA CACAAGCTCG CCTGCGCCAT AGTCAATACG GCCGGTCGCG AGACTGGGGG
21781 CGTACACTGG ATGGCCTTTG CCTGGAACCC GCACTCAAAA ACATGCTACC TCTTTGAGCC
21841 CTTTGGCTTT TCTGACCAGC GACTCAAGCA GGTTTACCAG TTTGAGTACG AGTCACTCCT
21901 GCGCCGTAGC GCCATTGCTT CTTCCCCCGA CCGCTGTATA ACGCTGGAAA AGTCCACCCA
21961 AAGCGTACAG GGGCCCAACT CGGCCGCCTG TGGACTATTC TGCTGCATGT TTCTCCACGC
22021 CTTTGCCAAC TGGCCCCAAA CTCCCATGGA TCACAACCCC ACCATGAACC TTATTACCGG
22081 GGTACCCAAC TCCATGCTCA ACAGTCCCCA GGTACAGCCC ACCCTGCGTC GCAACCAGGA
22141 ACAGCTCTAC AGCTTCCTGG AGCGCCACTC GCCCTACTTC CGCAGCCACA GTGCGCAGAT
22201 TAGGAGCGCC ACTTCTTTTT GTCACTTGAA AAACATGTAA AAATAATGTA CTAGAGACAC
22261 TTTCAATAAA GGCAAATGCT TTTATTTGTA CACTCTCGGG TGATTATTTA CCCCCACCCT
22321 TGCCGTCTGC GCCGTTTAAA AATCAAAGGG GTTCTGCCGC GCATCGCTAT GCGCCACTGG
22381 CAGGGACACG TTGCGATACT GGTGTTTAGT GCTCCACTTA AACTCAGGCA CAACCATCCG
22441 CGGCAGCTCG GTGAAGTTTT CACTCCACAG GCTGCGCACC ATCACCAACG CGTTTAGCAG
22501 GTCGGGCGCC GATATCTTGA AGTCGCAGTT GGGGCCTCCG CCCTGCGCGC GCGAGTTGCG
22561 ATACACAGGG TTGCAGCACT GGAACACTAT CAGCGCCGGG TGGTGCACGC TGGCCAGCAC
22621 GCTCTTGTCG GAGATCAGAT CCGCGTCCAG GTCCTCCGCG TTGCTCAGGG CGAACGGAGT
22681 CAACTTTGGT AGCTGCCTTC CCAAAAAGGG CGCGTGCCCA GGCTTTGAGT TGCACTCGCA
22741 CCGTAGTGGC ATCAAAAGGT GACCGTGCCC GGTCTGGGCG TTAGGATACA GCGCCTGCAT
22801 AAAAGCCTTG ATCTGCTTAA AAGCCACCTG AGCCTTTGCG CCTTCAGAGA AGAACATGCC
22861 GCAAGACTTG CCGGAAAACT GATTGGCCGG ACAGGCCGCG TCGTGCACGC AGCACCTTGC
22921 GTCGGTGTTG GAGATCTGCA CCACATTTCG GCCCCACCGG TTCTTCACGA TCTTGGCCTT

FIGURE 23
(SHEET 7)

```
22981 GCTAGACTGC TCCTTCAGCG CGCGCTGCCC GTTTTCGCTC GTCACATCCA TTTCAATCAC
23041 GTGCTCCTTA TTTATCATAA TGCTTCCGTG TAGACACTTA AGCTCGCCTT CGATCTCAGC
23101 GCAGCGGTGC AGCCACAACG CGCAGCCCGT GGGCTCGTGA TGCTTGTAGG TCACCTCTGC
23161 AAACGACTGC AGGTACGCCT GCAGGAATCG CCCCATCATC GTCACAAAGG TCTTGTTGCT
23221 GGTGAAGGTC AGCTGCAACC CGCGGTGCTC CTCGTTCAGC CAGGTCTTGC ATACGGCCGC
23281 CAGAGCTTCC ACTTGGTCAG GCAGTAGTTT GAAGTTCGCC TTTAGATCGT TATCCACGTG
23341 GTACTTGTCC ATCAGCGCGC GCGCAGCCTC CATGCCCTTC TCCCACGCAG ACACGATCGG
23401 CACACTCAGC GGGTTCATCA CCGTAATTTC ACTTTCCGCT TCGCTGGGCT CTTCCTCTTC
23461 CTCTTGCGTC CGCATACCAC GCGCCACTGG GTCGTCTTCA TTCAGCCGCC GCACTGTGCG
23521 CTTACCTCCT TTGCCATGCT TGATTAGCAC CGGTGGGTTG CTGAAACCCA CCATTTGTAG
23581 CGCCACATCT TCTCTTTCTT CCTCGCTGTC CACGATTACC TCTGGTGATG GCGGGCGCTC
23641 GGGCTTGGGA GAAGGGCGCT TCTTTTTCTT CTTGGGCGCA ATGGCCAAAT CCGCCGCCGA
23701 GGTCGATGGC CGCGGGCTGG GTGTGCGCGG CACCAGCGCG TCTTGTGATG AGTCTTCCTC
23761 GTCCTCGGAC TCGATACGCC GCCTCATCCG CTTTTTTGGG GGCGCCCGGG GAGGCGGCGG
23821 CGACGGGGAC GGGGACGACA CGTCCTCCAT GGTTGGGGGA CGTCGCGCCG CACCGCGTCC
23881 GCGCTCGGGG GTGGTTTCGC GCTGCTCCTC TTCCCGACTG GCCATTTCCT TCTCCTATAG
23941 GCAGAAAAAG ATCATGGAGT CAGTCGAGAA GAAGGACAGC CTAACCGCCC CCTCTGAGTT
24001 CGCCACCACC GCCTCCACCG ATGCCGCCAA CGCGCCTACC ACCTTCCCCG TCGAGGCACC
24061 CCCGCTTGAG GAGGAGGAAG TGATTATCGA GCAGGACCCA GGTTTTGTAA GCGAAGACGA
24121 CGAGGACCGC TCAGTACCAA CAGAGGATAA AAAGCAAGAC CAGGACAACG CAGAGGCAAA
24181 CGAGGAACAA GTCGGGCGGG GGGACGAAAG GCATGGCGAC TACCTAGATG TGGGAGACGA
24241 CGTGCTGTTG AAGCATCTGC AGCGCCAGTG CGCCATTATC TGCGACGCGT TGCAAGAGCG
24301 CAGCGATGTG CCCCTCGCCA TAGCGGATGT CAGCCTTGCC TACGAACGCC ACCTATTCTC
24361 ACCGCGCGTA CCCCCCAAAC GCCAAGAAAA CGGCACATGC GAGCCCAACC CGCGCCTCAA
24421 CTTCTACCCC GTATTTGCCG TGCCAGAGGT GCTTGCCACC TATCACATCT TTTTCCAAAA
24481 CTGCAAGATA CCCCTATCCT GCCGTGCCAA CCGCAGCCGA GCGGACAAGC AGCTGGCCTT
24541 GCGGCAGGGC GCTGTCATAC CTGATATCGC CTCGCTCAAC GAAGTGCCAA AAATCTTTGA
24601 GGGTCTTGGA CGCGACGAGA AGCGCGCGGC AAACGCTCTG CAACAGGAAA ACAGCGAAAA
24661 TGAAAGTCAC TCTGGAGTGT TGGTGGAACT CGAGGGTGAC AACGCGCGCC TAGCCGTACT
24721 AAAACGCAGC ATCGAGGTCA CCCACTTTGC CTACCCGGCA CTTAACCTAC CCCCCAAGGT
24781 CATGAGCACA GTCATGAGTG AGCTGATCGT GCGCCGTGCG CAGCCCCTGG AGAGGGATGC
24841 AAATTTGCAA GAACAAACAG AGGAGGGCCT ACCCGCAGTT GGCGACGAGC AGCTAGCGCG
24901 CTGGCTTCAA ACGCGCGAGC CTGCCGACTT GGAGGAGCGA CGCAAACTAA TGATGGCCGC
24961 AGTGCTCGTT ACCGTGGAGC TTGAGTGCAT GCAGCGGTTC TTTGCTGACC CGGAGATGCA
25021 GCGCAAGCTA GAGGAAACAT TGCACTACAC CTTTCGACAG GGCTACGTAC GCCAGGCCTG
25081 CAAGATCTCC AACGTGGAGC TCTGCAACCT GGTCTCCTAC CTTGGAATTT TGCACGAAAA
25141 CCGCCTTGGG CAAAACGTGC TTCATTCCAC GCTCAAGGGC GAGGCGCGCC GCGACTACGT
25201 CCGCGACTGC GTTTACTTAT TTCTATGCTA CACCTGGCAG ACGGCCATGG GCGTTTGGCA
25261 GCAGTGCTTG GAGGAGTGCA ACCTCAAGGA GCTGCAGAAA CTGCTAAAGC AAAACTTGAA
25321 GGACCTATGG ACGGCCTTCA ACGAGCGCTC CGTGGCCGCG CACCTGGCGG ACATCATTTT
25381 CCCCGAACGC CTGCTTAAAA CCCTGCAACA GGGTCTGCCA GACTTCACCA GTCAAAGCAT
25441 GTTGCAGAAC TTTAGGAACT TTATCCTAGA GCGCTCAGGA ATCTTGCCCG CCACCTGCTG
25501 TGCACTTCCT AGCGACTTTG TGCCCATTAA GTACCGCGAA TGCCCTCCGC CGCTTTGGGG
25561 CCACTGCTAC CTTCTGCAGC TAGCCAACTA CCTTGCCTAC CACTCTGACA TAATGGAAGA
25621 CGTGAGCGGT GACGGTCTAC TGGAGTGTCA CTGTCGCTGC AACCTATGCA CCCCGCACCG
25681 CTCCCTGGTT TGCAATTCGC AGCTGCTTAA CGAAAGTCAA ATTATCGGTA CCTTTGAGCT
25741 GCAGGGTCCC TCGCCTGACG AAAAGTCCGC GGCTCCGGGG TTGAAACTCA CTCCGGGGCT
25801 GTGGACGTCG GCTTACCTTC GCAAATTTGT ACCTGAGGAC TACCACGCCC ACGAGATTAG
25861 GTTCTACGAA GACCAATCCC GCCCGCCAAA TGCGGAGCTT ACCGCCTGCG TCATTACCCA
25921 GGGCCACATT CTTGGCCAAT TGCAAGCCAT CAACAAAGCC CGCCAAGAGT TTCTGCTACG
25981 AAAGGGACGG GGGGTTTACT TGGACCCCCA GTCCGGCGAG GAGCTCAACC CAATCCCCCC
26041 GCCGCCGCAG CCCTATCAGC AGCAGCCGCG GGCCCTTGCT TCCCAGGATG GCACCCAAAA
26101 AGAAGCTGCA GCTGCCGCCG CCACCCACGG ACGAGGAGGA ATACTGGGAC AGTCAGGCAG
26161 AGGAGGTTTT GGACGAGGAG GAGGAGGACA TGATGGAAGA CTGGGAGAGC CTAGACGAGG
26221 AAGCTTCCGA GGTCGAAGAG GTGTCAGACG AAACACCGTC ACCCTCGGTC GCATTCCCCT
26281 CGCCGGCGCC CCAGAAATCG GCAACCGGTT CCAGCATGGC TACAACCTCC GCTCCTCAGG
26341 CGCCGCCGGC ACTGCCCGTT CGCCGACCCA ACCGTAGATG GGACACCACT GGAACCAGGG
```

FIGURE 23
(SHEET 8)

26401 CCGGTAAGTC CAAGCAGCCG CCGCCGTTAG CCCAAGAGCA ACAACAGCGC CAAGGCTACC
26461 GCTCATGGCG CGGGCACAAG AACGCCATAG TTGCTTGCTT GCAAGACTGT GGGGGCAACA
26521 TCTCCTTCGC CCGCCGCTTT CTTCTCTACC ATCACGGCGT GGCCTTCCCC CGTAACATCC
26581 TGCATTACTA CCGTCATCTC TACAGCCCAT ACTGCACCGG CGGCAGCGGC AGCGGCAGCA
26641 ACAGCAGCGG CCACACAGAA GCAAAGGCGA CCGGATAGCA AGACTCTGAC AAAGCCCAAG
26701 AAATCCACAG CGGCGGCAGC AGCAGGAGGA GGAGCGCTGC GTCTGGCGCC CAACGAACCC
26761 GTATCGACCC GCGAGCTTAG AAACAGGATT TTTCCCACTC TGTATGCTAT ATTTCAACAG
26821 AGCAGGGGCC AAGAACAAGA GCTGAAAATA AAAAACAGGT CTCTGCGATC CCTCACCCGC
26881 AGCTGCCTGT ATCACAAAAG CGAAGATCAG CTTCGGCGCA CGCTGGAAGA CGCGGAGGCT
26941 CTCTTCAGTA AATACTGCGC GCTGACTCTT AAGGACTAGT TTCGCGCCCT TTCTCAAATT
27001 TAAGCGCGAA AACTACGTCA TCTCCAGCGG CCACACCCGG CGCCAGCACC TGTCGTCAGC
27061 GCCATTATGA GCAAGGAAAT TCCCACGCCC TACATGTGGA GTTACCAGCC ACAAATGGGA
27121 CTTGCGGCTG GAGCTGCCCA AGACTACTCA ACCCGAATAA ACTACATGAG CGCGGGACCC
27181 CACATGATAT CCCGGGTCAA CGGAATCCGC GCCCACCGAA ACCGAATTCT CTTGGAACAG
27241 GCGGCTATTA CCACCACACC TCGTAATAAC CTTAATCCCC GTAGTTGGCC CGCTGCCCTG
27301 GTGTACCAGG AAAGTCCCGC TCCCACCACT GTGGTACTTC CCAGAGACGC CCAGGCCGAA
27361 GTTCAGATGA CTAACTCAGG GGCGCAGCTT GCGGGCGGCT TTCGTCACAG GGTGCGGTCG
27421 CCCGGGCAGG GTATAACTCA CCTGACAATC AGAGGGCGAG GTATTCAGCT CAACGACGAG
27481 TCGGTGAGCT CCTCGCTTGG TCTCCGTCCG GACGGGACAT TTCAGATCGG CGGCGCCGGC
27541 CGTCCTTCAT TCACGCCTCG TCAGGCAATC CTAACTCTGC AGACCTCGTC CTCTGAGCCG
27601 CGCTCTGGAG GCATTGGAAC TCTGCAATTT ATTGAGGAGT TTGTGCCATC GGTCTACTTT
27661 AACCCCTTCT CGGGACCTCC CGGCCACTAT CCGGATCAAT TTATTCCTAA CTTTGACGCG
27721 GTAAAGGACT CGGCGGACGG CTACGACTGA ATGTTAAGTG GAGAGGCAGA GCAACTGCGC
27781 CTGAAACACC TGGTCCACTG TCGCCGCCAC AAGTGCTTTG CCCGCGACTC CGGTGAGTTT
27841 TGCTACTTTG AATTGCCCGA GGATCATATC GAGGGCCCGG CGCACGGCGT CCGGCTTACC
27901 GCCCAGGGAG AGCTTGCCCG TAGCCTGATT CGGGAGTTTA CCCAGCGCCC CCTGCTAGTT
27961 GAGCGGGACA GGGGACCCTG TGTTCTCACT GTGATTTGCA ACTGTCCTAA CCTTGGATTA
28021 CATCAAGATC TTTGTTGCCA TCTCTGTGCT GAGTATAATA AATACAGAAA TTAAAATATA
28081 CTGGGGCTCC TATCGCCATC CTGTAAACGC CACCGTCTTC ACCCGCCCAA GCAAACCAAG
28141 GCGAACCTTA CCTGGTACTT TTAACATCTC TCCCTCTGTG ATTTACAACA GTTTCAACCC
28201 AGACGGAGTG AGTCTACGAG AGAACCTCTC CGAGCTCAGC TACTCCATCA GAAAAAACAC
28261 CACCCTCCTT ACCTGCCGGG AACGTACGAG TGCGTCACCG GCCGCTGCAC CACACCTACC
28321 GCCTGACCGT AAACCAGACT TTTTCCGGAC AGACCTCAAT AACTCTGTTT ACCAGAACAG
28381 GAGGTGAGCT TAGAAAACCC TTAGGGTATT AGGCCAAAGG CGCAGCTACT GTGGGGTTTA
28441 TGAACAATTC AAGCAACTCT ACGGGCTATT CTAATTCAGG TTTCTCTAGA AGTCAGGCTT
28501 CCTGGATGTC AGCATCTGAC TTTGGCCAGC ACCTGTCCCG CGGATTTGTT CCAGTCCAAC
28561 TACAGCGACC CACCCTAACA GAGATGACCA ACACAACCAA CGCGGCCGCC GCTACCGGAC
28621 TTACATCTAC CACAAATACA CCCCAAGTTT CTGCCTTTGT CAATAACTGG GATAACTTGG
28681 GCATGTGGTG GTTCTCCATA GCGCTTATGT TTGTATGCCT TATTATTATG TGGCTCATCT
28741 GCTGCCTAAA GCGCAAACGC GCCCGACCAC CCATCTATAG TCCCATCATT GTGCTACACC
28801 CAAACAATGA TGGAATCCAT AGATTGGACG GACTGAAACA CATGTTCTTT TCTCTTACAG
28861 TATGATTAAA TGAGATCTAG AAATGGACGG AATTATTACA GAGCAGCGCC TGCTAGAAAG
28921 ACGCAGGGCA GCGGCCGAGC AACAGCGCAT GAATCAAGAG CTCCAAGACA TGGTTAACTT
28981 GCACCAGTGC AAAAGGGGTA TCTTTTGTCT GGTAAAGCAG GCCAAAGTCA CCTACGACAG
29041 TAATACCACC GGACACCGCC TTAGCTACAA GTTGCCAACC AAGCGTCAGA AATTGGTGGT
29101 CATGGTGGGA GAAAAGCCCA TTACCATAAC TCAGCACTCG GTAGAAACCG AAGGCTGCAT
29161 TCACTCACCT TGTCAAGGAC CTGAGGATCT CTGCACCCTT ATTAAGACCC TGTGCGGTCT
29221 CAAAGATCTT ATTCCCTTTA ACTAATAAAA AAAAATAATA AAGCATCACT TACTTAAAAT
29281 CAGTTAGCAA ATTTCTGTCC AGTTTATTCA GCAGCACCTC CTTGCCCTCC TCCCAGCTCT
29341 GGTATTGCAG CTTCCTCCTG GCTGCAAACT TTCTCCACAA TCTAAATGGA ATGTCAGTTT
29401 CCTCCTGTTC CTGTCCATCC GCACCCACTA TCTTCATGTT GTTGCAGATG AAGCGCGCAA
29461 GACCGTCTGA AGATACCTTC AACCCCGTGT ATCCATATGA CACGGAAACC GGTCCTCCAA
29521 CTGTGCCTTT TCTTACTCCT CCCTTTGTAT CCCCCAATGG GTTTCAAGAG AGTCCCCCTG
29581 GGGTACTCTC TTTGCGCCTA TCCGAACCTC TAGTTACCTC CAATGGCATG CTTGCGCTCA
29641 AAATGGGCAA CGGCCTCTCT CTGGACGAGG CCGGCAACCT TACCTCCCAA AATGTAACCA
29701 CTGTGAGCCC ACCTCTCAAA AAAACCAAGT CAAACATAAA CCTGGAAATA TCTGCACCCC
29761 TCACAGTTAC CTCAGAAGCC CTAACTGTGG CTGCCGCCGC ACCTCTAATG GTCGCGGGCA

FIGURE 23
(SHEET 9)

29821 ACACACTCAC CATGCAATCA CAGGCCCCGC TAACCGTGCA CGACTCCAAA CTTAGCATTG
29881 CCACCCAAGG ACCCCTCACA GTGTCAGAAG GAAAGCTAGC CCTGCAAACA TCAGGCCCCC
29941 TCACCACCAC CGATAGCAGT ACCCTTACTA TCACTGCCTC ACCCCCTCTA ACTACTGCCA
30001 CTGGTAGCTT GGGCATTGAC TTGAAAGAGC CCATTTATAC ACAAAATGGA AAACTAGGAC
30061 TAAAGTACGG GGCTCCTTTG CATGTAACAG ACGACCTAAA CACTTTGACC GTAGCAACTG
30121 GTCCAGGTGT GACTATTAAT AATACTTCCT TGCAAACTAA AGTTACTGGA GCCTTGGGTT
30181 TTGATTCACA AGGCAATATG CAACTTAATG TAGCAGGAGG ACTAAGGATT GATTCTCAAA
30241 ACAGACGCCT TATACTTGAT GTTAGTTATC CGTTTGATGC TCAAAACCAA CTAAATCTAA
30301 GACTAGGACA GGGCCCTCTT TTTATAAACT CAGCCCACAA CTTGGATATT AACTACAACA
30361 AAGGCCTTTA CTTGTTTACA GCTTCAAACA ATTCCAAAAA GCTTGAGGTT AACCTAAGCA
30421 CTGCCAAGGG GTTGATGTTT GACGCTACAG CCATAGCCAT TAATGCAGGA GATGGGCTTG
30481 AATTTGGTTC ACCTAATGCA CCAAACACAA ATCCCCTCAA AACAAAAATT GGCCATGGCC
30541 TAGAATTTGA TTCAAACAAG GCTATGGTTC CTAAACTAGG AACTGGCCTT AGTTTTGACA
30601 GCACAGGTGC CATTACAGTA GGAAACAAAA ATAATGATAA GCTAACTTTG TGGACCACAC
30661 CAGCTCCATC TCCTAACTGT AGACTAAATG CAGAGAAAGA TGCTAAACTC ACTTTGGTCT
30721 TAACAAAATG TGGCAGTCAA ATACTTGCTA CAGTTTCAGT TTTGGCTGTT AAAGGCAGTT
30781 TGGCTCCAAT ATCTGGAACA GTTCAAAGTG CTCATCTTAT TATAAGATTT GACGAAAATG
30841 GAGTGCTACT AAACAATTCC TTCCTGGACC CAGAATATTG GAACTTTAGA AATGGAGATC
30901 TTACTGAAGG CACAGCCTAT ACAAACGCTG TTGGATTTAT GCCTAACCTA TCAGCTTATC
30961 CAAAATCTCA CGGTAAAACT GCCAAAAGTA ACATTGTCAG TCAAGTTTAC TTAAACGGAG
31021 ACAAAACTAA ACCTGTAACA CTAACCATTA CACTAAACGG TACACAGGAA ACAGGAGACA
31081 CAACTCCAAG TGCATACTCT ATGTCATTTT CATGGGACTG GTCTGGCCAC AACTACATTA
31141 ATGAAATATT TGCCACATCC TCTTACACTT TTTCATACAT TGCCCAAGAA TAAAGAATCG
31201 TTTGTGTTAT GTTTCAACGT GTTTATTTTT CAATTGCAGA AAATTTCAAG TCATTTTTCA
31261 TTCAGTAGTA TAGCCCCACC ACCACATAGC TTATACAGAT CACCGTACCT TAATCAAACT
31321 CACAGAACCC TAGTATTCAA CCTGCCACCT CCCTCCCAAC ACACAGAGTA CACAGTCCTT
31381 TCTCCCCGGC TGGCCTTAAA AAGCATCATA TCATGGGTAA CAGACATATT CTTAGGTGTT
31441 ATATTCCACA CGGTTTCCTG TCGAGCCAAA CGCTCATCAG TGATATTAAT AAACTCCCCG
31501 GGCAGCTCAC TTAAGTTCAT GTCGCTGTCC AGCTGCTGAG CCACAGGCTG CTGTCCAACT
31561 TGCGGTTGCT TAACGGGCGG CGAAGGAGAA GTCCACGCCT ACATGGGGGT AGAGTCATAA
31621 TCGTGCATCA GGATAGGGCG GTGGTGCTGC AGCAGCGCGC GAATAAACTG CTGCCGCCGC
31681 CGCTCCGTCC TGCAGGAATA CAACATGGCA GTGGTCTCCT CAGCGATGAT TCGCACCGCC
31741 CGCAGCATAA GGCGCCTTGT CCTCCGGGCA CAGCAGCGCA CCCTGATCTC ACTTAAATCA
31801 GCACAGTAAC TGCAGCACAG CACCACAATA TTGTTCAAAA TCCCACAGTG CAAGGCGCTG
31861 TATCCAAAGC TCATGGCGGG GACCACAGAA CCCACGTGGC CATCATACCA CAAGCGCAGG
31921 TAGATTAAGT GGCGACCCCT CATAAACACG CTGGACATAA ACATTACCTC TTTTGGCATG
31981 TTGTAATTCA CCACCTCCCG GTACCATATA AACCTCTGAT TAAACATGGC GCCATCCACC
32041 ACCATCCTAA ACCAGCTGGC CAAAACCTGC CCGCCGGCTA TACACTGCAG GGAACCGGGA
32101 CTGGAACAAT GACAGTGGAG AGCCCAGGAC TCGTAACCAT GGATCATCAT GCTCGTCATG
32161 ATATCAATGT TGGCACAACA CAGGCACACG TGCATACACT TCCTCAGGAT TACAAGCTCC
32221 TCCCGCGTTA GAACCATATC CCAGGGAACA ACCCATTCCT GAATCAGCGT AAATCCCACA
32281 CTGCAGGGAA GACCTCGCAC GTAACTCACG TTGTGCATTG TCAAAGTGTT ACATTCGGGC
32341 AGCAGCGGAT GATCCTCCAG TATGGTAGCG CGGGTTTCTG TCTCAAAAGG AGGTAGACGA
32401 TCCCTACTGT ACGGAGTGCG CCGAGACAAC CGAGATCGTG TTGGTCGTAG TGTCATGCCA
32461 AATGGAACGC CGGACGTAGT CATATTTCCT GAAGCAAAAC CAGGTGCGGG CGTGACAAAC
32521 AGATCTGCGT CTCCGGTCTC GCCGCTTAGA TCGCTCTGTG TAGTAGTTGT AGTATATCCA
32581 CTCTCTCAAA GCATCCAGGC GCCCCCTGGC TTCGGGTTCT ATGTAAACTC CTTCATGCGC
32641 CGCTGCCCTG ATAACATCCA CCACCGCAGA ATAAGCCACA CCCAGCCAAC CTACACATTC
32701 GTTCTGCGAG TCACACACGG GAGGAGCGGG AAGAGCTGGA AGAACCATGT TTTTTTTTTT
32761 ATTCCAAAAG ATTATCCAAA ACCTCAAAAT GAAGATCTAT TAAGTGAACG CGCTCCCCTC
32821 CGGTGGCGTG GTCAAACTCT ACAGCCAAAG AACAGATAAT GGCATTTGTA AGATGTTGCA
32881 CAATGGCTTC CAAAAGGCAA ACGGCCCTCA CGTCCAAGTG GACGTAAAGG CTAAACCCTT
32941 CAGGGTGAAT CTCCTCTATA AACATTCCAG CACCTTCAAC CATGCCCAAA TAATTCTCAT
33001 CTCGCCACCT TCTCAATATA TCTCTAAGCA AATCCCGAAT ATTAAGTCCG GCCATTGTAA
33061 AAATCTGCTC CAGAGCGCCC TCCACCTTCA GCCTCAAGCA GCGAATCATG ATTGCAAAAA
33121 TTCAGGTTCC TCACAGACCT GTATAAGATT CAAAAGCGGA ACATTAACAA AAATACCGCG
33181 ATCCCGTAGG TCCCTTCGCA GGGCCAGCTG AACATAATCG TGCAGGTCTG CACGGACCAG

FIGURE 23
(SHEET 10)

33241 CGCGGCCACT TCCCCGCCAG GAACCTTGAC AAAAGAACCC ACACTGATTA TGACACGCAT
33301 ACTCGGAGCT ATGCTAACCA GCGTAGCCCC GATGTAAGCT TTGTTGCATG GGCGGCGATA
33361 TAAAATGCAA GGTGCTGCTC AAAAAATCAG GCAAAGCCTC GCGCAAAAAA GAAAGCACAT
33421 CGTAGTCATG CTCATGCAGA TAAAGGCAGG TAAGCTCCGG AACCACCACA GAAAAAGACA
33481 CCATTTTTCT CTCAAACATG TCTGCGGGTT TCTGCATAAA CACAAAATAA AATAACAAAA
33541 AAACATTTAA ACATTAGAAG CCTGTCTTAC AACAGGAAAA ACAACCCTTA TAAGCATAAG
33601 ACGGACTACG GCCATGCCGG CGTGACCGTA AAAAAACTGG TCACCGTGAT TAAAAAGCAC
33661 CACCGACAGC TCCTCGGTCA TGTCCGGAGT CATAATGTAA GACTCGGTAA ACACATCAGG
33721 TTGATTCATC GGTCAGTGCT AAAAAGCGAC CGAAATAGCC CGGGGGAATA CATACCCGCA
33781 GGCGTAGAGA CAACATTACA GCCCCCATAG GAGGTATAAC AAAATTAATA GGAGAGAAAA
33841 ACACATAAAC ACCTGAAAAA CCCTCCTGCC TAGGCAAAAT AGCACCCTCC CGCTCCAGAA
33901 CAACATACAG CGCTTCACAG CGGCAGCCTA ACAGTCAGCC TTACCAGTAA AAAAGAAAAC
33961 CTATTAAAAA AACACCACTC GACACGGCAC CAGCTCAATC AGTCACAGTG TAAAAAAGGG
34021 CCAAGTGCAG AGCGAGTATA TATAGGACTA AAAAATGACG TAACGGTTAA AGTCCACAAA
34081 AAACACCCAG AAAACCGCAC GCGAACCTAC GCCCAGAAAC GAAAGCCAAA AAACCCACAA
34141 CTTCCTCAAA TCGTCACTTC CGTTTTCCCA CGTTACGTAA CTTCCCATTT TAAGAAAACT
34201 ACAATTCCCA ACACATACAA GTTACTCCGC CCTAAAACCT ACGTCACCCG CCCCGTTCCC
34261 ACGCCCCGCG CCACGTCACA AACTCCACCC CCTCATTATC ATATTGGCTT CAATCCAAAA
34321 TAAGGTATAT TATTGATGAT G

FIGURE 23
(SHEET 11)

SEQUENCE LISTING

<160> NUMBER OF SEQ ID NOS: 28

<210> SEQ ID NO 1
<211> LENGTH: 33592
<212> TYPE: DNA
<213> ORGANISM: Adenovirus subgroup C

<400> SEQUENCE: 1
catcatcaat aatatacctt attttggatt gaagccaata tgataatgag ggggtggagt 60
ttgtgacgtg gcgcggggcg tgggaacggg gcgggtgacg tagtagtgtg gcggaagtgt 120
gatgttgcaa gtgtggcgga acacatgtaa gcgacggatg tggcaaaagt gacgtttttg 180
gtgtgcgccg gtgtacacag gaagtgacaa ttttcgcgcg gttttaggcg gatgttgtag 240
taaatttggg cgtaaccgag taagatttgg ccattttcgc gggaaaactg aataagagga 300
agtgaaatct gaataatttt gtgttactca tagcgcgtaa tatttgtcta gggccgcggg 360
gactttgacc gtttacgtgg agactcgccc aggtgttttt ctcaggtgtt ttccgcgttc 420
cgggtcaaag ttggcgtttt attattatag tcagctgacg tgtagtgtat ttatacccgg 480
tgagttcctc aagaggccac tcttgagtgc cagcgagtag agttttctcc tccgagccgc 540
tccgacaccg ggactgaaaa tgagacatga ggtactggct gataatcttc cacctcctag 600
ccattttgaa ccacctaccc ttcacgaact gtatgattta gacgtgacgg cccccgaaga 660
tcccaacgag gaggcggttt cgcagatttt tcccgactct gtaatgttgg cggtgcagga 720
agggattgac ttactcactt ttccgccggc gcccggttct ccggagccgc ctcacctttc 780
ccggcagccc gagcagccgg agcagagagc cttgggtccg gtttgccacg aggctggctt 840
tccacccagt gacgacgagg atgaagaggg tgaggagttt gtgttagatt atgtggagca 900
ccccgggcac ggttgcaggt cttgtcatta tcaccggagg aatacggggg acccagatat 960
tatgtgttcg ctttgctata tgaggacctg tggcatgttt gtctacagta agtgaaaatt 1020
atgggcagtg ggtgatagag tggtgggttt ggtgtggtaa tttttttttt aatttttaca 1080
gttttgtggt ttaaagaatt ttgtattgtg atttttttaa aaggtcctgt gtctgaacct 1140
gagcctgagc ccgagccaga accggagcct gcaagaccta cccgccgtcc taaaatggcg 1200
cctgctatcc tgagacgccc gacatcacct gtgtctagag aatgcaatag tagtacggat 1260
agctgtgact ccggtccttc taacacacct cctgagatac acccggtggt cccgctgtgc 1320
cccattaaac cagttgccgt gagagttggt gggcgtcgcc aggctgtgga atgtatcgag 1380
gacttgctta acgagcctgg gcaacctttg gacttgagct gtaaacgccc caggccataa 1440
ggtgtaaacc tgtgattgcg tgtgtggtta acgcctttgt ttgctgaatg agttgatgta 1500
agtttaataa agggtgagat aatgtttaac ttgcatggcg tgttaaatgg ggcggggctt 1560
aaagggtata taatgcgccg tgggctaatc ttggttacat ctgacctcat ggaggcttgg 1620
gagtgtttgg aagatttttc tgctgtgcgt aacttgctgg aacagagctc taacagtacc 1680
tcttggtttt ggaggtttct gtggggctca tcccaggcaa agttagtctg cagaattaag 1740
gaggattaca agtgggaatt tgaagagctt ttgaaatcct gtggtgagct gtttgattct 1800
ttgaatctgg gtcaccaggc gcttttccaa gagaaggtca tcaagacttt ggatttttcc 1860
acaccggggc gcgctgcggc tgctgttgct tttttgagtt ttataaagga taaatggagc 1920
gaagaaaccc atctgagcgg ggggtacctg ctggattttc tggccatgca tctgtggaga 1980
gcggttgtga gacacaagaa tcgcctgcta ctgttgtctt ccgtccgccc ggcgataata 2040

-continued

```
ccgacggagg agcagcagca gcagcaggag gaagccaggc ggcggcggca ggagcagagc   2100
ccatggaacc cgagagccgg cctggaccct cgggaatgaa tgttgtacag gtggctgaac   2160
tgtatccaga actgagacgc attttgacaa ttacagagga tgggcagggg ctaaaggggg   2220
taaagaggga gcggggggct tgtgaggcta cagaggaggc taggaatcta gcttttagct   2280
taatgaccag acaccgtcct gagtgtatta cttttcaaca gatcaaggat aattgcgcta   2340
atgagcttga tctgctggcg cagaagtatt ccatagagca gctgaccact tactggctgc   2400
agccagggga tgattttgag gaggctatta gggtatatgc aaaggtggca cttaggccag   2460
attgcaagta caagatcagc aaacttgtaa atatcaggaa ttgttgctac atttctggga   2520
acggggccga ggtggagata gatacggagg atagggtggc ctttagatgt agcatgataa   2580
atatgtggcc gggggtgctt ggcatggacg gggtggttat tatgaatgta aggtttactg   2640
gccccaattt tagcggtacg gttttcctgg ccaataccaa ccttatccta cacggtgtaa   2700
gcttctatgg gtttaacaat acctgtgtgg aagcctggac cgatgtaagg gttcggggct   2760
gtgcctttta ctgctgctgg aagggggtgg tgtgtcgccc caaaagcagg gcttcaatta   2820
agaaatgcct ctttgaaagg tgtaccttgg gtatcctgtc tgagggtaac tccagggtgc   2880
gccacaatgt ggcctccgac tgtggttgct tcatgctagt gaaaagcgtg gctgtgatta   2940
agcataacat ggtatgtggc aactgcgagg acagggcctc tcagatgctg acctgctcgg   3000
acggcaactg tcacctgctg aagaccattc acgtagccag ccactctcgc aaggcctggc   3060
cagtgtttga gcataacata ctgacccgct gttccttgca tttgggtaac aggagggggg   3120
tgttcctacc ttaccaatgc aatttgagtc acactaagat attgcttgag cccgagagca   3180
tgtccaaggt gaacctgaac ggggtgtttg acatgaccat gaagatctgg aaggtgctga   3240
ggtacgatga gacccgcacc aggtgcagac cctgcgagtg tggcggtaaa catattagga   3300
accagcctgt gatgctggat gtgaccgagg agctgaggcc cgatcacttg gtgctggcct   3360
gcacccgcgc tgagtttggc tctagcgatg aagatacaga ttgaggtact gaaatgtgtg   3420
ggcgtggctt aagggtggga aagaatatat aaggtggggg tcttatgtag ttttgtatct   3480
gttttgcagc agccgccgcc gccatgagca ccaactcgtt tgatggaagc attgtgagct   3540
catatttgac aacgcgcatg cccccatggg ccggggtgcg tcagaatgtg atgggctcca   3600
gcattgatgg tcgccccgtc ctgcccgcaa actctactac cttgacctac gagaccgtgt   3660
ctggaacgcc gttggagact gcagcctccg ccgccgcttc agccgctgca gccaccgccc   3720
gcgggattgt gactgacttt gctttcctga gcccgcttgc aagcagtgca gcttcccgtt   3780
catccgcccg cgatgacaag ttgacggctc ttttggcaca attggattct ttgacccggg   3840
aacttaatgt cgtttctcag cagctgttgg atctgcgcca gcaggtttct gccctgaagg   3900
cttcctcccc tcccaatgcg gtttaaaaca taaataaaaa accagactct gtttggattt   3960
ggatcaagca agtgtcttgc tgtctttatt taggggtttt gcgcgcgcgg taggcccggg   4020
accagcggtc tcggtcgttg agggtcctgt gtattttttc caggacgtgg taaaggtgac   4080
tctggatgtt cagatacatg ggcataagcc cgtctctggg gtggaggtag caccactgca   4140
gagcttcatg ctgcggggtg gtgttgtaga tgatccagtc gtagcaggag cgctgggcgt   4200
ggtgcctaaa aatgtctttc agtagcaagc tgattgccag ggcaggccc ttggtgtaag   4260
tgtttacaaa gcggttaagc tgggatgggt gcatacgtgg ggatatgaga tgcatcttgg   4320
actgtatttt taggttggct atgttcccag ccatatccct ccggggattc atgttgtgca   4380
```

-continued

```
gaaccaccag cacagtgtat ccggtgcact tgggaaattt gtcatgtagc ttagaaggaa   4440
atgcgtggaa gaacttggag acgcccttgt gacctccaag attttccatg cattcgtcca   4500
taatgatggc aatgggccca cgggcggcgg cctgggcgaa gatatttctg ggatcactaa   4560
cgtcatagtt gtgttccagg atgagatcgt cataggccat ttttacaaag cgcgggcgga   4620
gggtgccaga ctgcggtata atggttccat ccggcccagg ggcgtagtta ccctcacaga   4680
tttgcatttc ccacgctttg agttcagatg gggggatcat gtctacctgc ggggcgatga   4740
agaaaacggt ttccggggta ggggagatca gctgggaaga aagcaggttc ctgagcagct   4800
gcgacttacc gcagccggtg ggcccgtaaa tcacacctat taccgggtgc aactggtagt   4860
taagagagct gcagctgccg tcatccctga gcaggggggc cacttcgtta agcatgtccc   4920
tgactcgcat gttttccctg accaaatccg ccagaaggcg ctcgccgccc agcgatagca   4980
gttcttgcaa ggaagcaaag tttttcaacg gtttgagacc gtccgccgta ggcatgcttt   5040
tgagcgtttg accaagcagt tccaggcggt cccacagctc ggtcacctgc tctacggcat   5100
ctcgatccag catatctcct cgtttcgcgg gttggggcgg ctttcgctgt acggcagtag   5160
tcggtgctcg tccagacggg ccagggtcat gtctttccac gggcgcaggg tcctcgtcag   5220
cgtagtctgg gtcacggtga aggggtgcgc tccgggctgc gcgctggcca gggtgcgctt   5280
gaggctggtc ctgctggtgc tgaagcgctg ccggtcttcg ccctgcgcgt cggccaggta   5340
gcatttgacc atggtgtcat agtccagccc ctccgcggcg tggcccttgg cgcgcagctt   5400
gcccttggag gaggcgccgc acgaggggca gtgcagactt ttgagggcgt agagcttggg   5460
cgcgagaaat accgattccg gggagtaggc atccgcgccg caggccccgc agacggtctc   5520
gcattccacg agccaggtga gctctggccg ttcggggtca aaaaccaggt ttcccccatg   5580
ctttttgatg cgtttcttac ctctggtttc catgagccgg tgtccacgct cggtgacgaa   5640
aaggctgtcc gtgtccccgt atacagactt gagaggcctg tcctcgagcg gtgttccgcg   5700
gtcctcctcg tatagaaact cggaccactc tgagacaaag gctcgcgtcc aggccagcac   5760
gaaggaggct aagtgggagg ggtagcggtc gttgtccact agggggtcca ctcgctccag   5820
ggtgtgaaga cacatgtcgc cctcttcggc atcaaggaag gtgattggtt tgtaggtgta   5880
ggccacgtga ccgggtgttc ctgaaggggg gctataaaag ggggtggggg cgcgttcgtc   5940
ctcactctct tccgcatcgc tgtctgcgag ggccagctgt tggggtgagt actccctctg   6000
aaaagcgggc atgacttctg cgctaagatt gtcagtttcc aaaaacgagg aggatttgat   6060
attcacctgg cccgcggtga tgcctttgag ggtggccgca tccatctggt cagaaaagac   6120
aatctttttg ttgtcaagct tggtggcaaa cgacccgtag agggcgttgg acagcaactt   6180
ggcgatggag cgcagggttt ggtttttgtc gcgatcggcg cgctccttgg ccgcgatgtt   6240
tagctgcacg tattcgcgcg caacgcaccg ccattcggga aagacggtgg tgcgctcgtc   6300
gggcaccagg tgcacgcgcc aaccgcggtt gtgcagggtg acaaggtcaa cgctggtggc   6360
tacctctccg cgtaggcgct cgttggtcca gcagaggcgg ccgcccttgc gcgagcagaa   6420
tggcggtagg gggtctagct gcgtctcgtc cggggggtct gcgtccacgg taaagacccc   6480
gggcagcagg cgcgcgtcga agtagtctat cttgcatcct tgcaagtcta gcgcctgctg   6540
ccatgcgcgg gcggcaagcg cgcgctcgta tgggttgagt gggggacccc atggcatggg   6600
gtgggtgagc gcggaggcgt acatgccgca aatgtcgtaa acgtagaggg gctctctgag   6660
tattccaaga tatgtagggt agcatcttcc accgcggatg ctggcgcgca cgtaatcgta   6720
tagttcgtgc gagggagcga ggaggtcggg accgaggttg ctacgggcgg gctgctctgc   6780
```

-continued tcggaagact atctgcctga agatggcatg tgagttggat gatatggttg gacgctggaa 6840
gacgttgaag ctggcgtctg tgagacctac cgcgtcacgc acgaaggagg cgtaggagtc 6900
gcgcagcttg ttgaccagct cggcggtgac ctgcacgtct agggcgcagt agtccagggt 6960
ttccttgatg atgtcatact tatcctgtcc cttttttttc cacagctcgc ggttgaggac 7020
aaactcttcg cggtctttcc agtactcttg gatcggaaac ccgtcggcct ccgaacggta 7080
agagcctagc atgtagaact ggttgacggc ctggtaggcg cagcatccct tttctacggg 7140
tagcgcgtat gcctgcgcgg ccttccggag cgaggtgtgg gtgagcgcaa aggtgtccct 7200
gaccatgact ttgaggtact ggtatttgaa gtcagtgtcg tcgcatccgc cctgctccca 7260
gagcaaaaag tccgtgcgct ttttggaacg cggatttggc agggcgaagg tgacatcgtt 7320
gaagagtatc tttcccgcgc gaggcataaa gttgcgtgtg atgcggaagg gtcccggcac 7380
ctcggaacgg ttgttaatta cctgggcggc gagcacgatc tcgtcaaagc cgttgatgtt 7440
gtggcccaca atgtaaagtt ccaagaagcg cgggatgccc ttgatggaag gcaatttttt 7500
aagttcctcg taggtgagct cttcagggga gctgagcccg tgctctgaaa gggcccagtc 7560
tgcaagatga gggttggaag cgacgaatga gctccacagg tcacgggcca ttagcatttg 7620
caggtggtcg cgaaaggtcc taaactggcg acctatggcc atttttctg gggtgatgca 7680 gtagaaggta agcgggtctt gttcccagcg gtcccatcca aggttcgcgg ctaggtctcg 7740
cgcggcagtc actagaggct catctccgcc gaacttcatg accagcatga agggcacgag 7800
ctgcttccca aaggccccca tccaagtata ggtctctaca tcgtaggtga caaagagacg 7860
ctcggtgcga ggatgcgagc cgatcgggaa gaactggatc tcccgccacc aattggagga 7920
gtggctattg atgtggtgaa agtagaagtc cctgcgacgg gccgaacact cgtgctggct 7980
tttgtaaaaa cgtgcgcagt actggcagcg gtgcacgggc tgtacatcct gcacgaggtt 8040
gacctgacga ccgcgcacaa ggaagcagag tgggaatttg agcccctcgc ctggcgggtt 8100
tggctggtgg tcttctactt cggctgcttg tccttgaccg tctggctgct cgaggggagt 8160
tacggtggat cggaccacca cgccgcgcga gcccaaagtc cagatgtccg cgcgcggcgg 8220
tcggagcttg atgacaacat cgcgcagatg ggagctgtcc atggtctgga gctcccgcgg 8280
cgtcaggtca ggcgggagct cctgcaggtt tacctcgcat agacgggtca gggcgcgggc 8340
tagatccagg tgatacctaa tttccagggg ctggttggtg gcggcgtcga tggcttgcaa 8400
gaggccgcat ccccgcggcg cgactacggt accgcgcggc gggcggtggg ccgcgggggt 8460
gtccttggat gatgcatcta aaagcggtga cgcgggcgag cccccggagg tagggggggc 8520
tccggacccg ccgggagagg gggcaggggc acgtcggcgc cgcgcgcggg caggagctgg 8580
tgctgcgcgc gtaggttgct ggcgaacgcg acgacgcggc ggttgatctc ctgaatctgg 8640
cgcctctgcg tgaagacgac gggcccggtg agcttgagcc tgaaagagag ttcgacagaa 8700
tcaatttcgg tgtcgttgac ggcggcctgg cgcaaaatct cctgcacgtc tcctgagttg 8760
tcttgatagg cgatctcggc catgaactgc tcgatctctt cctcctggag atctccgcgt 8820
ccggctcgct ccacggtggc ggcgaggtcg ttggaaatgc gggccatgag ctgcgagaag 8880
gcgttgaggc ctccctcgtt ccagacgcgg ctgtagacca cgcccccttc ggcatcgcgg 8940
gcgcgcatga ccacctgcgc gagattgagc tccacgtgcc gggcgaagac ggcgtagttt 9000
cgcaggcgct gaaagaggta gttgagggtg gtggcggtgt gttctgccac gaagaagtac 9060
ataacccagc gtcgcaacgt ggattcgttg atatccccca aggcctcaag gcgctccatg 9120

-continued

```
gcctcgtaga agtccacggc gaagttgaaa aactgggagt tgcgcgccga cacggttaac   9180
tcctcctcca gaagacggat gagctcggcg acagtgtcgc gcacctcgcg ctcaaaggct   9240
acaggggcct cttcttcttc ttcaatctcc tcttccataa gggcctcccc ttcttcttct   9300
tctggcggcg gtgggggagg ggggacacgg cggcgacgac ggcgcaccgg gaggcggtcg   9360
acaaagcgct cgatcatctc cccgcggcga cggcgcatgg tctcggtgac ggcgcggccg   9420
ttctcgcggg ggcgcagttg gaagacgccg cccgtcatgt cccggttatg ggttggcggg   9480
gggctgccat gcggcaggga tacggcgcta acgatgcatc tcaacaattg ttgtgtaggt   9540
actccgccgc cgagggacct gagcgagtcc gcatcgaccg gatcggaaaa cctctcgaga   9600
aaggcgtcta accagtcaca gtcgcaaggt aggctgagca ccgtggcggg cggcagcggg   9660
cggcggtcgg ggttgtttct ggcggaggtg ctgctgatga tgtaattaaa gtaggcggtc   9720
ttgagacggc ggatggtcga cagaagcacc atgtccttgg gtccggcctg ctgaatgcgc   9780
aggcggtcgg ccatgcccca ggcttcgttt tgacatcggc gcaggtcttt gtagtagtct   9840
tgcatgagcc tttctaccgg cacttcttct tctccttcct cttgtcctgc atctcttgca   9900
tctatcgctg cggcggcggc ggagtttggc cgtaggtggc gccctcttcc tcccatgcgt   9960
gtgaccccga agcccctcat cggctgaagc agggctaggt cggcgacaac gcgctcggct  10020
aatatggcct gctgcacctg cgtgagggta gactggaagt catccatgtc cacaaagcgg  10080
tggtatgcgc ccgtgttgat ggtgtaagtg cagttggcca taacggacca gttaacggtc  10140
tggtgacccg gctgcgagag ctcggtgtac ctgagacgcg agtaagccct cgagtcaaat  10200
acgtagtcgt tgcaagtccg caccaggtac tggtatccca ccaaaaagtg cggcggcggc  10260
tggcggtaga ggggccagcg tagggtggcc ggggctccgg gggcgagatc ttccaacata  10320
aggcgatgat atccgtagat gtacctggac atccaggtga tgccggcggc ggtggtggag  10380
gcgcgcggaa agtcgcggac gcggttccag atgttgcgca gcggcaaaaa gtgctccatg  10440
gtcgggacgc tctggccggt caggcgcgcg caatcgttga cgctctagcg tgcaaaagga  10500
gagcctgtaa gcgggcactc ttccgtggtc tggtggataa attcgcaagg gtatcatggc  10560
ggacgaccgg ggttcgagcc ccgtatccgg ccgtccgccg tgatccatgc ggttaccgcc  10620
cgcgtgtcga acccaggtgt gcgacgtcag acaacggggg agtgctcctt ttggcttcct  10680
tccaggcgcg gcggctgctg cgctagcttt tttggccact ggccgcgcgc agcgtaagcg  10740
gttaggctgg aaagcgaaag cattaagtgg ctcgctccct gtagccggag ggttattttc  10800
caagggttga gtcgcgggac ccccggttcg agtctcggac cggccggact gcggcgaacg  10860
ggggtttgcc tccccgtcat gcaagacccc gcttgcaaat tcctccggaa acagggacga  10920
gccccttttt tgcttttccc agatgcatcc ggtgctgcgg cagatgcgcc cccctcctca  10980
gcagcggcaa gagcaagagc agcggcagac atgcagggca ccctcccctc ctcctaccgc  11040
gtcaggaggg gcgacatccg cggttgacgc ggcagcagat ggtgattacg aacccccgcg  11100
gcgccgggcc cggcactacc tggacttgga ggagggcgag ggcctggcgc ggctaggagc  11160
gccctctcct gagcggtacc caagggtgca gctgaagcgt gatacgcgtg aggcgtacgt  11220
gccgcggcag aacctgtttc gcgaccgcga gggagaggag cccgaggaga tgcgggatcg  11280
aaagttccac gcagggcgcg agctgcggca tggcctgaat cgcgagcggt tgctgcgcga  11340
ggaggacttt gagcccgacg cgcgaaccgg gattagtccc gcgcgcgcac acgtggcggc  11400
cgccgacctg gtaaccgcat acgagcagac ggtgaaccag gagattaact ttcaaaaaag  11460
ctttaacaac cacgtgcgta cgcttgtggc gcgcgaggag gtggctatag gactgatgca  11520
```

-continued

```
tctgtgggac tttgtaagcg cgctggagca aaacccaaat agcaagccgc tcatggcgca  11580
gctgttcctt atagtgcagc acagcaggga caacgaggca ttcagggatg cgctgctaaa  11640
catagtagag cccgagggcc gctggctgct cgatttgata aacatcctgc agagcatagt  11700
ggtgcaggag cgcagcttga gcctggctga caaggtggcc gccatcaact attccatgct  11760
tagcctgggc aagttttacg cccgcaagat ataccatacc ccttacgttc ccatagacaa  11820
ggaggtaaag atcgaggggt tctacatgcg catggcgctg aaggtgctta ccttgagcga  11880
cgacctgggc gtttatcgca acgagcgcat ccacaaggcc gtgagcgtga gccggcggcg  11940
cgagctcagc gaccgcgagc tgatgcacag cctgcaaagg gccctggctg gcacgggcag  12000
cggcgataga gaggccgagt cctactttga cgcgggcgct gacctgcgct gggccccaag  12060
ccgacgcgcc ctggaggcag ctggggccgg acctgggctg gcggtggcac ccgcgcgcgc  12120
tggcaacgtc ggcggcgtgg aggaatatga cgaggacgat gagtacgagc cagaggacgg  12180
cgagtactaa gcggtgatgt ttctgatcag atgatgcaag acgcaacgga cccggcggtg  12240
cgggcggcgc tgcagagcca gccgtccggc cttaactcca cggacgactg gcgccaggtc  12300
atggaccgca tcatgtcgct gactgcgcgc aatcctgacg cgttccggca gcagccgcag  12360
gccaaccggc tctccgcaat tctggaagcg gtggtcccgg cgcgcgcaaa ccccacgcac  12420
gagaaggtgc tggcgatcgt aaacgcgctg gccgaaaaca gggccatccg gcccgacgag  12480
gccggcctgg tctacgacgc gctgcttcag cgcgtggctc gttacaacag cggcaacgtg  12540
cagaccaacc tggaccggct ggtgggggat gtgcgcgagg ccgtggcgca gcgtgagcgc  12600
gcgcagcagc agggcaacct gggctccatg gttgcactaa acgccttcct gagtacacag  12660
cccgccaacg tgccgcgggg acaggaggac tacaccaact ttgtgagcgc actgcggcta  12720
atggtgactg agacaccgca aagtgaggtg taccagtctg ggccagacta tttttttccag  12780
accagtagac aaggcctgca gaccgtaaac ctgagccagg ctttcaaaaa cttgcagggg  12840
ctgtgggggg tgcgggctcc cacaggcgac cgcgcgaccg tgtctagctt gctgacgccc  12900
aactcgcgcc tgttgctgct gctaatagcg cccttcacgg acagtggcag cgtgtcccgg  12960
gacacatacc taggtcactt gctgacactg taccgcgagg ccataggtca ggcgcatgtg  13020
gacgagcata ctttccagga gattacaagt gtcagccgcg cgctggggca ggaggacacg  13080
ggcagcctgg aggcaaccct aaactacctg ctgaccaacc ggcggcagaa gatcccctcg  13140
ttgcacagtt taaacagcga ggaggagcgc attttgcgct acgtgcagca gagcgtgagc  13200
cttaacctga tgcgcgacgg ggtaacgccc agcgtggcgc tggacatgac cgcgcgcaac  13260
atggaaccgg gcatgtatgc ctcaaaccgg ccgtttatca accgcctaat ggactacttg  13320
catcgcgcgg ccgccgtgaa ccccgagtat ttcaccaatg ccatcttgaa cccgcactgg  13380
ctaccgcccc ctggtttcta caccggggga ttcgaggtgc ccgagggtaa cgatggattc  13440
ctctgggacg acatagacga cagcgtgttt tccccgcaac cgcagaccct gctagagttg  13500
caacagcgcg agcaggcaga ggcggcgctg cgaaaggaaa gcttccgcag gccaagcagc  13560
ttgtccgatc taggcgctgc ggccccgcgg tcagatgcta gtagcccatt tccaagcttg  13620
atagggtctc ttaccagcac tcgcaccacc cgcccgcgcc tgctgggcga ggaggagtac  13680
ctaaacaact cgctgctgca gccgcagcgc gaaaaaaacc tgcctccggc atttcccaac  13740
aacgggatag agagcctagt ggacaagatg agtagatgga agacgtacgc gcaggagcac  13800
agggacgtgc caggcccgcg cccgcccacc cgtcgtcaaa ggcacgaccg tcagcggggt  13860
```

-continued

```
ctggtgtggg aggacgatga ctcggcagac gacagcagcg tcctggattt gggagggagt  13920
ggcaacccgt ttgcgcacct tcgccccagg ctggggagaa tgttttaaaa aaaaaaaagc  13980
atgatgcaaa ataaaaaact caccaaggcc atggcaccga gcgttggttt tcttgtattc  14040
cccttagtat gcggcgcgcg gcgatgtatg aggaaggtcc tcctccctcc tacgagagtg  14100
tggtgagcgc ggcgccagtg gcggcggcgc tgggttctcc cttcgatgct cccctggacc  14160
cgccgtttgt gcctccgcgg tacctgcggc ctaccggggg gagaaacagc atccgttact  14220
ctgagttggc acccctattc gacaccaccc gtgtgtacct ggtggacaac aagtcaacgg  14280
atgtggcatc cctgaactac cagaacgacc acagcaactt tctgaccacg gtcattcaaa  14340
acaatgacta cagcccgggg gaggcaagca cacagaccat caatcttgac gaccggtcgc  14400
actggggcgg cgacctgaaa accatcctgc ataccaacat gccaaatgtg aacgagttca  14460
tgtttaccaa taagtttaag gcgcgggtga tggtgtcgcg cttgcctact aaggacaatc  14520
aggtggagct gaaatacgag tgggtggagt tcacgctgcc cgagggcaac tactccgaga  14580
ccatgaccat agaccttatg aacaacgcga tcgtggagca ctacttgaaa gtgggcagac  14640
agaacggggt tctggaaagc gacatcgggg taaagtttga cacccgcaac ttcagactgg  14700
ggtttgaccc cgtcactggt cttgtcatgc ctggggtata tacaaacgaa gccttccatc  14760
cagacatcat tttgctgcca ggatgcgggg tggacttcac ccacagccgc ctgagcaact  14820
tgttgggcat ccgcaagcgg caacccttcc aggagggctt taggatcacc tacgatgatc  14880
tggagggtgg taacattccc gcactgttgg atgtggacgc ctaccaggcg agcttgaaag  14940
atgacaccga acagggcggg ggtggcgcag gcggcagcaa cagcagtggc agcggcgcgg  15000
aagagaactc caacgcggca gccgcggcaa tgcagccggt ggaggacatg aacgatcatg  15060
ccattcgcgg cgacaccttt gccacacggg ctgaggagaa gcgcgctgag gccgaagcag  15120
cggccgaagc tgccgccccc gctgcgcaac ccgaggtcga gaagcctcag aagaaaccgg  15180
tgatcaaacc cctgacagag gacagcaaga aacgcagtta caacctaata agcaatgaca  15240
gcaccttcac ccagtaccgc agctggtacc ttgcatacaa ctacggcgac cctcagaccg  15300
gaatccgctc atggaccctg ctttgcactc ctgacgtaac ctgcggctcg gagcaggtct  15360
actggtcgtt gccagacatg atgcaagacc ccgtgacctt ccgctccacg cgccagatca  15420
gcaactttcc ggtggtgggc gccgagctgt tgcccgtgca ctccaagagc ttctacaacg  15480
accaggccgt ctactcccaa ctcatccgcc agtttacctc tctgacccac gtgttcaatc  15540
gctttcccga gaaccagatt ttggcgcgcc cgccagcccc caccatcacc accgtcagtg  15600
aaaacgttcc tgctctcaca gatcacggga cgctaccgct gcgcaacagc atcggaggag  15660
tccagcgagt gaccattact gacgccagac gccgcacctg cccctacgtt tacaaggccc  15720
tgggcatagt ctcgccgcgc gtcctatcga gccgcacttt ttgagcaagc atgtccatcc  15780
ttatatcgcc cagcaataac acaggctggg gcctgcgctt cccaagcaag atgtttggcg  15840
gggccaagaa gcgctccgac caacacccag tgcgcgtgcg cgggcactac cgcgcgccct  15900
ggggcgcgca caaacgcggc cgcactgggc gcaccaccgt cgatgacgcc atcgacgcgg  15960
tggtggagga ggcgcgcaac tacacgccca cgccgccacc agtgtccaca gtggacgcgg  16020
ccattcagac cgtggtgcgc ggagcccggc gctatgctaa aatgaagaga cggcggaggc  16080
gcgtagcacg tcgccaccgc cgccgacccg gcactgccgc ccaacgcgcg gcggcggccc  16140
tgcttaaccg cgcacgtcgc accggccgac gggcggccat gcgggccgct cgaaggctgg  16200
ccgcgggtat tgtcactgtg ccccccaggt ccaggcgacg agcggccgcc gcagcagccg  16260
```

-continued

```
cggccattag tgctatgact cagggtcgca ggggcaacgt gtattgggtg cgcgactcgg  16320
ttagcggcct gcgcgtgccc gtgcgcaccc gcccccccgcg caactagatt gcaagaaaaa  16380
actacttaga ctcgtactgt tgtatgtatc cagcggcggc ggcgcgcaac gaagctatgt  16440
ccaagcgcaa aatcaaagaa gagatgctcc aggtcatcgc gccggagatc tatggccccc  16500
cgaagaagga agagcaggat tacaagcccc gaaagctaaa gcgggtcaaa aagaaaaaga  16560
aagatgatga tgatgaactt gacgacgagg tggaactgct gcacgctacc gcgcccaggc  16620
gacgggtaca gtggaaaggt cgacgcgtaa aacgtgtttt gcgacccggc accaccgtag  16680
tctttacgcc cggtgagcgc tccacccgca cctacaagcg cgtgtatgat gaggtgtacg  16740
gcgacgagga cctgcttgag caggccaacg agcgcctcgg ggagtttgcc tacggaaagc  16800
ggcataagga catgctggcg ttgccgctgg acgagggcaa cccaacacct agcctaaagc  16860
ccgtaacact gcagcaggtg ctgcccgcgc ttgcaccgtc cgaagaaaag cgcggcctaa  16920
agcgcgagtc tggtgacttg gcacccaccg tgcagctgat ggtacccaag cgccagcgac  16980
tggaagatgt cttggaaaaa atgaccgtgg aacctgggct ggagcccgag gtccgcgtgc  17040
ggccaatcaa gcaggtggcg ccgggactgg gcgtgcagac cgtggacgtt cagataccca  17100
ctaccagtag caccagtatt gccaccgcca cagagggcat ggagacacaa acgtccccgg  17160
ttgcctcagc ggtggcggat gccgcggtgc aggcggtcgc tgcggccgcg tccaagacct  17220
ctacggaggt gcaaacggac ccgtggatgt ttcgcgtttc agccccccgg cgcccgcgcg  17280
gttcgaggaa gtacggcgcc gccagcgcgc tactgcccga atatgcccta catccttcca  17340
ttgcgcctac ccccggctat cgtggctaca cctaccgccc cagaagacga gcaactaccc  17400
gacgccgaac caccactgga acccgccgcc gccgtcgccg tcgccagccc gtgctggccc  17460
cgatttccgt gcgcagggtg gctcgcgaag gaggcaggac cctggtgctg ccaacagcgc  17520
gctaccaccc cagcatcgtt taaaagccgg tctttgtggt tcttgcagat atggccctca  17580
cctgccgcct ccgtttcccg gtgccgggat tccgaggaag aatgcaccgt aggaggggca  17640
tggccggcca cggcctgacg ggcggcatgc gtcgtgcgca ccaccggcgg cggcgcgcgt  17700
cgcaccgtcg catgcgcggc ggtatcctgc ccctccttat tccactgatc gccgcggcga  17760
ttggcgccgt gcccggaatt gcatccgtgg ccttgcaggc gcagagacac tgattaaaaa  17820
caagttgcat gtggaaaaat caaaataaaa agtctggact ctcacgctcg cttggtcctg  17880
taactatttt gtagaatgga agacatcaac tttgcgtctc tggccccgcg acacggctcg  17940
cgcccgttca tgggaaactg gcaagatatc ggcaccagca atatgagcgg tggcgccttc  18000
agctggggct cgctgtggag cggcattaaa aatttcggtt ccaccgttaa gaactatggc  18060
agcaaggcct ggaacagcag cacaggccag atgctgaggg ataagttgaa agagcaaaat  18120
ttccaacaaa aggtggtaga tggcctggcc tctggcatta gcggggtggt ggacctggcc  18180
aaccaggcag tgcaaaataa gattaacagt aagcttgatc cccgccctcc cgtagaggag  18240
cctccaccgg ccgtggagac agtgtctcca gaggggcgtg gcgaaaagcg tccgcgcccc  18300
gacagggaag aaactctggt gacgcaaata gacgagcctc cctcgtacga ggaggcacta  18360
aagcaaggcc tgcccaccac ccgtcccatc gcgcccatgg ctaccggagt gctgggccag  18420
cacacacccg taacgctgga cctgcctccc cccgccgaca cccagcagaa acctgtgctg  18480
ccaggcccga ccgccgttgt tgtaacccgt cctagccgcg cgtccctgcg ccgcgccgcc  18540
agcggtccgc gatcgttgcg gcccgtagcc agtggcaact ggcaaagcac actgaacagc  18600
```

-continued atcgtgggtc tgggggtgca atccctgaag cgccgacgat gcttctgaat agctaacgtg 18660
tcgtatgtgt gtcatgtatg cgtccatgtc gccgccagag gagctgctga gccgccgcgc 18720
gcccgctttc caagatggct accccttcga tgatgccgca gtggtcttac atgcacatct 18780
cgggccagga cgcctcggag tacctgagcc ccgggctggt gcagtttgcc cgcgccaccg 18840
agacgtactt cagcctgaat aacaagttta gaaaccccac ggtggcgcct acgcacgacg 18900
tgaccacaga ccggtcccag cgtttgacgc tgcggttcat ccctgtggac cgtgaggata 18960
ctgcgtactc gtacaaggcg cggttcaccc tagctgtggg tgataaccgt gtgctggaca 19020
tggcttccac gtactttgac atccgcggcg tgctggacag gggccctact tttaagccct 19080
actctggcac tgcctacaac gccctggctc ccaagggtgc cccaaatcct tgcgaatggg 19140
atgaagctgc tactgctctt gaaataaacc tagaagaaga ggacgatgac aacgaagacg 19200
aagtagacga gcaagctgag cagcaaaaaa ctcacgtatt tgggcaggcg ccttattctg 19260
gtataaatat tacaaaggag ggtattcaaa taggtgtcga aggtcaaaca cctaaatatg 19320
ccgataaaac atttcaacct gaacctcaaa taggagaatc tcagtggtac gaaactgaaa 19380
ttaatcatgc agctgggaga gtccttaaaa agactacccc aatgaaacca tgttacggtt 19440
catatgcaaa acccacaaat gaaaatggag ggcaaggcat tcttgtaaag caacaaaatg 19500
gaaagctaga aagtcaagtg gaaatgcaat tttctcaac tactgaggcg accgcaggca 19560
atggtgataa cttgactcct aaagtggtat tgtacagtga agatgtagat atagaaaccc 19620
cagacactca tatttcttac atgcccacta ttaaggaagg taactcacga gaactaatgg 19680
gccaacaatc tatgcccaac aggcctaatt acattgcttt tagggacaat tttattggtc 19740
taatgtatta caacagcacg ggtaatatgg gtgttctggc gggccaagca tcgcagttga 19800
atgctgttgt agatttgcaa gacagaaaca cagagctttc ataccagctt ttgcttgatt 19860
ccattggtga tagaaccagg tacttttcta tgtggaatca ggctgttgac agctatgatc 19920
cagatgttag aattattgaa aatcatggaa ctgaagatga acttccaaat tactgctttc 19980
cactgggagg tgtgattaat acagagactc ttaccaaggt aaaacctaaa acaggtcagg 20040
aaaatggatg ggaaaaagat gctacagaat tttcagataa aaatgaaata agagttggaa 20100
ataattttgc catggaaatc aatctaaatg ccaacctgtg gagaaatttc ctgtactcca 20160
acatagcgct gtatttgccc gacaagctaa agtacagtcc ttccaacgta aaaatttctg 20220
ataacccaaa cacctacgac tacatgaaca agcgagtggt ggctcccggg ttagtggact 20280
gctacattaa ccttggagca cgctggtccc ttgactatat ggacaacgtc aacccattta 20340
accaccaccg caatgctggc ctgcgctacc gctcaatgtt gctgggcaat ggtcgctatg 20400
tgcccttcca catccaggtg cctcagaagt tctttgccat taaaaacctc cttctcctgc 20460
cgggctcata cacctacgag tggaacttca ggaaggatgt taacatggtt ctgcagagct 20520
ccctaggaaa tgacctaagg gttgacggag ccagcattaa gtttgatagc atttgccttt 20580
acgccacctt cttccccatg gcccacaaca ccgcctccac gcttgaggcc atgcttagaa 20640
acgacaccaa cgaccagtcc tttaacgact atctctccgc cgccaacatg ctctacccta 20700
tacccgccaa cgctaccaac gtgcccatat ccatcccctc ccgcaactgg gcggctttcc 20760
gcggctgggc cttcacgcgc cttaagacta aggaaacccc atcactgggc tcgggctacg 20820
acccttatta cacctactct ggctctatac cctacctaga tggaaccttt tacctcaacc 20880
acacctttaa gaaggtggcc attacctttg actcttctgt cagctggcct ggcaatgacc 20940
gcctgcttac ccccaacgag tttgaaatta agcgctcagt tgacggggag ggttacaacg 21000

-continued

```
ttgcccagtg taacatgacc aaagactggt tcctggtaca aatgctagct aactacaaca  21060
ttggctacca gggcttctat atcccagaga gctacaagga ccgcatgtac tccttcttta  21120
gaaacttcca gcccatgagc cgtcaggtgg tggatgatac taaatacaag gactaccaac  21180
aggtgggcat cctacaccaa cacaacaact ctggatttgt tggctacctt gcccccacca  21240
tgcgcgaagg acaggcctac cctgctaact tcccctatcc gcttataggc aagaccgcag  21300
ttgacagcat tacccagaaa aagtttcttt gcgatcgcac cctttggcgc atcccattct  21360
ccagtaactt tatgtccatg ggcgcactca cagacctggg ccaaaacctt ctctacgcca  21420
actccgccca cgcgctagac atgacttttg aggtggatcc catggacgag cccacccttc  21480
tttatgtttt gtttgaagtc tttgacgtgg tccgtgtgca ccggccgcac cgcggcgtca  21540
tcgaaaccgt gtacctgcgc acgcccttct cggccggcaa cgccacaaca taaagaagca  21600
agcaacatca acaacagctg ccgccatggg ctccagtgag caggaactga aagccattgt  21660
caaagatctt ggttgtgggc catatttttt gggcacctat gacaagcgct ttccaggctt  21720
tgtttctcca cacaagctcg cctgcgccat agtcaatacg gccggtcgcg agactggggg  21780
cgtacactgg atggcctttg cctggaaccc gcactcaaaa acatgctacc tctttgagcc  21840
ctttggcttt tctgaccagc gactcaagca ggtttaccag tttgagtacg agtcactcct  21900
gcgccgtagc gccattgctt cttcccccga ccgctgtata acgctggaaa agtccaccca  21960
aagcgtacag gggcccaact cggccgcctg tggactattc tgctgcatgt ttctccacgc  22020
ctttgccaac tggccccaaa ctcccatgga tcacaacccc accatgaacc ttattaccgg  22080
ggtacccaac tccatgctca acagtcccca ggtacagccc accctgcgtc gcaaccagga  22140
acagctctac agcttcctgg agcgccactc gccctacttc cgcagccaca gtgcgcagat  22200
taggagcgcc acttcttttt gtcacttgaa aaacatgtaa aaataatgta ctagagacac  22260
tttcaataaa ggcaaatgct tttatttgta cactctcggg tgattattta cccccaccct  22320
tgccgtctgc gccgtttaaa aatcaaaggg gttctgccgc gcatcgctat gcgccactgg  22380
cagggacacg ttgcgatact ggtgtttagt gctccactta aactcaggca caaccatccg  22440
cggcagctcg gtgaagtttt cactccacag gctgcgcacc atcaccaacg cgtttagcag  22500
gtcgggcgcc gatatcttga agtcgcagtt ggggcctccg ccctgcgcgc gcgagttgcg  22560
atacacaggg ttgcagcact ggaacactat cagcgccggg tggtgcacgc tggccagcac  22620
gctcttgtcg gagatcagat ccgcgtccag gtcctccgcg ttgctcaggg cgaacggagt  22680
caactttggt agctgccttc ccaaaaaggg cgcgtgccca ggctttgagt tgcactcgca  22740
ccgtagtggc atcaaaaggt gaccgtgccc ggtctgggcg ttaggataca gcgcctgcat  22800
aaaagccttg atctgcttaa aagccacctg agcctttgcg ccttcagaga agaacatgcc  22860
gcaagacttg ccggaaaact gattggccgg acaggccgcg tcgtgcacgc agcaccttgc  22920
gtcggtgttg gagatctgca ccacatttcg gccccaccgg ttcttcacga tcttggcctt  22980
gctagactgc tccttcagcg cgcgctgccc gttttcgctc gtcacatcca tttcaatcac  23040
gtgctcctta tttatcataa tgcttccgtg tagacactta agctcgcctt cgatctcagc  23100
gcagcggtgc agccacaacg cgcagcccgt gggctcgtga tgcttgtagg tcacctctgc  23160
aaacgactgc aggtacgcct gcaggaatcg ccccatcatc gtcacaaagg tcttgttgct  23220
ggtgaaggtc agctgcaacc cgcggtgctc ctcgttcagc caggtcttgc atacggccgc  23280
cagagcttcc acttggtcag gcagtagttt gaagttcgcc tttagatcgt tatccacgtg  23340
```

-continued

```
gtacttgtcc atcagcgcgc gcgcagcctc catgcccttc tcccacgcag acacgatcgg  23400
cacactcagc gggttcatca ccgtaatttc actttccgct tcgctgggct cttcctcttc  23460
ctcttgcgtc cgcataccac gcgccactgg gtcgtcttca ttcagccgcc gcactgtgcg  23520
cttacctcct ttgccatgct tgattagcac cggtgggttg ctgaaaccca ccatttgtag  23580
cgccacatct tctctttctt cctcgctgtc cacgattacc tctggtgatg gcgggcgctc  23640
gggcttggga gaagggcgct tctttttctt cttgggcgca atggccaaat ccgccgccga  23700
ggtcgatggc cgcgggctgg gtgtgcgcgg caccagcgcg tcttgtgatg agtcttcctc  23760
gtcctcggac tcgatacgcc gcctcatccg ctttttttggg ggcgcccggg gaggcggcgg  23820
cgacggggac ggggacgaca cgtcctccat ggttggggga cgtcgcgccg caccgcgtcc  23880
gcgctcgggg gtggtttcgc gctgctcctc ttcccgactg gccatttcct tctcctatag  23940
gcagaaaaag atcatggagt cagtcgagaa gaaggacagc ctaaccgccc cctctgagtt  24000
cgccaccacc gcctccaccg atgccgccaa cgcgcctacc accttccccg tcgaggcacc  24060
cccgcttgag gaggaggaag tgattatcga gcaggaccca ggttttgtaa gcgaagacga  24120
cgaggaccgc tcagtaccaa cagaggataa aaagcaagac caggacaacg cagaggcaaa  24180
cgaggaacaa gtcgggcggg gggacgaaag gcatggcgac tacctagatg tgggagacga  24240
cgtgctgttg aagcatctgc agcgccagtg cgccattatc tgcgacgcgt tgcaagagcg  24300
cagcgatgtg cccctcgcca tagcggatgt cagccttgcc tacgaacgcc acctattctc  24360
accgcgcgta ccccccaaac gccaagaaaa cggcacatgc gagcccaacc cgcgcctcaa  24420
cttctacccc gtatttgccg tgccagaggt gcttgccacc tatcacatct tttccaaaa  24480
ctgcaagata cccctatcct gccgtgccaa ccgcagccga gcggacaagc agctggcctt  24540
gcggcagggc gctgtcatac ctgatatcgc ctcgctcaac gaagtgccaa aaatctttga  24600
gggtcttgga cgcgacgaga agcgcgcggc aaacgctctg caacaggaaa acagcgaaaa  24660
tgaaagtcac tctggagtgt tggtggaact cgagggtgac aacgcgcgcc tagccgtact  24720
aaaacgcagc atcgaggtca cccactttgc ctacccggca cttaacctac cccccaaggt  24780
catgagcaca gtcatgagtg agctgatcgt gcgccgtgcg cagcccctgg agagggatgc  24840
aaatttgcaa gaacaaacag aggagggcct acccgcagtt ggcgacgagc agctagcgcg  24900
ctggcttcaa acgcgcgagc ctgccgactt ggaggagcga cgcaaactaa tgatggccgc  24960
agtgctcgtt accgtggagc ttgagtgcat gcagcggttc tttgctgacc cggagatgca  25020
gcgcaagcta gaggaaacat tgcactacac ctttcgacag ggctacgtac gccaggcctg  25080
caagatctcc aacgtggagc tctgcaacct ggtctcctac cttggaattt tgcacgaaaa  25140
ccgccttggg caaaacgtgc ttcattccac gctcaagggc gaggcgcgcc gcgactacgt  25200
ccgcgactgc gtttacttat ttctatgcta cacctggcag acggccatgg gcgtttggca  25260
gcagtgcttg gaggagtgca acctcaagga gctgcagaaa ctgctaaagc aaaacttgaa  25320
ggacctatgg acggccttca acgagcgctc cgtggccgcg cacctggcgg acatcatttt  25380
ccccgaacgc ctgcttaaaa ccctgcaaca gggtctgcca gacttcacca gtcaaagcat  25440
gttgcagaac tttaggaact ttatcctaga gcgctcagga atcttgcccg ccacctgctg  25500
tgcacttcct agcgactttg tgcccattaa gtaccgcgaa tgccctccgc cgctttgggg  25560
ccactgctac cttctgcagc tagccaacta ccttgcctac cactctgaca taatggaaga  25620
cgtgagcggt gacggtctac tggagtgtca ctgtcgctgc aacctatgca ccccgcaccg  25680
ctccctggtt tgcaattcgc agctgcttaa cgaaagtcaa attatcggta cctttgagct  25740
```

-continued

```
gcagggtccc tcgcctgacg aaaagtccgc ggctccgggg ttgaaactca ctccggggct  25800
gtggacgtcg gcttaccttc gcaaatttgt acctgaggac taccacgccc acgagattag  25860
gttctacgaa gaccaatccc gcccgccaaa tgcggagctt accgcctgcg tcattaccca  25920
gggccacatt cttggccaat tgcaagccat caacaaagcc cgccaagagt ttctgctacg  25980
aaagggacgg ggggtttact tggacccca gtccggcgag gagctcaacc caatcccccc  26040
gccgccgcag ccctatcagc agcagccgcg ggcccttgct tcccaggatg gcacccaaaa  26100
agaagctgca gctgccgccg ccacccacgg acgaggagga atactgggac agtcaggcag  26160
aggaggtttt ggacgaggag gaggaggaca tgatggaaga ctgggagagc ctagacgagg  26220
aagcttccga ggtcgaagag gtgtcagacg aaacaccgtc accctcggtc gcattcccct  26280
cgccggcgcc ccagaaatcg gcaaccggtt ccagcatggc tacaacctcc gctcctcagg  26340
cgccgccggc actgcccgtt cgccgaccca accgtagatg ggacaccact ggaaccaggg  26400
ccggtaagtc caagcagccg ccgccgttag cccaagagca acaacagcgc caaggctacc  26460
gctcatggcg cgggcacaag aacgccatag ttgcttgctt gcaagactgt gggggcaaca  26520
tctccttcgc ccgccgcttt cttctctacc atcacggcgt ggccttcccc cgtaacatcc  26580
tgcattacta ccgtcatctc tacagcccat actgcaccgg cggcagcggc agcggcagca  26640
acagcagcgg ccacacagaa gcaaaggcga ccggatagca agactctgac aaagcccaag  26700
aaatccacag cggcggcagc agcaggagga ggagcgctgc gtctggcgcc caacgaaccc  26760
gtatcgaccc gcgagcttag aaacaggatt tttcccactc tgtatgctat atttcaacag  26820
agcaggggcc aagaacaaga gctgaaaata aaaaacaggt ctctgcgatc cctcacccgc  26880
agctgcctgt atcacaaaag cgaagatcag cttcggcgca cgctggaaga cgcggaggct  26940
ctcttcagta aatactgcgc gctgactctt aaggactagt ttcgcgccct ttctcaaatt  27000
taagcgcgaa aactacgtca tctccagcgg ccacacccgg cgccagcacc tgtcgtcagc  27060
gccattatga gcaaggaaat tcccacgccc tacatgtgga gttaccagcc acaaatggga  27120
cttgcggctg gagctgccca agactactca acccgaataa actacatgag cgcgggaccc  27180
cacatgatat cccgggtcaa cggaatccgc gcccaccgaa accgaattct cttggaacag  27240
gcggctatta ccaccacacc tcgtaataac cttaatcccc gtagttggcc cgctgccctg  27300
gtgtaccagg aaagtcccgc tcccaccact gtggtacttc ccagagacgc ccaggccgaa  27360
gttcagatga ctaactcagg ggcgcagctt gcgggcggct ttcgtcacag ggtgcggtcg  27420
cccgggcagg gtataactca cctgacaatc agagggcgag gtattcagct caacgacgag  27480
tcggtgagct cctcgcttgg tctccgtccg gacgggacat ttcagatcgg cggcgccggc  27540
cgtccttcat tcacgcctcg tcaggcaatc ctaactctgc agacctcgtc ctctgagccg  27600
cgctctggag gcattggaac tctgcaattt attgaggagt ttgtgccatc ggtctacttt  27660
aaccccttct cgggacctcc cggccactat ccggatcaat ttattcctaa ctttgacgcg  27720
gtaaaggact cggcggacgg ctacgactga taattaagtg gagaggcaga gcaactgcgc  27780
ctgaaacacc tggtccactg tcgccgccac aagtgctttg cccgcgactc cggtgagttt  27840
tgctactttg aattgcccga ggatcatatc gaggatcttt gttgccatct ctgtgctgag  27900
tataataaat acagaaatta aaatatactg gggctcctat cgccatcctg taaacgccac  27960
cgtcttcacc cgcccaagca aaccaaggcg aaccttacct ggtactttta acatctctcc  28020
ctctgtgatt tacaacagtt tcaacccaga cggagtgagt ctacgagaga acctctccga  28080
```

-continued gctcagctac tccatcagaa aaaacaccac cctccttacc tgccgggaac gtacccttaa 28140
ttaaaagtca ggcttcctgg atgtcagcat ctgactttgg ccagcacctg tcccgcggat 28200
ttgttccagt ccaactacag cgacccaccc taacagagat gaccaacaca accaacgcgg 28260
ccgccgctac cggacttaca tctaccacaa atacacccca agtttctgcc tttgtcaata 28320
actgggataa cttgggcatg tggtggttct ccatagcgct tatgtttgta tgccttatta 28380
ttatgtggct catctgctgc ctaaagcgca aacgcgcccg accacccatc tatagtccca 28440
tcattgtgct acacccaaac aatgatggaa tccatagatt ggacggactg aaacacatgt 28500
tcttttctct tacagtatga ttaaatgaga ttaattaagg aatttctgtc cagtttattc 28560
agcagcacct ccttgccctc ctcccagctc tggtattgca gcttcctcct ggctgcaaac 28620
tttctccaca atctaaatgg aatgtcagtt tcctcctgtt cctgtccatc cgcacccact 28680
atcttcatgt tgttgcagat gaagcgcgca agaccgtctg aagatacctt caaccccgtg 28740
tatccatatg acacggaaac cggtcctcca actgtgcctt ttcttactcc tccctttgta 28800
tcccccaatg ggtttcaaga gagtccccct ggggtactct ctttgcgcct atccgaacct 28860
ctagttacct ccaatggcat gcttgcgctc aaaatgggca acggcctctc tctggacgag 28920
gccggcaacc ttacctccca aaatgtaacc actgtgagcc cacctctcaa aaaaaccaag 28980
tcaaacataa acctggaaat atctgcaccc ctcacagtta cctcagaagc cctaactgtg 29040
gctgccgccg cacctctaat ggtcgcgggc aacacactca ccatgcaatc acaggccccg 29100
ctaaccgtgc acgactccaa acttagcatt gccacccaag gacccctcac agtgtcagaa 29160
ggaaagctag ccctgcaaac atcaggcccc ctcaccacca ccgatagcag tacccttact 29220
atcactgcct caccccctct aactactgcc actggtagct tgggcattga cttgaaagag 29280
cccatttata cacaaaatgg aaaactagga ctaaagtacg gggctccttt gcatgtaaca 29340
gacgacctaa acactttgac cgtagcaact ggtccaggtg tgactattaa taatacttcc 29400
ttgcaaacta aagttactgg agccttgggt tttgattcac aaggcaatat gcaacttaat 29460
gtagcaggag gactaaggat tgattctcaa aacagacgcc ttatacttga tgttagttat 29520
ccgtttgatg ctcaaaacca actaaatcta agactaggac agggccctct ttttataaac 29580
tcagcccaca acttggatat taactacaac aaaggccttt acttgtttac agcttcaaac 29640
aattccaaaa agcttgaggt taacctaagc actgccaagg ggttgatgtt tgacgctaca 29700
gccatagcca ttaatgcagg agatgggctt gaatttggtt cacctaatgc accaaacaca 29760
aatcccctca aaacaaaaat tggccatggc ctagaatttg attcaaacaa ggctatggtt 29820
cctaaactag gaactggcct tagttttgac agcacaggtg ccattacagt aggaaacaaa 29880
aataatgata agctaacttt gtggaccaca ccagctccat ctcctaactg tagactaaat 29940
gcagagaaag atgctaaact cactttggtc ttaacaaaat gtggcagtca aatacttgct 30000
acagtttcag ttttggctgt taaaggcagt ttggctccaa tatctggaac agttcaaagt 30060
gctcatctta ttataagatt tgacgaaaat ggagtgctac taaacaattc cttcctggac 30120
ccagaatatt ggaactttag aaatggagat cttactgaag gcacagccta tacaaacgct 30180
gttggattta tgcctaacct atcagcttat ccaaaatctc acggtaaaac tgccaaaagt 30240
aacattgtca gtcaagttta cttaaacgga gacaaaacta aacctgtaac actaaccatt 30300
acactaaacg gtacacagga aacaggagac acaactccaa gtgcatactc tatgtcattt 30360
tcatgggact ggtctggcca caactacatt aatgaaatat ttgccacatc ctcttacact 30420
ttttcataca ttgcccaaga ataaagaatc gtttgtgtta tgtttcaacg tgtttatttt 30480

-continued

```
tcaattgcag aaaatttcaa gtcatttttc attcagtagt atagccccac caccacatag  30540
cttatacaga tcaccgtacc ttaatcaaac tcacagaacc ctagtattca acctgccacc  30600
tccctcccaa cacacagagt acacagtcct ttctccccgg ctggccttaa aaagcatcat  30660
atcatgggta acagacatat tcttaggtgt tatattccac acggtttcct gtcgagccaa  30720
acgctcatca gtgatattaa taaactcccc gggcagctca cttaagttca tgtcgctgtc  30780
cagctgctga gccacaggct gctgtccaac ttgcggttgc ttaacgggcg gcgaaggaga  30840
agtccacgcc tacatggggg tagagtcata atcgtgcatc aggatagggc ggtggtgctg  30900
cagcagcgcg cgaataaact gctgccgccg ccgctccgtc ctgcaggaat acaacatggc  30960
agtggtctcc tcagcgatga ttcgcaccgc ccgcagcata aggcgccttg tcctccgggc  31020
acagcagcgc accctgatct cacttaaatc agcacagtaa ctgcagcaca gcaccacaat  31080
attgttcaaa atcccacagt gcaaggcgct gtatccaaag ctcatggcgg ggaccacaga  31140
acccacgtgg ccatcatacc acaagcgcag gtagattaag tggcgacccc tcataaacac  31200
gctggacata aacattacct cttttggcat gttgtaattc accacctccc ggtaccatat  31260
aaacctctga ttaaacatgg cgccatccac caccatccta aaccagctgg ccaaaacctg  31320
cccgccggct atacactgca gggaaccggg actggaacaa tgacagtgga gagcccagga  31380
ctcgtaacca tggatcatca tgctcgtcat gatatcaatg ttggcacaac acaggcacac  31440
gtgcatacac ttcctcagga ttacaagctc ctcccgcgtt agaaccatat cccagggaac  31500
aacccattcc tgaatcagcg taaatcccac actgcaggga agacctcgca cgtaactcac  31560
gttgtgcatt gtcaaagtgt tacattcggg cagcagcgga tgatcctcca gtatggtagc  31620
gcgggtttct gtctcaaaag gaggtagacg atccctactg tacggagtgc gccgagacaa  31680
ccgagatcgt gttggtcgta gtgtcatgcc aaatggaacg ccggacgtag tcatatttcc  31740
tgaagcaaaa ccaggtgcgg gcgtgacaaa cagatctgcg tctccggtct cgccgcttag  31800
atcgctctgt gtagtagttg tagtatatcc actctctcaa agcatccagg cgccccctgg  31860
cttcgggttc tatgtaaact ccttcatgcg ccgctgccct gataacatcc accaccgcag  31920
aataagccac acccagccaa cctacacatt cgttctgcga gtcacacacg ggaggagcgg  31980
gaagagctgg aagaaccatg tttttttttt tattccaaaa gattatccaa aacctcaaaa  32040
tgaagatcta ttaagtgaac gcgctcccct ccggtggcgt ggtcaaactc tacagccaaa  32100
gaacagataa tggcatttgt aagatgttgc acaatggctt ccaaaaggca aacggccctc  32160
acgtccaagt ggacgtaaag gctaaaccct tcagggtgaa tctcctctat aaacattcca  32220
gcaccttcaa ccatgcccaa ataattctca tctcgccacc ttctcaatat atctctaagc  32280
aaatcccgaa tattaagtcc ggccattgta aaaatctgct ccagagcgcc ctccaccttc  32340
agcctcaagc agcgaatcat gattgcaaaa attcaggttc ctcacagacc tgtataagat  32400
tcaaaagcgg aacattaaca aaaataccgc gatcccgtag gtcccttcgc agggccagct  32460
gaacataatc gtgcaggtct gcacggacca gcgcggccac ttccccgcca ggaaccttga  32520
caaaagaacc cacactgatt atgacacgca tactcggagc tatgctaacc agcgtagccc  32580
cgatgtaagc tttgttgcat gggcggcgat ataaaatgca aggtgctgct caaaaaatca  32640
ggcaaagcct cgcgcaaaaa agaaagcaca tcgtagtcat gctcatgcag ataaaggcag  32700
gtaagctccg gaaccaccac agaaaaagac accatttttc tctcaaacat gtctgcgggt  32760
ttctgcataa acacaaaata aaataacaaa aaaacattta aacattagaa gcctgtctta  32820
```

-continued caacaggaaa aacaaccctt ataagcataa gacggactac ggccatgccg gcgtgaccgt 32880
aaaaaaactg gtcaccgtga ttaaaaagca ccaccgacag ctcctcggtc atgtccggag 32940
tcataatgta agactcggta aacacatcag gttgattcat cggtcagtgc taaaaagcga 33000
ccgaaatagc ccgggggaat acatacccgc aggcgtagag acaacattac agccccata 33060 ggaggtataa caaaattaat aggagagaaa aacacataaa cacctgaaaa accctcctgc 33120
ctaggcaaaa tagcaccctc ccgctccaga acaacataca gcgcttcaca gcggcagcct 33180
aacagtcagc cttaccagta aaaaagaaaa cctattaaaa aaacaccact cgacacggca 33240
ccagctcaat cagtcacagt gtaaaaaagg gccaagtgca gagcgagtat atataggact 33300
aaaaaatgac gtaacggtta aagtccacaa aaaacaccca gaaaaccgca cgcgaaccta 33360
cgcccagaaa cgaaagccaa aaaacccaca acttcctcaa atcgtcactt ccgttttccc 33420
acgttacgta acttcccatt ttaagaaaac tacaattccc aacacataca agttactccg 33480
ccctaaaacc tacgtcaccc gccccgttcc cacgccccgc gccacgtcac aaactccacc 33540
ccctcattat catattggct tcaatccaaa ataaggtata ttattgatga tg 33592

<210> SEQ ID NO 2
<211> LENGTH: 34341
<212> TYPE: DNA
<213> ORGANISM: Adenovirus subgroup C

<400> SEQUENCE: 2
catcatcaat aatatacctt attttggatt gaagccaata tgataatgag ggggtggagt 60
ttgtgacgtg gcgcggggcg tgggaacggg gcgggtgacg tagtagtgtg gcggaagtgt 120
gatgttgcaa gtgtggcgga acacatgtaa gcgacggatg tggcaaaagt gacgtttttg 180
gtgtgcgccg gtgtacacag gaagtgacaa ttttcgcgcg gttttaggcg gatgttgtag 240
taaatttggg cgtaaccgag taagatttgg ccattttcgc gggaaaactg aataagagga 300
agtgaaatct gaataatttt gtgttactca tagcgcgtaa tatttgtcta gggccgcggg 360
gactttgacc gtttacgtgg agactcgccc aggtgttttt ctcaggtgtt ttccgcgttc 420
cgggtcaaag ttggcgtttt attattatag tcagctgacg tgtagtgtat ttatacccgg 480
tgagttcctc aagaggccac tcttgagtgc cagcgagtag agttttctcc tccgagccgc 540
tccgacaccg ggactgaaaa tgagacatga ggtactggct gataatcttc cacctcctag 600
ccattttgaa ccacctaccc ttcacgaact gtatgattta gacgtgacgg cccccgaaga 660
tcccaacgag gaggcggttt cgcagatttt tcccgactct gtaatgttgg cggtgcagga 720
agggattgac ttactcactt ttccgccggc gcccggttct ccggagccgc ctcacctttc 780
ccggcagccc gagcagccgg agcagagagc cttgggtccg gtttgccacg aggctggctt 840
tccacccagt gacgacgagg atgaagaggg tgaggagttt gtgttagatt atgtggagca 900
ccccgggcac ggttgcaggt cttgtcatta tcaccggagg aatacggggg acccagatat 960
tatgtgttcg ctttgctata tgaggacctg tggcatgttt gtctacagta agtgaaaatt 1020
atgggcagtg ggtgatagag tggtgggttt ggtgtggtaa tttttttttt aatttttaca 1080
gttttgtggt ttaaagaatt ttgtattgtg attttttaa aaggtcctgt gtctgaacct 1140
gagcctgagc ccgagccaga accggagcct gcaagaccta cccgccgtcc taaaatggcg 1200
cctgctatcc tgagacgccc gacatcacct gtgtctagag aatgcaatag tagtacggat 1260
agctgtgact ccggtccttc taacacacct cctgagatac acccggtggt cccgctgtgc 1320
cccattaaac cagttgccgt gagagttggt gggcgtcgcc aggctgtgga atgtatcgag 1380

-continued gacttgctta acgagcctgg gcaacctttg gacttgagct gtaaacgccc caggccataa 1440
ggtgtaaacc tgtgattgcg tgtgtggtta acgcctttgt ttgctgaatg agttgatgta 1500
agtttaataa agggtgagat aatgtttaac ttgcatggcg tgttaaatgg ggcggggctt 1560
aaagggtata taatgcgccg tgggctaatc ttggttacat ctgacctcat ggaggcttgg 1620
gagtgtttgg aagatttttc tgctgtgcgt aacttgctgg aacagagctc taacagtacc 1680
tcttggtttt ggaggtttct gtggggctca tcccaggcaa agttagtctg cagaattaag 1740
gaggattaca agtgggaatt tgaagagctt ttgaaatcct gtggtgagct gtttgattct 1800
ttgaatctgg gtcaccaggc gcttttccaa gagaaggtca tcaagacttt ggatttttcc 1860
acaccggggc gcgctgcggc tgctgttgct tttttgagtt ttataaagga taaatggagc 1920
gaagaaaccc atctgagcgg ggggtacctg ctggattttc tggccatgca tctgtggaga 1980
gcggttgtga gacacaagaa tcgcctgcta ctgttgtctt ccgtccgccc ggcgataata 2040
ccgacggagg agcagcagca gcagcaggag gaagccaggc ggcggcggca ggagcagagc 2100
ccatggaacc cgagagccgg cctggaccct cgggaatgaa tgttgtacag gtggctgaac 2160
tgtatccaga actgagacgc attttgacaa ttacagagga tgggcagggg ctaaaggggg 2220
taaagaggga gcgggggct tgtgaggcta cagaggaggc taggaatcta gcttttagct 2280
taatgaccag acaccgtcct gagtgtatta cttttcaaca gatcaaggat aattgcgcta 2340
atgagcttga tctgctggcg cagaagtatt ccatagagca gctgaccact tactggctgc 2400
agccagggga tgattttgag gaggctatta gggtatatgc aaaggtggca cttaggccag 2460
attgcaagta caagatcagc aaacttgtaa atatcaggaa ttgttgctac atttctggga 2520
acggggccga ggtggagata gatacggagg atagggtggc ctttagatgt agcatgataa 2580
atatgtggcc gggggtgctt ggcatggacg gggtggttat tatgaatgta aggtttactg 2640
gccccaattt tagcggtacg gttttcctgg ccaataccaa ccttatccta cacggtgtaa 2700
gcttctatgg gtttaacaat acctgtgtgg aagcctggac cgatgtaagg gttcggggct 2760
gtgcctttta ctgctgctgg aagggggtgg tgtgtcgccc caaaagcagg gcttcaatta 2820
agaaatgcct ctttgaaagg tgtaccttgg gtatcctgtc tgagggtaac tccagggtgc 2880
gccacaatgt ggcctccgac tgtggttgct tcatgctagt gaaaagcgtg gctgtgatta 2940
agcataacat ggtatgtggc aactgcgagg acagggcctc tcagatgctg acctgctcgg 3000
acggcaactg tcacctgctg aagaccattc acgtagccag ccactctcgc aaggcctggc 3060
cagtgtttga gcataacata ctgacccgct gttccttgca tttgggtaac aggaggggggg 3120
tgttcctacc ttaccaatgc aatttgagtc acactaagat attgcttgag cccgagagca 3180
tgtccaaggt gaacctgaac ggggtgtttg acatgaccat gaagatctgg aaggtgctga 3240
ggtacgatga gacccgcacc aggtgcagac cctgcgagtg tggcggtaaa catattagga 3300
accagcctgt gatgctggat gtgaccgagg agctgaggcc cgatcacttg gtgctggcct 3360
gcacccgcgc tgagtttggc tctagcgatg aagatacaga ttgaggtact gaaatgtgtg 3420
ggcgtggctt aagggtggga aagaatatat aaggtggggg tcttatgtag ttttgtatct 3480
gttttgcagc agccgccgcc gccatgagca ccaactcgtt tgatggaagc attgtgagct 3540
catatttgac aacgcgcatg cccccatggg ccggggtgcg tcagaatgtg atgggctcca 3600
gcattgatgg tcgccccgtc ctgcccgcaa actctactac cttgacctac gagaccgtgt 3660
ctggaacgcc gttggagact gcagcctccg ccgccgcttc agccgctgca gccaccgccc 3720

-continued gcgggattgt gactgacttt gctttcctga gcccgcttgc aagcagtgca gcttcccgtt 3780
catccgcccg cgatgacaag ttgacggctc ttttggcaca attggattct ttgacccggg 3840
aacttaatgt cgtttctcag cagctgttgg atctgcgcca gcaggtttct gccctgaagg 3900
cttcctcccc tcccaatgcg gtttaaaaca taaataaaaa accagactct gtttggattt 3960
ggatcaagca agtgtcttgc tgtctttatt taggggtttt gcgcgcgcgg taggcccggg 4020
accagcggtc tcggtcgttg agggtcctgt gtattttttc caggacgtgg taaaggtgac 4080
tctggatgtt cagatacatg ggcataagcc cgtctctggg gtggaggtag caccactgca 4140
gagcttcatg ctgcggggtg gtgttgtaga tgatccagtc gtagcaggag cgctgggcgt 4200
ggtgcctaaa aatgtctttc agtagcaagc tgattgccag gggcaggccc ttggtgtaag 4260
tgtttacaaa gcggttaagc tgggatgggt gcatacgtgg ggatatgaga tgcatcttgg 4320
actgtatttt taggttggct atgttcccag ccatatccct ccggggattc atgttgtgca 4380
gaaccaccag cacagtgtat ccggtgcact tgggaaattt gtcatgtagc ttagaaggaa 4440
atgcgtggaa gaacttggag acgcccttgt gacctccaag attttccatg cattcgtcca 4500
taatgatggc aatgggccca cgggcggcgg cctgggcgaa gatatttctg ggatcactaa 4560
cgtcatagtt gtgttccagg atgagatcgt cataggccat ttttacaaag cgcgggcgga 4620
gggtgccaga ctgcggtata atggttccat ccggcccagg ggcgtagtta ccctcacaga 4680
tttgcatttc ccacgctttg agttcagatg gggggatcat gtctacctgc ggggcgatga 4740
agaaaacggt ttccggggta ggggagatca gctgggaaga aagcaggttc ctgagcagct 4800
gcgacttacc gcagccggtg ggcccgtaaa tcacacctat taccgggtgc aactggtagt 4860
taagagagct gcagctgccg tcatccctga gcaggggggc cacttcgtta agcatgtccc 4920
tgactcgcat gttttccctg accaaatccg ccagaaggcg ctcgccgccc agcgatagca 4980
gttcttgcaa ggaagcaaag tttttcaacg gtttgagacc gtccgccgta ggcatgcttt 5040
tgagcgtttg accaagcagt tccaggcggt cccacagctc ggtcacctgc tctacggcat 5100
ctcgatccag catatctcct cgtttcgcgg gttggggcgg ctttcgctgt acggcagtag 5160
tcggtgctcg tccagacggg ccagggtcat gtctttccac gggcgcaggg tcctcgtcag 5220
cgtagtctgg gtcacggtga aggggtgcgc tccgggctgc gcgctggcca gggtgcgctt 5280
gaggctggtc ctgctggtgc tgaagcgctg ccggtcttcg ccctgcgcgt cggccaggta 5340
gcatttgacc atggtgtcat agtccagccc ctccgcggcg tggcccttgg cgcgcagctt 5400
gcccttggag gaggcgccgc acgaggggca gtgcagactt ttgagggcgt agagcttggg 5460
cgcgagaaat accgattccg gggagtaggc atccgcgccg caggccccgc agacggtctc 5520
gcattccacg agccaggtga gctctggccg ttcggggtca aaaaccaggt ttcccccatg 5580
ctttttgatg cgtttcttac ctctggtttc catgagccgg tgtccacgct cggtgacgaa 5640
aaggctgtcc gtgtccccgt atacagactt gagaggcctg tcctcgagcg gtgttccgcg 5700
gtcctcctcg tatagaaact cggaccactc tgagacaaag gctcgcgtcc aggccagcac 5760
gaaggaggct aagtgggagg ggtagcggtc gttgtccact agggggtcca ctcgctccag 5820
ggtgtgaaga cacatgtcgc cctcttcggc atcaaggaag gtgattggtt tgtaggtgta 5880
ggccacgtga ccgggtgttc ctgaaggggg gctataaaag gggtggggg cgcgttcgtc 5940 ctcactctct tccgcatcgc tgtctgcgag ggccagctgt tggggtgagt actccctctg 6000
aaaagcgggc atgacttctg cgctaagatt gtcagtttcc aaaaacgagg aggatttgat 6060
attcacctgg cccgcggtga tgcctttgag ggtggccgca tccatctggt cagaaaagac 6120

-continued

```
aatctttttg ttgtcaagct tggtggcaaa cgacccgtag agggcgttgg acagcaactt   6180
ggcgatggag cgcagggttt ggtttttgtc gcgatcggcg cgctccttgg ccgcgatgtt   6240
tagctgcacg tattcgcgcg caacgcaccg ccattcggga aagacggtgg tgcgctcgtc   6300
gggcaccagg tgcacgcgcc aaccgcggtt gtgcagggtg acaaggtcaa cgctggtggc   6360
tacctctccg cgtaggcgct cgttggtcca gcagaggcgg ccgcccttgc gcgagcagaa   6420
tggcggtagg gggtctagct gcgtctcgtc cggggggtct gcgtccacgg taaagacccc   6480
gggcagcagg cgcgcgtcga agtagtctat cttgcatcct tgcaagtcta gcgcctgctg   6540
ccatgcgcgg gcggcaagcg cgcgctcgta tgggttgagt gggggacccc atggcatggg   6600
gtgggtgagc gcggaggcgt acatgccgca aatgtcgtaa acgtagaggg gctctctgag   6660
tattccaaga tatgtagggt agcatcttcc accgcggatg ctggcgcgca cgtaatcgta   6720
tagttcgtgc gagggagcga ggaggtcggg accgaggttg ctacgggcgg gctgctctgc   6780
tcggaagact atctgcctga agatggcatg tgagttggat gatatggttg gacgctggaa   6840
gacgttgaag ctggcgtctg tgagacctac cgcgtcacgc acgaaggagg cgtaggagtc   6900
gcgcagcttg ttgaccagct cggcggtgac ctgcacgtct agggcgcagt agtccagggt   6960
ttccttgatg atgtcatact tatcctgtcc cttttttttc cacagctcgc ggttgaggac   7020
aaactcttcg cggtctttcc agtactcttg gatcggaaac ccgtcggcct ccgaacggta   7080
agagcctagc atgtagaact ggttgacggc ctggtaggcg cagcatccct tttctacggg   7140
tagcgcgtat gcctgcgcgg ccttccggag cgaggtgtgg gtgagcgcaa aggtgtccct   7200
gaccatgact ttgaggtact ggtatttgaa gtcagtgtcg tcgcatccgc cctgctccca   7260
gagcaaaaag tccgtgcgct ttttggaacg cggatttggc agggcgaagg tgacatcgtt   7320
gaagagtatc tttcccgcgc gaggcataaa gttgcgtgtg atgcggaagg gtcccggcac   7380
ctcggaacgg ttgttaatta cctgggcggc gagcacgatc tcgtcaaagc cgttgatgtt   7440
gtggcccaca atgtaaagtt ccaagaagcg cgggatgccc ttgatggaag gcaatttttt   7500
aagttcctcg taggtgagct cttcagggga gctgagcccg tgctctgaaa gggcccagtc   7560
tgcaagatga gggttggaag cgacgaatga gctccacagg tcacgggcca ttagcatttg   7620
caggtggtcg cgaaaggtcc taaactggcg acctatggcc atttttctg gggtgatgca   7680
gtagaaggta agcgggtctt gttcccagcg gtcccatcca aggttcgcgg ctaggtctcg   7740
cgcggcagtc actagaggct catctccgcc gaacttcatg accagcatga agggcacgag   7800
ctgcttccca aaggccccca tccaagtata ggtctctaca tcgtaggtga caaagagacg   7860
ctcggtgcga ggatgcgagc cgatcgggaa gaactggatc tcccgccacc aattggagga   7920
gtggctattg atgtggtgaa agtagaagtc cctgcgacgg gccgaacact cgtgctggct   7980
tttgtaaaaa cgtgcgcagt actggcagcg gtgcacgggc tgtacatcct gcacgaggtt   8040
gacctgacga ccgcgcacaa ggaagcagag tgggaatttg agcccctcgc ctggcgggtt   8100
tggctggtgg tcttctactt cggctgcttg tccttgaccg tctggctgct cgaggggagt   8160
tacggtggat cggaccacca cgccgcgcga gcccaaagtc cagatgtccg cgcgcggcgg   8220
tcggagcttg atgacaacat cgcgcagatg ggagctgtcc atggtctgga gctcccgcgg   8280
cgtcaggtca ggcgggagct cctgcaggtt tacctcgcat agacgggtca gggcgcgggc   8340
tagatccagg tgatacctaa tttccagggg ctggttggtg gcggcgtcga tggcttgcaa   8400
gaggccgcat ccccgcggcg cgactacggt accgcgcggc gggcggtggg ccgcgggggt   8460
```

-continued

```
gtccttggat gatgcatcta aaagcggtga cgcgggcgag cccccggagg tagggggggc   8520
tccggacccg ccgggagagg gggcaggggc acgtcggcgc cgcgcgcggg caggagctgg   8580
tgctgcgcgc gtaggttgct ggcgaacgcg acgacgcggc ggttgatctc ctgaatctgg   8640
cgcctctgcg tgaagacgac gggcccggtg agcttgagcc tgaaagagag ttcgacagaa   8700
tcaatttcgg tgtcgttgac ggcggcctgg cgcaaaatct cctgcacgtc tcctgagttg   8760
tcttgatagg cgatctcggc catgaactgc tcgatctctt cctcctggag atctccgcgt   8820
ccggctcgct ccacggtggc ggcgaggtcg ttggaaatgc gggccatgag ctgcgagaag   8880
gcgttgaggc ctccctcgtt ccagacgcgg ctgtagacca cgcccccttc ggcatcgcgg   8940
gcgcgcatga ccacctgcgc gagattgagc tccacgtgcc gggcgaagac ggcgtagttt   9000
cgcaggcgct gaaagaggta gttgagggtg gtggcggtgt gttctgccac gaagaagtac   9060
ataacccagc gtcgcaacgt ggattcgttg atatccccca aggcctcaag gcgctccatg   9120
gcctcgtaga agtccacggc gaagttgaaa aactgggagt tgcgcgccga cacggttaac   9180
tcctcctcca gaagacggat gagctcggcg acagtgtcgc gcacctcgcg ctcaaaggct   9240
acaggggcct cttcttcttc ttcaatctcc tcttccataa gggcctcccc ttcttcttct   9300
tctggcggcg gtgggggagg ggggacacgg cggcgacgac ggcgcaccgg gaggcggtcg   9360
acaaagcgct cgatcatctc cccgcggcga cggcgcatgg tctcggtgac ggcgcggccg   9420
ttctcgcggg ggcgcagttg gaagacgccg cccgtcatgt cccggttatg ggttggcggg   9480
gggctgccat gcggcaggga tacggcgcta acgatgcatc tcaacaattg ttgtgtaggt   9540
actccgccgc cgagggacct gagcgagtcc gcatcgaccg gatcggaaaa cctctcgaga   9600
aaggcgtcta accagtcaca gtcgcaaggt aggctgagca ccgtggcggg cggcagcggg   9660
cggcggtcgg ggttgtttct ggcggaggtg ctgctgatga tgtaattaaa gtaggcggtc   9720
ttgagacggc ggatggtcga cagaagcacc atgtccttgg gtccggcctg ctgaatgcgc   9780
aggcggtcgg ccatgcccca ggcttcgttt tgacatcggc gcaggtcttt gtagtagtct   9840
tgcatgagcc tttctaccgg cacttcttct tctccttcct cttgtcctgc atctcttgca   9900
tctatcgctg cggcggcggc ggagtttggc cgtaggtggc gccctcttcc tcccatgcgt   9960
gtgaccccga agcccctcat cggctgaagc agggctaggt cggcgacaac gcgctcggct  10020
aatatggcct gctgcacctg cgtgagggta gactggaagt catccatgtc cacaaagcgg  10080
tggtatgcgc ccgtgttgat ggtgtaagtg cagttggcca taacggacca gttaacggtc  10140
tggtgacccg gctgcgagag ctcggtgtac ctgagacgcg agtaagccct cgagtcaaat  10200
acgtagtcgt tgcaagtccg caccaggtac tggtatccca ccaaaaagtg cggcggcggc  10260
tggcggtaga ggggccagcg tagggtggcc ggggctccgg gggcgagatc ttccaacata  10320
aggcgatgat atccgtagat gtacctggac atccaggtga tgccggcggc ggtggtggag  10380
gcgcgcggaa agtcgcggac gcggttccag atgttgcgca gcggcaaaaa gtgctccatg  10440
gtcgggacgc tctggccggt caggcgcgcg caatcgttga cgctctagcg tgcaaaagga  10500
gagcctgtaa gcgggcactc ttccgtggtc tggtggataa attcgcaagg gtatcatggc  10560
ggacgaccgg ggttcgagcc ccgtatccgg ccgtccgccg tgatccatgc ggttaccgcc  10620
cgcgtgtcga acccaggtgt gcgacgtcag acaacggggg agtgctcctt ttggcttcct  10680
tccaggcgcg gcggctgctg cgctagcttt tttggccact ggccgcgcgc agcgtaagcg  10740
gttaggctgg aaagcgaaag cattaagtgg ctcgctccct gtagccggag ggttattttc  10800
caagggttga gtcgcgggac ccccggttcg agtctcggac cggccggact gcggcgaacg  10860
```

-continued

```
ggggtttgcc tccccgtcat gcaagacccc gcttgcaaat tcctccggaa acagggacga  10920
gcccctttt tgcttttccc agatgcatcc ggtgctgcgg cagatgcgcc cccctcctca  10980
gcagcggcaa gagcaagagc agcggcagac atgcagggca ccctcccctc ctcctaccgc  11040
gtcaggaggg gcgacatccg cggttgacgc ggcagcagat ggtgattacg aaccccgcg  11100
gcgccgggcc cggcactacc tggacttgga ggagggcgag ggcctggcgc ggctaggagc  11160
gccctctcct gagcggtacc caagggtgca gctgaagcgt gatacgcgtg aggcgtacgt  11220
gccgcggcag aacctgtttc gcgaccgcga gggagaggag cccgaggaga tgcgggatcg  11280
aaagttccac gcagggcgcg agctgcggca tggcctgaat cgcgagcggt tgctgcgcga  11340
ggaggacttt gagcccgacg cgcgaaccgg gattagtccc gcgcgcgcac acgtggcggc  11400
cgccgacctg gtaaccgcat acgagcagac ggtgaaccag gagattaact ttcaaaaaag  11460
ctttaacaac cacgtgcgta cgcttgtggc gcgcgaggag gtggctatag gactgatgca  11520
tctgtgggac tttgtaagcg cgctggagca aaacccaaat agcaagccgc tcatggcgca  11580
gctgttcctt atagtgcagc acagcaggga caacgaggca ttcagggatg cgctgctaaa  11640
catagtagag cccgagggcc gctggctgct cgatttgata aacatcctgc agagcatagt  11700
ggtgcaggag cgcagcttga gcctggctga caaggtggcc gccatcaact attccatgct  11760
tagcctgggc aagttttacg cccgcaagat ataccatacc ccttacgttc ccatagacaa  11820
ggaggtaaag atcgaggggt tctacatgcg catggcgctg aaggtgctta ccttgagcga  11880
cgacctgggc gtttatcgca acgagcgcat ccacaaggcc gtgagcgtga gccggcggcg  11940
cgagctcagc gaccgcgagc tgatgcacag cctgcaaagg gccctggctg gcacgggcag  12000
cggcgataga gaggccgagt cctactttga cgcgggcgct gacctgcgct gggccccaag  12060
ccgacgcgcc ctggaggcag ctggggccgg acctgggctg gcggtggcac ccgcgcgcgc  12120
tggcaacgtc ggcggcgtgg aggaatatga cgaggacgat gagtacgagc cagaggacgg  12180
cgagtactaa gcggtgatgt ttctgatcag atgatgcaag acgcaacgga cccggcggtg  12240
cgggcggcgc tgcagagcca gccgtccggc cttaactcca cggacgactg gcgccaggtc  12300
atggaccgca tcatgtcgct gactgcgcgc aatcctgacg cgttccggca gcagccgcag  12360
gccaaccggc tctccgcaat tctggaagcg gtggtcccgg cgcgcgcaaa ccccacgcac  12420
gagaaggtgc tggcgatcgt aaacgcgctg gccgaaaaca gggccatccg gcccgacgag  12480
gccggcctgg tctacgacgc gctgcttcag cgcgtggctc gttacaacag cggcaacgtg  12540
cagaccaacc tggaccggct ggtgggggat gtgcgcgagg ccgtggcgca gcgtgagcgc  12600
gcgcagcagc agggcaacct gggctccatg gttgcactaa acgccttcct gagtacacag  12660
cccgccaacg tgccgcgggg acaggaggac tacaccaact ttgtgagcgc actgcggcta  12720
atggtgactg agacaccgca aagtgaggtg taccagtctg ggccagacta tttttttccag  12780
accagtagac aaggcctgca gaccgtaaac ctgagccagg ctttcaaaaa cttgcagggg  12840
ctgtgggggg tgcgggctcc cacaggcgac cgcgcgaccg tgtctagctt gctgacgccc  12900
aactcgcgcc tgttgctgct gctaatagcg cccttcacgg acagtggcag cgtgtcccgg  12960
gacacatacc taggtcactt gctgacactg taccgcgagg ccataggtca ggcgcatgtg  13020
gacgagcata ctttccagga gattacaagt gtcagccgcg cgctggggca ggaggacacg  13080
ggcagcctgg aggcaaccct aaactacctg ctgaccaacc ggcggcagaa gatcccctcg  13140
ttgcacagtt taaacagcga ggaggagcgc attttgcgct acgtgcagca gagcgtgagc  13200
```

-continued cttaacctga tgcgcgacgg ggtaacgccc agcgtggcgc tggacatgac cgcgcgcaac 13260
atggaaccgg gcatgtatgc ctcaaaccgg ccgtttatca accgcctaat ggactacttg 13320
catcgcgcgg ccgccgtgaa ccccgagtat ttcaccaatg ccatcttgaa cccgcactgg 13380
ctaccgcccc ctggtttcta caccggggga ttcgaggtgc ccgagggtaa cgatggattc 13440
ctctgggacg acatagacga cagcgtgttt tccccgcaac cgcagaccct gctagagttg 13500
caacagcgcg agcaggcaga ggcggcgctg cgaaaggaaa gcttccgcag gccaagcagc 13560
ttgtccgatc taggcgctgc ggccccgcgg tcagatgcta gtagcccatt tccaagcttg 13620
atagggtctc ttaccagcac tcgcaccacc cgcccgcgcc tgctgggcga ggaggagtac 13680
ctaaacaact cgctgctgca gccgcagcgc gaaaaaaacc tgcctccggc atttcccaac 13740
aacgggatag agagcctagt ggacaagatg agtagatgga agacgtacgc gcaggagcac 13800
agggacgtgc caggcccgcg cccgcccacc cgtcgtcaaa ggcacgaccg tcagcggggt 13860
ctggtgtggg aggacgatga ctcggcagac gacagcagcg tcctggattt gggagggagt 13920
ggcaacccgt ttgcgcacct tcgccccagg ctggggagaa tgttttaaaa aaaaaaaagc 13980
atgatgcaaa ataaaaaact caccaaggcc atggcaccga gcgttggttt tcttgtattc 14040
cccttagtat gcggcgcgcg gcgatgtatg aggaaggtcc tcctccctcc tacgagagtg 14100
tggtgagcgc ggcgccagtg gcggcggcgc tgggttctcc cttcgatgct cccctggacc 14160
cgccgtttgt gcctccgcgg tacctgcggc ctaccggggg gagaaacagc atccgttact 14220
ctgagttggc acccctattc gacaccaccc gtgtgtacct ggtggacaac aagtcaacgg 14280
atgtggcatc cctgaactac cagaacgacc acagcaactt tctgaccacg gtcattcaaa 14340
acaatgacta cagcccgggg gaggcaagca cacagaccat caatcttgac gaccggtcgc 14400
actggggcgg cgacctgaaa accatcctgc ataccaacat gccaaatgtg aacgagttca 14460
tgtttaccaa taagtttaag gcgcgggtga tggtgtcgcg cttgcctact aaggacaatc 14520
aggtggagct gaaatacgag tgggtggagt tcacgctgcc cgagggcaac tactccgaga 14580
ccatgaccat agaccttatg aacaacgcga tcgtggagca ctacttgaaa gtgggcagac 14640
agaacggggt tctggaaagc gacatcgggg taaagtttga cacccgcaac ttcagactgg 14700
ggtttgaccc cgtcactggt cttgtcatgc ctggggtata tacaaacgaa gccttccatc 14760
cagacatcat tttgctgcca ggatgcgggg tggacttcac ccacagccgc ctgagcaact 14820
tgttgggcat ccgcaagcgg caacccttcc aggagggctt taggatcacc tacgatgatc 14880
tggagggtgg taacattccc gcactgttgg atgtggacgc ctaccaggcg agcttgaaag 14940
atgacaccga acagggcggg ggtggcgcag gcggcagcaa cagcagtggc agcggcgcgg 15000
aagagaactc caacgcggca gccgcggcaa tgcagccggt ggaggacatg aacgatcatg 15060
ccattcgcgg cgacaccttt gccacacggg ctgaggagaa gcgcgctgag gccgaagcag 15120
cggccgaagc tgccgccccc gctgcgcaac ccgaggtcga gaagcctcag aagaaaccgg 15180
tgatcaaacc cctgacagag gacagcaaga aacgcagtta caacctaata agcaatgaca 15240
gcaccttcac ccagtaccgc agctggtacc ttgcatacaa ctacggcgac cctcagaccg 15300
gaatccgctc atggaccctg ctttgcactc ctgacgtaac ctgcggctcg gagcaggtct 15360
actggtcgtt gccagacatg atgcaagacc ccgtgacctt ccgctccacg cgccagatca 15420
gcaactttcc ggtggtgggc gccgagctgt tgcccgtgca ctccaagagc ttctacaacg 15480
accaggccgt ctactcccaa ctcatccgcc agtttacctc tctgacccac gtgttcaatc 15540
gctttcccga gaaccagatt ttggcgcgcc cgccagcccc caccatcacc accgtcagtg 15600

-continued

```
aaaacgttcc tgctctcaca gatcacggga cgctaccgct gcgcaacagc atcggaggag  15660
tccagcgagt gaccattact gacgccagac gccgcacctg cccctacgtt tacaaggccc  15720
tgggcatagt ctcgccgcgc gtcctatcga gccgcacttt ttgagcaagc atgtccatcc  15780
ttatatcgcc cagcaataac acaggctggg gcctgcgctt cccaagcaag atgtttggcg  15840
gggccaagaa gcgctccgac caacacccag tgcgcgtgcg cgggcactac cgcgcgccct  15900
ggggcgcgca caaacgcggc cgcactgggc gcaccaccgt cgatgacgcc atcgacgcgg  15960
tggtggagga ggcgcgcaac tacacgccca cgccgccacc agtgtccaca gtggacgcgg  16020
ccattcagac cgtggtgcgc ggagcccggc gctatgctaa aatgaagaga cggcggaggc  16080
gcgtagcacg tcgccaccgc cgccgacccg gcactgccgc ccaacgcgcg gcggcggccc  16140
tgcttaaccg cgcacgtcgc accggccgac gggcggccat gcgggccgct cgaaggctgg  16200
ccgcgggtat tgtcactgtg ccccccaggt ccaggcgacg agcggccgcc gcagcagccg  16260
cggccattag tgctatgact cagggtcgca ggggcaacgt gtattgggtg cgcgactcgg  16320
ttagcggcct gcgcgtgccc gtgcgcaccc gcccccgcg caactagatt gcaagaaaaa  16380
actacttaga ctcgtactgt tgtatgtatc cagcggcggc ggcgcgcaac gaagctatgt  16440
ccaagcgcaa aatcaaagaa gagatgctcc aggtcatcgc gccggagatc tatggccccc  16500
cgaagaagga agagcaggat tacaagcccc gaaagctaaa gcgggtcaaa aagaaaaaga  16560
aagatgatga tgatgaactt gacgacgagg tggaactgct gcacgctacc gcgcccaggc  16620
gacgggtaca gtggaaaggt cgacgcgtaa aacgtgtttt gcgacccggc accaccgtag  16680
tctttacgcc cggtgagcgc tccacccgca cctacaagcg cgtgtatgat gaggtgtacg  16740
gcgacgagga cctgcttgag caggccaacg agcgcctcgg ggagtttgcc tacggaaagc  16800
ggcataagga catgctggcg ttgccgctgg acgagggcaa cccaacacct agcctaaagc  16860
ccgtaacact gcagcaggtg ctgcccgcgc ttgcaccgtc cgaagaaaag cgcggcctaa  16920
agcgcgagtc tggtgacttg gcacccaccg tgcagctgat ggtacccaag cgccagcgac  16980
tggaagatgt cttggaaaaa atgaccgtgg aacctgggct ggagcccgag gtccgcgtgc  17040
ggccaatcaa gcaggtggcg ccgggactgg gcgtgcagac cgtggacgtt cagataccca  17100
ctaccagtag caccagtatt gccaccgcca cagagggcat ggagacacaa acgtccccgg  17160
ttgcctcagc ggtggcggat gccgcggtgc aggcggtcgc tgcggccgcg tccaagacct  17220
ctacggaggt gcaaacggac ccgtggatgt ttcgcgtttc agccccccgg cgcccgcgcg  17280
gttcgaggaa gtacggcgcc gccagcgcgc tactgcccga atatgcccta catccttcca  17340
ttgcgcctac ccccggctat cgtggctaca cctaccgccc cagaagacga gcaactaccc  17400
gacgccgaac caccactgga acccgccgcc gccgtcgccg tcgccagccc gtgctggccc  17460
cgatttccgt gcgcagggtg gctcgcgaag gaggcaggac cctggtgctg ccaacagcgc  17520
gctaccaccc cagcatcgtt taaaagccgg tctttgtggt tcttgcagat atggccctca  17580
cctgccgcct ccgtttcccg gtgccgggat tccgaggaag aatgcaccgt aggaggggca  17640
tggccggcca cggcctgacg ggcggcatgc gtcgtgcgca ccaccggcgg cggcgcgcgt  17700
cgcaccgtcg catgcgcggc ggtatcctgc ccctccttat tccactgatc gccgcggcga  17760
ttggcgccgt gcccggaatt gcatccgtgg ccttgcaggc gcagagacac tgattaaaaa  17820
caagttgcat gtggaaaaat caaaataaaa agtctggact ctcacgctcg cttggtcctg  17880
taactatttt gtagaatgga agacatcaac tttgcgtctc tggccccgcg acacggctcg  17940
```

-continued cgcccgttca tgggaaactg gcaagatatc ggcaccagca atatgagcgg tggcgccttc 18000
agctggggct cgctgtggag cggcattaaa aatttcggtt ccaccgttaa gaactatggc 18060
agcaaggcct ggaacagcag cacaggccag atgctgaggg ataagttgaa agagcaaaat 18120
ttccaacaaa aggtggtaga tggcctggcc tctggcatta gcggggtggt ggacctggcc 18180
aaccaggcag tgcaaaataa gattaacagt aagcttgatc cccgccctcc cgtagaggag 18240
cctccaccgg ccgtggagac agtgtctcca gaggggcgtg gcgaaaagcg tccgcgcccc 18300
gacagggaag aaactctggt gacgcaaata gacgagcctc cctcgtacga ggaggcacta 18360
aagcaaggcc tgcccaccac ccgtcccatc gcgcccatgg ctaccggagt gctgggccag 18420
cacacacccg taacgctgga cctgcctccc cccgccgaca cccagcagaa acctgtgctg 18480
ccaggcccga ccgccgttgt tgtaacccgt cctagccgcg cgtccctgcg ccgcgccgcc 18540
agcggtccgc gatcgttgcg gcccgtagcc agtggcaact ggcaaagcac actgaacagc 18600
atcgtgggtc tgggggtgca atccctgaag cgccgacgat gcttctgaat agctaacgtg 18660
tcgtatgtgt gtcatgtatg cgtccatgtc gccgccagag gagctgctga gccgccgcgc 18720
gcccgctttc caagatggct accccttcga tgatgccgca gtggtcttac atgcacatct 18780
cgggccagga cgcctcggag tacctgagcc ccgggctggt gcagtttgcc cgcgccaccg 18840
agacgtactt cagcctgaat aacaagttta gaaaccccac ggtggcgcct acgcacgacg 18900
tgaccacaga ccggtcccag cgtttgacgc tgcggttcat ccctgtggac cgtgaggata 18960
ctgcgtactc gtacaaggcg cggttcaccc tagctgtggg tgataaccgt gtgctggaca 19020
tggcttccac gtactttgac atccgcggcg tgctggacag ggccctact tttaagccct 19080 actctggcac tgcctacaac gccctggctc ccaagggtgc cccaaatcct tgcgaatggg 19140
atgaagctgc tactgctctt gaaataaacc tagaagaaga ggacgatgac aacgaagacg 19200
aagtagacga gcaagctgag cagcaaaaaa ctcacgtatt tgggcaggcg ccttattctg 19260
gtataaatat tacaaaggag ggtattcaaa taggtgtcga aggtcaaaca cctaaatatg 19320
ccgataaaac atttcaacct gaacctcaaa taggagaatc tcagtggtac gaaactgaaa 19380
ttaatcatgc agctgggaga gtccttaaaa agactacccc aatgaaacca tgttacggtt 19440
catatgcaaa acccacaaat gaaaatggag ggcaaggcat tcttgtaaag caacaaaatg 19500
gaaagctaga aagtcaagtg gaaatgcaat tttctcaac tactgaggcg accgcaggca 19560
atggtgataa cttgactcct aaagtggtat tgtacagtga agatgtagat atagaaaccc 19620
cagacactca tatttcttac atgcccacta ttaaggaagg taactcacga gaactaatgg 19680
gccaacaatc tatgcccaac aggcctaatt acattgcttt tagggacaat tttattggtc 19740
taatgtatta caacagcacg ggtaatatgg gtgttctggc gggccaagca tcgcagttga 19800
atgctgttgt agatttgcaa gacagaaaca cagagctttc ataccagctt ttgcttgatt 19860
ccattggtga tagaaccagg tacttttcta tgtggaatca ggctgttgac agctatgatc 19920
cagatgttag aattattgaa aatcatggaa ctgaagatga acttccaaat tactgctttc 19980
cactgggagg tgtgattaat acagagactc ttaccaaggt aaaacctaaa acaggtcagg 20040
aaaatggatg ggaaaaagat gctacagaat tttcagataa aaatgaaata agagttggaa 20100
ataattttgc catggaaatc aatctaaatg ccaacctgtg gagaaatttc ctgtactcca 20160
acatagcgct gtatttgccc gacaagctaa agtacagtcc ttccaacgta aaaatttctg 20220
ataacccaaa cacctacgac tacatgaaca agcgagtggt ggctcccggg ttagtggact 20280
gctacattaa ccttggagca cgctggtccc ttgactatat ggacaacgtc aacccattta 20340

-continued

```
accaccaccg caatgctggc ctgcgctacc gctcaatgtt gctgggcaat ggtcgctatg  20400
tgcccttcca catccaggtg cctcagaagt tctttgccat taaaaacctc cttctcctgc  20460
cgggctcata cacctacgag tggaacttca ggaaggatgt taacatggtt ctgcagagct  20520
ccctaggaaa tgacctaagg gttgacggag ccagcattaa gtttgatagc atttgccttt  20580
acgccacctt cttccccatg gcccacaaca ccgcctccac gcttgaggcc atgcttagaa  20640
acgacaccaa cgaccagtcc tttaacgact atctctccgc cgccaacatg ctctacccta  20700
tacccgccaa cgctaccaac gtgcccatat ccatcccctc ccgcaactgg gcggctttcc  20760
gcggctgggc cttcacgcgc cttaagacta aggaaacccc atcactgggc tcgggctacg  20820
acccttatta cacctactct ggctctatac cctacctaga tggaaccttt tacctcaacc  20880
acacctttaa gaaggtggcc attacctttg actcttctgt cagctggcct ggcaatgacc  20940
gcctgcttac ccccaacgag tttgaaatta agcgctcagt tgacgggggag ggttacaacg  21000
ttgcccagtg taacatgacc aaagactggt tcctggtaca aatgctagct aactacaaca  21060
ttggctacca gggcttctat atcccagaga gctacaagga ccgcatgtac tccttcttta  21120
gaaacttcca gcccatgagc cgtcaggtgg tggatgatac taaatacaag gactaccaac  21180
aggtgggcat cctacaccaa cacaacaact ctggatttgt tggctacctt gcccccacca  21240
tgcgcgaagg acaggcctac cctgctaact tccccctatcc gcttataggc aagaccgcag  21300
ttgacagcat tacccagaaa aagtttcttt gcgatcgcac cctttggcgc atcccattct  21360
ccagtaactt tatgtccatg ggcgcactca cagacctggg ccaaaacctt ctctacgcca  21420
actccgccca cgcgctagac atgacttttg aggtggatcc catggacgag cccacccttc  21480
tttatgtttt gtttgaagtc tttgacgtgg tccgtgtgca ccggccgcac cgcggcgtca  21540
tcgaaaccgt gtacctgcgc acgcccttct cggccggcaa cgccacaaca taaagaagca  21600
agcaacatca acaacagctg ccgccatggg ctccagtgag caggaactga aagccattgt  21660
caaagatctt ggttgtgggc catatttttt gggcacctat gacaagcgct ttccaggctt  21720
tgtttctcca cacaagctcg cctgcgccat agtcaatacg gccggtcgcg agactggggg  21780
cgtacactgg atggcctttg cctggaaccc gcactcaaaa acatgctacc tctttgagcc  21840
ctttggcttt tctgaccagc gactcaagca ggtttaccag tttgagtacg agtcactcct  21900
gcgccgtagc gccattgctt cttcccccga ccgctgtata acgctggaaa agtccaccca  21960
aagcgtacag gggcccaact cggccgcctg tggactattc tgctgcatgt ttctccacgc  22020
ctttgccaac tggccccaaa ctcccatgga tcacaacccc accatgaacc ttattaccgg  22080
ggtacccaac tccatgctca acagtcccca ggtacagccc accctgcgtc gcaaccagga  22140
acagctctac agcttcctgg agcgccactc gccctacttc cgcagccaca gtgcgcagat  22200
taggagcgcc acttcttttt gtcacttgaa aaacatgtaa aaataatgta ctagagacac  22260
tttcaataaa ggcaaatgct tttatttgta cactctcggg tgattattta cccccaccct  22320
tgccgtctgc gccgtttaaa aatcaaaggg gttctgccgc gcatcgctat gcgccactgg  22380
cagggacacg ttgcgatact ggtgtttagt gctccactta aactcaggca caaccatccg  22440
cggcagctcg gtgaagtttt cactccacag gctgcgcacc atcaccaacg cgtttagcag  22500
gtcgggcgcc gatatcttga agtcgcagtt ggggcctccg ccctgcgcgc gcgagttgcg  22560
atacacaggg ttgcagcact ggaacactat cagcgccggg tggtgcacgc tggccagcac  22620
gctcttgtcg gagatcagat ccgcgtccag gtcctccgcg ttgctcaggg cgaacggagt  22680
```

-continued

```
caactttggt agctgccttc ccaaaaaggg cgcgtgccca ggctttgagt tgcactcgca  22740
ccgtagtggc atcaaaaggt gaccgtgccc ggtctgggcg ttaggataca gcgcctgcat  22800
aaaagccttg atctgcttaa aagccacctg agcctttgcg ccttcagaga agaacatgcc  22860
gcaagacttg ccggaaaact gattggccgg acaggccgcg tcgtgcacgc agcaccttgc  22920
gtcggtgttg gagatctgca ccacatttcg gccccaccgg ttcttcacga tcttggcctt  22980
gctagactgc tccttcagcg cgcgctgccc gttttcgctc gtcacatcca tttcaatcac  23040
gtgctcctta tttatcataa tgcttccgtg tagacactta agctcgcctt cgatctcagc  23100
gcagcggtgc agccacaacg cgcagcccgt gggctcgtga tgcttgtagg tcacctctgc  23160
aaacgactgc aggtacgcct gcaggaatcg ccccatcatc gtcacaaagg tcttgttgct  23220
ggtgaaggtc agctgcaacc cgcggtgctc ctcgttcagc caggtcttgc atacggccgc  23280
cagagcttcc acttggtcag gcagtagttt gaagttcgcc tttagatcgt tatccacgtg  23340
gtacttgtcc atcagcgcgc gcgcagcctc catgcccttc tcccacgcag acacgatcgg  23400
cacactcagc gggttcatca ccgtaatttc actttccgct tcgctgggct cttcctcttc  23460
ctcttgcgtc cgcataccac gcgccactgg gtcgtcttca ttcagccgcc gcactgtgcg  23520
cttacctcct ttgccatgct tgattagcac cggtgggttg ctgaaaccca ccatttgtag  23580
cgccacatct tctctttctt cctcgctgtc cacgattacc tctggtgatg gcgggcgctc  23640
gggcttggga gaagggcgct tctttttctt cttgggcgca atggccaaat ccgccgccga  23700
ggtcgatggc cgcgggctgg gtgtgcgcgg caccagcgcg tcttgtgatg agtcttcctc  23760
gtcctcggac tcgatacgcc gcctcatccg ctttttgggg ggcgcccggg gaggcggcgg  23820
cgacggggac ggggacgaca cgtcctccat ggttgggggga cgtcgcgccg caccgcgtcc  23880
gcgctcgggg gtggtttcgc gctgctcctc ttcccgactg gccatttcct tctcctatag  23940
gcagaaaaag atcatggagt cagtcgagaa gaaggacagc ctaaccgccc cctctgagtt  24000
cgccaccacc gcctccaccg atgccgccaa cgcgcctacc accttccccg tcgaggcacc  24060
cccgcttgag gaggaggaag tgattatcga gcaggaccca ggttttgtaa gcgaagacga  24120
cgaggaccgc tcagtaccaa cagaggataa aaagcaagac caggacaacg cagaggcaaa  24180
cgaggaacaa gtcgggcggg gggacgaaag gcatggcgac tacctagatg tgggagacga  24240
cgtgctgttg aagcatctgc agcgccagtg cgccattatc tgcgacgcgt tgcaagagcg  24300
cagcgatgtg cccctcgcca tagcggatgt cagccttgcc tacgaacgcc acctattctc  24360
accgcgcgta ccccccaaac gccaagaaaa cggcacatgc gagcccaacc cgcgcctcaa  24420
cttctacccc gtatttgccg tgccagaggt gcttgccacc tatcacatct ttttccaaaa  24480
ctgcaagata cccctatcct gccgtgccaa ccgcagccga gcggacaagc agctggcctt  24540
gcggcagggc gctgtcatac ctgatatcgc ctcgctcaac gaagtgccaa aaatctttga  24600
gggtcttgga cgcgacgaga agcgcgcggc aaacgctctg caacaggaaa acagcgaaaa  24660
tgaaagtcac tctggagtgt tggtggaact cgagggtgac aacgcgcgcc tagccgtact  24720
aaaacgcagc atcgaggtca cccactttgc ctacccggca cttaacctac cccccaaggt  24780
catgagcaca gtcatgagtg agctgatcgt gcgccgtgcg cagcccctgg agagggatgc  24840
aaatttgcaa gaacaaacag aggagggcct acccgcagtt ggcgacgagc agctagcgcg  24900
ctggcttcaa acgcgcgagc ctgccgactt ggaggagcga cgcaaactaa tgatggccgc  24960
agtgctcgtt accgtggagc ttgagtgcat gcagcggttc tttgctgacc cggagatgca  25020
gcgcaagcta gaggaaacat tgcactacac ctttcgacag ggctacgtac gccaggcctg  25080
```

-continued caagatctcc aacgtggagc tctgcaacct ggtctcctac cttggaattt tgcacgaaaa 25140
ccgccttggg caaaacgtgc ttcattccac gctcaagggc gaggcgcgcc gcgactacgt 25200
ccgcgactgc gtttacttat ttctatgcta cacctggcag acggccatgg gcgtttggca 25260
gcagtgcttg gaggagtgca acctcaagga gctgcagaaa ctgctaaagc aaaacttgaa 25320
ggacctatgg acggccttca acgagcgctc cgtggccgcg cacctggcgg acatcatttt 25380
ccccgaacgc ctgcttaaaa ccctgcaaca gggtctgcca gacttcacca gtcaaagcat 25440
gttgcagaac tttaggaact ttatcctaga gcgctcagga atcttgcccg ccacctgctg 25500
tgcacttcct agcgactttg tgcccattaa gtaccgcgaa tgccctccgc cgctttgggg 25560
ccactgctac cttctgcagc tagccaacta ccttgcctac cactctgaca taatggaaga 25620
cgtgagcggt gacggtctac tggagtgtca ctgtcgctgc aacctatgca ccccgcaccg 25680
ctccctggtt tgcaattcgc agctgcttaa cgaaagtcaa attatcggta cctttgagct 25740
gcagggtccc tcgcctgacg aaaagtccgc ggctccgggg ttgaaactca ctccggggct 25800
gtggacgtcg gcttaccttc gcaaatttgt acctgaggac taccacgccc acgagattag 25860
gttctacgaa gaccaatccc gcccgccaaa tgcggagctt accgcctgcg tcattaccca 25920
gggccacatt cttggccaat tgcaagccat caacaaagcc cgccaagagt ttctgctacg 25980
aaagggacgg ggggtttact tggacccccca gtccggcgag gagctcaacc caatcccccc 26040
gccgccgcag ccctatcagc agcagccgcg ggcccttgct tcccaggatg gcacccaaaa 26100
agaagctgca gctgccgccg ccacccacgg acgaggagga atactgggac agtcaggcag 26160
aggaggtttt ggacgaggag gaggaggaca tgatggaaga ctgggagagc ctagacgagg 26220
aagcttccga ggtcgaagag gtgtcagacg aaacaccgtc accctcggtc gcattcccct 26280
cgccggcgcc ccagaaatcg gcaaccggtt ccagcatggc tacaacctcc gctcctcagg 26340
cgccgccggc actgcccgtt cgccgaccca accgtagatg ggacaccact ggaaccaggg 26400
ccggtaagtc caagcagccg ccgccgttag cccaagagca acaacagcgc caaggctacc 26460
gctcatggcg cgggcacaag aacgccatag ttgcttgctt gcaagactgt gggggcaaca 26520
tctccttcgc ccgccgcttt cttctctacc atcacggcgt ggccttcccc cgtaacatcc 26580
tgcattacta ccgtcatctc tacagcccat actgcaccgg cggcagcggc agcggcagca 26640
acagcagcgg ccacacagaa gcaaaggcga ccggatagca agactctgac aaagcccaag 26700
aaatccacag cggcggcagc agcaggagga ggagcgctgc gtctggcgcc caacgaaccc 26760
gtatcgaccc gcgagcttag aaacaggatt tttcccactc tgtatgctat atttcaacag 26820
agcaggggcc aagaacaaga gctgaaaata aaaaacaggt ctctgcgatc cctcacccgc 26880
agctgcctgt atcacaaaag cgaagatcag cttcggcgca cgctggaaga cgcggaggct 26940
ctcttcagta aatactgcgc gctgactctt aaggactagt ttcgcgccct ttctcaaatt 27000
taagcgcgaa aactacgtca tctccagcgg ccacacccgg cgccagcacc tgtcgtcagc 27060
gccattatga gcaaggaaat tcccacgccc tacatgtgga gttaccagcc acaaatggga 27120
cttgcggctg gagctgccca agactactca acccgaataa actacatgag cgcgggaccc 27180
cacatgatat cccgggtcaa cggaatccgc gcccaccgaa accgaattct cttggaacag 27240
gcggctatta ccaccacacc tcgtaataac cttaatcccc gtagttggcc cgctgccctg 27300
gtgtaccagg aaagtcccgc tcccaccact gtggtacttc ccagagacgc ccaggccgaa 27360
gttcagatga ctaactcagg ggcgcagctt gcgggcggct ttcgtcacag ggtgcggtcg 27420

-continued

```
cccgggcagg gtataactca cctgacaatc agagggcgag gtattcagct caacgacgag  27480
tcggtgagct cctcgcttgg tctccgtccg gacgggacat ttcagatcgg cggcgccggc  27540
cgtccttcat tcacgcctcg tcaggcaatc ctaactctgc agacctcgtc ctctgagccg  27600
cgctctggag gcattggaac tctgcaattt attgaggagt ttgtgccatc ggtctacttt  27660
aaccccttct cgggacctcc cggccactat ccggatcaat ttattcctaa ctttgacgcg  27720
gtaaaggact cggcggacgg ctacgactga atgttaagtg gagaggcaga gcaactgcgc  27780
ctgaaacacc tggtccactg tcgccgccac aagtgctttg cccgcgactc cggtgagttt  27840
tgctactttg aattgcccga ggatcatatc gagggcccgg cgcacggcgt ccggcttacc  27900
gcccagggag agcttgcccg tagcctgatt cgggagttta cccagcgccc cctgctagtt  27960
gagcgggaca ggggaccctg tgttctcact gtgatttgca actgtcctaa ccttggatta  28020
catcaagatc tttgttgcca tctctgtgct gagtataata aatacagaaa ttaaaatata  28080
ctggggctcc tatcgccatc ctgtaaacgc caccgtcttc acccgcccaa gcaaaccaag  28140
gcgaacctta cctggtactt ttaacatctc tccctctgtg atttacaaca gtttcaaccc  28200
agacggagtg agtctacgag agaacctctc cgagctcagc tactccatca gaaaaaacac  28260
caccctcctt acctgccggg aacgtacgag tgcgtcaccg gccgctgcac cacacctacc  28320
gcctgaccgt aaaccagact ttttccggac agacctcaat aactctgttt accagaacag  28380
gaggtgagct tagaaaaccc ttagggtatt aggccaaagg cgcagctact gtggggttta  28440
tgaacaattc aagcaactct acgggctatt ctaattcagg tttctctaga agtcaggctt  28500
cctggatgtc agcatctgac tttggccagc acctgtcccg cggatttgtt ccagtccaac  28560
tacagcgacc caccctaaca gagatgacca acacaaccaa cgcggccgcc gctaccggac  28620
ttacatctac cacaaataca ccccaagttt ctgcctttgt caataactgg gataacttgg  28680
gcatgtggtg gttctccata gcgcttatgt ttgtatgcct tattattatg tggctcatct  28740
gctgcctaaa gcgcaaacgc gcccgaccac ccatctatag tcccatcatt gtgctacacc  28800
caaacaatga tggaatccat agattggacg gactgaaaca catgttcttt tctcttacag  28860
tatgattaaa tgagatctag aaatggacgg aattattaca gagcagcgcc tgctagaaag  28920
acgcagggca gcggccgagc aacagcgcat gaatcaagag ctccaagaca tggttaactt  28980
gcaccagtgc aaaaggggta tcttttgtct ggtaaagcag gccaaagtca cctacgacag  29040
taataccacc ggacaccgcc ttagctacaa gttgccaacc aagcgtcaga aattggtggt  29100
catggtggga gaaaagccca ttaccataac tcagcactcg gtagaaaccg aaggctgcat  29160
tcactcacct tgtcaaggac ctgaggatct ctgcaccctt attaagaccc tgtgcggtct  29220
caaagatctt attcccttta actaataaaa aaaaataata aagcatcact tacttaaaat  29280
cagttagcaa atttctgtcc agtttattca gcagcacctc cttgccctcc tcccagctct  29340
ggtattgcag cttcctcctg gctgcaaact ttctccacaa tctaaatgga atgtcagttt  29400
cctcctgttc ctgtccatcc gcacccacta tcttcatgtt gttgcagatg aagcgcgcaa  29460
gaccgtctga agataccttc aaccccgtgt atccatatga cacggaaacc ggtcctccaa  29520
ctgtgccttt tcttactcct ccctttgtat cccccaatgg gtttcaagag agtcccccctg  29580
ggtactctc tttgcgccta tccgaacctc tagttacctc caatggcatg cttgcgctca  29640
aaatgggcaa cggcctctct ctggacgagg ccggcaacct tacctcccaa aatgtaacca  29700
ctgtgagccc acctctcaaa aaaaccaagt caaacataaa cctggaaata tctgcacccc  29760
tcacagttac ctcagaagcc ctaactgtgg ctgccgccgc acctctaatg gtcgcgggca  29820
```

-continued

```
acacactcac catgcaatca caggccccgc taaccgtgca cgactccaaa cttagcattg  29880
ccacccaagg accccctcaca gtgtcagaag gaaagctagc cctgcaaaca tcaggccccc  29940
tcaccaccac cgatagcagt acccttacta tcactgcctc accccctcta actactgcca  30000
ctggtagctt gggcattgac ttgaaagagc ccatttatac acaaaatgga aaactaggac  30060
taaagtacgg ggctcctttg catgtaacag acgacctaaa cactttgacc gtagcaactg  30120
gtccaggtgt gactattaat aatacttcct tgcaaactaa agttactgga gccttgggtt  30180
ttgattcaca aggcaatatg caacttaatg tagcaggagg actaaggatt gattctcaaa  30240
acagacgcct tatacttgat gttagttatc cgtttgatgc tcaaaaccaa ctaaatctaa  30300
gactaggaca gggccctctt tttataaact cagcccacaa cttggatatt aactacaaca  30360
aaggccttta cttgtttaca gcttcaaaca attccaaaaa gcttgaggtt aacctaagca  30420
ctgccaaggg gttgatgttt gacgctacag ccatagccat taatgcagga gatgggcttg  30480
aatttggttc acctaatgca ccaaacacaa atcccctcaa aacaaaaatt ggccatggcc  30540
tagaatttga ttcaaacaag gctatggttc ctaaactagg aactggcctt agttttgaca  30600
gcacaggtgc cattacagta ggaaacaaaa ataatgataa gctaactttg tggaccacac  30660
cagctccatc tcctaactgt agactaaatg cagagaaaga tgctaaactc actttggtct  30720
taacaaaatg tggcagtcaa atacttgcta cagtttcagt tttggctgtt aaaggcagtt  30780
tggctccaat atctggaaca gttcaaagtg ctcatcttat tataagattt gacgaaaatg  30840
gagtgctact aaacaattcc ttcctggacc cagaatattg gaactttaga aatggagatc  30900
ttactgaagg cacagcctat acaaacgctg ttggatttat gcctaaccta tcagcttatc  30960
caaaatctca cggtaaaact gccaaaagta acattgtcag tcaagtttac ttaaacggag  31020
acaaaactaa acctgtaaca ctaaccatta cactaaacgg tacacaggaa acaggagaca  31080
caactccaag tgcatactct atgtcatttt catgggactg gtctggccac aactacatta  31140
atgaaatatt tgccacatcc tcttacactt tttcatacat tgcccaagaa taaagaatcg  31200
tttgtgttat gtttcaacgt gtttattttt caattgcaga aaatttcaag tcatttttca  31260
ttcagtagta tagccccacc accacatagc ttatacagat caccgtacct taatcaaact  31320
cacagaaccc tagtattcaa cctgccacct ccctcccaac acacagagta cacagtcctt  31380
tctccccggc tggccttaaa aagcatcata tcatgggtaa cagacatatt cttaggtgtt  31440
atattccaca cggtttcctg tcgagccaaa cgctcatcag tgatattaat aaactccccg  31500
ggcagctcac ttaagttcat gtcgctgtcc agctgctgag ccacaggctg ctgtccaact  31560
tgcggttgct taacgggcgg cgaaggagaa gtccacgcct acatgggggt agagtcataa  31620
tcgtgcatca ggatagggcg gtggtgctgc agcagcgcgc gaataaactg ctgccgccgc  31680
cgctccgtcc tgcaggaata caacatggca gtggtctcct cagcgatgat tcgcaccgcc  31740
cgcagcataa ggcgccttgt cctccgggca cagcagcgca ccctgatctc acttaaatca  31800
gcacagtaac tgcagcacag caccacaata ttgttcaaaa tcccacagtg caaggcgctg  31860
tatccaaagc tcatggcggg gaccacagaa cccacgtggc catcatacca caagcgcagg  31920
tagattaagt ggcgacccct cataaacacg ctggacataa acattacctc ttttggcatg  31980
ttgtaattca ccacctcccg gtaccatata aacctctgat taaacatggc gccatccacc  32040
accatcctaa accagctggc caaaacctgc ccgccggcta tacactgcag ggaaccggga  32100
ctggaacaat gacagtggag agcccaggac tcgtaaccat ggatcatcat gctcgtcatg  32160
```

-continued

```
atatcaatgt tggcacaaca caggcacacg tgcatacact tcctcaggat tacaagctcc  32220

tcccgcgtta gaaccatatc ccagggaaca acccattcct gaatcagcgt aaatcccaca  32280

ctgcagggaa gacctcgcac gtaactcacg ttgtgcattg tcaaagtgtt acattcgggc  32340

agcagcggat gatcctccag tatggtagcg cgggtttctg tctcaaaagg aggtagacga  32400

tccctactgt acggagtgcg ccgagacaac cgagatcgtg ttggtcgtag tgtcatgcca  32460

aatggaacgc cggacgtagt catatttcct gaagcaaaac caggtgcggg cgtgacaaac  32520

agatctgcgt ctccggtctc gccgcttaga tcgctctgtg tagtagttgt agtatatcca  32580

ctctctcaaa gcatccaggc gccccctggc ttcgggttct atgtaaactc cttcatgcgc  32640

cgctgccctg ataacatcca ccaccgcaga ataagccaca cccagccaac ctacacattc  32700

gttctgcgag tcacacacgg gaggagcggg aagagctgga agaaccatgt tttttttttt  32760

attccaaaag attatccaaa acctcaaaat gaagatctat taagtgaacg cgctcccctc  32820

cggtggcgtg gtcaaactct acagccaaag aacagataat ggcatttgta agatgttgca  32880

caatggcttc caaaaggcaa acggccctca cgtccaagtg gacgtaaagg ctaaaccctt  32940

cagggtgaat ctcctctata aacattccag caccttcaac catgcccaaa taattctcat  33000

ctcgccacct tctcaatata tctctaagca aatcccgaat attaagtccg gccattgtaa  33060

aaatctgctc cagagcgccc tccaccttca gcctcaagca gcgaatcatg attgcaaaaa  33120

ttcaggttcc tcacagacct gtataagatt caaaagcgga acattaacaa aaataccgcg  33180

atcccgtagg tcccttcgca gggccagctg aacataatcg tgcaggtctg cacggaccag  33240

cgcggccact tccccgccag gaaccttgac aaaagaaccc acactgatta tgacacgcat  33300

actcggagct atgctaacca gcgtagcccc gatgtaagct ttgttgcatg ggcggcgata  33360

taaaatgcaa ggtgctgctc aaaaaatcag gcaaagcctc gcgcaaaaaa gaaagcacat  33420

cgtagtcatg ctcatgcaga taaaggcagg taagctccgg aaccaccaca gaaaaagaca  33480

ccatttttct ctcaaacatg tctgcgggtt tctgcataaa cacaaaataa aataacaaaa  33540

aaacatttaa acattagaag cctgtcttac aacaggaaaa acaaccctta taagcataag  33600

acggactacg gccatgccgg cgtgaccgta aaaaaactgg tcaccgtgat taaaaagcac  33660

caccgacagc tcctcggtca tgtccggagt cataatgtaa gactcggtaa acacatcagg  33720

ttgattcatc ggtcagtgct aaaaagcgac cgaaatagcc cgggggaata catacccgca  33780

ggcgtagaga caacattaca gcccccatag gaggtataac aaaattaata ggagagaaaa  33840

acacataaac acctgaaaaa ccctcctgcc taggcaaaat agcaccctcc cgctccagaa  33900

caacatacag cgcttcacag cggcagccta acagtcagcc ttaccagtaa aaaagaaaac  33960

ctattaaaaa aacaccactc gacacggcac cagctcaatc agtcacagtg taaaaaaggg  34020

ccaagtgcag agcgagtata tataggacta aaaaatgacg taacggttaa agtccacaaa  34080

aaacacccag aaaaccgcac gcgaacctac gcccagaaac gaaagccaaa aaacccacaa  34140

cttcctcaaa tcgtcacttc cgttttccca cgttacgtaa cttcccattt taagaaaact  34200

acaattccca acacatacaa gttactccgc cctaaaacct acgtcacccg ccccgttccc  34260

acgccccgcg ccacgtcaca aactccaccc cctcattatc atattggctt caatccaaaa  34320

taaggtatat tattgatgat g                                            34341
```

<210> SEQ ID NO 3
<211> LENGTH: 33699
<212> TYPE: DNA
<213> ORGANISM: Adenovirus subgroup C -continued

<400> SEQUENCE: 3

```
catcatcaat aatatacctt attttggatt gaagccaata tgataatgag ggggtggagt     60
ttgtgacgtg gcgcggggcg tgggaacggg gcgggtgacg tagtagtgtg gcggaagtgt    120
gatgttgcaa gtgtggcgga acacatgtaa gcgacggatg tggcaaaagt gacgtttttg    180
gtgtgcgccg gtgtacacag gaagtgacaa ttttcgcgcg gttttaggcg gatgttgtag    240
taaatttggg cgtaaccgag taagatttgg ccattttcgc gggaaaactg aataagagga    300
agtgaaatct gaataatttt gtgttactca tagcgcgtaa tatttgtcta gggccgcggg    360
gactttgacc gtttacgtgg agactcgccc aggtgttttt ctcaggtgtt ttccgcgttc    420
cgggtcaaag ttggcgtttt attattatag tcagctgacg tgtagtgtat ttatacccgg    480
tgagttcctc aagaggccac tcttgagtgc cagcgagtag agttttctcc tccgagccgc    540
tccgacaccg ggactgaaaa tgagacatat tatctgccac ggaggtgtta ttaccgaaga    600
aatggccgcc agtcttttgg accagctgat cgaagaggta ctggctgata atcttccacc    660
tcctagccat tttgaaccac ctacccttca cgaactgtat gatttagacg tgacggcccc    720
cgaagatccc aacgaggagg cggtttcgca gatttttccc gactctgtaa tgttggcggt    780
gcaggaaggg attgacttac tcacttttcc gccggcgccc ggttctccgg agccgcctca    840
cctttcccgg cagcccgagc agccggagca gagagccttg ggtccggttt ctatgccaaa    900
ccttgtaccg gaggtgatcg atcttacctg ccacgaggct ggctttccac ccagtgacga    960
cgaggatgaa gagggtgagg agtttgtgtt agattatgtg gagcaccccg ggcacggttg   1020
caggtcttgt cattatcacc ggaggaatac gggggaccca gatattatgt gttcgctttg   1080
ctatatgagg acctgtggca tgtttgtcta cagtaagtga aaattatggg cagtgggtga   1140
tagagtggtg ggtttggtgt ggtaattttt tttttaattt ttacagtttt gtggtttaaa   1200
gaattttgta ttgtgatttt tttaaaaggt cctgtgtctg aacctgagcc tgagcccgag   1260
ccagaaccgg agcctgcaag acctacccgc cgtcctaaaa tggcgcctgc tatcctgaga   1320
cgcccgacat cacctgtgtc tagagaatgc aatagtagta cggatagctg tgactccggt   1380
ccttctaaca cacctcctga gatacacccg gtggtcccgc tgtgccccat taaaccagtt   1440
gccgtgagag ttggtgggcg tcgccaggct gtggaatgta tcgaggactt gcttaacgag   1500
cctgggcaac ctttggactt gagctgtaaa cgccccaggc cataaggtgt aaacctgtga   1560
ttgcgtgtgt ggttaacgcc tttgtttgct gaatgagttg atgtaagttt aataaagggt   1620
gagataatgt ttaacttgca tggcgtgtta aatggggcgg ggcttaaagg gtatataatg   1680
cgccgtgggc taatcttggt tacatctgac ctcatggagg cttgggagtg tttggaagat   1740
ttttctgctg tgcgtaactt gctggaacag agctctaaca gtacctcttg gttttggagg   1800
tttctgtggg gctcatccca ggcaaagtta gtctgcagaa ttaaggagga ttacaagtgg   1860
gaatttgaag agcttttgaa atcctgtggt gagctgtttg attctttgaa tctgggtcac   1920
caggcgcttt tccaagagaa ggtcatcaag actttggatt tttccacacc ggggcgcgct   1980
gcggctgctg ttgctttttt gagttttata aaggataaat ggagcgaaga aacccatctg   2040
agcggggggt acctgctgga ttttctggcc atgcatctgt ggagagcggt tgtgagacac   2100
aagaatcgcc tgctactgtt gtcttccgtc cgcccggcga taataccgac ggaggagcag   2160
cagcagcagc aggaggaagc caggcggcgg cggcaggagc agagcccatg gaacccgaga   2220
gccggcctgg accctcggga atgaatgttg tacaggtggc tgaactgtat ccagaactga   2280
```

-continued

```
gacgcatttt gacaattaca gaggatgggc aggggctaaa gggggtaaag agggagcggg   2340
gggcttgtga ggctacagag gaggctagga atctagcttt tagcttaatg accagacacc   2400
gtcctgagtg tattactttt caacagatca aggataattg cgctaatgag cttgatctgc   2460
tggcgcagaa gtattccata gagcagctga ccacttactg gctgcagcca ggggatgatt   2520
ttgaggaggc tattagggta tatgcaaagg tggcacttag gccagattgc aagtacaaga   2580
tcagcaaact tgtaaatatc aggaattgtt gctacatttc tgggaacggg gccgaggtgg   2640
agatagatac ggaggatagg gtggccttta gatgtagcat gataaatatg tggccggggg   2700
tgcttggcat ggacggggtg gttattatga atgtaaggtt tactggcccc aattttagcg   2760
gtacggtttt cctggccaat accaacctta tcctacacgg tgtaagcttc tatgggttta   2820
acaatacctg tgtggaagcc tggaccgatg taagggttcg ggctgtgcc ttttactgct    2880
gctggaaggg ggtggtgtgt cgccccaaaa gcagggcttc aattaagaaa tgcctctttg   2940
aaaggtgtac cttgggtatc ctgtctgagg gtaactccag ggtgcgccac aatgtggcct   3000
ccgactgtgg ttgcttcatg ctagtgaaaa gcgtggctgt gattaagcat aacatggtat   3060
gtggcaactg cgaggacagg gcctctcaga tgctgacctg ctcggacggc aactgtcacc   3120
tgctgaagac cattcacgta gccagccact ctcgcaaggc ctggccagtg tttgagcata   3180
acatactgac ccgctgttcc ttgcatttgg gtaacaggag gggggtgttc ctaccttacc   3240
aatgcaattt gagtcacact aagatattgc ttgagcccga gagcatgtcc aaggtgaacc   3300
tgaacggggt gtttgacatg accatgaaga tctggaaggt gctgaggtac gatgagaccc   3360
gcaccaggtg cagaccctgc gagtgtggcg gtaaacatat taggaaccag cctgtgatgc   3420
tggatgtgac cgaggagctg aggcccgatc acttggtgct ggcctgcacc cgcgctgagt   3480
ttggctctag cgatgaagat acagattgag gtactgaaat gtgtgggcgt ggcttaaggg   3540
tgggaaagaa tatataaggt gggggtctta tgtagttttg tatctgtttt gcagcagccg   3600
ccgccgccat gagcaccaac tcgtttgatg gaagcattgt gagctcatat ttgacaacgc   3660
gcatgccccc atgggccggg gtgcgtcaga atgtgatggg ctccagcatt gatggtcgcc   3720
ccgtcctgcc cgcaaactct actaccttga cctacgagac cgtgtctgga acgccgttgg   3780
agactgcagc ctccgccgcc gcttcagccg ctgcagccac cgcccgcggg attgtgactg   3840
actttgcttt cctgagcccg cttgcaagca gtgcagcttc ccgttcatcc gcccgcgatg   3900
acaagttgac ggctcttttg gcacaattgg attctttgac ccgggaactt aatgtcgttt   3960
ctcagcagct gttggatctg cgccagcagg tttctgccct gaaggcttcc tcccctccca   4020
atgcggttta aaacataaat aaaaaaccag actctgtttg gatttggatc aagcaagtgt   4080
cttgctgtct ttatttaggg gttttgcgcg cgcggtaggc ccgggaccag cggtctcggt   4140
cgttgagggt cctgtgtatt ttttccagga cgtggtaaag gtgactctgg atgttcagat   4200
acatgggcat aagcccgtct ctggggtgga ggtagcacca ctgcagagct tcatgctgcg   4260
gggtggtgtt gtagatgatc cagtcgtagc aggagcgctg ggcgtggtgc ctaaaaatgt   4320
ctttcagtag caagctgatt gccaggggca ggcccttggt gtaagtgttt acaaagcggt   4380
taagctggga tgggtgcata cgtggggata tgagatgcat cttggactgt atttttaggt   4440
tggctatgtt cccagccata tccctccggg gattcatgtt gtgcagaacc accagcacag   4500
tgtatccggt gcacttggga aatttgtcat gtagcttaga aggaaatgcg tggaagaact   4560
tggagacgcc cttgtgacct ccaagatttt ccatgcattc gtccataatg atggcaatgg   4620
gcccacgggc ggcggcctgg gcgaagatat ttctgggatc actaacgtca tagttgtgtt   4680
```

-continued

```
ccaggatgag atcgtcatag gccattttta caaagcgcgg gcggagggtg ccagactgcg   4740
gtataatggt tccatccggc ccaggggcgt agttaccctc acagatttgc atttcccacg   4800
ctttgagttc agatgggggg atcatgtcta cctgcggggc gatgaagaaa acggtttccg   4860
gggtagggga gatcagctgg gaagaaagca ggttcctgag cagctgcgac ttaccgcagc   4920
cggtgggccc gtaaatcaca cctattaccg ggtgcaactg gtagttaaga gagctgcagc   4980
tgccgtcatc cctgagcagg ggggccactt cgttaagcat gtccctgact cgcatgtttt   5040
ccctgaccaa atccgccaga aggcgctcgc cgcccagcga tagcagttct tgcaaggaag   5100
caaagttttt caacggtttg agaccgtccg ccgtaggcat gcttttgagc gtttgaccaa   5160
gcagttccag gcggtcccac agctcggtca cctgctctac ggcatctcga tccagcatat   5220
ctcctcgttt cgcgggttgg ggcggctttc gctgtacggc agtagtcggt gctcgtccag   5280
acgggccagg gtcatgtctt tccacgggcg cagggtcctc gtcagcgtag tctgggtcac   5340
ggtgaagggg tgcgctccgg gctgcgcgct ggccagggtg cgcttgaggc tggtcctgct   5400
ggtgctgaag cgctgccggt cttcgccctg cgcgtcggcc aggtagcatt tgaccatggt   5460
gtcatagtcc agcccctccg cggcgtggcc cttggcgcgc agcttgccct tggaggaggc   5520
gccgcacgag gggcagtgca gacttttgag ggcgtagagc ttgggcgcga gaaataccga   5580
ttccggggag taggcatccg cgccgcaggc cccgcagacg gtctcgcatt ccacgagcca   5640
ggtgagctct ggccgttcgg ggtcaaaaac caggtttccc ccatgctttt tgatgcgttt   5700
cttacctctg gtttccatga gccggtgtcc acgctcggtg acgaaaaggc tgtccgtgtc   5760
cccgtataca gacttgagag gcctgtcctc gagcggtgtt ccgcggtcct cctcgtatag   5820
aaactcggac cactctgaga caaaggctcg cgtccaggcc agcacgaagg aggctaagtg   5880
ggaggggtag cggtcgttgt ccactagggg gtccactcgc tccagggtgt gaagacacat   5940
gtcgccctct tcggcatcaa ggaaggtgat tggtttgtag gtgtaggcca cgtgaccggg   6000
tgttcctgaa ggggggctat aaaagggggt gggggcgcgt tcgtcctcac tctcttccgc   6060
atcgctgtct gcgagggcca gctgttgggg tgagtactcc ctctgaaaag cgggcatgac   6120
ttctgcgcta agattgtcag tttccaaaaa cgaggaggat ttgatattca cctggcccgc   6180
ggtgatgcct ttgagggtgg ccgcatccat ctggtcagaa aagacaatct ttttgttgtc   6240
aagcttggtg gcaaacgacc cgtagagggc gttggacagc aacttggcga tggagcgcag   6300
ggtttggttt ttgtcgcgat cggcgcgctc cttggccgcg atgtttagct gcacgtattc   6360
gcgcgcaacg caccgccatt cgggaaagac ggtggtgcgc tcgtcgggca ccaggtgcac   6420
gcgccaaccg cggttgtgca gggtgacaag gtcaacgctg gtggctacct ctccgcgtag   6480
gcgctcgttg gtccagcaga ggcggccgcc cttgcgcgag cagaatggcg gtagggggtc   6540
tagctgcgtc tcgtccgggg ggtctgcgtc cacggtaaag accccgggca gcaggcgcgc   6600
gtcgaagtag tctatcttgc atccttgcaa gtctagcgcc tgctgccatg cgcgggcggc   6660
aagcgcgcgc tcgtatgggt tgagtggggg accccatggc atggggtggg tgagcgcgga   6720
ggcgtacatg ccgcaaatgt cgtaaacgta gaggggctct ctgagtattc caagatatgt   6780
agggtagcat cttccaccgc ggatgctggc gcgcacgtaa tcgtatagtt cgtgcgaggg   6840
agcgaggagg tcgggaccga ggttgctacg ggcgggctgc tctgctcgga agactatctg   6900
cctgaagatg gcatgtgagt tggatgatat ggttggacgc tggaagacgt tgaagctggc   6960
gtctgtgaga cctaccgcgt cacgcacgaa ggaggcgtag gagtcgcgca gcttgttgac   7020
```

-continued cagctcggcg gtgacctgca cgtctagggc gcagtagtcc agggtttcct tgatgatgtc 7080
atacttatcc tgtccctttt ttttccacag ctcgcggttg aggacaaact cttcgcggtc 7140
tttccagtac tcttggatcg gaaacccgtc ggcctccgaa cggtaagagc ctagcatgta 7200
gaactggttg acggcctggt aggcgcagca tcccttttct acgggtagcg cgtatgcctg 7260
cgcggccttc cggagcgagg tgtgggtgag cgcaaaggtg tccctgacca tgactttgag 7320
gtactggtat ttgaagtcag tgtcgtcgca tccgccctgc tcccagagca aaaagtccgt 7380
gcgctttttg gaacgcggat ttggcagggc gaaggtgaca tcgttgaaga gtatctttcc 7440
cgcgcgaggc ataaagttgc gtgtgatgcg gaagggtccc ggcacctcgg aacggttgtt 7500
aattacctgg gcggcgagca cgatctcgtc aaagccgttg atgttgtggc ccacaatgta 7560
aagttccaag aagcgcggga tgcccttgat ggaaggcaat tttttaagtt cctcgtaggt 7620
gagctcttca ggggagctga gcccgtgctc tgaaagggcc cagtctgcaa gatgagggtt 7680
ggaagcgacg aatgagctcc acaggtcacg ggccattagc atttgcaggt ggtcgcgaaa 7740
ggtcctaaac tggcgaccta tggccatttt ttctggggtg atgcagtaga aggtaagcgg 7800
gtcttgttcc cagcggtccc atccaaggtt cgcggctagg tctcgcgcgg cagtcactag 7860
aggctcatct ccgccgaact tcatgaccag catgaagggc acgagctgct tcccaaaggc 7920
ccccatccaa gtataggtct ctacatcgta ggtgacaaag agacgctcgg tgcgaggatg 7980
cgagccgatc gggaagaact ggatctcccg ccaccaattg gaggagtggc tattgatgtg 8040
gtgaaagtag aagtccctgc gacgggccga acactcgtgc tggcttttgt aaaaacgtgc 8100
gcagtactgg cagcggtgca cgggctgtac atcctgcacg aggttgacct gacgaccgcg 8160
cacaaggaag cagagtggga atttgagccc ctcgcctggc gggtttggct ggtggtcttc 8220
tacttcggct gcttgtcctt gaccgtctgg ctgctcgagg ggagttacgg tggatcggac 8280
caccacgccg cgcgagccca aagtccagat gtccgcgcgc ggcggtcgga gcttgatgac 8340
aacatcgcgc agatgggagc tgtccatggt ctggagctcc cgcggcgtca ggtcaggcgg 8400
gagctcctgc aggtttacct cgcatagacg ggtcagggcg cgggctagat ccaggtgata 8460
cctaatttcc aggggctggt tggtggcggc gtcgatggct tgcaagaggc cgcatccccg 8520
cggcgcgact acggtaccgc gcggcgggcg gtgggccgcg ggggtgtcct tggatgatgc 8580
atctaaaagc ggtgacgcgg gcgagccccc ggaggtaggg ggggctccgg acccgccggg 8640
agagggggca ggggcacgtc ggcgccgcgc gcgggcagga gctggtgctg cgcgcgtagg 8700
ttgctggcga acgcgacgac gcggcggttg atctcctgaa tctggcgcct ctgcgtgaag 8760
acgacgggcc cggtgagctt gagcctgaaa gagagttcga cagaatcaat ttcggtgtcg 8820
ttgacggcgg cctggcgcaa aatctcctgc acgtctcctg agttgtcttg ataggcgatc 8880
tcggccatga actgctcgat ctcttcctcc tggagatctc cgcgtccggc tcgctccacg 8940
gtggcggcga ggtcgttgga aatgcgggcc atgagctgcg agaaggcgtt gaggcctccc 9000
tcgttccaga cgcggctgta gaccacgccc ccttcggcat cgcgggcgcg catgaccacc 9060
tgcgcgagat tgagctccac gtgccgggcg aagacggcgt agtttcgcag gcgctgaaag 9120
aggtagttga gggtggtggc ggtgtgttct gccacgaaga agtacataac ccagcgtcgc 9180
aacgtggatt cgttgatatc ccccaaggcc tcaaggcgct ccatggcctc gtagaagtcc 9240
acggcgaagt tgaaaaactg ggagttgcgc gccgacacgg ttaactcctc ctccagaaga 9300
cggatgagct cggcgacagt gtcgcgcacc tcgcgctcaa aggctacagg ggcctcttct 9360
tcttcttcaa tctcctcttc cataagggcc tccccttctt cttcttctgg cggcggtggg 9420

-continued

```
ggagggggga cacggcggcg acgacggcgc accgggaggc ggtcgacaaa gcgctcgatc   9480
atctccccgc ggcgacggcg catggtctcg gtgacggcgc ggccgttctc gcgggggcgc   9540
agttggaaga cgccgcccgt catgtcccgg ttatgggttg gcggggggct gccatgcggc   9600
agggatacgg cgctaacgat gcatctcaac aattgttgtg taggtactcc gccgccgagg   9660
gacctgagcg agtccgcatc gaccggatcg gaaaacctct cgagaaaggc gtctaaccag   9720
tcacagtcgc aaggtaggct gagcaccgtg gcgggcggca gcgggcggcg gtcggggttg   9780
tttctggcgg aggtgctgct gatgatgtaa ttaaagtagg cggtcttgag acggcggatg   9840
gtcgacagaa gcaccatgtc cttgggtccg gcctgctgaa tgcgcaggcg gtcggccatg   9900
ccccaggctt cgttttgaca tcggcgcagg tctttgtagt agtcttgcat gagcctttct   9960
accggcactt cttcttctcc ttcctcttgt cctgcatctc ttgcatctat cgctgcggcg  10020
gcggcggagt ttggccgtag gtggcgccct cttcctccca tgcgtgtgac cccgaagccc  10080
ctcatcggct gaagcagggc taggtcggcg acaacgcgct cggctaatat ggcctgctgc  10140
acctgcgtga gggtagactg gaagtcatcc atgtccacaa agcggtggta tgcgcccgtg  10200
ttgatggtgt aagtgcagtt ggccataacg gaccagttaa cggtctggtg acccggctgc  10260
gagagctcgg tgtacctgag acgcgagtaa gccctcgagt caaatacgta gtcgttgcaa  10320
gtccgcacca ggtactggta tcccaccaaa aagtgcggcg gcggctggcg gtagaggggc  10380
cagcgtaggg tggccggggc tccgggggcg agatcttcca acataaggcg atgatatccg  10440
tagatgtacc tggacatcca ggtgatgccg gcggcggtgg tggaggcgcg cggaaagtcg  10500
cggacgcggt tccagatgtt gcgcagcggc aaaaagtgct ccatggtcgg gacgctctgg  10560
ccggtcaggc gcgcgcaatc gttgacgctc tagaccgtgc aaaaggagag cctgtaagcg  10620
ggcactcttc cgtggtctgg tggataaatt cgcaagggta tcatggcgga cgaccggggt  10680
tcgagccccg tatccggccg tccgccgtga tccatgcggt taccgcccgc gtgtcgaacc  10740
caggtgtgcg acgtcagaca acgggggagt gctccttttg gcttccttcc aggcgcggcg  10800
gctgctgcgc tagctttttt ggccactggc cgcgcgcagc gtaagcggtt aggctggaaa  10860
gcgaaagcat taagtggctc gctccctgta gccggagggt tattttccaa gggttgagtc  10920
gcgggacccc cggttcgagt ctcggaccgg ccggactgcg gcgaacgggg gtttgcctcc  10980
ccgtcatgca agaccccgct tgcaaattcc tccggaaaca gggacgagcc cctttttgc   11040
ttttcccaga tgcatccggt gctgcggcag atgcgccccc ctcctcagca gcggcaagag  11100
caagagcagc ggcagacatg cagggcaccc tcccctcctc ctaccgcgtc aggaggggcg  11160
acatccgcgg ttgacgcggc agcagatggt gattacgaac cccgcggcg ccgggcccgg   11220
cactacctgg acttggagga gggcgagggc ctggcgcggc taggagcgcc ctctcctgag  11280
cggtacccaa gggtgcagct gaagcgtgat acgcgtgagg cgtacgtgcc gcggcagaac  11340
ctgtttcgcg accgcgaggg agaggagccc gaggagatgc gggatcgaaa gttccacgca  11400
gggcgcgagc tgcggcatgg cctgaatcgc gagcggttgc tgcgcgagga ggactttgag  11460
cccgacgcgc gaaccgggat tagtcccgcg cgcgcacacg tggcggccgc cgacctggta  11520
accgcatacg agcagacggt gaaccaggag attaactttc aaaaaagctt taacaaccac  11580
gtgcgtacgc ttgtggcgcg cgaggaggtg gctataggac tgatgcatct gtgggacttt  11640
gtaagcgcgc tggagcaaaa cccaaatagc aagccgctca tggcgcagct gttccttata  11700
gtgcagcaca gcagggacaa cgaggcattc agggatgcgc tgctaaacat agtagagccc  11760
```

-continued gagggccgct ggctgctcga tttgataaac atcctgcaga gcatagtggt gcaggagcgc 11820
agcttgagcc tggctgacaa ggtggccgcc atcaactatt ccatgcttag cctgggcaag 11880
ttttacgccc gcaagatata ccataccccct tacgttccca tagacaagga ggtaaagatc 11940
gaggggttct acatgcgcat ggcgctgaag gtgcttacct tgagcgacga cctgggcgtt 12000
tatcgcaacg agcgcatcca caaggccgtg agcgtgagcc ggcggcgcga gctcagcgac 12060
cgcgagctga tgcacagcct gcaaagggcc ctggctggca cgggcagcgg cgatagagag 12120
gccgagtcct actttgacgc gggcgctgac ctgcgctggg ccccaagccg acgcgccctg 12180
gaggcagctg gggccggacc tgggctggcg gtggcacccg cgcgcgctgg caacgtcggc 12240
ggcgtggagg aatatgacga ggacgatgag tacgagccag aggacggcga gtactaagcg 12300
gtgatgtttc tgatcagatg atgcaagacg caacggaccc ggcggtgcgg gcggcgctgc 12360
agagccagcc gtccggcctt aactccacgg acgactggcg ccaggtcatg gaccgcatca 12420
tgtcgctgac tgcgcgcaat cctgacgcgt tccggcagca gccgcaggcc aaccggctct 12480
ccgcaattct ggaagcggtg gtcccggcgc gcgcaaaccc cacgcacgag aaggtgctgg 12540
cgatcgtaaa cgcgctggcc gaaaacaggg ccatccggcc cgacgaggcc ggcctggtct 12600
acgacgcgct gcttcagcgc gtggctcgtt acaacagcgg caacgtgcag accaacctgg 12660
accggctggt gggggatgtg cgcgaggccg tggcgcagcg tgagcgcgcg cagcagcagg 12720
gcaacctggg ctccatggtt gcactaaacg ccttcctgag tacacagccc gccaacgtgc 12780
cgcggggaca ggaggactac accaactttg tgagcgcact gcggctaatg gtgactgaga 12840
caccgcaaag tgaggtgtac cagtctgggc cagactattt tttccagacc agtagacaag 12900
gcctgcagac cgtaaacctg agccaggctt tcaaaaactt gcaggggctg tggggggtgc 12960
gggctcccac aggcgaccgc gcgaccgtgt ctagcttgct gacgcccaac tcgcgcctgt 13020
tgctgctgct aatagcgccc ttcacggaca gtggcagcgt gtcccgggac acatacctag 13080
gtcacttgct gacactgtac cgcgaggcca taggtcaggc gcatgtggac gagcatactt 13140
tccaggagat tacaagtgtc agccgcgcgc tggggcagga ggacacgggc agcctggagg 13200
caaccctaaa ctacctgctg accaaccggc ggcagaagat cccctcgttg cacagtttaa 13260
acagcgagga ggagcgcatt ttgcgctacg tgcagcagag cgtgagcctt aacctgatgc 13320
gcgacggggt aacgcccagc gtggcgctgg acatgaccgc gcgcaacatg gaaccgggca 13380
tgtatgcctc aaaccggccg tttatcaacc gcctaatgga ctacttgcat cgcgcggccg 13440
ccgtgaaccc cgagtatttc accaatgcca tcttgaaccc gcactggcta ccgccccctg 13500
gtttctacac cgggggattc gaggtgcccg agggtaacga tggattcctc tgggacgaca 13560
tagacgacag cgtgttttcc ccgcaaccgc agaccctgct agagttgcaa cagcgcgagc 13620
aggcagaggc ggcgctgcga aaggaaagct tccgcaggcc aagcagcttg tccgatctag 13680
gcgctgcggc cccgcggtca gatgctagta gcccatttcc aagcttgata gggtctctta 13740
ccagcactcg caccacccgc ccgcgcctgc tgggcgagga ggagtaccta aacaactcgc 13800
tgctgcagcc gcagcgcgaa aaaaacctgc ctccggcatt tcccaacaac gggatagaga 13860
gcctagtgga caagatgagt agatggaaga cgtacgcgca ggagcacagg gacgtgccag 13920
gcccgcgccc gcccacccgt cgtcaaaggc acgaccgtca gcggggtctg gtgtgggagg 13980
acgatgactc ggcagacgac agcagcgtcc tggatttggg agggagtggc aacccgtttg 14040
cgcaccttcg ccccaggctg gggagaatgt tttaaaaaaa aaaaagcatg atgcaaaata 14100
aaaaactcac caaggccatg gcaccgagcg ttggttttct tgtattcccc ttagtatgcg 14160

-continued gcgcgcggcg atgtatgagg aaggtcctcc tccctcctac gagagtgtgg tgagcgcggc 14220
gccagtggcg gcggcgctgg gttctccctt cgatgctccc ctggacccgc cgtttgtgcc 14280
tccgcggtac ctgcggccta ccgggggggag aaacagcatc cgttactctg agttggcacc 14340
cctattcgac accacccgtg tgtacctggt ggacaacaag tcaacggatg tggcatccct 14400
gaactaccag aacgaccaca gcaactttct gaccacggtc attcaaaaca atgactacag 14460
cccgggggag gcaagcacac agaccatcaa tcttgacgac cggtcgcact ggggcggcga 14520
cctgaaaacc atcctgcata ccaacatgcc aaatgtgaac gagttcatgt ttaccaataa 14580
gtttaaggcg cgggtgatgg tgtcgcgctt gcctactaag gacaatcagg tggagctgaa 14640
atacgagtgg gtggagttca cgctgcccga gggcaactac tccgagacca tgaccataga 14700
ccttatgaac aacgcgatcg tggagcacta cttgaaagtg ggcagacaga acggggttct 14760
ggaaagcgac atcggggtaa agtttgacac ccgcaacttc agactggggt ttgaccccgt 14820
cactggtctt gtcatgcctg ggtatatac aaacgaagcc ttccatccag acatcatttt 14880
gctgccagga tgcggggtgg acttcaccca cagccgcctg agcaacttgt tgggcatccg 14940
caagcggcaa cccttccagg agggctttag gatcacctac gatgatctgg agggtggtaa 15000
cattcccgca ctgttggatg tggacgccta ccaggcgagc ttgaaagatg acaccgaaca 15060
gggcgggggt ggcgcaggcg gcagcaacag cagtggcagc ggcgcggaag agaactccaa 15120
cgcggcagcc gcggcaatgc agccggtgga ggacatgaac gatcatgcca ttcgcggcga 15180
cacctttgcc acacgggctg aggagaagcg cgctgaggcc gaagcagcgg ccgaagctgc 15240
cgcccccgct gcgcaacccg aggtcgagaa gcctcagaag aaaccggtga tcaaacccct 15300
gacagaggac agcaagaaac gcagttacaa cctaataagc aatgacagca ccttcaccca 15360
gtaccgcagc tggtaccttg catacaacta cggcgaccct cagaccggaa tccgctcatg 15420
gaccctgctt tgcactcctg acgtaacctg cggctcggag caggtctact ggtcgttgcc 15480
agacatgatg caagaccccg tgaccttccg ctccacgcgc cagatcagca actttccggt 15540
ggtgggcgcc gagctgttgc ccgtgcactc caagagcttc tacaacgacc aggccgtcta 15600
ctcccaactc atccgccagt ttacctctct gacccacgtg ttcaatcgct ttcccgagaa 15660
ccagattttg gcgcgcccgc cagcccccac catcaccacc gtcagtgaaa acgttcctgc 15720
tctcacagat cacgggacgc taccgctgcg caacagcatc ggaggagtcc agcgagtgac 15780
cattactgac gccagacgcc gcacctgccc ctacgtttac aaggccctgg gcatagtctc 15840
gccgcgcgtc ctatcgagcc gcactttttg agcaagcatg tccatcctta tatcgcccag 15900
caataacaca ggctggggcc tgcgcttccc aagcaagatg tttggcgggg ccaagaagcg 15960
ctccgaccaa cacccagtgc gcgtgcgcgg gcactaccgc gcgccctggg gcgcgcacaa 16020
acgcggccgc actgggcgca ccaccgtcga tgacgccatc gacgcggtgg tggaggaggc 16080
gcgcaactac acgcccacgc cgccaccagt gtccacagtg gacgcggcca ttcagaccgt 16140
ggtgcgcgga gcccggcgct atgctaaaat gaagagacgg cggaggcgcg tagcacgtcg 16200
ccaccgccgc cgacccggca ctgccgccca acgcgcggcg gcggccctgc ttaaccgcgc 16260
acgtcgcacc ggccgacggg cggccatgcg ggccgctcga aggctggccg cgggtattgt 16320
cactgtgccc cccaggtcca ggcgacgagc ggccgccgca gcagccgcgg ccattagtgc 16380
tatgactcag ggtcgcaggg gcaacgtgta ttgggtgcgc gactcggtta gcggcctgcg 16440
cgtgcccgtg cgcacccgcc ccccgcgcaa ctagattgca agaaaaaact acttagactc 16500

-continued

```
gtactgttgt atgtatccag cggcggcggc gcgcaacgaa gctatgtcca agcgcaaaat  16560
caaagaagag atgctccagg tcatcgcgcc ggagatctat ggcccccga agaaggaaga  16620
gcaggattac aagccccgaa agctaaagcg ggtcaaaaag aaaaagaaag atgatgatga  16680
tgaacttgac gacgaggtgg aactgctgca cgctaccgcg cccaggcgac gggtacagtg  16740
gaaaggtcga cgcgtaaaac gtgttttgcg acccggcacc accgtagtct ttacgcccgg  16800
tgagcgctcc acccgcacct acaagcgcgt gtatgatgag gtgtacggcg acgaggacct  16860
gcttgagcag gccaacgagc gcctcgggga gtttgcctac ggaaagcggc ataaggacat  16920
gctggcgttg ccgctggacg agggcaaccc aacacctagc ctaaagcccg taacactgca  16980
gcaggtgctg cccgcgcttg caccgtccga agaaaagcgc ggcctaaagc gcgagtctgg  17040
tgacttggca cccaccgtgc agctgatggt acccaagcgc cagcgactgg aagatgtctt  17100
ggaaaaaatg accgtggaac ctgggctgga gcccgaggtc cgcgtgcggc caatcaagca  17160
ggtggcgccg ggactgggcg tgcagaccgt ggacgttcag atacccacta ccagtagcac  17220
cagtattgcc accgccacag agggcatgga gacacaaacg tccccggttg cctcagcggt  17280
ggcggatgcc gcggtgcagg cggtcgctgc ggccgcgtcc aagacctcta cggaggtgca  17340
aacggacccg tggatgtttc gcgtttcagc cccccggcgc ccgcgcggtt cgaggaagta  17400
cggcgccgcc agcgcgctac tgcccgaata tgccctacat ccttccattg cgcctacccc  17460
cggctatcgt ggctacacct accgccccag aagacgagca actacccgac gccgaaccac  17520
cactggaacc cgccgccgcc gtcgccgtcg ccagcccgtg ctggccccga tttccgtgcg  17580
cagggtggct cgcgaaggag gcaggaccct ggtgctgcca acagcgcgct accaccccag  17640
catcgtttaa aagccggtct ttgtggttct tgcagatatg gccctcacct gccgcctccg  17700
tttcccggtg ccgggattcc gaggaagaat gcaccgtagg aggggcatgg ccggccacgg  17760
cctgacgggc ggcatgcgtc gtgcgcacca ccggcggcgg cgcgcgtcgc accgtcgcat  17820
gcgcggcggt atcctgcccc tccttattcc actgatcgcc gcggcgattg gcgccgtgcc  17880
cggaattgca tccgtggcct tgcaggcgca gagacactga ttaaaaacaa gttgcatgtg  17940
gaaaaatcaa aataaaaagt ctggactctc acgctcgctt ggtcctgtaa ctattttgta  18000
gaatggaaga catcaacttt gcgtctctgg ccccgcgaca cggctcgcgc ccgttcatgg  18060
gaaactggca agatatcggc accagcaata tgagcggtgg cgccttcagc tggggctcgc  18120
tgtggagcgg cattaaaaat ttcggttcca ccgttaagaa ctatggcagc aaggcctgga  18180
acagcagcac aggccagatg ctgagggata agttgaaaga gcaaaatttc caacaaaagg  18240
tggtagatgg cctggcctct ggcattagcg gggtggtgga cctggccaac caggcagtgc  18300
aaaataagat taacagtaag cttgatcccc gccctcccgt agaggagcct ccaccggccg  18360
tggagacagt gtctccagag ggcgtggcg aaaagcgtcc gcgccccgac agggaagaaa  18420
ctctggtgac gcaaatagac gagcctccct cgtacgagga ggcactaaag caaggcctgc  18480
ccaccacccg tcccatcgcg cccatggcta ccggagtgct gggccagcac acacccgtaa  18540
cgctggacct gcctcccccc gccgacaccc agcagaaacc tgtgctgcca ggcccgaccg  18600
ccgttgttgt aacccgtcct agccgcgcgt ccctgcgccg cgccgccagc ggtccgcgat  18660
cgttgcggcc cgtagccagt ggcaactggc aaagcacact gaacagcatc gtgggtctgg  18720
gggtgcaatc cctgaagcgc cgacgatgct tctgaatagc taacgtgtcg tatgtgtgtc  18780
atgtatgcgt ccatgtcgcc gccagaggag ctgctgagcc gccgcgcgcc cgctttccaa  18840
gatggctacc ccttcgatga tgccgcagtg gtcttacatg cacatctcgg gccaggacgc  18900
```

-continued

```
ctcggagtac ctgagccccg ggctggtgca gtttgcccgc gccaccgaga cgtacttcag  18960
cctgaataac aagtttagaa accccacggt ggcgcctacg cacgacgtga ccacagaccg  19020
gtcccagcgt ttgacgctgc ggttcatccc tgtggaccgt gaggatactg cgtactcgta  19080
caaggcgcgg ttcaccctag ctgtgggtga taaccgtgtg ctggacatgg cttccacgta  19140
ctttgacatc cgcggcgtgc tggacagggg ccctactttt aagccctact ctggcactgc  19200
ctacaacgcc ctggctccca agggtgcccc aaatccttgc gaatgggatg aagctgctac  19260
tgctcttgaa ataaacctag aagaagagga cgatgacaac gaagacgaag tagacgagca  19320
agctgagcag caaaaaactc acgtatttgg gcaggcgcct tattctggta taaatattac  19380
aaaggagggt attcaaatag gtgtcgaagg tcaaacacct aaatatgccg ataaaacatt  19440
tcaacctgaa cctcaaatag gagaatctca gtggtacgaa actgaaatta atcatgcagc  19500
tgggagagtc cttaaaaaga ctaccccaat gaaaccatgt tacggttcat atgcaaaacc  19560
cacaaatgaa aatggagggc aaggcattct tgtaaagcaa caaaatggaa agctagaaag  19620
tcaagtggaa atgcaatttt tctcaactac tgaggcgacc gcaggcaatg gtgataactt  19680
gactcctaaa gtggtattgt acagtgaaga tgtagatata gaaaccccag acactcatat  19740
ttcttacatg cccactatta aggaaggtaa ctcacgagaa ctaatgggcc aacaatctat  19800
gcccaacagg cctaattaca ttgcttttag ggacaatttt attggtctaa tgtattacaa  19860
cagcacgggt aatatgggtg ttctggcggg ccaagcatcg cagttgaatg ctgttgtaga  19920
tttgcaagac agaaacacag agctttcata ccagcttttg cttgattcca ttggtgatag  19980
aaccaggtac ttttctatgt ggaatcaggc tgttgacagc tatgatccag atgttagaat  20040
tattgaaaat catggaactg aagatgaact tccaaattac tgctttccac tgggaggtgt  20100
gattaataca gagactctta ccaaggtaaa acctaaaaca ggtcaggaaa atggatggga  20160
aaaagatgct acagaatttt cagataaaaa tgaaataaga gttggaaata attttgccat  20220
ggaaatcaat ctaaatgcca acctgtggag aaatttcctg tactccaaca tagcgctgta  20280
tttgcccgac aagctaaagt acagtccttc caacgtaaaa atttctgata acccaaacac  20340
ctacgactac atgaacaagc gagtggtggc tcccgggtta gtggactgct acattaacct  20400
tggagcacgc tggtcccttg actatatgga caacgtcaac ccatttaacc accaccgcaa  20460
tgctggcctg cgctaccgct caatgttgct gggcaatggt cgctatgtgc ccttccacat  20520
ccaggtgcct cagaagttct ttgccattaa aaacctcctt ctcctgccgg gctcatacac  20580
ctacgagtgg aacttcagga aggatgttaa catggttctg cagagctccc taggaaatga  20640
cctaagggtt gacggagcca gcattaagtt tgatagcatt tgcctttacg ccaccttctt  20700
ccccatggcc cacaacaccg cctccacgct tgaggccatg cttagaaacg acaccaacga  20760
ccagtccttt aacgactatc tctccgccgc caacatgctc taccctatac ccgccaacgc  20820
taccaacgtg cccatatcca tcccctcccg caactgggcg gctttccgcg gctgggcctt  20880
cacgcgcctt aagactaagg aaaccccatc actgggctcg ggctacgacc cttattacac  20940
ctactctggc tctataccct acctagatgg aaccttttac ctcaaccaca cctttaagaa  21000
ggtggccatt acctttgact cttctgtcag ctggcctggc aatgaccgcc tgcttacccc  21060
caacgagttt gaaattaagc gctcagttga cggggagggt tacaacgttg cccagtgtaa  21120
catgaccaaa gactggttcc tggtacaaat gctagctaac tacaacattg gctaccaggg  21180
cttctatatc ccagagagct acaaggaccg catgtactcc ttctttagaa acttccagcc  21240
```

-continued

```
catgagccgt caggtggtgg atgatactaa atacaaggac taccaacagg tgggcatcct  21300
acaccaacac aacaactctg gatttgttgg ctaccttgcc cccaccatgc gcgaaggaca  21360
ggcctaccct gctaacttcc cctatccgct tataggcaag accgcagttg acagcattac  21420
ccagaaaaag tttctttgcg atcgcaccct ttggcgcatc ccattctcca gtaactttat  21480
gtccatgggc gcactcacag acctgggcca aaaccttctc tacgccaact ccgcccacgc  21540
gctagacatg acttttgagg tggatcccat ggacgagccc acccttcttt atgttttgtt  21600
tgaagtcttt gacgtggtcc gtgtgcaccg gccgcaccgc ggcgtcatcg aaaccgtgta  21660
cctgcgcacg cccttctcgg ccggcaacgc cacaacataa agaagcaagc aacatcaaca  21720
acagctgccg ccatgggctc cagtgagcag gaactgaaag ccattgtcaa agatcttggt  21780
tgtgggccat atttttgggg cacctatgac aagcgctttc caggctttgt ttctccacac  21840
aagctcgcct gcgccatagt caatacggcc ggtcgcgaga ctgggggcgt acactggatg  21900
gcctttgcct ggaacccgca ctcaaaaaca tgctacctct ttgagccctt tggctttcct  21960
gaccagcgac tcaagcaggt ttaccagttt gagtacgagt cactcctgcg ccgtagcgcc  22020
attgcttctt cccccgaccg ctgtataacg ctggaaaagt ccacccaaag cgtacagggg  22080
cccaactcgg ccgcctgtgg actattctgc tgcatgtttc tccacgcctt tgccaactgg  22140
ccccaaactc ccatggatca caaccccacc atgaacctta ttaccggggt acccaactcc  22200
atgctcaaca gtccccaggt acagcccacc ctgcgtcgca accaggaaca gctctacagc  22260
ttcctggagc gccactcgcc ctacttccgc agccacagtg cgcagattag gagcgccact  22320
tctttttgtc acttgaaaaa catgtaaaaa taatgtacta gagacacttt caataaaggc  22380
aaatgctttt atttgtacac tctcgggtga ttatttaccc ccacccttgc cgtctgcgcc  22440
gtttaaaaat caaaggggtt ctgccgcgca tcgctatgcg ccactggcag ggacacgttg  22500
cgatactggt gtttagtgct ccacttaaac tcaggcacaa ccatccgcgg cagctcggtg  22560
aagttttcac tccacaggct gcgcaccatc accaacgcgt ttagcaggtc gggcgccgat  22620
atcttgaagt cgcagttggg gcctccgccc tgcgcgcgcg agttgcgata cacagggttg  22680
cagcactgga acactatcag cgccgggtgg tgcacgctgg ccagcacgct cttgtcggag  22740
atcagatccg cgtccaggtc ctccgcgttg ctcagggcga acggagtcaa ctttggtagc  22800
tgccttccca aaaagggcgc gtgcccaggc tttgagttgc actcgcaccg tagtggcatc  22860
aaaaggtgac cgtgcccggt ctgggcgtta ggatacagcg cctgcataaa agccttgatc  22920
tgcttaaaag ccacctgagc ctttgcgcct tcagagaaga acatgccgca agacttgccg  22980
gaaaactgat tggccggaca ggccgcgtcg tgcacgcagc accttgcgtc ggtgttggag  23040
atctgcacca catttcggcc ccaccggttc ttcacgatct tggccttgct agactgctcc  23100
ttcagcgcgc gctgcccgtt ttcgctcgtc acatccattt caatcacgtg ctccttattt  23160
atcataatgc ttccgtgtag acacttaagc tcgccttcga tctcagcgca gcggtgcagc  23220
cacaacgcgc agcccgtggg ctcgtgatgc ttgtaggtca cctctgcaaa cgactgcagg  23280
tacgcctgca ggaatcgccc catcatcgtc acaaaggtct tgttgctggt gaaggtcagc  23340
tgcaacccgc ggtgctcctc gttcagccag gtcttgcata cggccgccag agcttccact  23400
tggtcaggca gtagtttgaa gttcgccttt agatcgttat ccacgtggta cttgtccatc  23460
agcgcgcgcg cagcctccat gcccttctcc cacgcagaca cgatcggcac actcagcggg  23520
ttcatcaccg taatttcact ttccgcttcg ctgggctctt cctcttcctc ttgcgtccgc  23580
ataccacgcg ccactgggtc gtcttcattc agccgccgca ctgtgcgctt acctcctttg  23640
```

-continued

```
ccatgcttga ttagcaccgg tgggttgctg aaacccacca tttgtagcgc cacatcttct  23700
ctttcttcct cgctgtccac gattacctct ggtgatggcg ggcgctcggg cttgggagaa  23760
gggcgcttct ttttcttctt gggcgcaatg gccaaatccg ccgccgaggt cgatggccgc  23820
gggctgggtg tgcgcggcac cagcgcgtct tgtgatgagt cttcctcgtc ctcggactcg  23880
atacgccgcc tcatccgctt ttttgggggc gcccggggag gcggcggcga cggggacggg  23940
gacgacacgt cctccatggt tgggggacgt cgcgccgcac cgcgtccgcg ctcgggggtg  24000
gtttcgcgct gctcctcttc ccgactggcc atttccttct cctataggca gaaaaagatc  24060
atggagtcag tcgagaagaa ggacagccta accgccccct ctgagttcgc caccaccgcc  24120
tccaccgatg ccgccaacgc gcctaccacc ttccccgtcg aggcaccccc gcttgaggag  24180
gaggaagtga ttatcgagca ggacccaggt tttgtaagcg aagacgacga ggaccgctca  24240
gtaccaacag aggataaaaa gcaagaccag gacaacgcag aggcaaacga ggaacaagtc  24300
gggcgggggg acgaaaggca tggcgactac ctagatgtgg gagacgacgt gctgttgaag  24360
catctgcagc gccagtgcgc cattatctgc gacgcgttgc aagagcgcag cgatgtgccc  24420
ctcgccatag cggatgtcag ccttgcctac gaacgccacc tattctcacc gcgcgtaccc  24480
cccaaacgcc aagaaaacgg cacatgcgag cccaacccgc gcctcaactt ctaccccgta  24540
tttgccgtgc cagaggtgct tgccacctat cacatctttt tccaaaactg caagataccc  24600
ctatcctgcc gtgccaaccg cagccgagcg gacaagcagc tggccttgcg gcagggcgct  24660
gtcatacctg atatcgcctc gctcaacgaa gtgccaaaaa tctttgaggg tcttggacgc  24720
gacgagaagc gcgcggcaaa cgctctgcaa caggaaaaca gcgaaaatga aagtcactct  24780
ggagtgttgg tggaactcga gggtgacaac gcgcgcctag ccgtactaaa acgcagcatc  24840
gaggtcaccc actttgccta cccggcactt aacctacccc ccaaggtcat gagcacagtc  24900
atgagtgagc tgatcgtgcg ccgtgcgcag cccctggaga gggatgcaaa tttgcaagaa  24960
caaacagagg agggcctacc cgcagttggc gacgagcagc tagcgcgctg gcttcaaacg  25020
cgcgagcctg ccgacttgga ggagcgacgc aaactaatga tggccgcagt gctcgttacc  25080
gtggagcttg agtgcatgca gcggttcttt gctgacccgg agatgcagcg caagctagag  25140
gaaacattgc actacacctt tcgacagggc tacgtacgcc aggcctgcaa gatctccaac  25200
gtggagctct gcaacctggt ctcctacctt ggaattttgc acgaaaaccg ccttgggcaa  25260
aacgtgcttc attccacgct caagggcgag gcgcgccgcg actacgtccg cgactgcgtt  25320
tacttatttc tatgctacac ctggcagacg gccatgggcg tttggcagca gtgcttggag  25380
gagtgcaacc tcaaggagct gcagaaactg ctaaagcaaa acttgaagga cctatggacg  25440
gccttcaacg agcgctccgt ggccgcgcac ctggcggaca tcattttccc cgaacgcctg  25500
cttaaaaccc tgcaacaggg tctgccagac ttcaccagtc aaagcatgtt gcagaacttt  25560
aggaacttta tcctagagcg ctcaggaatc ttgcccgcca cctgctgtgc acttcctagc  25620
gactttgtgc ccattaagta ccgcgaatgc cctccgccgc tttggggcca ctgctacctt  25680
ctgcagctag ccaactacct tgcctaccac tctgacataa tggaagacgt gagcggtgac  25740
ggtctactgg agtgtcactg tcgctgcaac ctatgcaccc cgcaccgctc cctggtttgc  25800
aattcgcagc tgcttaacga aagtcaaatt atcggtacct ttgagctgca gggtccctcg  25860
cctgacgaaa agtccgcggc tccggggttg aaactcactc cggggctgtg gacgtcggct  25920
taccttcgca aatttgtacc tgaggactac cacgcccacg agattaggtt ctacgaagac  25980
```

-continued

```
caatcccgcc cgccaaatgc ggagcttacc gcctgcgtca ttacccaggg ccacattctt  26040

ggccaattgc aagccatcaa caaagcccgc caagagtttc tgctacgaaa gggacggggg  26100

gtttacttgg acccccagtc cggcgaggag ctcaacccaa tccccccgcc gccgcagccc  26160

tatcagcagc agccgcgggc ccttgcttcc caggatggca cccaaaaaga agctgcagct  26220

gccgccgcca cccacggacg aggaggaata ctgggacagt caggcagagg aggttttgga  26280

cgaggaggag gaggacatga tggaagactg ggagagccta gacgaggaag cttccgaggt  26340

cgaagaggtg tcagacgaaa caccgtcacc ctcggtcgca ttcccctcgc cggcgcccca  26400

gaaatcggca accggttcca gcatggctac aacctccgct cctcaggcgc cgccggcact  26460

gcccgttcgc cgacccaacc gtagatggga caccactgga accagggccg gtaagtccaa  26520

gcagccgccg ccgttagccc aagagcaaca acagcgccaa ggctaccgct catggcgcgg  26580

gcacaagaac gccatagttg cttgcttgca agactgtggg ggcaacatct ccttcgcccg  26640

ccgctttctt ctctaccatc acggcgtggc cttcccccgt aacatcctgc attactaccg  26700

tcatctctac agcccatact gcaccggcgg cagcggcagc ggcagcaaca gcagcggcca  26760

cacagaagca aaggcgaccg gatagcaaga ctctgacaaa gcccaagaaa tccacagcgg  26820

cggcagcagc aggaggagga gcgctgcgtc tggcgcccaa cgaacccgta tcgacccgcg  26880

agcttagaaa caggattttt cccactctgt atgctatatt tcaacagagc aggggccaag  26940

aacaagagct gaaaataaaa aacaggtctc tgcgatccct cacccgcagc tgcctgtatc  27000

acaaaagcga agatcagctt cggcgcacgc tggaagacgc ggaggctctc ttcagtaaat  27060

actgcgcgct gactcttaag gactagtttc gcgccctttc tcaaatttaa gcgcgaaaac  27120

tacgtcatct ccagcggcca cacccggcgc cagcacctgt cgtcagcgcc attatgagca  27180

aggaaattcc cacgccctac atgtggagtt accagccaca aatgggactt gcggctggag  27240

ctgcccaaga ctactcaacc cgaataaact acatgagcgc gggaccccac atgatatccc  27300

gggtcaacgg aatccgcgcc caccgaaacc gaattctctt ggaacaggcg gctattacca  27360

ccacacctcg taataacctt aatccccgta gttggcccgc tgccctggtg taccaggaaa  27420

gtcccgctcc caccactgtg gtacttccca gagacgccca ggccgaagtt cagatgacta  27480

actcaggggc gcagcttgcg ggcggctttc gtcacagggt gcggtcgccc gggcagggta  27540

taactcacct gacaatcaga gggcgaggta ttcagctcaa cgacgagtcg gtgagctcct  27600

cgcttggtct ccgtccggac gggacatttc agatcggcgg cgccggccgt ccttcattca  27660

cgcctcgtca ggcaatccta actctgcaga cctcgtcctc tgagccgcgc tctggaggca  27720

ttggaactct gcaatttatt gaggagtttg tgccatcggt ctactttaac cccttctcgg  27780

gacctcccgg ccactatccg gatcaattta ttcctaactt tgacgcggta aaggactcgg  27840

cggacggcta cgactgataa ttaagtggag aggcagagca actgcgcctg aaacacctgg  27900

tccactgtcg ccgccacaag tgctttgccc gcgactccgg tgagttttgc tactttgaat  27960

tgcccgagga tcatatcgag gatctttgtt gccatctctg tgctgagtat aataaataca  28020

gaaattaaaa tatactgggg ctcctatcgc catcctgtaa acgccaccgt cttcacccgc  28080

ccaagcaaac caaggcgaac cttacctggt acttttaaca tctctccctc tgtgatttac  28140

aacagtttca acccagacgg agtgagtcta cgagagaacc tctccgagct cagctactcc  28200

atcagaaaaa acaccaccct ccttacctgc cgggaacgta cccttaatta aaagtcaggc  28260

ttcctggatg tcagcatctg actttggcca gcacctgtcc cgcggatttg ttccagtcca  28320

actacagcga cccaccctaa cagagatgac caacacaacc aacgcggccg ccgctaccgg  28380
```

-continued

```
acttacatct accacaaata caccccaagt ttctgccttt gtcaataact gggataactt  28440
gggcatgtgg tggttctcca tagcgcttat gtttgtatgc cttattatta tgtggctcat  28500
ctgctgccta aagcgcaaac gcgcccgacc acccatctat agtcccatca ttgtgctaca  28560
cccaaacaat gatggaatcc atagattgga cggactgaaa cacatgttct tttctcttac  28620
agtatgatta aatgagatta attaaggaat ttctgtccag tttattcagc agcacctcct  28680
tgccctcctc ccagctctgg tattgcagct tcctcctggc tgcaaacttt ctccacaatc  28740
taaatggaat gtcagtttcc tcctgttcct gtccatccgc acccactatc ttcatgttgt  28800
tgcagatgaa gcgcgcaaga ccgtctgaag ataccttcaa ccccgtgtat ccatatgaca  28860
cggaaaccgg tcctccaact gtgccttttc ttactcctcc ctttgtatcc cccaatgggt  28920
ttcaagagag tcccccctggg gtactctctt tgcgcctatc cgaacctcta gttacctcca  28980
atggcatgct tgcgctcaaa atgggcaacg gcctctctct ggacgaggcc ggcaacctta  29040
cctcccaaaa tgtaaccact gtgagcccac ctctcaaaaa aaccaagtca aacataaacc  29100
tggaaatatc tgcacccctc acagttacct cagaagccct aactgtggct gccgccgcac  29160
ctctaatggt cgcgggcaac acactcacca tgcaatcaca ggccccgcta accgtgcacg  29220
actccaaact tagcattgcc acccaaggac ccctcacagt gtcagaagga aagctagccc  29280
tgcaaacatc aggcccccctc accaccaccg atagcagtac ccttactatc actgcctcac  29340
cccctctaac tactgccact ggtagcttgg gcattgactt gaaagagccc atttatacac  29400
aaaatggaaa actaggacta aagtacgggg ctcctttgca tgtaacagac gacctaaaca  29460
ctttgaccgt agcaactggt ccaggtgtga ctattaataa tacttccttg caaactaaag  29520
ttactggagc cttgggtttt gattcacaag gcaatatgca acttaatgta gcaggaggac  29580
taaggattga ttctcaaaac agacgcctta tacttgatgt tagttatccg tttgatgctc  29640
aaaaccaact aaatctaaga ctaggacagg gccctctttt tataaactca gcccacaact  29700
tggatattaa ctacaacaaa ggcctttact tgtttacagc ttcaaacaat tccaaaaagc  29760
ttgaggttaa cctaagcact gccaaggggt tgatgtttga cgctacagcc atagccatta  29820
atgcaggaga tgggcttgaa tttggttcac ctaatgcacc aaacacaaat cccctcaaaa  29880
caaaaattgg ccatggccta gaatttgatt caaacaaggc tatggttcct aaactaggaa  29940
ctggccttag ttttgacagc acaggtgcca ttacagtagg aaacaaaaat aatgataagc  30000
taactttgtg gaccacacca gctccatctc ctaactgtag actaaatgca gagaaagatg  30060
ctaaactcac tttggtctta acaaaatgtg gcagtcaaat acttgctaca gtttcagttt  30120
tggctgttaa aggcagtttg gctccaatat ctggaacagt tcaaagtgct catcttatta  30180
taagatttga cgaaaatgga gtgctactaa acaattcctt cctggaccca gaatattgga  30240
actttagaaa tggagatctt actgaaggca cagcctatac aaacgctgtt ggatttatgc  30300
ctaacctatc agcttatcca aaatctcacg gtaaaactgc caaaagtaac attgtcagtc  30360
aagtttactt aaacggagac aaaactaaac ctgtaacact aaccattaca ctaaacggta  30420
cacaggaaac aggagacaca actccaagtg catactctat gtcattttca tgggactggt  30480
ctggccacaa ctacattaat gaaatatttg ccacatcctc ttacactttt tcatacattg  30540
cccaagaata aagaatcgtt tgtgttatgt ttcaacgtgt ttatttttca attgcagaaa  30600
atttcaagtc atttttcatt cagtagtata gccccaccac cacatagctt atacagatca  30660
ccgtacctta atcaaactca cagaacccta gtattcaacc tgccacctcc ctcccaacac  30720
```

-continued

```
acagagtaca cagtcctttc tccccggctg gccttaaaaa gcatcatatc atgggtaaca  30780
gacatattct taggtgttat attccacacg gtttcctgtc gagccaaacg ctcatcagtg  30840
atattaataa actccccggg cagctcactt aagttcatgt cgctgtccag ctgctgagcc  30900
acaggctgct gtccaacttg cggttgctta acgggcggcg aaggagaagt ccacgcctac  30960
atgggggtag agtcataatc gtgcatcagg atagggcggt ggtgctgcag cagcgcgcga  31020
ataaactgct gccgccgccg ctccgtcctg caggaataca acatggcagt ggtctcctca  31080
gcgatgattc gcaccgcccg cagcataagg cgccttgtcc tccgggcaca gcagcgcacc  31140
ctgatctcac ttaaatcagc acagtaactg cagcacagca ccacaatatt gttcaaaatc  31200
ccacagtgca aggcgctgta tccaaagctc atggcgggga ccacagaacc cacgtggcca  31260
tcataccaca agcgcaggta gattaagtgg cgacccctca taaacacgct ggacataaac  31320
attacctctt ttggcatgtt gtaattcacc acctcccggt accatataaa cctctgatta  31380
aacatggcgc catccaccac catcctaaac cagctggcca aaacctgccc gccggctata  31440
cactgcaggg aaccgggact ggaacaatga cagtggagag cccaggactc gtaaccatgg  31500
atcatcatgc tcgtcatgat atcaatgttg gcacaacaca ggcacacgtg catacacttc  31560
ctcaggatta caagctcctc ccgcgttaga accatatccc agggaacaac ccattcctga  31620
atcagcgtaa atcccacact gcagggaaga cctcgcacgt aactcacgtt gtgcattgtc  31680
aaagtgttac attcgggcag cagcggatga tcctccagta tggtagcgcg ggtttctgtc  31740
tcaaaaggag gtagacgatc cctactgtac ggagtgcgcc gagacaaccg agatcgtgtt  31800
ggtcgtagtg tcatgccaaa tggaacgccg gacgtagtca tatttcctga agcaaaacca  31860
ggtgcgggcg tgacaaacag atctgcgtct ccggtctcgc cgcttagatc gctctgtgta  31920
gtagttgtag tatatccact ctctcaaagc atccaggcgc cccctggctt cgggttctat  31980
gtaaactcct tcatgcgccg ctgccctgat aacatccacc accgcagaat aagccacacc  32040
cagccaacct acacattcgt tctgcgagtc acacacggga ggagcgggaa gagctggaag  32100
aaccatgttt tttttttat tccaaaagat tatccaaaac ctcaaaatga agatctatta  32160
agtgaacgcg ctcccctccg gtggcgtggt caaactctac agccaaagaa cagataatgg  32220
catttgtaag atgttgcaca atggcttcca aaaggcaaac ggccctcacg tccaagtgga  32280
cgtaaaggct aaacccttca gggtgaatct cctctataaa cattccagca ccttcaacca  32340
tgcccaaata attctcatct cgccaccttc tcaatatatc tctaagcaaa tcccgaatat  32400
taagtccggc cattgtaaaa atctgctcca gagcgccctc caccttcagc ctcaagcagc  32460
gaatcatgat tgcaaaaatt caggttcctc acagacctgt ataagattca aaagcggaac  32520
attaacaaaa ataccgcgat cccgtaggtc ccttcgcagg gccagctgaa cataatcgtg  32580
caggtctgca cggaccagcg cggccacttc cccgccagga accttgacaa aagaacccac  32640
actgattatg acacgcatac tcggagctat gctaaccagc gtagccccga tgtaagcttt  32700
gttgcatggg cggcgatata aaatgcaagg tgctgctcaa aaaatcaggc aaagcctcgc  32760
gcaaaaaaga aagcacatcg tagtcatgct catgcagata aaggcaggta agctccggaa  32820
ccaccacaga aaaagacacc atttttctct caaacatgtc tgcgggtttc tgcataaaca  32880
caaaataaaa taacaaaaaa acatttaaac attagaagcc tgtcttacaa caggaaaaac  32940
aacccttata agcataagac ggactacggc catgccggcg tgaccgtaaa aaaactggtc  33000
accgtgatta aaaagcacca ccgacagctc ctcggtcatg tccggagtca taatgtaaga  33060
ctcggtaaac acatcaggtt gattcatcgg tcagtgctaa aaagcgaccg aaatagcccg  33120
```

-continued ggggaataca tacccgcagg cgtagagaca acattacagc ccccatagga ggtataacaa 33180
aattaatagg agagaaaaac acataaacac ctgaaaaacc ctcctgccta ggcaaaatag 33240
caccctcccg ctccagaaca acatacagcg cttcacagcg gcagcctaac agtcagcctt 33300
accagtaaaa aagaaaacct attaaaaaaa caccactcga cacggcacca gctcaatcag 33360
tcacagtgta aaaaagggcc aagtgcagag cgagtatata taggactaaa aaatgacgta 33420
acggttaaag tccacaaaaa acacccagaa aaccgcacgc gaacctacgc ccagaaacga 33480
aagccaaaaa acccacaact tcctcaaatc gtcacttccg ttttcccacg ttacgtaact 33540
tcccatttta agaaaactac aattcccaac acatacaagt tactccgccc taaaacctac 33600
gtcacccgcc ccgttcccac gccccgcgcc acgtcacaaa ctccaccccc tcattatcat 33660
attggcttca atccaaaata aggtatatta ttgatgatg 33699

<210> SEQ ID NO 4
<211> LENGTH: 34448
<212> TYPE: DNA
<213> ORGANISM: Adenovirus subgroup C

<400> SEQUENCE: 4
catcatcaat aatatacctt attttggatt gaagccaata tgataatgag ggggtggagt 60
ttgtgacgtg gcgcggggcg tgggaacggg gcgggtgacg tagtagtgtg gcggaagtgt 120
gatgttgcaa gtgtggcgga acacatgtaa gcgacggatg tggcaaaagt gacgtttttg 180
gtgtgcgccg gtgtacacag gaagtgacaa ttttcgcgcg gttttaggcg gatgttgtag 240
taaatttggg cgtaaccgag taagatttgg ccattttcgc gggaaaactg aataagagga 300
agtgaaatct gaataatttt gtgttactca tagcgcgtaa tatttgtcta gggccgcggg 360
gactttgacc gtttacgtgg agactcgccc aggtgttttt ctcaggtgtt ttccgcgttc 420
cgggtcaaag ttggcgtttt attattatag tcagctgacg tgtagtgtat ttatacccgg 480
tgagttcctc aagaggccac tcttgagtgc cagcgagtag agttttctcc tccgagccgc 540
tccgacaccg ggactgaaaa tgagacatat tatctgccac ggaggtgtta ttaccgaaga 600
aatggccgcc agtcttttgg accagctgat cgaagaggta ctggctgata atcttccacc 660
tcctagccat tttgaaccac ctacccttca cgaactgtat gatttagacg tgacggcccc 720
cgaagatccc aacgaggagg cggtttcgca gatttttccc gactctgtaa tgttggcggt 780
gcaggaaggg attgacttac tcacttttcc gccggcgccc ggttctccgg agccgcctca 840
cctttcccgg cagcccgagc agccggagca gagagccttg ggtccggttt ctatgccaaa 900
ccttgtaccg gaggtgatcg atcttacctg ccacgaggct ggctttccac ccagtgacga 960
cgaggatgaa gagggtgagg agtttgtgtt agattatgtg gagcaccccg ggcacggttg 1020
caggtcttgt cattatcacc ggaggaatac gggggaccca gatattatgt gttcgctttg 1080
ctatatgagg acctgtggca tgtttgtcta cagtaagtga aaattatggg cagtgggtga 1140
tagagtggtg ggtttggtgt ggtaattttt tttttaattt ttacagtttt gtggtttaaa 1200
gaattttgta ttgtgatttt tttaaaaggt cctgtgtctg aacctgagcc tgagcccgag 1260
ccagaaccgg agcctgcaag acctacccgc cgtcctaaaa tggcgcctgc tatcctgaga 1320
cgcccgacat cacctgtgtc tagagaatgc aatagtagta cggatagctg tgactccggt 1380
ccttctaaca cacctcctga gatacacccg gtggtcccgc tgtgccccat taaaccagtt 1440
gccgtgagag ttggtgggcg tcgccaggct gtggaatgta tcgaggactt gcttaacgag 1500

-continued

```
cctgggcaac ctttggactt gagctgtaaa cgccccaggc cataaggtgt aaacctgtga   1560
ttgcgtgtgt ggttaacgcc tttgtttgct gaatgagttg atgtaagttt aataaagggt   1620
gagataatgt ttaacttgca tggcgtgtta aatggggcgg ggcttaaagg gtatataatg   1680
cgccgtgggc taatcttggt tacatctgac ctcatggagg cttgggagtg tttggaagat   1740
ttttctgctg tgcgtaactt gctggaacag agctctaaca gtacctcttg gttttggagg   1800
tttctgtggg gctcatccca ggcaaagtta gtctgcagaa ttaaggagga ttacaagtgg   1860
gaatttgaag agcttttgaa atcctgtggt gagctgtttg attctttgaa tctgggtcac   1920
caggcgcttt tccaagagaa ggtcatcaag actttggatt tttccacacc ggggcgcgct   1980
gcggctgctg ttgctttttt gagttttata aaggataaat ggagcgaaga aacccatctg   2040
agcggggggt acctgctgga ttttctggcc atgcatctgt ggagagcggt tgtgagacac   2100
aagaatcgcc tgctactgtt gtcttccgtc cgcccggcga taataccgac ggaggagcag   2160
cagcagcagc aggaggaagc caggcggcgg cggcaggagc agagcccatg gaacccgaga   2220
gccggcctgg accctcggga atgaatgttg tacaggtggc tgaactgtat ccagaactga   2280
gacgcatttt gacaattaca gaggatgggc aggggctaaa gggggtaaag agggagcggg   2340
gggcttgtga ggctacagag gaggctagga atctagcttt tagcttaatg accagacacc   2400
gtcctgagtg tattactttt caacagatca aggataattg cgctaatgag cttgatctgc   2460
tggcgcagaa gtattccata gagcagctga ccacttactg gctgcagcca ggggatgatt   2520
ttgaggaggc tattagggta tatgcaaagg tggcacttag gccagattgc aagtacaaga   2580
tcagcaaact tgtaaatatc aggaattgtt gctacatttc tgggaacggg gccgaggtgg   2640
agatagatac ggaggatagg gtggccttta gatgtagcat gataaatatg tggccggggg   2700
tgcttggcat ggacggggtg gttattatga atgtaaggtt tactggcccc aattttagcg   2760
gtacggtttt cctggccaat accaacctta tcctacacgg tgtaagcttc tatgggttta   2820
acaatacctg tgtggaagcc tggaccgatg taagggttcg ggctgtgcc ttttactgct   2880
gctggaaggg ggtggtgtgt cgccccaaaa gcagggcttc aattaagaaa tgcctctttg   2940
aaaggtgtac cttgggtatc ctgtctgagg gtaactccag ggtgcgccac aatgtggcct   3000
ccgactgtgg ttgcttcatg ctagtgaaaa gcgtggctgt gattaagcat aacatggtat   3060
gtggcaactg cgaggacagg gcctctcaga tgctgacctg ctcggacggc aactgtcacc   3120
tgctgaagac cattcacgta gccagccact ctcgcaaggc ctggccagtg tttgagcata   3180
acatactgac ccgctgttcc ttgcatttgg gtaacaggag gggggtgttc ctaccttacc   3240
aatgcaattt gagtcacact aagatattgc ttgagcccga gagcatgtcc aaggtgaacc   3300
tgaacggggt gtttgacatg accatgaaga tctggaaggt gctgaggtac gatgagaccc   3360
gcaccaggtg cagaccctgc gagtgtggcg gtaaacatat taggaaccag cctgtgatgc   3420
tggatgtgac cgaggagctg aggcccgatc acttggtgct ggcctgcacc cgcgctgagt   3480
ttggctctag cgatgaagat acagattgag gtactgaaat gtgtgggcgt ggcttaaggg   3540
tgggaaagaa tatataaggt gggggtctta tgtagttttg tatctgtttt gcagcagccg   3600
ccgccgccat gagcaccaac tcgtttgatg gaagcattgt gagctcatat ttgacaacgc   3660
gcatgccccc atgggccggg gtgcgtcaga atgtgatggg ctccagcatt gatggtcgcc   3720
ccgtcctgcc cgcaaactct actaccttga cctacgagac cgtgtctgga acgccgttgg   3780
agactgcagc ctccgccgcc gcttcagccg ctgcagccac cgcccgcggg attgtgactg   3840
actttgcttt cctgagcccg cttgcaagca gtgcagcttc ccgttcatcc gcccgcgatg   3900
```

-continued

```
acaagttgac ggctcttttg gcacaattgg attctttgac ccgggaactt aatgtcgttt   3960
ctcagcagct gttggatctg cgccagcagg tttctgccct gaaggcttcc tcccctccca   4020
atgcggttta aaacataaat aaaaaaccag actctgtttg gatttggatc aagcaagtgt   4080
cttgctgtct ttatttaggg gttttgcgcg cgcggtaggc ccgggaccag cggtctcggt   4140
cgttgagggt cctgtgtatt ttttccagga cgtggtaaag gtgactctgg atgttcagat   4200
acatgggcat aagcccgtct ctggggtgga ggtagcacca ctgcagagct tcatgctgcg   4260
gggtggtgtt gtagatgatc cagtcgtagc aggagcgctg ggcgtggtgc ctaaaaatgt   4320
ctttcagtag caagctgatt gccaggggca ggcccttggt gtaagtgttt acaaagcggt   4380
taagctggga tgggtgcata cgtggggata tgagatgcat cttggactgt atttttaggt   4440
tggctatgtt cccagccata tccctccggg gattcatgtt gtgcagaacc accagcacag   4500
tgtatccggt gcacttggga aatttgtcat gtagcttaga aggaaatgcg tggaagaact   4560
tggagacgcc cttgtgacct ccaagatttt ccatgcattc gtccataatg atggcaatgg   4620
gcccacgggc ggcggcctgg gcgaagatat ttctgggatc actaacgtca tagttgtgtt   4680
ccaggatgag atcgtcatag gccattttta caaagcgcgg gcggagggtg ccagactgcg   4740
gtataatggt tccatccggc ccaggggcgt agttaccctc acagatttgc atttcccacg   4800
ctttgagttc agatgggggg atcatgtcta cctgcggggc gatgaagaaa acggtttccg   4860
gggtagggga gatcagctgg gaagaaagca ggttcctgag cagctgcgac ttaccgcagc   4920
cggtgggccc gtaaatcaca cctattaccg ggtgcaactg gtagttaaga gagctgcagc   4980
tgccgtcatc cctgagcagg ggggccactt cgttaagcat gtccctgact cgcatgtttt   5040
ccctgaccaa atccgccaga aggcgctcgc cgcccagcga tagcagttct tgcaaggaag   5100
caaagttttt caacggtttg agaccgtccg ccgtaggcat gcttttgagc gtttgaccaa   5160
gcagttccag gcggtcccac agctcggtca cctgctctac ggcatctcga tccagcatat   5220
ctcctcgttt cgcgggttgg ggcggctttc gctgtacggc agtagtcggt gctcgtccag   5280
acgggccagg gtcatgtctt tccacgggcg cagggtcctc gtcagcgtag tctgggtcac   5340
ggtgaagggg tgcgctccgg gctgcgcgct ggccagggtg cgcttgaggc tggtcctgct   5400
ggtgctgaag cgctgccggt cttcgccctg cgcgtcggcc aggtagcatt tgaccatggt   5460
gtcatagtcc agcccctccg cggcgtggcc cttggcgcgc agcttgccct tggaggaggc   5520
gccgcacgag ggcagtgca gacttttgag ggcgtagagc ttgggcgcga gaaataccga   5580
ttccggggag taggcatccg cgccgcaggc cccgcagacg gtctcgcatt ccacgagcca   5640
ggtgagctct ggccgttcgg ggtcaaaaac caggtttccc ccatgctttt tgatgcgttt   5700
cttacctctg gtttccatga gccggtgtcc acgctcggtg acgaaaaggc tgtccgtgtc   5760
cccgtataca gacttgagag gcctgtcctc gagcggtgtt ccgcggtcct cctcgtatag   5820
aaactcggac cactctgaga caaaggctcg cgtccaggcc agcacgaagg aggctaagtg   5880
ggaggggtag cggtcgttgt ccactagggg gtccactcgc tccagggtgt gaagacacat   5940
gtcgccctct tcggcatcaa ggaaggtgat tggtttgtag gtgtaggcca cgtgaccggg   6000
tgttcctgaa ggggggctat aaaagggggt gggggcgcgt tcgtcctcac tctcttccgc   6060
atcgctgtct gcgagggcca gctgttgggg tgagtactcc ctctgaaaag cgggcatgac   6120
ttctgcgcta agattgtcag tttccaaaaa cgaggaggat ttgatattca cctggcccgc   6180
ggtgatgcct ttgagggtgg ccgcatccat ctggtcagaa aagacaatct ttttgttgtc   6240
```

-continued aagcttggtg gcaaacgacc cgtagagggc gttggacagc aacttggcga tggagcgcag 6300
ggtttggttt ttgtcgcgat cggcgcgctc cttggccgcg atgtttagct gcacgtattc 6360
gcgcgcaacg caccgccatt cgggaaagac ggtggtgcgc tcgtcgggca ccaggtgcac 6420
gcgccaaccg cggttgtgca gggtgacaag gtcaacgctg gtggctacct ctccgcgtag 6480
gcgctcgttg gtccagcaga ggcggccgcc cttgcgcgag cagaatggcg gtagggggtc 6540
tagctgcgtc tcgtccgggg ggtctgcgtc cacggtaaag accccgggca gcaggcgcgc 6600
gtcgaagtag tctatcttgc atccttgcaa gtctagcgcc tgctgccatg cgcgggcggc 6660
aagcgcgcgc tcgtatgggt tgagtggggg accccatggc atggggtggg tgagcgcgga 6720
ggcgtacatg ccgcaaatgt cgtaaacgta gaggggctct ctgagtattc caagatatgt 6780
agggtagcat cttccaccgc ggatgctggc gcgcacgtaa tcgtatagtt cgtgcgaggg 6840
agcgaggagg tcgggaccga ggttgctacg ggcgggctgc tctgctcgga agactatctg 6900
cctgaagatg gcatgtgagt tggatgatat ggttggacgc tggaagacgt tgaagctggc 6960
gtctgtgaga cctaccgcgt cacgcacgaa ggaggcgtag gagtcgcgca gcttgttgac 7020
cagctcggcg gtgacctgca cgtctagggc gcagtagtcc agggtttcct tgatgatgtc 7080
atacttatcc tgtccctttt ttttccacag ctcgcggttg aggacaaact cttcgcggtc 7140
tttccagtac tcttggatcg gaaacccgtc ggcctccgaa cggtaagagc ctagcatgta 7200
gaactggttg acggcctggt aggcgcagca tccctttttct acgggtagcg cgtatgcctg 7260
cgcggccttc cggagcgagg tgtgggtgag cgcaaaggtg tccctgacca tgactttgag 7320
gtactggtat ttgaagtcag tgtcgtcgca tccgccctgc tcccagagca aaaagtccgt 7380
gcgctttttg gaacgcggat ttggcagggc gaaggtgaca tcgttgaaga gtatctttcc 7440
cgcgcgaggc ataaagttgc gtgtgatgcg gaagggtccc ggcacctcgg aacggttgtt 7500
aattacctgg gcggcgagca cgatctcgtc aaagccgttg atgttgtggc ccacaatgta 7560
aagttccaag aagcgcggga tgcccttgat ggaaggcaat tttttaagtt cctcgtaggt 7620
gagctcttca ggggagctga gcccgtgctc tgaaagggcc cagtctgcaa gatgagggtt 7680
ggaagcgacg aatgagctcc acaggtcacg ggccattagc atttgcaggt ggtcgcgaaa 7740
ggtcctaaac tggcgaccta tggccatttt ttctggggtg atgcagtaga aggtaagcgg 7800
gtcttgttcc cagcggtccc atccaaggtt cgcggctagg tctcgcgcgg cagtcactag 7860
aggctcatct ccgccgaact tcatgaccag catgaagggc acgagctgct tcccaaaggc 7920
ccccatccaa gtataggtct ctacatcgta ggtgacaaag agacgctcgg tgcgaggatg 7980
cgagccgatc gggaagaact ggatctcccg ccaccaattg gaggagtggc tattgatgtg 8040
gtgaaagtag aagtccctgc gacgggccga acactcgtgc tggcttttgt aaaaacgtgc 8100
gcagtactgg cagcggtgca cgggctgtac atcctgcacg aggttgacct gacgaccgcg 8160
cacaaggaag cagagtggga atttgagccc ctcgcctggc gggtttggct ggtggtcttc 8220
tacttcggct gcttgtcctt gaccgtctgg ctgctcgagg ggagttacgg tggatcggac 8280
caccacgccg cgcgagccca aagtccagat gtccgcgcgc ggcggtcgga gcttgatgac 8340
aacatcgcgc agatgggagc tgtccatggt ctggagctcc cgcggcgtca ggtcaggcgg 8400
gagctcctgc aggtttacct cgcatagacg ggtcagggcg cgggctagat ccaggtgata 8460
cctaatttcc aggggctggt tggtggcggc gtcgatggct tgcaagaggc cgcatccccg 8520
cggcgcgact acggtaccgc gcggcgggcg gtgggccgcg ggggtgtcct tggatgatgc 8580
atctaaaagc ggtgacgcgg gcgagccccc ggaggtaggg ggggctccgg acccgccggg 8640

-continued

```
agagggggca ggggcacgtc ggcgccgcgc gcgggcagga gctggtgctg cgcgcgtagg   8700
ttgctggcga acgcgacgac gcggcggttg atctcctgaa tctggcgcct ctgcgtgaag   8760
acgacgggcc cggtgagctt gagcctgaaa gagagttcga cagaatcaat ttcggtgtcg   8820
ttgacggcgg cctggcgcaa aatctcctgc acgtctcctg agttgtcttg ataggcgatc   8880
tcggccatga actgctcgat ctcttcctcc tggagatctc cgcgtccggc tcgctccacg   8940
gtggcggcga ggtcgttgga aatgcgggcc atgagctgcg agaaggcgtt gaggcctccc   9000
tcgttccaga cgcggctgta gaccacgccc ccttcggcat cgcgggcgcg catgaccacc   9060
tgcgcgagat tgagctccac gtgccgggcg aagacggcgt agtttcgcag gcgctgaaag   9120
aggtagttga gggtggtggc ggtgtgttct gccacgaaga agtacataac ccagcgtcgc   9180
aacgtggatt cgttgatatc ccccaaggcc tcaaggcgct ccatggcctc gtagaagtcc   9240
acggcgaagt tgaaaaactg ggagttgcgc gccgacacgg ttaactcctc ctccagaaga   9300
cggatgagct cggcgacagt gtcgcgcacc tcgcgctcaa aggctacagg ggcctcttct   9360
tcttcttcaa tctcctcttc cataagggcc tccccttctt cttcttctgg cggcggtggg   9420
ggagggggga cacggcggcg acgacggcgc accgggaggc ggtcgacaaa gcgctcgatc   9480
atctccccgc ggcgacggcg catggtctcg gtgacggcgc ggccgttctc gcgggggcgc   9540
agttggaaga cgccgcccgt catgtcccgg ttatgggttg gcggggggct gccatgcggc   9600
agggatacgg cgctaacgat gcatctcaac aattgttgtg taggtactcc gccgccgagg   9660
gacctgagcg agtccgcatc gaccggatcg gaaaacctct cgagaaaggc gtctaaccag   9720
tcacagtcgc aaggtaggct gagcaccgtg gcgggcggca gcgggcggcg gtcggggttg   9780
tttctggcgg aggtgctgct gatgatgtaa ttaaagtagg cggtcttgag acggcggatg   9840
gtcgacagaa gcaccatgtc cttgggtccg gcctgctgaa tgcgcaggcg gtcggccatg   9900
ccccaggctt cgttttgaca tcggcgcagg tctttgtagt agtcttgcat gagcctttct   9960
accggcactt cttcttctcc ttcctcttgt cctgcatctc ttgcatctat cgctgcggcg  10020
gcggcggagt ttggccgtag gtggcgccct cttcctccca tgcgtgtgac cccgaagccc  10080
ctcatcggct gaagcagggc taggtcggcg acaacgcgct cggctaatat ggcctgctgc  10140
acctgcgtga gggtagactg gaagtcatcc atgtccacaa agcggtggta tgcgcccgtg  10200
ttgatggtgt aagtgcagtt ggccataacg gaccagttaa cggtctggtg acccggctgc  10260
gagagctcgg tgtacctgag acgcgagtaa gccctcgagt caaatacgta gtcgttgcaa  10320
gtccgcacca ggtactggta tcccaccaaa aagtgcggcg gcggctggcg gtagaggggc  10380
cagcgtaggg tggccggggc tccgggggcg agatcttcca acataaggcg atgatatccg  10440
tagatgtacc tggacatcca ggtgatgccg gcggcggtgg tggaggcgcg cggaaagtcg  10500
cggacgcggt tccagatgtt gcgcagcggc aaaaagtgct ccatggtcgg gacgctctgg  10560
ccggtcaggc gcgcgcaatc gttgacgctc tagaccgtgc aaaaggagag cctgtaagcg  10620
ggcactcttc cgtggtctgg tggataaatt cgcaagggta tcatggcgga cgaccggggt  10680
tcgagccccg tatccggccg tccgccgtga tccatgcggt taccgcccgc gtgtcgaacc  10740
caggtgtgcg acgtcagaca acgggggagt gctccttttg gcttccttcc aggcgcggcg  10800
gctgctgcgc tagctttttt ggccactggc cgcgcgcagc gtaagcggtt aggctggaaa  10860
gcgaaagcat taagtggctc gctccctgta gccggagggt tattttccaa gggttgagtc  10920
gcgggacccc cggttcgagt ctcggaccgg ccggactgcg gcgaacgggg gtttgcctcc  10980
```

-continued

```
ccgtcatgca agaccccgct tgcaaattcc tccggaaaca gggacgagcc cctttttttgc  11040
ttttcccaga tgcatccggt gctgcggcag atgcgccccc ctcctcagca gcggcaagag  11100
caagagcagc ggcagacatg cagggcaccc tcccctcctc ctaccgcgtc aggaggggcg  11160
acatccgcgg ttgacgcggc agcagatggt gattacgaac cccgcggcg ccgggcccgg  11220
cactacctgg acttggagga gggcgagggc ctggcgcggc taggagcgcc ctctcctgag  11280
cggtacccaa gggtgcagct gaagcgtgat acgcgtgagg cgtacgtgcc gcggcagaac  11340
ctgtttcgcg accgcgaggg agaggagccc gaggagatgc gggatcgaaa gttccacgca  11400
gggcgcgagc tgcggcatgg cctgaatcgc gagcggttgc tgcgcgagga ggactttgag  11460
cccgacgcgc gaaccgggat tagtcccgcg cgcgcacacg tggcggccgc cgacctggta  11520
accgcatacg agcagacggt gaaccaggag attaactttc aaaaaagctt taacaaccac  11580
gtgcgtacgc ttgtggcgcg cgaggaggtg gctataggac tgatgcatct gtgggacttt  11640
gtaagcgcgc tggagcaaaa cccaaatagc aagccgctca tggcgcagct gttccttata  11700
gtgcagcaca gcagggacaa cgaggcattc agggatgcgc tgctaaacat agtagagccc  11760
gagggccgct ggctgctcga tttgataaac atcctgcaga gcatagtggt gcaggagcgc  11820
agcttgagcc tggctgacaa ggtggccgcc atcaactatt ccatgcttag cctgggcaag  11880
ttttacgccc gcaagatata ccatacccct tacgttccca tagacaagga ggtaaagatc  11940
gaggggttct acatgcgcat ggcgctgaag gtgcttacct tgagcgacga cctgggcgtt  12000
tatcgcaacg agcgcatcca caaggccgtg agcgtgagcc ggcggcgcga gctcagcgac  12060
cgcgagctga tgcacagcct gcaaagggcc ctggctggca cgggcagcgg cgatagagag  12120
gccgagtcct actttgacgc gggcgctgac ctgcgctggg ccccaagccg acgcgccctg  12180
gaggcagctg gggccggacc tgggctggcg gtggcacccg cgcgcgctgg caacgtcggc  12240
ggcgtggagg aatatgacga ggacgatgag tacgagccag aggacggcga gtactaagcg  12300
gtgatgtttc tgatcagatg atgcaagacg caacggaccc ggcggtgcgg gcggcgctgc  12360
agagccagcc gtccggcctt aactccacgg acgactggcg ccaggtcatg gaccgcatca  12420
tgtcgctgac tgcgcgcaat cctgacgcgt tccggcagca gccgcaggcc aaccggctct  12480
ccgcaattct ggaagcggtg gtcccggcgc gcgcaaaccc cacgcacgag aaggtgctgg  12540
cgatcgtaaa cgcgctggcc gaaaacaggg ccatccggcc cgacgaggcc ggcctggtct  12600
acgacgcgct gcttcagcgc gtggctcgtt acaacagcgg caacgtgcag accaacctgg  12660
accggctggt gggggatgtg cgcgaggccg tggcgcagcg tgagcgcgcg cagcagcagg  12720
gcaacctggg ctccatggtt gcactaaacg ccttcctgag tacacagccc gccaacgtgc  12780
cgcggggaca ggaggactac accaactttg tgagcgcact gcggctaatg gtgactgaga  12840
caccgcaaag tgaggtgtac cagtctgggc cagactattt tttccagacc agtagacaag  12900
gcctgcagac cgtaaacctg agccaggctt tcaaaaactt gcaggggctg tggggggtgc  12960
gggctcccac aggcgaccgc gcgaccgtgt ctagcttgct gacgcccaac tcgcgcctgt  13020
tgctgctgct aatagcgccc ttcacggaca gtggcagcgt gtcccgggac acatacctag  13080
gtcacttgct gacactgtac cgcgaggcca taggtcaggc gcatgtggac gagcatactt  13140
tccaggagat tacaagtgtc agccgcgcgc tggggcagga ggacacgggc agcctggagg  13200
caaccctaaa ctacctgctg accaaccggc ggcagaagat cccctcgttg cacagtttaa  13260
acagcgagga ggagcgcatt ttgcgctacg tgcagcagag cgtgagcctt aacctgatgc  13320
gcgacggggt aacgcccagc gtggcgctgg acatgaccgc gcgcaacatg gaaccgggca  13380
```

-continued tgtatgcctc aaaccggccg tttatcaacc gcctaatgga ctacttgcat cgcgcggccg 13440
ccgtgaaccc cgagtatttc accaatgcca tcttgaaccc gcactggcta ccgccccctg 13500
gtttctacac cgggggattc gaggtgcccg agggtaacga tggattcctc tgggacgaca 13560
tagacgacag cgtgttttcc ccgcaaccgc agaccctgct agagttgcaa cagcgcgagc 13620
aggcagaggc ggcgctgcga aaggaaagct tccgcaggcc aagcagcttg tccgatctag 13680
gcgctgcggc cccgcggtca gatgctagta gcccatttcc aagcttgata gggtctctta 13740
ccagcactcg caccacccgc ccgcgcctgc tgggcgagga ggagtaccta aacaactcgc 13800
tgctgcagcc gcagcgcgaa aaaaacctgc ctccggcatt tcccaacaac gggatagaga 13860
gcctagtgga caagatgagt agatggaaga cgtacgcgca ggagcacagg gacgtgccag 13920
gcccgcgccc gcccacccgt cgtcaaaggc acgaccgtca gcggggtctg gtgtgggagg 13980
acgatgactc ggcagacgac agcagcgtcc tggatttggg agggagtggc aacccgtttg 14040
cgcaccttcg ccccaggctg gggagaatgt tttaaaaaaa aaaaagcatg atgcaaaata 14100
aaaaactcac caaggccatg gcaccgagcg ttggttttct tgtattcccc ttagtatgcg 14160
gcgcgcggcg atgtatgagg aaggtcctcc tccctcctac gagagtgtgg tgagcgcggc 14220
gccagtggcg gcggcgctgg gttctccctt cgatgctccc ctggacccgc cgtttgtgcc 14280
tccgcggtac ctgcggccta ccggggggag aaacagcatc cgttactctg agttggcacc 14340
cctattcgac accacccgtg tgtacctggt ggacaacaag tcaacggatg tggcatccct 14400
gaactaccag aacgaccaca gcaactttct gaccacggtc attcaaaaca atgactacag 14460
cccgggggag gcaagcacac agaccatcaa tcttgacgac cggtcgcact ggggcggcga 14520
cctgaaaacc atcctgcata ccaacatgcc aaatgtgaac gagttcatgt ttaccaataa 14580
gtttaaggcg cgggtgatgg tgtcgcgctt gcctactaag gacaatcagg tggagctgaa 14640
atacgagtgg gtggagttca cgctgcccga gggcaactac tccgagacca tgaccataga 14700
ccttatgaac aacgcgatcg tggagcacta cttgaaagtg ggcagacaga acggggttct 14760
ggaaagcgac atcggggtaa agtttgacac ccgcaacttc agactggggt ttgaccccgt 14820
cactggtctt gtcatgcctg ggtatatac aaacgaagcc ttccatccag acatcatttt 14880
gctgccagga tgcggggtgg acttcaccca cagccgcctg agcaacttgt tgggcatccg 14940
caagcggcaa cccttccagg agggctttag gatcacctac gatgatctgg agggtggtaa 15000
cattcccgca ctgttggatg tggacgccta ccaggcgagc ttgaaagatg acaccgaaca 15060
gggcgggggt ggcgcaggcg gcagcaacag cagtggcagc ggcgcggaag agaactccaa 15120
cgcggcagcc gcggcaatgc agccggtgga ggacatgaac gatcatgcca ttcgcggcga 15180
cacctttgcc acacgggctg aggagaagcg cgctgaggcc gaagcagcgg ccgaagctgc 15240
cgcccccgct gcgcaacccg aggtcgagaa gcctcagaag aaaccggtga tcaaacccct 15300
gacagaggac agcaagaaac gcagttacaa cctaataagc aatgacagca ccttcaccca 15360
gtaccgcagc tggtaccttg catacaacta cggcgaccct cagaccggaa tccgctcatg 15420
gaccctgctt tgcactcctg acgtaacctg cggctcggag caggtctact ggtcgttgcc 15480
agacatgatg caagaccccg tgaccttccg ctccacgcgc cagatcagca actttccggt 15540
ggtgggcgcc gagctgttgc ccgtgcactc caagagcttc tacaacgacc aggccgtcta 15600
ctcccaactc atccgccagt ttacctctct gacccacgtg ttcaatcgct ttcccgagaa 15660
ccagattttg gcgcgcccgc cagcccccac catcaccacc gtcagtgaaa acgttcctgc 15720

-continued

```
tctcacagat cacgggacgc taccgctgcg caacagcatc ggaggagtcc agcgagtgac  15780
cattactgac gccagacgcc gcacctgccc ctacgtttac aaggccctgg gcatagtctc  15840
gccgcgcgtc ctatcgagcc gcactttttg agcaagcatg tccatcctta tatcgcccag  15900
caataacaca ggctggggcc tgcgcttccc aagcaagatg tttggcgggg ccaagaagcg  15960
ctccgaccaa cacccagtgc gcgtgcgcgg gcactaccgc gcgccctggg gcgcgcacaa  16020
acgcggccgc actgggcgca ccaccgtcga tgacgccatc gacgcggtgg tggaggaggc  16080
gcgcaactac acgcccacgc cgccaccagt gtccacagtg gacgcggcca ttcagaccgt  16140
ggtgcgcgga gcccggcgct atgctaaaat gaagagacgg cggaggcgcg tagcacgtcg  16200
ccaccgccgc cgacccggca ctgccgccca acgcgcggcg gcggccctgc ttaaccgcgc  16260
acgtcgcacc ggccgacggg cggccatgcg ggccgctcga aggctggccg cgggtattgt  16320
cactgtgccc cccaggtcca ggcgacgagc ggccgccgca gcagccgcgg ccattagtgc  16380
tatgactcag ggtcgcaggg gcaacgtgta ttgggtgcgc gactcggtta gcggcctgcg  16440
cgtgcccgtg cgcacccgcc ccccgcgcaa ctagattgca agaaaaaact acttagactc  16500
gtactgttgt atgtatccag cggcggcggc gcgcaacgaa gctatgtcca agcgcaaaat  16560
caaagaagag atgctccagg tcatcgcgcc ggagatctat ggccccccga agaaggaaga  16620
gcaggattac aagccccgaa agctaaagcg ggtcaaaaag aaaaagaaag atgatgatga  16680
tgaacttgac gacgaggtgg aactgctgca cgctaccgcg cccaggcgac gggtacagtg  16740
gaaaggtcga cgcgtaaaac gtgttttgcg acccggcacc accgtagtct ttacgcccgg  16800
tgagcgctcc acccgcacct acaagcgcgt gtatgatgag gtgtacggcg acgaggacct  16860
gcttgagcag gccaacgagc gcctcgggga gtttgcctac ggaaagcggc ataaggacat  16920
gctggcgttg ccgctggacg agggcaaccc aacacctagc ctaaagcccg taacactgca  16980
gcaggtgctg cccgcgcttg caccgtccga agaaaagcgc ggcctaaagc gcgagtctgg  17040
tgacttggca cccaccgtgc agctgatggt acccaagcgc cagcgactgg aagatgtctt  17100
ggaaaaaatg accgtggaac ctgggctgga gcccgaggtc cgcgtgcggc caatcaagca  17160
ggtggcgccg ggactgggcg tgcagaccgt ggacgttcag atacccacta ccagtagcac  17220
cagtattgcc accgccacag agggcatgga gacacaaacg tccccggttg cctcagcggt  17280
ggcggatgcc gcggtgcagg cggtcgctgc ggccgcgtcc aagacctcta cggaggtgca  17340
aacggacccg tggatgtttc gcgtttcagc cccccggcgc ccgcgcggtt cgaggaagta  17400
cggcgccgcc agcgcgctac tgcccgaata tgccctacat ccttccattg cgcctacccc  17460
cggctatcgt ggctacacct accgccccag aagacgagca actacccgac gccgaaccac  17520
cactggaacc cgccgccgcc gtcgccgtcg ccagcccgtg ctggccccga tttccgtgcg  17580
cagggtggct cgcgaaggag gcaggaccct ggtgctgcca acagcgcgct accaccccag  17640
catcgtttaa aagccggtct ttgtggttct tgcagatatg gccctcacct gccgcctccg  17700
tttcccggtg ccgggattcc gaggaagaat gcaccgtagg aggggcatgg ccggccacgg  17760
cctgacgggc ggcatgcgtc gtgcgcacca ccggcggcgg cgcgcgtcgc accgtcgcat  17820
gcgcggcggt atcctgcccc tccttattcc actgatcgcc gcggcgattg gcgccgtgcc  17880
cggaattgca tccgtggcct tgcaggcgca gagacactga ttaaaaacaa gttgcatgtg  17940
gaaaaatcaa aataaaaagt ctggactctc acgctcgctt ggtcctgtaa ctattttgta  18000
gaatggaaga catcaacttt gcgtctctgg ccccgcgaca cggctcgcgc ccgttcatgg  18060
gaaactggca agatatcggc accagcaata tgagcggtgg cgccttcagc tggggctcgc  18120
```

-continued

```
tgtggagcgg cattaaaaat ttcggttcca ccgttaagaa ctatggcagc aaggcctgga  18180
acagcagcac aggccagatg ctgagggata agttgaaaga gcaaaatttc caacaaaagg  18240
tggtagatgg cctggcctct ggcattagcg gggtggtgga cctggccaac caggcagtgc  18300
aaaataagat taacagtaag cttgatcccc gccctcccgt agaggagcct ccaccggccg  18360
tggagacagt gtctccagag gggcgtggcg aaaagcgtcc gcgccccgac agggaagaaa  18420
ctctggtgac gcaaatagac gagcctccct cgtacgagga ggcactaaag caaggcctgc  18480
ccaccacccg tcccatcgcg cccatggcta ccggagtgct gggccagcac acacccgtaa  18540
cgctggacct gcctcccccc gccgacaccc agcagaaacc tgtgctgcca ggcccgaccg  18600
ccgttgttgt aacccgtcct agccgcgcgt ccctgcgccg cgccgccagc ggtccgcgat  18660
cgttgcggcc cgtagccagt ggcaactggc aaagcacact gaacagcatc gtgggtctgg  18720
gggtgcaatc cctgaagcgc cgacgatgct tctgaatagc taacgtgtcg tatgtgtgtc  18780
atgtatgcgt ccatgtcgcc gccagaggag ctgctgagcc gccgcgcgcc cgctttccaa  18840
gatggctacc ccttcgatga tgccgcagtg gtcttacatg cacatctcgg gccaggacgc  18900
ctcggagtac ctgagccccg ggctggtgca gtttgcccgc gccaccgaga cgtacttcag  18960
cctgaataac aagtttagaa accccacggt ggcgcctacg cacgacgtga ccacagaccg  19020
gtcccagcgt ttgacgctgc ggttcatccc tgtggaccgt gaggatactg cgtactcgta  19080
caaggcgcgg ttcaccctag ctgtgggtga taaccgtgtg ctggacatgg cttccacgta  19140
ctttgacatc cgcggcgtgc tggacagggg ccctactttt aagccctact ctggcactgc  19200
ctacaacgcc ctggctccca agggtgcccc aaatccttgc gaatgggatg aagctgctac  19260
tgctcttgaa ataaacctag aagaagagga cgatgacaac gaagacgaag tagacgagca  19320
agctgagcag caaaaaactc acgtatttgg gcaggcgcct tattctggta taaatattac  19380
aaaggagggt attcaaatag gtgtcgaagg tcaaacacct aaatatgccg ataaaacatt  19440
tcaacctgaa cctcaaatag gagaatctca gtggtacgaa actgaaatta atcatgcagc  19500
tgggagagtc cttaaaaaga ctaccccaat gaaaccatgt tacggttcat atgcaaaacc  19560
cacaaatgaa aatggagggc aaggcattct tgtaaagcaa caaaatggaa agctagaaag  19620
tcaagtggaa atgcaatttt tctcaactac tgaggcgacc gcaggcaatg gtgataactt  19680
gactcctaaa gtggtattgt acagtgaaga tgtagatata gaaaccccag acactcatat  19740
ttcttacatg cccactatta aggaaggtaa ctcacgagaa ctaatgggcc aacaatctat  19800
gcccaacagg cctaattaca ttgcttttag ggacaatttt attggtctaa tgtattacaa  19860
cagcacgggt aatatgggtg ttctggcggg ccaagcatcg cagttgaatg ctgttgtaga  19920
tttgcaagac agaaacacag agctttcata ccagcttttg cttgattcca ttggtgatag  19980
aaccaggtac ttttctatgt ggaatcaggc tgttgacagc tatgatccag atgttagaat  20040
tattgaaaat catggaactg aagatgaact tccaaattac tgctttccac tgggaggtgt  20100
gattaataca gagactctta ccaaggtaaa acctaaaaca ggtcaggaaa atggatggga  20160
aaaagatgct acagaatttt cagataaaaa tgaaataaga gttggaaata attttgccat  20220
ggaaatcaat ctaaatgcca acctgtggag aaatttcctg tactccaaca tagcgctgta  20280
tttgcccgac aagctaaagt acagtccttc caacgtaaaa atttctgata acccaaacac  20340
ctacgactac atgaacaagc gagtggtggc tcccgggtta gtggactgct acattaacct  20400
tggagcacgc tggtcccttg actatatgga caacgtcaac ccatttaacc accaccgcaa  20460
```

-continued

```
tgctggcctg cgctaccgct caatgttgct gggcaatggt cgctatgtgc ccttccacat  20520
ccaggtgcct cagaagttct ttgccattaa aaacctcctt ctcctgccgg gctcatacac  20580
ctacgagtgg aacttcagga aggatgttaa catggttctg cagagctccc taggaaatga  20640
cctaagggtt gacggagcca gcattaagtt tgatagcatt tgcctttacg ccaccttctt  20700
ccccatggcc cacaacaccg cctccacgct tgaggccatg cttagaaacg acaccaacga  20760
ccagtccttt aacgactatc tctccgccgc caacatgctc taccctatac ccgccaacgc  20820
taccaacgtg cccatatcca tcccctcccg caactgggcg gctttccgcg gctgggcctt  20880
cacgcgcctt aagactaagg aaaccccatc actgggctcg ggctacgacc cttattacac  20940
ctactctggc tctataccct acctagatgg aacctttac ctcaaccaca cctttaagaa  21000
ggtggccatt acctttgact cttctgtcag ctggcctggc aatgaccgcc tgcttacccc  21060
caacgagttt gaaattaagc gctcagttga cggggagggt tacaacgttg cccagtgtaa  21120
catgaccaaa gactggttcc tggtacaaat gctagctaac tacaacattg gctaccaggg  21180
cttctatatc ccagagagct acaaggaccg catgtactcc ttctttagaa acttccagcc  21240
catgagccgt caggtggtgg atgatactaa atacaaggac taccaacagg tgggcatcct  21300
acaccaacac aacaactctg gatttgttgg ctaccttgcc cccaccatgc gcgaaggaca  21360
ggcctaccct gctaacttcc cctatccgct tataggcaag accgcagttg acagcattac  21420
ccagaaaaag tttctttgcg atcgcaccct ttggcgcatc ccattctcca gtaactttat  21480
gtccatgggc gcactcacag acctgggcca aaaccttctc tacgccaact ccgcccacgc  21540
gctagacatg acttttgagg tggatcccat ggacgagccc acccttcttt atgttttgtt  21600
tgaagtcttt gacgtggtcc gtgtgcaccg gccgcaccgc ggcgtcatcg aaaccgtgta  21660
cctgcgcacg cccttctcgg ccggcaacgc cacaacataa agaagcaagc aacatcaaca  21720
acagctgccg ccatgggctc cagtgagcag gaactgaaag ccattgtcaa agatcttggt  21780
tgtgggccat attttttggg cacctatgac aagcgctttc caggctttgt ttctccacac  21840
aagctcgcct gcgccatagt caatacggcc ggtcgcgaga ctgggggcgt acactggatg  21900
gcctttgcct ggaacccgca ctcaaaaaca tgctacctct ttgagccctt tggcttttct  21960
gaccagcgac tcaagcaggt ttaccagttt gagtacgagt cactcctgcg ccgtagcgcc  22020
attgcttctt cccccgaccg ctgtataacg ctggaaaagt ccacccaaag cgtacagggg  22080
cccaactcgg ccgcctgtgg actattctgc tgcatgtttc tccacgcctt tgccaactgg  22140
ccccaaactc ccatggatca caaccccacc atgaacctta ttaccggggt acccaactcc  22200
atgctcaaca gtccccaggt acagcccacc ctgcgtcgca accaggaaca gctctacagc  22260
ttcctggagc gccactcgcc ctacttccgc agccacagtg cgcagattag gagcgccact  22320
tctttttgtc acttgaaaaa catgtaaaaa taatgtacta gagacacttt caataaaggc  22380
aaatgctttt atttgtacac tctcgggtga ttatttaccc ccacccttgc cgtctgcgcc  22440
gtttaaaaat caaaggggtt ctgccgcgca tcgctatgcg ccactggcag ggacacgttg  22500
cgatactggt gtttagtgct ccacttaaac tcaggcacaa ccatccgcgg cagctcggtg  22560
aagttttcac tccacaggct gcgcaccatc accaacgcgt ttagcaggtc gggcgccgat  22620
atcttgaagt cgcagttggg gcctccgccc tgcgcgcgcg agttgcgata cacagggttg  22680
cagcactgga acactatcag cgccgggtgg tgcacgctgg ccagcacgct cttgtcggag  22740
atcagatccg cgtccaggtc ctccgcgttg ctcagggcga acggagtcaa ctttggtagc  22800
tgccttccca aaaagggcgc gtgcccaggc tttgagttgc actcgcaccg tagtggcatc  22860
```

-continued

```
aaaaggtgac cgtgcccggt ctgggcgtta ggatacagcg cctgcataaa agccttgatc  22920
tgcttaaaag ccacctgagc ctttgcgcct tcagagaaga acatgccgca agacttgccg  22980
gaaaactgat tggccggaca ggccgcgtcg tgcacgcagc accttgcgtc ggtgttggag  23040
atctgcacca catttcggcc ccaccggttc ttcacgatct tggccttgct agactgctcc  23100
ttcagcgcgc gctgcccgtt ttcgctcgtc acatccattt caatcacgtg ctccttattt  23160
atcataatgc ttccgtgtag acacttaagc tcgccttcga tctcagcgca gcggtgcagc  23220
cacaacgcgc agcccgtggg ctcgtgatgc ttgtaggtca cctctgcaaa cgactgcagg  23280
tacgcctgca ggaatcgccc catcatcgtc acaaaggtct tgttgctggt gaaggtcagc  23340
tgcaacccgc ggtgctcctc gttcagccag gtcttgcata cggccgccag agcttccact  23400
tggtcaggca gtagtttgaa gttcgccttt agatcgttat ccacgtggta cttgtccatc  23460
agcgcgcgcg cagcctccat gcccttctcc cacgcagaca cgatcggcac actcagcggg  23520
ttcatcaccg taatttcact ttccgcttcg ctgggctctt cctcttcctc ttgcgtccgc  23580
ataccacgcg ccactgggtc gtcttcattc agccgccgca ctgtgcgctt acctcctttg  23640
ccatgcttga ttagcaccgg tgggttgctg aaacccacca tttgtagcgc cacatcttct  23700
ctttcttcct cgctgtccac gattacctct ggtgatggcg ggcgctcggg cttgggagaa  23760
gggcgcttct ttttcttctt gggcgcaatg gccaaatccg ccgccgaggt cgatggccgc  23820
gggctgggtg tgcgcggcac cagcgcgtct tgtgatgagt cttcctcgtc ctcggactcg  23880
atacgccgcc tcatccgctt ttttgggggc gcccggggag gcggcggcga cggggacggg  23940
gacgacacgt cctccatggt tgggggacgt cgcgccgcac cgcgtccgcg ctcgggggtg  24000
gtttcgcgct gctcctcttc ccgactggcc atttccttct cctataggca gaaaaagatc  24060
atggagtcag tcgagaagaa ggacagccta accgcccccct ctgagttcgc caccaccgcc  24120
tccaccgatg ccgccaacgc gcctaccacc ttccccgtcg aggcaccccc gcttgaggag  24180
gaggaagtga ttatcgagca ggacccaggt tttgtaagcg aagacgacga ggaccgctca  24240
gtaccaacag aggataaaaa gcaagaccag gacaacgcag aggcaaacga ggaacaagtc  24300
gggcgggggg acgaaaggca tggcgactac ctagatgtgg gagacgacgt gctgttgaag  24360
catctgcagc gccagtgcgc cattatctgc gacgcgttgc aagagcgcag cgatgtgccc  24420
ctcgccatag cggatgtcag ccttgcctac gaacgccacc tattctcacc gcgcgtaccc  24480
cccaaacgcc aagaaaacgg cacatgcgag cccaacccgc gcctcaactt ctaccccgta  24540
tttgccgtgc cagaggtgct tgccacctat cacatctttt tccaaaactg caagataccc  24600
ctatcctgcc gtgccaaccg cagccgagcg gacaagcagc tggccttgcg gcagggcgct  24660
gtcatacctg atatcgcctc gctcaacgaa gtgccaaaaa tctttgaggg tcttggacgc  24720
gacgagaagc gcgcggcaaa cgctctgcaa caggaaaaca gcgaaaatga aagtcactct  24780
ggagtgttgg tggaactcga gggtgacaac gcgcgcctag ccgtactaaa acgcagcatc  24840
gaggtcaccc actttgccta cccggcactt aacctacccc ccaaggtcat gagcacagtc  24900
atgagtgagc tgatcgtgcg ccgtgcgcag cccctggaga gggatgcaaa tttgcaagaa  24960
caaacagagg agggcctacc cgcagttggc gacgagcagc tagcgcgctg gcttcaaacg  25020
cgcgagcctg ccgacttgga ggagcgacgc aaactaatga tggccgcagt gctcgttacc  25080
gtggagcttg agtgcatgca gcggttcttt gctgacccgg agatgcagcg caagctagag  25140
gaaacattgc actacacctt tcgacagggc tacgtacgcc aggcctgcaa gatctccaac  25200
```

-continued

```
gtggagctct gcaacctggt ctcctacctt ggaattttgc acgaaaaccg ccttgggcaa  25260
aacgtgcttc attccacgct caagggcgag gcgcgccgcg actacgtccg cgactgcgtt  25320
tacttatttc tatgctacac ctggcagacg gccatgggcg tttggcagca gtgcttggag  25380
gagtgcaacc tcaaggagct gcagaaactg ctaaagcaaa acttgaagga cctatggacg  25440
gccttcaacg agcgctccgt ggccgcgcac ctggcggaca tcattttccc cgaacgcctg  25500
cttaaaaccc tgcaacaggg tctgccagac ttcaccagtc aaagcatgtt gcagaacttt  25560
aggaacttta tcctagagcg ctcaggaatc ttgcccgcca cctgctgtgc acttcctagc  25620
gactttgtgc ccattaagta ccgcgaatgc cctccgccgc tttggggcca ctgctacctt  25680
ctgcagctag ccaactacct tgcctaccac tctgacataa tggaagacgt gagcggtgac  25740
ggtctactgg agtgtcactg tcgctgcaac ctatgcaccc cgcaccgctc cctggtttgc  25800
aattcgcagc tgcttaacga aagtcaaatt atcggtacct ttgagctgca gggtccctcg  25860
cctgacgaaa agtccgcggc tccggggttg aaactcactc cggggctgtg gacgtcggct  25920
taccttcgca aatttgtacc tgaggactac cacgcccacg agattaggtt ctacgaagac  25980
caatcccgcc cgccaaatgc ggagcttacc gcctgcgtca ttacccaggg ccacattctt  26040
ggccaattgc aagccatcaa caaagcccgc caagagtttc tgctacgaaa gggacggggg  26100
gtttacttgg acccccagtc cggcgaggag ctcaacccaa tcccccgcc gccgcagccc  26160
tatcagcagc agccgcgggc ccttgcttcc caggatggca cccaaaaaga agctgcagct  26220
gccgccgcca cccacggacg aggaggaata ctgggacagt caggcagagg aggttttgga  26280
cgaggaggag gaggacatga tggaagactg ggagagccta gacgaggaag cttccgaggt  26340
cgaagaggtg tcagacgaaa caccgtcacc ctcggtcgca ttcccctcgc cggcgcccca  26400
gaaatcggca accggttcca gcatggctac aacctccgct cctcaggcgc cgccggcact  26460
gcccgttcgc cgacccaacc gtagatggga caccactgga accagggccg gtaagtccaa  26520
gcagccgccg ccgttagccc aagagcaaca acagcgccaa ggctaccgct catggcgcgg  26580
gcacaagaac gccatagttg cttgcttgca agactgtggg ggcaacatct ccttcgcccg  26640
ccgctttctt ctctaccatc acggcgtggc cttcccccgt aacatcctgc attactaccg  26700
tcatctctac agcccatact gcaccggcgg cagcggcagc ggcagcaaca gcagcggcca  26760
cacagaagca aaggcgaccg gatagcaaga ctctgacaaa gcccaagaaa tccacagcgg  26820
cggcagcagc aggaggagga gcgctgcgtc tggcgcccaa cgaacccgta tcgacccgcg  26880
agcttagaaa caggattttt cccactctgt atgctatatt tcaacagagc aggggccaag  26940
aacaagagct gaaaataaaa aacaggtctc tgcgatccct cacccgcagc tgcctgtatc  27000
acaaaagcga agatcagctt cggcgcacgc tggaagacgc ggaggctctc ttcagtaaat  27060
actgcgcgct gactcttaag gactagtttc gcgccctttc tcaaatttaa gcgcgaaaac  27120
tacgtcatct ccagcggcca cacccggcgc cagcacctgt cgtcagcgcc attatgagca  27180
aggaaattcc cacgccctac atgtggagtt accagccaca aatgggactt gcggctggag  27240
ctgcccaaga ctactcaacc cgaataaact acatgagcgc gggaccccac atgatatccc  27300
gggtcaacgg aatccgcgcc caccgaaacc gaattctctt ggaacaggcg gctattacca  27360
ccacacctcg taataacctt aatccccgta gttggcccgc tgccctggtg taccaggaaa  27420
gtcccgctcc caccactgtg gtacttccca gagacgccca ggccgaagtt cagatgacta  27480
actcaggggc gcagcttgcg ggcggctttc gtcacagggt gcggtcgccc gggcagggta  27540
taactcacct gacaatcaga gggcgaggta ttcagctcaa cgacgagtcg gtgagctcct  27600
```

-continued

```
cgcttggtct ccgtccggac gggacatttc agatcggcgg cgccggccgt ccttcattca  27660
cgcctcgtca ggcaatccta actctgcaga cctcgtcctc tgagccgcgc tctggaggca  27720
ttggaactct gcaatttatt gaggagtttg tgccatcggt ctactttaac cccttctcgg  27780
gacctcccgg ccactatccg gatcaattta ttcctaactt tgacgcggta aaggactcgg  27840
cggacggcta cgactgaatg ttaagtggag aggcagagca actgcgcctg aaacacctgg  27900
tccactgtcg ccgccacaag tgctttgccc gcgactccgg tgagttttgc tactttgaat  27960
tgcccgagga tcatatcgag ggcccggcgc acggcgtccg gcttaccgcc cagggagagc  28020
ttgcccgtag cctgattcgg gagtttaccc agcgccccct gctagttgag cgggacaggg  28080
gaccctgtgt tctcactgtg atttgcaact gtcctaacct tggattacat caagatcttt  28140
gttgccatct ctgtgctgag tataataaat acagaaatta aaatatactg gggctcctat  28200
cgccatcctg taaacgccac cgtcttcacc cgcccaagca aaccaaggcg aaccttacct  28260
ggtactttta acatctctcc ctctgtgatt tacaacagtt tcaacccaga cggagtgagt  28320
ctacgagaga acctctccga gctcagctac tccatcagaa aaaacaccac cctccttacc  28380
tgccgggaac gtacgagtgc gtcaccggcc gctgcaccac acctaccgcc tgaccgtaaa  28440
ccagactttt tccggacaga cctcaataac tctgtttacc agaacaggag gtgagcttag  28500
aaaaccctta gggtattagg ccaaaggcgc agctactgtg gggtttatga acaattcaag  28560
caactctacg ggctattcta attcaggttt ctctagaagt caggcttcct ggatgtcagc  28620
atctgacttt ggccagcacc tgtcccgcgg atttgttcca gtccaactac agcgacccac  28680
cctaacagag atgaccaaca caaccaacgc ggccgccgct accggactta catctaccac  28740
aaatacaccc caagtttctg cctttgtcaa taactgggat aacttgggca tgtggtggtt  28800
ctccatagcg cttatgtttg tatgccttat tattatgtgg ctcatctgct gcctaaagcg  28860
caaacgcgcc cgaccaccca tctatagtcc catcattgtg ctacacccaa acaatgatgg  28920
aatccataga ttggacggac tgaaacacat gttcttttct cttacagtat gattaaatga  28980
gatctagaaa tggacggaat tattacagag cagcgcctgc tagaaagacg cagggcagcg  29040
gccgagcaac agcgcatgaa tcaagagctc caagacatgg ttaacttgca ccagtgcaaa  29100
aggggtatct tttgtctggt aaagcaggcc aaagtcacct acgacagtaa taccaccgga  29160
caccgcctta gctacaagtt gccaaccaag cgtcagaaat tggtggtcat ggtgggagaa  29220
aagcccatta ccataactca gcactcggta gaaaccgaag gctgcattca ctcaccttgt  29280
caaggacctg aggatctctg cacccttatt aagaccctgt gcggtctcaa agatcttatt  29340
ccctttaact aataaaaaaa aataataaag catcacttac ttaaaatcag ttagcaaatt  29400
tctgtccagt ttattcagca gcacctcctt gccctcctcc cagctctggt attgcagctt  29460
cctcctggct gcaaactttc tccacaatct aaatggaatg tcagtttcct cctgttcctg  29520
tccatccgca cccactatct tcatgttgtt gcagatgaag cgcgcaagac cgtctgaaga  29580
taccttcaac cccgtgtatc catatgacac ggaaaccggt cctccaactg tgccttttct  29640
tactcctccc tttgtatccc ccaatgggtt tcaagagagt ccccctgggg tactctcttt  29700
gcgcctatcc gaacctctag ttacctccaa tggcatgctt gcgctcaaaa tgggcaacgg  29760
cctctctctg gacgaggccg gcaaccttac ctcccaaaat gtaaccactg tgagcccacc  29820
tctcaaaaaa accaagtcaa acataaacct ggaaatatct gcacccctca cagttacctc  29880
agaagcccta actgtggctg ccgccgcacc tctaatggtc gcgggcaaca cactcaccat  29940
```

-continued

```
gcaatcacag gccccgctaa ccgtgcacga ctccaaactt agcattgcca cccaaggacc  30000
cctcacagtg tcagaaggaa agctagccct gcaaacatca ggccccctca ccaccaccga  30060
tagcagtacc cttactatca ctgcctcacc ccctctaact actgccactg gtagcttggg  30120
cattgacttg aaagagccca tttatacaca aaatggaaaa ctaggactaa agtacggggc  30180
tcctttgcat gtaacagacg acctaaacac tttgaccgta gcaactggtc caggtgtgac  30240
tattaataat acttccttgc aaactaaagt tactggagcc ttgggttttg attcacaagg  30300
caatatgcaa cttaatgtag caggaggact aaggattgat tctcaaaaca gacgccttat  30360
acttgatgtt agttatccgt ttgatgctca aaaccaacta aatctaagac taggacaggg  30420
ccctcttttt ataaactcag cccacaactt ggatattaac tacaacaaag gcctttactt  30480
gtttacagct tcaaacaatt ccaaaaagct tgaggttaac ctaagcactg ccaaggggtt  30540
gatgtttgac gctacagcca tagccattaa tgcaggagat gggcttgaat ttggttcacc  30600
taatgcacca aacacaaatc ccctcaaaac aaaaattggc catggcctag aatttgattc  30660
aaacaaggct atggttccta aactaggaac tggccttagt tttgacagca caggtgccat  30720
tacagtagga aacaaaaata atgataagct aactttgtgg accacaccag ctccatctcc  30780
taactgtaga ctaaatgcag agaaagatgc taaactcact ttggtcttaa caaaatgtgg  30840
cagtcaaata cttgctacag tttcagtttt ggctgttaaa ggcagtttgg ctccaatatc  30900
tggaacagtt caaagtgctc atcttattat aagatttgac gaaaatggag tgctactaaa  30960
caattccttc ctggacccag aatattggaa ctttagaaat ggagatctta ctgaaggcac  31020
agcctataca aacgctgttg gatttatgcc taacctatca gcttatccaa aatctcacgg  31080
taaaactgcc aaaagtaaca ttgtcagtca agtttactta aacggagaca aaactaaacc  31140
tgtaacacta accattacac taaacggtac acaggaaaca ggagacacaa ctccaagtgc  31200
atactctatg tcattttcat gggactggtc tggccacaac tacattaatg aaatatttgc  31260
cacatcctct tacacttttt catacattgc ccaagaataa agaatcgttt gtgttatgtt  31320
tcaacgtgtt tatttttcaa ttgcagaaaa tttcaagtca tttttcattc agtagtatag  31380
ccccaccacc acatagctta tacagatcac cgtaccttaa tcaaactcac agaaccctag  31440
tattcaacct gccacctccc tcccaacaca cagagtacac agtcctttct ccccggctgg  31500
ccttaaaaag catcatatca tgggtaacag acatattctt aggtgttata ttccacacgg  31560
tttcctgtcg agccaaacgc tcatcagtga tattaataaa ctccccgggc agctcactta  31620
agttcatgtc gctgtccagc tgctgagcca caggctgctg tccaacttgc ggttgcttaa  31680
cgggcggcga aggagaagtc cacgcctaca tgggggtaga gtcataatcg tgcatcagga  31740
tagggcggtg gtgctgcagc agcgcgcgaa taaactgctg ccgccgccgc tccgtcctgc  31800
aggaatacaa catggcagtg gtctcctcag cgatgattcg caccgcccgc agcataaggc  31860
gccttgtcct ccgggcacag cagcgcaccc tgatctcact taaatcagca cagtaactgc  31920
agcacagcac cacaatattg ttcaaaatcc cacagtgcaa ggcgctgtat ccaaagctca  31980
tggcggggac cacagaaccc acgtggccat cataccacaa gcgcaggtag attaagtggc  32040
gacccctcat aaacacgctg gacataaaca ttacctcttt tggcatgttg taattcacca  32100
cctcccggta ccatataaac ctctgattaa acatggcgcc atccaccacc atcctaaacc  32160
agctggccaa aacctgcccg ccggctatac actgcaggga accgggactg gaacaatgac  32220
agtggagagc ccaggactcg taaccatgga tcatcatgct cgtcatgata tcaatgttgg  32280
cacaacacag gcacacgtgc atacacttcc tcaggattac aagctcctcc cgcgttagaa  32340
```

-continued

```
ccatatccca gggaacaacc cattcctgaa tcagcgtaaa tcccacactg cagggaagac  32400
ctcgcacgta actcacgttg tgcattgtca aagtgttaca ttcgggcagc agcggatgat  32460
cctccagtat ggtagcgcgg gtttctgtct caaaaggagg tagacgatcc ctactgtacg  32520
gagtgcgccg agacaaccga gatcgtgttg gtcgtagtgt catgccaaat ggaacgccgg  32580
acgtagtcat atttcctgaa gcaaaaccag gtgcgggcgt gacaaacaga tctgcgtctc  32640
cggtctcgcc gcttagatcg ctctgtgtag tagttgtagt atatccactc tctcaaagca  32700
tccaggcgcc ccctggcttc gggttctatg taaactcctt catgcgccgc tgccctgata  32760
acatccacca ccgcagaata agccacaccc agccaaccta cacattcgtt ctgcgagtca  32820
cacacgggag gagcgggaag agctggaaga accatgtttt ttttttttatt ccaaaagatt  32880
atccaaaacc tcaaaatgaa gatctattaa gtgaacgcgc tcccctccgg tggcgtggtc  32940
aaactctaca gccaaagaac agataatggc atttgtaaga tgttgcacaa tggcttccaa  33000
aaggcaaacg gccctcacgt ccaagtggac gtaaaggcta aacccttcag ggtgaatctc  33060
ctctataaac attccagcac cttcaaccat gcccaaataa ttctcatctc gccaccttct  33120
caatatatct ctaagcaaat cccgaatatt aagtccggcc attgtaaaaa tctgctccag  33180
agcgccctcc accttcagcc tcaagcagcg aatcatgatt gcaaaaattc aggttcctca  33240
cagacctgta taagattcaa aagcggaaca ttaacaaaaa taccgcgatc ccgtaggtcc  33300
cttcgcaggg ccagctgaac ataatcgtgc aggtctgcac ggaccagcgc ggccacttcc  33360
ccgccaggaa ccttgacaaa agaacccaca ctgattatga cacgcatact cggagctatg  33420
ctaaccagcg tagccccgat gtaagctttg ttgcatgggc ggcgatataa aatgcaaggt  33480
gctgctcaaa aaatcaggca aagcctcgcg caaaaaagaa agcacatcgt agtcatgctc  33540
atgcagataa aggcaggtaa gctccggaac caccacagaa aaagacacca tttttctctc  33600
aaacatgtct gcgggtttct gcataaacac aaaataaaat aacaaaaaaa catttaaaca  33660
ttagaagcct gtcttacaac aggaaaaaca acccttataa gcataagacg gactacggcc  33720
atgccggcgt gaccgtaaaa aaactggtca ccgtgattaa aaagcaccac cgacagctcc  33780
tcggtcatgt ccggagtcat aatgtaagac tcggtaaaca catcaggttg attcatcggt  33840
cagtgctaaa aagcgaccga aatagcccgg gggaatacat acccgcaggc gtagagacaa  33900
cattacagcc cccataggag gtataacaaa attaatagga gagaaaaaca cataaacacc  33960
tgaaaaaccc tcctgcctag gcaaaatagc accctcccgc tccagaacaa catacagcgc  34020
ttcacagcgg cagcctaaca gtcagcctta ccagtaaaaa agaaaaccta ttaaaaaaac  34080
accactcgac acggcaccag ctcaatcagt cacagtgtaa aaaagggcca agtgcagagc  34140
gagtatatat aggactaaaa aatgacgtaa cggttaaagt ccacaaaaaa cacccagaaa  34200
accgcacgcg aacctacgcc cagaaacgaa agccaaaaaa cccacaactt cctcaaatcg  34260
tcacttccgt tttcccacgt tacgtaactt cccattttaa gaaaactaca attcccaaca  34320
catacaagtt actccgccct aaaacctacg tcacccgccc cgttcccacg ccccgcgcca  34380
cgtcacaaac tccacccccct cattatcata ttggcttcaa tccaaaataa ggtatattat  34440
tgatgatg                                                           34448
```

<210> SEQ ID NO 5
<211> LENGTH: 94
<212> TYPE: PRT
<213> ORGANISM: Adenovirus subgroup C -continued

<400> SEQUENCE: 5

Met Val Asp Thr Val Asn Ser Tyr Asn Thr Ala Thr Gly Leu Thr Ser
1 5 10 15

Ala Leu Asn Leu Pro Gln Val Ser Thr Phe Val Asn Asn Trp Ala Asn
20 25 30

Leu Gly Met Trp Trp Phe Ser Ile Ala Leu Met Phe Val Cys Leu Ile
35 40 45

Ile Met Trp Leu Ser Cys Cys Leu Lys Arg Lys Arg Ala Arg Pro Pro
50 55 60

Ile Tyr Lys Pro Ile Ile Val Leu Asn Pro Asn Asn Asp Gly Ile His
65 70 75 80

Arg Leu Asp Gly Leu Asn Thr Cys Ser Phe Ser Phe Ala Val
85 90

<210> SEQ ID NO 6
<211> LENGTH: 101
<212> TYPE: PRT
<213> ORGANISM: Adenovirus subgroup C

<400> SEQUENCE: 6

Met Thr Gly Ser Thr Ile Ala Pro Thr Thr Asp Tyr Arg Asn Thr Thr
1 5 10 15

Ala Thr Gly Leu Thr Ser Ala Leu Asn Leu Pro Gln Val His Ala Phe
20 25 30

Val Asn Asp Trp Ala Ser Leu Asp Met Trp Trp Phe Ser Ile Ala Leu
35 40 45

Met Phe Val Cys Leu Ile Ile Met Trp Leu Ile Cys Cys Leu Lys Arg
50 55 60

Arg Arg Ala Arg Pro Pro Ile Tyr Arg Pro Ile Ile Val Leu Asn Pro
65 70 75 80

His Asn Glu Lys Ile His Arg Leu Asp Gly Leu Lys Pro Cys Ser Leu
85 90 95

Leu Leu Gln Tyr Asp
100

<210> SEQ ID NO 7
<211> LENGTH: 93
<212> TYPE: PRT
<213> ORGANISM: Adenovirus subgroup C

<400> SEQUENCE: 7

Met Thr Asn Thr Thr Asn Ala Ala Ala Ala Thr Gly Leu Thr Ser Thr
1 5 10 15

Thr Asn Thr Pro Gln Val Ser Ala Phe Val Asn Asn Trp Asp Asn Leu
20 25 30

Gly Met Trp Trp Phe Ser Ile Ala Leu Met Phe Val Cys Leu Ile Ile
35 40 45

Met Trp Leu Ile Cys Cys Leu Lys Arg Lys Arg Ala Arg Pro Pro Ile
50 55 60

Tyr Ser Pro Ile Ile Val Leu His Pro Asn Asn Asp Gly Ile His Arg
65 70 75 80

Leu Asp Gly Leu Lys His Met Phe Phe Ser Leu Thr Val
85 90

<210> SEQ ID NO 8
<211> LENGTH: 95
<212> TYPE: PRT

-continued

```
<213> ORGANISM: Adenovirus subgroup C

<400> SEQUENCE: 8

Met Val Asp Thr Val Asn Ser Tyr Asn Thr Ala Thr Gly Leu Lys Ser
1               5                   10                  15

Ala Leu Asn Leu Pro Gln Val His Ala Phe Val Asn Asp Trp Ala Ser
            20                  25                  30

Leu Gly Met Trp Trp Phe Ser Ile Ala Leu Met Phe Val Cys Leu Ile
        35                  40                  45

Ile Met Trp Leu Ile Cys Cys Leu Lys Arg Arg Arg Ala Arg Pro Pro
    50                  55                  60

Ile Tyr Arg Pro Ile Ile Val Leu Asn Pro His Asn Glu Lys Ile His
65                  70                  75                  80

Arg Leu Asp Gly Leu Lys Pro Cys Ser Leu Leu Leu Gln Tyr Asp
                85                  90                  95


<210> SEQ ID NO 9
<211> LENGTH: 78
<212> TYPE: PRT
<213> ORGANISM: Adenovirus subgroup C

<400> SEQUENCE: 9

Met Thr Gly Ser Thr Ile Ala Pro Thr Thr Asp Tyr Arg Asn Thr Thr
1               5                   10                  15

Ala Thr Gly Leu Thr Ser Ala Leu Asn Leu Pro Gln Val His Ala Phe
            20                  25                  30

Val Asn Asp Trp Ala Ser Leu Asp Met Trp Trp Phe Ser Ile Ala Leu
        35                  40                  45

Met Phe Val Cys Leu Ile Ile Met Trp Leu Ile Cys Cys Leu Lys Arg
    50                  55                  60

Arg Arg Ala Arg Pro Pro Ile Tyr Arg Pro Ile Ile Val Leu
65                  70                  75


<210> SEQ ID NO 10
<211> LENGTH: 87
<212> TYPE: PRT
<213> ORGANISM: Adenovirus subgroup C

<400> SEQUENCE: 10

Met Thr Gly Ser Thr Ile Ala Pro Thr Thr Asp Tyr Arg Asn Thr Thr
1               5                   10                  15

Ala Thr Gly Leu Thr Ser Ala Leu Asn Leu Pro Gln Val His Ala Phe
            20                  25                  30

Val Asn Asp Trp Ala Ser Leu Asp Met Trp Trp Phe Ser Ile Ala Leu
        35                  40                  45

Met Phe Val Cys Leu Ile Ile Met Trp Leu Ile Cys Cys Leu Lys Arg
    50                  55                  60

Arg Arg Ala Arg Pro Pro Ile Tyr Arg Pro Ile Gly Leu Lys Pro Cys
65                  70                  75                  80

Ser Leu Leu Leu Gln Tyr Asp
                85


<210> SEQ ID NO 11
<211> LENGTH: 77
<212> TYPE: PRT
<213> ORGANISM: Adenovirus subgroup C

<400> SEQUENCE: 11
```

-continued

```
Met Thr Gly Ser Thr Ile Ala Pro Thr Thr Asp Tyr Arg Asn Thr Thr
1               5                   10                  15

Ala Thr Gly Leu Thr Ser Ala Leu Asn Leu Pro Gln Val His Ala Phe
            20                  25                  30

Val Asn Asp Trp Ala Ser Leu Asp Met Trp Trp Phe Ser Ile Ala Leu
        35                  40                  45

Met Phe Val Cys Leu Ile Ile Met Trp Leu Ile Cys Cys Leu Lys Arg
    50                  55                  60

Arg Arg Ala Arg Pro Pro Ser Leu Leu Leu Gln Tyr Asp
65                  70                  75


<210> SEQ ID NO 12
<211> LENGTH: 84
<212> TYPE: PRT
<213> ORGANISM: Adenovirus subgroup C

<400> SEQUENCE: 12

Met Thr Gly Ser Thr Ile Ala Pro Thr Thr Asp Tyr Arg Asn Thr Thr
1               5                   10                  15

Ala Thr Gly Leu Thr Ser Ala Leu Asn Leu Pro Gln Ile Ala Leu Met
            20                  25                  30

Phe Val Cys Leu Ile Ile Met Trp Leu Ile Cys Cys Leu Lys Arg Arg
        35                  40                  45

Arg Ala Arg Pro Pro Ile Tyr Arg Pro Ile Ile Val Leu Asn Pro His
    50                  55                  60

Asn Glu Lys Ile His Arg Leu Asp Gly Leu Lys Pro Cys Ser Leu Leu
65                  70                  75                  80

Leu Gln Tyr Asp


<210> SEQ ID NO 13
<211> LENGTH: 35724
<212> TYPE: DNA
<213> ORGANISM: Adenovirus subgroup C

<400> SEQUENCE: 13

catcatcaat aatatacctt attttggatt gaagccaata tgataatgag ggggtggagt      60

ttgtgacgtg gcgcggggcg tgggaacggg gcgggtgacg tagtagtgtg gcggaagtgt     120

gatgttgcaa gtgtggcgga acacatgtaa gcgacggatg tggcaaaagt gacgtttttg     180

gtgtgcgccg gtgtacacag gaagtgacaa ttttcgcgcg gttttaggcg gatgttgtag     240

taaatttggg cgtaaccgag taagatttgg ccattttcgc gggaaaactg aataagagga     300

agtgaaatct gaataatttt gtgttactca tagcgcgtaa tatttgtcta gggccgcggg     360

gactttgacc gtttacgtgg agactcgccc aggtgttttt ctcaggtgtt ttccgcgttc     420

cgggtcaaag ttggcgtttt attattatag tcagctgacg tgtagtgtat ttatacccgg     480

tgagttcctc aagaggccac tcttgagtgc cagcgagtag agttttctcc tccgagccgc     540

tccgacaccg ggactgaaaa tgagacatga ggtactggct gataatcttc cacctcctag     600

ccattttgaa ccacctaccc ttcacgaact gtatgattta gacgtgacgg cccccgaaga     660

tcccaacgag gaggcggttt cgcagatttt tcccgactct gtaatgttgg cggtgcagga     720

agggattgac ttactcactt ttccgccggc gcccggttct ccggagccgc ctcacctttc     780

ccggcagccc gagcagccgg agcagagagc cttgggtccg gtttgccacg aggctggctt     840

tccacccagt gacgacgagg atgaagaggg tgaggagttt gtgttagatt atgtggagca     900

ccccgggcac ggttgcaggt cttgtcatta tcaccggagg aatacggggg acccagatat     960
```

-continued

```
tatgtgttcg ctttgctata tgaggacctg tggcatgttt gtctacagta agtgaaaatt   1020
atgggcagtg ggtgatagag tggtgggttt ggtgtggtaa tttttttttt aatttttaca   1080
gttttgtggt ttaaagaatt ttgtattgtg atttttttaa aaggtcctgt gtctgaacct   1140
gagcctgagc ccgagccaga accggagcct gcaagaccta cccgccgtcc taaaatggcg   1200
cctgctatcc tgagacgccc gacatcacct gtgtctagag aatgcaatag tagtacggat   1260
agctgtgact ccggtccttc taacacacct cctgagatac acccggtggt cccgctgtgc   1320
cccattaaac cagttgccgt gagagttggt gggcgtcgcc aggctgtgga atgtatcgag   1380
gacttgctta acgagcctgg gcaacctttg gacttgagct gtaaacgccc caggccataa   1440
ggtgtaaacc tgtgattgcg tgtgtggtta acgcctttgt ttgctgaatg agttgatgta   1500
agtttaataa agggtgagat aatgtttaac ttgcatggcg tgttaaatgg ggcggggctt   1560
aaagggtata taatgcgccg tggctaatc ttggttacat ctgacctcat ggaggcttgg   1620
gagtgtttgg aagatttttc tgctgtgcgt aacttgctgg aacagagctc taacagtacc   1680
tcttggtttt ggaggtttct gtggggctca tcccaggcaa agttagtctg cagaattaag   1740
gaggattaca agtgggaatt tgaagagctt ttgaaatcct gtggtgagct gtttgattct   1800
ttgaatctgg gtcaccaggc gcttttccaa gagaaggtca tcaagacttt ggatttttcc   1860
acaccggggc gcgctgcggc tgctgttgct tttttgagtt ttataaagga taaatggagc   1920
gaagaaaccc atctgagcgg ggggtacctg ctggattttc tggccatgca tctgtggaga   1980
gcggttgtga gacacaagaa tcgcctgcta ctgttgtctt ccgtccgccc ggcgataata   2040
ccgacggagg agcagcagca gcagcaggag gaagccaggc ggcggcggca ggagcagagc   2100
ccatggaacc cgagagccgg cctggaccct cgggaatgaa tgttgtacag gtggctgaac   2160
tgtatccaga actgagacgc attttgacaa ttacagagga tgggcagggg ctaaaggggg   2220
taaagaggga gcggggggct tgtgaggcta cagaggaggc taggaatcta gcttttagct   2280
taatgaccag acaccgtcct gagtgtatta cttttcaaca gatcaaggat aattgcgcta   2340
atgagcttga tctgctggcg cagaagtatt ccatagagca gctgaccact tactggctgc   2400
agccagggga tgattttgag gaggctatta gggtatatgc aaaggtggca cttaggccag   2460
attgcaagta caagatcagc aaacttgtaa atatcaggaa ttgttgctac atttctggga   2520
acggggccga ggtggagata gatacggagg atagggtggc ctttagatgt agcatgataa   2580
atatgtggcc gggggtgctt ggcatggacg gggtggttat tatgaatgta aggtttactg   2640
gccccaattt tagcggtacg gttttcctgg ccaataccaa ccttatccta cacggtgtaa   2700
gcttctatgg gtttaacaat acctgtgtgg aagcctggac cgatgtaagg gttcggggct   2760
gtgcctttta ctgctgctgg aagggggtgg tgtgtcgccc caaaagcagg gcttcaatta   2820
agaaatgcct ctttgaaagg tgtaccttgg gtatcctgtc tgagggtaac tccagggtgc   2880
gccacaatgt ggcctccgac tgtggttgct tcatgctagt gaaaagcgtg gctgtgatta   2940
agcataacat ggtatgtggc aactgcgagg acagggcctc tcagatgctg acctgctcgg   3000
acggcaactg tcacctgctg aagaccattc acgtagccag ccactctcgc aaggcctggc   3060
cagtgtttga gcataacata ctgacccgct gttccttgca tttgggtaac aggagggggg   3120
tgttcctacc ttaccaatgc aatttgagtc acactaagat attgcttgag cccgagagca   3180
tgtccaaggt gaacctgaac ggggtgtttg acatgaccat gaagatctgg aaggtgctga   3240
ggtacgatga gacccgcacc aggtgcagac cctgcgagtg tggcggtaaa catattagga   3300
```

-continued

```
accagcctgt gatgctggat gtgaccgagg agctgaggcc cgatcacttg gtgctggcct   3360
gcacccgcgc tgagtttggc tctagcgatg aagatacaga ttgaggtact gaaatgtgtg   3420
ggcgtggctt aagggtggga aagaatatat aaggtggggg tcttatgtag ttttgtatct   3480
gttttgcagc agccgccgcc gccatgagca ccaactcgtt tgatggaagc attgtgagct   3540
catatttgac aacgcgcatg cccccatggg ccggggtgcg tcagaatgtg atgggctcca   3600
gcattgatgg tcgccccgtc ctgcccgcaa actctactac cttgacctac gagaccgtgt   3660
ctggaacgcc gttggagact gcagcctccg ccgccgcttc agccgctgca gccaccgccc   3720
gcgggattgt gactgacttt gctttcctga gcccgcttgc aagcagtgca gcttcccgtt   3780
catccgcccg cgatgacaag ttgacggctc ttttggcaca attggattct ttgacccggg   3840
aacttaatgt cgtttctcag cagctgttgg atctgcgcca gcaggtttct gccctgaagg   3900
cttcctcccc tcccaatgcg gtttaaaaca taaataaaaa accagactct gtttggattt   3960
ggatcaagca agtgtcttgc tgtctttatt taggggtttt gcgcgcgcgg taggcccggg   4020
accagcggtc tcggtcgttg agggtcctgt gtattttttc caggacgtgg taaaggtgac   4080
tctggatgtt cagatacatg ggcataagcc cgtctctggg gtggaggtag caccactgca   4140
gagcttcatg ctgcggggtg gtgttgtaga tgatccagtc gtagcaggag cgctgggcgt   4200
ggtgcctaaa aatgtctttc agtagcaagc tgattgccag gggcaggccc ttggtgtaag   4260
tgtttacaaa gcggttaagc tgggatgggt gcatacgtgg ggatatgaga tgcatcttgg   4320
actgtatttt taggttggct atgttcccag ccatatccct ccggggattc atgttgtgca   4380
gaaccaccag cacagtgtat ccggtgcact tgggaaattt gtcatgtagc ttagaaggaa   4440
atgcgtggaa gaacttggag acgcccttgt gacctccaag attttccatg cattcgtcca   4500
taatgatggc aatgggccca cgggcggcgg cctgggcgaa gatatttctg ggatcactaa   4560
cgtcatagtt gtgttccagg atgagatcgt cataggccat ttttacaaag cgcgggcgga   4620
gggtgccaga ctgcggtata atggttccat ccggcccagg ggcgtagtta ccctcacaga   4680
tttgcatttc ccacgctttg agttcagatg gggggatcat gtctacctgc ggggcgatga   4740
agaaaacggt ttccggggta ggggagatca gctgggaaga aagcaggttc ctgagcagct   4800
gcgacttacc gcagccggtg ggcccgtaaa tcacacctat taccgggtgc aactggtagt   4860
taagagagct gcagctgccg tcatccctga gcaggggggc cacttcgtta agcatgtccc   4920
tgactcgcat gttttccctg accaaatccg ccagaaggcg ctcgccgccc agcgatagca   4980
gttcttgcaa ggaagcaaag tttttcaacg gtttgagacc gtccgccgta ggcatgcttt   5040
tgagcgtttg accaagcagt tccaggcggt cccacagctc ggtcacctgc tctacggcat   5100
ctcgatccag catatctcct cgtttcgcgg gttggggcgg ctttcgctgt acggcagtag   5160
tcggtgctcg tccagacggg ccagggtcat gtctttccac gggcgcaggg tcctcgtcag   5220
cgtagtctgg gtcacggtga aggggtgcgc tccgggctgc gcgctggcca gggtgcgctt   5280
gaggctggtc ctgctggtgc tgaagcgctg ccggtcttcg ccctgcgcgt cggccaggta   5340
gcatttgacc atggtgtcat agtccagccc ctccgcggcg tggcccttgg cgcgcagctt   5400
gcccttggag gaggcgccgc acgaggggca gtgcagactt ttgagggcgt agagcttggg   5460
cgcgagaaat accgattccg gggagtaggc atccgcgccg caggccccgc agacggtctc   5520
gcattccacg agccaggtga gctctggccg ttcggggtca aaaaccaggt ttcccccatg   5580
ctttttgatg cgtttcttac ctctggtttc catgagccgg tgtccacgct cggtgacgaa   5640
aaggctgtcc gtgtccccgt atacagactt gagaggcctg tcctcgagcg gtgttccgcg   5700
```

-continued

```
gtcctcctcg tatagaaact cggaccactc tgagacaaag gctcgcgtcc aggccagcac   5760
gaaggaggct aagtgggagg ggtagcggtc gttgtccact agggggtcca ctcgctccag   5820
ggtgtgaaga cacatgtcgc cctcttcggc atcaaggaag gtgattggtt tgtaggtgta   5880
ggccacgtga ccgggtgttc ctgaaggggg gctataaaag ggggtggggg cgcgttcgtc   5940
ctcactctct tccgcatcgc tgtctgcgag ggccagctgt tggggtgagt actccctctg   6000
aaaagcgggc atgacttctg cgctaagatt gtcagtttcc aaaaacgagg aggatttgat   6060
attcacctgg cccgcggtga tgcctttgag ggtggccgca tccatctggt cagaaaagac   6120
aatctttttg ttgtcaagct tggtggcaaa cgacccgtag agggcgttgg acagcaactt   6180
ggcgatggag cgcagggttt ggtttttgtc gcgatcggcg cgctccttgg ccgcgatgtt   6240
tagctgcacg tattcgcgcg caacgcaccg ccattcggga aagacggtgg tgcgctcgtc   6300
gggcaccagg tgcacgcgcc aaccgcggtt gtgcagggtg acaaggtcaa cgctggtggc   6360
tacctctccg cgtaggcgct cgttggtcca gcagaggcgg ccgcccttgc gcgagcagaa   6420
tggcggtagg gggtctagct gcgtctcgtc cggggggtct gcgtccacgg taaagacccc   6480
gggcagcagg cgcgcgtcga agtagtctat cttgcatcct tgcaagtcta gcgcctgctg   6540
ccatgcgcgg gcggcaagcg cgcgctcgta tgggttgagt gggggacccc atggcatggg   6600
gtgggtgagc gcggaggcgt acatgccgca aatgtcgtaa acgtagaggg gctctctgag   6660
tattccaaga tatgtagggt agcatcttcc accgcggatg ctggcgcgca cgtaatcgta   6720
tagttcgtgc gagggagcga ggaggtcggg accgaggttg ctacgggcgg gctgctctgc   6780
tcggaagact atctgcctga agatggcatg tgagttggat gatatggttg gacgctggaa   6840
gacgttgaag ctggcgtctg tgagacctac cgcgtcacgc acgaaggagg cgtaggagtc   6900
gcgcagcttg ttgaccagct cggcggtgac ctgcacgtct agggcgcagt agtccagggt   6960
ttccttgatg atgtcatact tatcctgtcc cttttttttc cacagctcgc ggttgaggac   7020
aaactcttcg cggtctttcc agtactcttg gatcggaaac ccgtcggcct ccgaacggta   7080
agagcctagc atgtagaact ggttgacggc ctggtaggcg cagcatccct tttctacggg   7140
tagcgcgtat gcctgcgcgg ccttccggag cgaggtgtgg gtgagcgcaa aggtgtccct   7200
gaccatgact ttgaggtact ggtatttgaa gtcagtgtcg tcgcatccgc cctgctccca   7260
gagcaaaaag tccgtgcgct tttggaacg cggatttggc agggcgaagg tgacatcgtt   7320
gaagagtatc tttcccgcgc gaggcataaa gttgcgtgtg atgcggaagg gtcccggcac   7380
ctcggaacgg ttgttaatta cctgggcggc gagcacgatc tcgtcaaagc cgttgatgtt   7440
gtggcccaca atgtaaagtt ccaagaagcg cgggatgccc ttgatggaag gcaatttttt   7500
aagttcctcg taggtgagct cttcagggga gctgagcccg tgctctgaaa gggcccagtc   7560
tgcaagatga gggttggaag cgacgaatga gctccacagg tcacgggcca ttagcatttg   7620
caggtggtcg cgaaaggtcc taaactggcg acctatggcc atttttctg gggtgatgca   7680
gtagaaggta agcgggtctt gttcccagcg gtcccatcca aggttcgcgg ctaggtctcg   7740
cgcggcagtc actagaggct catctccgcc gaacttcatg accagcatga agggcacgag   7800
ctgcttccca aaggccccca tccaagtata ggtctctaca tcgtaggtga caaagagacg   7860
ctcggtgcga ggatgcgagc cgatcgggaa gaactggatc tcccgccacc aattggagga   7920
gtggctattg atgtggtgaa agtagaagtc cctgcgacgg gccgaacact cgtgctggct   7980
tttgtaaaaa cgtgcgcagt actggcagcg gtgcacgggc tgtacatcct gcacgaggtt   8040
```

-continued gacctgacga ccgcgcacaa ggaagcagag tgggaatttg agcccctcgc ctggcgggtt 8100
tggctggtgg tcttctactt cggctgcttg tccttgaccg tctggctgct cgaggggagt 8160
tacggtggat cggaccacca cgccgcgcga gcccaaagtc cagatgtccg cgcgcggcgg 8220
tcggagcttg atgacaacat cgcgcagatg ggagctgtcc atggtctgga gctcccgcgg 8280
cgtcaggtca ggcgggagct cctgcaggtt tacctcgcat agacgggtca gggcgcgggc 8340
tagatccagg tgatacctaa tttccagggg ctggttggtg gcggcgtcga tggcttgcaa 8400
gaggccgcat ccccgcggcg cgactacggt accgcgcggc gggcggtggg ccgcgggggt 8460
gtccttggat gatgcatcta aaagcggtga cgcgggcgag cccccggagg tagggggggc 8520
tccggacccg ccgggagagg gggcaggggc acgtcggcgc cgcgcgcggg caggagctgg 8580
tgctgcgcgc gtaggttgct ggcgaacgcg acgacgcggc ggttgatctc ctgaatctgg 8640
cgcctctgcg tgaagacgac gggcccggtg agcttgagcc tgaaagagag ttcgacagaa 8700
tcaatttcgg tgtcgttgac ggcggcctgg cgcaaaatct cctgcacgtc tcctgagttg 8760
tcttgatagg cgatctcggc catgaactgc tcgatctctt cctcctggag atctccgcgt 8820
ccggctcgct ccacggtggc ggcgaggtcg ttggaaatgc gggccatgag ctgcgagaag 8880
gcgttgaggc ctccctcgtt ccagacgcgg ctgtagacca cgcccccttc ggcatcgcgg 8940
gcgcgcatga ccacctgcgc gagattgagc tccacgtgcc gggcgaagac ggcgtagttt 9000
cgcaggcgct gaaagaggta gttgagggtg gtggcggtgt gttctgccac gaagaagtac 9060
ataacccagc gtcgcaacgt ggattcgttg atatccccca aggcctcaag gcgctccatg 9120
gcctcgtaga agtccacggc gaagttgaaa aactgggagt tgcgcgccga cacggttaac 9180
tcctcctcca gaagacggat gagctcggcg acagtgtcgc gcacctcgcg ctcaaaggct 9240
acaggggcct cttcttcttc ttcaatctcc tcttccataa gggcctcccc ttcttcttct 9300
tctggcggcg gtgggggagg ggggacacgg cggcgacgac ggcgcaccgg gaggcggtcg 9360
acaaagcgct cgatcatctc cccgcggcga cggcgcatgg tctcggtgac ggcgcggccg 9420
ttctcgcggg ggcgcagttg gaagacgccg cccgtcatgt cccggttatg ggttggcggg 9480
gggctgccat gcggcaggga tacggcgcta acgatgcatc tcaacaattg ttgtgtaggt 9540
actccgccgc cgagggacct gagcgagtcc gcatcgaccg gatcggaaaa cctctcgaga 9600
aaggcgtcta accagtcaca gtcgcaaggt aggctgagca ccgtggcggg cggcagcggg 9660
cggcggtcgg ggttgtttct ggcggaggtg ctgctgatga tgtaattaaa gtaggcggtc 9720
ttgagacggc ggatggtcga cagaagcacc atgtccttgg gtccggcctg ctgaatgcgc 9780
aggcggtcgg ccatgcccca ggcttcgttt tgacatcggc gcaggtcttt gtagtagtct 9840
tgcatgagcc tttctaccgg cacttcttct tctccttcct cttgtcctgc atctcttgca 9900
tctatcgctg cggcggcggc ggagtttggc cgtaggtggc gccctcttcc tcccatgcgt 9960
gtgaccccga agcccctcat cggctgaagc agggctaggt cggcgacaac gcgctcggct 10020
aatatggcct gctgcacctg cgtgagggta gactggaagt catccatgtc cacaaagcgg 10080
tggtatgcgc ccgtgttgat ggtgtaagtg cagttggcca taacggacca gttaacggtc 10140
tggtgacccg gctgcgagag ctcggtgtac ctgagacgcg agtaagccct cgagtcaaat 10200
acgtagtcgt tgcaagtccg caccaggtac tggtatccca ccaaaaagtg cggcggcggc 10260
tggcggtaga ggggccagcg tagggtggcc ggggctccgg gggcgagatc ttccaacata 10320
aggcgatgat atccgtagat gtacctggac atccaggtga tgccggcggc ggtggtggag 10380
gcgcgcggaa agtcgcggac gcggttccag atgttgcgca gcggcaaaaa gtgctccatg 10440

-continued

```
gtcgggacgc tctggccggt caggcgcgcg caatcgttga cgctctagcg tgcaaaagga  10500
gagcctgtaa gcgggcactc ttccgtggtc tggtggataa attcgcaagg gtatcatggc  10560
ggacgaccgg ggttcgagcc ccgtatccgg ccgtccgccg tgatccatgc ggttaccgcc  10620
cgcgtgtcga acccaggtgt gcgacgtcag acaacggggg agtgctcctt ttggcttcct  10680
tccaggcgcg gcggctgctg cgctagcttt tttggccact ggccgcgcgc agcgtaagcg  10740
gttaggctgg aaagcgaaag cattaagtgg ctcgctccct gtagccggag ggttattttc  10800
caagggttga gtcgcgggac ccccggttcg agtctcggac cggccggact gcggcgaacg  10860
ggggtttgcc tccccgtcat gcaagacccc gcttgcaaat tcctccggaa acagggacga  10920
gccccttttt tgcttttccc agatgcatcc ggtgctgcgg cagatgcgcc cccctcctca  10980
gcagcggcaa gagcaagagc agcggcagac atgcagggca ccctcccctc ctcctaccgc  11040
gtcaggaggg gcgacatccg cggttgacgc ggcagcagat ggtgattacg aacccccgcg  11100
gcgccgggcc cggcactacc tggacttgga ggagggcgag ggcctggcgc ggctaggagc  11160
gccctctcct gagcggtacc caagggtgca gctgaagcgt gatacgcgtg aggcgtacgt  11220
gccgcggcag aacctgtttc gcgaccgcga gggagaggag cccgaggaga tgcgggatcg  11280
aaagttccac gcagggcgcg agctgcggca tggcctgaat cgcgagcggt tgctgcgcga  11340
ggaggacttt gagcccgacg cgcgaaccgg gattagtccc gcgcgcgcac acgtggcggc  11400
cgccgacctg gtaaccgcat acgagcagac ggtgaaccag gagattaact ttcaaaaaag  11460
ctttaacaac cacgtgcgta cgcttgtggc gcgcgaggag gtggctatag gactgatgca  11520
tctgtgggac tttgtaagcg cgctggagca aaacccaaat agcaagccgc tcatggcgca  11580
gctgttcctt atagtgcagc acagcaggga caacgaggca ttcagggatg cgctgctaaa  11640
catagtagag cccgagggcc gctggctgct cgatttgata aacatcctgc agagcatagt  11700
ggtgcaggag cgcagcttga gcctggctga caaggtggcc gccatcaact attccatgct  11760
tagcctgggc aagttttacg cccgcaagat ataccatacc ccttacgttc ccatagacaa  11820
ggaggtaaag atcgaggggt tctacatgcg catggcgctg aaggtgctta ccttgagcga  11880
cgacctgggc gtttatcgca acgagcgcat ccacaaggcc gtgagcgtga gccggcggcg  11940
cgagctcagc gaccgcgagc tgatgcacag cctgcaaagg gccctggctg gcacgggcag  12000
cggcgataga gaggccgagt cctactttga cgcgggcgct gacctgcgct gggccccaag  12060
ccgacgcgcc ctggaggcag ctggggccgg acctgggctg gcggtggcac ccgcgcgcgc  12120
tggcaacgtc ggcggcgtgg aggaatatga cgaggacgat gagtacgagc cagaggacgg  12180
cgagtactaa gcggtgatgt ttctgatcag atgatgcaag acgcaacgga cccggcggtg  12240
cgggcggcgc tgcagagcca gccgtccggc cttaactcca cggacgactg gcgccaggtc  12300
atggaccgca tcatgtcgct gactgcgcgc aatcctgacg cgttccggca gcagccgcag  12360
gccaaccggc tctccgcaat tctggaagcg gtggtcccgg cgcgcgcaaa ccccacgcac  12420
gagaaggtgc tggcgatcgt aaacgcgctg gccgaaaaca gggccatccg gcccgacgag  12480
gccggcctgg tctacgacgc gctgcttcag cgcgtggctc gttacaacag cggcaacgtg  12540
cagaccaacc tggaccggct ggtgggggat gtgcgcgagg ccgtggcgca gcgtgagcgc  12600
gcgcagcagc agggcaacct gggctccatg gttgcactaa acgccttcct gagtacacag  12660
cccgccaacg tgccgcgggg acaggaggac tacaccaact ttgtgagcgc actgcggcta  12720
atggtgactg agacaccgca aagtgaggtg taccagtctg ggccagacta tttttccag  12780
```

-continued

```
accagtagac aaggcctgca gaccgtaaac ctgagccagg ctttcaaaaa cttgcagggg  12840
ctgtgggggg tgcgggctcc cacaggcgac cgcgcgaccg tgtctagctt gctgacgccc  12900
aactcgcgcc tgttgctgct gctaatagcg cccttcacgg acagtggcag cgtgtcccgg  12960
gacacatacc taggtcactt gctgacactg taccgcgagg ccataggtca ggcgcatgtg  13020
gacgagcata ctttccagga gattacaagt gtcagccgcg cgctggggca ggaggacacg  13080
ggcagcctgg aggcaaccct aaactacctg ctgaccaacc ggcggcagaa gatcccctcg  13140
ttgcacagtt taaacagcga ggaggagcgc attttgcgct acgtgcagca gagcgtgagc  13200
cttaacctga tgcgcgacgg ggtaacgccc agcgtggcgc tggacatgac cgcgcgcaac  13260
atggaaccgg gcatgtatgc ctcaaaccgg ccgtttatca accgcctaat ggactacttg  13320
catcgcgcgg ccgccgtgaa ccccgagtat ttcaccaatg ccatcttgaa cccgcactgg  13380
ctaccgcccc ctggtttcta caccggggga ttcgaggtgc ccgagggtaa cgatggattc  13440
ctctgggacg acatagacga cagcgtgttt tccccgcaac cgcagaccct gctagagttg  13500
caacagcgcg agcaggcaga ggcggcgctg cgaaaggaaa gcttccgcag gccaagcagc  13560
ttgtccgatc taggcgctgc ggccccgcgg tcagatgcta gtagcccatt tccaagcttg  13620
atagggtctc ttaccagcac tcgcaccacc cgcccgcgcc tgctgggcga ggaggagtac  13680
ctaaacaact cgctgctgca gccgcagcgc gaaaaaaacc tgcctccggc atttcccaac  13740
aacgggatag agagcctagt ggacaagatg agtagatgga agacgtacgc gcaggagcac  13800
agggacgtgc caggcccgcg cccgcccacc cgtcgtcaaa ggcacgaccg tcagcggggt  13860
ctggtgtggg aggacgatga ctcggcagac gacagcagcg tcctggattt gggagggagt  13920
ggcaacccgt ttgcgcacct tcgccccagg ctggggagaa tgttttaaaa aaaaaaaagc  13980
atgatgcaaa ataaaaaact caccaaggcc atggcaccga gcgttggttt tcttgtattc  14040
cccttagtat gcggcgcgcg gcgatgtatg aggaaggtcc tcctccctcc tacgagagtg  14100
tggtgagcgc ggcgccagtg gcggcggcgc tgggttctcc cttcgatgct cccctggacc  14160
cgccgtttgt gcctccgcgg tacctgcggc ctaccggggg gagaaacagc atccgttact  14220
ctgagttggc acccctattc gacaccaccc gtgtgtacct ggtggacaac aagtcaacgg  14280
atgtggcatc cctgaactac cagaacgacc acagcaactt tctgaccacg gtcattcaaa  14340
acaatgacta cagcccgggg gaggcaagca cacagaccat caatcttgac gaccggtcgc  14400
actggggcgg cgacctgaaa accatcctgc ataccaacat gccaaatgtg aacgagttca  14460
tgtttaccaa taagtttaag gcgcgggtga tggtgtcgcg cttgcctact aaggacaatc  14520
aggtggagct gaaatacgag tgggtggagt tcacgctgcc cgagggcaac tactccgaga  14580
ccatgaccat agaccttatg aacaacgcga tcgtggagca ctacttgaaa gtgggcagac  14640
agaacggggt tctggaaagc gacatcgggg taaagtttga cacccgcaac ttcagactgg  14700
ggtttgaccc cgtcactggt cttgtcatgc ctggggtata tacaaacgaa gccttccatc  14760
cagacatcat tttgctgcca ggatgcgggg tggacttcac ccacagccgc ctgagcaact  14820
tgttgggcat ccgcaagcgg caacccttcc aggagggctt taggatcacc tacgatgatc  14880
tggagggtgg taacattccc gcactgttgg atgtggacgc ctaccaggcg agcttgaaag  14940
atgacaccga acagggcggg ggtggcgcag gcggcagcaa cagcagtggc agcggcgcgg  15000
aagagaactc caacgcggca gccgcggcaa tgcagccggt ggaggacatg aacgatcatg  15060
ccattcgcgg cgacaccttt gccacacggg ctgaggagaa gcgcgctgag gccgaagcag  15120
cggccgaagc tgccgccccc gctgcgcaac ccgaggtcga gaagcctcag aagaaaccgg  15180
```

-continued tgatcaaacc cctgacagag gacagcaaga aacgcagtta caacctaata agcaatgaca 15240
gcaccttcac ccagtaccgc agctggtacc ttgcatacaa ctacggcgac cctcagaccg 15300
gaatccgctc atggaccctg ctttgcactc ctgacgtaac ctgcggctcg gagcaggtct 15360
actggtcgtt gccagacatg atgcaagacc ccgtgacctt ccgctccacg cgccagatca 15420
gcaactttcc ggtggtgggc gccgagctgt tgcccgtgca ctccaagagc ttctacaacg 15480
accaggccgt ctactcccaa ctcatccgcc agtttacctc tctgacccac gtgttcaatc 15540
gctttcccga gaaccagatt ttggcgcgcc cgccagcccc caccatcacc accgtcagtg 15600
aaaacgttcc tgctctcaca gatcacggga cgctaccgct gcgcaacagc atcggaggag 15660
tccagcgagt gaccattact gacgccagac gccgcacctg cccctacgtt tacaaggccc 15720
tgggcatagt ctcgccgcgc gtcctatcga gccgcacttt ttgagcaagc atgtccatcc 15780
ttatatcgcc cagcaataac acaggctggg gcctgcgctt cccaagcaag atgtttggcg 15840
gggccaagaa gcgctccgac caacacccag tgcgcgtgcg cgggcactac cgcgcgccct 15900
ggggcgcgca caaacgcggc cgcactgggc gcaccaccgt cgatgacgcc atcgacgcgg 15960
tggtggagga ggcgcgcaac tacacgccca cgccgccacc agtgtccaca gtggacgcgg 16020
ccattcagac cgtggtgcgc ggagcccggc gctatgctaa aatgaagaga cggcggaggc 16080
gcgtagcacg tcgccaccgc cgccgacccg gcactgccgc ccaacgcgcg gcggcggccc 16140
tgcttaaccg cgcacgtcgc accggccgac gggcggccat gcgggccgct cgaaggctgg 16200
ccgcgggtat tgtcactgtg ccccccaggt ccaggcgacg agcggccgcc gcagcagccg 16260
cggccattag tgctatgact cagggtcgca ggggcaacgt gtattgggtg cgcgactcgg 16320
ttagcggcct gcgcgtgccc gtgcgcaccc gcccccgcg caactagatt gcaagaaaaa 16380
actacttaga ctcgtactgt tgtatgtatc cagcggcggc ggcgcgcaac gaagctatgt 16440
ccaagcgcaa aatcaaagaa gagatgctcc aggtcatcgc gccggagatc tatggccccc 16500
cgaagaagga agagcaggat tacaagcccc gaaagctaaa gcgggtcaaa aagaaaaaga 16560
aagatgatga tgatgaactt gacgacgagg tggaactgct gcacgctacc gcgcccaggc 16620
gacgggtaca gtggaaaggt cgacgcgtaa aacgtgtttt gcgacccggc accaccgtag 16680
tctttacgcc cggtgagcgc tccacccgca cctacaagcg cgtgtatgat gaggtgtacg 16740
gcgacgagga cctgcttgag caggccaacg agcgcctcgg ggagtttgcc tacggaaagc 16800
ggcataagga catgctggcg ttgccgctgg acgagggcaa cccaacacct agcctaaagc 16860
ccgtaacact gcagcaggtg ctgcccgcgc ttgcaccgtc cgaagaaaag cgcggcctaa 16920
agcgcgagtc tggtgacttg gcacccaccg tgcagctgat ggtacccaag cgccagcgac 16980
tggaagatgt cttggaaaaa atgaccgtgg aacctgggct ggagcccgag gtccgcgtgc 17040
ggccaatcaa gcaggtggcg ccgggactgg gcgtgcagac cgtggacgtt cagataccca 17100
ctaccagtag caccagtatt gccaccgcca cagagggcat ggagacacaa acgtccccgg 17160
ttgcctcagc ggtggcggat gccgcggtgc aggcggtcgc tgcggccgcg tccaagacct 17220
ctacggaggt gcaaacggac ccgtggatgt ttcgcgtttc agccccccgg cgcccgcgcg 17280
gttcgaggaa gtacggcgcc gccagcgcgc tactgcccga atatgcccta catccttcca 17340
ttgcgcctac ccccggctat cgtggctaca cctaccgccc cagaagacga gcaactaccc 17400
gacgccgaac caccactgga acccgccgcc gccgtcgccg tcgccagccc gtgctggccc 17460
cgatttccgt gcgcagggtg gctcgcgaag gaggcaggac cctggtgctg ccaacagcgc 17520

-continued

```
gctaccaccc cagcatcgtt taaaagccgg tctttgtggt tcttgcagat atggccctca  17580
cctgccgcct ccgtttcccg gtgccgggat tccgaggaag aatgcaccgt aggaggggca  17640
tggccggcca cggcctgacg ggcggcatgc gtcgtgcgca ccaccggcgg cggcgcgcgt  17700
cgcaccgtcg catgcgcggc ggtatcctgc cctccttat tccactgatc gccgcggcga  17760
ttggcgccgt gcccggaatt gcatccgtgg ccttgcaggc gcagagacac tgattaaaaa  17820
caagttgcat gtggaaaaat caaaataaaa agtctggact ctcacgctcg cttggtcctg  17880
taactatttt gtagaatgga agacatcaac tttgcgtctc tggccccgcg acacggctcg  17940
cgcccgttca tgggaaactg gcaagatatc ggcaccagca atatgagcgg tggcgccttc  18000
agctggggct cgctgtggag cggcattaaa aatttcggtt ccaccgttaa gaactatggc  18060
agcaaggcct ggaacagcag cacaggccag atgctgaggg ataagttgaa agagcaaaat  18120
ttccaacaaa aggtggtaga tggcctggcc tctggcatta gcggggtggt ggacctggcc  18180
aaccaggcag tgcaaaataa gattaacagt aagcttgatc cccgccctcc cgtagaggag  18240
cctccaccgg ccgtggagac agtgtctcca gaggggcgtg gcgaaaagcg tccgcgcccc  18300
gacagggaag aaactctggt gacgcaaata gacgagcctc cctcgtacga ggaggcacta  18360
aagcaaggcc tgcccaccac ccgtcccatc gcgcccatgg ctaccggagt gctgggccag  18420
cacacacccg taacgctgga cctgcctccc cccgccgaca cccagcagaa acctgtgctg  18480
ccaggcccga ccgccgttgt tgtaacccgt cctagccgcg cgtccctgcg ccgcgccgcc  18540
agcggtccgc gatcgttgcg gcccgtagcc agtggcaact ggcaaagcac actgaacagc  18600
atcgtgggtc tgggggtgca atccctgaag cgccgacgat gcttctgaat agctaacgtg  18660
tcgtatgtgt gtcatgtatg cgtccatgtc gccgccagag gagctgctga gccgccgcgc  18720
gcccgctttc caagatggct accccttcga tgatgccgca gtggtcttac atgcacatct  18780
cgggccagga cgcctcggag tacctgagcc ccgggctggt gcagtttgcc cgcgccaccg  18840
agacgtactt cagcctgaat aacaagttta gaaaccccac ggtggcgcct acgcacgacg  18900
tgaccacaga ccggtcccag cgtttgacgc tgcggttcat ccctgtggac cgtgaggata  18960
ctgcgtactc gtacaaggcg cggttcaccc tagctgtggg tgataaccgt gtgctggaca  19020
tggcttccac gtactttgac atccgcggcg tgctggacag ggccctact tttaagccct  19080
actctggcac tgcctacaac gccctggctc ccaagggtgc cccaaatcct tgcgaatggg  19140
atgaagctgc tactgctctt gaaataaacc tagaagaaga ggacgatgac aacgaagacg  19200
aagtagacga gcaagctgag cagcaaaaaa ctcacgtatt tgggcaggcg ccttattctg  19260
gtataaatat tacaaaggag ggtattcaaa taggtgtcga aggtcaaaca cctaaatatg  19320
ccgataaaac atttcaacct gaacctcaaa taggagaatc tcagtggtac gaaactgaaa  19380
ttaatcatgc agctgggaga gtccttaaaa agactacccc aatgaaacca tgttacggtt  19440
catatgcaaa acccacaaat gaaaatggag ggcaaggcat tcttgtaaag caacaaaatg  19500
gaaagctaga aagtcaagtg gaaatgcaat ttttctcaac tactgaggcg accgcaggca  19560
atggtgataa cttgactcct aaagtggtat tgtacagtga agatgtagat atagaaaccc  19620
cagacactca tatttcttac atgcccacta ttaaggaagg taactcacga gaactaatgg  19680
gccaacaatc tatgcccaac aggcctaatt acattgcttt tagggacaat tttattggtc  19740
taatgtatta caacagcacg ggtaatatgg gtgttctggc gggccaagca tcgcagttga  19800
atgctgttgt agatttgcaa gacagaaaca cagagctttc ataccagctt ttgcttgatt  19860
ccattggtga tagaaccagg tacttttcta tgtggaatca ggctgttgac agctatgatc  19920
```

-continued cagatgttag aattattgaa aatcatggaa ctgaagatga acttccaaat tactgctttc 19980
cactgggagg tgtgattaat acagagactc ttaccaaggt aaaacctaaa acaggtcagg 20040
aaaatggatg ggaaaaagat gctacagaat tttcagataa aaatgaaata agagttggaa 20100
ataattttgc catggaaatc aatctaaatg ccaacctgtg gagaaatttc ctgtactcca 20160
acatagcgct gtatttgccc gacaagctaa agtacagtcc ttccaacgta aaaatttctg 20220
ataacccaaa cacctacgac tacatgaaca agcgagtggt ggctcccggg ttagtggact 20280
gctacattaa ccttggagca cgctggtccc ttgactatat ggacaacgtc aacccattta 20340
accaccaccg caatgctggc ctgcgctacc gctcaatgtt gctgggcaat ggtcgctatg 20400
tgcccttcca catccaggtg cctcagaagt tctttgccat taaaaacctc cttctcctgc 20460
cgggctcata cacctacgag tggaacttca ggaaggatgt taacatggtt ctgcagagct 20520
ccctaggaaa tgacctaagg gttgacggag ccagcattaa gtttgatagc atttgccttt 20580
acgccacctt cttccccatg gcccacaaca ccgcctccac gcttgaggcc atgcttagaa 20640
acgacaccaa cgaccagtcc tttaacgact atctctccgc cgccaacatg ctctacccta 20700
tacccgccaa cgctaccaac gtgcccatat ccatcccctc ccgcaactgg gcggctttcc 20760
gcggctgggc cttcacgcgc cttaagacta aggaaacccc atcactgggc tcgggctacg 20820
acccttatta cacctactct ggctctatac cctacctaga tggaaccttt tacctcaacc 20880
acacctttaa gaaggtggcc attacctttg actcttctgt cagctggcct ggcaatgacc 20940
gcctgcttac ccccaacgag tttgaaatta agcgctcagt tgacggggag ggttacaacg 21000
ttgcccagtg taacatgacc aaagactggt tcctggtaca aatgctagct aactacaaca 21060
ttggctacca gggcttctat atcccagaga gctacaagga ccgcatgtac tccttcttta 21120
gaaacttcca gcccatgagc cgtcaggtgg tggatgatac taaatacaag gactaccaac 21180
aggtgggcat cctacaccaa cacaacaact ctggatttgt tggctacctt gcccccacca 21240
tgcgcgaagg acaggcctac cctgctaact tcccctatcc gcttataggc aagaccgcag 21300
ttgacagcat tacccagaaa aagtttcttt gcgatcgcac cctttggcgc atcccattct 21360
ccagtaactt tatgtccatg ggcgcactca cagacctggg ccaaaacctt ctctacgcca 21420
actccgccca cgcgctagac atgacttttg aggtggatcc catggacgag cccacccttc 21480
tttatgtttt gtttgaagtc tttgacgtgg tccgtgtgca ccggccgcac cgcggcgtca 21540
tcgaaaccgt gtacctgcgc acgcccttct cggccggcaa cgccacaaca taaagaagca 21600
agcaacatca acaacagctg ccgccatggg ctccagtgag caggaactga aagccattgt 21660
caaagatctt ggttgtgggc catatttttt gggcacctat gacaagcgct ttccaggctt 21720
tgtttctcca cacaagctcg cctgcgccat agtcaatacg gccggtcgcg agactggggg 21780
cgtacactgg atggcctttg cctggaaccc gcactcaaaa acatgctacc tctttgagcc 21840
ctttggcttt tctgaccagc gactcaagca ggtttaccag tttgagtacg agtcactcct 21900
gcgccgtagc gccattgctt cttcccccga ccgctgtata acgctggaaa agtccaccca 21960
aagcgtacag gggcccaact cggccgcctg tggactattc tgctgcatgt ttctccacgc 22020
ctttgccaac tggccccaaa ctcccatgga tcacaacccc accatgaacc ttattaccgg 22080
ggtacccaac tccatgctca acagtcccca ggtacagccc accctgcgtc gcaaccagga 22140
acagctctac agcttcctgg agcgccactc gccctacttc cgcagccaca gtgcgcagat 22200
taggagcgcc acttcttttt gtcacttgaa aaacatgtaa aaataatgta ctagagacac 22260

-continued

```
tttcaataaa ggcaaatgct tttatttgta cactctcggg tgattattta cccccaccct  22320
tgccgtctgc gccgtttaaa aatcaaaggg gttctgccgc gcatcgctat gcgccactgg  22380
cagggacacg ttgcgatact ggtgtttagt gctccactta aactcaggca caaccatccg  22440
cggcagctcg gtgaagtttt cactccacag gctgcgcacc atcaccaacg cgtttagcag  22500
gtcgggcgcc gatatcttga agtcgcagtt ggggcctccg ccctgcgcgc gcgagttgcg  22560
atacacaggg ttgcagcact ggaacactat cagcgccggg tggtgcacgc tggccagcac  22620
gctcttgtcg gagatcagat ccgcgtccag gtcctccgcg ttgctcaggg cgaacggagt  22680
caactttggt agctgccttc ccaaaaaggg cgcgtgccca ggctttgagt tgcactcgca  22740
ccgtagtggc atcaaaaggt gaccgtgccc ggtctgggcg ttaggataca gcgcctgcat  22800
aaaagccttg atctgcttaa aagccacctg agcctttgcg ccttcagaga agaacatgcc  22860
gcaagacttg ccggaaaact gattggccgg acaggccgcg tcgtgcacgc agcaccttgc  22920
gtcggtgttg gagatctgca ccacatttcg gccccaccgg ttcttcacga tcttggcctt  22980
gctagactgc tccttcagcg cgcgctgccc gttttcgctc gtcacatcca tttcaatcac  23040
gtgctcctta tttatcataa tgcttccgtg tagacactta agctcgcctt cgatctcagc  23100
gcagcggtgc agccacaacg cgcagcccgt gggctcgtga tgcttgtagg tcacctctgc  23160
aaacgactgc aggtacgcct gcaggaatcg ccccatcatc gtcacaaagg tcttgttgct  23220
ggtgaaggtc agctgcaacc cgcggtgctc ctcgttcagc caggtcttgc atacggccgc  23280
cagagcttcc acttggtcag gcagtagttt gaagttcgcc tttagatcgt tatccacgtg  23340
gtacttgtcc atcagcgcgc gcgcagcctc catgcccttc tcccacgcag acacgatcgg  23400
cacactcagc gggttcatca ccgtaatttc actttccgct tcgctgggct cttcctcttc  23460
ctcttgcgtc cgcataccac gcgccactgg gtcgtcttca ttcagccgcc gcactgtgcg  23520
cttacctcct ttgccatgct tgattagcac cggtgggttg ctgaaaccca ccatttgtag  23580
cgccacatct tctctttctt cctcgctgtc cacgattacc tctggtgatg gcgggcgctc  23640
gggcttggga gaagggcgct tctttttctt cttgggcgca atggccaaat ccgccgccga  23700
ggtcgatggc cgcgggctgg gtgtgcgcgg caccagcgcg tcttgtgatg agtcttcctc  23760
gtcctcggac tcgatacgcc gcctcatccg cttttttggg ggcgcccggg gaggcggcgg  23820
cgacggggac ggggacgaca cgtcctccat ggttggggga cgtcgcgccg caccgcgtcc  23880
gcgctcgggg gtggtttcgc gctgctcctc ttcccgactg gccatttcct tctcctatag  23940
gcagaaaaag atcatggagt cagtcgagaa gaaggacagc ctaaccgccc cctctgagtt  24000
cgccaccacc gcctccaccg atgccgccaa cgcgcctacc accttccccg tcgaggcacc  24060
cccgcttgag gaggaggaag tgattatcga gcaggaccca ggttttgtaa gcgaagacga  24120
cgaggaccgc tcagtaccaa cagaggataa aaagcaagac caggacaacg cagaggcaaa  24180
cgaggaacaa gtcgggcggg gggacgaaag gcatggcgac tacctagatg tgggagacga  24240
cgtgctgttg aagcatctgc agcgccagtg cgccattatc tgcgacgcgt tgcaagagcg  24300
cagcgatgtg cccctcgcca tagcggatgt cagccttgcc tacgaacgcc acctattctc  24360
accgcgcgta ccccccaaac gccaagaaaa cggcacatgc gagcccaacc cgcgcctcaa  24420
cttctacccc gtatttgccg tgccagaggt gcttgccacc tatcacatct tttccaaaaa  24480
ctgcaagata cccctatcct gccgtgccaa ccgcagccga gcggacaagc agctggcctt  24540
gcggcagggc gctgtcatac ctgatatcgc ctcgctcaac gaagtgccaa aaatctttga  24600
gggtcttgga cgcgacgaga agcgcgcggc aaacgctctg caacaggaaa acagcgaaaa  24660
```

-continued

```
tgaaagtcac tctggagtgt tggtggaact cgagggtgac aacgcgcgcc tagccgtact  24720
aaaacgcagc atcgaggtca cccactttgc ctacccggca cttaacctac cccccaaggt  24780
catgagcaca gtcatgagtg agctgatcgt gcgccgtgcg cagcccctgg agagggatgc  24840
aaatttgcaa gaacaaacag aggagggcct acccgcagtt ggcgacgagc agctagcgcg  24900
ctggcttcaa acgcgcgagc ctgccgactt ggaggagcga cgcaaactaa tgatggccgc  24960
agtgctcgtt accgtggagc ttgagtgcat gcagcggttc tttgctgacc cggagatgca  25020
gcgcaagcta gaggaaacat tgcactacac ctttcgacag ggctacgtac gccaggcctg  25080
caagatctcc aacgtggagc tctgcaacct ggtctcctac cttggaattt tgcacgaaaa  25140
ccgccttggg caaaacgtgc ttcattccac gctcaagggc gaggcgcgcc gcgactacgt  25200
ccgcgactgc gtttacttat ttctatgcta cacctggcag acggccatgg gcgtttggca  25260
gcagtgcttg gaggagtgca acctcaagga gctgcagaaa ctgctaaagc aaaacttgaa  25320
ggacctatgg acggccttca acgagcgctc cgtggccgcg cacctggcgg acatcatttt  25380
ccccgaacgc ctgcttaaaa ccctgcaaca gggtctgcca gacttcacca gtcaaagcat  25440
gttgcagaac tttaggaact ttatcctaga gcgctcagga atcttgcccg ccacctgctg  25500
tgcacttcct agcgactttg tgcccattaa gtaccgcgaa tgccctccgc cgctttgggg  25560
ccactgctac cttctgcagc tagccaacta ccttgcctac cactctgaca taatggaaga  25620
cgtgagcggt gacggtctac tggagtgtca ctgtcgctgc aacctatgca ccccgcaccg  25680
ctccctggtt tgcaattcgc agctgcttaa cgaaagtcaa attatcggta cctttgagct  25740
gcagggtccc tcgcctgacg aaaagtccgc ggctccgggg ttgaaactca ctccggggct  25800
gtggacgtcg gcttaccttc gcaaatttgt acctgaggac taccacgccc acgagattag  25860
gttctacgaa gaccaatccc gcccgccaaa tgcggagctt accgcctgcg tcattaccca  25920
gggccacatt cttggccaat tgcaagccat caacaaagcc cgccaagagt ttctgctacg  25980
aaagggacgg ggggtttact tggaccccca gtccggcgag gagctcaacc caatcccccc  26040
gccgccgcag ccctatcagc agcagccgcg ggcccttgct tcccaggatg gcacccaaaa  26100
agaagctgca gctgccgccg ccacccacgg acgaggagga atactgggac agtcaggcag  26160
aggaggtttt ggacgaggag gaggaggaca tgatggaaga ctgggagagc ctagacgagg  26220
aagcttccga ggtcgaagag gtgtcagacg aaacaccgtc accctcggtc gcattcccct  26280
cgccggcgcc ccagaaatcg gcaaccggtt ccagcatggc tacaacctcc gctcctcagg  26340
cgccgccggc actgcccgtt cgccgaccca accgtagatg ggacaccact ggaaccaggg  26400
ccggtaagtc caagcagccg ccgccgttag cccaagagca acaacagcgc caaggctacc  26460
gctcatggcg cgggcacaag aacgccatag ttgcttgctt gcaagactgt gggggcaaca  26520
tctccttcgc ccgccgcttt cttctctacc atcacggcgt ggccttcccc cgtaacatcc  26580
tgcattacta ccgtcatctc tacagcccat actgcaccgg cggcagcggc agcggcagca  26640
acagcagcgg ccacacagaa gcaaaggcga ccggatagca agactctgac aaagcccaag  26700
aaatccacag cggcggcagc agcaggagga ggagcgctgc gtctggcgcc caacgaaccc  26760
gtatcgaccc gcgagcttag aaacaggatt tttcccactc tgtatgctat atttcaacag  26820
agcaggggcc aagaacaaga gctgaaaata aaaaacaggt ctctgcgatc cctcacccgc  26880
agctgcctgt atcacaaaag cgaagatcag cttcggcgca cgctggaaga cgcggaggct  26940
ctcttcagta aatactgcgc gctgactctt aaggactagt ttcgcgccct ttctcaaatt  27000
```

-continued

```
taagcgcgaa aactacgtca tctccagcgg ccacacccgg cgccagcacc tgtcgtcagc  27060
gccattatga gcaaggaaat tcccacgccc tacatgtgga gttaccagcc acaaatggga  27120
cttgcggctg gagctgccca agactactca acccgaataa actacatgag cgcgggaccc  27180
cacatgatat cccgggtcaa cggaatccgc gcccaccgaa accgaattct cttggaacag  27240
gcggctatta ccaccacacc tcgtaataac cttaatcccc gtagttggcc cgctgccctg  27300
gtgtaccagg aaagtcccgc tcccaccact gtggtacttc ccagagacgc ccaggccgaa  27360
gttcagatga ctaactcagg ggcgcagctt gcgggcggct ttcgtcacag ggtgcggtcg  27420
cccgggcagg gtataactca cctgacaatc agagggcgag gtattcagct caacgacgag  27480
tcggtgagct cctcgcttgg tctccgtccg gacgggacat ttcagatcgg cggcgccggc  27540
cgtccttcat tcacgcctcg tcaggcaatc ctaactctgc agacctcgtc ctctgagccg  27600
cgctctggag gcattggaac tctgcaattt attgaggagt ttgtgccatc ggtctacttt  27660
aaccccttct cgggacctcc cggccactat ccggatcaat ttattcctaa ctttgacgcg  27720
gtaaaggact cggcggacgg ctacgactga atgttaagtg gagaggcaga gcaactgcgc  27780
ctgaaacacc tggtccactg tcgccgccac aagtgctttg cccgcgactc cggtgagttt  27840
tgctactttg aattgcccga ggatcatatc gagggcccgg cgcacggcgt ccggcttacc  27900
gcccagggag agcttgcccg tagcctgatt cgggagttta cccagcgccc cctgctagtt  27960
gagcgggaca ggggaccctg tgttctcact gtgatttgca actgtcctaa ccttggatta  28020
catcaagatc tttgttgcca tctctgtgct gagtataata aatacagaaa ttaaaatata  28080
ctggggctcc tatcgccatc ctgtaaacgc caccgtcttc acccgcccaa gcaaaccaag  28140
gcgaacctta cctggtactt ttaacatctc tccctctgtg atttacaaca gtttcaaccc  28200
agacggagtg agtctacgag agaacctctc cgagctcagc tactccatca gaaaaaacac  28260
caccctcctt acctgccggg aacgtacgag tgcgtcaccg gccgctgcac cacacctacc  28320
gcctgaccgt aaaccagact ttttccggac agacctcaat aactctgttt accagaacag  28380
gaggtgagct tagaaaaccc ttagggtatt aggccaaagg cgcagctact gtggggttta  28440
tgaacaattc aagcaactct acgggctatt ctaattcagg tttctctagg gttggggtta  28500
ttctctgtct tgtgattctc tttattctta tactaacgct tctctgccta aggctcgccg  28560
cctgctgtgt gcacatttgc atttattgtc agctttttaa acgctggggt cgccacccaa  28620
gatgattagg tacataatcc taggtttact caccettgcg tcagcccacg gtacttaatt  28680
aacccaaaag gtggatttta aggagccagc ctgtaatgtt acattcgcag ctgaagctaa  28740
tgagtgcacc actcttataa aatgcaccac agaacatgaa aagctgctta ttcgccacaa  28800
aaacaaaatt ggcaagtatg ctgtttatgc tatttggcag ccaggtgaca ctacagagta  28860
taatgttaca gttttccagg gtaaaagtca taaaactttt atgtatactt ttccatttta  28920
tgaaatgtgc gacattacca tgtacatgag caaacagtat aagttgtggc ccccacaaaa  28980
ttgtgtggaa aacactggca ctttctgctg cactgctatg ctaattacag tgctcgcttt  29040
ggtctgtacc ctactctata ttaaatacaa aagcagacgc agctttattg aggaaaagaa  29100
aatgccttaa tttactaagt tacaaagcta atgtcaccac taactgcttt actcgctgct  29160
tgcaaaacaa attcaaaaag ttagcattat aattagaata ggatttaaac cccccggtca  29220
tttcctgctc aataccattc ccctgaacaa ttgactctat gtgggatatg ctccagcgct  29280
acaaccttga agtcaggctt cctggatgtc agcatctgac tttggccagc acctgtcccg  29340
cggatttgtt ccagtccaac tacagcgacc caccctaaca gagatgacca acacaaccaa  29400
```

-continued

```
cgcggccgcc gctaccggac ttacatctac cacaaataca ccccaagttt ctgcctttgt  29460
caataactgg gataacttgg gcatgtggtg gttctccata gcgcttatgt ttgtatgcct  29520
tattattatg tggctcatct gctgcctaaa gcgcaaacgc gcccgaccac ccatctatag  29580
tcccatcatt gtgctacacc caaacaatga tggaatccat agattggacg gactgaaaca  29640
catgttcttt tctcttacag tatgattaaa tgagacatga ttcctcgagt ttttatatta  29700
ctgacccttg ttgcgctttt ttgtgcgtgc tccacattgg ctgcggtttc tcacatcgaa  29760
gtagactgca ttccagcctt cacagtctat ttgctttacg gatttgtcac cctcacgctc  29820
atctgcagcc tcatcactgt ggtcatcgcc tttatccagt gcattgactg ggtctgtgtg  29880
cgctttgcat atctcagctg ctgccatgtt gtgttgctac catgttgttt tcatgtgttg  29940
ctgccatgct cttgtcgcct tagatctctc tttatgtagt gttgtggtgt ctctcttgtc  30000
gtgatgtgtg ttttgtccta tatattttaa tttttaatcc aaacccctgt ccccgcagag  30060
gcctttgcgt tctggtaggc cgtcattgaa aactgactta actcgttaaa ttaaaaaaat  30120
gtaaaaaaata atggttgaga ctcagcccaa catcggcaga tgaggtggat tgagactcag  30180
cccaacatcg gcagatgagg tggattgaga ctcaacccca acattggcag atgaggtgaa  30240
ttagatgagg tggattgaga ctcatgaggg tggtatgagg gcccgacgtc cacaggtggg  30300
agttgtgctt tacagtccaa cgtgcaggac gcttggcatt tgccagagaa caccaagatt  30360
ggcaaattcg caactggcgc cctgtgctct tcacagacgg aaaaatgacc aaaatctgat  30420
tatttttgta aaacggaaac cgaatgtccg acaaagttca tttgatgact tcccggtagg  30480
tctgccctgc cgctgggccg acgccgtccg ggaattttac aaacgatttc ggacgtctag  30540
cattcactca ccttgtcaag gacctgagga tctctgcacc cttattaaga ccctgtgcgg  30600
tctcaaagat cttattccct ttaactaata aaaaaaaata ataaagcatc acttacttaa  30660
aatcagttag caaatttctg tccagtttat tcagcagcac ctccttgccc tcctcccagc  30720
tctggtattg cagcttcctc ctggctgcaa actttctcca caatctaaat ggaatgtcag  30780
tttcctcctg ttcctgtcca tccgcaccca ctatcttcat gttgttgcag atgaagcgcg  30840
caagaccgtc tgaagatacc ttcaaccccg tgtatccata tgacacggaa accggtcctc  30900
caactgtgcc ttttcttact cctccctttg tatcccccaa tgggtttcaa gagagtcccc  30960
ctggggtact ctctttgcgc ctatccgaac ctctagttac ctccaatggc atgcttgcgc  31020
tcaaaatggg caacggcctc tctctggacg aggccggcaa ccttacctcc caaaatgtaa  31080
ccactgtgag cccacctctc aaaaaaacca agtcaaacat aaacctggaa atatctgcac  31140
ccctcacagt tacctcagaa gccctaactg tggctgccgc cgcacctcta atggtcgcgg  31200
gcaacacact caccatgcaa tcacaggccc cgctaaccgt gcacgactcc aaacttagca  31260
ttgccaccca aggacccctc acagtgtcag aaggaaagct agccctgcaa acatcaggcc  31320
ccctcaccac caccgatagc agtacccttta ctatcactgc ctcacccccct ctaactactg  31380
ccactggtag cttgggcatt gacttgaaag agcccattta tacacaaaat ggaaaactag  31440
gactaaagta cggggctcct ttgcatgtaa cagacgacct aaacactttg accgtagcaa  31500
ctggtccagg tgtgactatt aataatactt ccttgcaaac taaagttact ggagccttgg  31560
gttttgattc acaaggcaat atgcaactta atgtagcagg aggactaagg attgattctc  31620
aaaacagacg ccttatactt gatgttagtt atccgtttga tgctcaaaac caactaaatc  31680
taagactagg acagggccct ctttttataa actcagccca caacttggat attaactaca  31740
```

-continued

```
acaaaggcct ttacttgttt acagcttcaa acaattccaa aaagcttgag gttaacctaa  31800
gcactgccaa ggggttgatg tttgacgcta cagccatagc cattaatgca ggagatgggc  31860
ttgaatttgg ttcacctaat gcaccaaaca caaatcccct caaaacaaaa attggccatg  31920
gcctagaatt tgattcaaac aaggctatgg ttcctaaact aggaactggc cttagttttg  31980
acagcacagg tgccattaca gtaggaaaca aaaataatga taagctaact ttgtggacca  32040
caccagctcc atctcctaac tgtagactaa atgcagagaa agatgctaaa ctcactttgg  32100
tcttaacaaa atgtggcagt caaatacttg ctacagtttc agttttggct gttaaaggca  32160
gtttggctcc aatatctgga acagttcaaa gtgctcatct tattataaga tttgacgaaa  32220
atggagtgct actaaacaat tccttcctgg acccagaata ttggaacttt agaaatggag  32280
atcttactga aggcacagcc tatacaaacg ctgttggatt tatgcctaac ctatcagctt  32340
atccaaaatc tcacggtaaa actgccaaaa gtaacattgt cagtcaagtt tacttaaacg  32400
gagacaaaac taaacctgta acactaacca ttacactaaa cggtacacag gaaacaggag  32460
acacaactcc aagtgcatac tctatgtcat tttcatggga ctggtctggc cacaactaca  32520
ttaatgaaat atttgccaca tcctcttaca ctttttcata cattgcccaa gaataaagaa  32580
tcgtttgtgt tatgtttcaa cgtgtttatt tttcaattgc agaaaatttc aagtcatttt  32640
tcattcagta gtatagcccc accaccacat agcttataca gatcaccgta ccttaatcaa  32700
actcacagaa ccctagtatt caacctgcca cctccctccc aacacacaga gtacacagtc  32760
ctttctcccc ggctggcctt aaaaagcatc atatcatggg taacagacat attcttaggt  32820
gttatattcc acacggtttc ctgtcgagcc aaacgctcat cagtgatatt aataaactcc  32880
ccgggcagct cacttaagtt catgtcgctg tccagctgct gagccacagg ctgctgtcca  32940
acttgcggtt gcttaacggg cggcgaagga gaagtccacg cctacatggg ggtagagtca  33000
taatcgtgca tcaggatagg gcggtggtgc tgcagcagcg cgcgaataaa ctgctgccgc  33060
cgccgctccg tcctgcagga atacaacatg gcagtggtct cctcagcgat gattcgcacc  33120
gcccgcagca taaggcgcct tgtcctccgg gcacagcagc gcaccctgat ctcacttaaa  33180
tcagcacagt aactgcagca cagcaccaca atattgttca aaatcccaca gtgcaaggcg  33240
ctgtatccaa agctcatggc ggggaccaca gaacccacgt ggccatcata ccacaagcgc  33300
aggtagatta agtggcgacc cctcataaac acgctggaca taaacattac ctcttttggc  33360
atgttgtaat tcaccacctc ccggtaccat ataaacctct gattaaacat ggcgccatcc  33420
accaccatcc taaaccagct ggccaaaacc tgcccgccgg ctatacactg cagggaaccg  33480
ggactggaac aatgacagtg gagagcccag gactcgtaac catggatcat catgctcgtc  33540
atgatatcaa tgttggcaca acacaggcac acgtgcatac acttcctcag gattacaagc  33600
tcctcccgcg ttagaaccat atcccaggga acaacccatt cctgaatcag cgtaaatccc  33660
acactgcagg gaagacctcg cacgtaactc acgttgtgca ttgtcaaagt gttacattcg  33720
ggcagcagcg gatgatcctc cagtatggta gcgcgggttt ctgtctcaaa aggaggtaga  33780
cgatccctac tgtacggagt gcgccgagac aaccgagatc gtgttggtcg tagtgtcatg  33840
ccaaatggaa cgccggacgt agtcatattt cctgaagcaa aaccaggtgc gggcgtgaca  33900
aacagatctg cgtctccggt ctcgccgctt agatcgctct gtgtagtagt tgtagtatat  33960
ccactctctc aaagcatcca ggcgccccct ggcttcgggt tctatgtaaa ctccttcatg  34020
cgccgctgcc ctgataacat ccaccaccgc agaataagcc acacccagcc aacctacaca  34080
ttcgttctgc gagtcacaca cgggaggagc gggaagagct ggaagaacca tgttttttt  34140
```

-continued

```
tttattccaa aagattatcc aaaacctcaa aatgaagatc tattaagtga acgcgctccc  34200

ctccggtggc gtggtcaaac tctacagcca aagaacagat aatggcattt gtaagatgtt  34260

gcacaatggc ttccaaaagg caaacggccc tcacgtccaa gtggacgtaa aggctaaacc  34320

cttcagggtg aatctcctct ataaacattc cagcaccttc aaccatgccc aaataattct  34380

catctcgcca ccttctcaat atatctctaa gcaaatcccg aatattaagt ccggccattg  34440

taaaaatctg ctccagagcg ccctccacct tcagcctcaa gcagcgaatc atgattgcaa  34500

aaattcaggt tcctcacaga cctgtataag attcaaaagc ggaacattaa caaaaatacc  34560

gcgatcccgt aggtcccttc gcagggccag ctgaacataa tcgtgcaggt ctgcacggac  34620

cagcgcggcc acttccccgc caggaacctt gacaaaagaa cccacactga ttatgacacg  34680

catactcgga gctatgctaa ccagcgtagc cccgatgtaa gctttgttgc atgggcggcg  34740

atataaaatg caaggtgctg ctcaaaaaat caggcaaagc ctcgcgcaaa aaagaaagca  34800

catcgtagtc atgctcatgc agataaaggc aggtaagctc cggaaccacc acagaaaaag  34860

acaccatttt tctctcaaac atgtctgcgg gtttctgcat aaacacaaaa taaaataaca  34920

aaaaaacatt taaacattag aagcctgtct tacaacagga aaaacaaccc ttataagcat  34980

aagacggact acggccatgc cggcgtgacc gtaaaaaaac tggtcaccgt gattaaaaag  35040

caccaccgac agctcctcgg tcatgtccgg agtcataatg taagactcgg taaacacatc  35100

aggttgattc atcggtcagt gctaaaaagc gaccgaaata gcccggggga atacataccc  35160

gcaggcgtag agacaacatt acagccccca taggaggtat aacaaaatta ataggagaga  35220

aaaacacata aacacctgaa aaaccctcct gcctaggcaa aatagcaccc tcccgctcca  35280

gaacaacata cagcgcttca cagcggcagc ctaacagtca gccttaccag taaaaaagaa  35340

aacctattaa aaaaacacca ctcgacacgg caccagctca atcagtcaca gtgtaaaaaa  35400

gggccaagtg cagagcgagt atatatagga ctaaaaaatg acgtaacggt taaagtccac  35460

aaaaaacacc cagaaaaccg cacgcgaacc tacgcccaga aacgaaagcc aaaaaaccca  35520

caacttcctc aaatcgtcac ttccgttttc ccacgttacg taacttccca ttttaagaaa  35580

actacaattc ccaacacata caagttactc cgccctaaaa cctacgtcac ccgccccgtt  35640

cccacgcccc gcgccacgtc acaaactcca ccccctcatt atcatattgg cttcaatcca  35700

aaataaggta tattattgat gatg                                          35724
```

<210> SEQ ID NO 14
<211> LENGTH: 33988
<212> TYPE: DNA
<213> ORGANISM: Adenovirus subgroup C

<400> SEQUENCE: 14

```
catcatcaat aatatacctt attttggatt gaagccaata tgataatgag ggggtggagt     60

ttgtgacgtg gcgcggggcg tgggaacggg gcgggtgacg tagtagtgtg gcggaagtgt    120

gatgttgcaa gtgtggcgga acacatgtaa gcgacggatg tggcaaaagt gacgtttttg    180

gtgtgcgccg gtgtacacag gaagtgacaa ttttcgcgcg gttttaggcg gatgttgtag    240

taaatttggg cgtaaccgag taagatttgg ccattttcgc gggaaaactg aataagagga    300

agtgaaatct gaataatttt gtgttactca tagcgcgtaa tatttgtcta gggccgcggg    360

gactttgacc gtttacgtgg agactcgccc aggtgttttt ctcaggtgtt ttccgcgttc    420

cgggtcaaag ttggcgtttt attattatag tcagctgacg tgtagtgtat ttatacccgg    480
```

-continued

```
tgagttcctc aagaggccac tcttgagtgc cagcgagtag agttttctcc tccgagccgc    540
tccgacaccg ggactgaaaa tgagacatga ggtactggct gataatcttc cacctcctag    600
ccattttgaa ccacctaccc ttcacgaact gtatgattta gacgtgacgg cccccgaaga    660
tcccaacgag gaggcggttt cgcagatttt tcccgactct gtaatgttgg cggtgcagga    720
agggattgac ttactcactt ttccgccggc gcccggttct ccggagccgc ctcacctttc    780
ccggcagccc gagcagccgg agcagagagc cttgggtccg gtttgccacg aggctggctt    840
tccacccagt gacgacgagg atgaagaggg tgaggagttt gtgttagatt atgtggagca    900
ccccgggcac ggttgcaggt cttgtcatta tcaccggagg aatacggggg acccagatat    960
tatgtgttcg ctttgctata tgaggacctg tggcatgttt gtctacagta agtgaaaatt   1020
atgggcagtg ggtgatagag tggtgggttt ggtgtggtaa tttttttttt aatttttaca   1080
gttttgtggt ttaaagaatt ttgtattgtg atttttttaa aaggtcctgt gtctgaacct   1140
gagcctgagc ccgagccaga accggagcct gcaagaccta cccgccgtcc taaaatggcg   1200
cctgctatcc tgagacgccc gacatcacct gtgtctagag aatgcaatag tagtacggat   1260
agctgtgact ccggtccttc taacacacct cctgagatac acccggtggt cccgctgtgc   1320
cccattaaac cagttgccgt gagagttggt gggcgtcgcc aggctgtgga atgtatcgag   1380
gacttgctta acgagcctgg gcaacctttg gacttgagct gtaaacgccc caggccataa   1440
ggtgtaaacc tgtgattgcg tgtgtggtta acgcctttgt ttgctgaatg agttgatgta   1500
agtttaataa agggtgagat aatgtttaac ttgcatggcg tgttaaatgg ggcggggctt   1560
aaagggtata taatgcgccg tgggctaatc ttggttacat ctgacctcat ggaggcttgg   1620
gagtgtttgg aagatttttc tgctgtgcgt aacttgctgg aacagagctc taacagtacc   1680
tcttggtttt ggaggtttct gtggggctca tcccaggcaa agttagtctg cagaattaag   1740
gaggattaca agtgggaatt tgaagagctt ttgaaatcct gtggtgagct gtttgattct   1800
ttgaatctgg gtcaccaggc gcttttccaa gagaaggtca tcaagacttt ggatttttcc   1860
acaccggggc gcgctgcggc tgctgttgct tttttgagtt ttataaagga taaatggagc   1920
gaagaaaccc atctgagcgg ggggtacctg ctggattttc tggccatgca tctgtggaga   1980
gcggttgtga gacacaagaa tcgcctgcta ctgttgtctt ccgtccgccc ggcgataata   2040
ccgacggagg agcagcagca gcagcaggag gaagccaggc ggcggcggca ggagcagagc   2100
ccatggaacc cgagagccgg cctggaccct cgggaatgaa tgttgtacag gtggctgaac   2160
tgtatccaga actgagacgc attttgacaa ttacagagga tgggcagggg ctaaaggggg   2220
taaagaggga gcgggggct tgtgaggcta cagaggaggc taggaatcta gcttttagct   2280
taatgaccag acaccgtcct gagtgtatta cttttcaaca gatcaaggat aattgcgcta   2340
atgagcttga tctgctggcg cagaagtatt ccatagagca gctgaccact tactggctgc   2400
agccagggga tgattttgag gaggctatta gggtatatgc aaaggtggca cttaggccag   2460
attgcaagta caagatcagc aaacttgtaa atatcaggaa ttgttgctac atttctggga   2520
acggggccga ggtggagata gatacggagg atagggtggc ctttagatgt agcatgataa   2580
atatgtggcc gggggtgctt ggcatggacg gggtggttat tatgaatgta aggtttactg   2640
gccccaattt tagcggtacg gttttcctgg ccaataccaa ccttatccta cacggtgtaa   2700
gcttctatgg gtttaacaat acctgtgtgg aagcctggac cgatgtaagg gttcggggct   2760
gtgcctttta ctgctgctgg aagggggtgg tgtgtcgccc caaaagcagg gcttcaatta   2820
agaaatgcct ctttgaaagg tgtaccttgg gtatcctgtc tgagggtaac tccagggtgc   2880
```

-continued

```
gccacaatgt ggcctccgac tgtggttgct tcatgctagt gaaaagcgtg gctgtgatta   2940
agcataacat ggtatgtggc aactgcgagg acagggcctc tcagatgctg acctgctcgg   3000
acggcaactg tcacctgctg aagaccattc acgtagccag ccactctcgc aaggcctggc   3060
cagtgtttga gcataacata ctgacccgct gttccttgca tttgggtaac aggagggggg   3120
tgttcctacc ttaccaatgc aatttgagtc acactaagat attgcttgag cccgagagca   3180
tgtccaaggt gaacctgaac ggggtgtttg acatgaccat gaagatctgg aaggtgctga   3240
ggtacgatga gacccgcacc aggtgcagac cctgcgagtg tggcggtaaa catattagga   3300
accagcctgt gatgctggat gtgaccgagg agctgaggcc cgatcacttg gtgctggcct   3360
gcacccgcgc tgagtttggc tctagcgatg aagatacaga ttgaggtact gaaatgtgtg   3420
ggcgtggctt aagggtggga aagaatatat aaggtggggg tcttatgtag ttttgtatct   3480
gttttgcagc agccgccgcc gccatgagca ccaactcgtt tgatggaagc attgtgagct   3540
catatttgac aacgcgcatg cccccatggg ccggggtgcg tcagaatgtg atgggctcca   3600
gcattgatgg tcgccccgtc ctgcccgcaa actctactac cttgacctac gagaccgtgt   3660
ctggaacgcc gttggagact gcagcctccg ccgccgcttc agccgctgca gccaccgccc   3720
gcgggattgt gactgacttt gctttcctga gcccgcttgc aagcagtgca gcttcccgtt   3780
catccgcccg cgatgacaag ttgacggctc ttttggcaca attggattct ttgacccggg   3840
aacttaatgt cgtttctcag cagctgttgg atctgcgcca gcaggtttct gccctgaagg   3900
cttcctcccc tcccaatgcg gtttaaaaca taaataaaaa accagactct gtttggattt   3960
ggatcaagca agtgtcttgc tgtctttatt taggggtttt gcgcgcgcgg taggcccggg   4020
accagcggtc tcggtcgttg agggtcctgt gtattttttc caggacgtgg taaaggtgac   4080
tctggatgtt cagatacatg ggcataagcc cgtctctggg gtggaggtag caccactgca   4140
gagcttcatg ctgcggggtg gtgttgtaga tgatccagtc gtagcaggag cgctgggcgt   4200
ggtgcctaaa aatgtctttc agtagcaagc tgattgccag gggcaggccc ttggtgtaag   4260
tgtttacaaa gcggttaagc tgggatgggt gcatacgtgg ggatatgaga tgcatcttgg   4320
actgtatttt taggttggct atgttcccag ccatatccct ccggggattc atgttgtgca   4380
gaaccaccag cacagtgtat ccggtgcact tgggaaattt gtcatgtagc ttagaaggaa   4440
atgcgtggaa gaacttggag acgcccttgt gacctccaag attttccatg cattcgtcca   4500
taatgatggc aatgggccca cgggcggcgg cctgggcgaa gatatttctg ggatcactaa   4560
cgtcatagtt gtgttccagg atgagatcgt cataggccat ttttacaaag cgcgggcgga   4620
gggtgccaga ctgcggtata atggttccat ccggcccagg ggcgtagtta ccctcacaga   4680
tttgcatttc ccacgctttg agttcagatg gggggatcat gtctacctgc ggggcgatga   4740
agaaaacggt ttccggggta ggggagatca gctgggaaga aagcaggttc ctgagcagct   4800
gcgacttacc gcagccggtg ggcccgtaaa tcacacctat taccgggtgc aactggtagt   4860
taagagagct gcagctgccg tcatccctga gcaggggggc cacttcgtta agcatgtccc   4920
tgactcgcat gttttccctg accaaatccg ccagaaggcg ctcgccgccc agcgatagca   4980
gttcttgcaa ggaagcaaag tttttcaacg gtttgagacc gtccgccgta ggcatgcttt   5040
tgagcgtttg accaagcagt tccaggcggt cccacagctc ggtcacctgc tctacggcat   5100
ctcgatccag catatctcct cgtttcgcgg gttggggcgg ctttcgctgt acggcagtag   5160
tcggtgctcg tccagacggg ccagggtcat gtctttccac gggcgcaggg tcctcgtcag   5220
```

-continued

```
cgtagtctgg gtcacggtga aggggtgcgc tccgggctgc gcgctggcca gggtgcgctt   5280
gaggctggtc ctgctggtgc tgaagcgctg ccggtcttcg ccctgcgcgt cggccaggta   5340
gcatttgacc atggtgtcat agtccagccc ctccgcggcg tggcccttgg cgcgcagctt   5400
gcccttggag gaggcgccgc acgaggggca gtgcagactt ttgagggcgt agagcttggg   5460
cgcgagaaat accgattccg gggagtaggc atccgcgccg caggccccgc agacggtctc   5520
gcattccacg agccaggtga gctctggccg ttcggggtca aaaaccaggt ttcccccatg   5580
ctttttgatg cgtttcttac ctctggtttc catgagccgg tgtccacgct cggtgacgaa   5640
aaggctgtcc gtgtccccgt atacagactt gagaggcctg tcctcgagcg gtgttccgcg   5700
gtcctcctcg tatagaaact cggaccactc tgagacaaag gctcgcgtcc aggccagcac   5760
gaaggaggct aagtgggagg ggtagcggtc gttgtccact agggggtcca ctcgctccag   5820
ggtgtgaaga cacatgtcgc cctcttcggc atcaaggaag gtgattggtt tgtaggtgta   5880
ggccacgtga ccgggtgttc ctgaaggggg gctataaaag gggtgggggg cgcgttcgtc   5940
ctcactctct tccgcatcgc tgtctgcgag ggccagctgt tggggtgagt actccctctg   6000
aaaagcgggc atgacttctg cgctaagatt gtcagtttcc aaaaacgagg aggatttgat   6060
attcacctgg cccgcggtga tgcctttgag ggtggccgca tccatctggt cagaaaagac   6120
aatctttttg ttgtcaagct tggtggcaaa cgacccgtag agggcgttgg acagcaactt   6180
ggcgatggag cgcagggttt ggtttttgtc gcgatcggcg cgctccttgg ccgcgatgtt   6240
tagctgcacg tattcgcgcg caacgcaccg ccattcggga aagacggtgg tgcgctcgtc   6300
gggcaccagg tgcacgcgcc aaccgcggtt gtgcagggtg acaaggtcaa cgctggtggc   6360
tacctctccg cgtaggcgct cgttggtcca gcagaggcgg ccgcccttgc gcgagcagaa   6420
tggcggtagg gggtctagct gcgtctcgtc cggggggtct gcgtccacgg taaagacccc   6480
gggcagcagg cgcgcgtcga agtagtctat cttgcatcct tgcaagtcta gcgcctgctg   6540
ccatgcgcgg gcggcaagcg cgcgctcgta tgggttgagt gggggacccc atggcatggg   6600
gtgggtgagc gcggaggcgt acatgccgca aatgtcgtaa acgtagaggg gctctctgag   6660
tattccaaga tatgtagggt agcatcttcc accgcggatg ctggcgcgca cgtaatcgta   6720
tagttcgtgc gagggagcga ggaggtcggg accgaggttg ctacgggcgg gctgctctgc   6780
tcggaagact atctgcctga agatggcatg tgagttggat gatatggttg gacgctggaa   6840
gacgttgaag ctggcgtctg tgagacctac cgcgtcacgc acgaaggagg cgtaggagtc   6900
gcgcagcttg ttgaccagct cggcggtgac ctgcacgtct agggcgcagt agtccagggt   6960
ttccttgatg atgtcatact tatcctgtcc cttttttttc cacagctcgc ggttgaggac   7020
aaactcttcg cggtctttcc agtactcttg gatcggaaac ccgtcggcct ccgaacggta   7080
agagcctagc atgtagaact ggttgacggc ctggtaggcg cagcatccct tttctacggg   7140
tagcgcgtat gcctgcgcgg ccttccggag cgaggtgtgg gtgagcgcaa aggtgtccct   7200
gaccatgact ttgaggtact ggtatttgaa gtcagtgtcg tcgcatccgc cctgctccca   7260
gagcaaaaag tccgtgcgct ttttggaacg cggatttggc agggcgaagg tgacatcgtt   7320
gaagagtatc tttcccgcgc gaggcataaa gttgcgtgtg atgcggaagg gtcccggcac   7380
ctcggaacgg ttgttaatta cctgggcggc gagcacgatc tcgtcaaagc cgttgatgtt   7440
gtggcccaca atgtaaagtt ccaagaagcg cgggatgccc ttgatggaag gcaatttttt   7500
aagttcctcg taggtgagct cttcagggga gctgagcccg tgctctgaaa gggcccagtc   7560
tgcaagatga gggttggaag cgacgaatga gctccacagg tcacgggcca ttagcatttg   7620
```

-continued caggtggtcg cgaaaggtcc taaactggcg acctatggcc atttttttctg gggtgatgca 7680 gtagaaggta agcgggtctt gttcccagcg gtcccatcca aggttcgcgg ctaggtctcg 7740
cgcggcagtc actagaggct catctccgcc gaacttcatg accagcatga agggcacgag 7800
ctgcttccca aaggcccccca tccaagtata ggtctctaca tcgtaggtga caaagagacg 7860
ctcggtgcga ggatgcgagc cgatcgggaa gaactggatc tcccgccacc aattggagga 7920
gtggctattg atgtggtgaa agtagaagtc cctgcgacgg gccgaacact cgtgctggct 7980
tttgtaaaaa cgtgcgcagt actggcagcg gtgcacgggc tgtacatcct gcacgaggtt 8040
gacctgacga ccgcgcacaa ggaagcagag tgggaatttg agcccctcgc ctggcgggtt 8100
tggctggtgg tcttctactt cggctgcttg tccttgaccg tctggctgct cgaggggagt 8160
tacggtggat cggaccacca cgccgcgcga gcccaaagtc cagatgtccg cgcgcggcgg 8220
tcggagcttg atgacaacat cgcgcagatg ggagctgtcc atggtctgga gctcccgcgg 8280
cgtcaggtca ggcgggagct cctgcaggtt tacctcgcat agacgggtca gggcgcgggc 8340
tagatccagg tgatacctaa tttccagggg ctggttggtg gcggcgtcga tggcttgcaa 8400
gaggccgcat ccccgcggcg cgactacggt accgcgcggc gggcggtggg ccgcgggggt 8460
gtccttggat gatgcatcta aaagcggtga cgcgggcgag cccccggagg taggggggggc 8520 tccggacccg ccgggagagg gggcaggggc acgtcggcgc cgcgcgcggg caggagctgg 8580
tgctgcgcgc gtaggttgct ggcgaacgcg acgacgcggc ggttgatctc ctgaatctgg 8640
cgcctctgcg tgaagacgac gggcccggtg agcttgagcc tgaaagagag ttcgacagaa 8700
tcaatttcgg tgtcgttgac ggcggcctgg cgcaaaatct cctgcacgtc tcctgagttg 8760
tcttgatagg cgatctcggc catgaactgc tcgatctctt cctcctggag atctccgcgt 8820
ccggctcgct ccacggtggc ggcgaggtcg ttggaaatgc gggccatgag ctgcgagaag 8880
gcgttgaggc ctccctcgtt ccagacgcgg ctgtagacca cgcccccttc ggcatcgcgg 8940
gcgcgcatga ccacctgcgc gagattgagc tccacgtgcc gggcgaagac ggcgtagttt 9000
cgcaggcgct gaaagaggta gttgagggtg gtggcggtgt gttctgccac gaagaagtac 9060
ataacccagc gtcgcaacgt ggattcgttg atatccccca aggcctcaag gcgctccatg 9120
gcctcgtaga agtccacggc gaagttgaaa aactgggagt tgcgcgccga cacggttaac 9180
tcctcctcca gaagacggat gagctcggcg acagtgtcgc gcacctcgcg ctcaaaggct 9240
acaggggcct cttcttcttc ttcaatctcc tcttccataa gggcctcccc ttcttcttct 9300
tctggcggcg gtgggggagg ggggacacgg cggcgacgac ggcgcaccgg gaggcggtcg 9360
acaaagcgct cgatcatctc cccgcggcga cggcgcatgg tctcggtgac ggcgcggccg 9420
ttctcgcggg ggcgcagttg gaagacgccg cccgtcatgt cccggttatg ggttggcggg 9480
gggctgccat gcggcaggga tacggcgcta acgatgcatc tcaacaattg ttgtgtaggt 9540
actccgccgc cgagggacct gagcgagtcc gcatcgaccg gatcggaaaa cctctcgaga 9600
aaggcgtcta accagtcaca gtcgcaaggt aggctgagca ccgtggcggg cggcagcggg 9660
cggcggtcgg ggttgtttct ggcggaggtg ctgctgatga tgtaattaaa gtaggcggtc 9720
ttgagacggc ggatggtcga cagaagcacc atgtccttgg gtccggcctg ctgaatgcgc 9780
aggcggtcgg ccatgcccca ggcttcgttt tgacatcggc gcaggtcttt gtagtagtct 9840
tgcatgagcc tttctaccgg cacttcttct tctccttcct cttgtcctgc atctcttgca 9900
tctatcgctg cggcggcggc ggagtttggc cgtaggtggc gccctcttcc tcccatgcgt 9960

-continued

```
gtgaccccga agcccctcat cggctgaagc agggctaggt cggcgacaac gcgctcggct  10020
aatatggcct gctgcacctg cgtgagggta gactggaagt catccatgtc cacaaagcgg  10080
tggtatgcgc ccgtgttgat ggtgtaagtg cagttggcca taacggacca gttaacggtc  10140
tggtgacccg gctgcgagag ctcggtgtac ctgagacgcg agtaagccct cgagtcaaat  10200
acgtagtcgt tgcaagtccg caccaggtac tggtatccca ccaaaaagtg cggcggcggc  10260
tggcggtaga ggggccagcg tagggtggcc ggggctccgg gggcgagatc ttccaacata  10320
aggcgatgat atccgtagat gtacctggac atccaggtga tgccggcggc ggtggtggag  10380
gcgcgcggaa agtcgcggac gcggttccag atgttgcgca gcggcaaaaa gtgctccatg  10440
gtcgggacgc tctggccggt caggcgcgcg caatcgttga cgctctagcg tgcaaaagga  10500
gagcctgtaa gcgggcactc ttccgtggtc tggtggataa attcgcaagg gtatcatggc  10560
ggacgaccgg ggttcgagcc ccgtatccgg ccgtccgccg tgatccatgc ggttaccgcc  10620
cgcgtgtcga acccaggtgt gcgacgtcag acaacggggg agtgctcctt ttggcttcct  10680
tccaggcgcg gcggctgctg cgctagcttt tttggccact ggccgcgcgc agcgtaagcg  10740
gttaggctgg aaagcgaaag cattaagtgg ctcgctccct gtagccggag ggttattttc  10800
caagggttga gtcgcgggac ccccggttcg agtctcggac cggccggact gcggcgaacg  10860
ggggtttgcc tccccgtcat gcaagacccc gcttgcaaat tcctccggaa acagggacga  10920
gcccctttt tgcttttccc agatgcatcc ggtgctgcgg cagatgcgcc cccctcctca  10980
gcagcggcaa gagcaagagc agcggcagac atgcagggca ccctcccctc ctcctaccgc  11040
gtcaggaggg gcgacatccg cggttgacgc ggcagcagat ggtgattacg aaccccgcg  11100
gcgccgggcc cggcactacc tggacttgga ggagggcgag ggcctggcgc ggctaggagc  11160
gccctctcct gagcggtacc caagggtgca gctgaagcgt gatacgcgtg aggcgtacgt  11220
gccgcggcag aacctgtttc gcgaccgcga gggagaggag cccgaggaga tgcgggatcg  11280
aaagttccac gcagggcgcg agctgcggca tggcctgaat cgcgagcggt tgctgcgcga  11340
ggaggacttt gagcccgacg cgcgaaccgg gattagtccc gcgcgcgcac acgtggcggc  11400
cgccgacctg gtaaccgcat acgagcagac ggtgaaccag gagattaact ttcaaaaaag  11460
ctttaacaac cacgtgcgta cgcttgtggc gcgcgaggag gtggctatag gactgatgca  11520
tctgtgggac tttgtaagcg cgctggagca aaacccaaat agcaagccgc tcatggcgca  11580
gctgttcctt atagtgcagc acagcaggga caacgaggca ttcagggatg cgctgctaaa  11640
catagtagag cccgagggcc gctggctgct cgatttgata aacatcctgc agagcatagt  11700
ggtgcaggag cgcagcttga gcctggctga caaggtggcc gccatcaact attccatgct  11760
tagcctgggc aagttttacg cccgcaagat ataccatacc ccttacgttc ccatagacaa  11820
ggaggtaaag atcgaggggt tctacatgcg catggcgctg aaggtgctta ccttgagcga  11880
cgacctgggc gtttatcgca acgagcgcat ccacaaggcc gtgagcgtga gccggcggcg  11940
cgagctcagc gaccgcgagc tgatgcacag cctgcaaagg gccctggctg gcacgggcag  12000
cggcgataga gaggccgagt cctactttga cgcgggcgct gacctgcgct gggccccaag  12060
ccgacgcgcc ctggaggcag ctggggccgg acctgggctg gcggtggcac ccgcgcgcgc  12120
tggcaacgtc ggcggcgtgg aggaatatga cgaggacgat gagtacgagc cagaggacgg  12180
cgagtactaa gcggtgatgt ttctgatcag atgatgcaag acgcaacgga cccggcggtg  12240
cgggcggcgc tgcagagcca gccgtccggc cttaactcca cggacgactg gcgccaggtc  12300
atggaccgca tcatgtcgct gactgcgcgc aatcctgacg cgttccggca gcagccgcag  12360
```

-continued gccaaccggc tctccgcaat tctggaagcg gtggtcccgg cgcgcgcaaa ccccacgcac 12420
gagaaggtgc tggcgatcgt aaacgcgctg gccgaaaaca gggccatccg gcccgacgag 12480
gccggcctgg tctacgacgc gctgcttcag cgcgtggctc gttacaacag cggcaacgtg 12540
cagaccaacc tggaccggct ggtgggggat gtgcgcgagg ccgtggcgca gcgtgagcgc 12600
gcgcagcagc agggcaacct gggctccatg gttgcactaa acgccttcct gagtacacag 12660
cccgccaacg tgccgcgggg acaggaggac tacaccaact ttgtgagcgc actgcggcta 12720
atggtgactg agacaccgca aagtgaggtg taccagtctg ggccagacta tttttttccag 12780
accagtagac aaggcctgca gaccgtaaac ctgagccagg ctttcaaaaa cttgcagggg 12840
ctgtgggggg tgcgggctcc cacaggcgac cgcgcgaccg tgtctagctt gctgacgccc 12900
aactcgcgcc tgttgctgct gctaatagcg cccttcacgg acagtggcag cgtgtcccgg 12960
gacacatacc taggtcactt gctgacactg taccgcgagg ccataggtca ggcgcatgtg 13020
gacgagcata ctttccagga gattacaagt gtcagccgcg cgctggggca ggaggacacg 13080
ggcagcctgg aggcaaccct aaactacctg ctgaccaacc ggcggcagaa gatcccctcg 13140
ttgcacagtt taaacagcga ggaggagcgc attttgcgct acgtgcagca gagcgtgagc 13200
cttaacctga tgcgcgacgg ggtaacgccc agcgtggcgc tggacatgac cgcgcgcaac 13260
atggaaccgg gcatgtatgc ctcaaaccgg ccgtttatca accgcctaat ggactacttg 13320
catcgcgcgg ccgccgtgaa ccccgagtat ttcaccaatg ccatcttgaa cccgcactgg 13380
ctaccgcccc ctggtttcta caccggggga ttcgaggtgc ccgagggtaa cgatggattc 13440
ctctgggacg acatagacga cagcgtgttt tccccgcaac cgcagaccct gctagagttg 13500
caacagcgcg agcaggcaga ggcggcgctg cgaaaggaaa gcttccgcag gccaagcagc 13560
ttgtccgatc taggcgctgc ggccccgcgg tcagatgcta gtagcccatt tccaagcttg 13620
atagggtctc ttaccagcac tcgcaccacc cgcccgcgcc tgctgggcga ggaggagtac 13680
ctaaacaact cgctgctgca gccgcagcgc gaaaaaaacc tgcctccggc atttcccaac 13740
aacgggatag agagcctagt ggacaagatg agtagatgga agacgtacgc gcaggagcac 13800
agggacgtgc caggcccgcg cccgcccacc cgtcgtcaaa ggcacgaccg tcagcggggt 13860
ctggtgtggg aggacgatga ctcggcagac gacagcagcg tcctggattt gggagggagt 13920
ggcaacccgt ttgcgcacct tcgccccagg ctggggagaa tgttttaaaa aaaaaaaagc 13980
atgatgcaaa ataaaaaact caccaaggcc atggcaccga gcgttggttt tcttgtattc 14040
cccttagtat gcggcgcgcg gcgatgtatg aggaaggtcc tcctccctcc tacgagagtg 14100
tggtgagcgc ggcgccagtg gcggcggcgc tgggttctcc cttcgatgct cccctggacc 14160
cgccgtttgt gcctccgcgg tacctgcggc ctaccggggg gagaaacagc atccgttact 14220
ctgagttggc acccctattc gacaccaccc gtgtgtacct ggtggacaac aagtcaacgg 14280
atgtggcatc cctgaactac cagaacgacc acagcaactt tctgaccacg gtcattcaaa 14340
acaatgacta cagcccgggg gaggcaagca cacagaccat caatcttgac gaccggtcgc 14400
actggggcgg cgacctgaaa accatcctgc ataccaacat gccaaatgtg aacgagttca 14460
tgtttaccaa taagtttaag gcgcgggtga tggtgtcgcg cttgcctact aaggacaatc 14520
aggtggagct gaaatacgag tgggtggagt tcacgctgcc cgagggcaac tactccgaga 14580
ccatgaccat agaccttatg aacaacgcga tcgtggagca ctacttgaaa gtgggcagac 14640
agaacggggt tctggaaagc gacatcgggg taaagtttga cacccgcaac ttcagactgg 14700

-continued

```
ggtttgaccc cgtcactggt cttgtcatgc ctggggtata tacaaacgaa gccttccatc  14760
cagacatcat tttgctgcca ggatgcgggg tggacttcac ccacagccgc ctgagcaact  14820
tgttgggcat ccgcaagcgg caacccttcc aggagggctt taggatcacc tacgatgatc  14880
tggagggtgg taacattccc gcactgttgg atgtggacgc ctaccaggcg agcttgaaag  14940
atgacaccga acagggcggg ggtggcgcag gcggcagcaa cagcagtggc agcggcgcgg  15000
aagagaactc caacgcggca gccgcggcaa tgcagccggt ggaggacatg aacgatcatg  15060
ccattcgcgg cgacaccttt gccacacggg ctgaggagaa gcgcgctgag gccgaagcag  15120
cggccgaagc tgccgccccc gctgcgcaac ccgaggtcga gaagcctcag aagaaaccgg  15180
tgatcaaacc cctgacagag gacagcaaga aacgcagtta caacctaata agcaatgaca  15240
gcaccttcac ccagtaccgc agctggtacc ttgcatacaa ctacggcgac cctcagaccg  15300
gaatccgctc atggaccctg ctttgcactc ctgacgtaac ctgcggctcg gagcaggtct  15360
actggtcgtt gccagacatg atgcaagacc ccgtgacctt ccgctccacg cgccagatca  15420
gcaactttcc ggtggtgggc gccgagctgt tgcccgtgca ctccaagagc ttctacaacg  15480
accaggccgt ctactcccaa ctcatccgcc agtttacctc tctgacccac gtgttcaatc  15540
gctttcccga gaaccagatt ttggcgcgcc cgccagcccc caccatcacc accgtcagtg  15600
aaaacgttcc tgctctcaca gatcacggga cgctaccgct gcgcaacagc atcggaggag  15660
tccagcgagt gaccattact gacgccagac gccgcacctg cccctacgtt tacaaggccc  15720
tgggcatagt ctcgccgcgc gtcctatcga gccgcacttt ttgagcaagc atgtccatcc  15780
ttatatcgcc cagcaataac acaggctggg gcctgcgctt cccaagcaag atgtttggcg  15840
gggccaagaa gcgctccgac caacacccag tgcgcgtgcg cgggcactac cgcgcgccct  15900
ggggcgcgca caaacgcggc cgcactgggc gcaccaccgt cgatgacgcc atcgacgcgg  15960
tggtggagga ggcgcgcaac tacacgccca cgccgccacc agtgtccaca gtggacgcgg  16020
ccattcagac cgtggtgcgc ggagcccggc gctatgctaa aatgaagaga cggcggaggc  16080
gcgtagcacg tcgccaccgc cgccgacccg gcactgccgc ccaacgcgcg gcggcggccc  16140
tgcttaaccg cgcacgtcgc accggccgac gggcggccat gcgggccgct cgaaggctgg  16200
ccgcgggtat tgtcactgtg ccccccaggt ccaggcgacg agcggccgcc gcagcagccg  16260
cggccattag tgctatgact cagggtcgca ggggcaacgt gtattgggtg cgcgactcgg  16320
ttagcggcct gcgcgtgccc gtgcgcaccc gcccccgcg caactagatt gcaagaaaaa  16380
actacttaga ctcgtactgt tgtatgtatc cagcggcggc ggcgcgcaac gaagctatgt  16440
ccaagcgcaa aatcaaagaa gagatgctcc aggtcatcgc gccggagatc tatggccccc  16500
cgaagaagga agagcaggat tacaagcccc gaaagctaaa gcgggtcaaa aagaaaaaga  16560
aagatgatga tgatgaactt gacgacgagg tggaactgct gcacgctacc gcgcccaggc  16620
gacgggtaca gtggaaaggt cgacgcgtaa aacgtgtttt gcgacccggc accaccgtag  16680
tctttacgcc cggtgagcgc tccacccgca cctacaagcg cgtgtatgat gaggtgtacg  16740
gcgacgagga cctgcttgag caggccaacg agcgcctcgg ggagtttgcc tacggaaagc  16800
ggcataagga catgctggcg ttgccgctgg acgagggcaa cccaacacct agcctaaagc  16860
ccgtaacact gcagcaggtg ctgcccgcgc ttgcaccgtc cgaagaaaag cgcggcctaa  16920
agcgcgagtc tggtgacttg gcacccaccg tgcagctgat ggtacccaag cgccagcgac  16980
tggaagatgt cttggaaaaa atgaccgtgg aacctgggct ggagcccgag gtccgcgtgc  17040
ggccaatcaa gcaggtggcg ccgggactgg gcgtgcagac cgtggacgtt cagataccca  17100
```

-continued

```
ctaccagtag caccagtatt gccaccgcca cagagggcat ggagacacaa acgtccccgg  17160
ttgcctcagc ggtggcggat gccgcggtgc aggcggtcgc tgcggccgcg tccaagacct  17220
ctacggaggt gcaaacggac ccgtggatgt ttcgcgtttc agcccccgg cgcccgcgcg  17280
gttcgaggaa gtacggcgcc gccagcgcgc tactgcccga atatgcccta catccttcca  17340
ttgcgcctac ccccggctat cgtggctaca cctaccgccc cagaagacga gcaactaccc  17400
gacgccgaac caccactgga acccgccgcc gccgtcgccg tcgccagccc gtgctggccc  17460
cgatttccgt gcgcagggtg gctcgcgaag gaggcaggac cctggtgctg ccaacagcgc  17520
gctaccaccc cagcatcgtt taaaagccgg tctttgtggt tcttgcagat atggccctca  17580
cctgccgcct ccgtttcccg gtgccgggat tccgaggaag aatgcaccgt aggaggggca  17640
tggccggcca cggcctgacg ggcggcatgc gtcgtgcgca ccaccggcgg cggcgcgcgt  17700
cgcaccgtcg catgcgcggc ggtatcctgc ccctccttat tccactgatc gccgcggcga  17760
ttggcgccgt gcccggaatt gcatccgtgg ccttgcaggc gcagagacac tgattaaaaa  17820
caagttgcat gtggaaaaat caaaataaaa agtctggact ctcacgctcg cttggtcctg  17880
taactatttt gtagaatgga agacatcaac tttgcgtctc tggccccgcg acacggctcg  17940
cgcccgttca tgggaaactg gcaagatatc ggcaccagca atatgagcgg tggcgccttc  18000
agctggggct cgctgtggag cggcattaaa aatttcggtt ccaccgttaa gaactatggc  18060
agcaaggcct ggaacagcag cacaggccag atgctgaggg ataagttgaa agagcaaaat  18120
ttccaacaaa aggtggtaga tggcctggcc tctggcatta gcggggtggt ggacctggcc  18180
aaccaggcag tgcaaaataa gattaacagt aagcttgatc cccgccctcc cgtagaggag  18240
cctccaccgg ccgtggagac agtgtctcca gaggggcgtg gcgaaaagcg tccgcgcccc  18300
gacagggaag aaactctggt gacgcaaata gacgagcctc cctcgtacga ggaggcacta  18360
aagcaaggcc tgcccaccac ccgtcccatc gcgcccatgg ctaccggagt gctgggccag  18420
cacacacccg taacgctgga cctgcctccc cccgccgaca cccagcagaa acctgtgctg  18480
ccaggcccga ccgccgttgt tgtaacccgt cctagccgcg cgtccctgcg ccgcgccgcc  18540
agcggtccgc gatcgttgcg gcccgtagcc agtggcaact ggcaaagcac actgaacagc  18600
atcgtgggtc tgggggtgca atccctgaag cgccgacgat gcttctgaat agctaacgtg  18660
tcgtatgtgt gtcatgtatg cgtccatgtc gccgccagag gagctgctga gccgccgcgc  18720
gcccgctttc caagatggct accccttcga tgatgccgca gtggtcttac atgcacatct  18780
cgggccagga cgcctcggag tacctgagcc ccgggctggt gcagtttgcc cgcgccaccg  18840
agacgtactt cagcctgaat aacaagttta gaaaccccac ggtggcgcct acgcacgacg  18900
tgaccacaga ccggtcccag cgtttgacgc tgcggttcat ccctgtggac cgtgaggata  18960
ctgcgtactc gtacaaggcg cggttcaccc tagctgtggg tgataaccgt gtgctggaca  19020
tggcttccac gtactttgac atccgcggcg tgctggacag gggccctact tttaagccct  19080
actctggcac tgcctacaac gccctggctc ccaagggtgc cccaaatcct tgcgaatggg  19140
atgaagctgc tactgctctt gaaataaacc tagaagaaga ggacgatgac aacgaagacg  19200
aagtagacga gcaagctgag cagcaaaaaa ctcacgtatt tgggcaggcg ccttattctg  19260
gtataaatat tacaaaggag ggtattcaaa taggtgtcga aggtcaaaca cctaaatatg  19320
ccgataaaac atttcaacct gaacctcaaa taggagaatc tcagtggtac gaaactgaaa  19380
ttaatcatgc agctgggaga gtccttaaaa agactacccc aatgaaacca tgttacggtt  19440
```

-continued

```
catatgcaaa acccacaaat gaaaatggag ggcaaggcat tcttgtaaag caacaaaatg  19500
gaaagctaga aagtcaagtg gaaatgcaat ttttctcaac tactgaggcg accgcaggca  19560
atggtgataa cttgactcct aaagtggtat tgtacagtga agatgtagat atagaaaccc  19620
cagacactca tatttcttac atgcccacta ttaaggaagg taactcacga gaactaatgg  19680
gccaacaatc tatgcccaac aggcctaatt acattgcttt tagggacaat tttattggtc  19740
taatgtatta caacagcacg ggtaatatgg gtgttctggc gggccaagca tcgcagttga  19800
atgctgttgt agatttgcaa gacagaaaca cagagctttc ataccagctt ttgcttgatt  19860
ccattggtga tagaaccagg tacttttcta tgtggaatca ggctgttgac agctatgatc  19920
cagatgttag aattattgaa aatcatggaa ctgaagatga acttccaaat tactgctttc  19980
cactgggagg tgtgattaat acagagactc ttaccaaggt aaaacctaaa acaggtcagg  20040
aaaatggatg ggaaaaagat gctacagaat tttcagataa aaatgaaata agagttggaa  20100
ataattttgc catggaaatc aatctaaatg ccaacctgtg gagaaatttc ctgtactcca  20160
acatagcgct gtatttgccc gacaagctaa agtacagtcc ttccaacgta aaaatttctg  20220
ataacccaaa cacctacgac tacatgaaca agcgagtggt ggctcccggg ttagtggact  20280
gctacattaa ccttggagca cgctggtccc ttgactatat ggacaacgtc aacccattta  20340
accaccaccg caatgctggc ctgcgctacc gctcaatgtt gctgggcaat ggtcgctatg  20400
tgcccttcca catccaggtg cctcagaagt tctttgccat taaaaacctc cttctcctgc  20460
cgggctcata cacctacgag tggaacttca ggaaggatgt taacatggtt ctgcagagct  20520
ccctaggaaa tgacctaagg gttgacggag ccagcattaa gtttgatagc atttgccttt  20580
acgccacctt cttccccatg gcccacaaca ccgcctccac gcttgaggcc atgcttagaa  20640
acgacaccaa cgaccagtcc tttaacgact atctctccgc cgccaacatg ctctaccct a  20700
tacccgccaa cgctaccaac gtgcccatat ccatcccctc ccgcaactgg gcggctttcc  20760
gcggctgggc cttcacgcgc cttaagacta aggaaacccc atcactgggc tcgggctacg  20820
acccttatta cacctactct ggctctatac cctacctaga tggaaccttt tacctcaacc  20880
acacctttaa gaaggtggcc attacctttg actcttctgt cagctggcct ggcaatgacc  20940
gcctgcttac ccccaacgag tttgaaatta agcgctcagt tgacggggag ggttacaacg  21000
ttgcccagtg taacatgacc aaagactggt tcctggtaca aatgctagct aactacaaca  21060
ttggctacca gggcttctat atcccagaga gctacaagga ccgcatgtac tccttcttta  21120
gaaacttcca gcccatgagc cgtcaggtgg tggatgatac taaatacaag gactaccaac  21180
aggtgggcat cctacaccaa cacaacaact ctggatttgt tggctacctt gcccccacca  21240
tgcgcgaagg acaggcctac cctgctaact tcccctatcc gcttataggc aagaccgcag  21300
ttgacagcat tacccagaaa aagtttcttt gcgatcgcac cctttggcgc atcccattct  21360
ccagtaactt tatgtccatg ggcgcactca cagacctggg ccaaaacctt ctctacgcca  21420
actccgccca cgcgctagac atgacttttg aggtggatcc catggacgag cccacccttc  21480
tttatgtttt gtttgaagtc tttgacgtgg tccgtgtgca ccggccgcac cgcggcgtca  21540
tcgaaaccgt gtacctgcgc acgcccttct cggccggcaa cgccacaaca taaagaagca  21600
agcaacatca acaacagctg ccgccatggg ctccagtgag caggaactga aagccattgt  21660
caaagatctt ggttgtgggc catatttttt gggcacctat gacaagcgct ttccaggctt  21720
tgtttctcca cacaagctcg cctgcgccat agtcaatacg gccggtcgcg agactggggg  21780
cgtacactgg atggcctttg cctggaaccc gcactcaaaa acatgctacc tctttgagcc  21840
```

-continued

```
ctttggcttt tctgaccagc gactcaagca ggtttaccag tttgagtacg agtcactcct  21900
gcgccgtagc gccattgctt cttcccccga ccgctgtata acgctggaaa agtccaccca  21960
aagcgtacag gggcccaact cggccgcctg tggactattc tgctgcatgt ttctccacgc  22020
ctttgccaac tggccccaaa ctcccatgga tcacaacccc accatgaacc ttattaccgg  22080
ggtacccaac tccatgctca acagtcccca ggtacagccc accctgcgtc gcaaccagga  22140
acagctctac agcttcctgg agcgccactc gccctacttc cgcagccaca gtgcgcagat  22200
taggagcgcc acttcttttt gtcacttgaa aaacatgtaa aaataatgta ctagagacac  22260
tttcaataaa ggcaaatgct tttatttgta cactctcggg tgattattta cccccaccct  22320
tgccgtctgc gccgtttaaa aatcaaaggg gttctgccgc gcatcgctat gcgccactgg  22380
cagggacacg ttgcgatact ggtgtttagt gctccactta aactcaggca caaccatccg  22440
cggcagctcg gtgaagtttt cactccacag gctgcgcacc atcaccaacg cgtttagcag  22500
gtcgggcgcc gatatcttga agtcgcagtt ggggcctccg ccctgcgcgc gcgagttgcg  22560
atacacaggg ttgcagcact ggaacactat cagcgccggg tggtgcacgc tggccagcac  22620
gctcttgtcg gagatcagat ccgcgtccag gtcctccgcg ttgctcaggg cgaacggagt  22680
caactttggt agctgccttc ccaaaaaggg cgcgtgccca ggctttgagt tgcactcgca  22740
ccgtagtggc atcaaaaggt gaccgtgccc ggtctgggcg ttaggataca gcgcctgcat  22800
aaaagccttg atctgcttaa aagccacctg agcctttgcg ccttcagaga agaacatgcc  22860
gcaagacttg ccggaaaact gattggccgg acaggccgcg tcgtgcacgc agcaccttgc  22920
gtcggtgttg gagatctgca ccacatttcg gccccaccgg ttcttcacga tcttggcctt  22980
gctagactgc tccttcagcg cgcgctgccc gttttcgctc gtcacatcca tttcaatcac  23040
gtgctcctta tttatcataa tgcttccgtg tagacactta agctcgcctt cgatctcagc  23100
gcagcggtgc agccacaacg cgcagcccgt gggctcgtga tgcttgtagg tcacctctgc  23160
aaacgactgc aggtacgcct gcaggaatcg ccccatcatc gtcacaaagg tcttgttgct  23220
ggtgaaggtc agctgcaacc cgcggtgctc ctcgttcagc caggtcttgc atacggccgc  23280
cagagcttcc acttggtcag gcagtagttt gaagttcgcc tttagatcgt tatccacgtg  23340
gtacttgtcc atcagcgcgc gcgcagcctc catgcccttc tcccacgcag acacgatcgg  23400
cacactcagc gggttcatca ccgtaatttc actttccgct tcgctgggct cttcctcttc  23460
ctcttgcgtc cgcataccac gcgccactgg gtcgtcttca ttcagccgcc gcactgtgcg  23520
cttacctcct ttgccatgct tgattagcac cggtgggttg ctgaaaccca ccatttgtag  23580
cgccacatct tctctttctt cctcgctgtc cacgattacc tctggtgatg gcgggcgctc  23640
gggcttggga gaagggcgct tctttttctt cttgggcgca atggccaaat ccgccgccga  23700
ggtcgatggc cgcgggctgg gtgtgcgcgg caccagcgcg tcttgtgatg agtcttcctc  23760
gtcctcggac tcgatacgcc gcctcatccg ctttttgggg ggcgcccggg gaggcggcgg  23820
cgacggggac ggggacgaca cgtcctccat ggttgggggga cgtcgcgccg caccgcgtcc  23880
gcgctcgggg gtggtttcgc gctgctcctc ttcccgactg gccatttcct tctcctatag  23940
gcagaaaaag atcatggagt cagtcgagaa gaaggacagc ctaaccgccc cctctgagtt  24000
cgccaccacc gcctccaccg atgccgccaa cgcgcctacc accttccccg tcgaggcacc  24060
cccgcttgag gaggaggaag tgattatcga gcaggaccca ggttttgtaa gcgaagacga  24120
cgaggaccgc tcagtaccaa cagaggataa aaagcaagac caggacaacg cagaggcaaa  24180
```

-continued

```
cgaggaacaa gtcgggcggg gggacgaaag gcatggcgac tacctagatg tgggagacga  24240
cgtgctgttg aagcatctgc agcgccagtg cgccattatc tgcgacgcgt tgcaagagcg  24300
cagcgatgtg cccctcgcca tagcggatgt cagccttgcc tacgaacgcc acctattctc  24360
accgcgcgta ccccccaaac gccaagaaaa cggcacatgc gagcccaacc cgcgcctcaa  24420
cttctacccc gtatttgccg tgccagaggt gcttgccacc tatcacatct ttttccaaaa  24480
ctgcaagata cccctatcct gccgtgccaa ccgcagccga gcggacaagc agctggcctt  24540
gcggcagggc gctgtcatac ctgatatcgc ctcgctcaac gaagtgccaa aaatctttga  24600
gggtcttgga cgcgacgaga agcgcgcggc aaacgctctg caacaggaaa acagcgaaaa  24660
tgaaagtcac tctggagtgt tggtggaact cgagggtgac aacgcgcgcc tagccgtact  24720
aaaacgcagc atcgaggtca cccactttgc ctacccggca cttaacctac cccccaaggt  24780
catgagcaca gtcatgagtg agctgatcgt gcgccgtgcg cagcccctgg agagggatgc  24840
aaatttgcaa gaacaaacag aggagggcct acccgcagtt ggcgacgagc agctagcgcg  24900
ctggcttcaa acgcgcgagc ctgccgactt ggaggagcga cgcaaactaa tgatggccgc  24960
agtgctcgtt accgtggagc ttgagtgcat gcagcggttc tttgctgacc cggagatgca  25020
gcgcaagcta gaggaaacat tgcactacac ctttcgacag ggctacgtac gccaggcctg  25080
caagatctcc aacgtggagc tctgcaacct ggtctcctac cttggaattt tgcacgaaaa  25140
ccgccttggg caaaacgtgc ttcattccac gctcaagggc gaggcgcgcc gcgactacgt  25200
ccgcgactgc gtttacttat ttctatgcta cacctggcag acggccatgg gcgtttggca  25260
gcagtgcttg gaggagtgca acctcaagga gctgcagaaa ctgctaaagc aaaacttgaa  25320
ggacctatgg acggccttca acgagcgctc cgtggccgcg cacctggcgg acatcatttt  25380
ccccgaacgc ctgcttaaaa ccctgcaaca gggtctgcca gacttcacca gtcaaagcat  25440
gttgcagaac tttaggaact ttatcctaga gcgctcagga atcttgcccg ccacctgctg  25500
tgcacttcct agcgactttg tgcccattaa gtaccgcgaa tgccctccgc cgctttgggg  25560
ccactgctac cttctgcagc tagccaacta ccttgcctac cactctgaca taatggaaga  25620
cgtgagcggt gacggtctac tggagtgtca ctgtcgctgc aacctatgca ccccgcaccg  25680
ctccctggtt tgcaattcgc agctgcttaa cgaaagtcaa attatcggta cctttgagct  25740
gcagggtccc tcgcctgacg aaaagtccgc ggctccgggg ttgaaactca ctccggggct  25800
gtggacgtcg gcttaccttc gcaaatttgt acctgaggac taccacgccc acgagattag  25860
gttctacgaa gaccaatccc gcccgccaaa tgcggagctt accgcctgcg tcattaccca  25920
gggccacatt cttggccaat tgcaagccat caacaaagcc cgccaagagt ttctgctacg  25980
aaagggacgg ggggtttact tggaccccca gtccggcgag gagctcaacc caatcccccc  26040
gccgccgcag ccctatcagc agcagccgcg ggcccttgct tcccaggatg gcacccaaaa  26100
agaagctgca gctgccgccg ccacccacgg acgaggagga atactgggac agtcaggcag  26160
aggaggtttt ggacgaggag gaggaggaca tgatggaaga ctgggagagc ctagacgagg  26220
aagcttccga ggtcgaagag gtgtcagacg aaacaccgtc accctcggtc gcattcccct  26280
cgccggcgcc ccagaaatcg gcaaccggtt ccagcatggc tacaacctcc gctcctcagg  26340
cgccgccggc actgcccgtt cgccgaccca accgtagatg ggacaccact ggaaccaggg  26400
ccggtaagtc caagcagccg ccgccgttag cccaagagca acaacagcgc caaggctacc  26460
gctcatggcg cgggcacaag aacgccatag ttgcttgctt gcaagactgt gggggcaaca  26520
tctccttcgc ccgccgcttt cttctctacc atcacggcgt ggccttcccc cgtaacatcc  26580
```

-continued

```
tgcattacta ccgtcatctc tacagcccat actgcaccgg cggcagcggc agcggcagca  26640
acagcagcgg ccacacagaa gcaaaggcga ccggatagca agactctgac aaagcccaag  26700
aaatccacag cggcggcagc agcaggagga ggagcgctgc gtctggcgcc caacgaaccc  26760
gtatcgaccc gcgagcttag aaacaggatt tttcccactc tgtatgctat atttcaacag  26820
agcaggggcc aagaacaaga gctgaaaata aaaaacaggt ctctgcgatc cctcacccgc  26880
agctgcctgt atcacaaaag cgaagatcag cttcggcgca cgctggaaga cgcggaggct  26940
ctcttcagta aatactgcgc gctgactctt aaggactagt ttcgcgccct ttctcaaatt  27000
taagcgcgaa aactacgtca tctccagcgg ccacacccgg cgccagcacc tgtcgtcagc  27060
gccattatga gcaaggaaat tcccacgccc tacatgtgga gttaccagcc acaaatggga  27120
cttgcggctg gagctgccca agactactca acccgaataa actacatgag cgcgggaccc  27180
cacatgatat cccgggtcaa cggaatccgc gcccaccgaa accgaattct cttggaacag  27240
gcggctatta ccaccacacc tcgtaataac cttaatcccc gtagttggcc cgctgccctg  27300
gtgtaccagg aaagtcccgc tcccaccact gtggtacttc ccagagacgc ccaggccgaa  27360
gttcagatga ctaactcagg ggcgcagctt gcgggcggct ttcgtcacag ggtgcggtcg  27420
cccgggcagg gtataactca cctgacaatc agagggcgag gtattcagct caacgacgag  27480
tcggtgagct cctcgcttgg tctccgtccg gacgggacat ttcagatcgg cggcgccggc  27540
cgtccttcat tcacgcctcg tcaggcaatc ctaactctgc agacctcgtc ctctgagccg  27600
cgctctggag gcattggaac tctgcaattt attgaggagt ttgtgccatc ggtctacttt  27660
aaccccttct cgggacctcc cggccactat ccggatcaat ttattcctaa ctttgacgcg  27720
gtaaaggact cggcggacgg ctacgactga taattaagtg gagaggcaga gcaactgcgc  27780
ctgaaacacc tggtccactg tcgccgccac aagtgctttg cccgcgactc cggtgagttt  27840
tgctactttg aattgcccga ggatcatatc gaggatcttt gttgccatct ctgtgctgag  27900
tataataaat acagaaatta aaatatactg gggctcctat cgccatcctg taaacgccac  27960
cgtcttcacc cgcccaagca aaccaaggcg aaccttacct ggtactttta acatctctcc  28020
ctctgtgatt tacaacagtt tcaacccaga cggagtgagt ctacgagaga acctctccga  28080
gctcagctac tccatcagaa aaaacaccac cctccttacc tgccgggaac gtacccttaa  28140
ttaaaagtca ggcttcctgg atgtcagcat ctgactttgg ccagcacctg tcccgcggat  28200
ttgttccagt ccaactacag cgacccaccc taacagagat gaccaacaca accaacgcgg  28260
ccgccgctac cggacttaca tctaccacaa atacacccca agtttctgcc tttgtcaata  28320
actgggataa cttgggcatg tggtggttct ccatagcgct tatgtttgta tgccttatta  28380
ttatgtggct catctgctgc ctaaagcgca aacgcgcccg accacccatc tatagtccca  28440
tcattgtgct acacccaaac aatgatggaa tccatagatt ggacggactg aaacacatgt  28500
tcttttctct tacagtatga ttaaatgaga ttaattaagg aatttctgtc cagtttattc  28560
agcagcacct ccttgccctc ctcccagctc tggtattgca gcttcctcct ggctgcaaac  28620
tttctccaca atctaaatgg aatgtcagtt tcctcctgtt cctgtccatc cgcacccact  28680
atcttcatgt tgttgcagat gaagcgcgca agaccgtctg aagatacctt caaccccgtg  28740
tatccatatg acacggaaac cggtcctcca actgtgcctt ttcttactcc tccctttgta  28800
tcccccaatg ggtttcaaga gagtccccct ggggtactct ctttgcgcct atccgaacct  28860
ctagttacct ccaatggcat gcttgcgctc aaaatgggca acggcctctc tctggacgag  28920
```

-continued

```
gccggcaacc ttacctccca aaatgtaacc actgtgagcc cacctctcaa aaaaaccaag  28980
tcaaacataa acctggaaat atctgcaccc ctcacagtta cctcagaagc cctaactgtg  29040
gctgccgccg cacctctaat ggtcgcgggc aacacactca ccatgcaatc acaggccccg  29100
ctaaccgtgc acgactccaa acttagcatt gccacccaag gacccctcac agtgtcagaa  29160
ggaaagctag ccctgcaaac atcaggcccc ctcaccacca ccgatagcag tacccttact  29220
atcactgcct caccccctct aactactgcc actggtagct tgggcattga cttgaaagag  29280
cccatttata cacaaaatgg aaaactagga ctaaagtacg gggctccttt gcatgtaaca  29340
gacgacctaa acactttgac cgtagcaact ggtccaggtg tgactattaa taatacttcc  29400
ttgcaaacta aagttactgg agccttgggt tttgattcac aaggcaatat gcaacttaat  29460
gtagcaggag gactaaggat tgattctcaa aacagacgcc ttatacttga tgttagttat  29520
ccgtttgatg ctcaaaacca actaaatcta agactaggac agggccctct ttttataaac  29580
tcagcccaca acttggatat taactacaac aaaggccttt acttgtttac agcttcaaac  29640
aattccaaaa agcttgaggt taacctaagc actgccaagg ggttgatgtt tgacgctaca  29700
gccatagcca ttaatgcagg agatgggctt gaatttggtt cacctaatgc accaaacaca  29760
aatcccctca aaacaaaaat tggccatggc ctagaatttg attcaaacaa ggctatggtt  29820
cctaaactag gaactggcct tagttttgac agcacaggtg ccattacagt aggaaacaaa  29880
aataatgata agctaacttt gtggaccaca ccagctccat ctcctaactg tagactaaat  29940
gcagagaaag atgctaaact cactttggtc ttaacaaaat gtggcagtca aatacttgct  30000
acagtttcag ttttggctgt taaaggcagt ttggctccaa tatctggaac agttcaaagt  30060
gctcatctta ttataagatt tgacgaaaat ggagtgctac taaacaattc cttcctggac  30120
ccagaatatt ggaactttag aaatggagat cttactgaag gcacagccta tacaaacgct  30180
gttggattta tgcctaacct atcagcttat ccaaaatctc acggtaaaac tgccaaaagt  30240
aacattgtca gtcaagttta cttaaacgga gacaaaacta aacctgtaac actaaccatt  30300
acactaaacg gtacacagga aacaggagac acaactccaa gtgcatactc tatgtcattt  30360
tcatgggact ggtctggcca caactacatt aatgaaatat ttgccacatc ctcttacact  30420
ttttcataca ttgcccaaga ataaagaatc gtttgtgtta tgtttcaacg tgtttatttt  30480
tcaattgcag aaaatttcaa gtcatttttc attcagtagt atagccccac caccacatag  30540
cttatacaga tcaccgtacc ttaatcaaac tcacagaacc ctagtattca acctgccacc  30600
tccctcccaa cacacagagt acacagtcct ttctccccgg ctggccttaa aaagcatcat  30660
atcatgggta acagacatat tcttaggtgt tatattccac acggtttcct gtcgagccaa  30720
acgctcatca gtgatattaa taaactcccc gggcagctca cttaagttca tgtcgctgtc  30780
cagctgctga gccacaggct gctgtccaac ttgcggttgc ttaacgggcg gcgaaggaga  30840
agtccacgcc tacatggggg tagagtcata atcgtgcatc aggatagggc ggtggtgctg  30900
cagcagcgcg cgaataaact gctgccgccg ccgctccgtc ctgcaggaat acaacatggc  30960
agtggtctcc tcagcgatga ttcgcaccgc ccgcagcata aggcgccttg tcctccgggc  31020
acagcagcgc accctgatct cacttaaatc agcacagtaa ctgcagcaca gcaccacaat  31080
attgttcaaa atcccacagt gcaaggcgct gtatccaaag ctcatggcgg ggaccacaga  31140
acccacgtgg ccatcatacc acaagcgcag gtagattaag tggcgacccc tcataaacac  31200
gctggacata aacattacct cttttggcat gttgtaattc accacctccc ggtaccatat  31260
aaacctctga ttaaacatgg cgccatccac caccatccta aaccagctgg ccaaaacctg  31320
```

-continued

```
cccgccggct atacactgca gggaaccggg actggaacaa tgacagtgga gagcccagga  31380
ctcgtaacca tggatcatca tgctcgtcat gatatcaatg ttggcacaac acaggcacac  31440
gtgcatacac ttcctcagga ttacaagctc ctcccgcgtt agaaccatat cccagggaac  31500
aacccattcc tgaatcagcg taaatcccac actgcaggga agacctcgca cgtaactcac  31560
gttgtgcatt gtcaaagtgt tacattcggg cagcagcgga tgatcctcca gtatggtagc  31620
gcgggtttct gtctcaaaag gaggtagacg atccctactg tacggagtgc gccgagacaa  31680
ccgagatcgt gttggtcgta gtgtcatgcc aaatggaacg ccggacgtag tcatatttcc  31740
tgaagcaaaa ccaggtgcgg gcgtgacaaa cagatctgcg tctccggtct cgccgcttag  31800
atcgctctgt gtagtagttg tagtatatcc actctctcaa agcatccagg cgccccctgg  31860
cttcgggttc tatgtaaact ccttcatgcg ccgctgccct gataacatcc accaccgcag  31920
aataagccac acccagccaa cctacacatt cgttctgcga gtcacacacg ggaggagcgg  31980
gaagagctgg aagaaccatg ttttttttt tattccaaaa gattatccaa aacctcaaaa  32040
tgaagatcta ttaagtgaac gcgctcccct ccggtggcgt ggtcaaactc tacagccaaa  32100
gaacagataa tggcatttgt aagatgttgc acaatggctt ccaaaaggca aacggccctc  32160
acgtccaagt ggacgtaaag gctaaaccct tcagggtgaa tctcctctat aaacattcca  32220
gcaccttcaa ccatgcccaa ataattctca tctcgccacc ttctcaatat atctctaagc  32280
aaatcccgaa tattaagtcc ggccattgta aaaatctgct ccagagcgcc ctccaccttc  32340
agcctcaagc agcgaatcat gattgcaaaa attcaggttc ctcacagacc tgtataagat  32400
tcaaaagcgg aacattaaca aaaataccgc gatcccgtag gtcccttcgc agggccagct  32460
gaacataatc gtgcaggtct gcacggacca gcgcggccac ttccccgcca ggaaccttga  32520
caaaagaacc cacactgatt atgacacgca tactcggagc tatgctaacc agcgtagccc  32580
cgatgtaagc tttgttgcat gggcggcgat ataaaatgca aggtgctgct caaaaaatca  32640
ggcaaagcct cgcgcaaaaa agaaagcaca tcgtagtcat gctcatgcag ataaaggcag  32700
gtaagctccg gaaccaccac agaaaaagac accatttttc tctcaaacat gtctgcgggt  32760
ttctgcataa acacaaaata aaataacaaa aaaacattta aacattagaa gcctgtctta  32820
caacaggaaa aacaaccctt ataagcataa gacggactac ggccatgccg gcgtgaccgt  32880
aaaaaaactg gtcaccgtga ttaaaaagca ccaccgacag ctcctcggtc atgtccggag  32940
tcataatgta agactcggta aacacatcag gttgattcat cggtcagtgc taaaaagcga  33000
ccgaaatagc ccgggggaat acatacccgc aggcgtagag acaacattac agccccata  33060
ggaggtataa caaaattaat aggagagaaa aacacataaa cacctgaaaa accctcctgc  33120
ctaggcaaaa tagcaccctc ccgctccaga acaacataca gcgcttcaca gcggcagcct  33180
aacagtcagc cttaccagta aaaaagaaaa cctattaaaa aaacaccact cgacacggca  33240
ccagctcaat cagtcacagt gtaaaaaagg gccaagtgcg ttacactgca gcaggtgtga  33300
ctcagccatg gcacctctgc agcctgggta ccctgcttgg ggcatggccc cttatagctg  33360
ggcggggcgt gggggctctg taggagtggc agcgacctca gtgtttgtct ttgctctgaa  33420
gagccctcca ggtgcttgat cccacctttt cccagcagga acactcctgc ctgccttacc  33480
acctgtcctg gctgatggcc tgttcctgcc tcctttgccc cctgcccaga ctcccatgtt  33540
cctggacttg tggcttcctc caaccagggg ctctcaagcc tccatacctg gtcccacctc  33600
tccaggccgt gggagggagg ttgaggaggg tggagggcat ctggttgggg gcagcctggg  33660
```

-continued tgttcccctc ccatcccctc cctgggcctc ccaggccccc tctactcttg agcaatgctc 33720
ttgagagctt cctgcctggc tcttaaccca gggcaagccc tggaagggca gacccaggac 33780
actctcacca cctccttacc ttttccccctg gaaaaatctt ctgtatactt cccattttaa 33840
gaaaactaca attcccaaca catacaagtt actccgccct aaaacctacg tcacccgccc 33900
cgttcccacg ccccgcgcca cgtcacaaac tccacccccct cattatcata ttggcttcaa 33960
tccaaaataa ggtatattat tgatgatg 33988

<210> SEQ ID NO 15
<211> LENGTH: 34737
<212> TYPE: DNA
<213> ORGANISM: Adenovirus subgroup C

<400> SEQUENCE: 15
catcatcaat aatatacctt attttggatt gaagccaata tgataatgag ggggtggagt 60
ttgtgacgtg gcgcggggcg tgggaacggg gcgggtgacg tagtagtgtg gcggaagtgt 120
gatgttgcaa gtgtggcgga acacatgtaa gcgacggatg tggcaaaagt gacgtttttg 180
gtgtgcgccg gtgtacacag gaagtgacaa ttttcgcgcg gttttaggcg gatgttgtag 240
taaatttggg cgtaaccgag taagatttgg ccattttcgc gggaaaactg aataagagga 300
agtgaaatct gaataatttt gtgttactca tagcgcgtaa tatttgtcta gggccgcggg 360
gactttgacc gtttacgtgg agactcgccc aggtgttttt ctcaggtgtt ttccgcgttc 420
cgggtcaaag ttggcgtttt attattatag tcagctgacg tgtagtgtat ttatacccgg 480
tgagttcctc aagaggccac tcttgagtgc cagcgagtag agttttctcc tccgagccgc 540
tccgacaccg ggactgaaaa tgagacatga ggtactggct gataatcttc cacctcctag 600
ccattttgaa ccacctaccc ttcacgaact gtatgattta gacgtgacgg cccccgaaga 660
tcccaacgag gaggcggttt cgcagatttt tcccgactct gtaatgttgg cggtgcagga 720
agggattgac ttactcactt ttccgccggc gcccggttct ccggagccgc ctcacctttc 780
ccggcagccc gagcagccgg agcagagagc cttgggtccg gtttgccacg aggctggctt 840
tccacccagt gacgacgagg atgaagaggg tgaggagttt gtgttagatt atgtggagca 900
ccccgggcac ggttgcaggt cttgtcatta tcaccggagg aatacggggg acccagatat 960
tatgtgttcg ctttgctata tgaggacctg tggcatgttt gtctacagta agtgaaaatt 1020
atgggcagtg ggtgatagag tggtgggttt ggtgtggtaa tttttttttt aatttttaca 1080
gttttgtggt ttaaagaatt ttgtattgtg atttttttaa aaggtcctgt gtctgaacct 1140
gagcctgagc ccgagccaga accggagcct gcaagaccta cccgccgtcc taaaatggcg 1200
cctgctatcc tgagacgccc gacatcacct gtgtctagag aatgcaatag tagtacggat 1260
agctgtgact ccggtccttc taacacacct cctgagatac acccggtggt cccgctgtgc 1320
cccattaaac cagttgccgt gagagttggt gggcgtcgcc aggctgtgga atgtatcgag 1380
gacttgctta acgagcctgg gcaacctttg gacttgagct gtaaacgccc caggccataa 1440
ggtgtaaacc tgtgattgcg tgtgtggtta acgcctttgt ttgctgaatg agttgatgta 1500
agtttaataa agggtgagat aatgtttaac ttgcatggcg tgttaaatgg ggcggggctt 1560
aaagggtata taatgcgccg tgggctaatc ttggttacat ctgacctcat ggaggcttgg 1620
gagtgtttgg aagatttttc tgctgtgcgt aacttgctgg aacagagctc taacagtacc 1680
tcttggtttt ggaggtttct gtggggctca tcccaggcaa agttagtctg cagaattaag 1740
gaggattaca agtgggaatt tgaagagctt ttgaaatcct gtggtgagct gtttgattct 1800

-continued

```
ttgaatctgg gtcaccaggc gcttttccaa gagaaggtca tcaagacttt ggatttttcc   1860
acaccggggc gcgctgcggc tgctgttgct tttttgagtt ttataaagga taaatggagc   1920
gaagaaaccc atctgagcgg ggggtacctg ctggattttc tggccatgca tctgtggaga   1980
gcggttgtga gacacaagaa tcgcctgcta ctgttgtctt ccgtccgccc ggcgataata   2040
ccgacggagg agcagcagca gcagcaggag gaagccaggc ggcggcggca ggagcagagc   2100
ccatggaacc cgagagccgg cctggaccct cgggaatgaa tgttgtacag gtggctgaac   2160
tgtatccaga actgagacgc attttgacaa ttacagagga tgggcagggg ctaaaggggg   2220
taaagaggga gcgggggct tgtgaggcta cagaggaggc taggaatcta gcttttagct   2280
taatgaccag acaccgtcct gagtgtatta cttttcaaca gatcaaggat aattgcgcta   2340
atgagcttga tctgctggcg cagaagtatt ccatagagca gctgaccact tactggctgc   2400
agccagggga tgattttgag gaggctatta gggtatatgc aaaggtggca cttaggccag   2460
attgcaagta caagatcagc aaacttgtaa atatcaggaa ttgttgctac atttctggga   2520
acggggccga ggtggagata gatacggagg atagggtggc ctttagatgt agcatgataa   2580
atatgtggcc gggggtgctt ggcatggacg gggtggttat tatgaatgta aggtttactg   2640
gccccaattt tagcggtacg gttttcctgg ccaataccaa ccttatccta cacggtgtaa   2700
gcttctatgg gtttaacaat acctgtgtgg aagcctggac cgatgtaagg gttcggggct   2760
gtgcctttta ctgctgctgg aagggggtgg tgtgtcgccc caaaagcagg gcttcaatta   2820
agaaatgcct ctttgaaagg tgtaccttgg gtatcctgtc tgagggtaac tccagggtgc   2880
gccacaatgt ggcctccgac tgtggttgct tcatgctagt gaaaagcgtg gctgtgatta   2940
agcataacat ggtatgtggc aactgcgagg acagggcctc tcagatgctg acctgctcgg   3000
acggcaactg tcacctgctg aagaccattc acgtagccag ccactctcgc aaggcctggc   3060
cagtgtttga gcataacata ctgacccgct gttccttgca tttgggtaac aggagggggg   3120
tgttcctacc ttaccaatgc aatttgagtc acactaagat attgcttgag cccgagagca   3180
tgtccaaggt gaacctgaac ggggtgtttg acatgaccat gaagatctgg aaggtgctga   3240
ggtacgatga gacccgcacc aggtgcagac cctgcgagtg tggcggtaaa catattagga   3300
accagcctgt gatgctggat gtgaccgagg agctgaggcc cgatcacttg gtgctggcct   3360
gcacccgcgc tgagtttggc tctagcgatg aagatacaga ttgaggtact gaaatgtgtg   3420
ggcgtggctt aagggtggga aagaatatat aaggtggggg tcttatgtag ttttgtatct   3480
gttttgcagc agccgccgcc gccatgagca ccaactcgtt tgatggaagc attgtgagct   3540
catatttgac aacgcgcatg cccccatggg ccggggtgcg tcagaatgtg atgggctcca   3600
gcattgatgg tcgccccgtc ctgcccgcaa actctactac cttgacctac gagaccgtgt   3660
ctggaacgcc gttggagact gcagcctccg ccgccgcttc agccgctgca gccaccgccc   3720
gcgggattgt gactgacttt gctttcctga gcccgcttgc aagcagtgca gcttcccgtt   3780
catccgcccg cgatgacaag ttgacggctc ttttggcaca attggattct ttgacccggg   3840
aacttaatgt cgtttctcag cagctgttgg atctgcgcca gcaggtttct gccctgaagg   3900
cttcctcccc tcccaatgcg gtttaaaaca taaataaaaa accagactct gtttggattt   3960
ggatcaagca agtgtcttgc tgtctttatt taggggtttt gcgcgcgcgg taggcccggg   4020
accagcggtc tcggtcgttg agggtcctgt gtattttttc caggacgtgg taaaggtgac   4080
tctggatgtt cagatacatg ggcataagcc cgtctctggg gtggaggtag caccactgca   4140
```

-continued

```
gagcttcatg ctgcggggtg gtgttgtaga tgatccagtc gtagcaggag cgctgggcgt   4200
ggtgcctaaa aatgtctttc agtagcaagc tgattgccag gggcaggccc ttggtgtaag   4260
tgtttacaaa gcggttaagc tgggatgggt gcatacgtgg ggatatgaga tgcatcttgg   4320
actgtatttt taggttggct atgttcccag ccatatccct ccggggattc atgttgtgca   4380
gaaccaccag cacagtgtat ccggtgcact tgggaaattt gtcatgtagc ttagaaggaa   4440
atgcgtggaa gaacttggag acgcccttgt gacctccaag attttccatg cattcgtcca   4500
taatgatggc aatgggccca cgggcggcgg cctgggcgaa gatatttctg ggatcactaa   4560
cgtcatagtt gtgttccagg atgagatcgt cataggccat ttttacaaag cgcgggcgga   4620
gggtgccaga ctgcggtata atggttccat ccggcccagg ggcgtagtta ccctcacaga   4680
tttgcatttc ccacgctttg agttcagatg gggggatcat gtctacctgc ggggcgatga   4740
agaaaacggt ttccggggta ggggagatca gctgggaaga aagcaggttc ctgagcagct   4800
gcgacttacc gcagccggtg ggcccgtaaa tcacacctat taccgggtgc aactggtagt   4860
taagagagct gcagctgccg tcatccctga gcaggggggc cacttcgtta agcatgtccc   4920
tgactcgcat gttttccctg accaaatccg ccagaaggcg ctcgccgccc agcgatagca   4980
gttcttgcaa ggaagcaaag tttttcaacg gtttgagacc gtccgccgta ggcatgcttt   5040
tgagcgtttg accaagcagt tccaggcggt cccacagctc ggtcacctgc tctacggcat   5100
ctcgatccag catatctcct cgtttcgcgg gttggggcgg ctttcgctgt acggcagtag   5160
tcggtgctcg tccagacggg ccagggtcat gtctttccac gggcgcaggg tcctcgtcag   5220
cgtagtctgg gtcacggtga aggggtgcgc tccgggctgc gcgctggcca gggtgcgctt   5280
gaggctggtc ctgctggtgc tgaagcgctg ccggtcttcg ccctgcgcgt cggccaggta   5340
gcatttgacc atggtgtcat agtccagccc ctccgcggcg tggcccttgg cgcgcagctt   5400
gcccttggag gaggcgccgc acgaggggca gtgcagactt ttgagggcgt agagcttggg   5460
cgcgagaaat accgattccg gggagtaggc atccgcgccg caggccccgc agacggtctc   5520
gcattccacg agccaggtga gctctggccg ttcggggtca aaaaccaggt ttcccccatg   5580
ctttttgatg cgtttcttac ctctggtttc catgagccgg tgtccacgct cggtgacgaa   5640
aaggctgtcc gtgtccccgt atacagactt gagaggcctg tcctcgagcg gtgttccgcg   5700
gtcctcctcg tatagaaact cggaccactc tgagacaaag gctcgcgtcc aggccagcac   5760
gaaggaggct aagtgggagg ggtagcggtc gttgtccact agggggtcca ctcgctccag   5820
ggtgtgaaga cacatgtcgc cctcttcggc atcaaggaag gtgattggtt tgtaggtgta   5880
ggccacgtga ccgggtgttc ctgaaggggg gctataaaag gggggtgggg cgcgttcgtc   5940
ctcactctct tccgcatcgc tgtctgcgag ggccagctgt tggggtgagt actccctctg   6000
aaaagcgggc atgacttctg cgctaagatt gtcagtttcc aaaaacgagg aggatttgat   6060
attcacctgg cccgcggtga tgcctttgag ggtggccgca tccatctggt cagaaaagac   6120
aatctttttg ttgtcaagct tggtggcaaa cgacccgtag agggcgttgg acagcaactt   6180
ggcgatggag cgcagggttt ggtttttgtc gcgatcggcg cgctccttgg ccgcgatgtt   6240
tagctgcacg tattcgcgcg caacgcaccg ccattcggga aagacggtgg tgcgctcgtc   6300
gggcaccagg tgcacgcgcc aaccgcggtt gtgcagggtg acaaggtcaa cgctggtggc   6360
tacctctccg cgtaggcgct cgttggtcca gcagaggcgg ccgcccttgc gcgagcagaa   6420
tggcggtagg gggtctagct gcgtctcgtc cggggggtct gcgtccacgg taaagacccc   6480
gggcagcagg cgcgcgtcga agtagtctat cttgcatcct tgcaagtcta gcgcctgctg   6540
```

```
ccatgcgcgg gcggcaagcg cgcgctcgta tgggttgagt gggggacccc atggcatggg    6600
gtgggtgagc gcggaggcgt acatgccgca aatgtcgtaa acgtagaggg gctctctgag    6660
tattccaaga tatgtagggt agcatcttcc accgcggatg ctggcgcgca cgtaatcgta    6720
tagttcgtgc gagggagcga ggaggtcggg accgaggttg ctacgggcgg gctgctctgc    6780
tcggaagact atctgcctga agatggcatg tgagttggat gatatggttg gacgctggaa    6840
gacgttgaag ctggcgtctg tgagacctac cgcgtcacgc acgaaggagg cgtaggagtc    6900
gcgcagcttg ttgaccagct cggcggtgac ctgcacgtct agggcgcagt agtccagggt    6960
ttccttgatg atgtcatact tatcctgtcc cttttttttc cacagctcgc ggttgaggac    7020
aaactcttcg cggtctttcc agtactcttg gatcggaaac ccgtcggcct ccgaacggta    7080
agagcctagc atgtagaact ggttgacggc ctggtaggcg cagcatccct tttctacggg    7140
tagcgcgtat gcctgcgcgg ccttccgagg cgaggtgtgg gtgagcgcaa aggtgtccct    7200
gaccatgact ttgaggtact ggtatttgaa gtcagtgtcg tcgcatccgc cctgctccca    7260
gagcaaaaag tccgtgcgct ttttggaacg cggatttggc agggcgaagg tgacatcgtt    7320
gaagagtatc tttcccgcgc gaggcataaa gttgcgtgtg atgcggaagg gtcccggcac    7380
ctcggaacgg ttgttaatta cctgggcggc gagcacgatc tcgtcaaagc cgttgatgtt    7440
gtggcccaca atgtaaagtt ccaagaagcg cgggatgccc ttgatggaag gcaattttt    7500
aagttcctcg taggtgagct cttcagggga gctgagcccg tgctctgaaa gggcccagtc    7560
tgcaagatga gggttggaag cgacgaatga gctccacagg tcacgggcca ttagcatttg    7620
caggtggtcg cgaaaggtcc taaactggcg acctatggcc attttttctg gggtgatgca    7680
gtagaaggta agcgggtctt gttcccagcg gtcccatcca aggttcgcgg ctaggtctcg    7740
cgcggcagtc actagaggct catctccgcc gaacttcatg accagcatga agggcacgag    7800
ctgcttccca aaggccccca tccaagtata ggtctctaca tcgtaggtga caaagagacg    7860
ctcggtgcga ggatgcgagc cgatcgggaa gaactggatc tcccgccacc aattggagga    7920
gtggctattg atgtggtgaa agtagaagtc cctgcgacgg gccgaacact cgtgctggct    7980
tttgtaaaaa cgtgcgcagt actggcagcg gtgcacgggc tgtacatcct gcacgaggtt    8040
gacctgacga ccgcgcacaa ggaagcagag tgggaatttg agcccctcgc ctggcgggtt    8100
tggctggtgg tcttctactt cggctgcttg tccttgaccg tctggctgct cgaggggagt    8160
tacggtggat cggaccacca cgccgcgcga gcccaaagtc cagatgtccg cgcgcggcgg    8220
tcggagcttg atgacaacat cgcgcagatg ggagctgtcc atggtctgga gctcccgcgg    8280
cgtcaggtca ggcgggagct cctgcaggtt tacctcgcat agacgggtca gggcgcgggc    8340
tagatccagg tgatacctaa tttccagggg ctggttggtg gcggcgtcga tggcttgcaa    8400
gaggccgcat ccccgcggcg cgactacggt accgcgcggc gggcggtggg ccgcgggggt    8460
gtccttggat gatgcatcta aaagcggtga cgcgggcgag cccccggagg tagggggggc    8520
tccggacccg ccgggagagg gggcaggggc acgtcggcgc cgcgcgcggg caggagctgg    8580
tgctgcgcgc gtaggttgct ggcgaacgcg acgacgcggc ggttgatctc ctgaatctgg    8640
cgcctctgcg tgaagacgac gggcccggtg agcttgagcc tgaaagagag ttcgacagaa    8700
tcaatttcgg tgtcgttgac ggcggcctgg cgcaaaatct cctgcacgtc tcctgagttg    8760
tcttgatagg cgatctcggc catgaactgc tcgatctctt cctcctggag atctccgcgt    8820
ccggctcgct ccacggtggc ggcgaggtcg ttggaaatgc gggccatgag ctgcgagaag    8880
```

-continued

```
gcgttgaggc ctccctcgtt ccagacgcgg ctgtagacca cgccccccttc ggcatcgcgg   8940
gcgcgcatga ccacctgcgc gagattgagc tccacgtgcc gggcgaagac ggcgtagttt   9000
cgcaggcgct gaaagaggta gttgagggtg gtggcggtgt gttctgccac gaagaagtac   9060
ataacccagc gtcgcaacgt ggattcgttg atatccccca aggcctcaag gcgctccatg   9120
gcctcgtaga agtccacggc gaagttgaaa aactgggagt tgcgcgccga cacggttaac   9180
tcctcctcca gaagacggat gagctcggcg acagtgtcgc gcacctcgcg ctcaaaggct   9240
acaggggcct cttcttcttc ttcaatctcc tcttccataa gggcctcccc ttcttcttct   9300
tctggcggcg gtgggggagg ggggacacgg cggcgacgac ggcgcaccgg gaggcggtcg   9360
acaaagcgct cgatcatctc cccgcggcga cggcgcatgg tctcggtgac ggcgcggccg   9420
ttctcgcggg ggcgcagttg gaagacgccg cccgtcatgt cccggttatg ggttggcggg   9480
gggctgccat gcggcaggga tacggcgcta acgatgcatc tcaacaattg ttgtgtaggt   9540
actccgccgc cgagggacct gagcgagtcc gcatcgaccg gatcggaaaa cctctcgaga   9600
aaggcgtcta accagtcaca gtcgcaaggt aggctgagca ccgtggcggg cggcagcggg   9660
cggcggtcgg ggttgtttct ggcggaggtg ctgctgatga tgtaattaaa gtaggcggtc   9720
ttgagacggc ggatggtcga cagaagcacc atgtccttgg gtccggcctg ctgaatgcgc   9780
aggcggtcgg ccatgcccca ggcttcgttt tgacatcggc gcaggtcttt gtagtagtct   9840
tgcatgagcc tttctaccgg cacttcttct tctccttcct cttgtcctgc atctcttgca   9900
tctatcgctg cggcggcggc ggagtttggc cgtaggtggc gccctcttcc tcccatgcgt   9960
gtgaccccga agcccctcat cggctgaagc agggctaggt cggcgacaac gcgctcggct  10020
aatatggcct gctgcacctg cgtgagggta gactggaagt catccatgtc cacaaagcgg  10080
tggtatgcgc ccgtgttgat ggtgtaagtg cagttggcca taacggacca gttaacggtc  10140
tggtgacccg gctgcgagag ctcggtgtac ctgagacgcg agtaagccct cgagtcaaat  10200
acgtagtcgt tgcaagtccg caccaggtac tggtatccca ccaaaaagtg cggcggcggc  10260
tggcggtaga ggggccagcg tagggtggcc ggggctccgg gggcgagatc ttccaacata  10320
aggcgatgat atccgtagat gtacctggac atccaggtga tgccggcggc ggtggtggag  10380
gcgcgcggaa agtcgcggac gcggttccag atgttgcgca gcggcaaaaa gtgctccatg  10440
gtcgggacgc tctggccggt caggcgcgcg caatcgttga cgctctagcg tgcaaaagga  10500
gagcctgtaa gcgggcactc ttccgtggtc tggtggataa attcgcaagg gtatcatggc  10560
ggacgaccgg ggttcgagcc ccgtatccgg ccgtccgccg tgatccatgc ggttaccgcc  10620
cgcgtgtcga acccaggtgt gcgacgtcag acaacggggg agtgctcctt ttggcttcct  10680
tccaggcgcg gcggctgctg cgctagcttt tttggccact ggccgcgcgc agcgtaagcg  10740
gttaggctgg aaagcgaaag cattaagtgg ctcgctccct gtagccggag ggttattttc  10800
caagggttga gtcgcgggac ccccggttcg agtctcggac cggccggact gcggcgaacg  10860
ggggtttgcc tccccgtcat gcaagacccc gcttgcaaat tcctccggaa acagggacga  10920
gcccctttttt tgcttttccc agatgcatcc ggtgctgcgg cagatgcgcc cccctcctca  10980
gcagcggcaa gagcaagagc agcggcagac atgcagggca ccctcccctc ctcctaccgc  11040
gtcaggaggg gcgacatccg cggttgacgc ggcagcagat ggtgattacg aaccccccgcg  11100
gcgccgggcc cggcactacc tggacttgga ggagggcgag ggcctggcgc ggctaggagc  11160
gccctctcct gagcggtacc caagggtgca gctgaagcgt gatacgcgtg aggcgtacgt  11220
gccgcggcag aacctgtttc gcgaccgcga gggagaggag cccgaggaga tgcgggatcg  11280
```

-continued

```
aaagttccac gcagggcgcg agctgcggca tggcctgaat cgcgagcggt tgctgcgcga  11340
ggaggacttt gagcccgacg cgcgaaccgg gattagtccc gcgcgcgcac acgtggcggc  11400
cgccgacctg gtaaccgcat acgagcagac ggtgaaccag gagattaact ttcaaaaaag  11460
ctttaacaac cacgtgcgta cgcttgtggc gcgcgaggag gtggctatag gactgatgca  11520
tctgtgggac tttgtaagcg cgctggagca aaacccaaat agcaagccgc tcatggcgca  11580
gctgttcctt atagtgcagc acagcaggga caacgaggca ttcagggatg cgctgctaaa  11640
catagtagag cccgagggcc gctggctgct cgatttgata aacatcctgc agagcatagt  11700
ggtgcaggag cgcagcttga gcctggctga caaggtggcc gccatcaact attccatgct  11760
tagcctgggc aagttttacg cccgcaagat ataccatacc ccttacgttc ccatagacaa  11820
ggaggtaaag atcgaggggt tctacatgcg catggcgctg aaggtgctta ccttgagcga  11880
cgacctgggc gtttatcgca acgagcgcat ccacaaggcc gtgagcgtga gccggcggcg  11940
cgagctcagc gaccgcgagc tgatgcacag cctgcaaagg gccctggctg gcacgggcag  12000
cggcgataga gaggccgagt cctactttga cgcgggcgct gacctgcgct gggccccaag  12060
ccgacgcgcc ctggaggcag ctggggccgg acctgggctg gcggtggcac ccgcgcgcgc  12120
tggcaacgtc ggcggcgtgg aggaatatga cgaggacgat gagtacgagc cagaggacgg  12180
cgagtactaa gcggtgatgt ttctgatcag atgatgcaag acgcaacgga cccggcggtg  12240
cgggcggcgc tgcagagcca gccgtccggc cttaactcca cggacgactg gcgccaggtc  12300
atggaccgca tcatgtcgct gactgcgcgc aatcctgacg cgttccggca gcagccgcag  12360
gccaaccggc tctccgcaat tctggaagcg gtggtcccgg cgcgcgcaaa ccccacgcac  12420
gagaaggtgc tggcgatcgt aaacgcgctg gccgaaaaca gggccatccg gcccgacgag  12480
gccggcctgg tctacgacgc gctgcttcag cgcgtggctc gttacaacag cggcaacgtg  12540
cagaccaacc tggaccggct ggtgggggat gtgcgcgagg ccgtggcgca gcgtgagcgc  12600
gcgcagcagc agggcaacct gggctccatg gttgcactaa acgccttcct gagtacacag  12660
cccgccaacg tgccgcgggg acaggaggac tacaccaact ttgtgagcgc actgcggcta  12720
atggtgactg agacaccgca aagtgaggtg taccagtctg ggccagacta tttttttccag  12780
accagtagac aaggcctgca gaccgtaaac ctgagccagg ctttcaaaaa cttgcagggg  12840
ctgtgggggg tgcgggctcc cacaggcgac cgcgcgaccg tgtctagctt gctgacgccc  12900
aactcgcgcc tgttgctgct gctaatagcg cccttcacgg acagtggcag cgtgtcccgg  12960
gacacatacc taggtcactt gctgacactg taccgcgagg ccataggtca ggcgcatgtg  13020
gacgagcata ctttccagga gattacaagt gtcagccgcg cgctggggca ggaggacacg  13080
ggcagcctgg aggcaaccct aaactacctg ctgaccaacc ggcggcagaa gatcccctcg  13140
ttgcacagtt taaacagcga ggaggagcgc attttgcgct acgtgcagca gagcgtgagc  13200
cttaacctga tgcgcgacgg ggtaacgccc agcgtggcgc tggacatgac cgcgcgcaac  13260
atggaaccgg gcatgtatgc ctcaaaccgg ccgtttatca accgcctaat ggactacttg  13320
catcgcgcgg ccgccgtgaa ccccgagtat ttcaccaatg ccatcttgaa cccgcactgg  13380
ctaccgcccc ctggtttcta caccggggga ttcgaggtgc ccgagggtaa cgatggattc  13440
ctctgggacg acatagacga cagcgtgttt tccccgcaac cgcagaccct gctagagttg  13500
caacagcgcg agcaggcaga ggcggcgctg cgaaaggaaa gcttccgcag gccaagcagc  13560
ttgtccgatc taggcgctgc ggccccgcgg tcagatgcta gtagcccatt tccaagcttg  13620
```

-continued

```
atagggtctc ttaccagcac tcgcaccacc cgcccgcgcc tgctgggcga ggaggagtac  13680
ctaaacaact cgctgctgca gccgcagcgc gaaaaaaacc tgcctccggc atttcccaac  13740
aacgggatag agagcctagt ggacaagatg agtagatgga agacgtacgc gcaggagcac  13800
agggacgtgc caggcccgcg cccgcccacc cgtcgtcaaa ggcacgaccg tcagcggggt  13860
ctggtgtggg aggacgatga ctcggcagac gacagcagcg tcctggattt gggagggagt  13920
ggcaacccgt ttgcgcacct tcgccccagg ctggggagaa tgttttaaaa aaaaaaaagc  13980
atgatgcaaa ataaaaaact caccaaggcc atggcaccga gcgttggttt tcttgtattc  14040
cccttagtat gcggcgcgcg gcgatgtatg aggaaggtcc tcctccctcc tacgagagtg  14100
tggtgagcgc ggcgccagtg gcggcggcgc tgggttctcc cttcgatgct cccctggacc  14160
cgccgtttgt gcctccgcgg tacctgcggc ctaccggggg gagaaacagc atccgttact  14220
ctgagttggc acccctattc gacaccaccc gtgtgtacct ggtggacaac aagtcaacgg  14280
atgtggcatc cctgaactac cagaacgacc acagcaactt tctgaccacg gtcattcaaa  14340
acaatgacta cagcccgggg gaggcaagca cacagaccat caatcttgac gaccggtcgc  14400
actggggcgg cgacctgaaa accatcctgc ataccaacat gccaaatgtg aacgagttca  14460
tgtttaccaa taagtttaag gcgcgggtga tggtgtcgcg cttgcctact aaggacaatc  14520
aggtggagct gaaatacgag tgggtggagt tcacgctgcc cgagggcaac tactccgaga  14580
ccatgaccat agaccttatg aacaacgcga tcgtggagca ctacttgaaa gtgggcagac  14640
agaacggggt tctggaaagc gacatcgggg taaagtttga cacccgcaac ttcagactgg  14700
ggtttgaccc cgtcactggt cttgtcatgc ctggggtata tacaaacgaa gccttccatc  14760
cagacatcat tttgctgcca ggatgcgggg tggacttcac ccacagccgc ctgagcaact  14820
tgttgggcat ccgcaagcgg caacccttcc aggagggctt taggatcacc tacgatgatc  14880
tggagggtgg taacattccc gcactgttgg atgtggacgc ctaccaggcg agcttgaaag  14940
atgacaccga acagggcggg ggtggcgcag gcggcagcaa cagcagtggc agcggcgcgg  15000
aagagaactc caacgcggca gccgcggcaa tgcagccggt ggaggacatg aacgatcatg  15060
ccattcgcgg cgacaccttt gccacacggg ctgaggagaa gcgcgctgag gccgaagcag  15120
cggccgaagc tgccgccccc gctgcgcaac ccgaggtcga gaagcctcag aagaaaccgg  15180
tgatcaaacc cctgacagag gacagcaaga aacgcagtta caacctaata agcaatgaca  15240
gcaccttcac ccagtaccgc agctggtacc ttgcatacaa ctacggcgac cctcagaccg  15300
gaatccgctc atggaccctg ctttgcactc ctgacgtaac ctgcggctcg gagcaggtct  15360
actggtcgtt gccagacatg atgcaagacc ccgtgacctt ccgctccacg cgccagatca  15420
gcaactttcc ggtggtgggc gccgagctgt tgcccgtgca ctccaagagc ttctacaacg  15480
accaggccgt ctactcccaa ctcatccgcc agtttacctc tctgacccac gtgttcaatc  15540
gctttcccga gaaccagatt ttggcgcgcc cgccagcccc caccatcacc accgtcagtg  15600
aaaacgttcc tgctctcaca gatcacggga cgctaccgct gcgcaacagc atcggaggag  15660
tccagcgagt gaccattact gacgccagac gccgcacctg cccctacgtt tacaaggccc  15720
tgggcatagt ctcgccgcgc gtcctatcga gccgcacttt ttgagcaagc atgtccatcc  15780
ttatatcgcc cagcaataac acaggctggg gcctgcgctt cccaagcaag atgtttggcg  15840
gggccaagaa gcgctccgac caacacccag tgcgcgtgcg cgggcactac cgcgcgccct  15900
ggggcgcgca caaacgcggc cgcactgggc gcaccaccgt cgatgacgcc atcgacgcgg  15960
tggtggagga ggcgcgcaac tacacgccca cgccgccacc agtgtccaca gtggacgcgg  16020
```

-continued ccattcagac cgtggtgcgc ggagcccggc gctatgctaa aatgaagaga cggcggaggc 16080
gcgtagcacg tcgccaccgc cgccgacccg gcactgccgc ccaacgcgcg gcggcggccc 16140
tgcttaaccg cgcacgtcgc accggccgac gggcggccat gcgggccgct cgaaggctgg 16200
ccgcgggtat tgtcactgtg ccccccaggt ccaggcgacg agcggccgcc gcagcagccg 16260
cggccattag tgctatgact cagggtcgca ggggcaacgt gtattgggtg cgcgactcgg 16320
ttagcggcct gcgcgtgccc gtgcgcaccc gccccccgcg caactagatt gcaagaaaaa 16380
actacttaga ctcgtactgt tgtatgtatc cagcggcggc ggcgcgcaac gaagctatgt 16440
ccaagcgcaa aatcaaagaa gagatgctcc aggtcatcgc gccggagatc tatggccccc 16500
cgaagaagga agagcaggat tacaagcccc gaaagctaaa gcgggtcaaa aagaaaaaga 16560
aagatgatga tgatgaactt gacgacgagg tggaactgct gcacgctacc gcgcccaggc 16620
gacgggtaca gtggaaaggt cgacgcgtaa aacgtgtttt gcgacccggc accaccgtag 16680
tctttacgcc cggtgagcgc tccacccgca cctacaagcg cgtgtatgat gaggtgtacg 16740
gcgacgagga cctgcttgag caggccaacg agcgcctcgg ggagtttgcc tacggaaagc 16800
ggcataagga catgctggcg ttgccgctgg acgagggcaa cccaacacct agcctaaagc 16860
ccgtaacact gcagcaggtg ctgcccgcgc ttgcaccgtc cgaagaaaag cgcggcctaa 16920
agcgcgagtc tggtgacttg gcacccaccg tgcagctgat ggtacccaag cgccagcgac 16980
tggaagatgt cttggaaaaa atgaccgtgg aacctgggct ggagcccgag gtccgcgtgc 17040
ggccaatcaa gcaggtggcg ccgggactgg gcgtgcagac cgtggacgtt cagataccca 17100
ctaccagtag caccagtatt gccaccgcca cagagggcat ggagacacaa acgtccccgg 17160
ttgcctcagc ggtggcggat gccgcggtgc aggcggtcgc tgcggccgcg tccaagacct 17220
ctacggaggt gcaaacggac ccgtggatgt ttcgcgtttc agccccccgg cgcccgcgcg 17280
gttcgaggaa gtacggcgcc gccagcgcgc tactgcccga atatgcccta catccttcca 17340
ttgcgcctac ccccggctat cgtggctaca cctaccgccc cagaagacga gcaactaccc 17400
gacgccgaac caccactgga acccgccgcc gccgtcgccg tcgccagccc gtgctggccc 17460
cgatttccgt gcgcagggtg gctcgcgaag gaggcaggac cctggtgctg ccaacagcgc 17520
gctaccaccc cagcatcgtt taaaagccgg tctttgtggt tcttgcagat atggccctca 17580
cctgccgcct ccgtttcccg gtgccgggat tccgaggaag aatgcaccgt aggaggggca 17640
tggccggcca cggcctgacg ggcggcatgc gtcgtgcgca ccaccggcgg cggcgcgcgt 17700
cgcaccgtcg catgcgcggc ggtatcctgc ccctccttat tccactgatc gccgcggcga 17760
ttggcgccgt gcccggaatt gcatccgtgg ccttgcaggc gcagagacac tgattaaaaa 17820
caagttgcat gtggaaaaat caaaataaaa agtctggact ctcacgctcg cttggtcctg 17880
taactatttt gtagaatgga agacatcaac tttgcgtctc tggccccgcg acacggctcg 17940
cgcccgttca tgggaaactg gcaagatatc ggcaccagca atatgagcgg tggcgccttc 18000
agctggggct cgctgtggag cggcattaaa aatttcggtt ccaccgttaa gaactatggc 18060
agcaaggcct ggaacagcag cacaggccag atgctgaggg ataagttgaa agagcaaaat 18120
ttccaacaaa aggtggtaga tggcctggcc tctggcatta gcggggtggt ggacctggcc 18180
aaccaggcag tgcaaaataa gattaacagt aagcttgatc cccgccctcc cgtagaggag 18240
cctccaccgg ccgtggagac agtgtctcca gaggggcgtg gcgaaaagcg tccgcgcccc 18300
gacagggaag aaactctggt gacgcaaata gacgagcctc cctcgtacga ggaggcacta 18360

-continued

```
aagcaaggcc tgcccaccac ccgtcccatc gcgcccatgg ctaccggagt gctgggccag  18420
cacacacccg taacgctgga cctgcctccc cccgccgaca cccagcagaa acctgtgctg  18480
ccaggcccga ccgccgttgt tgtaacccgt cctagccgcg cgtccctgcg ccgcgccgcc  18540
agcggtccgc gatcgttgcg gcccgtagcc agtggcaact ggcaaagcac actgaacagc  18600
atcgtgggtc tgggggtgca atccctgaag cgccgacgat gcttctgaat agctaacgtg  18660
tcgtatgtgt gtcatgtatg cgtccatgtc gccgccagag gagctgctga gccgccgcgc  18720
gcccgctttc caagatggct accccttcga tgatgccgca gtggtcttac atgcacatct  18780
cgggccagga cgcctcggag tacctgagcc ccgggctggt gcagtttgcc cgcgccaccg  18840
agacgtactt cagcctgaat aacaagttta gaaaccccac ggtggcgcct acgcacgacg  18900
tgaccacaga ccggtcccag cgtttgacgc tgcggttcat ccctgtggac cgtgaggata  18960
ctgcgtactc gtacaaggcg cggttcaccc tagctgtggg tgataaccgt gtgctggaca  19020
tggcttccac gtactttgac atccgcggcg tgctggacag gggccctact tttaagccct  19080
actctggcac tgcctacaac gccctggctc ccaagggtgc cccaaatcct tgcgaatggg  19140
atgaagctgc tactgctctt gaaataaacc tagaagaaga ggacgatgac aacgaagacg  19200
aagtagacga gcaagctgag cagcaaaaaa ctcacgtatt tgggcaggcg ccttattctg  19260
gtataaatat tacaaaggag ggtattcaaa taggtgtcga aggtcaaaca cctaaatatg  19320
ccgataaaac atttcaacct gaacctcaaa taggagaatc tcagtggtac gaaactgaaa  19380
ttaatcatgc agctgggaga gtccttaaaa agactacccc aatgaaacca tgttacggtt  19440
catatgcaaa acccacaaat gaaaatggag ggcaaggcat tcttgtaaag caacaaaatg  19500
gaaagctaga aagtcaagtg gaaatgcaat tttctcaac tactgaggcg accgcaggca  19560
atggtgataa cttgactcct aaagtggtat tgtacagtga agatgtagat atagaaaccc  19620
cagacactca tatttcttac atgcccacta ttaaggaagg taactcacga gaactaatgg  19680
gccaacaatc tatgcccaac aggcctaatt acattgcttt tagggacaat tttattggtc  19740
taatgtatta caacagcacg ggtaatatgg gtgttctggc gggccaagca tcgcagttga  19800
atgctgttgt agatttgcaa gacagaaaca cagagctttc ataccagctt ttgcttgatt  19860
ccattggtga tagaaccagg tacttttcta tgtggaatca ggctgttgac agctatgatc  19920
cagatgttag aattattgaa aatcatggaa ctgaagatga acttccaaat tactgctttc  19980
cactgggagg tgtgattaat acagagactc ttaccaaggt aaaacctaaa acaggtcagg  20040
aaaatggatg ggaaaaagat gctacagaat tttcagataa aaatgaaata agagttggaa  20100
ataattttgc catggaaatc aatctaaatg ccaacctgtg gagaaatttc ctgtactcca  20160
acatagcgct gtatttgccc gacaagctaa agtacagtcc ttccaacgta aaaatttctg  20220
ataacccaaa cacctacgac tacatgaaca agcgagtggt ggctcccggg ttagtggact  20280
gctacattaa ccttggagca cgctggtccc ttgactatat ggacaacgtc aacccattta  20340
accaccaccg caatgctggc ctgcgctacc gctcaatgtt gctgggcaat ggtcgctatg  20400
tgcccttcca catccaggtg cctcagaagt tctttgccat taaaaacctc cttctcctgc  20460
cgggctcata cacctacgag tggaacttca ggaaggatgt taacatggtt ctgcagagct  20520
ccctaggaaa tgacctaagg gttgacggag ccagcattaa gtttgatagc atttgccttt  20580
acgccacctt cttccccatg gcccacaaca ccgcctccac gcttgaggcc atgcttagaa  20640
acgacaccaa cgaccagtcc tttaacgact atctctccgc cgccaacatg ctctacccta  20700
tacccgccaa cgctaccaac gtgcccatat ccatcccctc ccgcaactgg gcggctttcc  20760
```

-continued gcggctgggc cttcacgcgc cttaagacta aggaaacccc atcactgggc tcgggctacg 20820
acccttatta cacctactct ggctctatac cctacctaga tggaaccttt tacctcaacc 20880
acacctttaa gaaggtggcc attacctttg actcttctgt cagctggcct ggcaatgacc 20940
gcctgcttac ccccaacgag tttgaaatta agcgctcagt tgacggggag ggttacaacg 21000
ttgcccagtg taacatgacc aaagactggt tcctggtaca aatgctagct aactacaaca 21060
ttggctacca gggcttctat atcccagaga gctacaagga ccgcatgtac tccttcttta 21120
gaaacttcca gcccatgagc cgtcaggtgg tggatgatac taaatacaag gactaccaac 21180
aggtgggcat cctacaccaa cacaacaact ctggatttgt tggctacctt gcccccacca 21240
tgcgcgaagg acaggcctac cctgctaact tcccctatcc gcttataggc aagaccgcag 21300
ttgacagcat tacccagaaa aagtttcttt gcgatcgcac cctttggcgc atcccattct 21360
ccagtaactt tatgtccatg ggcgcactca cagacctggg ccaaaacctt ctctacgcca 21420
actccgccca cgcgctagac atgacttttg aggtggatcc catggacgag cccacccttc 21480
tttatgtttt gtttgaagtc tttgacgtgg tccgtgtgca ccggccgcac cgcggcgtca 21540
tcgaaaccgt gtacctgcgc acgcccttct cggccggcaa cgccacaaca taaagaagca 21600
agcaacatca acaacagctg ccgccatggg ctccagtgag caggaactga aagccattgt 21660
caaagatctt ggttgtgggc catatttttt gggcacctat gacaagcgct ttccaggctt 21720
tgtttctcca cacaagctcg cctgcgccat agtcaatacg gccggtcgcg agactggggg 21780
cgtacactgg atggcctttg cctggaaccc gcactcaaaa acatgctacc tctttgagcc 21840
ctttggcttt tctgaccagc gactcaagca ggtttaccag tttgagtacg agtcactcct 21900
gcgccgtagc gccattgctt cttcccccga ccgctgtata acgctggaaa agtccaccca 21960
aagcgtacag gggcccaact cggccgcctg tggactattc tgctgcatgt ttctccacgc 22020
ctttgccaac tggccccaaa ctcccatgga tcacaacccc accatgaacc ttattaccgg 22080
ggtacccaac tccatgctca acagtcccca ggtacagccc accctgcgtc gcaaccagga 22140
acagctctac agcttcctgg agcgccactc gccctacttc cgcagccaca gtgcgcagat 22200
taggagcgcc acttcttttt gtcacttgaa aaacatgtaa aaataatgta ctagagacac 22260
tttcaataaa ggcaaatgct tttatttgta cactctcggg tgattattta cccccaccct 22320
tgccgtctgc gccgtttaaa aatcaaaggg gttctgccgc gcatcgctat gcgccactgg 22380
cagggacacg ttgcgatact ggtgtttagt gctccactta aactcaggca caaccatccg 22440
cggcagctcg gtgaagtttt cactccacag gctgcgcacc atcaccaacg cgtttagcag 22500
gtcgggcgcc gatatcttga agtcgcagtt ggggcctccg ccctgcgcgc gcgagttgcg 22560
atacacaggg ttgcagcact ggaacactat cagcgccggg tggtgcacgc tggccagcac 22620
gctcttgtcg gagatcagat ccgcgtccag gtcctccgcg ttgctcaggg cgaacggagt 22680
caactttggt agctgccttc ccaaaaaggg cgcgtgccca ggctttgagt tgcactcgca 22740
ccgtagtggc atcaaaaggt gaccgtgccc ggtctgggcg ttaggataca gcgcctgcat 22800
aaaagccttg atctgcttaa aagccacctg agcctttgcg ccttcagaga agaacatgcc 22860
gcaagacttg ccggaaaact gattggccgg acaggccgcg tcgtgcacgc agcaccttgc 22920
gtcggtgttg gagatctgca ccacatttcg gccccaccgg ttcttcacga tcttggcctt 22980
gctagactgc tccttcagcg cgcgctgccc gttttcgctc gtcacatcca tttcaatcac 23040
gtgctcctta tttatcataa tgcttccgtg tagacactta agctcgcctt cgatctcagc 23100

-continued gcagcggtgc agccacaacg cgcagcccgt gggctcgtga tgcttgtagg tcacctctgc 23160
aaacgactgc aggtacgcct gcaggaatcg ccccatcatc gtcacaaagg tcttgttgct 23220
ggtgaaggtc agctgcaacc cgcggtgctc ctcgttcagc caggtcttgc atacggccgc 23280
cagagcttcc acttggtcag gcagtagttt gaagttcgcc tttagatcgt tatccacgtg 23340
gtacttgtcc atcagcgcgc gcgcagcctc catgcccttc tcccacgcag acacgatcgg 23400
cacactcagc gggttcatca ccgtaatttc actttccgct tcgctgggct cttcctcttc 23460
ctcttgcgtc cgcataccac gcgccactgg gtcgtcttca ttcagccgcc gcactgtgcg 23520
cttacctcct ttgccatgct tgattagcac cggtgggttg ctgaaaccca ccatttgtag 23580
cgccacatct tctctttctt cctcgctgtc cacgattacc tctggtgatg gcgggcgctc 23640
gggcttggga gaagggcgct tctttttctt cttgggcgca atggccaaat ccgccgccga 23700
ggtcgatggc cgcgggctgg gtgtgcgcgg caccagcgcg tcttgtgatg agtcttcctc 23760
gtcctcggac tcgatacgcc gcctcatccg cttttttggg ggcgcccggg gaggcggcgg 23820
cgacggggac ggggacgaca cgtcctccat ggttggggga cgtcgcgccg caccgcgtcc 23880
gcgctcgggg gtggtttcgc gctgctcctc ttcccgactg gccatttcct tctcctatag 23940
gcagaaaaag atcatggagt cagtcgagaa gaaggacagc ctaaccgccc cctctgagtt 24000
cgccaccacc gcctccaccg atgccgccaa cgcgcctacc accttccccg tcgaggcacc 24060
cccgcttgag gaggaggaag tgattatcga gcaggaccca ggttttgtaa gcgaagacga 24120
cgaggaccgc tcagtaccaa cagaggataa aaagcaagac caggacaacg cagaggcaaa 24180
cgaggaacaa gtcgggcggg gggacgaaag gcatggcgac tacctagatg tgggagacga 24240
cgtgctgttg aagcatctgc agcgccagtg cgccattatc tgcgacgcgt tgcaagagcg 24300
cagcgatgtg cccctcgcca tagcggatgt cagccttgcc tacgaacgcc acctattctc 24360
accgcgcgta ccccccaaac gccaagaaaa cggcacatgc gagcccaacc cgcgcctcaa 24420
cttctacccc gtatttgccg tgccagaggt gcttgccacc tatcacatct tttccaaaa 24480 ctgcaagata cccctatcct gccgtgccaa ccgcagccga gcggacaagc agctggcctt 24540
gcggcagggc gctgtcatac ctgatatcgc ctcgctcaac gaagtgccaa aaatctttga 24600
gggtcttgga cgcgacgaga agcgcgcggc aaacgctctg caacaggaaa acagcgaaaa 24660
tgaaagtcac tctggagtgt tggtggaact cgagggtgac aacgcgcgcc tagccgtact 24720
aaaacgcagc atcgaggtca cccactttgc ctacccggca cttaacctac cccccaaggt 24780
catgagcaca gtcatgagtg agctgatcgt gcgccgtgcg cagcccctgg agagggatgc 24840
aaatttgcaa gaacaaacag aggagggcct acccgcagtt ggcgacgagc agctagcgcg 24900
ctggcttcaa acgcgcgagc ctgccgactt ggaggagcga cgcaaactaa tgatggccgc 24960
agtgctcgtt accgtggagc ttgagtgcat gcagcggttc tttgctgacc cggagatgca 25020
gcgcaagcta gaggaaacat tgcactacac ctttcgacag ggctacgtac gccaggcctg 25080
caagatctcc aacgtggagc tctgcaacct ggtctcctac cttggaattt tgcacgaaaa 25140
ccgccttggg caaaacgtgc ttcattccac gctcaagggc gaggcgcgcc gcgactacgt 25200
ccgcgactgc gtttacttat ttctatgcta cacctggcag acggccatgg gcgtttggca 25260
gcagtgcttg gaggagtgca acctcaagga gctgcagaaa ctgctaaagc aaaacttgaa 25320
ggacctatgg acggccttca acgagcgctc cgtggccgcg cacctggcgg acatcatttt 25380
ccccgaacgc ctgcttaaaa ccctgcaaca gggtctgcca gacttcacca gtcaaagcat 25440
gttgcagaac tttaggaact ttatcctaga gcgctcagga atcttgcccg ccacctgctg 25500

-continued tgcacttcct agcgactttg tgcccattaa gtaccgcgaa tgccctccgc cgctttgggg 25560
ccactgctac cttctgcagc tagccaacta ccttgcctac cactctgaca taatggaaga 25620
cgtgagcggt gacggtctac tggagtgtca ctgtcgctgc aacctatgca ccccgcaccg 25680
ctccctggtt tgcaattcgc agctgcttaa cgaaagtcaa attatcggta cctttgagct 25740
gcagggtccc tcgcctgacg aaaagtccgc ggctccgggg ttgaaactca ctccggggct 25800
gtggacgtcg gcttaccttc gcaaatttgt acctgaggac taccacgccc acgagattag 25860
gttctacgaa gaccaatccc gcccgccaaa tgcggagctt accgcctgcg tcattaccca 25920
gggccacatt cttggccaat tgcaagccat caacaaagcc cgccaagagt ttctgctacg 25980
aaagggacgg ggggtttact tggacccccca gtccggcgag gagctcaacc caatcccccc 26040
gccgccgcag ccctatcagc agcagccgcg ggcccttgct tcccaggatg gcacccaaaa 26100
agaagctgca gctgccgccg ccacccacgg acgaggagga atactgggac agtcaggcag 26160
aggaggtttt ggacgaggag gaggaggaca tgatggaaga ctgggagagc ctagacgagg 26220
aagcttccga ggtcgaagag gtgtcagacg aaacaccgtc accctcggtc gcattcccct 26280
cgccggcgcc ccagaaatcg gcaaccggtt ccagcatggc tacaacctcc gctcctcagg 26340
cgccgccggc actgcccgtt cgccgaccca accgtagatg ggacaccact ggaaccaggg 26400
ccggtaagtc caagcagccg ccgccgttag cccaagagca acaacagcgc caaggctacc 26460
gctcatggcg cgggcacaag aacgccatag ttgcttgctt gcaagactgt gggggcaaca 26520
tctccttcgc ccgccgcttt cttctctacc atcacggcgt ggccttcccc cgtaacatcc 26580
tgcattacta ccgtcatctc tacagcccat actgcaccgg cggcagcggc agcggcagca 26640
acagcagcgg ccacacagaa gcaaaggcga ccggatagca agactctgac aaagcccaag 26700
aaatccacag cggcggcagc agcaggagga ggagcgctgc gtctggcgcc caacgaaccc 26760
gtatcgaccc gcgagcttag aaacaggatt tttcccactc tgtatgctat atttcaacag 26820
agcaggggcc aagaacaaga gctgaaaata aaaaacaggt ctctgcgatc cctcacccgc 26880
agctgcctgt atcacaaaag cgaagatcag cttcggcgca cgctggaaga cgcggaggct 26940
ctcttcagta aatactgcgc gctgactctt aaggactagt ttcgcgccct ttctcaaatt 27000
taagcgcgaa aactacgtca tctccagcgg ccacacccgg cgccagcacc tgtcgtcagc 27060
gccattatga gcaaggaaat tcccacgccc tacatgtgga gttaccagcc acaaatggga 27120
cttgcggctg gagctgccca agactactca acccgaataa actacatgag cgcgggaccc 27180
cacatgatat cccgggtcaa cggaatccgc gcccaccgaa accgaattct cttggaacag 27240
gcggctatta ccaccacacc tcgtaataac cttaatcccc gtagttggcc cgctgccctg 27300
gtgtaccagg aaagtcccgc tcccaccact gtggtacttc ccagagacgc ccaggccgaa 27360
gttcagatga ctaactcagg ggcgcagctt gcgggcggct ttcgtcacag ggtgcggtcg 27420
cccgggcagg gtataactca cctgacaatc agagggcgag gtattcagct caacgacgag 27480
tcggtgagct cctcgcttgg tctccgtccg gacgggacat ttcagatcgg cggcgccggc 27540
cgtccttcat tcacgcctcg tcaggcaatc ctaactctgc agacctcgtc ctctgagccg 27600
cgctctggag gcattggaac tctgcaattt attgaggagt ttgtgccatc ggtctacttt 27660
aacccccttct cgggacctcc cggccactat ccggatcaat ttattcctaa ctttgacgcg 27720
gtaaaggact cggcggacgg ctacgactga atgttaagtg gagaggcaga gcaactgcgc 27780
ctgaaacacc tggtccactg tcgccgccac aagtgctttg cccgcgactc cggtgagttt 27840

-continued tgctactttg aattgcccga ggatcatatc gagggcccgg cgcacggcgt ccggcttacc 27900
gcccagggag agcttgcccg tagcctgatt cgggagttta cccagcgccc cctgctagtt 27960
gagcgggaca ggggaccctg tgttctcact gtgatttgca actgtcctaa ccttggatta 28020
catcaagatc tttgttgcca tctctgtgct gagtataata aatacagaaa ttaaaatata 28080
ctggggctcc tatcgccatc ctgtaaacgc caccgtcttc acccgcccaa gcaaaccaag 28140
gcgaacctta cctggtactt ttaacatctc tccctctgtg atttacaaca gtttcaaccc 28200
agacggagtg agtctacgag agaacctctc cgagctcagc tactccatca gaaaaaacac 28260
caccctcctt acctgccggg aacgtacgag tgcgtcaccg gccgctgcac cacacctacc 28320
gcctgaccgt aaaccagact ttttccggac agacctcaat aactctgttt accagaacag 28380
gaggtgagct tagaaaaccc ttagggtatt aggccaaagg cgcagctact gtggggttta 28440
tgaacaattc aagcaactct acgggctatt ctaattcagg tttctctaga agtcaggctt 28500
cctggatgtc agcatctgac tttggccagc acctgtcccg cggatttgtt ccagtccaac 28560
tacagcgacc caccctaaca gagatgacca acacaaccaa cgcggccgcc gctaccggac 28620
ttacatctac cacaaataca ccccaagttt ctgcctttgt caataactgg gataacttgg 28680
gcatgtggtg gttctccata gcgcttatgt ttgtatgcct tattattatg tggctcatct 28740
gctgcctaaa gcgcaaacgc gcccgaccac ccatctatag tcccatcatt gtgctacacc 28800
caaacaatga tggaatccat agattggacg gactgaaaca catgttcttt tctcttacag 28860
tatgattaaa tgagatctag aaatggacgg aattattaca gagcagcgcc tgctagaaag 28920
acgcagggca gcggccgagc aacagcgcat gaatcaagag ctccaagaca tggttaactt 28980
gcaccagtgc aaaaggggta tcttttgtct ggtaaagcag gccaaagtca cctacgacag 29040
taataccacc ggacaccgcc ttagctacaa gttgccaacc aagcgtcaga aattggtggt 29100
catggtggga gaaaagccca ttaccataac tcagcactcg gtagaaaccg aaggctgcat 29160
tcactcacct tgtcaaggac ctgaggatct ctgcaccctt attaagaccc tgtgcggtct 29220
caaagatctt attcccttta actaataaaa aaaaataata aagcatcact tacttaaaat 29280
cagttagcaa atttctgtcc agtttattca gcagcacctc cttgccctcc tcccagctct 29340
ggtattgcag cttcctcctg gctgcaaact ttctccacaa tctaaatgga atgtcagttt 29400
cctcctgttc ctgtccatcc gcacccacta tcttcatgtt gttgcagatg aagcgcgcaa 29460
gaccgtctga agataccttc aaccccgtgt atccatatga cacggaaacc ggtcctccaa 29520
ctgtgccttt tcttactcct ccctttgtat cccccaatgg gtttcaagag agtccccctg 29580
gggtactctc tttgcgccta tccgaacctc tagttacctc caatggcatg cttgcgctca 29640
aaatgggcaa cggcctctct ctggacgagg ccggcaacct tacctcccaa aatgtaacca 29700
ctgtgagccc acctctcaaa aaaaccaagt caaacataaa cctggaaata tctgcacccc 29760
tcacagttac ctcagaagcc ctaactgtgg ctgccgccgc acctctaatg gtcgcgggca 29820
acacactcac catgcaatca caggccccgc taaccgtgca cgactccaaa cttagcattg 29880
ccacccaagg acccctcaca gtgtcagaag gaaagctagc cctgcaaaca tcaggccccc 29940
tcaccaccac cgatagcagt acccttacta tcactgcctc acccccctcta actactgcca 30000 ctggtagctt gggcattgac ttgaaagagc ccatttatac acaaaatgga aaactaggac 30060
taaagtacgg ggctcctttg catgtaacag acgacctaaa cactttgacc gtagcaactg 30120
gtccaggtgt gactattaat aatacttcct tgcaaactaa agttactgga gccttgggtt 30180
ttgattcaca aggcaatatg caacttaatg tagcaggagg actaaggatt gattctcaaa 30240

-continued

```
acagacgcct tatacttgat gttagttatc cgtttgatgc tcaaaaccaa ctaaatctaa  30300
gactaggaca gggccctctt tttataaact cagcccacaa cttggatatt aactacaaca  30360
aaggccttta cttgtttaca gcttcaaaca attccaaaaa gcttgaggtt aacctaagca  30420
ctgccaaggg gttgatgttt gacgctacag ccatagccat taatgcagga gatgggcttg  30480
aatttggttc acctaatgca ccaaacacaa atcccctcaa aacaaaaatt ggccatggcc  30540
tagaatttga ttcaaacaag gctatggttc ctaaactagg aactggcctt agttttgaca  30600
gcacaggtgc cattacagta ggaaacaaaa ataatgataa gctaactttg tggaccacac  30660
cagctccatc tcctaactgt agactaaatg cagagaaaga tgctaaactc actttggtct  30720
taacaaaatg tggcagtcaa atacttgcta cagtttcagt tttggctgtt aaaggcagtt  30780
tggctccaat atctggaaca gttcaaagtg ctcatcttat tataagattt gacgaaaatg  30840
gagtgctact aaacaattcc ttcctggacc cagaatattg gaactttaga aatggagatc  30900
ttactgaagg cacagcctat acaaacgctg ttggatttat gcctaaccta tcagcttatc  30960
caaaatctca cggtaaaact gccaaaagta acattgtcag tcaagtttac ttaaacggag  31020
acaaaactaa acctgtaaca ctaaccatta cactaaacgg tacacaggaa acaggagaca  31080
caactccaag tgcatactct atgtcatttt catgggactg gtctggccac aactacatta  31140
atgaaatatt tgccacatcc tcttacactt tttcatacat tgcccaagaa taaagaatcg  31200
tttgtgttat gtttcaacgt gtttattttt caattgcaga aaatttcaag tcatttttca  31260
ttcagtagta tagccccacc accacatagc ttatacagat caccgtacct taatcaaact  31320
cacagaaccc tagtattcaa cctgccacct ccctcccaac acacagagta cacagtcctt  31380
tctccccggc tggccttaaa aagcatcata tcatgggtaa cagacatatt cttaggtgtt  31440
atattccaca cggtttcctg tcgagccaaa cgctcatcag tgatattaat aaactccccg  31500
ggcagctcac ttaagttcat gtcgctgtcc agctgctgag ccacaggctg ctgtccaact  31560
tgcggttgct taacgggcgg cgaaggagaa gtccacgcct acatgggggt agagtcataa  31620
tcgtgcatca ggatagggcg gtggtgctgc agcagcgcgc gaataaactg ctgccgccgc  31680
cgctccgtcc tgcaggaata caacatggca gtggtctcct cagcgatgat tcgcaccgcc  31740
cgcagcataa ggcgccttgt cctccgggca cagcagcgca ccctgatctc acttaaatca  31800
gcacagtaac tgcagcacag caccacaata ttgttcaaaa tcccacagtg caaggcgctg  31860
tatccaaagc tcatggcggg gaccacagaa cccacgtggc catcatacca caagcgcagg  31920
tagattaagt ggcgacccct cataaacacg ctggacataa acattacctc ttttggcatg  31980
ttgtaattca ccacctcccg gtaccatata aacctctgat taaacatggc gccatccacc  32040
accatcctaa accagctggc caaaacctgc ccgccggcta tacactgcag ggaaccggga  32100
ctggaacaat gacagtggag agcccaggac tcgtaaccat ggatcatcat gctcgtcatg  32160
atatcaatgt tggcacaaca caggcacacg tgcatacact tcctcaggat tacaagctcc  32220
tcccgcgtta gaaccatatc ccagggaaca acccattcct gaatcagcgt aaatcccaca  32280
ctgcagggaa gacctcgcac gtaactcacg ttgtgcattg tcaaagtgtt acattcgggc  32340
agcagcggat gatcctccag tatggtagcg cgggtttctg tctcaaaagg aggtagacga  32400
tccctactgt acggagtgcg ccgagacaac cgagatcgtg ttggtcgtag tgtcatgcca  32460
aatggaacgc cggacgtagt catatttcct gaagcaaaac caggtgcggg cgtgacaaac  32520
agatctgcgt ctccggtctc gccgcttaga tcgctctgtg tagtagttgt agtatatcca  32580
```

-continued

```
ctctctcaaa gcatccaggc gccccctggc ttcgggttct atgtaaactc cttcatgcgc  32640
cgctgccctg ataacatcca ccaccgcaga ataagccaca cccagccaac ctacacattc  32700
gttctgcgag tcacacacgg gaggagcggg aagagctgga agaaccatgt ttttttttt   32760
attccaaaag attatccaaa acctcaaaat gaagatctat taagtgaacg cgctcccctc  32820
cggtggcgtg gtcaaactct acagccaaag aacagataat ggcatttgta agatgttgca  32880
caatggcttc caaaaggcaa acggccctca cgtccaagtg gacgtaaagg ctaaaccctt  32940
cagggtgaat ctcctctata aacattccag caccttcaac catgcccaaa taattctcat  33000
ctcgccacct tctcaatata tctctaagca aatcccgaat attaagtccg gccattgtaa  33060
aaatctgctc cagagcgccc tccaccttca gcctcaagca gcgaatcatg attgcaaaaa  33120
ttcaggttcc tcacagacct gtataagatt caaaagcgga acattaacaa aaataccgcg  33180
atcccgtagg tcccttcgca gggccagctg aacataatcg tgcaggtctg cacggaccag  33240
cgcggccact tccccgccag gaaccttgac aaaagaaccc acactgatta tgacacgcat  33300
actcggagct atgctaacca gcgtagcccc gatgtaagct ttgttgcatg ggcggcgata  33360
taaaatgcaa ggtgctgctc aaaaaatcag gcaaagcctc gcgcaaaaaa gaaagcacat  33420
cgtagtcatg ctcatgcaga taaaggcagg taagctccgg aaccaccaca gaaaaagaca  33480
ccatttttct ctcaaacatg tctgcgggtt tctgcataaa cacaaaataa aataacaaaa  33540
aaacatttaa acattagaag cctgtcttac aacaggaaaa acaaccctta taagcataag  33600
acggactacg gccatgccgg cgtgaccgta aaaaaactgg tcaccgtgat taaaaagcac  33660
caccgacagc tcctcggtca tgtccggagt cataatgtaa gactcggtaa acacatcagg  33720
ttgattcatc ggtcagtgct aaaaagcgac cgaaatagcc cgggggaata catacccgca  33780
ggcgtagaga caacattaca gcccccatag gaggtataac aaaattaata ggagagaaaa  33840
acacataaac acctgaaaaa ccctcctgcc taggcaaaat agcaccctcc cgctccagaa  33900
caacatacag cgcttcacag cggcagccta acagtcagcc ttaccagtaa aaaagaaaac  33960
ctattaaaaa aacaccactc gacacggcac cagctcaatc agtcacagtg taaaaaaggg  34020
ccaagtgcgt tacactgcag caggtgtgac tcagccatgg cacctctgca gcctgggtac  34080
cctgcttggg gcatggcccc ttatagctgg gcggggcgtg gggctctgt aggagtggca   34140
gcgacctcag tgtttgtctt tgctctgaag agccctccag gtgcttgatc ccaccttttc  34200
ccagcaggaa cactcctgcc tgccttacca cctgtcctgg ctgatggcct gttcctgcct  34260
cctttgcccc ctgcccagac tcccatgttc ctggacttgt ggcttcctcc aaccaggggc  34320
tctcaagcct ccatacctgg tcccacctct ccaggccgtg ggagggaggt tgaggagggt  34380
ggagggcatc tggttggggg cagcctgggt gttcccctcc catcccctcc ctgggcctcc  34440
caggccccct ctactcttga gcaatgctct tgagagcttc ctgcctggct cttaacccag  34500
ggcaagccct ggaagggcag acccaggaca ctctcaccac ctccttacct tttcccctgg  34560
aaaaatcttc tgtatacttc ccattttaag aaaactacaa ttcccaacac atacaagtta  34620
ctccgcccta aaacctacgt cacccgcccc gttcccacgc cccgcgccac gtcacaaact  34680
ccaccccctc attatcatat tggcttcaat ccaaaataag gtatattatt gatgatg     34737
```

<210> SEQ ID NO 16
<211> LENGTH: 36114
<212> TYPE: DNA
<213> ORGANISM: Adenovirus subgroup C

<400> SEQUENCE: 16

-continued

```
catcatcaat aatatacctt attttggatt gaagccaata tgataatgag ggggtggagt     60
ttgtgacgtg gcgcggggcg tgggaacggg gcgggtgacg tagtagtgtg gcggaagtgt    120
gatgttgcaa gtgtggcgga acacatgtaa gcgacggatg tggcaaaagt gacgtttttg    180
gtgtgcgccg gtgtacacag gaagtgacaa ttttcgcgcg gttttaggcg gatgttgtag    240
taaatttggg cgtaaccgag taagatttgg ccattttcgc gggaaaactg aataagagga    300
agtgaaatct gaataatttt gtgttactca tagcgcgtaa tatttgtcta gggccgcggg    360
gactttgacc gtttacgtgg agactcgccc aggtgttttt ctcaggtgtt ttccgcgttc    420
cgggtcaaag ttggcgtttt attattatag tcagctgacg tgtagtgtat ttatacccgg    480
tgagttcctc aagaggccac tcttgagtgc cagcgagtag agttttctcc tccgagccgc    540
tccgacaccg ggactgaaaa tgagacatga ggtactggct gataatcttc cacctcctag    600
ccattttgaa ccacctaccc ttcacgaact gtatgattta gacgtgacgg cccccgaaga    660
tcccaacgag gaggcggttt cgcagatttt tcccgactct gtaatgttgg cggtgcagga    720
agggattgac ttactcactt ttccgccggc gcccggttct ccggagccgc ctcacctttc    780
ccggcagccc gagcagccgg agcagagagc cttgggtccg gtttgccacg aggctggctt    840
tccacccagt gacgacgagg atgaagaggg tgaggagttt gtgttagatt atgtggagca    900
ccccgggcac ggttgcaggt cttgtcatta tcaccggagg aatacggggg acccagatat    960
tatgtgttcg ctttgctata tgaggacctg tggcatgttt gtctacagta agtgaaaatt   1020
atgggcagtg ggtgatagag tggtgggttt ggtgtggtaa tttttttttt aatttttaca   1080
gttttgtggt ttaaagaatt ttgtattgtg atttttttaa aaggtcctgt gtctgaacct   1140
gagcctgagc ccgagccaga accggagcct gcaagaccta cccgccgtcc taaaatggcg   1200
cctgctatcc tgagacgccc gacatcacct gtgtctagag aatgcaatag tagtacggat   1260
agctgtgact ccggtccttc taacacacct cctgagatac acccggtggt cccgctgtgc   1320
cccattaaac cagttgccgt gagagttggt gggcgtcgcc aggctgtgga atgtatcgag   1380
gacttgctta acgagcctgg gcaacctttg gacttgagct gtaaacgccc caggccataa   1440
ggtgtaaacc tgtgattgcg tgtgtggtta acgcctttgt ttgctgaatg agttgatgta   1500
agtttaataa agggtgagat aatgtttaac ttgcatggcg tgttaaatgg ggcggggctt   1560
aaagggtata taatgcgccg tgggctaatc ttggttacat ctgacctcat ggaggcttgg   1620
gagtgtttgg aagatttttc tgctgtgcgt aacttgctgg aacagagctc taacagtacc   1680
tcttggtttt ggaggtttct gtggggctca tcccaggcaa agttagtctg cagaattaag   1740
gaggattaca agtgggaatt tgaagagctt ttgaaatcct gtggtgagct gtttgattct   1800
ttgaatctgg gtcaccaggc gcttttccaa gagaaggtca tcaagacttt ggatttttcc   1860
acaccggggc gcgctgcggc tgctgttgct tttttgagtt ttataaagga taaatggagc   1920
gaagaaaccc atctgagcgg ggggtacctg ctggattttc tggccatgca tctgtggaga   1980
gcggttgtga gacacaagaa tcgcctgcta ctgttgtctt ccgtccgccc ggcgataata   2040
ccgacggagg agcagcagca gcagcaggag gaagccaggc ggcggcggca ggagcagagc   2100
ccatggaacc cgagagccgg cctggaccct cgggaatgaa tgttgtacag gtggctgaac   2160
tgtatccaga actgagacgc attttgacaa ttacagagga tgggcagggg ctaaaggggg   2220
taaagaggga gcgggggggct tgtgaggcta cagaggaggc taggaatcta gcttttagct   2280
taatgaccag acaccgtcct gagtgtatta cttttcaaca gatcaaggat aattgcgcta   2340
```

-continued atgagcttga tctgctggcg cagaagtatt ccatagagca gctgaccact tactggctgc 2400
agccagggga tgattttgag gaggctatta gggtatatgc aaaggtggca cttaggccag 2460
attgcaagta caagatcagc aaacttgtaa atatcaggaa ttgttgctac atttctggga 2520
acggggccga ggtggagata gatacggagg atagggtggc ctttagatgt agcatgataa 2580
atatgtggcc gggggtgctt ggcatggacg gggtggttat tatgaatgta aggtttactg 2640
gccccaattt tagcggtacg gttttcctgg ccaataccaa ccttatccta cacggtgtaa 2700
gcttctatgg gtttaacaat acctgtgtgg aagcctggac cgatgtaagg gttcggggct 2760
gtgcctttta ctgctgctgg aagggggtgg tgtgtcgccc caaaagcagg gcttcaatta 2820
agaaatgcct ctttgaaagg tgtaccttgg gtatcctgtc tgagggtaac tccagggtgc 2880
gccacaatgt ggcctccgac tgtggttgct tcatgctagt gaaaagcgtg gctgtgatta 2940
agcataacat ggtatgtggc aactgcgagg acagggcctc tcagatgctg acctgctcgg 3000
acggcaactg tcacctgctg aagaccattc acgtagccag ccactctcgc aaggcctggc 3060
cagtgtttga gcataacata ctgacccgct gttccttgca tttgggtaac aggagggggg 3120
tgttcctacc ttaccaatgc aatttgagtc acactaagat attgcttgag cccgagagca 3180
tgtccaaggt gaacctgaac ggggtgtttg acatgaccat gaagatctgg aaggtgctga 3240
ggtacgatga gacccgcacc aggtgcagac cctgcgagtg tggcggtaaa catattagga 3300
accagcctgt gatgctggat gtgaccgagg agctgaggcc cgatcacttg gtgctggcct 3360
gcacccgcgc tgagtttggc tctagcgatg aagatacaga ttgaggtact gaaatgtgtg 3420
ggcgtggctt aagggtggga aagaatatat aaggtggggg tcttatgtag ttttgtatct 3480
gttttgcagc agccgccgcc gccatgagca ccaactcgtt tgatggaagc attgtgagct 3540
catatttgac aacgcgcatg cccccatggg ccggggtgcg tcagaatgtg atgggctcca 3600
gcattgatgg tcgccccgtc ctgcccgcaa actctactac cttgacctac gagaccgtgt 3660
ctggaacgcc gttggagact gcagcctccg ccgccgcttc agccgctgca gccaccgccc 3720
gcgggattgt gactgacttt gctttcctga gcccgcttgc aagcagtgca gcttcccgtt 3780
catccgcccg cgatgacaag ttgacggctc ttttggcaca attggattct ttgacccggg 3840
aacttaatgt cgtttctcag cagctgttgg atctgcgcca gcaggtttct gccctgaagg 3900
cttcctcccc tcccaatgcg gtttaaaaca taaataaaaa accagactct gtttggattt 3960
ggatcaagca agtgtcttgc tgtctttatt taggggtttt gcgcgcgcgg taggcccggg 4020
accagcggtc tcggtcgttg agggtcctgt gtattttttc caggacgtgg taaaggtgac 4080
tctggatgtt cagatacatg ggcataagcc cgtctctggg gtggaggtag caccactgca 4140
gagcttcatg ctgcggggtg gtgttgtaga tgatccagtc gtagcaggag cgctgggcgt 4200
ggtgcctaaa aatgtctttc agtagcaagc tgattgccag gggcaggccc ttggtgtaag 4260
tgtttacaaa gcggttaagc tgggatgggt gcatacgtgg ggatatgaga tgcatcttgg 4320
actgtatttt taggttggct atgttcccag ccatatccct ccggggattc atgttgtgca 4380
gaaccaccag cacagtgtat ccggtgcact tgggaaattt gtcatgtagc ttagaaggaa 4440
atgcgtggaa gaacttggag acgcccttgt gacctccaag attttccatg cattcgtcca 4500
taatgatggc aatgggccca cgggcggcgg cctgggcgaa gatatttctg ggatcactaa 4560
cgtcatagtt gtgttccagg atgagatcgt cataggccat tttacaaag cgcgggcgga 4620 gggtgccaga ctgcggtata atggttccat ccggcccagg ggcgtagtta ccctcacaga 4680
tttgcatttc ccacgctttg agttcagatg gggggatcat gtctacctgc ggggcgatga 4740

-continued

```
agaaaacggt ttccggggta ggggagatca gctgggaaga aagcaggttc ctgagcagct   4800
gcgacttacc gcagccggtg ggcccgtaaa tcacacctat taccgggtgc aactggtagt   4860
taagagagct gcagctgccg tcatccctga gcagggggc cacttcgtta agcatgtccc   4920
tgactcgcat gttttccctg accaaatccg ccagaaggcg ctcgccgccc agcgatagca   4980
gttcttgcaa ggaagcaaag tttttcaacg gtttgagacc gtccgccgta ggcatgcttt   5040
tgagcgtttg accaagcagt tccaggcggt cccacagctc ggtcacctgc tctacggcat   5100
ctcgatccag catatctcct cgtttcgcgg gttggggcgg ctttcgctgt acggcagtag   5160
tcggtgctcg tccagacggg ccagggtcat gtctttccac gggcgcaggg tcctcgtcag   5220
cgtagtctgg gtcacggtga aggggtgcgc tccgggctgc gcgctggcca gggtgcgctt   5280
gaggctggtc ctgctggtgc tgaagcgctg ccggtcttcg ccctgcgcgt cggccaggta   5340
gcatttgacc atggtgtcat agtccagccc ctccgcggcg tggcccttgg cgcgcagctt   5400
gcccttggag gaggcgccgc acgaggggca gtgcagactt ttgagggcgt agagcttggg   5460
cgcgagaaat accgattccg gggagtaggc atccgcgccg caggccccgc agacggtctc   5520
gcattccacg agccaggtga gctctggccg ttcggggtca aaaaccaggt ttcccccatg   5580
ctttttgatg cgtttcttac ctctggtttc catgagccgg tgtccacgct cggtgacgaa   5640
aaggctgtcc gtgtccccgt atacagactt gagaggcctg tcctcgagcg gtgttccgcg   5700
gtcctcctcg tatagaaact cggaccactc tgagacaaag gctcgcgtcc aggccagcac   5760
gaaggaggct aagtgggagg ggtagcggtc gttgtccact agggggtcca ctcgctccag   5820
ggtgtgaaga cacatgtcgc cctcttcggc atcaaggaag gtgattggtt tgtaggtgta   5880
ggccacgtga ccgggtgttc ctgaaggggg gctataaaag gggtgggggg cgcgttcgtc   5940
ctcactctct tccgcatcgc tgtctgcgag ggccagctgt tggggtgagt actccctctg   6000
aaaagcgggc atgacttctg cgctaagatt gtcagtttcc aaaaacgagg aggatttgat   6060
attcacctgg cccgcggtga tgcctttgag ggtggccgca tccatctggt cagaaaagac   6120
aatctttttg ttgtcaagct tggtggcaaa cgacccgtag agggcgttgg acagcaactt   6180
ggcgatggag cgcagggttt ggtttttgtc gcgatcggcg cgctccttgg ccgcgatgtt   6240
tagctgcacg tattcgcgcg caacgcaccg ccattcggga aagacggtgg tgcgctcgtc   6300
gggcaccagg tgcacgcgcc aaccgcggtt gtgcagggtg acaaggtcaa cgctggtggc   6360
tacctctccg cgtaggcgct cgttggtcca gcagaggcgg ccgcccttgc gcgagcagaa   6420
tggcggtagg gggtctagct gcgtctcgtc cggggggtct gcgtccacgg taaagacccc   6480
gggcagcagg cgcgcgtcga agtagtctat cttgcatcct tgcaagtcta gcgcctgctg   6540
ccatgcgcgg gcggcaagcg cgcgctcgta tgggttgagt gggggacccc atggcatggg   6600
gtgggtgagc gcggaggcgt acatgccgca aatgtcgtaa acgtagaggg gctctctgag   6660
tattccaaga tatgtagggt agcatcttcc accgcggatg ctggcgcgca cgtaatcgta   6720
tagttcgtgc gagggagcga ggaggtcggg accgaggttg ctacgggcgg gctgctctgc   6780
tcggaagact atctgcctga agatggcatg tgagttggat gatatggttg gacgctggaa   6840
gacgttgaag ctggcgtctg tgagacctac cgcgtcacgc acgaaggagg cgtaggagtc   6900
gcgcagcttg ttgaccagct cggcggtgac ctgcacgtct agggcgcagt agtccagggt   6960
ttccttgatg atgtcatact tatcctgtcc cttttttttc cacagctcgc ggttgaggac   7020
aaactcttcg cggtctttcc agtactcttg gatcggaaac ccgtcggcct ccgaacggta   7080
```

-continued agagcctagc atgtagaact ggttgacggc ctggtaggcg cagcatccct tttctacggg 7140
tagcgcgtat gcctgcgcgg ccttccggag cgaggtgtgg gtgagcgcaa aggtgtccct 7200
gaccatgact ttgaggtact ggtatttgaa gtcagtgtcg tcgcatccgc cctgctccca 7260
gagcaaaaag tccgtgcgct tttggaacg cggatttggc agggcgaagg tgacatcgtt 7320
gaagagtatc tttcccgcgc gaggcataaa gttgcgtgtg atgcggaagg gtcccggcac 7380
ctcggaacgg ttgttaatta cctgggcggc gagcacgatc tcgtcaaagc cgttgatgtt 7440
gtggcccaca atgtaaagtt ccaagaagcg cgggatgccc ttgatggaag gcaatttttt 7500
aagttcctcg taggtgagct cttcagggga gctgagcccg tgctctgaaa gggcccagtc 7560
tgcaagatga gggttggaag cgacgaatga gctccacagg tcacgggcca ttagcatttg 7620
caggtggtcg cgaaaggtcc taaactggcg acctatggcc attttttctg ggtgatgca 7680 gtagaaggta agcgggtctt gttcccagcg gtcccatcca aggttcgcgg ctaggtctcg 7740
cgcggcagtc actagaggct catctccgcc gaacttcatg accagcatga agggcacgag 7800
ctgcttccca aaggccccca tccaagtata ggtctctaca tcgtaggtga caaagagacg 7860
ctcggtgcga ggatgcgagc cgatcgggaa gaactggatc tcccgccacc aattggagga 7920
gtggctattg atgtggtgaa agtagaagtc cctgcgacgg gccgaacact cgtgctggct 7980
tttgtaaaaa cgtgcgcagt actggcagcg gtgcacgggc tgtacatcct gcacgaggtt 8040
gacctgacga ccgcgcacaa ggaagcagag tgggaatttg agcccctcgc ctggcgggtt 8100
tggctggtgg tcttctactt cggctgcttg tccttgaccg tctggctgct cgaggggagt 8160
tacggtggat cggaccacca cgccgcgcga gcccaaagtc cagatgtccg cgcgcggcgg 8220
tcggagcttg atgacaacat cgcgcagatg ggagctgtcc atggtctgga gctcccgcgg 8280
cgtcaggtca ggcgggagct cctgcaggtt tacctcgcat agacgggtca gggcgcgggc 8340
tagatccagg tgatacctaa tttccagggg ctggttggtg gcggcgtcga tggcttgcaa 8400
gaggccgcat ccccgcggcg cgactacggt accgcgcggc gggcggtggg ccgcgggggt 8460
gtccttggat gatgcatcta aaagcggtga cgcgggcgag cccccggagg taggggggc 8520 tccggacccg ccgggagagg gggcaggggc acgtcggcgc cgcgcgcggg caggagctgg 8580
tgctgcgcgc gtaggttgct ggcgaacgcg acgacgcggc ggttgatctc ctgaatctgg 8640
cgcctctgcg tgaagacgac gggcccggtg agcttgagcc tgaaagagag ttcgacagaa 8700
tcaatttcgg tgtcgttgac ggcggcctgg cgcaaaatct cctgcacgtc tcctgagttg 8760
tcttgatagg cgatctcggc catgaactgc tcgatctctt cctcctggag atctccgcgt 8820
ccggctcgct ccacggtggc ggcgaggtcg ttggaaatgc gggccatgag ctgcgagaag 8880
gcgttgaggc ctccctcgtt ccagacgcgg ctgtagacca cgcccccttc ggcatcgcgg 8940
gcgcgcatga ccacctgcgc gagattgagc tccacgtgcc gggcgaagac ggcgtagttt 9000
cgcaggcgct gaaagaggta gttgagggtg gtggcggtgt gttctgccac gaagaagtac 9060
ataacccagc gtcgcaacgt ggattcgttg atatccccca aggcctcaag gcgctccatg 9120
gcctcgtaga agtccacggc gaagttgaaa aactgggagt tgcgcgccga cacggttaac 9180
tcctcctcca gaagacggat gagctcggcg acagtgtcgc gcacctcgcg ctcaaaggct 9240
acaggggcct cttcttcttc ttcaatctcc tcttccataa gggcctcccc ttcttcttct 9300
tctggcggcg gtgggggagg ggggacacgg cggcgacgac ggcgcaccgg gaggcggtcg 9360
acaaagcgct cgatcatctc cccgcggcga cggcgcatgg tctcggtgac ggcgcggccg 9420
ttctcgcggg ggcgcagttg gaagacgccg cccgtcatgt cccggttatg ggttggcggg 9480

-continued

```
gggctgccat gcggcaggga tacggcgcta acgatgcatc tcaacaattg ttgtgtaggt   9540
actccgccgc cgagggacct gagcgagtcc gcatcgaccg gatcggaaaa cctctcgaga   9600
aaggcgtcta accagtcaca gtcgcaaggt aggctgagca ccgtggcggg cggcagcggg   9660
cggcggtcgg ggttgtttct ggcggaggtg ctgctgatga tgtaattaaa gtaggcggtc   9720
ttgagacggc ggatggtcga cagaagcacc atgtccttgg gtccggcctg ctgaatgcgc   9780
aggcggtcgg ccatgcccca ggcttcgttt tgacatcggc gcaggtcttt gtagtagtct   9840
tgcatgagcc tttctaccgg cacttcttct tctccttcct cttgtcctgc atctcttgca   9900
tctatcgctg cggcggcggc ggagtttggc cgtaggtggc gccctcttcc tcccatgcgt   9960
gtgaccccga agcccctcat cggctgaagc agggctaggt cggcgacaac gcgctcggct  10020
aatatggcct gctgcacctg cgtgagggta gactggaagt catccatgtc cacaaagcgg  10080
tggtatgcgc ccgtgttgat ggtgtaagtg cagttggcca taacggacca gttaacggtc  10140
tggtgacccg gctgcgagag ctcggtgtac ctgagacgcg agtaagccct cgagtcaaat  10200
acgtagtcgt tgcaagtccg caccaggtac tggtatccca ccaaaaagtg cggcggcggc  10260
tggcggtaga ggggccagcg tagggtggcc ggggctccgg gggcgagatc ttccaacata  10320
aggcgatgat atccgtagat gtacctggac atccaggtga tgccggcggc ggtggtggag  10380
gcgcgcggaa agtcgcggac gcggttccag atgttgcgca gcggcaaaaa gtgctccatg  10440
gtcgggacgc tctggccggt caggcgcgcg caatcgttga cgctctagcg tgcaaaagga  10500
gagcctgtaa gcgggcactc ttccgtggtc tggtggataa attcgcaagg gtatcatggc  10560
ggacgaccgg ggttcgagcc ccgtatccgg ccgtccgccg tgatccatgc ggttaccgcc  10620
cgcgtgtcga acccaggtgt gcgacgtcag acaacggggg agtgctcctt ttggcttcct  10680
tccaggcgcg gcggctgctg cgctagcttt tttggccact ggccgcgcgc agcgtaagcg  10740
gttaggctgg aaagcgaaag cattaagtgg ctcgctccct gtagccggag ggttattttc  10800
caagggttga gtcgcgggac ccccggttcg agtctcggac cggccggact gcggcgaacg  10860
ggggtttgcc tccccgtcat gcaagacccc gcttgcaaat tcctccggaa acagggacga  10920
gcccctttt  tgcttttccc agatgcatcc ggtgctgcgg cagatgcgcc cccctcctca  10980
gcagcggcaa gagcaagagc agcggcagac atgcagggca ccctcccctc ctcctaccgc  11040
gtcaggaggg gcgacatccg cggttgacgc ggcagcagat ggtgattacg aacccccgcg  11100
gcgccgggcc cggcactacc tggacttgga ggagggcgag ggcctggcgc ggctaggagc  11160
gccctctcct gagcggtacc caagggtgca gctgaagcgt gatacgcgtg aggcgtacgt  11220
gccgcggcag aacctgtttc gcgaccgcga gggagaggag cccgaggaga tgcgggatcg  11280
aaagttccac gcagggcgcg agctgcggca tggcctgaat cgcgagcggt tgctgcgcga  11340
ggaggacttt gagcccgacg cgcgaaccgg gattagtccc gcgcgcgcac acgtggcggc  11400
cgccgacctg gtaaccgcat acgagcagac ggtgaaccag gagattaact ttcaaaaaag  11460
ctttaacaac cacgtgcgta cgcttgtggc gcgcgaggag gtggctatag gactgatgca  11520
tctgtgggac tttgtaagcg cgctggagca aaacccaaat agcaagccgc tcatggcgca  11580
gctgttcctt atagtgcagc acagcaggga caacgaggca ttcagggatg cgctgctaaa  11640
catagtagag cccgagggcc gctggctgct cgatttgata aacatcctgc agagcatagt  11700
ggtgcaggag cgcagcttga gcctggctga caaggtggcc gccatcaact attccatgct  11760
tagcctgggc aagttttacg cccgcaagat ataccatacc ccttacgttc ccatagacaa  11820
```

-continued ggaggtaaag atcgaggggt tctacatgcg catggcgctg aaggtgctta ccttgagcga 11880
cgacctgggc gtttatcgca acgagcgcat ccacaaggcc gtgagcgtga gccggcggcg 11940
cgagctcagc gaccgcgagc tgatgcacag cctgcaaagg gccctggctg gcacgggcag 12000
cggcgataga gaggccgagt cctactttga cgcgggcgct gacctgcgct gggccccaag 12060
ccgacgcgcc ctggaggcag ctggggccgg acctgggctg gcggtggcac ccgcgcgcgc 12120
tggcaacgtc ggcggcgtgg aggaatatga cgaggacgat gagtacgagc cagaggacgg 12180
cgagtactaa gcggtgatgt ttctgatcag atgatgcaag acgcaacgga cccggcggtg 12240
cgggcggcgc tgcagagcca gccgtccggc cttaactcca cggacgactg gcgccaggtc 12300
atggaccgca tcatgtcgct gactgcgcgc aatcctgacg cgttccggca gcagccgcag 12360
gccaaccggc tctccgcaat tctggaagcg gtggtcccgg cgcgcgcaaa ccccacgcac 12420
gagaaggtgc tggcgatcgt aaacgcgctg gccgaaaaca gggccatccg gcccgacgag 12480
gccggcctgg tctacgacgc gctgcttcag cgcgtggctc gttacaacag cggcaacgtg 12540
cagaccaacc tggaccggct ggtgggggat gtgcgcgagg ccgtggcgca gcgtgagcgc 12600
gcgcagcagc agggcaacct gggctccatg gttgcactaa acgccttcct gagtacacag 12660
cccgccaacg tgccgcgggg acaggaggac tacaccaact ttgtgagcgc actgcggcta 12720
atggtgactg agacaccgca aagtgaggtg taccagtctg ggccagacta tttttttccag 12780 accagtagac aaggcctgca gaccgtaaac ctgagccagg ctttcaaaaa cttgcagggg 12840
ctgtgggggg tgcgggctcc cacaggcgac cgcgcgaccg tgtctagctt gctgacgccc 12900
aactcgcgcc tgttgctgct gctaatagcg cccttcacgg acagtggcag cgtgtcccgg 12960
gacacatacc taggtcactt gctgacactg taccgcgagg ccataggtca ggcgcatgtg 13020
gacgagcata ctttccagga gattacaagt gtcagccgcg cgctggggca ggaggacacg 13080
ggcagcctgg aggcaaccct aaactacctg ctgaccaacc ggcggcagaa gatcccctcg 13140
ttgcacagtt taaacagcga ggaggagcgc attttgcgct acgtgcagca gagcgtgagc 13200
cttaacctga tgcgcgacgg ggtaacgccc agcgtggcgc tggacatgac cgcgcgcaac 13260
atggaaccgg gcatgtatgc ctcaaaccgg ccgtttatca accgcctaat ggactacttg 13320
catcgcgcgg ccgccgtgaa ccccgagtat ttcaccaatg ccatcttgaa cccgcactgg 13380
ctaccgcccc ctggtttcta caccggggga ttcgaggtgc ccgagggtaa cgatggattc 13440
ctctgggacg acatagacga cagcgtgttt tccccgcaac cgcagaccct gctagagttg 13500
caacagcgcg agcaggcaga ggcggcgctg cgaaaggaaa gcttccgcag gccaagcagc 13560
ttgtccgatc taggcgctgc ggccccgcgg tcagatgcta gtagcccatt tccaagcttg 13620
atagggtctc ttaccagcac tcgcaccacc cgcccgcgcc tgctgggcga ggaggagtac 13680
ctaaacaact cgctgctgca gccgcagcgc gaaaaaaacc tgcctccggc atttcccaac 13740
aacgggatag agagcctagt ggacaagatg agtagatgga agacgtacgc gcaggagcac 13800
agggacgtgc caggcccgcg cccgcccacc cgtcgtcaaa ggcacgaccg tcagcggggt 13860
ctggtgtggg aggacgatga ctcggcagac gacagcagcg tcctggattt gggagggagt 13920
ggcaacccgt ttgcgcacct tcgccccagg ctggggagaa tgttttaaaa aaaaaaaagc 13980
atgatgcaaa ataaaaaact caccaaggcc atggcaccga gcgttggttt tcttgtattc 14040
cccttagtat gcggcgcgcg gcgatgtatg aggaaggtcc tcctccctcc tacgagagtg 14100
tggtgagcgc ggcgccagtg gcggcggcgc tgggttctcc cttcgatgct cccctggacc 14160
cgccgtttgt gcctccgcgg tacctgcggc ctaccggggg gagaaacagc atccgttact 14220

-continued

```
ctgagttggc accccctattc gacaccaccc gtgtgtacct ggtggacaac aagtcaacgg  14280
atgtggcatc cctgaactac cagaacgacc acagcaactt tctgaccacg gtcattcaaa  14340
acaatgacta cagcccgggg gaggcaagca cacagaccat caatcttgac gaccggtcgc  14400
actggggcgg cgacctgaaa accatcctgc ataccaacat gccaaatgtg aacgagttca  14460
tgtttaccaa taagtttaag gcgcgggtga tggtgtcgcg cttgcctact aaggacaatc  14520
aggtggagct gaaatacgag tgggtggagt tcacgctgcc cgagggcaac tactccgaga  14580
ccatgaccat agaccttatg aacaacgcga tcgtggagca ctacttgaaa gtgggcagac  14640
agaacggggt tctggaaagc gacatcgggg taaagtttga cacccgcaac ttcagactgg  14700
ggtttgaccc cgtcactggt cttgtcatgc ctggggtata tacaaacgaa gccttccatc  14760
cagacatcat tttgctgcca ggatgcgggg tggacttcac ccacagccgc ctgagcaact  14820
tgttgggcat ccgcaagcgg caacccttcc aggagggctt taggatcacc tacgatgatc  14880
tggagggtgg taacattccc gcactgttgg atgtggacgc ctaccaggcg agcttgaaag  14940
atgacaccga acagggcggg ggtggcgcag gcggcagcaa cagcagtggc agcggcgcgg  15000
aagagaactc caacgcggca gccgcggcaa tgcagccggt ggaggacatg aacgatcatg  15060
ccattcgcgg cgacaccttt gccacacggg ctgaggagaa gcgcgctgag gccgaagcag  15120
cggccgaagc tgccgccccc gctgcgcaac ccgaggtcga gaagcctcag aagaaaccgg  15180
tgatcaaacc cctgacagag gacagcaaga aacgcagtta caacctaata agcaatgaca  15240
gcaccttcac ccagtaccgc agctggtacc ttgcatacaa ctacggcgac cctcagaccg  15300
gaatccgctc atggaccctg ctttgcactc ctgacgtaac ctgcggctcg gagcaggtct  15360
actggtcgtt gccagacatg atgcaagacc ccgtgacctt ccgctccacg cgccagatca  15420
gcaactttcc ggtggtgggc gccgagctgt tgcccgtgca ctccaagagc ttctacaacg  15480
accaggccgt ctactcccaa ctcatccgcc agtttacctc tctgacccac gtgttcaatc  15540
gctttcccga gaaccagatt ttggcgcgcc cgccagcccc caccatcacc accgtcagtg  15600
aaaacgttcc tgctctcaca gatcacggga cgctaccgct gcgcaacagc atcggaggag  15660
tccagcgagt gaccattact gacgccagac gccgcacctg cccctacgtt tacaaggccc  15720
tgggcatagt ctcgccgcgc gtcctatcga gccgcacttt ttgagcaagc atgtccatcc  15780
ttatatcgcc cagcaataac acaggctggg gcctgcgctt cccaagcaag atgtttggcg  15840
gggccaagaa gcgctccgac caacacccag tgcgcgtgcg cgggcactac cgcgcgccct  15900
ggggcgcgca caaacgcggc cgcactgggc gcaccaccgt cgatgacgcc atcgacgcgg  15960
tggtggagga ggcgcgcaac tacacgccca cgccgccacc agtgtccaca gtggacgcgg  16020
ccattcagac cgtggtgcgc ggagcccggc gctatgctaa aatgaagaga cggcggaggc  16080
gcgtagcacg tcgccaccgc cgccgacccg gcactgccgc ccaacgcgcg gcggcggccc  16140
tgcttaaccg cgcacgtcgc accggccgac gggcggccat gcgggccgct cgaaggctgg  16200
ccgcgggtat tgtcactgtg ccccccaggt ccaggcgacg agcggccgcc gcagcagccg  16260
cggccattag tgctatgact cagggtcgca ggggcaacgt gtattgggtg cgcgactcgg  16320
ttagcggcct gcgcgtgccc gtgcgcaccc gccccccgcg caactagatt gcaagaaaaa  16380
actacttaga ctcgtactgt tgtatgtatc cagcggcggc ggcgcgcaac gaagctatgt  16440
ccaagcgcaa aatcaaagaa gagatgctcc aggtcatcgc gccggagatc tatggccccc  16500
cgaagaagga agagcaggat tacaagcccc gaaagctaaa gcgggtcaaa aagaaaaaga  16560
```

-continued

```
aagatgatga tgatgaactt gacgacgagg tggaactgct gcacgctacc gcgcccaggc  16620
gacgggtaca gtggaaaggt cgacgcgtaa aacgtgtttt gcgacccggc accaccgtag  16680
tctttacgcc cggtgagcgc tccacccgca cctacaagcg cgtgtatgat gaggtgtacg  16740
gcgacgagga cctgcttgag caggccaacg agcgcctcgg ggagtttgcc tacggaaagc  16800
ggcataagga catgctggcg ttgccgctgg acgagggcaa cccaacacct agcctaaagc  16860
ccgtaacact gcagcaggtg ctgcccgcgc ttgcaccgtc cgaagaaaag cgcggcctaa  16920
agcgcgagtc tggtgacttg gcacccaccg tgcagctgat ggtacccaag cgccagcgac  16980
tggaagatgt cttggaaaaa atgaccgtgg aacctgggct ggagcccgag gtccgcgtgc  17040
ggccaatcaa gcaggtggcg ccgggactgg gcgtgcagac cgtggacgtt cagataccca  17100
ctaccagtag caccagtatt gccaccgcca cagagggcat ggagacacaa acgtccccgg  17160
ttgcctcagc ggtggcggat gccgcggtgc aggcggtcgc tgcggccgcg tccaagacct  17220
ctacggaggt gcaaacggac ccgtggatgt ttcgcgtttc agcccccccgg cgcccgcgcg  17280
gttcgaggaa gtacggcgcc gccagcgcgc tactgcccga atatgcccta catccttcca  17340
ttgcgcctac ccccggctat cgtggctaca cctaccgccc cagaagacga gcaactaccc  17400
gacgccgaac caccactgga acccgccgcc gccgtcgccg tcgccagccc gtgctggccc  17460
cgatttccgt gcgcagggtg gctcgcgaag gaggcaggac cctggtgctg ccaacagcgc  17520
gctaccaccc cagcatcgtt taaaagccgg tctttgtggt tcttgcagat atggccctca  17580
cctgccgcct ccgtttcccg gtgccgggat tccgaggaag aatgcaccgt aggaggggca  17640
tggccggcca cggcctgacg ggcggcatgc gtcgtgcgca ccaccggcgg cggcgcgcgt  17700
cgcaccgtcg catgcgcggc ggtatcctgc ccctccttat tccactgatc gccgcggcga  17760
ttggcgccgt gcccggaatt gcatccgtgg ccttgcaggc gcagagacac tgattaaaaa  17820
caagttgcat gtggaaaaat caaaataaaa agtctggact ctcacgctcg cttggtcctg  17880
taactatttt gtagaatgga agacatcaac tttgcgtctc tggccccgcg acacggctcg  17940
cgcccgttca tgggaaactg gcaagatatc ggcaccagca atatgagcgg tggcgccttc  18000
agctggggct cgctgtggag cggcattaaa aatttcggtt ccaccgttaa gaactatggc  18060
agcaaggcct ggaacagcag cacaggccag atgctgaggg ataagttgaa agagcaaaat  18120
ttccaacaaa aggtggtaga tggcctggcc tctggcatta gcggggtggt ggacctggcc  18180
aaccaggcag tgcaaaataa gattaacagt aagcttgatc cccgccctcc cgtagaggag  18240
cctccaccgg ccgtggagac agtgtctcca gaggggcgtg gcgaaaagcg tccgcgcccc  18300
gacagggaag aaactctggt gacgcaaata gacgagcctc cctcgtacga ggaggcacta  18360
aagcaaggcc tgcccaccac ccgtcccatc gcgcccatgg ctaccggagt gctgggccag  18420
cacacacccg taacgctgga cctgcctccc cccgccgaca cccagcagaa acctgtgctg  18480
ccaggcccga ccgccgttgt tgtaacccgt cctagccgcg cgtccctgcg ccgcgccgcc  18540
agcggtccgc gatcgttgcg gcccgtagcc agtggcaact ggcaaagcac actgaacagc  18600
atcgtgggtc tgggggtgca atccctgaag cgccgacgat gcttctgaat agctaacgtg  18660
tcgtatgtgt gtcatgtatg cgtccatgtc gccgccagag gagctgctga gccgccgcgc  18720
gcccgctttc caagatggct accccttcga tgatgccgca gtggtcttac atgcacatct  18780
cgggccagga cgcctcggag tacctgagcc ccgggctggt gcagtttgcc cgcgccaccg  18840
agacgtactt cagcctgaat aacaagttta gaaaccccac ggtggcgcct acgcacgacg  18900
tgaccacaga ccggtcccag cgtttgacgc tgcggttcat ccctgtggac cgtgaggata  18960
```

-continued

```
ctgcgtactc gtacaaggcg cggttcaccc tagctgtggg tgataaccgt gtgctggaca  19020
tggcttccac gtactttgac atccgcggcg tgctggacag gggccctact tttaagccct  19080
actctggcac tgcctacaac gccctggctc ccaagggtgc cccaaatcct tgcgaatggg  19140
atgaagctgc tactgctctt gaaataaacc tagaagaaga ggacgatgac aacgaagacg  19200
aagtagacga gcaagctgag cagcaaaaaa ctcacgtatt tgggcaggcg ccttattctg  19260
gtataaatat tacaaaggag ggtattcaaa taggtgtcga aggtcaaaca cctaaatatg  19320
ccgataaaac atttcaacct gaacctcaaa taggagaatc tcagtggtac gaaactgaaa  19380
ttaatcatgc agctgggaga gtccttaaaa agactacccc aatgaaacca tgttacggtt  19440
catatgcaaa acccacaaat gaaaatggag ggcaaggcat tcttgtaaag caacaaaatg  19500
gaaagctaga aagtcaagtg gaaatgcaat tttctcaac tactgaggcg accgcaggca  19560
atggtgataa cttgactcct aaagtggtat tgtacagtga agatgtagat atagaaaccc  19620
cagacactca tatttcttac atgcccacta ttaaggaagg taactcacga gaactaatgg  19680
gccaacaatc tatgcccaac aggcctaatt acattgcttt tagggacaat tttattggtc  19740
taatgtatta caacagcacg ggtaatatgg gtgttctggc gggccaagca tcgcagttga  19800
atgctgttgt agatttgcaa gacagaaaca cagagctttc ataccagctt ttgcttgatt  19860
ccattggtga tagaaccagg tacttttcta tgtggaatca ggctgttgac agctatgatc  19920
cagatgttag aattattgaa aatcatggaa ctgaagatga acttccaaat tactgctttc  19980
cactgggagg tgtgattaat acagagactc ttaccaaggt aaaacctaaa acaggtcagg  20040
aaaatggatg ggaaaaagat gctacagaat tttcagataa aaatgaaata agagttggaa  20100
ataattttgc catggaaatc aatctaaatg ccaacctgtg gagaaatttc ctgtactcca  20160
acatagcgct gtatttgccc gacaagctaa agtacagtcc ttccaacgta aaaatttctg  20220
ataacccaaa cacctacgac tacatgaaca agcgagtggt ggctcccggg ttagtggact  20280
gctacattaa ccttggagca cgctggtccc ttgactatat ggacaacgtc aacccattta  20340
accaccaccg caatgctggc ctgcgctacc gctcaatgtt gctgggcaat ggtcgctatg  20400
tgcccttcca catccaggtg cctcagaagt tctttgccat taaaaacctc cttctcctgc  20460
cgggctcata cacctacgag tggaacttca ggaaggatgt taacatggtt ctgcagagct  20520
ccctaggaaa tgacctaagg gttgacggag ccagcattaa gtttgatagc atttgccttt  20580
acgccacctt cttccccatg gcccacaaca ccgcctccac gcttgaggcc atgcttagaa  20640
acgacaccaa cgaccagtcc tttaacgact atctctccgc cgccaacatg ctctacccta  20700
tacccgccaa cgctaccaac gtgcccatat ccatcccctc ccgcaactgg gcggctttcc  20760
gcggctgggc cttcacgcgc cttaagacta aggaaacccc atcactgggc tcgggctacg  20820
acccttatta cacctactct ggctctatac cctacctaga tggaaccttt tacctcaacc  20880
acacctttaa gaaggtggcc attacctttg actcttctgt cagctggcct ggcaatgacc  20940
gcctgcttac ccccaacgag tttgaaatta agcgctcagt tgacggggag ggttacaacg  21000
ttgcccagtg taacatgacc aaagactggt tcctggtaca aatgctagct aactacaaca  21060
ttggctacca gggcttctat atcccagaga gctacaagga ccgcatgtac tccttcttta  21120
gaaacttcca gcccatgagc cgtcaggtgg tggatgatac taaatacaag gactaccaac  21180
aggtgggcat cctacaccaa cacaacaact ctggatttgt tggctacctt gcccccacca  21240
tgcgcgaagg acaggcctac cctgctaact tcccctatcc gcttataggc aagaccgcag  21300
```

-continued

```
ttgacagcat tacccagaaa aagtttcttt gcgatcgcac cctttggcgc atcccattct  21360
ccagtaactt tatgtccatg ggcgcactca cagacctggg ccaaaacctt ctctacgcca  21420
actccgccca cgcgctagac atgacttttg aggtggatcc catggacgag cccacccttc  21480
tttatgtttt gtttgaagtc tttgacgtgg tccgtgtgca ccggccgcac cgcggcgtca  21540
tcgaaaccgt gtacctgcgc acgcccttct cggccggcaa cgccacaaca taaagaagca  21600
agcaacatca acaacagctg ccgccatggg ctccagtgag caggaactga aagccattgt  21660
caaagatctt ggttgtgggc catatttttt gggcacctat gacaagcgct ttccaggctt  21720
tgtttctcca cacaagctcg cctgcgccat agtcaatacg gccggtcgcg agactggggg  21780
cgtacactgg atggcctttg cctggaaccc gcactcaaaa acatgctacc tctttgagcc  21840
ctttggcttt tctgaccagc gactcaagca ggtttaccag tttgagtacg agtcactcct  21900
gcgccgtagc gccattgctt cttcccccga ccgctgtata acgctggaaa agtccaccca  21960
aagcgtacag gggcccaact cggccgcctg tggactattc tgctgcatgt ttctccacgc  22020
ctttgccaac tggccccaaa ctcccatgga tcacaacccc accatgaacc ttattaccgg  22080
ggtacccaac tccatgctca acagtcccca ggtacagccc accctgcgtc gcaaccagga  22140
acagctctac agcttcctgg agcgccactc gccctacttc cgcagccaca gtgcgcagat  22200
taggagcgcc acttcttttt gtcacttgaa aaacatgtaa aaataatgta ctagagacac  22260
tttcaataaa ggcaaatgct tttatttgta cactctcggg tgattattta cccccaccct  22320
tgccgtctgc gccgtttaaa aatcaaaggg gttctgccgc gcatcgctat gcgccactgg  22380
cagggacacg ttgcgatact ggtgtttagt gctccactta aactcaggca caaccatccg  22440
cggcagctcg gtgaagtttt cactccacag gctgcgcacc atcaccaacg cgtttagcag  22500
gtcgggcgcc gatatcttga agtcgcagtt ggggcctccg ccctgcgcgc gcgagttgcg  22560
atacacaggg ttgcagcact ggaacactat cagcgccggg tggtgcacgc tggccagcac  22620
gctcttgtcg gagatcagat ccgcgtccag gtcctccgcg ttgctcaggg cgaacggagt  22680
caactttggt agctgccttc ccaaaaaggg cgcgtgccca ggctttgagt tgcactcgca  22740
ccgtagtggc atcaaaaggt gaccgtgccc ggtctgggcg ttaggataca gcgcctgcat  22800
aaaagccttg atctgcttaa aagccacctg agcctttgcg ccttcagaga agaacatgcc  22860
gcaagacttg ccggaaaact gattggccgg acaggccgcg tcgtgcacgc agcaccttgc  22920
gtcggtgttg gagatctgca ccacatttcg gccccaccgg ttcttcacga tcttggcctt  22980
gctagactgc tccttcagcg cgcgctgccc gttttcgctc gtcacatcca tttcaatcac  23040
gtgctcctta tttatcataa tgcttccgtg tagacactta agctcgcctt cgatctcagc  23100
gcagcggtgc agccacaacg cgcagcccgt gggctcgtga tgcttgtagg tcacctctgc  23160
aaacgactgc aggtacgcct gcaggaatcg ccccatcatc gtcacaaagg tcttgttgct  23220
ggtgaaggtc agctgcaacc cgcggtgctc ctcgttcagc caggtcttgc atacggccgc  23280
cagagcttcc acttggtcag gcagtagttt gaagttcgcc tttagatcgt tatccacgtg  23340
gtacttgtcc atcagcgcgc gcgcagcctc catgcccttc tcccacgcag acacgatcgg  23400
cacactcagc gggttcatca ccgtaatttc actttccgct tcgctgggct cttcctcttc  23460
ctcttgcgtc cgcataccac gcgccactgg gtcgtcttca ttcagccgcc gcactgtgcg  23520
cttacctcct ttgccatgct tgattagcac cggtgggttg ctgaaaccca ccatttgtag  23580
cgccacatct tctctttctt cctcgctgtc cacgattacc tctggtgatg gcgggcgctc  23640
gggcttggga gaagggcgct tctttttctt cttgggcgca atggccaaat ccgccgccga  23700
```

-continued ggtcgatggc cgcgggctgg gtgtgcgcgg caccagcgcg tcttgtgatg agtcttcctc 23760
gtcctcggac tcgatacgcc gcctcatccg cttttttggg ggcgcccggg gaggcggcgg 23820
cgacggggac ggggacgaca cgtcctccat ggttgggggga cgtcgcgccg caccgcgtcc 23880
gcgctcgggg gtggtttcgc gctgctcctc ttcccgactg gccatttcct tctcctatag 23940
gcagaaaaag atcatggagt cagtcgagaa gaaggacagc ctaaccgccc cctctgagtt 24000
cgccaccacc gcctccaccg atgccgccaa cgcgcctacc accttccccg tcgaggcacc 24060
cccgcttgag gaggaggaag tgattatcga gcaggaccca ggttttgtaa gcgaagacga 24120
cgaggaccgc tcagtaccaa cagaggataa aaagcaagac caggacaacg cagaggcaaa 24180
cgaggaacaa gtcgggcggg gggacgaaag gcatggcgac tacctagatg tgggagacga 24240
cgtgctgttg aagcatctgc agcgccagtg cgccattatc tgcgacgcgt tgcaagagcg 24300
cagcgatgtg cccctcgcca tagcggatgt cagccttgcc tacgaacgcc acctattctc 24360
accgcgcgta ccccccaaac gccaagaaaa cggcacatgc gagcccaacc cgcgcctcaa 24420
cttctacccc gtatttgccg tgccagaggt gcttgccacc tatcacatct tttccaaaa 24480
ctgcaagata cccctatcct gccgtgccaa ccgcagccga gcggacaagc agctggcctt 24540
gcggcagggc gctgtcatac ctgatatcgc ctcgctcaac gaagtgccaa aaatctttga 24600
gggtcttgga cgcgacgaga agcgcgcggc aaacgctctg caacaggaaa acagcgaaaa 24660
tgaaagtcac tctggagtgt tggtggaact cgagggtgac aacgcgcgcc tagccgtact 24720
aaaacgcagc atcgaggtca cccactttgc ctacccggca cttaacctac cccccaaggt 24780
catgagcaca gtcatgagtg agctgatcgt gcgccgtgcg cagcccctgg agagggatgc 24840
aaatttgcaa gaacaaacag aggagggcct acccgcagtt ggcgacgagc agctagcgcg 24900
ctggcttcaa acgcgcgagc ctgccgactt ggaggagcga cgcaaactaa tgatggccgc 24960
agtgctcgtt accgtggagc ttgagtgcat gcagcggttc tttgctgacc cggagatgca 25020
gcgcaagcta gaggaaacat tgcactacac ctttcgacag ggctacgtac gccaggcctg 25080
caagatctcc aacgtggagc tctgcaacct ggtctcctac cttggaattt tgcacgaaaa 25140
ccgccttggg caaaacgtgc ttcattccac gctcaagggc gaggcgcgcc gcgactacgt 25200
ccgcgactgc gtttacttat ttctatgcta cacctggcag acggccatgg gcgtttggca 25260
gcagtgcttg gaggagtgca acctcaagga gctgcagaaa ctgctaaagc aaaacttgaa 25320
ggacctatgg acggccttca acgagcgctc cgtggccgcg cacctggcgg acatcatttt 25380
ccccgaacgc ctgcttaaaa ccctgcaaca gggtctgcca gacttcacca gtcaaagcat 25440
gttgcagaac tttaggaact ttatcctaga gcgctcagga atcttgcccg ccacctgctg 25500
tgcacttcct agcgactttg tgcccattaa gtaccgcgaa tgccctccgc cgctttgggg 25560
ccactgctac cttctgcagc tagccaacta ccttgcctac cactctgaca taatggaaga 25620
cgtgagcggt gacggtctac tggagtgtca ctgtcgctgc aacctatgca ccccgcaccg 25680
ctccctggtt tgcaattcgc agctgcttaa cgaaagtcaa attatcggta cctttgagct 25740
gcagggtccc tcgcctgacg aaaagtccgc ggctccgggg ttgaaactca ctccggggct 25800
gtggacgtcg gcttaccttc gcaaatttgt acctgaggac taccacgccc acgagattag 25860
gttctacgaa gaccaatccc gcccgccaaa tgcggagctt accgcctgcg tcattaccca 25920
gggccacatt cttggccaat tgcaagccat caacaaagcc cgccaagagt ttctgctacg 25980
aaagggacgg ggggtttact tggaccccca gtccggcgag gagctcaacc caatcccccc 26040

-continued

```
gccgccgcag ccctatcagc agcagccgcg ggcccttgct tcccaggatg gcacccaaaa  26100
agaagctgca gctgccgccg ccacccacgg acgaggagga atactgggac agtcaggcag  26160
aggaggtttt ggacgaggag gaggaggaca tgatggaaga ctgggagagc ctagacgagg  26220
aagcttccga ggtcgaagag gtgtcagacg aaacaccgtc accctcggtc gcattcccct  26280
cgccggcgcc ccagaaatcg gcaaccggtt ccagcatggc tacaacctcc gctcctcagg  26340
cgccgccggc actgcccgtt cgccgaccca accgtagatg ggacaccact ggaaccaggg  26400
ccggtaagtc caagcagccg ccgccgttag cccaagagca acaacagcgc caaggctacc  26460
gctcatggcg cgggcacaag aacgccatag ttgcttgctt gcaagactgt gggggcaaca  26520
tctccttcgc ccgccgcttt cttctctacc atcacggcgt ggccttcccc cgtaacatcc  26580
tgcattacta ccgtcatctc tacagcccat actgcaccgg cggcagcggc agcggcagca  26640
acagcagcgg ccacacagaa gcaaaggcga ccggatagca agactctgac aaagcccaag  26700
aaatccacag cggcggcagc agcaggagga ggagcgctgc gtctggcgcc caacgaaccc  26760
gtatcgaccc gcgagcttag aaacaggatt tttcccactc tgtatgctat atttcaacag  26820
agcaggggcc aagaacaaga gctgaaaata aaaaacaggt ctctgcgatc cctcacccgc  26880
agctgcctgt atcacaaaag cgaagatcag cttcggcgca cgctggaaga cgcggaggct  26940
ctcttcagta aatactgcgc gctgactctt aaggactagt ttcgcgccct ttctcaaatt  27000
taagcgcgaa aactacgtca tctccagcgg ccacacccgg cgccagcacc tgtcgtcagc  27060
gccattatga gcaaggaaat tcccacgccc tacatgtgga gttaccagcc acaaatggga  27120
cttgcggctg gagctgccca agactactca acccgaataa actacatgag cgcgggaccc  27180
cacatgatat cccgggtcaa cggaatccgc gcccaccgaa accgaattct cttggaacag  27240
gcggctatta ccaccacacc tcgtaataac cttaatcccc gtagttggcc cgctgccctg  27300
gtgtaccagg aaagtcccgc tcccaccact gtggtacttc ccagagacgc ccaggccgaa  27360
gttcagatga ctaactcagg ggcgcagctt gcgggcggct ttcgtcacag ggtgcggtcg  27420
cccgggcagg gtataactca cctgacaatc agagggcgag gtattcagct caacgacgag  27480
tcggtgagct cctcgcttgg tctccgtccg gacgggacat ttcagatcgg cggcgccggc  27540
cgtccttcat tcacgcctcg tcaggcaatc ctaactctgc agacctcgtc ctctgagccg  27600
cgctctggag gcattggaac tctgcaattt attgaggagt ttgtgccatc ggtctacttt  27660
aaccccttct cgggacctcc cggccactat ccggatcaat ttattcctaa ctttgacgcg  27720
gtaaaggact cggcggacgg ctacgactga atgttaagtg gagaggcaga gcaactgcgc  27780
ctgaaacacc tggtccactg tcgccgccac aagtgctttg cccgcgactc cggtgagttt  27840
tgctactttg aattgcccga ggatcatatc gagggcccgg cgcacggcgt ccggcttacc  27900
gcccagggag agcttgcccg tagcctgatt cgggagttta cccagcgccc cctgctagtt  27960
gagcgggaca ggggaccctg tgttctcact gtgatttgca actgtcctaa ccttggatta  28020
catcaagatc tttgttgcca tctctgtgct gagtataata aatacagaaa ttaaaatata  28080
ctggggctcc tatcgccatc ctgtaaacgc caccgtcttc acccgcccaa gcaaaccaag  28140
gcgaacctta cctggtactt ttaacatctc tccctctgtg atttacaaca gtttcaaccc  28200
agacggagtg agtctacgag agaacctctc cgagctcagc tactccatca gaaaaaacac  28260
caccctcctt acctgccggg aacgtacgag tgcgtcaccg gccgctgcac cacacctacc  28320
gcctgaccgt aaaccagact tttccggac  agacctcaat aactctgttt accagaacag  28380
gaggtgagct tagaaaaccc ttagggtatt aggccaaagg cgcagctact gtggggttta  28440
```

-continued

```
tgaacaattc aagcaactct acgggctatt ctaattcagg tttctctagg gttggggtta  28500
ttctctgtct tgtgattctc tttattctta tactaacgct tctctgccta aggctcgccg  28560
cctgctgtgt gcacatttgc atttattgtc agctttttaa acgctggggt cgccacccaa  28620
gatgattagg tacataatcc taggtttact caccccttgcg tcagcccacg gtaccaccca  28680
aaaggtggat tttaaggagc cagcctgtaa tgttacattc gcagctgaag ctaatgagtg  28740
caccactctt ataaaatgca ccacagaaca tgaaaagctg cttattcgcc acaaaaacaa  28800
aattggcaag tatgctgttt atgctatttg gcagccaggt gacactacag agtataatgt  28860
tacagttttc cagggtaaaa gtcataaaac ttttatgtat acttttccat tttatgaaat  28920
gtgcgacatt accatgtaca tgagcaaaca gtataagttg tggcccccac aaaattgtgt  28980
ggaaaacact ggcactttct gctgcactgc tatgctaatt acagtgctcg ctttggtctg  29040
taccctactc tatattaaat acaaaagcag acgcagcttt attgaggaaa agaaaatgcc  29100
ttaatttact aagttacaaa gctaatgtca ccactaactg ctttactcgc tgcttgcaaa  29160
acaaattcaa aaagttagca ttataattag aataggattt aaaccccccg gtcatttcct  29220
gctcaatacc attcccctga acaattgact ctatgtggga tatgctccag cgctacaacc  29280
ttgaagtcag gcttcctgga tgtcagcatc tgactttggc cagcacctgt cccgcggatt  29340
tgttccagtc caactacagc gacccaccct aacagagatg accaacacaa ccaacgcggc  29400
cgccgctacc ggacttacat ctaccacaaa tacaccccaa gtttctgcct ttgtcaataa  29460
ctgggataac ttgggcatgt ggtggttctc catagcgctt atgtttgtat gccttattat  29520
tatgtggctc atctgctgcc taaagcgcaa acgcgcccga ccacccatct atagtcccat  29580
cattgtgcta cacccaaaca atgatggaat ccatagattg gacggactga aacacatgtt  29640
cttttctctt acagtatgat taaatgagac atgattcctc gagtttttat attactgacc  29700
cttgttgcgc ttttttgtgc gtgctccaca ttggctgcgg tttctcacat cgaagtagac  29760
tgcattccag ccttcacagt ctatttgctt tacggatttg tcaccctcac gctcatctgc  29820
agcctcatca ctgtggtcat cgcctttatc cagtgcattg actgggtctg tgtgcgcttt  29880
gcatatctca gctgctgcca tgttgtgttg ctaccatgtt gttttcatgt gttgctgcca  29940
tgctcttgtc gccttagatc tctctttatg tagtgttgtg gtgtctctct tgtcgtgatg  30000
tgtgttttgt cctatatatt ttaattttta atccaaaccc ctgtccccgc agaggccttt  30060
gcgttctggt aggccgtcat tgaaaactga cttaactcgt taaattaaaa aaatgtaaaa  30120
aataatggtt gagactcagc ccaacatcgg cagatgaggt ggattgagac tcagcccaac  30180
atcggcagat gaggtggatt gagactcaac cccaacattg gcagatgagg tgaattagat  30240
gaggtggatt gagactcatg agggtggtat gagggcccga cgtccacagg tgggagttgt  30300
gctttacagt ccaacgtgca ggacgcttgg catttgccag agaacaccaa gattggcaaa  30360
ttcgcaactg gcgccctgtg ctcttcacag acggaaaaat gaccaaaatc tgattatttt  30420
tgtaaaacgg aaaccgaatg tccgacaaag ttcatttgat gacttcccgg taggtctgcc  30480
ctgccgctgg gccgacgccg tccgggaatt ttacaaacga tttcggacgt ctagcattca  30540
ctcaccttgt caaggacctg aggatctctg caccccttatt aagaccctgt gcggtctcaa  30600
agatcttatt ccctttaact aataaaaaaa aataataaag catcacttac ttaaaatcag  30660
ttagcaaatt tctgtccagt ttattcagca gcacctcctt gccctcctcc cagctctggt  30720
attgcagctt cctcctggct gcaaactttc tccacaatct aaatggaatg tcagtttcct  30780
```

-continued cctgttcctg tccatccgca cccactatct tcatgttgtt gcagatgaag cgcgcaagac 30840
cgtctgaaga taccttcaac cccgtgtatc catatgacac ggaaaccggt cctccaactg 30900
tgccttttct tactcctccc tttgtatccc ccaatgggtt tcaagagagt ccccctgggg 30960
tactctcttt gcgcctatcc gaacctctag ttacctccaa tggcatgctt gcgctcaaaa 31020
tgggcaacgg cctctctctg gacgaggccg gcaaccttac ctcccaaaat gtaaccactg 31080
tgagcccacc tctcaaaaaa accaagtcaa acataaacct ggaaatatct gcacccctca 31140
cagttacctc agaagcccta actgtggctg ccgccgcacc tctaatggtc gcgggcaaca 31200
cactcaccat gcaatcacag gccccgctaa ccgtgcacga ctccaaactt agcattgcca 31260
cccaaggacc cctcacagtg tcagaaggaa agctagccct gcaaacatca ggcccctca 31320 ccaccaccga tagcagtacc cttactatca ctgcctcacc ccctctaact actgccactg 31380
gtagcttggg cattgacttg aaagagccca tttatacaca aaatggaaaa ctaggactaa 31440
agtacggggc tcctttgcat gtaacagacg acctaaacac tttgaccgta gcaactggtc 31500
caggtgtgac tattaataat acttccttgc aaactaaagt tactggagcc ttgggttttg 31560
attcacaagg caatatgcaa cttaatgtag caggaggact aaggattgat tctcaaaaca 31620
gacgccttat acttgatgtt agttatccgt ttgatgctca aaaccaacta aatctaagac 31680
taggacaggg ccctcttttt ataaactcag cccacaactt ggatattaac tacaacaaag 31740
gcctttactt gtttacagct tcaaacaatt ccaaaaagct tgaggttaac ctaagcactg 31800
ccaaggggtt gatgtttgac gctacagcca tagccattaa tgcaggagat gggcttgaat 31860
ttggttcacc taatgcacca aacacaaatc ccctcaaaac aaaaaattggc catggcctag 31920 aatttgattc aaacaaggct atggttccta aactaggaac tggccttagt tttgacagca 31980
caggtgccat tacagtagga aacaaaaata atgataagct aactttgtgg accacaccag 32040
ctccatctcc taactgtaga ctaaatgcag agaaagatgc taaactcact ttggtcttaa 32100
caaaatgtgg cagtcaaata cttgctacag tttcagtttt ggctgttaaa ggcagtttgg 32160
ctccaatatc tggaacagtt caaagtgctc atcttattat aagatttgac gaaaatggag 32220
tgctactaaa caattccttc ctggacccag aatattggaa ctttagaaat ggagatctta 32280
ctgaaggcac agcctataca aacgctgttg gatttatgcc taacctatca gcttatccaa 32340
aatctcacgg taaaactgcc aaaagtaaca ttgtcagtca agtttactta aacggagaca 32400
aaactaaacc tgtaacacta accattacac taaacggtac acaggaaaca ggagacacaa 32460
ctccaagtgc atactctatg tcattttcat gggactggtc tggccacaac tacattaatg 32520
aaatatttgc cacatcctct tacacttttt catacattgc ccaagaataa agaatcgttt 32580
gtgttatgtt tcaacgtgtt tatttttcaa ttgcagaaaa tttcaagtca tttttcattc 32640
agtagtatag ccccaccacc acatagctta tacagatcac cgtaccttaa tcaaactcac 32700
agaaccctag tattcaacct gccacctccc tcccaacaca cagagtacac agtcctttct 32760
ccccggctgg ccttaaaaag catcatatca tgggtaacag acatattctt aggtgttata 32820
ttccacacgg tttcctgtcg agccaaacgc tcatcagtga tattaataaa ctccccgggc 32880
agctcactta agttcatgtc gctgtccagc tgctgagcca caggctgctg tccaacttgc 32940
ggttgcttaa cgggcggcga aggagaagtc cacgcctaca tgggggtaga gtcataatcg 33000
tgcatcagga tagggcggtg gtgctgcagc agcgcgcgaa taaactgctg ccgccgccgc 33060
tccgtcctgc aggaatacaa catggcagtg gtctcctcag cgatgattcg caccgcccgc 33120
agcataaggc gccttgtcct ccgggcacag cagcgcaccc tgatctcact taaatcagca 33180

-continued cagtaactgc agcacagcac cacaatattg ttcaaaatcc cacagtgcaa ggcgctgtat 33240
ccaaagctca tggcggggac cacagaaccc acgtggccat cataccacaa gcgcaggtag 33300
attaagtggc gacccctcat aaacacgctg gacataaaca ttacctcttt tggcatgttg 33360
taattcacca cctcccggta ccatataaac ctctgattaa acatggcgcc atccaccacc 33420
atcctaaacc agctggccaa aacctgcccg ccggctatac actgcaggga accgggactg 33480
gaacaatgac agtggagagc ccaggactcg taaccatgga tcatcatgct cgtcatgata 33540
tcaatgttgg cacaacacag gcacacgtgc atacacttcc tcaggattac aagctcctcc 33600
cgcgttagaa ccatatccca gggaacaacc cattcctgaa tcagcgtaaa tcccacactg 33660
cagggaagac ctcgcacgta actcacgttg tgcattgtca aagtgttaca ttcgggcagc 33720
agcggatgat cctccagtat ggtagcgcgg gtttctgtct caaaaggagg tagacgatcc 33780
ctactgtacg gagtgcgccg agacaaccga gatcgtgttg gtcgtagtgt catgccaaat 33840
ggaacgccgg acgtagtcat atttcctgaa gcaaaaccag gtgcgggcgt gacaaacaga 33900
tctgcgtctc cggtctcgcc gcttagatcg ctctgtgtag tagttgtagt atatccactc 33960
tctcaaagca tccaggcgcc ccctggcttc gggttctatg taaactcctt catgcgccgc 34020
tgccctgata acatccacca ccgcagaata agccacaccc agccaaccta cacattcgtt 34080
ctgcgagtca cacacgggag gagcgggaag agctggaaga accatgtttt tttttttatt 34140
ccaaaagatt atccaaaacc tcaaaatgaa gatctattaa gtgaacgcgc tcccctccgg 34200
tggcgtggtc aaactctaca gccaaagaac agataatggc atttgtaaga tgttgcacaa 34260
tggcttccaa aaggcaaacg gccctcacgt ccaagtggac gtaaaggcta aacccttcag 34320
ggtgaatctc ctctataaac attccagcac cttcaaccat gcccaaataa ttctcatctc 34380
gccaccttct caatatatct ctaagcaaat cccgaatatt aagtccggcc attgtaaaaa 34440
tctgctccag agcgccctcc accttcagcc tcaagcagcg aatcatgatt gcaaaaattc 34500
aggttcctca cagacctgta taagattcaa aagcggaaca ttaacaaaaa taccgcgatc 34560
ccgtaggtcc cttcgcaggg ccagctgaac ataatcgtgc aggtctgcac ggaccagcgc 34620
ggccacttcc ccgccaggaa ccttgacaaa agaacccaca ctgattatga cacgcatact 34680
cggagctatg ctaaccagcg tagccccgat gtaagctttg ttgcatgggc ggcgatataa 34740
aatgcaaggt gctgctcaaa aaatcaggca aagcctcgcg caaaaaagaa agcacatcgt 34800
agtcatgctc atgcagataa aggcaggtaa gctccggaac caccacagaa aaagacacca 34860
tttttctctc aaacatgtct gcgggtttct gcataaacac aaaataaaat aacaaaaaaa 34920
catttaaaca ttagaagcct gtcttacaac aggaaaaaca acccttataa gcataagacg 34980
gactacggcc atgccggcgt gaccgtaaaa aaactggtca ccgtgattaa aaagcaccac 35040
cgacagctcc tcggtcatgt ccggagtcat aatgtaagac tcggtaaaca catcaggttg 35100
attcatcggt cagtgctaaa aagcgaccga aatagcccgg gggaatacat acccgcaggc 35160
gtagagacaa cattacagcc cccataggag gtataacaaa attaatagga gagaaaaaca 35220
cataaacacc tgaaaaaccc tcctgcctag gcaaaatagc accctcccgc tccagaacaa 35280
catacagcgc ttcacagcgg cagcctaaca gtcagcctta ccagtaaaaa agaaaaccta 35340
ttaaaaaaac accactcgac acggcaccag ctcaatcagt cacagtgtaa aaaagggcca 35400
agtgcgttac actgcagcag gtgtgactca gccatggcac ctctgcagcc tgggtaccct 35460
gcttggggca tggcccctta tagctgggcg gggcgtgggg gctctgtagg agtggcagcg 35520

-continued

```
acctcagtgt ttgtctttgc tctgaagagc cctccaggtg cttgatccca ccttttccca  35580

gcaggaacac tcctgcctgc cttaccacct gtcctggctg atggcctgtt cctgcctcct  35640

ttgccccctg cccagactcc catgttcctg gacttgtggc ttcctccaac caggggctct  35700

caagcctcca tacctggtcc cacctctcca ggccgtggga gggaggttga ggagggtgga  35760

gggcatctgg ttgggggcag cctgggtgtt cccctcccat cccctccctg ggcctcccag  35820

gccccctcta ctcttgagca atgctcttga gagcttcctg cctggctctt aacccagggc  35880

aagccctgga agggcagacc caggacactc tcaccacctc cttacctttt cccctggaaa  35940

aatcttctgt atacttccca ttttaagaaa actacaattc ccaacacata caagttactc  36000

cgccctaaaa cctacgtcac ccgccccgtt cccacgcccc gcgccacgtc acaaactcca  36060

ccccctcatt atcatattgg cttcaatcca aaataaggta tattattgat gatg        36114
```

<210> SEQ ID NO 17
<211> LENGTH: 40
<212> TYPE: PRT
<213> ORGANISM: Adenovirus subgroup C

<400> SEQUENCE: 17

```
Met Thr Gly Ser Thr Ile Ala Pro Thr Thr Asp Tyr Arg Asn Thr Thr
1               5                   10                  15

Ala Thr Gly Leu Thr Ser Ala Leu Asn Leu Pro Gln Val His Ala Phe
            20                  25                  30

Val Asn Asp Trp Ala Ser Leu Asp
        35                  40
```

<210> SEQ ID NO 18
<211> LENGTH: 19
<212> TYPE: PRT
<213> ORGANISM: Adenovirus subgroup C

<400> SEQUENCE: 18

```
Met Trp Trp Phe Ser Ile Ala Leu Met Phe Val Cys Leu Ile Ile Met
1               5                   10                  15

Trp Leu Ile
```

<210> SEQ ID NO 19
<211> LENGTH: 8
<212> TYPE: PRT
<213> ORGANISM: Adenovirus subgroup C

<400> SEQUENCE: 19

```
Lys Arg Arg Arg Ala Arg Pro Pro
1               5
```

<210> SEQ ID NO 20
<211> LENGTH: 42
<212> TYPE: PRT
<213> ORGANISM: Adenovirus subgroup C

<400> SEQUENCE: 20

```
Cys Cys Leu Lys Arg Arg Arg Ala Arg Pro Pro Ile Tyr Arg Pro Ile
1               5                   10                  15

Ile Val Leu Asn Pro His Asn Glu Lys Ile His Arg Leu Asp Gly Leu
            20                  25                  30

Lys Pro Cys Ser Leu Leu Leu Gln Tyr Asp
        35                  40
```

```
<210> SEQ ID NO 21
<211> LENGTH: 11
<212> TYPE: DNA
<213> ORGANISM: Adenovirus subgroup C

<400> SEQUENCE: 21

ccttaattaa a                                                            11

<210> SEQ ID NO 22
<211> LENGTH: 10
<212> TYPE: DNA
<213> ORGANISM: Adenovirus subgroup C

<400> SEQUENCE: 22

ttaattaagg                                                              10

<210> SEQ ID NO 23
<211> LENGTH: 8
<212> TYPE: DNA
<213> ORGANISM: Adenovirus subgroup C

<400> SEQUENCE: 23

ttaattaa                                                                 8

<210> SEQ ID NO 24
<211> LENGTH: 11
<212> TYPE: DNA
<213> ORGANISM: Adenovirus subgroup C

<400> SEQUENCE: 24

ccttaattaa a                                                            11

<210> SEQ ID NO 25
<211> LENGTH: 10
<212> TYPE: DNA
<213> ORGANISM: Adenovirus subgroup C

<400> SEQUENCE: 25

ttaattaagg                                                              10

<210> SEQ ID NO 26
<211> LENGTH: 11
<212> TYPE: DNA
<213> ORGANISM: Adenovirus subgroup C

<400> SEQUENCE: 26

ccttaattaa a                                                            11

<210> SEQ ID NO 27
<211> LENGTH: 10
<212> TYPE: DNA
<213> ORGANISM: Adenovirus subgroup C

<400> SEQUENCE: 27

ttaattaagg                                                              10

<210> SEQ ID NO 28
<211> LENGTH: 35935
<212> TYPE: DNA
<213> ORGANISM: Adenovirus subgroup C

<400> SEQUENCE: 28

catcatcaat aatatacctt attttggatt gaagccaata tgataatgag ggggtggagt        60
```

-continued

```
ttgtgacgtg gcgcggggcg tgggaacggg gcgggtgacg tagtagtgtg gcggaagtgt    120

gatgttgcaa gtgtggcgga acacatgtaa gcgacggatg tggcaaaagt gacgtttttg    180

gtgtgcgccg gtgtacacag gaagtgacaa ttttcgcgcg gttttaggcg gatgttgtag    240

taaatttggg cgtaaccgag taagatttgg ccattttcgc gggaaaactg aataagagga    300

agtgaaatct gaataatttt gtgttactca tagcgcgtaa tatttgtcta gggccgcggg    360

gactttgacc gtttacgtgg agactcgccc aggtgttttt ctcaggtgtt ttccgcgttc    420

cgggtcaaag ttggcgtttt attattatag tcagctgacg tgtagtgtat ttatacccgg    480

tgagttcctc aagaggccac tcttgagtgc cagcgagtag agttttctcc tccgagccgc    540

tccgacaccg ggactgaaaa tgagacatat tatctgccac ggaggtgtta ttaccgaaga    600

aatggccgcc agtcttttgg accagctgat cgaagaggta ctggctgata atcttccacc    660

tcctagccat tttgaaccac ctacccttca cgaactgtat gatttagacg tgacggcccc    720

cgaagatccc aacgaggagg cggtttcgca gatttttccc gactctgtaa tgttggcggt    780

gcaggaaggg attgacttac tcacttttcc gccggcgccc ggttctccgg agccgcctca    840

cctttcccgg cagcccgagc agccggagca gagagccttg ggtccggttt ctatgccaaa    900

ccttgtaccg gaggtgatcg atcttacctg ccacgaggct ggctttccac ccagtgacga    960

cgaggatgaa gagggtgagg agtttgtgtt agattatgtg gagcaccccg ggcacggttg   1020

caggtcttgt cattatcacc ggaggaatac gggggaccca gatattatgt gttcgctttg   1080

ctatatgagg acctgtggca tgtttgtcta cagtaagtga aaattatggg cagtgggtga   1140

tagagtggtg ggtttggtgt ggtaattttt tttttaattt ttacagtttt gtggtttaaa   1200

gaattttgta ttgtgatttt tttaaaaggt cctgtgtctg aacctgagcc tgagcccgag   1260

ccagaaccgg agcctgcaag acctacccgc cgtcctaaaa tggcgcctgc tatcctgaga   1320

cgcccgacat cacctgtgtc tagagaatgc aatagtagta cggatagctg tgactccggt   1380

ccttctaaca cacctcctga gatacacccg gtggtcccgc tgtgccccat taaaccagtt   1440

gccgtgagag ttggtgggcg tcgccaggct gtggaatgta tcgaggactt gcttaacgag   1500

cctgggcaac ctttggactt gagctgtaaa cgccccaggc cataaggtgt aaacctgtga   1560

ttgcgtgtgt ggttaacgcc tttgtttgct gaatgagttg atgtaagttt aataaagggt   1620

gagataatgt ttaacttgca tggcgtgtta aatggggcgg ggcttaaagg gtatataatg   1680

cgccgtgggc taatcttggt tacatctgac ctcatggagg cttgggagtg tttggaagat   1740

ttttctgctg tgcgtaactt gctggaacag agctctaaca gtacctcttg gttttggagg   1800

tttctgtggg gctcatccca ggcaaagtta gtctgcagaa ttaaggagga ttacaagtgg   1860

gaatttgaag agcttttgaa atcctgtggt gagctgtttg attctttgaa tctgggtcac   1920

caggcgcttt tccaagagaa ggtcatcaag actttggatt tttccacacc ggggcgcgct   1980

gcggctgctg ttgctttttt gagttttata aaggataaat ggagcgaaga aacccatctg   2040

agcggggggt acctgctgga ttttctggcc atgcatctgt ggagagcggt tgtgagacac   2100

aagaatcgcc tgctactgtt gtcttccgtc cgcccggcga taataccgac ggaggagcag   2160

cagcagcagc aggaggaagc caggcggcgg cggcaggagc agagcccatg gaacccgaga   2220

gccggcctgg accctcggga atgaatgttg tacaggtggc tgaactgtat ccagaactga   2280

gacgcatttt gacaattaca gaggatgggc aggggctaaa gggggtaaag agggagcggg   2340

gggcttgtga ggctacagag gaggctagga atctagcttt tagcttaatg accagacacc   2400

gtcctgagtg tattactttt caacagatca aggataattg cgctaatgag cttgatctgc   2460
```

-continued

```
tggcgcagaa gtattccata gagcagctga ccacttactg gctgcagcca ggggatgatt   2520
ttgaggaggc tattagggta tatgcaaagg tggcacttag gccagattgc aagtacaaga   2580
tcagcaaact tgtaaatatc aggaattgtt gctacatttc tgggaacggg gccgaggtgg   2640
agatagatac ggaggatagg gtggccttta gatgtagcat gataaatatg tggccggggg   2700
tgcttggcat ggacggggtg gttattatga atgtaaggtt tactggcccc aattttagcg   2760
gtacggtttt cctggccaat accaacctta tcctacacgg tgtaagcttc tatgggttta   2820
acaatacctg tgtggaagcc tggaccgatg taagggttcg ggctgtgcc ttttactgct   2880
gctggaaggg ggtggtgtgt cgccccaaaa gcagggcttc aattaagaaa tgcctctttg   2940
aaaggtgtac cttgggtatc ctgtctgagg gtaactccag ggtgcgccac aatgtggcct   3000
ccgactgtgg ttgcttcatg ctagtgaaaa gcgtggctgt gattaagcat aacatggtat   3060
gtggcaactg cgaggacagg gcctctcaga tgctgacctg ctcggacggc aactgtcacc   3120
tgctgaagac cattcacgta gccagccact ctcgcaaggc ctggccagtg tttgagcata   3180
acatactgac ccgctgttcc ttgcatttgg gtaacaggag gggggtgttc ctaccttacc   3240
aatgcaattt gagtcacact aagatattgc ttgagcccga gagcatgtcc aaggtgaacc   3300
tgaacggggt gtttgacatg accatgaaga tctggaaggt gctgaggtac gatgagaccc   3360
gcaccaggtg cagaccctgc gagtgtggcg gtaaacatat taggaaccag cctgtgatgc   3420
tggatgtgac cgaggagctg aggcccgatc acttggtgct ggcctgcacc cgcgctgagt   3480
ttggctctag cgatgaagat acagattgag gtactgaaat gtgtgggcgt ggcttaaggg   3540
tgggaaagaa tatataaggt gggggtctta tgtagttttg tatctgtttt gcagcagccg   3600
ccgccgccat gagcaccaac tcgtttgatg gaagcattgt gagctcatat ttgacaacgc   3660
gcatgccccc atgggccggg gtgcgtcaga atgtgatggg ctccagcatt gatggtcgcc   3720
ccgtcctgcc cgcaaactct actaccttga cctacgagac cgtgtctgga acgccgttgg   3780
agactgcagc ctccgccgcc gcttcagccg ctgcagccac cgcccgcggg attgtgactg   3840
actttgcttt cctgagcccg cttgcaagca gtgcagcttc ccgttcatcc gcccgcgatg   3900
acaagttgac ggctcttttg gcacaattgg attctttgac ccgggaactt aatgtcgttt   3960
ctcagcagct gttggatctg cgccagcagg tttctgccct gaaggcttcc tcccctccca   4020
atgcggttta aaacataaat aaaaaaccag actctgtttg gatttggatc aagcaagtgt   4080
cttgctgtct ttatttaggg gttttgcgcg cgcggtaggc ccgggaccag cggtctcggt   4140
cgttgagggt cctgtgtatt ttttccagga cgtggtaaag gtgactctgg atgttcagat   4200
acatgggcat aagcccgtct ctggggtgga ggtagcacca ctgcagagct tcatgctgcg   4260
gggtggtgtt gtagatgatc cagtcgtagc aggagcgctg ggcgtggtgc ctaaaaatgt   4320
ctttcagtag caagctgatt gccaggggca ggcccttggt gtaagtgttt acaaagcggt   4380
taagctggga tgggtgcata cgtggggata tgagatgcat cttggactgt atttttaggt   4440
tggctatgtt cccagccata tccctccggg gattcatgtt gtgcagaacc accagcacag   4500
tgtatccggt gcacttggga aatttgtcat gtagcttaga aggaaatgcg tggaagaact   4560
tggagacgcc cttgtgacct ccaagatttt ccatgcattc gtccataatg atggcaatgg   4620
gcccacgggc ggcggcctgg gcgaagatat ttctgggatc actaacgtca tagttgtgtt   4680
ccaggatgag atcgtcatag gccattttta caaagcgcgg gcggagggtg ccagactgcg   4740
gtataatggt tccatccggc ccaggggcgt agttaccctc acagatttgc atttcccacg   4800
```

-continued

```
ctttgagttc agatgggggg atcatgtcta cctgcggggc gatgaagaaa acggtttccg   4860
gggtagggga gatcagctgg gaagaaagca ggttcctgag cagctgcgac ttaccgcagc   4920
cggtgggccc gtaaatcaca cctattaccg ggtgcaactg gtagttaaga gagctgcagc   4980
tgccgtcatc cctgagcagg ggggccactt cgttaagcat gtccctgact cgcatgtttt   5040
ccctgaccaa atccgccaga aggcgctcgc cgcccagcga tagcagttct tgcaaggaag   5100
caaagttttt caacggtttg agaccgtccg ccgtaggcat gcttttgagc gtttgaccaa   5160
gcagttccag gcggtcccac agctcggtca cctgctctac ggcatctcga tccagcatat   5220
ctcctcgttt cgcgggttgg ggcggctttc gctgtacggc agtagtcggt gctcgtccag   5280
acgggccagg gtcatgtctt tccacgggcg cagggtcctc gtcagcgtag tctgggtcac   5340
ggtgaagggg tgcgctccgg gctgcgcgct ggccagggtg cgcttgaggc tggtcctgct   5400
ggtgctgaag cgctgccggt cttcgccctg cgcgtcggcc aggtagcatt tgaccatggt   5460
gtcatagtcc agcccctccg cggcgtggcc cttggcgcgc agcttgccct tggaggaggc   5520
gccgcacgag gggcagtgca gacttttgag ggcgtagagc ttgggcgcga gaaataccga   5580
ttccggggag taggcatccg cgccgcaggc cccgcagacg gtctcgcatt ccacgagcca   5640
ggtgagctct ggccgttcgg ggtcaaaaac caggtttccc ccatgctttt tgatgcgttt   5700
cttacctctg gtttccatga gccggtgtcc acgctcggtg acgaaaaggc tgtccgtgtc   5760
cccgtataca gacttgagag gcctgtcctc gagcggtgtt ccgcggtcct cctcgtatag   5820
aaactcggac cactctgaga caaaggctcg cgtccaggcc agcacgaagg aggctaagtg   5880
ggaggggtag cggtcgttgt ccactagggg gtccactcgc tccagggtgt gaagacacat   5940
gtcgccctct tcggcatcaa ggaaggtgat tggtttgtag gtgtaggcca cgtgaccggg   6000
tgttcctgaa ggggggctat aaaagggggt gggggcgcgt tcgtcctcac tctcttccgc   6060
atcgctgtct gcgagggcca gctgttgggg tgagtactcc ctctgaaaag cgggcatgac   6120
ttctgcgcta agattgtcag tttccaaaaa cgaggaggat ttgatattca cctggcccgc   6180
ggtgatgcct ttgagggtgg ccgcatccat ctggtcagaa aagacaatct ttttgttgtc   6240
aagcttggtg gcaaacgacc cgtagagggc gttggacagc aacttggcga tggagcgcag   6300
ggtttggttt ttgtcgcgat cggcgcgctc cttggccgcg atgtttagct gcacgtattc   6360
gcgcgcaacg caccgccatt cgggaaagac ggtggtgcgc tcgtcgggca ccaggtgcac   6420
gcgccaaccg cggttgtgca gggtgacaag gtcaacgctg gtggctacct ctccgcgtag   6480
gcgctcgttg gtccagcaga ggcggccgcc cttgcgcgag cagaatggcg gtagggggtc   6540
tagctgcgtc tcgtccgggg ggtctgcgtc cacggtaaag accccgggca gcaggcgcgc   6600
gtcgaagtag tctatcttgc atccttgcaa gtctagcgcc tgctgccatg cgcgggcggc   6660
aagcgcgcgc tcgtatgggt tgagtggggg accccatggc atggggtggg tgagcgcgga   6720
ggcgtacatg ccgcaaatgt cgtaaacgta gaggggctct ctgagtattc caagatatgt   6780
agggtagcat cttccaccgc ggatgctggc gcgcacgtaa tcgtatagtt cgtgcgaggg   6840
agcgaggagg tcgggaccga ggttgctacg ggcgggctgc tctgctcgga agactatctg   6900
cctgaagatg gcatgtgagt tggatgatat ggttggacgc tggaagacgt tgaagctggc   6960
gtctgtgaga cctaccgcgt cacgcacgaa ggaggcgtag gagtcgcgca gcttgttgac   7020
cagctcggcg gtgacctgca cgtctagggc gcagtagtcc agggtttcct tgatgatgtc   7080
atacttatcc tgtccctttt ttttccacag ctcgcggttg aggacaaact cttcgcggtc   7140
tttccagtac tcttggatcg gaaacccgtc ggcctccgaa cggtaagagc ctagcatgta   7200
```

-continued

```
gaactggttg acggcctggt aggcgcagca tccctttttct acgggtagcg cgtatgcctg   7260
cgcggccttc cggagcgagg tgtgggtgag cgcaaaggtg tccctgacca tgactttgag   7320
gtactggtat ttgaagtcag tgtcgtcgca tccgccctgc tcccagagca aaaagtccgt   7380
gcgctttttg gaacgcggat ttggcagggc gaaggtgaca tcgttgaaga gtatctttcc   7440
cgcgcgaggc ataaagttgc gtgtgatgcg gaagggtccc ggcacctcgg aacggttgtt   7500
aattacctgg gcggcgagca cgatctcgtc aaagccgttg atgttgtggc ccacaatgta   7560
aagttccaag aagcgcggga tgcccttgat ggaaggcaat tttttaagtt cctcgtaggt   7620
gagctcttca ggggagctga gcccgtgctc tgaaagggcc cagtctgcaa gatgagggtt   7680
ggaagcgacg aatgagctcc acaggtcacg ggccattagc atttgcaggt ggtcgcgaaa   7740
ggtcctaaac tggcgaccta tggccatttt ttctggggtg atgcagtaga aggtaagcgg   7800
gtcttgttcc cagcggtccc atccaaggtt cgcggctagg tctcgcgcgg cagtcactag   7860
aggctcatct ccgccgaact tcatgaccag catgaagggc acgagctgct tcccaaaggc   7920
ccccatccaa gtataggtct ctacatcgta ggtgacaaag agacgctcgg tgcgaggatg   7980
cgagccgatc gggaagaact ggatctcccg ccaccaattg gaggagtggc tattgatgtg   8040
gtgaaagtag aagtccctgc gacgggccga acactcgtgc tggcttttgt aaaaacgtgc   8100
gcagtactgg cagcggtgca cgggctgtac atcctgcacg aggttgacct gacgaccgcg   8160
cacaaggaag cagagtggga atttgagccc ctcgcctggc gggtttggct ggtggtcttc   8220
tacttcggct gcttgtcctt gaccgtctgg ctgctcgagg ggagttacgg tggatcggac   8280
caccacgccg cgcgagccca aagtccagat gtccgcgcgc ggcggtcgga gcttgatgac   8340
aacatcgcgc agatgggagc tgtccatggt ctggagctcc cgcggcgtca ggtcaggcgg   8400
gagctcctgc aggtttacct cgcatagacg ggtcagggcg cgggctagat ccaggtgata   8460
cctaatttcc aggggctggt tggtggcggc gtcgatggct tgcaagaggc cgcatccccg   8520
cggcgcgact acggtaccgc gcggcgggcg gtgggccgcg ggggtgtcct tggatgatgc   8580
atctaaaagc ggtgacgcgg gcgagccccc ggaggtaggg ggggctccgg acccgccggg   8640
agagggggca ggggcacgtc ggcgccgcgc gcgggcagga gctggtgctg cgcgcgtagg   8700
ttgctggcga acgcgacgac gcggcggttg atctcctgaa tctggcgcct ctgcgtgaag   8760
acgacgggcc cggtgagctt gagcctgaaa gagagttcga cagaatcaat ttcggtgtcg   8820
ttgacggcgg cctggcgcaa aatctcctgc acgtctcctg agttgtcttg ataggcgatc   8880
tcggccatga actgctcgat ctcttcctcc tggagatctc cgcgtccggc tcgctccacg   8940
gtggcggcga ggtcgttgga aatgcgggcc atgagctgcg agaaggcgtt gaggcctccc   9000
tcgttccaga cgcggctgta gaccacgccc ccttcggcat cgcgggcgcg catgaccacc   9060
tgcgcgagat tgagctccac gtgccgggcg aagacggcgt agtttcgcag gcgctgaaag   9120
aggtagttga gggtggtggc ggtgtgttct gccacgaaga agtacataac ccagcgtcgc   9180
aacgtggatt cgttgatatc ccccaaggcc tcaaggcgct ccatggcctc gtagaagtcc   9240
acggcgaagt tgaaaaactg ggagttgcgc gccgacacgg ttaactcctc ctccagaaga   9300
cggatgagct cggcgacagt gtcgcgcacc tcgcgctcaa aggctacagg ggcctcttct   9360
tcttcttcaa tctcctcttc cataagggcc tccccttctt cttcttctgg cggcggtggg   9420
ggagggggga cacggcggcg acgacggcgc accgggaggc ggtcgacaaa gcgctcgatc   9480
atctccccgc ggcgacggcg catggtctcg gtgacggcgc ggccgttctc gcgggggcgc   9540
```

-continued

```
agttggaaga cgccgcccgt catgtcccgg ttatgggttg gcggggggct gccatgcggc   9600
agggatacgg cgctaacgat gcatctcaac aattgttgtg taggtactcc gccgccgagg   9660
gacctgagcg agtccgcatc gaccggatcg gaaaacctct cgagaaaggc gtctaaccag   9720
tcacagtcgc aaggtaggct gagcaccgtg gcgggcggca gcgggcggcg gtcggggttg   9780
tttctggcgg aggtgctgct gatgatgtaa ttaaagtagg cggtcttgag acggcggatg   9840
gtcgacagaa gcaccatgtc cttgggtccg gcctgctgaa tgcgcaggcg gtcggccatg   9900
ccccaggctt cgttttgaca tcggcgcagg tctttgtagt agtcttgcat gagcctttct   9960
accggcactt cttcttctcc ttcctcttgt cctgcatctc ttgcatctat cgctgcggcg  10020
gcggcggagt ttggccgtag gtggcgccct cttcctccca tgcgtgtgac cccgaagccc  10080
ctcatcggct gaagcagggc taggtcggcg acaacgcgct cggctaatat ggcctgctgc  10140
acctgcgtga gggtagactg gaagtcatcc atgtccacaa agcggtggta tgcgcccgtg  10200
ttgatggtgt aagtgcagtt ggccataacg gaccagttaa cggtctggtg acccggctgc  10260
gagagctcgg tgtacctgag acgcgagtaa gccctcgagt caaatacgta gtcgttgcaa  10320
gtccgcacca ggtactggta tcccaccaaa aagtgcggcg gcggctggcg gtagaggggc  10380
cagcgtaggg tggccggggc tccgggggcg agatcttcca acataaggcg atgatatccg  10440
tagatgtacc tggacatcca ggtgatgccg gcggcggtgg tggaggcgcg cggaaagtcg  10500
cggacgcggt tccagatgtt gcgcagcggc aaaaagtgct ccatggtcgg gacgctctgg  10560
ccggtcaggc gcgcgcaatc gttgacgctc tagaccgtgc aaaaggagag cctgtaagcg  10620
ggcactcttc cgtggtctgg tggataaatt cgcaagggta tcatggcgga cgaccggggt  10680
tcgagccccg tatccggccg tccgccgtga tccatgcggt taccgcccgc gtgtcgaacc  10740
caggtgtgcg acgtcagaca acgggggagt gctccttttg gcttccttcc aggcgcggcg  10800
gctgctgcgc tagctttttt ggccactggc cgcgcgcagc gtaagcggtt aggctggaaa  10860
gcgaaagcat taagtggctc gctccctgta gccggagggt tattttccaa gggttgagtc  10920
gcgggacccc cggttcgagt ctcggaccgg ccggactgcg gcgaacgggg gtttgcctcc  10980
ccgtcatgca agaccccgct tgcaaattcc tccggaaaca gggacgagcc cctttttttgc  11040
ttttcccaga tgcatccggt gctgcggcag atgcgccccc ctcctcagca gcggcaagag  11100
caagagcagc ggcagacatg cagggcaccc tcccctcctc ctaccgcgtc aggaggggcg  11160
acatccgcgg ttgacgcggc agcagatggt gattacgaac cccgcggcg ccgggcccgg  11220
cactacctgg acttggagga gggcgagggc ctggcgcggc taggagcgcc ctctcctgag  11280
cggtacccaa gggtgcagct gaagcgtgat acgcgtgagg cgtacgtgcc gcggcagaac  11340
ctgtttcgcg accgcgaggg agaggagccc gaggagatgc gggatcgaaa gttccacgca  11400
gggcgcgagc tgcggcatgg cctgaatcgc gagcggttgc tgcgcgagga ggactttgag  11460
cccgacgcgc gaaccgggat tagtcccgcg cgcgcacacg tggcggccgc cgacctggta  11520
accgcatacg agcagacggt gaaccaggag attaactttc aaaaaagctt taacaaccac  11580
gtgcgtacgc ttgtggcgcg cgaggaggtg gctataggac tgatgcatct gtgggacttt  11640
gtaagcgcgc tggagcaaaa cccaaatagc aagccgctca tggcgcagct gttccttata  11700
gtgcagcaca gcagggacaa cgaggcattc agggatgcgc tgctaaacat agtagagccc  11760
gagggccgct ggctgctcga tttgataaac atcctgcaga gcatagtggt gcaggagcgc  11820
agcttgagcc tggctgacaa ggtggccgcc atcaactatt ccatgcttag cctgggcaag  11880
ttttacgccc gcaagatata ccatacccct tacgttccca tagacaagga ggtaaagatc  11940
```

-continued gaggggttct acatgcgcat ggcgctgaag gtgcttacct tgagcgacga cctgggcgtt 12000
tatcgcaacg agcgcatcca caaggccgtg agcgtgagcc ggcggcgcga gctcagcgac 12060
cgcgagctga tgcacagcct gcaaagggcc ctggctggca cgggcagcgg cgatagagag 12120
gccgagtcct actttgacgc gggcgctgac ctgcgctggg ccccaagccg acgcgccctg 12180
gaggcagctg gggccggacc tgggctggcg gtggcacccg cgcgcgctgg caacgtcggc 12240
ggcgtggagg aatatgacga ggacgatgag tacgagccag aggacggcga gtactaagcg 12300
gtgatgtttc tgatcagatg atgcaagacg caacggaccc ggcggtgcgg gcggcgctgc 12360
agagccagcc gtccggcctt aactccacgg acgactggcg ccaggtcatg gaccgcatca 12420
tgtcgctgac tgcgcgcaat cctgacgcgt tccggcagca gccgcaggcc aaccggctct 12480
ccgcaattct ggaagcggtg gtcccggcgc gcgcaaaccc cacgcacgag aaggtgctgg 12540
cgatcgtaaa cgcgctggcc gaaaacaggg ccatccggcc cgacgaggcc ggcctggtct 12600
acgacgcgct gcttcagcgc gtggctcgtt acaacagcgg caacgtgcag accaacctgg 12660
accggctggt gggggatgtg cgcgaggccg tggcgcagcg tgagcgcgcg cagcagcagg 12720
gcaacctggg ctccatggtt gcactaaacg ccttcctgag tacacagccc gccaacgtgc 12780
cgcggggaca ggaggactac accaactttg tgagcgcact gcggctaatg gtgactgaga 12840
caccgcaaag tgaggtgtac cagtctgggc cagactattt tttccagacc agtagacaag 12900
gcctgcagac cgtaaacctg agccaggctt tcaaaaactt gcaggggctg tggggggtgc 12960
gggctcccac aggcgaccgc gcgaccgtgt ctagcttgct gacgcccaac tcgcgcctgt 13020
tgctgctgct aatagcgccc ttcacggaca gtggcagcgt gtcccgggac acatacctag 13080
gtcacttgct gacactgtac cgcgaggcca taggtcaggc gcatgtggac gagcatactt 13140
tccaggagat tacaagtgtc agccgcgcgc tggggcagga ggacacgggc agcctggagg 13200
caaccctaaa ctacctgctg accaaccggc ggcagaagat cccctcgttg cacagtttaa 13260
acagcgagga ggagcgcatt ttgcgctacg tgcagcagag cgtgagcctt aacctgatgc 13320
gcgacggggt aacgcccagc gtggcgctgg acatgaccgc gcgcaacatg gaaccgggca 13380
tgtatgcctc aaaccggccg tttatcaacc gcctaatgga ctacttgcat cgcgcggccg 13440
ccgtgaaccc cgagtatttc accaatgcca tcttgaaccc gcactggcta ccgccccctg 13500
gtttctacac cgggggattc gaggtgcccg agggtaacga tggattcctc tgggacgaca 13560
tagacgacag cgtgttttcc ccgcaaccgc agaccctgct agagttgcaa cagcgcgagc 13620
aggcagaggc ggcgctgcga aaggaaagct tccgcaggcc aagcagcttg tccgatctag 13680
gcgctgcggc cccgcggtca gatgctagta gcccatttcc aagcttgata gggtctctta 13740
ccagcactcg caccacccgc ccgcgcctgc tgggcgagga ggagtaccta aacaactcgc 13800
tgctgcagcc gcagcgcgaa aaaaacctgc ctccggcatt tcccaacaac gggatagaga 13860
gcctagtgga caagatgagt agatggaaga cgtacgcgca ggagcacagg gacgtgccag 13920
gcccgcgccc gcccacccgt cgtcaaaggc acgaccgtca gcggggtctg gtgtgggagg 13980
acgatgactc ggcagacgac agcagcgtcc tggatttggg agggagtggc aacccgtttg 14040
cgcaccttcg ccccaggctg gggagaatgt tttaaaaaaa aaaaagcatg atgcaaaata 14100
aaaaactcac caaggccatg gcaccgagcg ttggttttct tgtattcccc ttagtatgcg 14160
gcgcgcggcg atgtatgagg aaggtcctcc tccctcctac gagagtgtgg tgagcgcggc 14220
gccagtggcg gcggcgctgg gttctccctt cgatgctccc ctggacccgc cgtttgtgcc 14280

-continued

```
tccgcggtac ctgcggccta ccggggggag aaacagcatc cgttactctg agttggcacc  14340
cctattcgac accacccgtg tgtacctggt ggacaacaag tcaacggatg tggcatccct  14400
gaactaccag aacgaccaca gcaactttct gaccacggtc attcaaaaca atgactacag  14460
cccgggggag gcaagcacac agaccatcaa tcttgacgac cggtcgcact ggggcggcga  14520
cctgaaaacc atcctgcata ccaacatgcc aaatgtgaac gagttcatgt ttaccaataa  14580
gtttaaggcg cgggtgatgg tgtcgcgctt gcctactaag gacaatcagg tggagctgaa  14640
atacgagtgg gtggagttca cgctgcccga gggcaactac tccgagacca tgaccataga  14700
ccttatgaac aacgcgatcg tggagcacta cttgaaagtg ggcagacaga acggggttct  14760
ggaaagcgac atcggggtaa agtttgacac ccgcaacttc agactggggt ttgaccccgt  14820
cactggtctt gtcatgcctg ggtatatac aaacgaagcc ttccatccag acatcatttt  14880
gctgccagga tgcggggtgg acttcaccca cagccgcctg agcaacttgt tgggcatccg  14940
caagcggcaa cccttccagg agggctttag gatcacctac gatgatctgg agggtggtaa  15000
cattcccgca ctgttggatg tggacgccta ccaggcgagc ttgaaagatg acaccgaaca  15060
gggcgggggt ggcgcaggcg gcagcaacag cagtggcagc ggcgcggaag agaactccaa  15120
cgcggcagcc gcggcaatgc agccggtgga ggacatgaac gatcatgcca ttcgcggcga  15180
cacctttgcc acacgggctg aggagaagcg cgctgaggcc gaagcagcgg ccgaagctgc  15240
cgcccccgct gcgcaacccg aggtcgagaa gcctcagaag aaaccggtga tcaaacccct  15300
gacagaggac agcaagaaac gcagttacaa cctaataagc aatgacagca ccttcaccca  15360
gtaccgcagc tggtaccttg catacaacta cggcgaccct cagaccggaa tccgctcatg  15420
gaccctgctt tgcactcctg acgtaacctg cggctcggag caggtctact ggtcgttgcc  15480
agacatgatg caagaccccg tgaccttccg ctccacgcgc cagatcagca actttccggt  15540
ggtgggcgcc gagctgttgc ccgtgcactc caagagcttc tacaacgacc aggccgtcta  15600
ctcccaactc atccgccagt ttacctctct gacccacgtg ttcaatcgct ttcccgagaa  15660
ccagattttg gcgcgcccgc cagcccccac catcaccacc gtcagtgaaa acgttcctgc  15720
tctcacagat cacgggacgc taccgctgcg caacagcatc ggaggagtcc agcgagtgac  15780
cattactgac gccagacgcc gcacctgccc ctacgtttac aaggccctgg gcatagtctc  15840
gccgcgcgtc ctatcgagcc gcactttttg agcaagcatg tccatcctta tatcgcccag  15900
caataacaca ggctggggcc tgcgcttccc aagcaagatg tttggcgggg ccaagaagcg  15960
ctccgaccaa cacccagtgc gcgtgcgcgg gcactaccgc gcgccctggg gcgcgcacaa  16020
acgcggccgc actgggcgca ccaccgtcga tgacgccatc gacgcggtgg tggaggaggc  16080
gcgcaactac acgcccacgc cgccaccagt gtccacagtg gacgcggcca ttcagaccgt  16140
ggtgcgcgga gcccggcgct atgctaaaat gaagagacgg cggaggcgcg tagcacgtcg  16200
ccaccgccgc cgacccggca ctgccgccca acgcgcggcg gcggccctgc ttaaccgcgc  16260
acgtcgcacc ggccgacggg cggccatgcg ggccgctcga aggctggccg cgggtattgt  16320
cactgtgccc cccaggtcca ggcgacgagc ggccgccgca gcagccgcgg ccattagtgc  16380
tatgactcag ggtcgcaggg gcaacgtgta ttgggtgcgc gactcggtta gcggcctgcg  16440
cgtgcccgtg cgcacccgcc ccccgcgcaa ctagattgca agaaaaaact acttagactc  16500
gtactgttgt atgtatccag cggcggcggc gcgcaacgaa gctatgtcca agcgcaaaat  16560
caaagaagag atgctccagg tcatcgcgcc ggagatctat ggcccccga agaaggaaga  16620
gcaggattac aagccccgaa agctaaagcg ggtcaaaaag aaaaagaaag atgatgatga  16680
```

-continued

```
tgaacttgac gacgaggtgg aactgctgca cgctaccgcg cccaggcgac gggtacagtg  16740
gaaaggtcga cgcgtaaaac gtgttttgcg acccggcacc accgtagtct ttacgcccgg  16800
tgagcgctcc acccgcacct acaagcgcgt gtatgatgag gtgtacggcg acgaggacct  16860
gcttgagcag gccaacgagc gcctcgggga gtttgcctac ggaaagcggc ataaggacat  16920
gctggcgttg ccgctggacg agggcaaccc aacacctagc ctaaagcccg taacactgca  16980
gcaggtgctg cccgcgcttg caccgtccga agaaaagcgc ggcctaaagc gcgagtctgg  17040
tgacttggca cccaccgtgc agctgatggt acccaagcgc cagcgactgg aagatgtctt  17100
ggaaaaaatg accgtggaac ctgggctgga gcccgaggtc cgcgtgcggc caatcaagca  17160
ggtggcgccg ggactgggcg tgcagaccgt ggacgttcag atacccacta ccagtagcac  17220
cagtattgcc accgccacag agggcatgga gacacaaacg tccccggttg cctcagcggt  17280
ggcggatgcc gcggtgcagg cggtcgctgc ggccgcgtcc aagacctcta cggaggtgca  17340
aacggacccg tggatgtttc gcgtttcagc cccccggcgc ccgcgcggtt cgaggaagta  17400
cggcgccgcc agcgcgctac tgcccgaata tgccctacat ccttccattg cgcctacccc  17460
cggctatcgt ggctacacct accgccccag aagacgagca actacccgac gccgaaccac  17520
cactggaacc cgccgccgcc gtcgccgtcg ccagcccgtg ctggccccga tttccgtgcg  17580
cagggtggct cgcgaaggag gcaggaccct ggtgctgcca acagcgcgct accaccccag  17640
catcgtttaa aagccggtct ttgtggttct tgcagatatg gccctcacct gccgcctccg  17700
tttcccggtg ccgggattcc gaggaagaat gcaccgtagg aggggcatgg ccggccacgg  17760
cctgacgggc ggcatgcgtc gtgcgcacca ccggcggcgg cgcgcgtcgc accgtcgcat  17820
gcgcggcggt atcctgcccc tccttattcc actgatcgcc gcggcgattg gcgccgtgcc  17880
cggaattgca tccgtggcct tgcaggcgca gagacactga ttaaaaacaa gttgcatgtg  17940
gaaaaatcaa aataaaaagt ctggactctc acgctcgctt ggtcctgtaa ctattttgta  18000
gaatggaaga catcaacttt gcgtctctgg ccccgcgaca cggctcgcgc ccgttcatgg  18060
gaaactggca agatatcggc accagcaata tgagcggtgg cgccttcagc tggggctcgc  18120
tgtggagcgg cattaaaaat ttcggttcca ccgttaagaa ctatggcagc aaggcctgga  18180
acagcagcac aggccagatg ctgagggata agttgaaaga gcaaaatttc caacaaaagg  18240
tggtagatgg cctggcctct ggcattagcg gggtggtgga cctggccaac caggcagtgc  18300
aaaataagat taacagtaag cttgatcccc gccctcccgt agaggagcct ccaccggccg  18360
tggagacagt gtctccagag gggcgtggcg aaaagcgtcc gcgccccgac agggaagaaa  18420
ctctggtgac gcaaatagac gagcctccct cgtacgagga ggcactaaag caaggcctgc  18480
ccaccacccg tcccatcgcg cccatggcta ccggagtgct gggccagcac acacccgtaa  18540
cgctggacct gcctcccccc gccgacaccc agcagaaacc tgtgctgcca ggcccgaccg  18600
ccgttgttgt aacccgtcct agccgcgcgt ccctgcgccg cgccgccagc ggtccgcgat  18660
cgttgcggcc cgtagccagt ggcaactggc aaagcacact gaacagcatc gtgggtctgg  18720
gggtgcaatc cctgaagcgc cgacgatgct tctgaatagc taacgtgtcg tatgtgtgtc  18780
atgtatgcgt ccatgtcgcc gccagaggag ctgctgagcc gccgcgcgcc cgctttccaa  18840
gatggctacc ccttcgatga tgccgcagtg gtcttacatg cacatctcgg gccaggacgc  18900
ctcggagtac ctgagccccg ggctggtgca gtttgcccgc gccaccgaga cgtacttcag  18960
cctgaataac aagtttagaa accccacggt ggcgcctacg cacgacgtga ccacagaccg  19020
```

-continued

```
gtcccagcgt ttgacgctgc ggttcatccc tgtggaccgt gaggatactg cgtactcgta  19080
caaggcgcgg ttcaccctag ctgtgggtga taaccgtgtg ctggacatgg cttccacgta  19140
ctttgacatc cgcggcgtgc tggacagggg ccctactttt aagccctact ctggcactgc  19200
ctacaacgcc ctggctccca agggtgcccc aaatccttgc gaatgggatg aagctgctac  19260
tgctcttgaa ataaacctag aagaagagga cgatgacaac gaagacgaag tagacgagca  19320
agctgagcag caaaaaactc acgtatttgg gcaggcgcct tattctggta taaatattac  19380
aaaggagggt attcaaatag gtgtcgaagg tcaaacacct aaatatgccg ataaaacatt  19440
tcaacctgaa cctcaaatag gagaatctca gtggtacgaa actgaaatta atcatgcagc  19500
tgggagagtc cttaaaaaga ctaccccaat gaaaccatgt tacggttcat atgcaaaacc  19560
cacaaatgaa aatggagggc aaggcattct tgtaaagcaa caaaatggaa agctagaaag  19620
tcaagtggaa atgcaatttt tctcaactac tgaggcgacc gcaggcaatg gtgataactt  19680
gactcctaaa gtggtattgt acagtgaaga tgtagatata gaaaccccag acactcatat  19740
ttcttacatg cccactatta aggaaggtaa ctcacgagaa ctaatgggcc aacaatctat  19800
gcccaacagg cctaattaca ttgcttttag ggacaatttt attggtctaa tgtattacaa  19860
cagcacgggt aatatgggtg ttctggcggg ccaagcatcg cagttgaatg ctgttgtaga  19920
tttgcaagac agaaacacag agctttcata ccagcttttg cttgattcca ttggtgatag  19980
aaccaggtac ttttctatgt ggaatcaggc tgttgacagc tatgatccag atgttagaat  20040
tattgaaaat catggaactg aagatgaact tccaaattac tgctttccac tgggaggtgt  20100
gattaataca gagactctta ccaaggtaaa acctaaaaca ggtcaggaaa atggatggga  20160
aaaagatgct acagaatttt cagataaaaa tgaaataaga gttggaaata attttgccat  20220
ggaaatcaat ctaaatgcca acctgtggag aaatttcctg tactccaaca tagcgctgta  20280
tttgcccgac aagctaaagt acagtccttc caacgtaaaa atttctgata acccaaacac  20340
ctacgactac atgaacaagc gagtggtggc tcccgggtta gtggactgct acattaacct  20400
tggagcacgc tggtcccttg actatatgga caacgtcaac ccatttaacc accaccgcaa  20460
tgctggcctg cgctaccgct caatgttgct gggcaatggt cgctatgtgc ccttccacat  20520
ccaggtgcct cagaagttct ttgccattaa aaacctcctt ctcctgccgg gctcatacac  20580
ctacgagtgg aacttcagga aggatgttaa catggttctg cagagctccc taggaaatga  20640
cctaagggtt gacggagcca gcattaagtt tgatagcatt tgcctttacg ccaccttctt  20700
ccccatggcc cacaacaccg cctccacgct tgaggccatg cttagaaacg acaccaacga  20760
ccagtccttt aacgactatc tctccgccgc caacatgctc taccctatac ccgccaacgc  20820
taccaacgtg cccatatcca tcccctcccg caactgggcg gctttccgcg gctgggcctt  20880
cacgcgcctt aagactaagg aaaccccatc actgggctcg ggctacgacc cttattacac  20940
ctactctggc tctataccct acctagatgg aaccttttac ctcaaccaca cctttaagaa  21000
ggtggccatt acctttgact cttctgtcag ctggcctggc aatgaccgcc tgcttacccc  21060
caacgagttt gaaattaagc gctcagttga cggggagggt tacaacgttg cccagtgtaa  21120
catgaccaaa gactggttcc tggtacaaat gctagctaac tacaacattg gctaccaggg  21180
cttctatatc ccagagagct acaaggaccg catgtactcc ttctttagaa acttccagcc  21240
catgagccgt caggtggtgg atgatactaa atacaaggac taccaacagg tgggcatcct  21300
acaccaacac aacaactctg gatttgttgg ctaccttgcc cccaccatgc gcgaaggaca  21360
ggcctaccct gctaacttcc cctatccgct tataggcaag accgcagttg acagcattac  21420
```

-continued

```
ccagaaaaag tttctttgcg atcgcaccct ttggcgcatc ccattctcca gtaactttat  21480
gtccatgggc gcactcacag acctgggcca aaaccttctc tacgccaact ccgcccacgc  21540
gctagacatg acttttgagg tggatcccat ggacgagccc acccttcttt atgttttgtt  21600
tgaagtcttt gacgtggtcc gtgtgcaccg gccgcaccgc ggcgtcatcg aaaccgtgta  21660
cctgcgcacg cccttctcgg ccggcaacgc cacaacataa agaagcaagc aacatcaaca  21720
acagctgccg ccatgggctc cagtgagcag gaactgaaag ccattgtcaa agatcttggt  21780
tgtgggccat atttttgggg cacctatgac aagcgctttc caggctttgt ttctccacac  21840
aagctcgcct gcgccatagt caatacggcc ggtcgcgaga ctgggggcgt acactggatg  21900
gcctttgcct ggaacccgca ctcaaaaaca tgctacctct ttgagccctt tggcttttct  21960
gaccagcgac tcaagcaggt ttaccagttt gagtacgagt cactcctgcg ccgtagcgcc  22020
attgcttctt cccccgaccg ctgtataacg ctggaaaagt ccacccaaag cgtacagggg  22080
cccaactcgg ccgcctgtgg actattctgc tgcatgtttc tccacgcctt tgccaactgg  22140
ccccaaactc ccatggatca caaccccacc atgaacctta ttaccggggt acccaactcc  22200
atgctcaaca gtccccaggt acagcccacc ctgcgtcgca accaggaaca gctctacagc  22260
ttcctggagc gccactcgcc ctacttccgc agccacagtg cgcagattag gagcgccact  22320
tctttttgtc acttgaaaaa catgtaaaaa taatgtacta gagacacttt caataaaggc  22380
aaatgctttt atttgtacac tctcgggtga ttatttaccc ccacccttgc cgtctgcgcc  22440
gtttaaaaat caaaggggtt ctgccgcgca tcgctatgcg ccactggcag ggacacgttg  22500
cgatactggt gtttagtgct ccacttaaac tcaggcacaa ccatccgcgg cagctcggtg  22560
aagttttcac tccacaggct gcgcaccatc accaacgcgt ttagcaggtc gggcgccgat  22620
atcttgaagt cgcagttggg gcctccgccc tgcgcgcgcg agttgcgata cacagggttg  22680
cagcactgga acactatcag cgccgggtgg tgcacgctgg ccagcacgct cttgtcggag  22740
atcagatccg cgtccaggtc ctccgcgttg ctcagggcga acggagtcaa ctttggtagc  22800
tgccttccca aaaagggcgc gtgcccaggc tttgagttgc actcgcaccg tagtggcatc  22860
aaaaggtgac cgtgcccggt ctgggcgtta ggatacagcg cctgcataaa agccttgatc  22920
tgcttaaaag ccacctgagc ctttgcgcct tcagagaaga acatgccgca agacttgccg  22980
gaaaactgat tggccggaca ggccgcgtcg tgcacgcagc accttgcgtc ggtgttggag  23040
atctgcacca catttcggcc ccaccggttc ttcacgatct tggccttgct agactgctcc  23100
ttcagcgcgc gctgcccgtt ttcgctcgtc acatccattt caatcacgtg ctccttattt  23160
atcataatgc ttccgtgtag acacttaagc tcgccttcga tctcagcgca gcggtgcagc  23220
cacaacgcgc agcccgtggg ctcgtgatgc ttgtaggtca cctctgcaaa cgactgcagg  23280
tacgcctgca ggaatcgccc catcatcgtc acaaaggtct tgttgctggt gaaggtcagc  23340
tgcaacccgc ggtgctcctc gttcagccag gtcttgcata cggccgccag agcttccact  23400
tggtcaggca gtagtttgaa gttcgccttt agatcgttat ccacgtggta cttgtccatc  23460
agcgcgcgcg cagcctccat gcccttctcc cacgcagaca cgatcggcac actcagcggg  23520
ttcatcaccg taatttcact ttccgcttcg ctgggctctt cctcttcctc ttgcgtccgc  23580
ataccacgcg ccactgggtc gtcttcattc agccgccgca ctgtgcgctt acctcctttg  23640
ccatgcttga ttagcaccgg tgggttgctg aaacccacca tttgtagcgc cacatcttct  23700
ctttcttcct cgctgtccac gattacctct ggtgatggcg ggcgctcggg cttgggagaa  23760
```

-continued

```
gggcgcttct tttcttctt gggcgcaatg gccaaatccg ccgccgaggt cgatggccgc  23820
gggctgggtg tgcgcggcac cagcgcgtct tgtgatgagt cttcctcgtc ctcggactcg  23880
atacgccgcc tcatccgctt ttttgggggc gcccggggag gcggcggcga cggggacggg  23940
gacgacacgt cctccatggt tgggggacgt cgcgccgcac cgcgtccgcg ctcgggggtg  24000
gtttcgcgct gctcctcttc ccgactggcc atttccttct cctataggca gaaaaagatc  24060
atggagtcag tcgagaagaa ggacagccta accgccccct ctgagttcgc caccaccgcc  24120
tccaccgatg ccgccaacgc gcctaccacc ttccccgtcg aggcaccccc gcttgaggag  24180
gaggaagtga ttatcgagca ggacccaggt tttgtaagcg aagacgacga ggaccgctca  24240
gtaccaacag aggataaaaa gcaagaccag gacaacgcag aggcaaacga ggaacaagtc  24300
gggcgggggg acgaaaggca tggcgactac ctagatgtgg gagacgacgt gctgttgaag  24360
catctgcagc gccagtgcgc cattatctgc gacgcgttgc aagagcgcag cgatgtgccc  24420
ctcgccatag cggatgtcag ccttgcctac gaacgccacc tattctcacc gcgcgtaccc  24480
cccaaacgcc aagaaaacgg cacatgcgag cccaacccgc gcctcaactt ctaccccgta  24540
tttgccgtgc cagaggtgct tgccacctat cacatctttt tccaaaactg caagataccc  24600
ctatcctgcc gtgccaaccg cagccgagcg gacaagcagc tggccttgcg gcagggcgct  24660
gtcatacctg atatcgcctc gctcaacgaa gtgccaaaaa tctttgaggg tcttggacgc  24720
gacgagaagc gcgcggcaaa cgctctgcaa caggaaaaca gcgaaaatga aagtcactct  24780
ggagtgttgg tggaactcga gggtgacaac gcgcgcctag ccgtactaaa acgcagcatc  24840
gaggtcaccc actttgccta cccggcactt aacctacccc ccaaggtcat gagcacagtc  24900
atgagtgagc tgatcgtgcg ccgtgcgcag cccctggaga gggatgcaaa tttgcaagaa  24960
caaacagagg agggcctacc cgcagttggc gacgagcagc tagcgcgctg gcttcaaacg  25020
cgcgagcctg ccgacttgga ggagcgacgc aaactaatga tggccgcagt gctcgttacc  25080
gtggagcttg agtgcatgca gcggttcttt gctgacccgg agatgcagcg caagctagag  25140
gaaacattgc actacacctt tcgacagggc tacgtacgcc aggcctgcaa gatctccaac  25200
gtggagctct gcaacctggt ctcctacctt ggaattttgc acgaaaaccg ccttgggcaa  25260
aacgtgcttc attccacgct caagggcgag gcgcgccgcg actacgtccg cgactgcgtt  25320
tacttatttc tatgctacac ctggcagacg gccatgggcg tttggcagca gtgcttggag  25380
gagtgcaacc tcaaggagct gcagaaactg ctaaagcaaa acttgaagga cctatggacg  25440
gccttcaacg agcgctccgt ggccgcgcac ctggcggaca tcattttccc cgaacgcctg  25500
cttaaaaccc tgcaacaggg tctgccagac ttcaccagtc aaagcatgtt gcagaacttt  25560
aggaacttta tcctagagcg ctcaggaatc ttgcccgcca cctgctgtgc acttcctagc  25620
gactttgtgc ccattaagta ccgcgaatgc cctccgccgc tttggggcca ctgctacctt  25680
ctgcagctag ccaactacct tgcctaccac tctgacataa tggaagacgt gagcggtgac  25740
ggtctactgg agtgtcactg tcgctgcaac ctatgcaccc cgcaccgctc cctggtttgc  25800
aattcgcagc tgcttaacga aagtcaaatt atcggtacct ttgagctgca gggtccctcg  25860
cctgacgaaa agtccgcggc tccggggttg aaactcactc cggggctgtg gacgtcggct  25920
taccttcgca aatttgtacc tgaggactac cacgcccacg agattaggtt ctacgaagac  25980
caatcccgcc cgccaaatgc ggagcttacc gcctgcgtca ttacccaggg ccacattctt  26040
ggccaattgc aagccatcaa caaagcccgc caagagtttc tgctacgaaa gggacggggg  26100
gtttacttgg acccccagtc cggcgaggag ctcaacccaa tccccccgcc gccgcagccc  26160
```

-continued

```
tatcagcagc agccgcgggc ccttgcttcc caggatggca cccaaaaaga agctgcagct  26220
gccgccgcca cccacggacg aggaggaata ctgggacagt caggcagagg aggttttgga  26280
cgaggaggag gaggacatga tggaagactg ggagagccta gacgaggaag cttccgaggt  26340
cgaagaggtg tcagacgaaa caccgtcacc ctcggtcgca ttcccctcgc cggcgcccca  26400
gaaatcggca accggttcca gcatggctac aacctccgct cctcaggcgc cgccggcact  26460
gcccgttcgc cgacccaacc gtagatggga caccactgga accagggccg gtaagtccaa  26520
gcagccgccg ccgttagccc aagagcaaca acagcgccaa ggctaccgct catggcgcgg  26580
gcacaagaac gccatagttg cttgcttgca agactgtggg ggcaacatct ccttcgcccg  26640
ccgctttctt ctctaccatc acggcgtggc cttcccccgt aacatcctgc attactaccg  26700
tcatctctac agcccatact gcaccggcgg cagcggcagc ggcagcaaca gcagcggcca  26760
cacagaagca aaggcgaccg gatagcaaga ctctgacaaa gcccaagaaa tccacagcgg  26820
cggcagcagc aggaggagga gcgctgcgtc tggcgcccaa cgaacccgta tcgacccgcg  26880
agcttagaaa caggattttt cccactctgt atgctatatt tcaacagagc aggggccaag  26940
aacaagagct gaaaataaaa aacaggtctc tgcgatccct cacccgcagc tgcctgtatc  27000
acaaaagcga agatcagctt cggcgcacgc tggaagacgc ggaggctctc ttcagtaaat  27060
actgcgcgct gactcttaag gactagtttc gcgccctttc tcaaatttaa gcgcgaaaac  27120
tacgtcatct ccagcggcca cacccggcgc cagcacctgt cgtcagcgcc attatgagca  27180
aggaaattcc cacgccctac atgtggagtt accagccaca aatgggactt gcggctggag  27240
ctgcccaaga ctactcaacc cgaataaact acatgagcgc gggaccccac atgatatccc  27300
gggtcaacgg aatccgcgcc caccgaaacc gaattctctt ggaacaggcg gctattacca  27360
ccacacctcg taataacctt aatccccgta gttggcccgc tgccctggtg taccaggaaa  27420
gtcccgctcc caccactgtg gtacttccca gagacgccca ggccgaagtt cagatgacta  27480
actcaggggc gcagcttgcg ggcggctttc gtcacagggt gcggtcgccc gggcagggta  27540
taactcacct gacaatcaga gggcgaggta ttcagctcaa cgacgagtcg gtgagctcct  27600
cgcttggtct ccgtccggac gggacatttc agatcggcgg cgccggccgt ccttcattca  27660
cgcctcgtca ggcaatccta actctgcaga cctcgtcctc tgagccgcgc tctggaggca  27720
ttggaactct gcaatttatt gaggagtttg tgccatcggt ctactttaac cccttctcgg  27780
gacctcccgg ccactatccg gatcaattta ttcctaactt tgacgcggta aaggactcgg  27840
cggacggcta cgactgaatg ttaagtggag aggcagagca actgcgcctg aaacacctgg  27900
tccactgtcg ccgccacaag tgctttgccc gcgactccgg tgagttttgc tactttgaat  27960
tgcccgagga tcatatcgag ggcccggcgc acggcgtccg gcttaccgcc cagggagagc  28020
ttgcccgtag cctgattcgg gagtttaccc agcgcccccct gctagttgag cgggacaggg  28080
gaccctgtgt tctcactgtg atttgcaact gtcctaacct tggattacat caagatcttt  28140
gttgccatct ctgtgctgag tataataaat acagaaatta aaatatactg gggctcctat  28200
cgccatcctg taaacgccac cgtcttcacc cgcccaagca aaccaaggcg aaccttacct  28260
ggtactttta acatctctcc ctctgtgatt tacaacagtt tcaacccaga cggagtgagt  28320
ctacgagaga acctctccga gctcagctac tccatcagaa aaaacaccac cctccttacc  28380
tgccgggaac gtacgagtgc gtcaccggcc gctgcaccac acctaccgcc tgaccgtaaa  28440
ccagactttt tccggacaga cctcaataac tctgtttacc agaacaggag gtgagcttag  28500
```

-continued

```
aaaaccctta gggtattagg ccaaaggcgc agctactgtg gggtttatga acaattcaag  28560
caactctacg ggctattcta attcaggttt ctctagaatc ggggttgggg ttattctctg  28620
tcttgtgatt ctctttattc ttatactaac gcttctctgc ctaaggctcg ccgcctgctg  28680
tgtgcacatt tgcatttatt gtcagctttt taaacgctgg ggtcgccacc caagatgatt  28740
aggtacataa tcctaggttt actcaccctt gcgtcagccc acggtaccac ccaaaaggtg  28800
gattttaagg agccagcctg taatgttaca ttcgcagctg aagctaatga gtgcaccact  28860
cttataaaat gcaccacaga acatgaaaag ctgcttattc gccacaaaaa caaaattggc  28920
aagtatgctg tttatgctat ttggcagcca ggtgacacta cagagtataa tgttacagtt  28980
ttccagggta aaagtcataa aacttttatg tatacttttc cattttatga aatgtgcgac  29040
attaccatgt acatgagcaa acagtataag ttgtggcccc cacaaaattg tgtggaaaac  29100
actggcactt tctgctgcac tgctatgcta attacagtgc tcgctttggt ctgtacccta  29160
ctctatatta aatacaaaag cagacgcagc tttattgagg aaaagaaaat gccttaattt  29220
actaagttac aaagctaatg tcaccactaa ctgctttact cgctgcttgc aaaacaaatt  29280
caaaaagtta gcattataat tagaatagga tttaaacccc ccggtcattt cctgctcaat  29340
accattcccc tgaacaattg actctatgtg ggatatgctc cagcgctaca accttgaagt  29400
caggcttcct ggatgtcagc atctgacttt ggccagcacc tgtcccgcgg atttgttcca  29460
gtccaactac agcgacccac cctaacagag atgaccaaca caaccaacgc ggccgccgct  29520
accggactta catctaccac aaatacaccc caagtttctg cctttgtcaa taactgggat  29580
aacttgggca tgtggtggtt ctccatagcg cttatgtttg tatgccttat tattatgtgg  29640
ctcatctgct gcctaaagcg caaacgcgcc cgaccaccca tctatagtcc catcattgtg  29700
ctacacccaa acaatgatgg aatccataga ttggacggac tgaaacacat gttcttttct  29760
cttacagtat gattaaatga gacatgattc ctcgagtttt tatattactg acccttgttg  29820
cgcttttttg tgcgtgctcc acattggctg cggtttctca catcgaagta gactgcattc  29880
cagccttcac agtctatttg ctttacggat ttgtcaccct cacgctcatc tgcagcctca  29940
tcactgtggt catcgccttt atccagtgca ttgactgggt ctgtgtgcgc tttgcatatc  30000
tcagacacca tccccagtac agggacagga ctatagctga gcttcttaga attctttaat  30060
tatgaaattt actgtgactt ttctgctgat tatttgcacc ctatctgcgt tttgttcccc  30120
gacctccaag cctcaaagac atatatcatg cagattcact cgtatatgga atattccaag  30180
ttgctacaat gaaaaaagcg atctttccga agcctggtta tatgcaatca tctctgttat  30240
ggtgttctgc agtaccatct tagccctagc tatatatccc taccttgaca ttggctggaa  30300
acgaatagat gccatgaacc acccaacttt ccccgcgccc gctatgcttc cactgcaaca  30360
agttgttgcc ggcggctttg tcccagccaa tcagcctcgc cccacttctc ccaccccccac  30420
tgaaatcagc tactttaatc taacaggagg agatgactga caccctagat ctagaaatgg  30480
acggaattat tacagagcag cgcctgctag aaagacgcag ggcagcggcc gagcaacagc  30540
gcatgaatca agagctccaa gacatggtta acttgcacca gtgcaaaagg ggtatctttt  30600
gtctggtaaa gcaggccaaa gtcacctacg acagtaatac caccggacac cgccttagct  30660
acaagttgcc aaccaagcgt cagaaattgg tggtcatggt gggagaaaag cccattacca  30720
taactcagca ctcggtagaa accgaaggct gcattcactc accttgtcaa ggacctgagg  30780
atctctgcac ccttattaag accctgtgcg gtctcaaaga tcttattccc tttaactaat  30840
aaaaaaaaat aataaagcat cacttactta aaatcagtta gcaaatttct gtccagttta  30900
```

-continued ttcagcagca cctccttgcc ctcctcccag ctctggtatt gcagcttcct cctggctgca 30960
aactttctcc acaatctaaa tggaatgtca gtttcctcct gttcctgtcc atccgcaccc 31020
actatcttca tgttgttgca gatgaagcgc gcaagaccgt ctgaagatac cttcaacccc 31080
gtgtatccat atgacacgga aaccggtcct ccaactgtgc cttttcttac tcctcccttt 31140 gtatcccccca atgggtttca agagagtccc cctggggtac tctctttgcg cctatccgaa 31200
cctctagtta cctccaatgg catgcttgcg ctcaaaatgg gcaacggcct ctctctggac 31260
gaggccggca accttacctc ccaaaatgta accactgtga gcccacctct caaaaaaacc 31320
aagtcaaaca taaacctgga aatatctgca cccctcacag ttacctcaga agccctaact 31380
gtggctgccg ccgcacctct aatggtcgcg ggcaacacac tcaccatgca atcacaggcc 31440
ccgctaaccg tgcacgactc caaacttagc attgccaccc aaggacccct cacagtgtca 31500
gaaggaaagc tagccctgca aacatcaggc cccctcacca ccaccgatag cagtaccctt 31560
actatcactg cctcaccccc tctaactact gccactggta gcttgggcat tgacttgaaa 31620
gagcccattt atacacaaaa tggaaaacta ggactaaagt acggggctcc tttgcatgta 31680
acagacgacc taaacacttt gaccgtagca actggtccag gtgtgactat taataatact 31740
tccttgcaaa ctaaagttac tggagccttg ggttttgatt cacaaggcaa tatgcaactt 31800
aatgtagcag gaggactaag gattgattct caaaacagac gccttatact tgatgttagt 31860
tatccgtttg atgctcaaaa ccaactaaat ctaagactag gacagggccc tctttttata 31920
aactcagccc acaacttgga tattaactac aacaaaggcc tttacttgtt tacagcttca 31980
aacaattcca aaaagcttga ggttaaccta agcactgcca aggggttgat gtttgacgct 32040
acagccatag ccattaatgc aggagatggg cttgaatttg gttcacctaa tgcaccaaac 32100
acaaatcccc tcaaaacaaa aattggccat ggcctagaat ttgattcaaa caaggctatg 32160
gttcctaaac taggaactgg ccttagtttt gacagcacag gtgccattac agtaggaaac 32220
aaaaataatg ataagctaac tttgtggacc acaccagctc catctcctaa ctgtagacta 32280
aatgcagaga aagatgctaa actcactttg gtcttaacaa aatgtggcag tcaaatactt 32340
gctacagttt cagttttggc tgttaaaggc agtttggctc caatatctgg aacagttcaa 32400
agtgctcatc ttattataag atttgacgaa aatggagtgc tactaaacaa ttccttcctg 32460
gacccagaat attggaactt tagaaatgga gatcttactg aaggcacagc ctatacaaac 32520
gctgttggat ttatgcctaa cctatcagct tatccaaaat ctcacggtaa aactgccaaa 32580
agtaacattg tcagtcaagt ttacttaaac ggagacaaaa ctaaacctgt aacactaacc 32640
attacactaa acggtacaca ggaaacagga gacacaactc caagtgcata ctctatgtca 32700
ttttcatggg actggtctgg ccacaactac attaatgaaa tatttgccac atcctcttac 32760
actttttcat acattgccca agaataaaga atcgtttgtg ttatgtttca acgtgtttat 32820
ttttcaattg cagaaaattt caagtcattt ttcattcagt agtatagccc caccaccaca 32880
tagcttatac agatcaccgt accttaatca aactcacaga accctagtat tcaacctgcc 32940
acctccctcc caacacacag agtacacagt cctttctccc cggctggcct taaaaagcat 33000
catatcatgg gtaacagaca tattcttagg tgttatattc cacacggttt cctgtcgagc 33060
caaacgctca tcagtgatat taataaactc cccgggcagc tcacttaagt tcatgtcgct 33120
gtccagctgc tgagccacag gctgctgtcc aacttgcggt tgcttaacgg gcggcgaagg 33180
agaagtccac gcctacatgg gggtagagtc ataatcgtgc atcaggatag ggcggtggtg 33240

-continued

```
ctgcagcagc gcgcgaataa actgctgccg ccgccgctcc gtcctgcagg aatacaacat  33300
ggcagtggtc tcctcagcga tgattcgcac cgcccgcagc ataaggcgcc ttgtcctccg  33360
ggcacagcag cgcaccctga tctcacttaa atcagcacag taactgcagc acagcaccac  33420
aatattgttc aaaatcccac agtgcaaggc gctgtatcca aagctcatgg cggggaccac  33480
agaacccacg tggccatcat accacaagcg caggtagatt aagtggcgac ccctcataaa  33540
cacgctggac ataaacatta cctcttttgg catgttgtaa ttcaccacct cccggtacca  33600
tataaacctc tgattaaaca tggcgccatc caccaccatc ctaaaccagc tggccaaaac  33660
ctgcccgccg gctatacact gcagggaacc gggactggaa caatgacagt ggagagccca  33720
ggactcgtaa ccatggatca tcatgctcgt catgatatca atgttggcac aacacaggca  33780
cacgtgcata cacttcctca ggattacaag ctcctcccgc gttagaacca tatcccaggg  33840
aacaacccat tcctgaatca gcgtaaatcc cacactgcag ggaagacctc gcacgtaact  33900
cacgttgtgc attgtcaaag tgttacattc gggcagcagc ggatgatcct ccagtatggt  33960
agcgcgggtt tctgtctcaa aaggaggtag acgatcccta ctgtacggag tgcgccgaga  34020
caaccgagat cgtgttggtc gtagtgtcat gccaaatgga acgccggacg tagtcatatt  34080
tcctgaagca aaaccaggtg cgggcgtgac aaacagatct gcgtctccgg tctcgccgct  34140
tagatcgctc tgtgtagtag ttgtagtata tccactctct caaagcatcc aggcgccccc  34200
tggcttcggg ttctatgtaa actccttcat gcgccgctgc cctgataaca tccaccaccg  34260
cagaataagc cacacccagc caacctacac attcgttctg cgagtcacac acgggaggag  34320
cgggaagagc tggaagaacc atgttttttt ttttattcca aaagattatc caaaacctca  34380
aaatgaagat ctattaagtg aacgcgctcc cctccggtgg cgtggtcaaa ctctacagcc  34440
aaagaacaga taatggcatt tgtaagatgt tgcacaatgg cttccaaaag gcaaacggcc  34500
ctcacgtcca agtggacgta aaggctaaac ccttcagggt gaatctcctc tataaacatt  34560
ccagcacctt caaccatgcc caaataattc tcatctcgcc accttctcaa tatatctcta  34620
agcaaatccc gaatattaag tccggccatt gtaaaaatct gctccagagc gccctccacc  34680
ttcagcctca agcagcgaat catgattgca aaaattcagg ttcctcacag acctgtataa  34740
gattcaaaag cggaacatta acaaaaatac cgcgatcccg taggtccctt cgcagggcca  34800
gctgaacata atcgtgcagg tctgcacgga ccagcgcggc cacttccccg ccaggaacct  34860
tgacaaaaga acccacactg attatgacac gcatactcgg agctatgcta accagcgtag  34920
ccccgatgta agctttgttg catgggcggc gatataaaat gcaaggtgct gctcaaaaaa  34980
tcaggcaaag cctcgcgcaa aaaagaaagc acatcgtagt catgctcatg cagataaagg  35040
caggtaagct ccggaaccac cacagaaaaa gacaccattt ttctctcaaa catgtctgcg  35100
ggtttctgca taaacacaaa ataaaataac aaaaaaacat ttaaacatta gaagcctgtc  35160
ttacaacagg aaaaacaacc cttataagca taagacggac tacggccatg ccggcgtgac  35220
cgtaaaaaaa ctggtcaccg tgattaaaaa gcaccaccga cagctcctcg gtcatgtccg  35280
gagtcataat gtaagactcg gtaaacacat caggttgatt catcggtcag tgctaaaaag  35340
cgaccgaaat agcccggggg aatacatacc cgcaggcgta gagacaacat tacagccccc  35400
ataggaggta taacaaaatt aataggagag aaaaacacat aaacacctga aaaaccctcc  35460
tgcctaggca aaatagcacc ctcccgctcc agaacaacat acagcgcttc acagcggcag  35520
cctaacagtc agccttacca gtaaaaaaga aaacctatta aaaaaacacc actcgacacg  35580
gcaccagctc aatcagtcac agtgtaaaaa agggccaagt gcagagcgag tatatatagg  35640
```

```
actaaaaaat gacgtaacgg ttaaagtcca caaaaaacac ccagaaaacc gcacgcgaac    35700

ctacgcccag aaacgaaagc caaaaaaccc acaacttcct caaatcgtca cttccgtttt    35760

cccacgttac gtaacttccc attttaagaa aactacaatt cccaacacat acaagttact    35820

ccgccctaaa acctacgtca cccgccccgt tcccacgccc cgcgccacgt cacaaactcc    35880

accccctcat tatcatattg gcttcaatcc aaaataaggt atattattga tgatg         35935
```

REPLICATION-COMPETENT ANTI-CANCER VECTORS

REFERENCE TO GOVERNMENT GRANT

This invention was made with government support under a grant from the National Institutes of Health, Grant Number RO1 CA71704. The government has certain rights in this invention.

BACKGROUND OF THE INVENTION (1) Field of the Invention

This invention relates generally to the treatment of cancer and more particularly to vectors which replicate in neoplastic cells and which overexpress an adenovirus death protein (ADP) and to the use of these vectors in treating human cancer.

(2) Description of the Related Art

Cancer is a leading cause of death in the United States and elsewhere. Depending on the type of cancer, it is typically treated with surgery, chemotherapy, and/or radiation. These treatments often fail: surgery may not remove all the cancer; some cancers are resistant to chemotherapy and radiation therapy; and chemotherapy-resistant tumors frequently develop. New therapies are necessary, to be used alone or in combination with classical techniques.

One potential therapy under active investigation is treating tumors with recombinant viral vectors expressing anti-cancer therapeutic proteins. Adenovirus-based vectors contain several characteristics that make them conceptually appealing for use in treating cancer, as well as for therapy of genetic disorders. Adenoviruses (hereinafter used interchangeably with "Ads") can easily be grown in culture to high titer stocks that are stable. They have a broad host range, replicating in most human cancer cell types. Their genome can be manipulated by site-directed mutation and insertion of foreign genes expressed from foreign promoters.

The adenovirion consists of a DNA-protein core within a protein capsid (reviewed by Stewart et al., "Adenovirus structure by x-ray crystallography and electron microscopy." in: *The Molecular Repertoire of Adenoviruses*, Doerfler, W. et al., (ed)., Springer-Verlag, Heidelberg, Germany, p. 25-38). Virions bind to a specific cellular receptor, are endocytosed, and the genome is extruded from endosomes and transported to the nucleus. The genome is a linear duplex DNA of about 36 kbp, encoding about 36 genes (FIG. 1A). In the nucleus, the "immediate early" E1A proteins are expressed initially, and these proteins induce expression of the "delayed early" proteins encoded by the E1B, E2, E3, and E4 transcription units (reviewed by Shenk, T. "Adenoviridae: the viruses and their replication" in: Fields Virology, Field, B. N. et al., Lippencott-Raven, Philadelphia, p. 2111-2148). E1A proteins also induce or repress cellular genes, resulting in stimulation of the cell cycle. About 23 early proteins function to usurp the cell and initiate viral DNA replication. Viral DNA replicates at about 7 h post-infection (p.i.), then late genes are expressed from the "major late" transcription unit. Major late mRNAs are synthesized from the common "major late promoter" by alternative pre-mRNA processing. Each late mRNA contains a common "tripartite leader" at its 5'-terminus (exons 1, 2, and 3 in FIG. 1), which allows for efficient translation of Ad late mRNAs. Cellular protein synthesis is shut off, and the cell becomes a factory for making viral proteins. Virions assemble in the nucleus at about 1 day p.i., and after 2-3 days the cell lyses and releases progeny virus. Cell lysis is mediated by the E3 11.6K protein, which has been renamed "adenovirus death protein" (ADP) (Tollefson et al., *J. Virol.* 70:2296-2306, 1996; Tollefson et al., *Virol.* 220:152-162, 1996). The term ADP as used herein in a generic sense refers collectively to ADP's from adenoviruses such as, e.g. Ad type 1 (Ad1), Ad type 2 (Ad2), Ad type 5 (Ad5) or Ad type 6 (Ad6) all of which express homologous ADP's with a high degree of sequence similarity.

The Ad vectors being investigated for use in anti-cancer and gene therapy are based on recombinant Ad's that are either replication-defective or replication-competent. Typical replication-defective Ad vectors lack the E1A and E1B genes (collectively known as E1) and contain in their place an expression cassette consisting of a promoter and pre-mRNA processing signals which drive expression of a foreign gene. These vectors are unable to replicate because they lack the E1A genes required to induce Ad gene expression and DNA replication. In addition, the E3 genes are usually deleted because they are not essential for virus replication in cultured cells.

A number of investigators have constructed replication-defective Ad vectors expressing anti-cancer therapeutic proteins. Usually, these vectors have been tested by direct injection of human tumors growing in mouse models. Most commonly, these vectors express the thymidine kinase gene from herpes simplex virus, and the mice are treated with gancyclovir to kill cells transduced by the vector (see e.g., Felzmann et al., *Gene Ther.* 4:1322-1329, 1997). Another suicide gene therapy approach involves injecting tumors with a replication defective Ad vector expressing cytosine deaminase, followed by administration of 5-fluorocytosine (Topf et al., *Gene Ther.* 5::507-513, 1998). Investigators have also prepared and tested replication-defective Ad vectors expressing a cytokine-such as IL-2, IL-12, IL-6, tumor necrosis factor (TNF), type I interferons, or the co-stimulatory molecule B7-1 in the anticipation that the Ad-expressed cytokine will stimulate an immune response, including cytotoxic T-lymphocytes (CTL), against the tumor (Felzmann et al., supra; Putzer et al., *Proc. Natl. Acad. Sci. USA* 94:10889-10894, 1997). Other vectors express tumor antigens (e.g. melanoma MART1), proteins that de-regulate the cell cycle and induce apoptosis (p53, pRB, $p21^{Kip1/WAF1}$, $p16^{CDKN2}$, and even Ad E1A), and ribozymes. An Ad vector expressing FasL induces apoptosis and tumor regression of a mouse tumor (Arai et al., *Proc. Natl. Acad. Sci. USA* 94:13862-13867, 1997).

Despite these generally positive reports, it is recognized in the art that replication-defective Ad vectors have several characteristics that make them suboptimal for use in therapy. For example, production of replication-defective vectors requires that they be grown on a complementing cell line that provides the E1A proteins in trans. Such cell lines are fastidious, and generation of virus stocks is time-consuming and expensive. In addition, although many foreign proteins have been expressed from such vectors, the level of expression is low compared to Ad late proteins.

To address these problems, several groups have proposed using replication-competent Ad vectors for therapeutic use. Replication-competent vectors retain Ad genes essential for replication and thus do not require complementing cell lines to replicate. Replication-competent Ad vectors lyse cells as a natural part of the life cycle of the vector. Another advantage of replication-competent Ad vectors occurs when the vector is engineered to encode and express a foreign protein. Such vectors would be expected to greatly amplify synthesis of the encoded protein in vivo as the vector replicates. For use as anti-cancer agents, replication-competent viral vectors would theoretically also be advantageous in that they should replicate and spread throughout the tumor, not just in the initial infected cells as is the case with replication-defective vectors.

Wyeth Laboratories developed replication-competent Ad vectors for vaccination purposes, using vaccine strains of Ad serotypes 4, 7, and 5 (Lubeck et al., *AIDS Res. Hum. Retroviruses* 10:1443-1449, 1994). Foreign genes were inserted into the E3 region (with the E3 genes deleted) or into a site at the right end of the genome. Two foreign genes used were hepatitis B surface antigen and the HIV envelope protein. They obtained good expression in culture, and were able to raise antisera in animal models. Phase I human trials were ambiguous, and the project was mostly abandoned.

Onyx Pharmaceuticals recently reported on adenovirus-based anti-cancer vectors which are replication deficient in non-neoplastic cells but which exhibit a replication phenotype in neoplastic cells lacking functional p53 and/or retinoblastoma (pRB) tumor suppressor proteins (U.S. Pat. No. 5,677,178; Heise et al., *Nature Med.* 6:639-645, 1997; Bischoff et al., *Science* 274:373-376, 1996). This phenotype is reportedly accomplished by using recombinant adenoviruses containing a mutation in the E1B region that make the encoded E1B-55K protein incapable of binding to p53 and/or a mutation(s) in the E1A region which make the encoded E1A protein (p289R or p243R) incapable of binding to pRB and/or the cellular 300 kD polypeptide and/or the 107 kD polypeptide. E1B-55K has at least two independent functions: it binds and inactivates the tumor suppressor protein p53, and it is required for efficient transport of Ad mRNA from the nucleus. Because these E1B and E1A viral proteins are involved in forcing cells into S-phase, which is required for replication of adenovirus DNA, and because the p53 and pRB proteins block cell cycle progression, the recombinant adenovirus vectors described by Onyx should replicate in cells defective in p53 and/or pRB, which is the case for many cancer cells, but not in cells with wild-type p53 and/or pRB. Onyx has reported that replication of an adenovirus lacking E1B-55K, which is named ONYX-015, was restricted to p53-minus cancer cell lines (Bischoff et al., supra), and that ONYX-015 slowed the growth or caused regression of a p53-minus human tumor growing in nude mice (Heise et al., supra). Others have challenged the Onyx report claiming that replication of ONYX-015 is independent of p53 genotype and occurs efficiently in some primary cultured human cells (Harada and Berk, *J. Virol* 73:5333-5344, 1999). ONYX-015 does not replicate as well as wild-type adenovirus because E1B-55K is not available to facilitate viral mRNA transport from the nucleus. Also, ONYX-015 expresses less ADP than wild-type virus (see Example 1 below).

As an extension of the ONYX-015 concept, a replication-competent adenovirus vector was designed that has the gene for E1B-55K replaced with the herpes simplex virus thymidine kinase gene (Wilder et al., *Gene Therapy* 6:57-62, 1999). The group that constructed this vector reported that the combination of the vector plus gancyclovir showed a therapeutic effect on a human colon cancer in a nude mouse model (Wilder et al., *Cancer Res.* 59:410-413, 1999). However, this vector lacks the gene for ADP, and accordingly, the vector will lyse cells and spread from cell-to-cell less efficiently than an equivalent vector that expresses ADP. The gene for ADP is also lacking in another replication-competent adenovirus vector that has been described, in which a minimal enhancer/promoter of the human prostate specific antigen was inserted into the adenovirus E1A enhancer/promoter (Rodriguez et al., *Cancer Res.* 57:2559-2563, 1997).

Thus, there is a continuing need for vectors that replicate and spread efficiently in tumors but that can be modified such that they replicate poorly or not at all in normal tissue.

SUMMARY OF THE INVENTION

Briefly, therefore, the present invention is directed to novel vectors which are replication competent in neoplastic cells and which overexpress an adenovirus death protein (ADP). The work reported herein demonstrates the discovery that overexpression of ADP by a recombinant adenovirus allows the construction of a replication-competent adenovirus that kills neoplastic cells and spreads from cell-to-cell at a rate similar to or faster than that exhibited by adenoviruses expressing wild-type levels of ADP, even when the recombinant adenovirus contains a mutation that would otherwise reduce its replication rate in non-neoplastic cells. This discovery was unexpected because it could not have been predicted from what was known about adenovirus biology that Ad vectors overexpressing ADP remain viable and that the infected cells are not killed by the higher amounts of ADP before the Ad vector produces new virus particles that can spread to other tumor cells. Indeed, naturally-occurring adenoviruses express ADP in low amounts from the E3 promoter at early stages of infection, and begin to make ADP in large amounts only at 24-30 h p.i., once virions have been assembled in the cell nucleus. It is believed that other non-adenoviral vectors can be used to deliver ADP's cell-killing activity to neoplastic cells, including other viral vectors and plasmid expression vectors.

Thus, in one preferred embodiment, the ADP-expressing vector comprises a recombinant adenovirus lacking expression of at least one E3 protein selected from the group consisting of: gp19K; RIDα (also known as 10.4K); RIDβ (also known as 14.5K) and 14.7K. Because these E3 proteins inhibit immune-mediated inflammation and/or apoptosis of Ad-infected cells, it is believed that a recombinant adenovirus lacking one or more of these E3 proteins will stimulate infiltration of inflammatory and immune cells into a tumor treated with the adenovirus and that this host immune response will aid in destruction of the tumor as well as tumors that have metastasized. The ADP expressed by preferred embodiments comprises a naturally-occurring amino acid sequence from a human adenovirus of subgroup C, namely Ad1, Ad2, Ad5 and Ad6.

In another embodiment, replication of the vector is restricted to neoplastic cells. Such replication-restricted vectors are useful in treating cancer patients in which it is desirable to eliminate or reduce damage to normal cells and tissues that might be caused by the vector, particularly viral vectors that kill the host cell as part of their life cycle. In preferred embodiments, a recombinant adenovirus has a replication-restricted phenotype because the recombinant adenovirus is incapable of expressing an E1A viral protein which binds the pRB and the p300/CBP proteins or because the E4 promoter has been substituted with a promoter that is activated only in neoplastic cells.

In yet another embodiment, the invention provides a vector which overexpresses ADP and whose replication is under the control of a tissue specific promoter or an inducible promoter. In preferred embodiments, the vector comprises a recombinant adenovirus in which the tissue specific promoter or inducible promoter is substituted for the E4 promoter. Such vectors are useful for restricting replication of the vector and its ADP-mediated cell killing to cells of a particular type or to cells exposed to an exogenous agent that activates the promoter. A preferred tissue-specific or inducible vector also expresses a phenotype that restricts its replication to neoplastic cells.

In yet another embodiment, the invention provides a vector which overexpresses ADP but which is not restricted to tumors by a specific genetic modification. Such a vector is more destructive to neoplastic cells than even the naturally occurring Ad's of subgroup C. In preferred embodiments, this vector could be used for patients with terminal cancer not treatable by another method, and who have pre-existing neutralizing antibodies to Ad or to which neutralizing antibodies can be administered.

In still another embodiment, the invention provides a composition comprising a first recombinant virus which is replication competent in a neoplastic cell and overexpresses the adenovirus death protein. In one embodiment, the recombinant virus is contained within a delivery vehicle comprising a targeting moiety that limits delivery of the virus to cells of a certain type. With this embodiment, the replication-competent vector can be of any ADP-overexpressing configuration described herein. In some embodiments, the composition also comprises a second recombinant virus which is replication-defective and which expresses an anti-cancer gene product. The recombinant virus complements spread of the replication-defective virus, as well as its encoded anti-cancer product, throughout a tumor. In preferred embodiments, the first recombinant virus is a recombinant adenovirus whose replication is restricted to neoplastic cells and/or which lacks expression of one or more of the E3 gp19K; RIDα; RIDβ; and 14.7K proteins.

The ADP-expressing vectors and compositions of the invention are useful in a method for promoting death of a neoplastic cell. The method comprises contacting the neoplastic cell with a vector which is replication-competent in the neoplastic cell and which overexpresses ADP. Where the neoplastic cell comprises a tumor in a patient, the vector is administered directly to the tumor or, in other embodiments, the vector is administered to the patient systemically or in a delivery vehicle containing a targeting moiety that directs delivery of the vector to the tumor. In embodiments where the vector is a recombinant virus, the method can also comprise passively immunizing the patient against the virus.

In yet another embodiment of the invention, the vector may be used in combination with radiation therapy. The radiation therapy can be any form of radiation therapy used in the art such as for example, external beam radiation such as x-ray treatment, radiation delivered by insertion of radioactive materials within the body near or at the tumor site such as treatment with gamma ray emitting radionuclides, particle beam therapy which utilizes neutrons or charged particles and the like. In addition, this embodiment encompasses the use of more than one of the vectors of the present invention in a cocktail in combination with radiation therapy.

Another embodiment of the invention involves the use of the recombinant vector in combination with chemotherapy as has been disclosed for other adenovirus vectors (U.S. Pat. No. 5,846,945). Chemotherapeutic agents are known in the art and include antimetabolites including pyrimidine-analogue and purine-analogue antimetabolies, plant alkaloids, antitumor antibiotics, alkylating agents and the like. The use of more than one of the vectors of the present invention with a chemotherapeutic agent or agents is also contemplated within this embodiment.

Among the several advantages found to be achieved by the present invention, therefore, may be noted the provision of replication-competent vectors, particularly viruses, which rapidly kill cancer cells and spread from cell-to-cell in a tumor; the provision of such vectors whose replication can be induced or which is restricted to tumors and/or to cells of a certain tissue type; and the provision of compositions and methods for anti-cancer therapy which cause little to no side effects in normal tissues.

BRIEF DESCRIPTION OF THE DRAWINGS

FIG. 20 depicts the amino acid sequence, shown in single letter code, for the ADP proteins of Ad1, Ad2, Ad5, and Ad6 (SEQ ID NOS:5-8), for the Ad2 ADP mutants dl716, dl715, dl714, and dl737 (SEQ ID NOS:9-12), and for putative lumenal Domain (SEQ ID NO:17), transmembrane domain (SEQ ID NO:18), the cytosolic basic-proline domain (SEQ ID NO:19), and the remainder of the cystosolic domain (SEQ ID NO:20) of the ADP protein of Ad2.

FIG. 21 presents the complete nucleotide sequence of the genome of Ad5 (SEQ ID NO:28).

FIG. 22 presents the complete nucleotide sequence of the genome of KD1 (SEQ ID NO:1).

FIG. 23 presents the complete nucleotide sequence of the genome of KD3 (SEQ ID NO:2).

DESCRIPTION OF THE PREFERRED EMBODIMENTS

Figure 1:
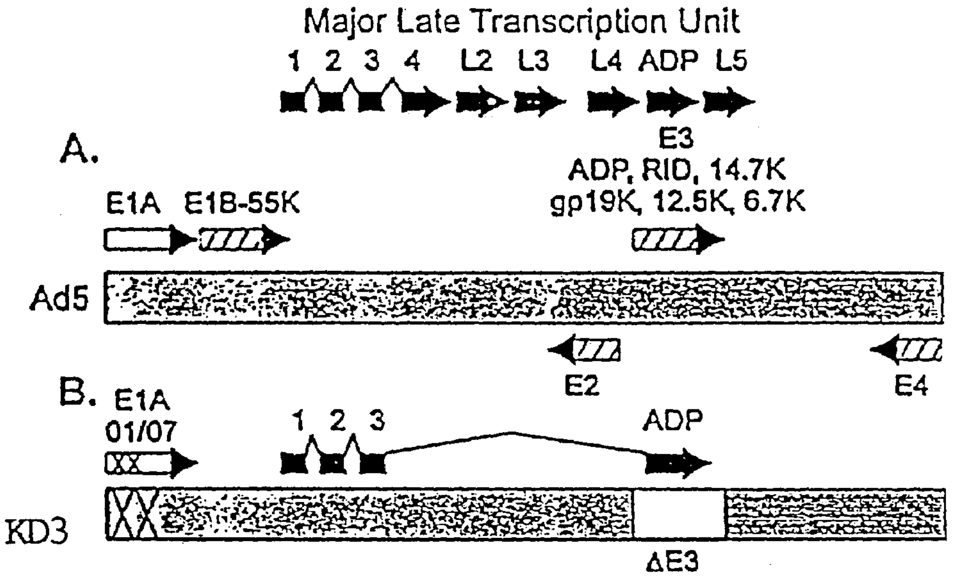
FIG. 1 is a schematic of gene expression in Ad5 (FIG. 1A) and KD3, a preferred embodiment of the invention (FIG. 1B), in which the respective genomes are represented by the stippled bars and transcription units represented by arrows above and below the bars, with the E3 proteins listed above the arrows for the E3 transcription unit, and the L1 to L5 families of late mRNA's indicated.

In accordance with the present invention, it has been discovered that overexpression of ADP by a recombinant adenovirus results in faster lysis of cells and spread of the virus throughout a cell monolayer than viruses expressing wild-type levels of ADP. It has also been discovered that this function for ADP is manifest in an adenovirus which contains E1A mutations that restrict adenoviral replication to neoplastic cells. Thus, vectors which are both replication competent in neoplastic cells and which overexpress ADP should be useful in anti-cancer therapy.

In the context of this disclosure, the following terms will be defined as follows unless otherwise indicated:

"Naturally-occurring" as applied to an object such as a polynucleotide, polypeptide, or virus means that the object can be isolated from a source in nature and has not been intentionally modified by a human.

"Neoplastic cell" means a cell which exhibits an aberrant growth phenotype characterized by a significant loss of control of cell proliferation and includes actively replicating cells as well as cells in a temporary non-replicative resting state ($G_1$ or $G_2$). A neoplastic cell may have a well-differentiated phenotype or a poorly-differentiated phenotype and may comprise a benign neoplasm or a malignant neoplasm.

"Recombinant virus" means any viral genome or virion which is different than a wild-type virus due to a deletion, insertion, or substitution of one or more nucleotides in the wild-type viral genome. The recombinant virus can have changes in the number of amino acid sequences encoded and expressed or in the amount or activity of proteins expressed by the virus. In particular, the term includes recombinant viruses generated by the intervention of a human.

"Replication-competent" as applied to a vector means that the vector is capable of replicating in normal and/or neoplastic cells. As applied to a recombinant virus, "replication-competent" means that the virus exhibits the following phenotypic characteristics in normal and/or neoplastic cells: cell infection; replication of the viral genome; and production and release of new virus particles; although one or more of these characteristics need not occur at the same rate as they occur in the same cell type infected by a wild-type virus, and may occur at a faster or slower rate. Where the recombinant virus is derived from a virus such as adenovirus that lyses the cell as part of its life cycle, it is preferred that at least 5 to 25% of the cells in a cell culture monolayer are dead 5 days after infection. Preferably, a replication-competent virus infects and lyses at least 25 to 50%, more preferably at least 75%, and most preferably at least 90% of the cells of the monolayer by 5 days post infection (p.i.).

"Replication-defective" as applied to a recombinant virus means the virus is incapable of or is greatly compromised in, replicating its genome in any cell type in the absence of a complementing replication-competent virus. Exceptions to this are cell lines such as 293 cells that have been engineered to express adenovirus E1A and E1B proteins.

"Replication-restricted" as applied to a vector of the invention means the vector replicates better in a dividing cell, i.e. either a neoplastic cell or a non-neoplastic, dividing cell, than in a cell of the same type that is not neoplastic and/or not dividing, which is also referenced herein as a normal, non-dividing cell. Preferably, a replication-restricted virus kills at least 10% more neoplastic cells than normal, non-dividing cells in cell culture monolayers of the same size, as measured by the number of cells showing cytopathic effects (CPE) at 5 days p.i. More preferably, between 25% and 50%, and even more preferably, between 50% and 75% more neoplastic than normal cells are killed by a replication-restricted virus. Most preferably, a replication-restricted adenovirus kills between 75% and 100% more neoplastic than normal cells in equal sized monolayers by 5 days p.i.

In one embodiment the invention provides a vector that is replication-competent in neoplastic cells and which overexpresses an ADP. Vectors useful in the invention include but are not limited to plasmid-expression vectors, bacterial vectors such as *Salmonella* species that are able to invade and survive in a number of different cell types, vectors derived from DNA viruses such as human and non-human adenoviruses, adenovirus associated viruses (AAVs), poxviruses, herpesviruses, and vectors derived from RNA viruses such as retroviruses and alphaviruses. Preferred vectors include recombinant viruses engineered to overexpress an ADP. Recombinant adenoviruses are particularly preferred for use as the vector, especially vectors derived from Ad1, Ad2, Ad5 or Ad6.

Vectors according to the invention overexpress ADP. As applied to recombinant Ad and AAV vectors, the term "overexpresses ADP" means that more ADP molecules are made per viral genome present in a dividing cell infected by the vector than expressed by any previously known recombinant adenoviral vector or AAV in a dividing cell of the same type. As applied to other, non-adenoviral vectors, "overexpresses ADP" means that the virus expresses sufficient ADP to lyse a cell containing the vector.

Vectors overexpressing ADP can be prepared using routine methodology. (See, e.g., *A Laboratory Cloning Manual,* 2nd Ed., vol. 3, Sambrook et al., eds., Cold Spring Harbor Laboratory Press, 1989). For example, a polynucleotide encoding the ADP can be cloned into a plasmid expression vector known to efficiently express heterologous proteins in mammalian cells. The polynucleotide should also include appropriate termination and polyadenylation signals. Enhancer elements may also be added to the plasmid to increase the amount of ADP expression. Viral vectors overexpressing ADP can be prepared using similar materials and techniques.

Where the virus is a recombinant adenovirus, overexpression of ADP can be achieved in a multitude of ways. In general, any type of deletion in the E3 region that removes a splice site for any of the E3 mRNAs will lead to overexpression of the mRNA for ADP, inasmuch as more of the E3 pre-mRNA molecules will be processed into the mRNA for ADP. This is exemplified in the KD1, KD3, GZ1 and GZ3 vectors (SEQ ID NOS:1-4) whose construction is described below. Other means of achieving overexpression of ADP in Ad vectors include, but are not limited to: insertion of pre-mRNA splicing and cleavage/polyadenylation signals at sites flanking the gene for ADP; expression of ADP from another promoter, e.g. the human cytomegalovirus promoter, inserted into a variety of sites in the Ad genome; and insertion of the gene for ADP behind the gene for another Ad mRNA, together with a sequence on the 5' side of the ADP sequence that allows for internal initiation of translation of ADP, e.g. the Ad tripartite leader or a viral internal ribosome initiation sequence.

The ADP expressed by a vector according to the invention is any polypeptide comprising a naturally-occurring full-length ADP amino acid sequence or variant thereof that confers upon a vector expressing the ADP the ability to lyse a cell containing the vector such that replicated copies of the vector are released from the infected cell. A preferred full-length ADP comprises the ADP amino acid sequence encoded by Ad1, Ad2, Ad5 or Ad6. These naturally-occurring ADP sequences are set forth in SEQ ID NOS:5-8, respectively. ADP variants include fragments and deletion mutants of naturally-occurring adenovirus death proteins, as well as full-length molecules, fragments and deletion mutants containing conservative amino acid substitutions, provided that such variants retain the ability, when expressed by a vector inside a cell, to lyse the cell.

Conservative amino acid substitutions refer to the interchangeability of residues having similar side chains. Conservatively substituted amino acids can be grouped according to the chemical properties of their side chains. For example, one grouping of amino acids includes those amino acids having neutral and hydrophobic side chains (A, V, L, I, P, W, F, and M); another grouping is those amino acids having neutral and polar side chains (G, S, T, Y, C, N, and Q); another grouping is those amino acids having basic side chains (K, R, and H); another grouping is those amino acids having acidic side chains (D and E); another grouping is those amino acids having aliphatic side chains (G, A, V, L, and I); another grouping is those amino acids having aliphatic-hydroxyl side chains (S and T); another grouping is those amino acids having amine-containing side chains (N, Q, K, R, and H); another grouping is those amino acids having aromatic side chains (F, Y, and W); and another grouping is those amino acids having sulfur-containing side chains (C and M). Preferred conservative amino acid substitutions groups are: R-K; E-D, Y-F, L-M; V-I, and Q-H.

As used herein, an ADP variant can also include modifications of a naturally-occurring ADP in which one or more amino acids have been inserted, deleted or replaced with a different amino acid or a modified or unusual amino acid, as well as modifications such as glycosylation or phosphorylation of one or more amino acids so long as the ADP variant containing the modified sequence retains cell lysing activity.

As described below, the inventors herein performed a structure-function analysis of ADP which defined specific domains in ADP required to promote cell death. Using this information, when combined with known recombinant DNA and cloning methodology, it is believed the skilled artisan can readily construct ADP variants of a naturally-occurring adenovirus death protein and test them for cell lysing activity. A preferred ADP deletion mutant comprises an ADP amino acid sequence from any of the deletion mutants dl716, dl715, dl714 and dl737, whose ADP sequences are set forth in SEQ ID NOS:9-12, respectively).

Where the vector is derived from a virus, it is preferred that the virus lack expression of one or more viral proteins involved in avoiding host anti-viral defenses such as immune-mediated inflammation and/or apoptosis of infected cells. For example, adenovirus contains a cassette of genes that prevents killing of Ad-infected cells by the immune system (Wold et al., *Semin. Virol.,* 1998 (8:515-523, 1998). The E3-14.7K protein and the E3 RID (Receptor Internalization and Degradation) protein, which is a complex consisting of RIDα and RIDβ, inhibit apoptosis of Ad-infected cells induced by tumor necrosis factor (TNF) and the Fas ligand which are expressed on, or secreted by, activated macrophages, natural killer (NK) cells, and cytotoxic lymphocytes (CTLs) (Tollefson et al., *Nature* 392:727-730, 1998). The E3-gp19K protein inhibits CTL-killing of infected cells by blocking transport of MHC class I antigens to the cell surface (Wold et al., supra). Thus, it is believed that infection of tumor cells by such viral vectors will stimulate infiltration of inflammatory cells and lymphocytes into the tumor, and will not prevent infected tumor cells from apoptosis induced by cytolytic cells of the immune system, or against apoptosis inducing cytokines. For example, it is known that when mice are infected with Ad mutants lacking the E3 gp19K, RID and 14.7K proteins there is a dramatic increase (as compared to E3-positive Ad) in infiltration of inflammatory cells and lymphocytes into the infected tissue (Sparer et al., *J. Virol.* 70:2431-2439, 1996). A similar infiltration of tumors infected by an ADP-expressing viral vector of the invention would be expected to further promote destruction of the tumor by adding an immune system attack to the ADP-mediated killing activity. For example, it is believed that the viral infection will stimulate formation of tumor-specific CTL's that can kill neoplastic cells not only in the tumor but also ones that have metastasized. In addition, it is also expected that vector-specific CTL's will be generated which could attack vector-infected cells if the vector spreads away from the tumor into normal cells. Because viral vectors overexpressing ADP will spread rapidly through the tumor, it is believed these immune mechanisms will have little effect on spread of the vector.

Where the vector is a recombinant adenovirus, it is preferred that the adenovirus lack expression of each of the E3 gp19K, RID, and 14.7K proteins. By "lack expression" and "lacking expression" of a protein(s), "it is meant" that the viral genome contains one or more mutations that inactivates expression of a functional protein, i.e., one having all the functions of the wild-type protein. The inactivating mutation includes but is not limited to substitution or deletion of one or more nucleotides in the encoding gene(s) that prevents expression of functional transcripts or that results in transcripts encoding nonfunctional translation products. A particularly preferred way to inactivate expression of the Ad E3 gp19K, RID, and 14.7K proteins is by deleting the E3 region containing the genes encoding these proteins. Preferably, one or both of the E3 genes encoding the E3 6.7K and 12.5K proteins are also deleted because, as discussed in the Examples below, it is believed that deletion of most or all of the E3 genes other than the ADP gene facilitates overexpression of ADP mRNA by reducing competition for splicing of the major late pre-mRNAs. Preferred Ad vectors containing an E3 deletion that overexpress ADP are GZ1 (SEQ ID NO:3) and GZ3 (SEQ ID NO:4), whose construction and properties are described in the Examples below.

The invention also provides ADP-expressing vectors whose replication is restricted to dividing cells. Any means known to provide such a replication-restricted phenotype may be used. For example, WO 96/40238 describes microbes that preferentially invade tumor cells as well as methods for identifying and isolating bacterial promoters that are selectively activated in tumors. It is also contemplated that expression of one or more vector proteins essential for replication can be placed under the control of the promoter for a cellular gene whose expression is known to be upregulated in neoplastic cells. Examples of such genes include but are not limited to: the breast cancer markers mammaglobin (Watson et al., *Oncogene* 16:817-824, 1998); BRCA1 (Norris et al., *J. Biol. Chem.* 270:22777-22782, 1995) and her2/neu (Scott et al., *J. Biol. Chem.* 269:19848-19858, 1994); and prostate specific antigen (U.S. Pat. No. 5,698,443); surfactant protein B for lung alveoli (Yan et al., *J. Biol. Chem.* 270:24852-24857, 1995); factor VII for liver (Greenberg et al., *Proc. Natl. Acad. Sci. USA* 92:12347-12351, 1995); and surviving for cancer in general (Li et al., *Nature* 396:580-584). Where the vector is an adenovirus, it is contemplated that such tumor-specific promoters can be substituted for the E4 promoter. Because E4 gene products are essential for Ad replication, placing their expression under the control of a tumor-specific promoter should restrict replication of the vector to tumor cells in which the promoter is activated.

Another strategy for restricting replication of ADP-expressing Ad vectors to neoplastic cells is exemplified by the KD1 (SEQ ID NO:1), KD2 (SEQ ID NO:13) and KD3 (SEQ ID NO:2) vectors, whose construction and properties are described in the Examples below. This strategy exploits a pre-existing Ad5 mutant in the E1A gene, named dl1101/1107 (Howe et al., *Proc. Natl. Acad. Sci.,* 87:5883-5887, 1990), also referred to herein as dl01/07, and which can only grow well in cancer cells. The role of E1A is to drive cells from the $G_0$ and $G_1$ phases of the cell cycle into S-phase. This is achieved by two mechanisms, one involving pRB (and family members), and the other involving p300 and the related protein CBP (DePinho, R. A., *Nature* 391:533-536, 1998). One domain in E1A binds members of the pRB family. pRB normally exists in the cell as a complex with the transcription factor E2F-1 and E2F family members (E2F), tethered via-E2F to E-2F binding sites in promoters of cells expressed in S-phase. Here, pRB acts as a transcriptional co-repressor. E1A binding to pRB relieves this repression, and causes the release of E2F from pRB/E2F complexes. Free E2F then activates promoters of genes expressed in S-phase, e.g. thymidine kinase, ribonucleotide reductase, etc. Another domain in E1A binds the p300/CBP transcription adaptor protein complex. p300/CBP is a transcriptional co-activator that binds many different transcription factors and accordingly is targeted to promoters. p300/CBP has intrinsic histone acetyltransferase activity. E1A binding to p300/CBP is believed to inhibit this histone acetyltransferase activity, allowing acetylation of histones and repression of transcription (Chakravarti et al., *Cell* 96:393-403, 1999; Hamamori et al., *Cell* 96:405-413, 1999). Conceivably, some of the genes that are repressed as a result of E1A interacting with p300/CBP to play a role in blocking the cell cycle, although this is not known. Cancer cells are cycling, so they have free E2F and presumably some p300/CBP-regulated genes are repressed. Consistent with these ideas, E1A must bind both p300/CBP and the pRB family in order to transform primary cells to a constitutively cycling state (Howe et al., supra). The mutant dl01/07 lacks both the p300/CBP- and pRB-binding domains and, as expected, it replicates very poorly in non-dividing "normal" cells or serum-starved cancer cells, but well in growing cancer cells. As described below, the growth of the KD1 and KD3 vectors, which contain the dl01/07 E1A mutation, is very much better in dividing cancer cells as compared to non-dividing cells. Because the dl01/07 mutant is completely defective in oncogenic transformation of rat cells (Howe et al., supra), vectors according to the invention that contain this E1A mutation cannot induce cancer in humans (remote as that may be) through an E1A-dependent mechanism.

The invention also includes vectors overexpressing ADP whose replication is restricted to specific tissues by placing expression of one or more proteins essential for replication under the control of a tissue specific promoter. A number of tissue-specific promoters have been described in the art such as the surfactant protein B promoter which is only active in cells containing the TTF1 transcription factor, i.e., type II alveolar cells (Yan et al., supra) the transcriptional regulatory element described in U.S. Pat. No. 5,466,596 to Breitman et al., that directs gene expression specifically in cells of endothelial lineage; prostate specific antigen which is expressed in prostate cells (Rodriguez et al., supra); and human alpha-lactalburn gene which is expressed in breast cancer cells (Anderson et al., *Gene Therapy* 6:854-864, 1999). Many other tissue-specific or tissue-preferred enhancer/promoters have been reported (Miller and Whelan, *Human Gene Therapy* 8:803-815, 1997).

Replication of vectors according to the invention can also be controlled by placing one or more genes essential for vector replication under the control of a promoter that is activated by an exogenous inducing agent, such as metals, hormones, antibiotics, and temperature changes. Examples of such inducible promoters include but are not limited to metallothionein promoters, the glucocorticoid promoter, the tetracycline response promoter, and heat shock protein (hsp) promoters such as the hsp 65 and 70 promoters.

The invention also provides compositions comprising a recombinant vector that overexpresses ADP in an amount effective for promoting death of neoplastic cells and a method comprising administering a therapeutically effective amount of the vector to a neoplastic cell in a patient. It is believed the compositions and methods of the present invention are useful for killing neoplastic cells of any origin and include neoplastic cells comprising tumors as well as metastatic neoplastic cells.

It is also contemplated that ADP-expressing viral vectors can be administered to neoplastic cells along with a replication-defective virus that expresses an anti-cancer gene product. For example, many replication-defective $E1^-$ Ad vectors for use in cancer therapy are well characterized. A limitation of replication-defective vectors is that they only synthesize the therapeutic protein in the cell they initially infect, they cannot spread to other cells. Also, since the genome does not replicate, transcription can only occur from the input genomes, and this could be as low as one copy per cell. In contrast, the genome of replication-competent Ad vectors are amplified by about $10^4$ in the cell that was initially infected, providing more templates for transcription. More amplification is achieved as the vector spreads to other cells. By combining replication-defective viral vectors expressing an anti-cancer gene product with replication-competent viral vectors described herein, it is expected that the result will be template amplification and rapid spread of both vectors to surrounding cells. For example, with Ad-based vectors, the burst size for each vector should be large, $\sim 10^4$ PFU/cell, so the probability of co-infection of surrounding cells by both vectors will be high. Thus, both the replication-competent and replication-defective vectors should spread simultaneously through the tumor, providing even more effective anti-cancer therapy.

Expression of the anti-cancer gene product encoded by the replication-defective vector can be under the control of either constitutive, inducible or cell-type specific promoters. The anti-cancer gene product can be any substance that promotes death of a neoplastic cell. The term "gene product" as used herein refers to any biological product or products produced as a result of the biochemical reactions that occur under the control of a gene. The gene product can be, for example, an RNA molecule, a peptide, a protein, or a product produced under the control of an enzyme or other molecule that is the initial product of the gene, i.e., a metabolic product. For example, a gene can first control the synthesis of an RNA molecule which is translated by the action of ribosomes into a prodrug converting enzyme which converts a nontoxic prodrug administered to a cancer patient to a cell-killing agent; the RNA molecule, enzyme, and the cell-killing agent generated by the enzyme are all gene products as the term is used here. Examples of anti-cancer gene products include but are not limited to cell-killing agents such as apoptosis-promoting agents and toxins; prodrug converting enzymes; angiogenesis inhibitors; and immunoregulatory molecules and antigens capable of stimulating an immune response, humoral and/or cellular, against the neoplastic cell.

Apoptosis-promoting agents include but are not limited to the pro-apoptotic members of the BCL-2 family such as BAX, BAD, BID and BIK, as well as antisense molecules which block expression of anti-apoptotic members of the BCL-2 family. Examples of immunoregulatory molecules are cytokines such as tumor necrosis factor, Fas/Apo1/CD95 ligand, tumor necrosis factor related apoptosis inducing ligand, interleukins, macrophage activating factor and interferon $\gamma$. Angiogenesis inhibitors include but are not limited to endostatin and angiostatin. Toxins include but are not limited to tumor necrosis factor, lymphotoxin, the plant toxin ricin, which is not toxic to humans due to the lack of ricin receptors in animal cells, and the toxic subunit of bacterial toxins. Examples of pro-drug converting enzymes and pro-drug combinations are described in WO 96/40238 and include: thymidine kinase and acyclovir or gancyclovir; and bacterial cytosine deaminase and 5-fluorocytosine.

The therapeutic or pharmaceutical compositions of the present invention can be administered by any suitable route known in the art including for example by direct injection into a tumor or by other injection routes such as intravenous, subcutaneous, intramuscular, transdermal, intrathecal and intracerebral. Administration can be either rapid as by injection or over a period of time as by slow infusion or administration of slow release formulation. For treating tissues in the central nervous system, administration can be by injection or infusion into the cerebrospinal fluid (CSF). When it is intended that a recombinant vector of the invention be administered to cells in the central nervous system, administration can be with one or more agents capable of promoting penetration of the vector across the blood-brain barrier. Preferably, vectors of the invention are administered with a carrier such as liposomes or polymers containing a targeting moiety to limit delivery of the vector to targeted cells. Examples of targeting moieties include but are not limited to antibodies, ligands or receptors to specific cell surface molecules.

Compositions according to the invention can be employed in the form of pharmaceutical preparations. Such preparations are made in a manner well known in the pharmaceutical art. One preferred preparation-utilizes a vehicle of physiological saline solution, but it is contemplated that other pharmaceutically acceptable carriers such as physiological concentrations of other non-toxic salts, five percent aqueous glucose solution, sterile water or the like may also be used. It may also be desirable that a suitable buffer be present in the composition. Such solutions can, if desired, be lyophilized and stored in a sterile ampoule ready for reconstitution by the addition of sterile water for ready injection. The primary solvent can be aqueous or alternatively non-aqueous.

The carrier can also contain other pharmaceutically-acceptable excipients for modifying or maintaining the pH, osmolarity, viscosity, clarity, color, sterility, stability, rate of dissolution, or odor of the formulation. Similarly, the carrier may contain still other pharmaceutically-acceptable excipients for modifying or maintaining release or absorption or penetration across the blood-brain barrier. Such excipients are those substances usually and customarily employed to formulate dosages for parenteral administration in either unit dosage or multi-dose form or for direct infusion into the cerebrospinal fluid by continuous or periodic infusion.

It is also contemplated that certain formulations containing ADP-expressing vectors are to be administered orally. Such formulations are preferably encapsulated and formulated with suitable carriers in solid dosage forms. Some examples of suitable carriers, excipients, and diluents include lactose, dextrose, sucrose, sorbitol, mannitol, starches, gum acacia, calcium phosphate, alginates, calcium silicate, microcrystalline cellulose, polyvinylpyrrolidone, cellulose, gelatin, syrup, methyl cellulose, methyl- and propylhydroxybenzoates, talc, magnesium, stearate, water, mineral oil, and the like. The formulations can additionally include lubricating agents, wetting agents, emulsifying and suspending agents, preserving agents, sweetening agents or flavoring agents. The compositions may be formulated so as to provide rapid, sustained, or delayed release of the active ingredients after administration to the patient by employing procedures well known in the art. The formulations can also contain substances that diminish proteolytic degradation and promote absorption such as, for example, surface active agents.

The specific dose is calculated according to the approximate body weight or body surface area of the patient or the volume of body space to be occupied. The dose will also be calculated dependent upon the particular route of administration selected. Further refinement of the calculations necessary to determine the appropriate dosage for treatment is routinely made by those of ordinary skill in the art. Such calculations can be made without undue experimentation by one skilled in the art. Exact dosages are determined in conjunction with standard dose-response studies. It will be understood that the amount of the composition actually administered will be determined by a practitioner, in the light of the relevant circumstances including the condition or conditions to be treated, the choice of composition to be administered, the age, weight, and response of the individual patient, the severity of the patient's symptoms, and the chosen route of administration. Dose administration can be repeated depending upon the pharmacokinetic parameters of the dosage formulation and the route of administration used.

The invention also contemplates passively immunizing patients who have been treated with a viral vector overexpressing ADP. Passive immunization can include administering to the patient antiserum raised against the viral vector, or gamma-globulin or vector-specific purified polyclonal or monoclonal antibodies isolated from the antiserum. Preferably, the patient is passively immunized after a time period sufficient for the viral vector to replicate in and spread through the tumor.

Preferred embodiments of the invention are described in the following examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims which follow the examples.

EXAMPLE 1

This example illustrates the construction and characterization of the KD1 and KD3 anti-cancer vectors.

To construct KD1, the inventors deleted the entire E3 region of a unique plasmid, leaving behind only a unique PacI site for cloning. The starting plasmid was pCRII, purchased from Invitrogen, containing the Ad5 BamHIA fragment having a deletion of all the E3 genes; the E3 deletion is identical to that for KD1 and GZ3, the sequences of which are given in SEQ ID NO:1 and SEQ ID NO:4, respectively. The ADP gene from Ad5 was cloned into the PacI site, then built into the E3 region of the genome of the Ad5 E1A mutant named dl01/07. This was done by co-transfecting into human embryonic kidney 293 cells the aforementioned BamHIA fragment containing the ADP gene together with the overlapping EcoRIA restriction fragment obtained from dl01/07. Complete viral genomes are formed within the cell by overlap recombination between the Ad sequences in the BamHIA fragment in the plasmid and the EcoRIA fragment. KD3 was constructed in the same way except the E3 gene for the 12.5K protein was retained in the starting plasmid. A vector named KD2, which marginally overexpress ADP, was also prepared. Plaques of each recombinant Ad were picked, screened, purified, expanded into CsCl-banded stocks, sequenced, titered, and characterized. GZ1 and GZ3 are Ad vectors that are identical to KD1 and KD3, respectively, except that GZ1 and GZ3 have wild-type E1A sequences as found in AD5 or in the Ad5 mutant dl309. GZ1 and GZ3 were constructed as described for KD1 and KD3 except that the EcoRIA fragment of Ad5 was used for GZ1 and GZ3.

KD1 and KD3 were characterized in cell culture by infecting the human A549 lung carcinoma cell line with high titer ($1-8\times10^{10}$ plaque forming units [PFU] per ml) virus stocks of one of these recombinant vectors, or with one of the control viruses dl01/07, dl309, dl327, and Ad5 (wt). Fifty PFU per cell were used for each virus. The descriptions of these viruses as well as some other viruses used in these examples are presented in Table 1.

TABLE 1

Description of mutations in viruses:

| | RNA REGION | | | |
|---|---|---|---|---|
| Virus | E1 | VA | E3 | E4 |
| dl1101/1107 | dl1101: deletion of Ad5 bp 569-634 dl1107: deletion of Ad5 bp 890-928 | From dl309 deletion of Ad5 bp 10594-10595 | From dl309 deletion of Ad5 bp 28597-28602; deletion-substitution Ad5 bp 3005-30750, insert 642 bp DNA of unknown origin | wild type |
| KD1 | dl1101: deletion of Ad5 bp 569-634 dl1107: deletion of Ad5 bp 890-928 | From dl309 deletion of Ad5 bp 10594-10595 | deletion of Ad5 bp 27858-27860, TAA inserted; deletion of Ad5 bp 27982-28134; deletion of Ad5 bp 28395-29397, insert CCTTAATTAAA; deletion of Ad5 bp 29783-30883, insert TTAATTAAGG | wild type |
| KD2 | dl1101: deletion of Ad5 bp 569-634 dl1107: deletion of Ad5 bp 890-928 | From dl309 deletion of Ad5 bp 10594-10595 | dl309 background, gp19K mutated deletion of Ad5 bp 28597-28602; deletion-substitution Ad5 bp 3005-30750, insert 642 bp DNA of unknown origin; deletion of Ad5 bp 28788-28789, insert TTAATTAA | wild type |

TABLE 1-continued

Description of mutations in viruses:

| | RNA REGION | | | |
|---|---|---|---|---|
| Virus | E1 | VA | E3 | E4 |
| KD3 | dl1101: deletion of Ad5 bp 569-634 dl1107: deletion of Ad5 bp 890-928 | From dl309 deletion of Ad5 bp 10594-10595 | deletion of Ad5 bp 28598-29397; deletion of Ad5 bp 29783-30469 | wild type |
| GZ1 | wt | wild type | deletion of Ad5 bp 27858-27860, TAA inserted; deletion of Ad5 bp 27982-28314; deletion of Ad5 bp 28395-29397, insert CCTTAATTAAA; deletion of Ad5 bp 29783-30883, insert TTAATTAAGG | wild type |
| GZ3 | wild type | wild type | deletion of AD5 bp 28598-29397; deletion of Ad5 bp 29783-30469 | wild type |
| dl1101/1107-SPB | dl1101: deletion of Ad5 bp 569-634 dl1107: deletion of Ad5 bp 890-928 | From dl309 deletion of Ad5 bp 10594-10595 | From dl309 deletion of Ad5 bp 28597-28602; deletion-substitution Ad5 bp 3005-30750, insert 642 bp DNA of unknown origin | E4 promoter deletion-substitution: deletion of Ad5 bp 35623-35775, insert SP-B 500 promoter flanked |
| KD1-SPB | dl1101: deletion of Ad5 bp 569-634 dl1107: deletion of Ad5 bp 890-928 | From dl309 deletion of Ad5 bp 10594-10595 | deletion of Ad5 bp 27848-27860, TAA inserted; deletion of Ad5 bp 27982-28134; deletion of Ad5 bp 28395-29397, insert CCTTAATTAAA; deletion of Ad5 bp 29783-30883, insert TTAATTAAGG | E4 promoter deletion-substitution: deletion of Ad5 bp 35623-35775, insert SP-B 500 promoter flanked by Bst1 107l sites |
| KD3-SPB | dl1101: deletion of Ad5 bp 569-634 dl1107: deletion of Ad5 bp 890-928 | From dl309 deletion of Ad5 bp 10594-10595 | deletion of Ad5 bp 28598-29397; deletion of Ad5 bp 29783-30469 | E4 promoter deletion-substitution: deletion of Ad5 bp 35623-35775, insert SP-B 500 promoter flanked by Bst1 107l sites |

Using a polymerase chain reaction (PCR)-based protocol, an in-frame stop codon was introduced into the gene for the E3-gp19K protein in the E3 region of the Ad5 mutant dl309 (Jones and Shenk, *Cell* 17:683-689, 1979). The mutagenesis was conducted using a SunI-Bst1107I fragment, nucleotides 28,390 to 29,012 in the Ad5 genome, which was then substituted for the equivalent fragment in dl309. dl01/07 is the parent for KD1 and KD3. In turn, the Ad5 mutant named dl309 is the parent of dl01/07, i.e. dl309 is identical to dl01/07 except that dl309 does not have the E1A mutation. Both dl01/07 and dl309 have deletions of the genes for the E3 RIDα, RIDβ and 14.7K proteins but retain the gene for ADP. The Ad5 mutant dl327 has wild-type E1A, it lacks the gene for ADP, and its lacks all other E3 genes except the one for the 12.5K protein.

Figure 2:
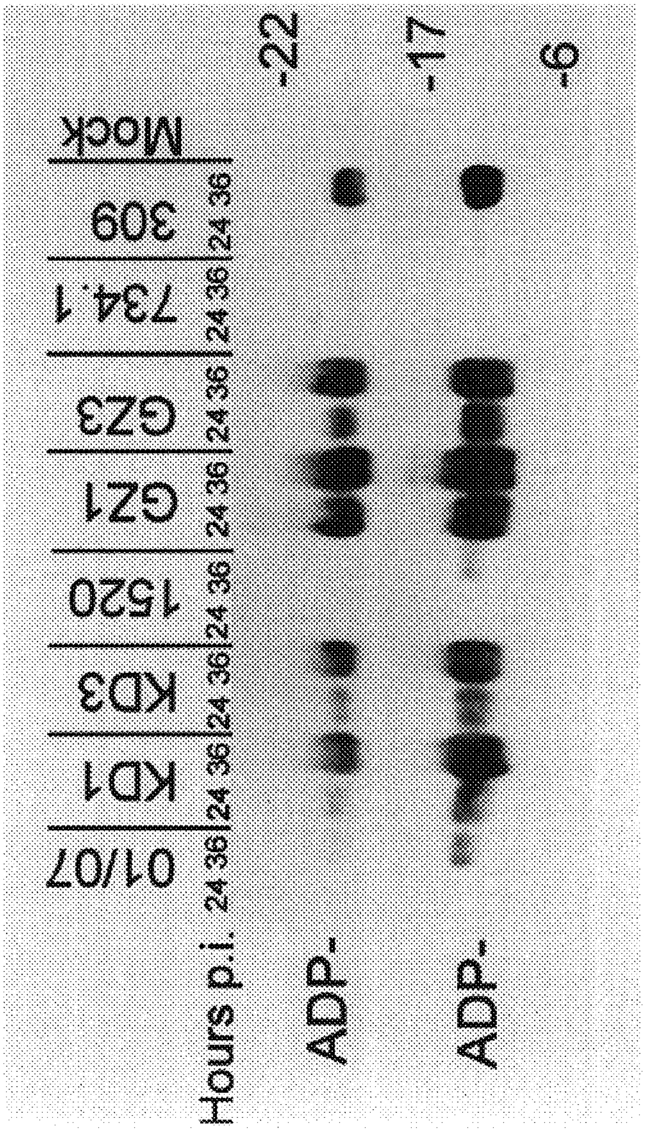
FIG. 2 illustrates the overexpression of ADP by KD1, KD3, GZ1, and GZ3 showing an immunoblot of proteins isolated from human A549 cells infected with the indicated viruses and probed with an anti-ADP antibody, with ADP indicating differently glycosylated and proteolytically processed forms of ADP.
Figure 3:
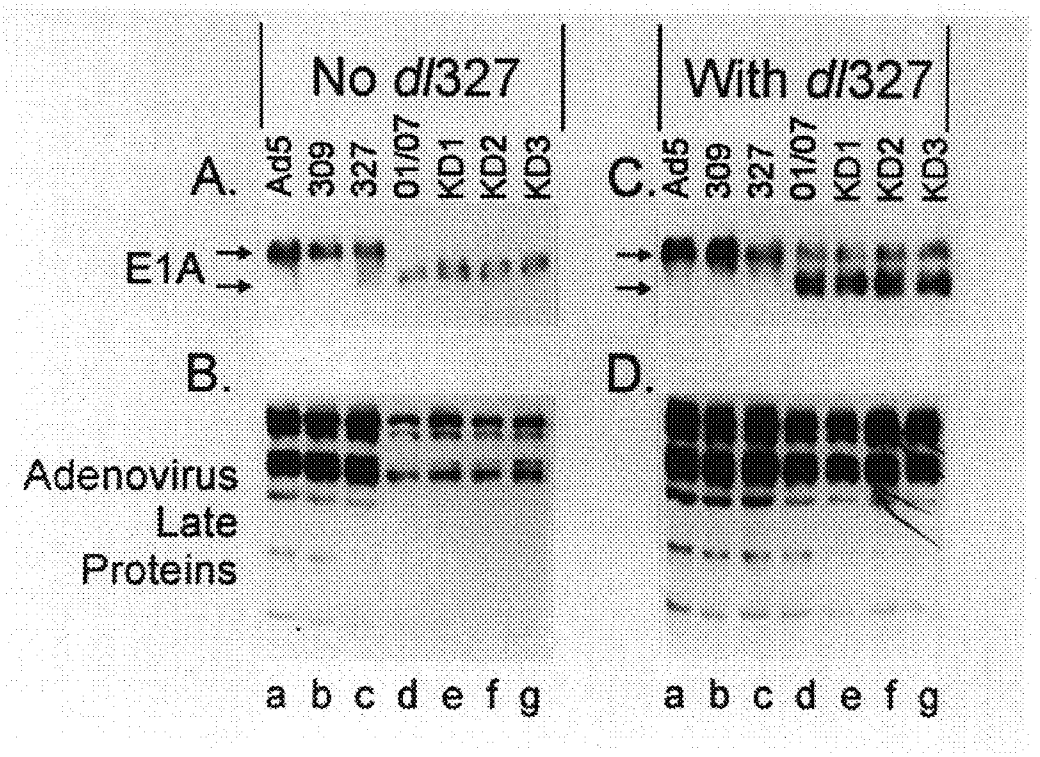
FIG. 3 illustrates that the E1A dl1101/1107 mutation referred to in the figure and hereinafter as dl01/07, retards expression of late proteins, showing an immunoblot of E1A proteins and late proteins in A549 cells infected with the indicated viruses in the absence (FIGS. 3A and 3B) or presence (FIGS. 3C and 3D) of dl327, which has a wild-type E1A region and has a deletion of all E3 genes but the gene encoding the 12.5K protein (FIGS. 3C and 3D). An antiserum specific to the E1A proteins was used for FIGS. 3A and 3C. An antiserum raised against Ad5 virions was used for FIGS. 3B and 3D.

At 24 and 36 hours post-infection (h p.i.), proteins were extracted from the A549 cells and analyzed for ADP by immunoblot using a rabbit antiserum against ADP (Tollefson et al., *J. Virol.* 66:3633-3642, 1992). The results are shown in FIG. 2. Much more ADP was detected at 24 and 36 h p.i. in KD1- and KD3-infected cells than in cells infected with dl01/07. Also, much more ADP was synthesized by GZ1 and GZ3 than dl309 or the other viruses. Most importantly, KD1, KD3, GZ1, and GZ3 expressed much more ADP at 24 h p.i. than did dl01/07 or dl309 (FIG. 2). This result is consistent with an observation discussed below that the cells infected with KD1, KD3, GZ1, or GZ3 lyse faster, and that these viruses spread from cell to cell faster than dl01/07 or dl309. It is noteworthy that KD1, KD3, GZ1, and GZ3 express much more ADP at 24 and 36 h p.i. than the Ad5 mutant dl1520 (FIG. 2); dl1520 is the original name given to ONYX-015 (Heise et al., *Nature Medicine* 3:639-645, 1997). As expected, no ADP was detected in cells infected with pm734.1 (FIG. 2), a mutant that lacks amino acids 1 to 48 in ADP (Tollefson et al., *J. Virol.* 70:2296-2306, 1996). Expression of the E1A proteins by dl01/07, KD1, KD2, and KD3 was slightly less than by Ad5, dl309, or dl327, and as expected from the dl01/07 deletion, the proteins were smaller (FIG. 3A). dl327 is isogenic with dl324 (Thimmappaya et al., 1982 *Cell* 31:543-51, 1983), and it lacks the gene for ADP and all other E3 proteins except the 12.5K protein.

The amount of ADP detected in the KD1 and KD3 infected cells is significantly higher than the amount detected in the dl309 infected cells (FIG. 2). If one takes into consideration the fact that the viruses with the E1A mutation replicate somewhat slower, as evidenced in by the delayed appearance of the late proteins (FIG. 3B), it is clear that KD1 and KD3 express much more ADP per viral genome present in the cell than dl309. This finding is supported by the fact that when A549 cells are coinfected with a virus containing the E1A mutation and dl327, which lacks ADP but has wild-type E1A, the replication rates of the E1A mutant viruses speed up, as indicated by earlier appearance of late proteins (compare FIGS. 3B and 3D). Thus, dl327 complements the E1A mutation. In conclusion, these experiments demonstrate that ADP is dramatically overexpressed by KD1, KD3, GZ1, and GZ3. ADP is marginally overexpressed by KD2 (not shown).

EXAMPLE 2

This example illustrates that KD1 and KD3 lyse cells more rapidly and spread from cell-to cell faster than other adenoviruses.

Figure 4:
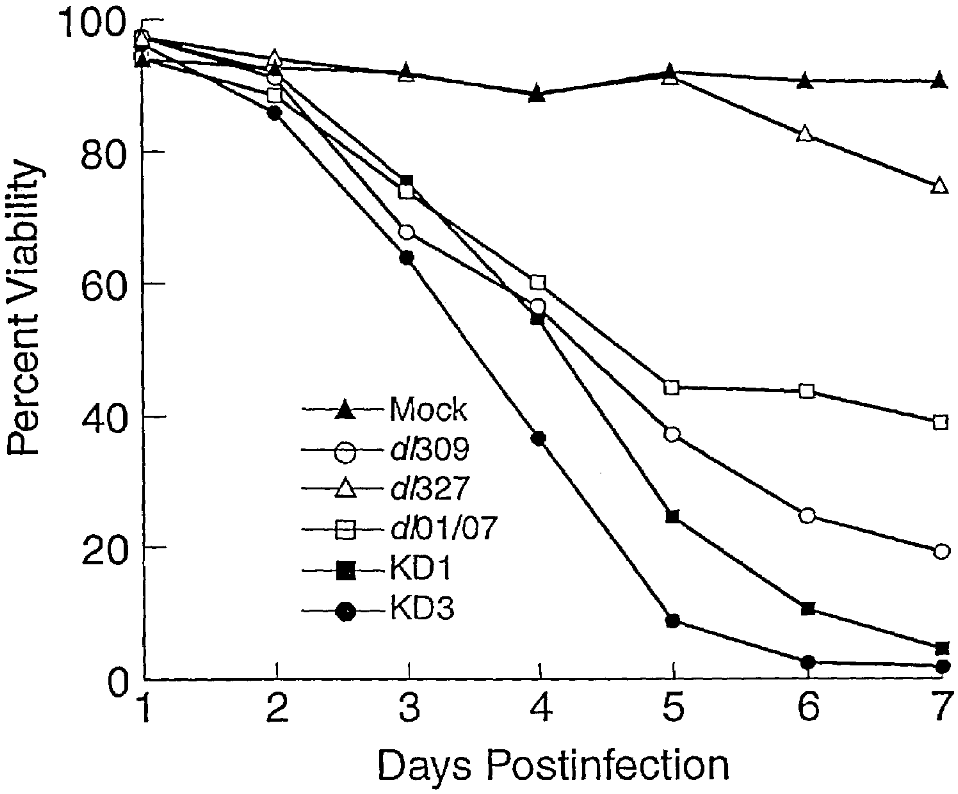
FIG. 4 illustrates that KD1 and KD3 kill cells more efficiently than control viruses that express less or no ADP, showing a graph of the percent of A549 cells infected with the indicated viruses that were viable at the indicated days p.i. as determined by trypan blue exclusion.

The ability of KD1 and KD3 to lyse cells was examined by a trypan blue exclusion cell viability assay which was performed essentially as described by Tollefson et al., *J. Virol.* 70:2296-2306, 1996. In brief, A549 cells were mock-infected or infected with 20 PFU/cell of KD1, KD3, dl01/07, dl327 or dl309. At various days p.i., the number of viable cells was determined using a hemacytometer (600 to 1000 cells were counted per time point) and the results are shown in FIG. 4.

Only 25% of the KD1-infected cells and 9% of the KD3-infected cells were alive at 5 days p.i. as compared to 44% of cells infected with dl01/07, which has the same E1A mutation as KD1 and KD3. The KD1 and KD3 vectors also lysed cells faster than dl309, which has a wild-type E1A region. When infected with dl327 ($ADP^-$, $E1A^+$), 94% of the cells were alive after 5 days. When cell lysis was estimated by release of lactate dehydrogenase, KD1 and KD3 once again lysed cells faster than dl01/07 and dl309, and dl327 caused little cell lysis (data not shown). Thus, ADP is required for efficient cell lysis, and over-expression of ADP increases the rate of cell lysis.

As another means to measure cell lysis and to examine virus replication in cancer cells, separate groups of A549 cells were infected with 20 PFU/cell of KD1, KD3, dl01/07, or dl309 and the amount of intracellular and extracellular virus was determined by plaque assay on A549 cells. At 2 days p.i., the total amount of virus formed in each group was similar, $2–4\times10^8$ PFU/ml, indicating that replication of all the viruses is similar. However, when the ratio of extracellular to intracellular virus was calculated, the value for KD1 and KD3 was 2-3 logs higher than for Ad5, dl309, or dl01/07 (data not shown). Thus, virus is released much more rapidly from cells infected with KD1 and KD3, which overexpress ADP, than with viruses expressing wild-type amounts of ADP.

Figure 5:
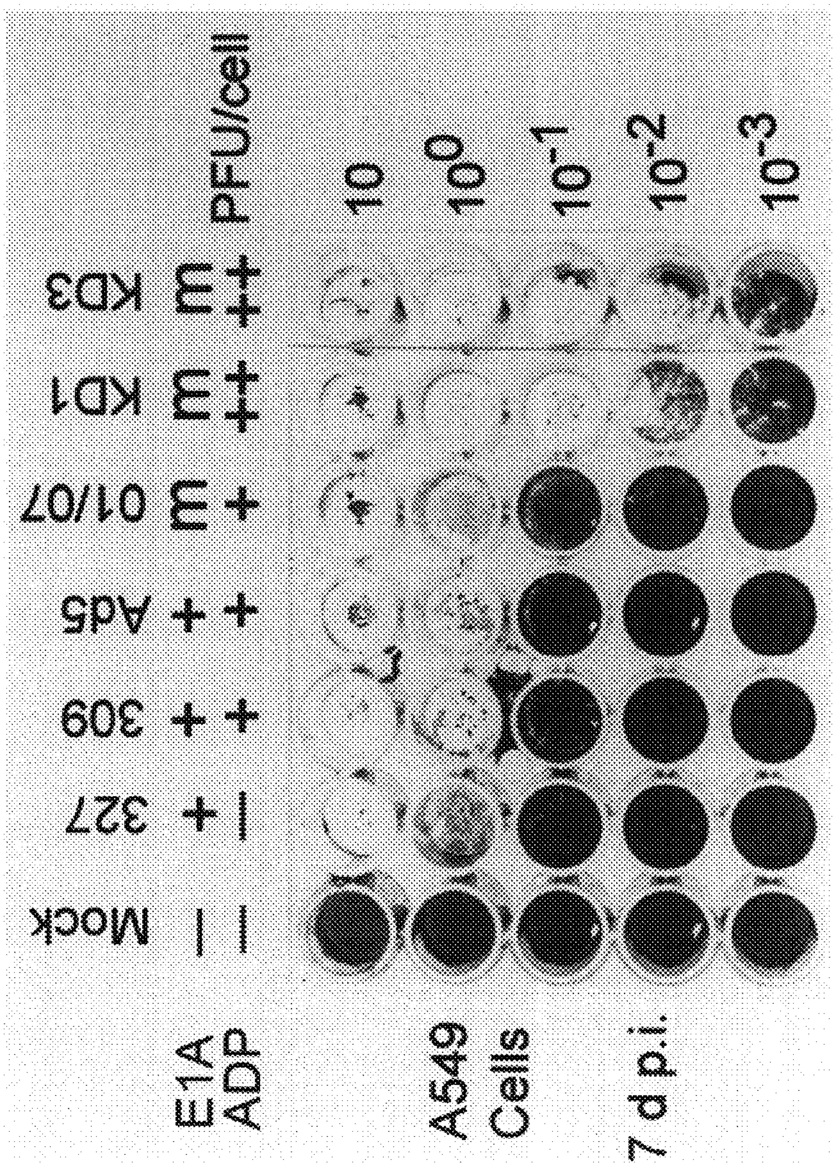
FIG. 5 is a cell spread assay illustrating that overexpression of ADP enhances spread of virus from cell to cell, showing monolayers infected with the indicated viruses at the indicated PFU/cell which were treated at 7 days p.i. with crystal violet, which stains live cells but not dead cells.

The ability of KD1 and KD3 to spread from cell-to-cell was measured in a "cell spreading" assay. In this assay monolayers of A549 cells in a 48 well culture dish were mock-infected or infected with $10^{-3}$, $10^{-2}$, $10^{-1}$, $10^{0}$, or 10 PFU/cell of dl327, dl309, Ad5, dl01/07, KD1 or KD3. At low PFU/cell, the viruses must go through two or three rounds of replication in order to infect every cell in the monolayer. At 1.0 and 10 PFU/cell, the monolayer should be destroyed by the virus that initially infected the cells. To assess the amount of spread in the monolayers by 7 days p.i., crystal violet, which stains live cells but not dead cells, was added to the monolayers. The results are shown in FIG. 5.

Remarkably, at 7 days p.i., the monolayer was virtually eliminated by KD1 and KD3 at $10^{-3}$ PFU/cell, whereas 1.0 PFU/cell was required with dl01/07, dl309 and Ad5. This result attests to the potency of ADP in mediating cell lysis and virus spread in A549 cells. KD1 and KD3 are also more effective that dl01/07 in killing other types of human cancer cell fines (most purchased from the American Type Culture Collection [ATCC]) as determined in this cell spreading assay. KD1 and/or KD3 killed HeLa (cervical carcinoma), DU145 (prostate), and pC3 (prostate) cells at $10^{-2}$ PFU/cell, ME-180 (cervix) and Hep3B (liver) at $10^{-1}$ PFU/cell, and U118 (glioblastoma) and U373 (glioblastoma) at 10 PFU/cell. From 10- to 100-fold more dl01/07 was required to kill these cells (data not shown). These results indicate that KD1 and KD3 may be effective against many types of cancer.

An important aspect of the finding that ADP overexpressing vectors lyse cells at very low multiplicities of infection is that the multiplicity of infection in human tumors is likely to be low at sites distal to the sight of vector injection or distal to blood vessels that carry the vector to the tumor. Thus, ADP overexpressing vectors have an advantage over vectors that express less ADP or no ADP at all.

EXAMPLE 3

This example illustrates that KD1 and KD3 replicate poorly in non-growing non-cancerous cells. The replication phenotype of KD1 and KD3 was evaluated using "normal" HEL-299 human fibroblast cells, either growing in 10% serum or rendered quiescent using 0.1% serum. All Ads should replicate well in growing cells, but viruses with the dl01/07 E1A mutation should do poorly in quiescent cells because E1A is required to drive them out of $G_0$. dl309, which has wild-type E1A, should replicate well in both growing and growth-arrested cells.

Figure 6:
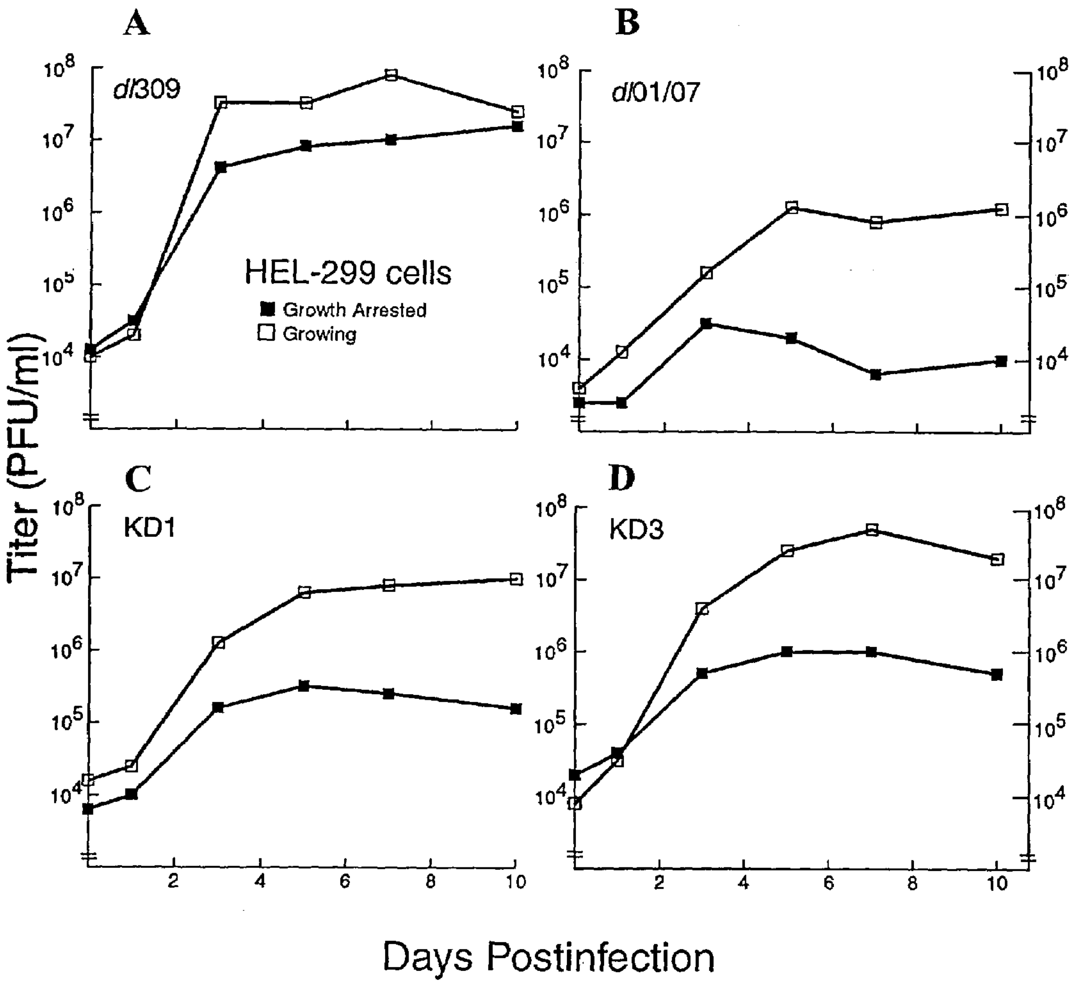
FIG. 6 illustrates that KD1 and KD3 replicate well in growing cells but not in growth-arrested cells showing the virus titer extracted from growing or growth arrested HEL-229 cells at various times following infection with 100 PFU/ml of the following viruses: dl309 (FIG. 6A), dl01/07 (FIG. 6B), KD1 (FIG. 6C) and KD3 (FIG. 6D).

Cells were infected with 100 PFU/cell of KD1, KD3, dl01/07, or dl309. At different days p.i., virus was extracted and titered. In 10% serum, KD1, KD3, and dl01/07 replicated well, reaching titers of $10^6$-$10^7$ PFU/ml, only slightly less than dl309 (FIG. 6). However, in quiescent cells, replication of KD1, KD3, and dl01/07 was 1.5-2 logs lower than in growing cells, ranging from $10^4$ to $2\times10^5$ PFU/ml. The titer of dl309 reached $10^7$ PFU/ml, nearly the level achieved in growing cells. At 10 days p.i., quiescent HEL-299 cell monolayers infected with 100 PFU/cell of KD1, KD3, or dl01/07 were intact, whereas those infected with dl309 or dl327, which have wild-type E1A, showed strong typical Ad cytopathic effect indicative of cell death (data not shown). Thus, replication of KD1 and KD3 is severely restricted to growing cell lines.

Figure 7:
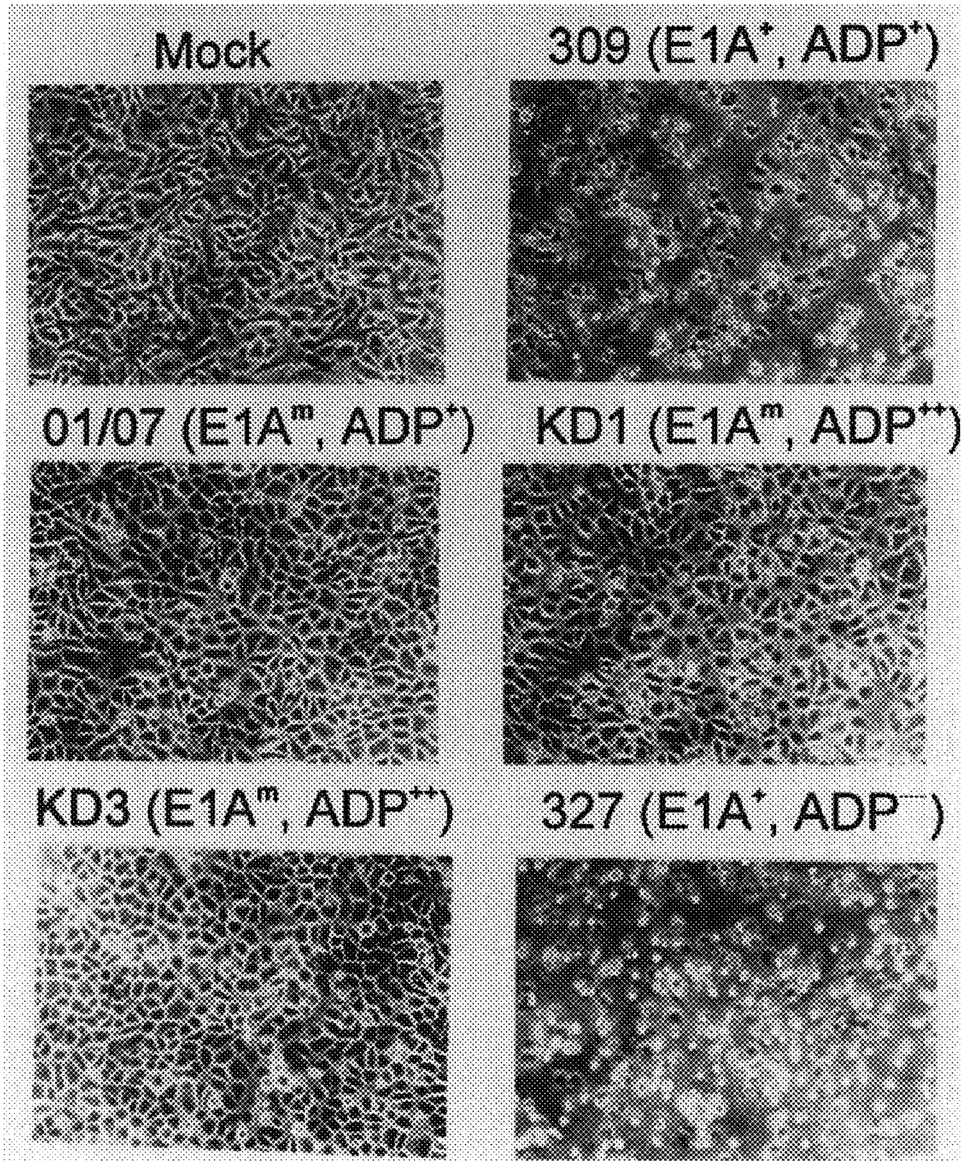
FIG. 7 illustrates that KD1 and KD3 are defective in killing primary human bronchial epithelial cells showing these cell monolayers infected at 30% confluency with 10 PFU/ml of the indicated viruses and stained at 5 days p.i. with neutral red.

The restriction associated with the dl01/07 E1A mutation was also tested in primary human cells (purchased from Clonetics) growing as monolayers. Bronchial epithelial cells (FIG. 7) and small airway epithelial cells were not killed by 10 PFU/cell of KD1, KD3, or dl01/07 at 5 days p.i., whereas they were killed by 10 PFU/cell of dl309 or dl327 (data not shown). Lung endothelial cells also were not killed after 10 days by KD1, KD3, or dl01/07 at 10 PFU/cell, but they were killed by 1 PFU/cell of dl309. These monolayers were subconfluent when initially infected, then grew to confluency. The exciting result here is that although these primary cells were growing, they did not support replication in this time frame and were not killed by KD1 or KD3. Thus, it is believed these vectors will be restricted to cancerous cells, and will have little to no effect on cells such as basal cells that are normally dividing in the body. In addition, it is unlikely that KD1 and KD3 will affect dividing leukocytes because such cells are poorly infected by Ad.

In summary, the above experiments demonstrate that KD1 and KD3 lyse cancer cells, spread from cell-to-cell rapidly, and replicate poorly in quiescent and non-cancerous cells. These properties should make them useful in anti-cancer therapy.

EXAMPLE 4

This example illustrates that KD1 and KD3 inhibit the growth of human tumors in an animal model.

We could not evaluate mouse or rat tumors in normal mice or rats because they are totally non-permissive. Human cancer cell lines growing in nude mice have been used by Onyx Pharmaceuticals (Richmond, Calif.) to evaluate the efficacy of ONYX-015, an Ad vector lacking expression of the E1B 55 kDa protein (Heise et al., *Nature Med.* 3:639-645, 1997). We have found that A549 cells, which were used in many of our cell culture studies, form excellent rapidly growing solid tumors when injected subcutaneously into nude mice. The average tumor reaches ca. 500 μl in four weeks, and is encapsulated, vascularized, and attached to the mouse skin (usually) or muscle.

Nude mice were inoculated into each hind flank with $2\times10^7$ A549 cells. After 1 week tumors had formed, ranging in size from about 20 μl to 50 μl. Individual tumors were injected three days later, and at subsequent weeks for 4 weeks (total of 5 injections), with 50 μl of buffer or 50 μl of buffer containing $5\times10^7$ PFU of dl309, dl01/07, KD1, KD3, or pm734.1, with a total virus dose per tumor of $3\times10^8$ PFU. The mutant pm734.1 lacks ADP activity due to two nonsense mutations in the gene for ADP, but all other Ad proteins are expected to be synthesized at wild-type levels (Tollefson et al., *J. Virol.* 70:2296-2306, 1996). The efficacy of each virus (or buffer) was tested on six tumors. At weekly intervals, the length (L) and width (W) of tumors were measured using a Mitutoyo digital caliper. Tumor volumes were calculated by multiplying L×W×W/2. This value was divided by the tumor volume at the time of the initial virus injection, the fold-increase in tumor growth was calculated, and the average for the six tumors was graphed.

Figure 8A:
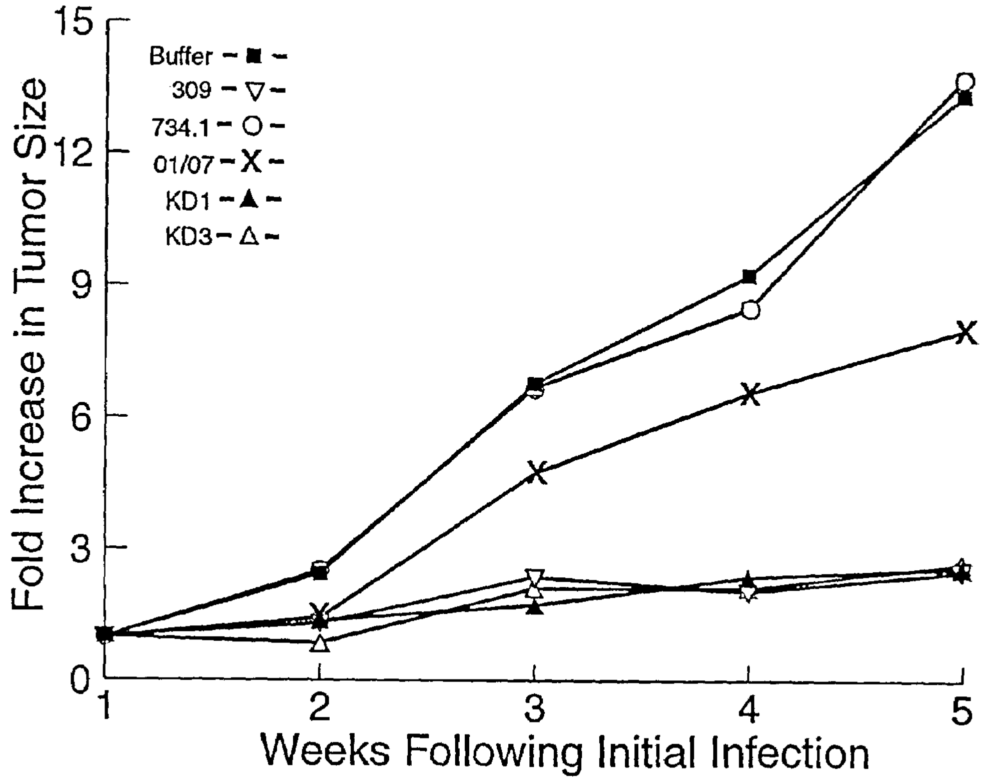
FIG. 8 illustrates that KD1 and KD3 reduce the growth rate of human A549 cell tumors growing in nude mice, showing in FIG. 8A a graph of average-fold increase in tumor size plotted against the number of weeks following infection of the tumor with buffer or with $5\times10^7$ PFU at weekly intervals of or the indicated viruses, and showing in FIG. 8B a similar graph of tumors injected once with $5\times10^8$ PFU of KD3 or GZ3.

As shown in FIG. 8A, tumors that received buffer continued to grow, increasing about 14-fold by 5 weeks. In contrast, tumors injected with d/309, which expresses normal amounts of ADP and lacks the E3 RID and 14.7K and proteins, only grew about 2.5-fold by 5 weeks. With pm734.1, which lacks ADP, the tumors grew as well as those that received buffer. Thus, dl309 markedly decreases the rate of tumor growth, and ADP is required for this decrease. Tumors inoculated with dl01/07 grew about 8-fold over 5 weeks. Since dl01/07 is identical to dl309 except for the E1A mutation, this result indicates that the E1A mutation significantly reduces the ability of Ad to prevent growth of the tumors. This effect is probably due to a reduction in virus replication in the tumors resulting in lower ADP expression, but it could also reflect other properties of E1A in the tumor cells, e.g. the inability of the mutant E1A proteins to induce apoptosis. Most importantly, tumors inoculated with KD1 or KD3 only grew about 2.5-fold. Thus, the overexpression of ADP by KD1 and KD3 allows KD1 and KD3 to reduce tumor growth to a rate markedly slower than dl01/07 (their parental control virus), and even to a rate similar to that of dl309.

The finding that KD1 and KD3 are as effective as wild-type Ad (i.e. dl309) in reducing the rate of A549 tumor growth is highly significant in the context of cancer treatment, inasmuch as KD1 and KD3 are restricted to cancer cells whereas wild-type Ad does not have such a restriction.

Figure 8B:
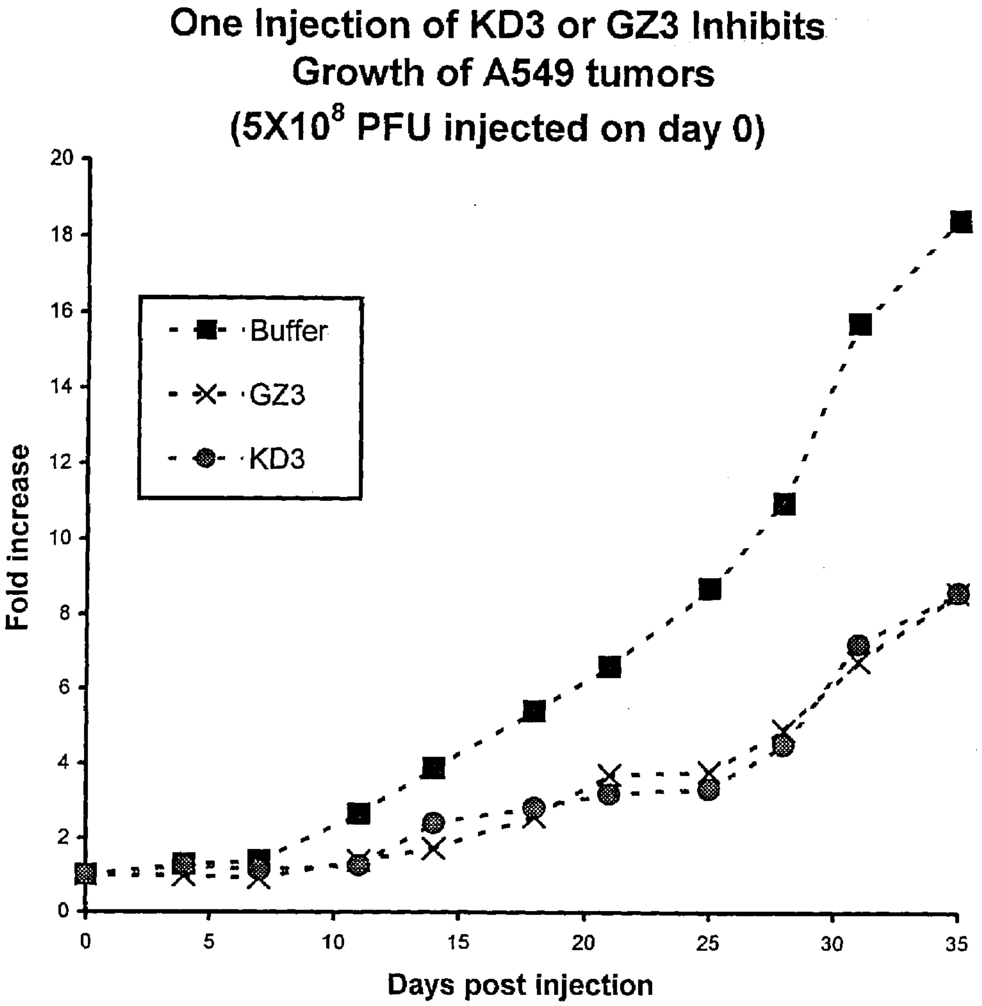

The tumors in FIG. 8A received five injections of vectors, but only one dose of vector, in this case $5\times10^8$ of each of KD3 or GZ3, is sufficient to significantly reduce the rate of A549 tumor growth (FIG. 8B).

Figure 9:
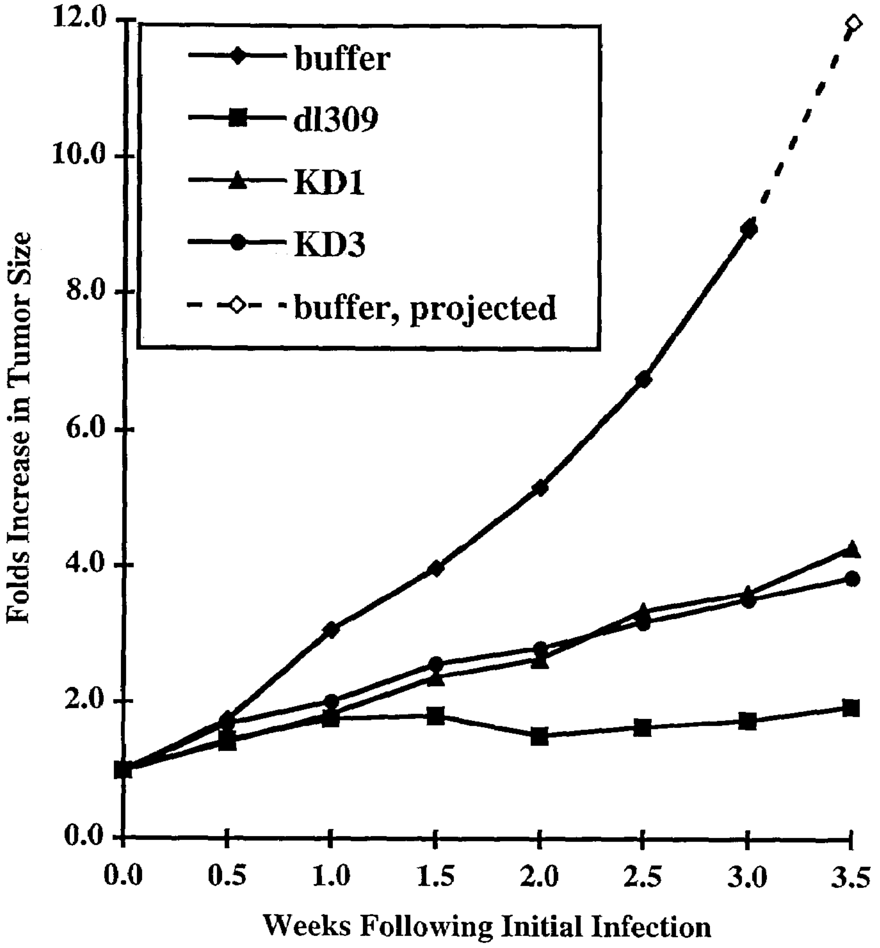
FIG. 9 illustrates that KD1 and KD3 reduce the growth rate of human Hep3B cell tumors growing in nude mice, showing a graph of average-fold increase in tumor size plotted against the number of weeks following injection of the tumor with buffer or with $5\times10^7$ PFU of dl309, KD1 or KD3 at twice weekly intervals of the indicated viruses.

We have also found that KD1 and KD3 reduce the rate of growth in nude mice of a human liver cancer cell line, Hep3B cells. These cells form rapidly growing tumors that are highly vascularized. Nude mice were inoculated into each hind flank with $1\times10^7$ of Hep3B cells. After tumors reached about 100 μl, they were injected twice per week for 3 weeks with 50 μl of buffer or $5\times10^7$ PFU of KD1, KD3, or dl309. There were typically 8-10 tumors per test virus. The tumor sizes were measured and the fold increase in size at 0 to 3.5 following the initial virus injection was graphed as described above for the A549 tumors. Tumors that received buffer alone grew 9-fold over 3 weeks and were projected to grow about 12-fold over 3.5 weeks (after 3 weeks the mice had to be sacrificed because the tumors were becoming too large) (FIG. 9). Tumors that received KD1 or KD3 grew about 4-fold, establishing that KD1 and KD3 reduce the growth of Hep3B tumors in nude mice. Tumors that were injected with d/309 grew 2-fold (FIG. 9). The finding that KD1 and KD3 were somewhat less effective than dl309 is probably due to the fact that they do not grow as well as dl309 in Hep3B cells, as indicated by a cell spread assay in culture (data not shown). In any case, the important points are that KD1 and KD3 are effective against the Hep3B tumors, and that they contain the E1A mutation that limits their replication to cancer cells.

These results point to the potency of ADP as an anti-tumor agent when expressed in an Ad vector. It is highly probable that KD1 and KD3 will provide significant clinical benefit when used to infect tumors growing in humans.

EXAMPLE 5

This example illustrates the use of replication-defective Ad vectors in combination with KD1 or KD3.

It is well established that replication-competent (RC) viruses complement replication-defective (RD) mutants. That is, when the same cell is infected, the competent virus will supply the protein(s) that cannot be made from the mutant genome, and both viruses will grow. To test the ability of KD1 and KD3 to complement RD viruses, two RD vectors expressing β-galactosidase were constructed. The first, named Ad-β-gal, has a cDNA encoding β-gal under the control of the Rous Sarcoma Virus promoter substituted for the deleted E1 region. Ad-β-gal also has the E3 region deleted, including the gene for ADP. The second, named Ad-β-gal/FasL is identical to Ad-β-gal, except that it also expresses murine FasL from the human cytomegalovirus promoter/enhancer. These vectors were constructed by overlap recombination in human 293 cells that constitutively express the Ad E1A and E1B genes and complement replication of the E1-minus vectors.

These RD vectors should infect and express β-gal in A549 cells, but should not replicate because the E1A proteins are lacking. However, the vectors should replicate when cells are co-infected with RC Ads. To prove this, A549 cells were infected with 10 PFU/cell of Ad-β-gal alone, or with 10 PFU/cell of Ad-β-gal plus 10 PFU/cell of KD1, KD3, dl01/07, dl309, or dl327. At 2 days p.i., virus was extracted and Ad-β-gal titers determined by -gal expression in A549 cells. The yields are shown in Table 2 below.

TABLE 2

| Virus | Yield (blue plaques per ml) |
|---|---|
| Ad-β-gal | $1\times10^2$ |
| Ad-β-gal + KD1 | $2\times10^5$ |
| Ad-β-gal + KD3 | $3\times10^5$ |
| Ad-β-gal + dl01/07 | $4\times10^4$ |
| Ad-β-gal + dl309 | $3\times10^5$ |
| Ad-β-gal + dl327 | $3.0\times10^5$ |

The data in Table 2 indicate that the complementing viruses increased the yield of Ad-β-gal by about $10^3$.

Figure 10:
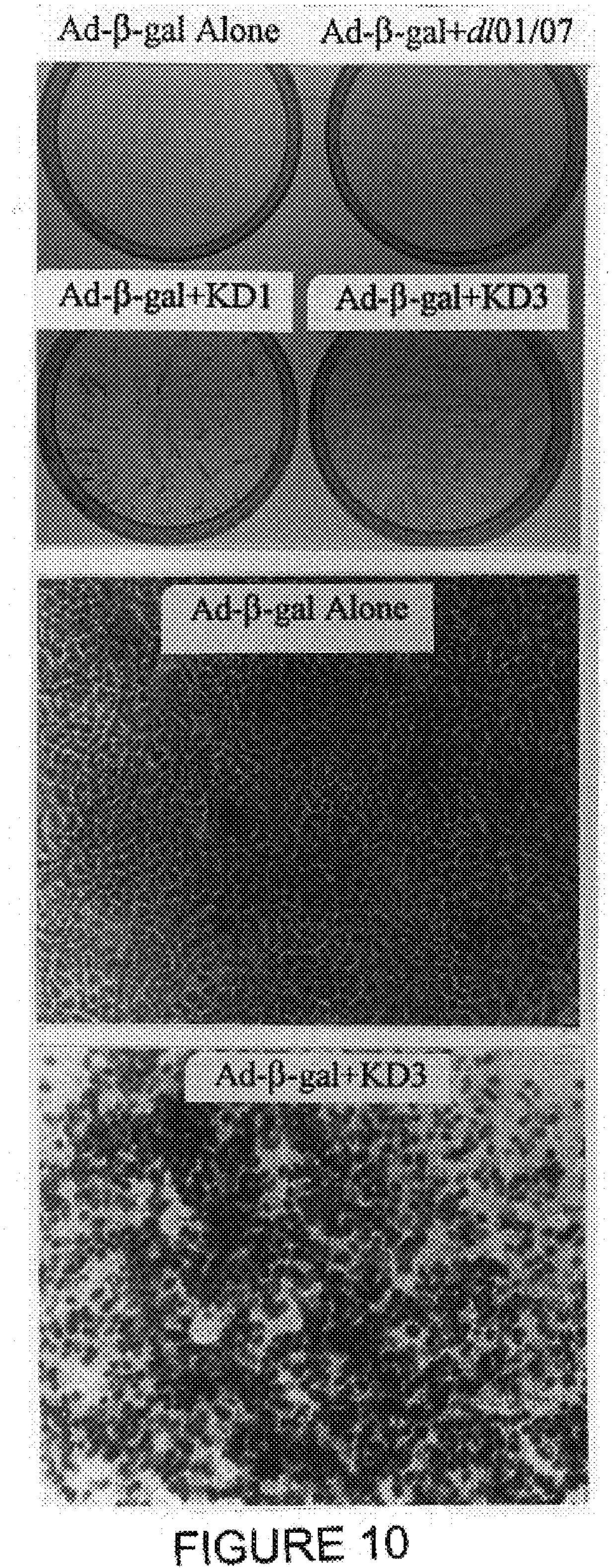
FIG. 10 illustrates that KD1 and KD3 complement the replication and spread of Ad-β-gal, a replication-defective vector that expresses β-galactosidase, using an infectious center assay showing in FIG. 10A a picture of A549 cell monolayers seeded with A549 cells infected with Ad-β-gal alone or with the indicated viruses, with FIGS. 10B and 10C showing close-up views of two of the monolayers of FIG. 10A.

A key feature of KD1 and KD3 is that they spread from cell-to-cell faster than other Ads. Accordingly, they should complement the spread of Ad-β-gal. To test this, an infectious center assay was conducted. A549 cells were infected with Ad-β-gal plus KD1, KD3, or dl01/07. After 2 h, cells were collected, diluted, and seeded onto monolayers of fresh A549 cells. After 4 days, the cells were stained with X-gal and the results are shown in FIG. 10.

With Ad-β-gal alone, only the originally infected cell (before seeding) should be stained, and the vector should not spread to other cells on the seeded monolayer. This was indeed the case. In monolayers seeded with A549 cells infected with Ad-β-gal alone (dish shown in the top left of FIG. 10A) contained a number of individual blue cells (not visible in the print); examples are shown in the enlarged view FIG. 10B. However, when the monolayers were seeded with A549 cells coinfected with Ad-β-gal and KD1 or KD3, there were numerous "comets" of blue cells (FIG. 10A). Each comet represents Ad-β-gal which has spread from one initially-infected cell. Most of the cells within a comet were stained with X-gal (FIG. 10C). Comets were also observed with dl01/07, but not to the extent of KD1 and KD3 (FIG. 10A). With dl327 ($ADP^-$), there was little spread from the originally infected cell (data not shown). In summary, KD1 and KD3 not only complement the replication of Ad-β-gal, they also enhance its rapid spread.

It is expected that KD1 and KD3 will also complement and enhance the spread of RD vectors expressing anti-cancer therapeutic gene products, and this expectation can be readily verified using the Ad-β-gal/FasL in replication and infectious center assays as described above.

Figure 11:
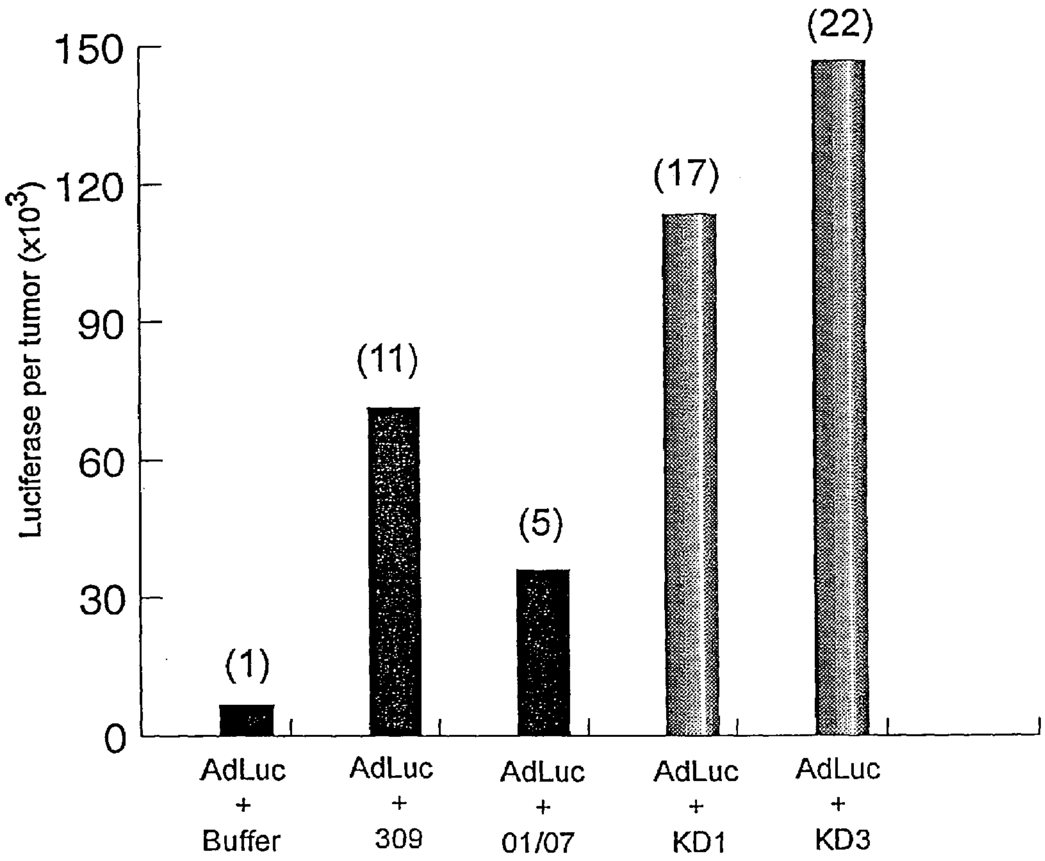
FIG. 11 is a bar graph illustrating that KD1 and KD3 increase the expression of luciferase in human Hep3B cell tumors growing in nude mice, using an assay in which tumors were injected with the indicated combinations of viruses, then were extracted 2 weeks p.i. and assayed for luciferase activity. The numbers in parentheses indicated the fold increase in luciferase activity compared to that of the Adluc vector plus buffer.

KD1 and KD3 not only complement the replication of RD vectors in cell culture, they also do so in Hep3B tumors growing in the hind flanks of nude mice. The RD vector used was AdLuc, an Ad that lacks the E1 and E3 regions, and has inserted into the E1 region an expression cassette where the firefly luciferase gene is expressed from the Rous Sarcoma Virus promoter (Harrod et al., *Human Gene Therapy* 9:1885-1898, 1998). The Hep3B tumors were injected with $1\times10^7$ PFU of AdLuc plus buffer, or $1\times10^7$ PFU of AdLuc plus $5\times10^7$ PFU of KD1, KD3, dl01/07, or dl309. After 2 weeks, mice were sacrificed and tumors excised. Proteins were extracted from the tumors and luciferase activity determined using a luminometer. The luciferase counts per tumor were 6,800 for AdLuc plus buffer, 113,500 for KD1, and 146,900 for KD3 (FIG. 11). Thus, KD3 and KD1 respectively caused a 22-fold and 17-fold increase in luciferase activity. This increase could be due to elevated synthesis of luciferase in cells that were initially coinfected the AdLuc and KD1 or KD3, and it could also be due to spread of AdLuc from cell to cell in the tumor as mediated by KD1 or KD3.

In summary, infecting a tumor with a replication-competent ADP-overexpressing vector according to the invention together with a RD vector expressing an anti-cancer gene product should greatly increase the amount of anti-cancer protein synthesized in the tumor thereby increasing the ability of the replication-defective vector to promote destruction of the tumor.

EXAMPLE 6

This example illustrates the construction and characterization of a recombinant Ad vector according to the invention which is replication-restricted to cancerous type II alveolar cells.

As demonstrated above, the dl01/07 mutation in KD1 and KD3 limits growth of these vectors to cancer cells. To further restrict their replication phenotype, the E4 promoter in each virus was deleted and replaced by the surfactant protein B (SPB) promoter to produce vectors named KD1-SPB (SEQ ID NO:14), KD3-SPB (SEQ ID NO:15), and dl01/07-SPB (SEQ ID NO:16). The SPB promoter is only active in cells containing the TTF1 transcription factor, which has thus far been found primarily in type II alveolar cells of the human lung (Lazzaro et al., *Development* 113:1093-1104, 1991). Thus, KD1-SPB, KD3-SPB, and dl01/07-SPB should be severely restricted to cancerous type II alveolar cells of the human lung. Many lung cancers are of this type.

The KD1-SPB and KD3-SPB vectors were prepared as follows. The E4 promoter is located at the right end of the Ad genome (FIG. 1). Using a pCRII-based plasmid (Invitrogen) containing the Ad5 DNA sequences from the BamHI site (59 map units) to the right hand end of the genome, and using and a PCR-based protocol, nearly all the transcription factor binding sites were deleted from the E4 promoter Ad5 base pairs 35,623 to 35,775 and replaced with a 500 base pair fragment containing the SPB promoter (Yan et al., *J. Biol. Chem.* 270: 24852-24857, 1995). The final plasmids contain the E4-SPB substitution in the E4 region and the dl01/07, KD1, or KD3 versions of the E3 region, respectively, for the viruses dl01/07-SPF, KD1-SPB, and KD3-SPB. These plasmids were co-transfected into 293 cells with a fragment containing the left portion of the genome of dl01/07, and plaques were allowed to develop. Plaques were screened for the expected features, purified, then expanded into a stock.

The A549-TTF1 cell line was developed in order to test the prediction that replication of dl01/07-SPB, KD1-SPB, and KD3-SPB would be restricted to cancerous cells expressing the TTF1 transcription factor. These cells were co-transfected with two plasmids, one in which TTF1 is expressed from the CMV promoter, and the other coding for resistance to neomycin Resistant clones were isolated and shown to express TTF1 activity as determined by transient transfection with a plasmid expressing chloramphenicol acetyltransferase from the TTF1-requiring surfactant protein C promoter.

Figure 12:
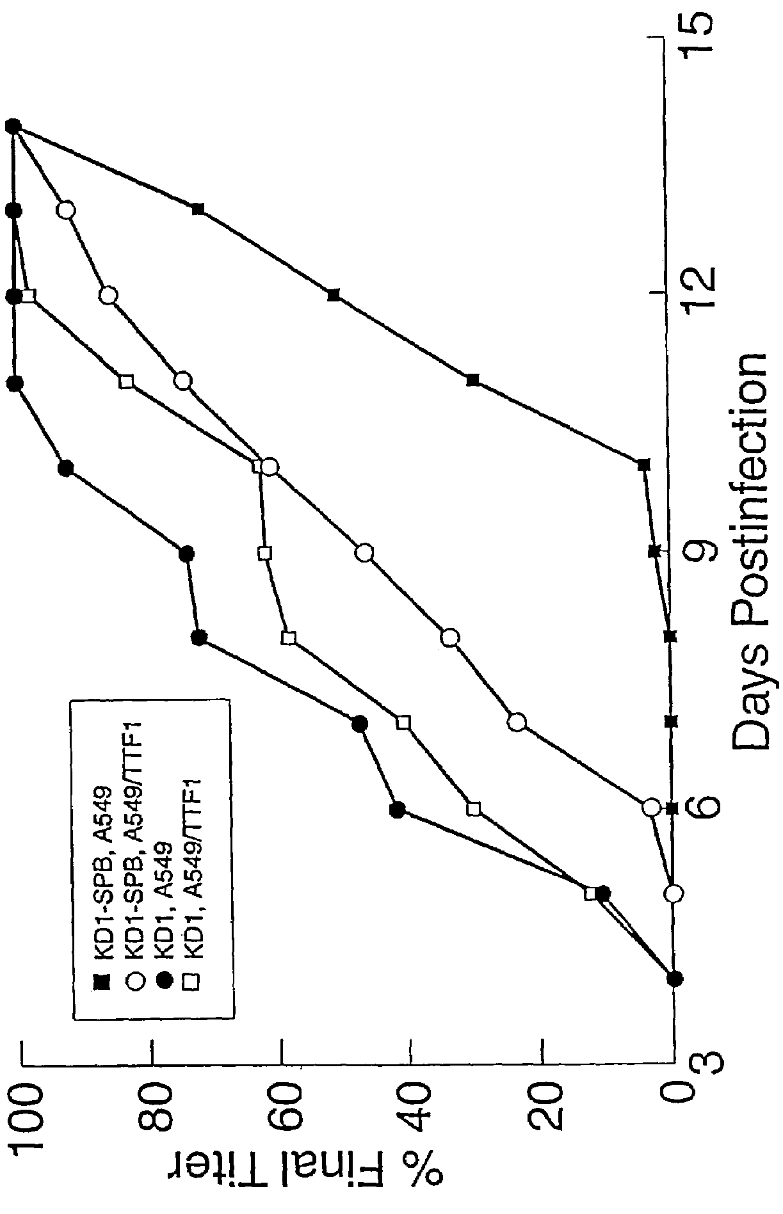
FIG. 12 is a graph showing the results of a standard plaque development assay for KD1 and KD1-SPB on A549 cells engineered to express the TTF1 transcription factor (A549/TTF1) and the parental 549 cells, in which data are plotted as the number of plaques observed on a particular day in the assay divided by the final number of plaques observed for that virus multiplied by 100.

KD1-SPB and KD1 were subjected to a standard plaque development assay on A549-TTF1 cells and parental A549 cells. The results are shown in FIG. 12. With KD1-SPB on A549 cells, plaques were not visible after 8 days, only about 4% of the final number of plaques were seen after 10 days, and about 50% of final plaques were seen after 12 days. With KD1-SPB on A549-TTF1 cells, plaques were visible after 6 days, and about 60% of plaques were seen after 10 days. Thus, as expected, KD1-SPB grew significantly faster on the cells containing TTF1. KD1 formed plaques more quickly than KD1-SPB on both A549 and A549-TTF1 cells, indicating that the E4 promoter-SPB substitution is not as effective the wild-type E4 promoter in inducing Ad replication. However, this difference between KD1-SPB and KD1 on A549-TTF1 cells is tolerable, with KD1-SPB delayed only about 1 day. Curiously, the final titer obtained for all virus stocks by day 16 was similar, indicating that A549 cells may contain a very small amount of endogenous TTF1 activity. It is predicted that KD3-SPB and dl01/07-SPB will behave similarly to KD1-SPB when grown in A549-TTF1 cells and A549 cells.

Figure 13:
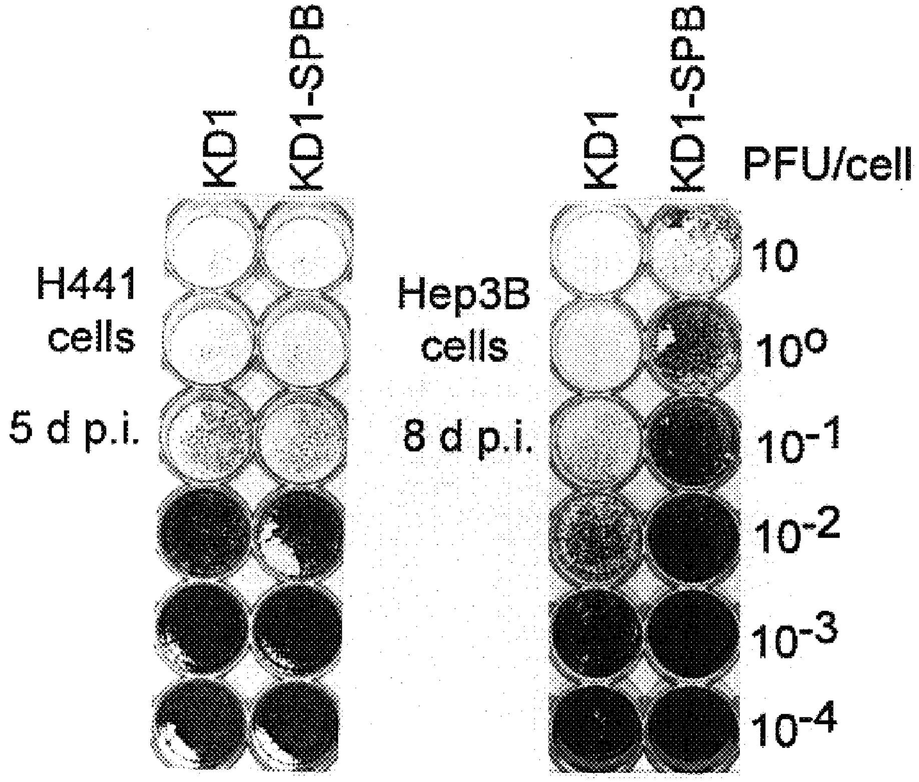
FIG. 13 is a cell spread assay for KD1 and KD1-SPB on H441 cells and Hep3B cells, where cells were infected with the indicated amounts of KD1 or KD1-SPB and H441 cells and Hep3B cells were strained with crystal violet at 5 days p.i. and 8 days p.i., respectively.

The restriction of KD1-SPB to cells containing TTF1 was further examined in a cell spread assay using H441 cells, a TTF1-expressing human pulmonary adenocarcinoma cell line (Yan et al., supra), and Hep3B cells, a liver cancer cell line not expected to express TTF1. Culture dish wells containing H441 or Hep3B cells were infected with KD1-SPB or KD1 at multiplicities ranging from 10 to $10^{-4}$ PFU/cell. The H441 and Hep3B cells were stained with crystal violet at 5 days and 8 days p.i., respectively. KD1-SPB and KD1 grew and spread equally well on H441 cells, causing destruction of the monolayer at $10^{-1}$ PFU per cell (FIG. 13). (Some of the H441 monolayer has peeled off in the well with KD1-SPB at $10^{-2}$ PFU per cell, and in the wells with KD1 and KD1-SPB at $10^{-4}$ PFU per cell; this occasionally occurs in cell spread assays, and it does not reflect virus infection). With Hep3B cells, KD1 grew and spread very much better than KD1-SPB, with $10^{-2}$ PFU per cell of KD1 causing more destruction of the monolayer as 1.0 PFU per cell of KD1-SPB (FIG. 13).

In summary, this example demonstrates that a replication-competent Ad, which replicates well on cells expressing the appropriate transcription factor, can be constructed with a tissue-specific promoter substituted in place of the E4 promoter. This methodology should be applicable to many other tissue specific and cell type specific promoters. One possibility would be a liver-specific promoter. Another possibility would be to use the E2F promoter, or another promoter with E2F sites, inasmuch as that promoter would be active only in cells such as cancer cells that have free E2F. A third possibility would be to use a regulatable promoter, e.g. the synthetic tetracycline response promoter (Massie et al., *J. Virol.* 72:2289-2296, 1998), where the activity of the promoter is controlled by the level of tetracycline or a tetracyclin analog in the patient.

EXAMPLE 7

This example illustrates the construction and characterization of vectors which overexpress ADP and are not replication restricted.

As demonstrated above, the dl01/07 E1A mutation in KD1 and KD3 is attenuating, inhibiting growth in non-dividing and even in dividing primary human epithelial and endothelial cells. Ads with this mutation are able to replicate well in dividing cancer cells. However, replication of such E1A mutants is not as efficient as, e.g. dl309 which has a wild-type E1A gene. For instance, the rate of replication of dl01/07, as determined by the rate at which plaques develop, is reduced such that dl01/07 plaques appear one day later than those of dl309 (data not shown). This delay is due in part to a delay in expression of Ad late genes (see FIG. 3). The idea that the dl01/07 mutation retards the rate of replication in A549 cells is further supported by the data in FIG. 8A, where dl01/07 did not prevent tumor growth nearly as well as dl309. Despite this negative effect of the dl01/07 E1A mutation, there are theoretical and practical aspects of having this mutation in the KD1 and KD3 vectors, as has been discussed. Nevertheless, one can easily imagine scenarios (e.g. patients with terminal cancer) where the ability of an Ad vector to destroy the tumor supercedes the requirement that the vector be totally restricted to tumor cells. In such cases, it would be advantageous to have vectors similar to KD1 and KD3, but with the wild-type E1A gene. The rates at which such vectors express their genes, lyse cells, and spread from cell to cell should be higher than those of KD1 and KD3. Such vectors might cause some damage to non-cancerous cells and tissue, but this is also true for other modes of anti-cancer treatment such as surgery, chemotherapy, and radiation therapy.

In light of these considerations, vectors named GZ1 and GZ3 have been constructed that are identical to KD1 and KD3, respectively, except they have a wild-type E1A region. These vectors were constructed by overlap recombination in A549 cells. The left hand fragment contained the wild-type E1A region of Ad5, and the right end fragment contained the E3 modifications of KD1 or KD3. Plaques were picked, analyzed for the expected genotype, plaque-purified, and expanded into CsCl-banded stocks. The titers of these stocks on A549 cells were $2.9\times10^{10}$ PFU/ml for GZ1 and $1.6\times10^{11}$ PFU/ml for GZ3. Thus, these vectors can be grown into high titer stocks comparable to wild-type Ad. The GZ1 and GZ3 plaques are larger and appear much sooner than the plaques for dl309. Large rapidly-appearing plaques reflect the ability of Ad to lyse cells and spread from cell-to-cell (Tollefson et al., *J. Virol.* 70:2296-2306, 1996; Tollefson et al., Virology 220:152-162, 1996), and this property, as discussed, is due to the function of ADP.

Figure 14:
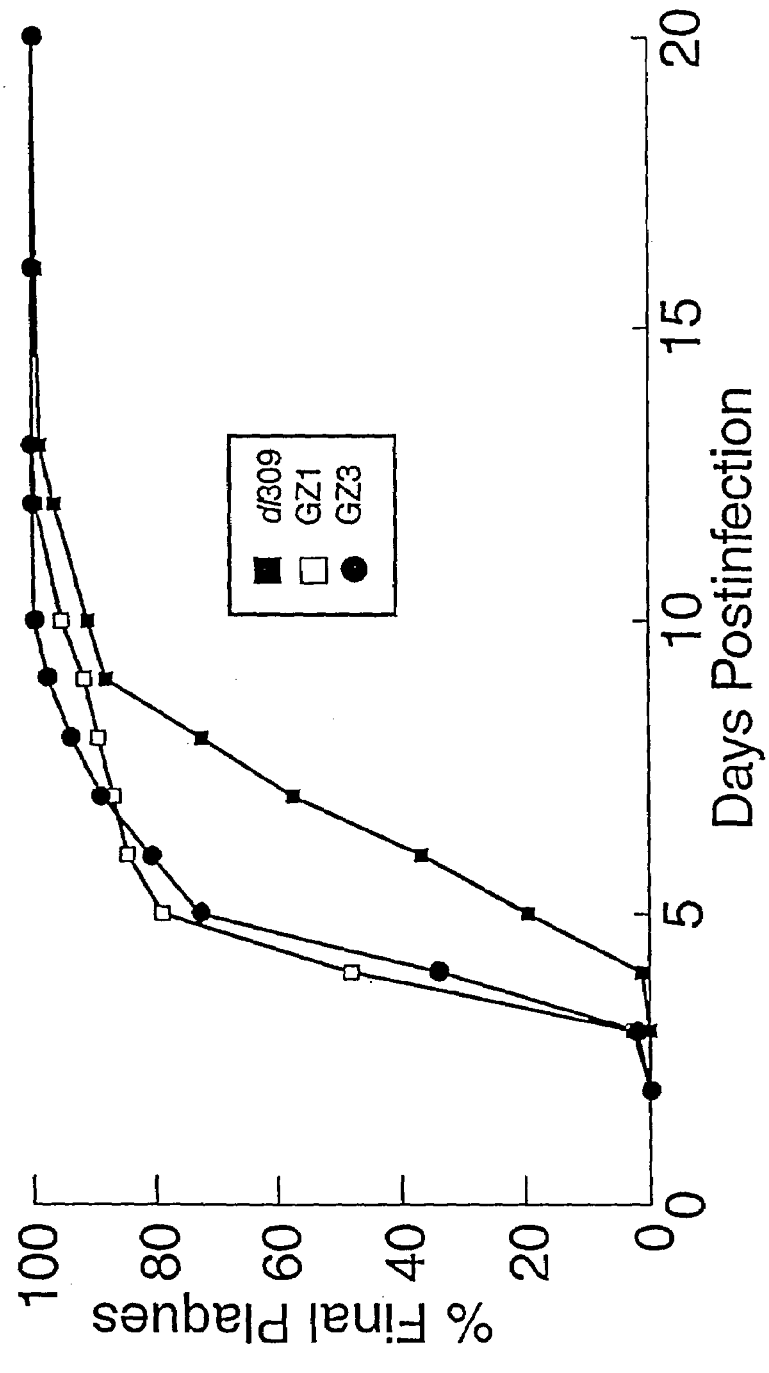
FIG. 14 is a graph showing the results of a standard plaque development assay for dl309 and two preferred embodiments of the invention, GZ1 and GZ3, in which data are plotted as the number of plaques observed on a particular day in the assay divided by the final number of plaques observed for that virus multiplied by 100.

The rate of plaque appearance can be quantitated in a plaque development assay (Tollefson et al., supra). Here, a typical plaque assay is performed, and the plaques observed on subsequent days of the assay are calculated as a percentage of the number of plaques observed at the end of the plaque assay. As shown in FIG. 14, after 4 days of plaque assay on A549 cells, GZ1 and GZ3 had 48% and 34%, respectively, of the final number of plaques, whereas dl309 had only 1%. It is very unusual in Ad plaque assays in A549 cells for plaques to appear after only 4 days. These large plaques reflect the overexpression of ADP. These GZ1 and GZ3 plaques appear sooner than those of KD1 and KD3 (data not shown), no doubt because GZ1 and GZ3 replicate faster because they have a wild-type E1A region.

Figure 15:
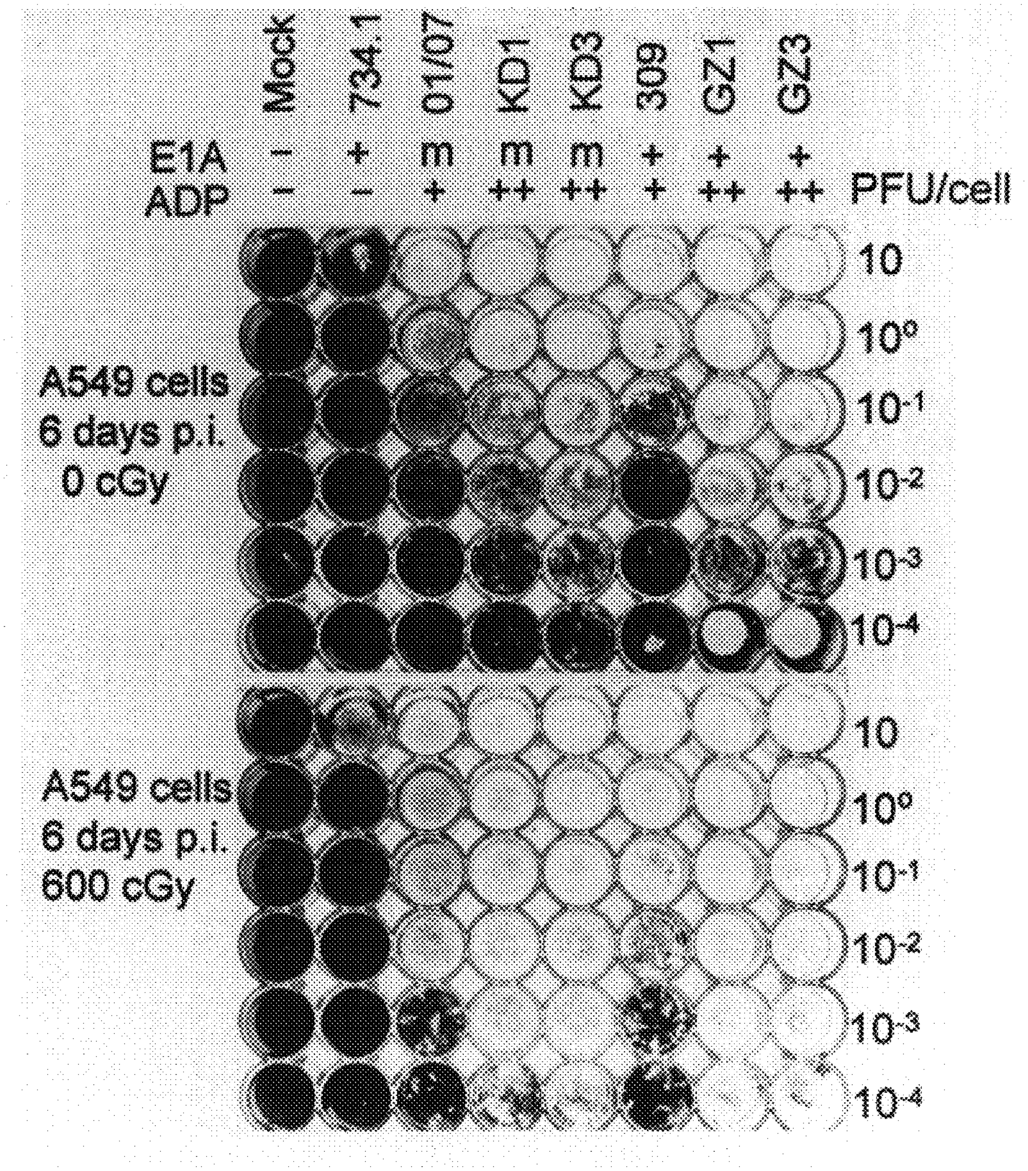
FIG. 15 is a cell spread assay illustrating that the combination of KD1, KD3, GZ1, or GZ3 with x-ray radiation is more effective in destroying A549 cell monolayers than is virus vector alone or radiation alone, wherein cells were infected with the indicated amounts of the indicated viruses, radiated with 600 centigreys (cGy) of x-radiation (bottom panel), or mock radiated (top panel), then stained with crystal violet at 6 days p.i.

GZ1 and GZ3 lyse cells and spread from cell to cell much more effectively than dl309. At 6 days p.i. of A549 cells, approximately as much monolayer destruction was observed with GZ1 and GZ3 at $10^{-3}$ PFU per cell as was observed with dl309 at $10^{-1}$ PFU per cell (FIG. 15, top panel). This result further underscores the conclusion that overexpression of ADP promotes cell lysis and virus spread.

In theory, GZ1 and GZ3 should be able to replicate not only in tumor cells but also in normal cells. Although they can replicate in normal cells, it is quite possible that GZ1 and GZ3 may be useful as anti-cancer vectors. First, GZ1 and GZ3 could be injected directly into the tumor. Many tumors are self-contained (encapsulated) except for the blood supply. The physical barriers of the tumor could minimize dissemination of the virus to other tissues. Second, Ads are in general quite benign. Most infections of Ad5 are in infants and result in mild or asymptomatic disease, and are held in check by strong humoral and cellular immunity. Anti-Ad immunity appears to be life-long. GZ1 and GZ3 could be used only in patients who have an intact immune system, and perhaps also with pre-existing anti-Ad immunity. Further, patients could be passively immunized against Ad, using gamma-globulin or even specific purified anti-Ad neutralizing antibodies. Third, considering that Ad5 is a respiratory virus which most efficiently infects lung epithelial cells displaying the specific Ad5 receptor (named CAR) as well as specific integrins (e.g. $a_v$ b5), replication-competent vectors derived from Ad5 may not spread efficiently in many non-cancer tissues of the body. In addition, it is believed that versions of GZ1 and GZ3 can be constructed that have the E4 promoter substituted with a tumor-specific, tissue-specific, cell-specific, or synthetic promoter. Such vectors would have the positive features associated with wild-type E1A and ADP, and yet be replication-restricted to tumor tissue and/or to particular cell types.

EXAMPLE 8

This example illustrates that the combination of KD1, KD3, GZ1, or GZ3 with radiation is more effective in destroying A549 cells, growing in culture or growing as tumors in nude mice, than the vectors alone or radiation alone.

This was shown in a cell spread assay. A549 cells growing in three 48 well culture dishes were mock-infected or infected with different viruses at multiplicities of infection ranging from 10 to $10^{-4}$ PFU per cell as indicated in FIG. 15. One dish was not radiated. A second dish received 600 centrigreys (cGy) of radiation at 24 h p.i., and a third dish received 2000 cGy of radiation at the same time. All dishes were stained with crystal violet at 6 days p.i. With the cells that were not radiated (top panel in FIG. 15), KD1 and KD3 caused monolayer destruction at lower multiplicities of infection than their parental control, dl01/07. This was also true for GZ1 and GZ3 as compared to their parental control dl309. (The paucity of cells in the cells infected with GZ1 or GZ3 at $10^{-4}$ PFU per cell is an experimental artifact, and is not caused by infection by GZ1 or GZ3). These KD1, KD3, GZ1 and GZ3 results are consistent with earlier results showing that overexpression of ADP leads to increased cell lysis and virus spread.

With the dish that was infected then radiated with 600 cGy there was markedly increased cell killing and virus spread as compared to the non-radiated cells (compare the bottom panel of FIG. 15 with the top panel). For example, with KD1, KD3, GZ1, and GZ3 there was about the same amount of cell destruction in the radiated wells at $10^{-4}$ PFU per cell as in the non-radiated wells at $10^{-2}$ PFU per cell. Similar results were seen with the dish that received 2000 cGy of radiation (data not shown), and also with dishes that received 600 or 2000 cGy of radiation 24 h prior to infection (data not shown).

The amount of cell destruction was quantitated by extracting the crystal violet from the cells with 33% acetic acid, then measuring the absorbance at 490 nm (data not shown). The absorbance with non-radiated mock-infected cells was set at 100% cell viability. With mock-infected cells that received 600 cGy there was a 15% loss in viability (i.e. 15% less crystal violet was extracted). With KD1 at $10^{-3}$ PFU per cell, the non-radiated cells were 80% viable whereas the cells receiving 600 cGy of radiation were only about 30% viable. Similar differences in viability between radiated and non-radiated cells were seen with KD3, GZ1, and GZ3. These results argue that the combination of radiation plus vector has a syngergistic effect on cell lysis and vector spread, rather than an additive effect. If the effect were only additive, then with the KD1 samples at $10^{-3}$ PFU per cell, the cell viability should have been 65% (15% reduction in viability due to radiation alone, 20% reduction due to KD1 alone). In fact, the cell viability was 30% rather than 65%.

Figure 16:
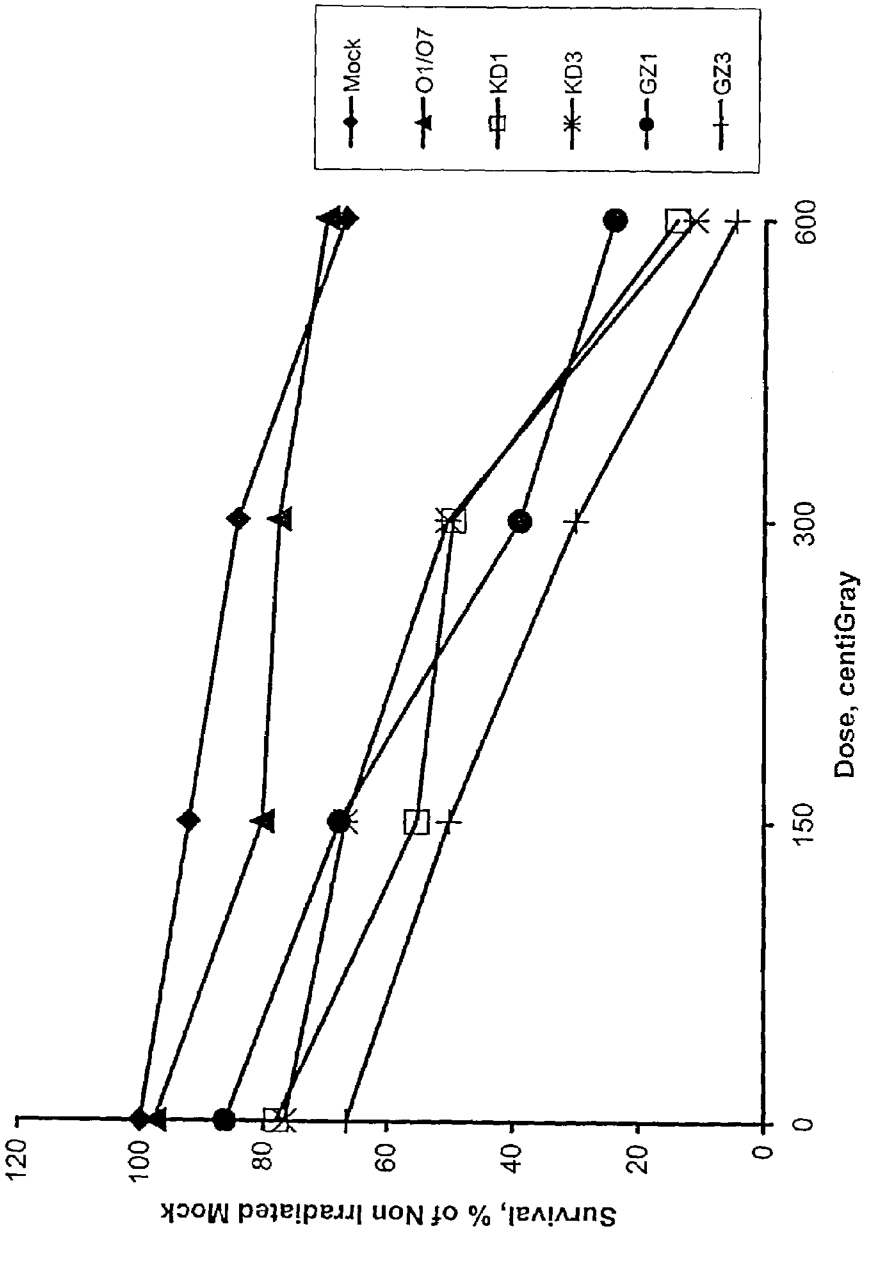
FIG. 16 is a graph of a cell spread assay illustrating that $10^{-3}$ PFU of KD1, KD3, GZ1, or GZ3 used in combination with 150, 300, or 600 centigreys of radiation is more effective in destroying A549 cell monolayers than virus vector alone or radiation alone. Cell viability is based on the amount of crystal violet extracted from the culture wells, using the mock-infected non-radiated well as 100% viability.

As mentioned, approximately as much cell lysis and virus spread were observed with 600 cGy as with 2000 cGy. To determine the optimal dose of radiation to synergize with the vectors, an experiment similar to the one described above was conducted with mock-, dl01/07-, KD1-, KD3-, dl309, GZ1-, or GZ3-infected A549 cells. The 48 well plates received 0, 150, 300, or 600 cGy of radiation at 24 h p.i. Cells were stained with crystal violet. The results with cells receiving 0 versus 600 cGy of radiation were similar to those in FIG. 15. The crystal violet was extracted from the cells infected with $10^{-3}$ PFU per cell of the difference viruses. The absorbance of crystal violet was determined, and the percent cell viability was graphed, using the absorbance of the non-radiated mock-infected cells as 100% cell viability. As illustrated in FIG. 16, an approximately linear decrease in cell viability in all wells was obtained with increasing radiation dose, although the slope of the line was more negative with KD1, KD3, GZ1, or GZ3 than with mock, dl01/07, or dl309. With KD1, KD3, GZ1, and GZ3, there was much more cell lysis and vector spread with their parental control viruses, and there was synergy between the vectors and radiation. For example, with mock-infected cells, 600 cGy reduced cell viability by about 30% (70% of cells were viable). KD1 without radiation reduced cell viability by about 23%. The combination of 600 cGy radiation plus KD1 reduced cell viability to about 85%, more than 53% of which is the sum of radiation alone and KD1 alone. When considering the data in FIGS. 15 and 16 together, a dose of about 600 cGy is optimal in this type of cell culture experiment.

Figure 17:
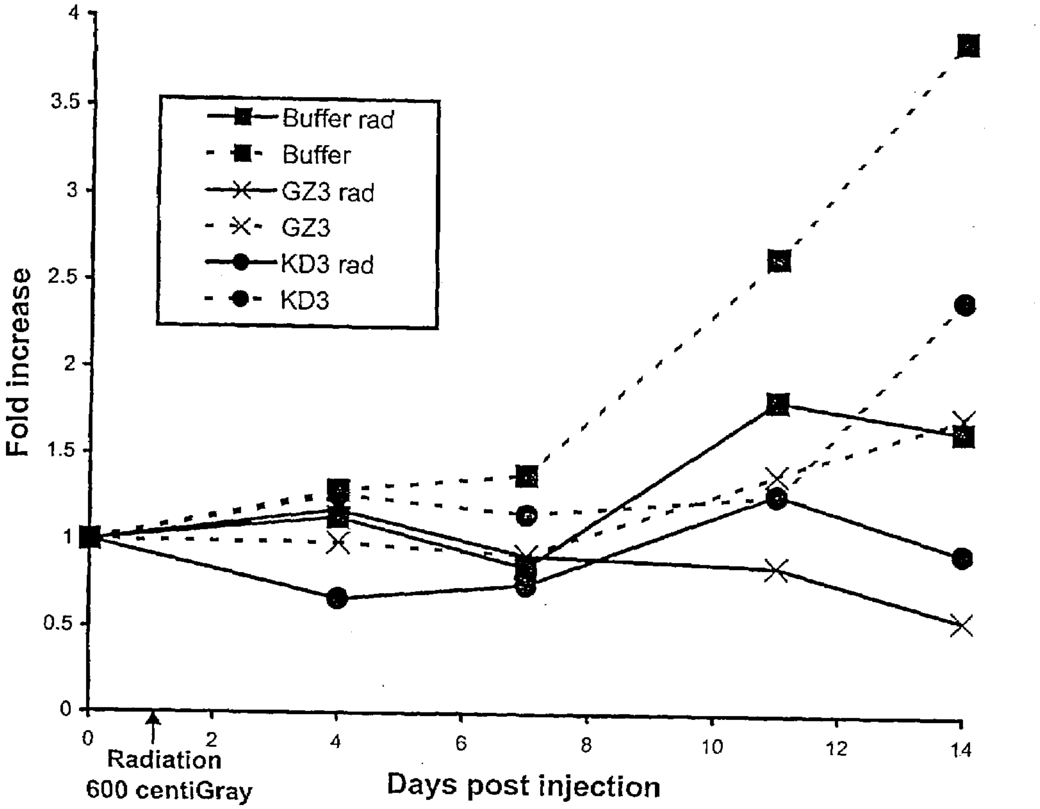
FIG. 17 illustrates that the combination of KD3 or GZ3 plus x-ray radiation is more effective in reducing the growth of A549 cell tumors growing in nude mice than KD3 alone or GZ3 alone.

The combination of KD3 or GZ3 with radiation was also examined in the A549 tumor-nude mouse model (see Example 4). A549 cells were injected into the hind flanks of nude mice, and tumors were allowed to form. When tumors reached approximately 50-μl, they were injected with buffer or with $5\times10^8$ PFU of KD3 or GZ3. Eight to ten tumors were injected per test condition. At 1 day p.i., half the mice received 600 cGy of whole body radiation. Tumor size was measured over time, and was plotted as a fold-increase in tumor size versus days p.i. (as described in Example 4). As shown in FIG. 17, the non-radiated buffer-injected tumors grew faster than those injected with KD3 or GZ3. Tumors that received the combination of KD3 and radiation did not grow, and those that received the combination of GZ3 and radiation shrank in size after 14 days. These results indicate that the combination of KD3 plus radiation or GZ3 plus radiation is more effective than either vector alone or radiation alone in reducing the rate of A549 tumor growth in nude mice. It is likely that radiation would increase the effectiveness in treating tumors of KD1 and GZ1, or indeed any other replication-competent or replication-defective Ad vector.

The mechanism by which radiation causes the ADP overexpressing vectors to lyse cells and spread from cell-to-cell more effectively is not understood. Radiation is expected to induce cellular DNA repair mechanisms, and that may allow for more efficient synthesis of Ad DNA. Radiation may enhance the function of ADP. ADP probably functions by interacting with one or more cellular proteins, and radiation may affect this protein(s) such that ADP functions more efficiently.

It is believed that KD1, KD3, GZ1, or GZ3, or any other replication-competent Ad vector, when used in combination with radiation, will be more effective than vector alone or radiation alone in providing clinical benefit to patients with cancer. The vectors should allow more tumor destruction with a given amount of radiation. Stated another way, radiation should cause more tumor destruction with a given amount of vector. These vectors should also allow the radiation oncologist to use less radiation to achieve the same amount of tumor destruction. Less radiation would reduce the side effects of the radiation.

It is also believed that a cocktail of vectors when used in combination with radiation will be more effective than the cocktail alone or radiation alone. The cocktail could consist of ADP producing vectors plus one or more replication defective vectors expressing an anticancer therapeutic protein (see Example 5).

EXAMPLE 9

This example illustrates a structure-function analysis of adenovirus death protein.

Figure 18B:
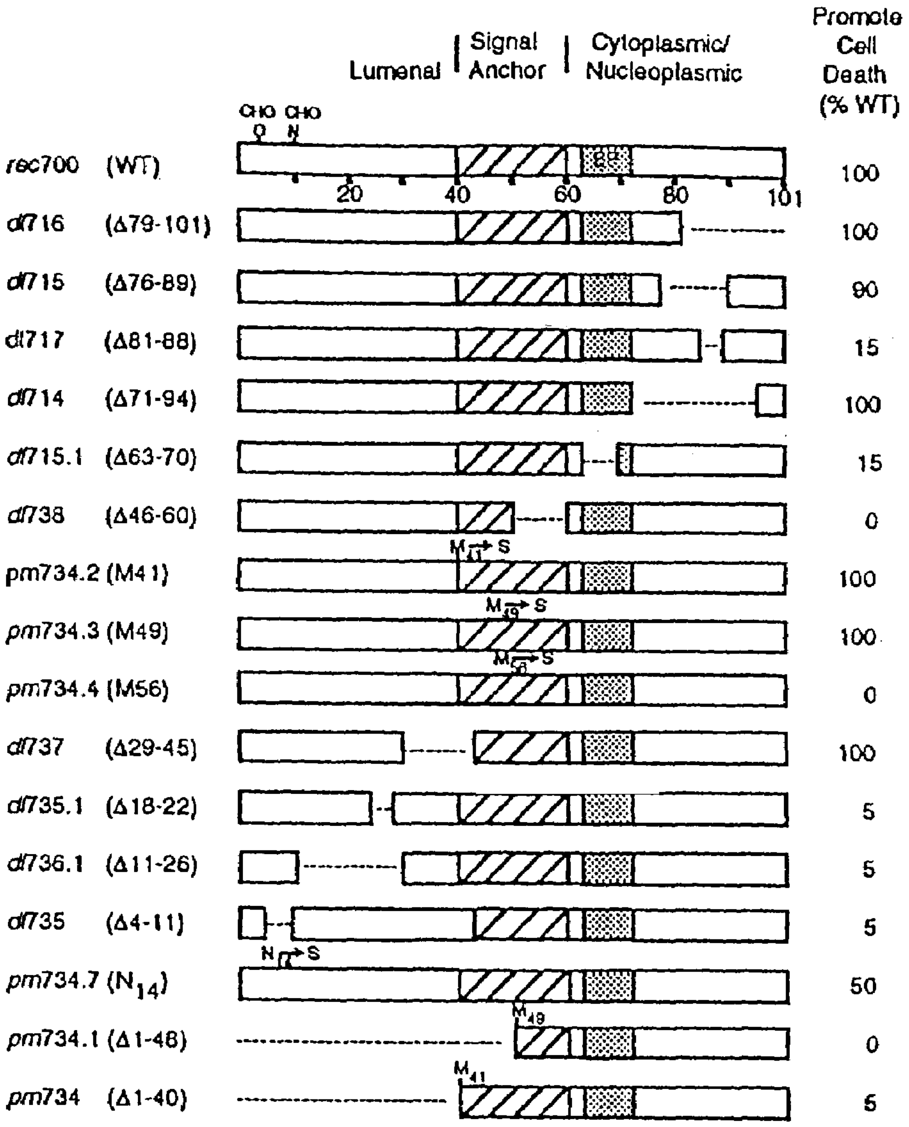
FIG. 18 illustrates a structure-function analysis of ADP, showing in FIG. 18A the amino acid sequence of the adenovirus death protein encoded by Ad2 (SEQ ID NO:6), with the various putative domains and glycosylation sites labeled and showing in FIG. 18B a schematic of the ADP gene in rec700 and in the indicated deletion mutants, with the right column summarizing the death promoting phenotype of the various mutants as a percentage of the wild-type phenotype.

ADP is an 11.6 kDa N-linked O-linked integral membrane glycoprotein that localizes to the inner nuclear membrane (NM) (Scaria et al., Virology 191:743-753). As illustrated in FIG. 18, the Ad2-encoded ADP (SEQ ID NO:6) consists of 101 amino acids; aa 1-40 (SEQ ID NO:17) are lumenal, aa 41-59 (SEQ ID NO:18) constitute the transmembrane signal-anchor (SA) domain, aa 63-70 (SEQ ID NO:19) constitute a basic proline (BP) domain within the nucleoplasmic (NP) domain, which constitutes aa 61-101 (SEQ ID NO:20). To determine which domains in ADP are required to promote cell death, a number of deletion mutants of rec700 were prepared which lacked various portions of the ADP gene and examined for the ability of ADP to localize to the NM and promote death. The rec700 virus is an Ad5-Ad-Ad5 recombinant which has been described elsewhere (Wold et al., *Virology* 148:168-180, 1986).

The structure of ADP in rec700 and in each deletion mutant is schematically illustrated in FIG. 18. The ADP gene in each deletion mutant has been sequenced using PCR methods to insure that the mutations are correct. The structure and activity of ADP in the deletion mutants was tested by infecting A549 cells followed by immunoblot analysis of the ADP mutant proteins as well as the ability to lyse cells. All deletion mutants expressed a stable ADP protein except pm734.1 (Δ1-48, i.e. aa 1-48 are deleted). The pm734.7 (N14) ADP, which has $Asn_{14}$ mutated to Ser, is O-glycosylated but not N-glycosylated because $Asn_{14}$ is the only N-glycosylation site (data not shown). The dl735 (Δ4-11) ADP is N-glycosylated but not O-glycosylated because the sites for O-glycosylation are deleted (data not shown). The pm734.4 (M56) ADP, which has $Met_{56}$ in the SA domain mutated to Ser, contains exclusively N-linked high-mannose oligosaccharides (data not shown); this occurs because the $Met_{56}$ mutation precludes exit of ADP from the endoplasmic reticulum (ER). The dl738 ADP, which lacks aa 46-60 in the signal-anchor domain, forms insoluble aggregates in the cytoplasm; therefore, aa 41-59 do in fact include the signal-anchor domain. The pm734 (Δ1-40) ADP, which initiates at $Met_{41}$ at the N-terminus of the SA domain, comigrated with the lower group of bands generated by proteolytic processing (data not shown). This indicates that the proteolytic cleavage sites occur near $Met_{41}$. Consistent with this, the proteolytic products were not seen with dl737 (Δ29-45) (data not shown). Also, the size of the products decreased in all mutants with deletions within aa 41-101 (dl175.1, dl715, dl714, dl716) (data not shown).

Figure 19A:
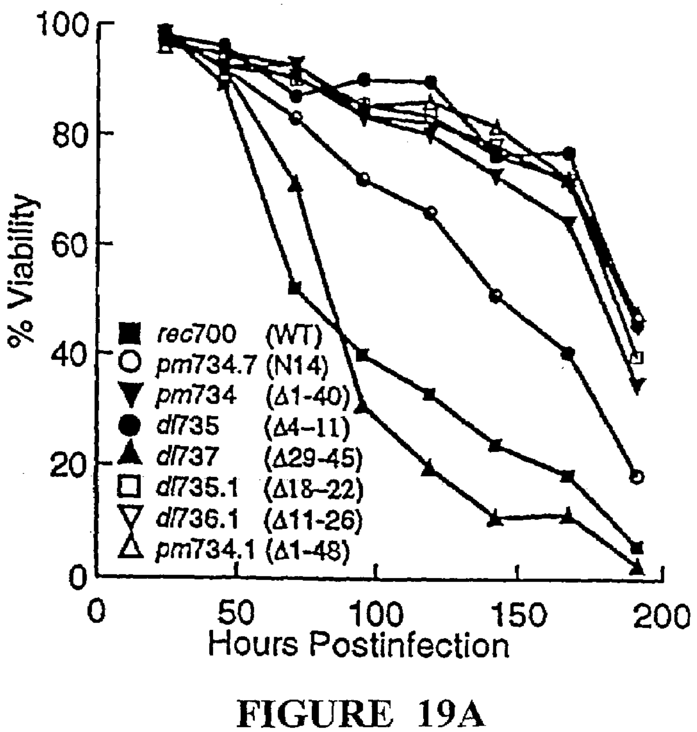
FIGS. 19A and 19B illustrate a cell viability assay of the indicated ADP mutants showing a graph of viability as determined by trypan blue exclusion plotted against hours (FIG. 19A) or days (FIG. 19B) postinfection.
Figure 19B:
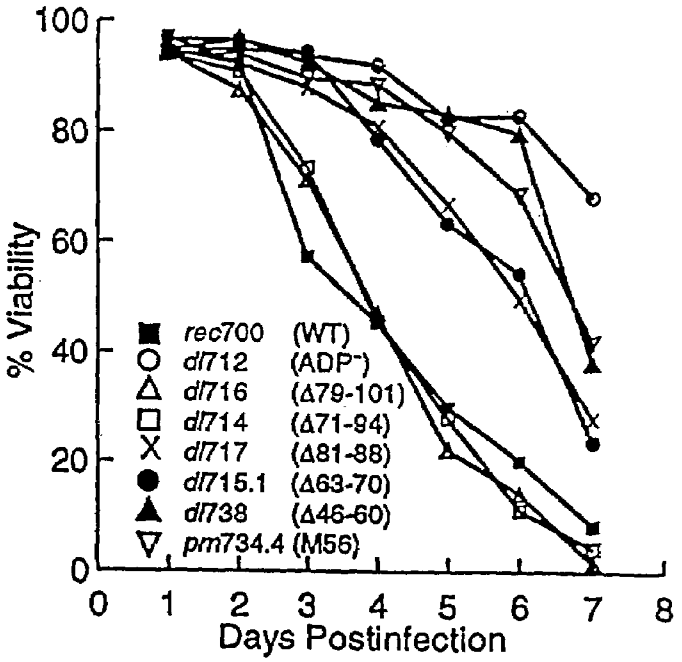

The ability of these mutants to promote cell death was monitored by trypan blue exclusion, plaque development, and lactate dehydrogenase release assays (Tollefson et al., *J. Virol.* 70:2296-2306, 1996). The trypan blue results in FIG. 15A indicate that the death-promoting function of ADP was abolished by deletion of aa 1-40 (pm734), aa 11-26 (dl736.1), aa 18-22 (dl735.1), or aa4-11 (dl735). Mutation of the N-glycosylation site at $Asn_{14}$ (pm734.7) reduced the death-promoting activity to about 50% of rec700 (WT). dl737 (Δ29-45) was efficient as rec700 in promoting cell death; this indicates that the proteolytic processing products must not be required to promote cell death because they are not formed with dl737. The SA domain is essential for death because dl738 (Δ46-60) and pm734.4 (M56) were completely defective (FIG. 19). dl715.1 was nearly completely defective, indicating that the BP domain is extremely important. Surprisingly, aa 71-94 (dl714), 76-89 (dl715), and 79-101 (dl716) could be deleted without affecting the death-promoting activity of ADP (FIG. 19). On the other hand, deletion of aa 81-88 (dl717) nearly completely abolished the activity of ADP (FIG. 19); this is probably the result of aberrant-sorting of ADP (see below). Similar results were obtained when the ability of these ADP mutants to promote cell death was examined with standard plaque development, LDH-release and MTT assays.

The effects of these mutations on the intracellular localization of ADP are extremely interesting. When examined by immunofluorescence (IF) at 33 h p.i. (data not shown), ADP from rec700 (WT) localized crisply to the NM; localization to the Golgi was also apparent. With dl714 (Δ71-94) and dl715 (Δ76-89), ADP localized to all membranes, i.e. the ER, Golgi, plasma membrane, and NM. This was even more apparent at 45 h p.i. (data not shown) Thus, aa 71-94 appear to include a signal that directs ADP specifically to the NM. ADP is very likely sorted from the trans-Golgi network (TGN) to the NM, so this putative signal in ADP probably functions in this sorting pathway. ADP from dl717 (Δ81-88) is intriguing: it localized to the NM and Golgi, but in many cells "dots" and circular structures were observed. Again, this was more apparent at 45 h p.i. when these structures were the prominent feature. dl717-infected cells have not begun to die at 45 h p.i., so these structures are not cellular remnants. The intriguing possibility is that these structures are membrane vesicles that have pinched off from the TGN but are defective in targeting to and/or fusing with the NM.

With dl738 (Δ46-60 in the SA domain), ADP aggregated in the cytoplasm. This again indicates that aa 46-60 include the SA sequence. Withpm734.4 (M56), ADP localized primarily to the NM. As discussed above, the pm734.4 ADP has exclusively high-mannose N-linked oligosaccharides, indicating that it never leaves the ER. Perhaps the putative NM-localization signal in the C-terminal region of the pm734.4 ADP targets ADP to the NM by lateral diffusion from the ER (which is continuous with the outer and inner NM).

With dl737 (Δ29-45), ADP localized to the NM. ADP from pm734 (Δ1-40), pm734.7 (N14) (N-linked glycosylation cannot occur), and dl735 (Δ4-11; the O-glycosylation sites are deleted) localized much more prominently to the Golgi than the NM. ADP from dl735.1 (Δ18-22) and dl736.1 (Δ11-26) also localized much more strongly to the Golgi than the NM. Thus, residues 1-26 and/or glycosylation appear to be required for efficient transport of ADP from the Golgi/TGN to the NM.

In summary, aa 41-59 include the SA domain, $Met_{56}$ in the SA domain is required for exit from the ER, aa 1-26 are required for efficient exit from the Golgi, and aa 76-94 are required to target ADP specifically to the NM. With respect to promoting cell death, the essential regions are aa 1-26, the SA domain (ADP does not enter membranes), $Met_{56}$ in the SA domain, and the BP domain (aa 63-70). It is not clear whether the defective death-promoting phenotype of pm734 (Δ1-40), dl735 (Δ4-11), dl735.1 (Δ18-22), dl736.1 (Δ11-26), and pm734.7 (N14) is due to lack of sequences (or oligosaccharides) that promote death or to much slower exit of ADP from the Golgi to the NM. dl714 (Δ71-94) and dl715 (Δ76-89) express a wild-type phenotype for promoting death even though they are defective in localizing specifically to the NM; this is probably because sufficient ADP still enters the NM to promote death. Even though the deletion in dl717 (Δ81-88) lies within the deletions in dl715 (Δ76-89) and dl714 (Δ71-94), the dl717 ADP is only about 15% as efficient as rec700 (WT), dl715 and *d/*714 in promoting death. This may be because the dl717 ADP tends to remain in vesicles rather than localizing to the NM. Altogether, these data indicate that ADP must localize to the NM in order to promote cell death.

In view of the above, it will be seen that the several advantages of the invention are achieved and other advantageous results attained.

As various changes could be made in the above methods and compositions without departing from the scope of the invention, it is intended that all matter contained in the above description and shown in the accompanying drawings shall be interpreted as illustrative and not in a limiting sense.

All references cited in this specification, including patents and patent applications, are hereby incorporated by reference. The discussion of references herein is intended merely to summarize the assertions made by their authors and no admission is made that any reference constitutes prior art. Applicants reserve the right to challenge the accuracy and pertinency of the cited references.

What is claimed is:

1. A method for treating cancer in an animal having a tumor comprising administering to the tumor an adenovirus vector wherein
said adenovirus vector is replication-competent in neoplastic cells and overexpresses an adenovirus death protein (ADP), wherein overexpression is defined as overexpression relative to dl309.

2. The method of claim 1 wherein the adenovirus death protein comprises SEQ ID NO:5, SEQ ID NO:6, SEQ ID NO:7, or SEQ ID NO:8, SEQ ID NO:9, SEQ ID NO:10, SEQ ID NO:11 or SEQ ID NO:12.

3. The method of claim 1, wherein the adenovirus vector comprises a recombinant adenovirus lacking expression of at least one E3 protein selected from the group consisting of: gp19K; RIDα; RIDβ and 14.7K.

4. The method of claim 3, wherein the vector is replication-restricted to neoplastic cells.

5. The method of claim 4, wherein the vector is a recombinant adenovirus comprising SEQ ID NO:1 or SEQ ID NO:2.

6. The method of claim 3, wherein the adenovirus vector comprises a tumor specific promoter.

7. The method of claim 6, wherein the adenovirus vector comprises SEQ ID NO:14, SEQ ID NO:15 or SEQ ID NO:16.

8. The method of claim 1, further comprising the step of passively immunizing the animal against the adenovirus vector.

9. The method of claim 8, wherein the adenovirus vector comprises SEQ ID NO:1 or SEQ ID NO:2.

10. The method of claim 1, further comprising treating the tumor with radiation.

11. The method of claim 10 comprising administering more than one distinct type of recombinant adenovirus to the tumor and treating the tumor with radiation, wherein at least one recombinant adenovirus is replication-defective.

12. The method of claim 1, further comprising treating the tumor with chemotherapy.

13. The method of claim 12 comprising administering more than one recombinant adenovirus to the tumor and treating the tumor with chemotherapy.

14. The method of claim 1, further comprising administering to the tumor one or more replication-defective adenoviruses, wherein each replication-defective adenovirus expresses an anti-cancer gene product, and wherein the adenovirus vector facilitates the spread of the replication-defective adenovirus in the tumor.

15. The method of claim 1, wherein the adenovirus vector is replication-restricted to dividing cells or neoplastic cells.

16. The method of claim 1, wherein the adenovirus vector comprises a mutation in an E1A gene that renders the adenovirus incapable of expressing an E1A viral protein which binds the pRB and the p300/CBP proteins.

17. The method of claim 15, wherein an E4 promoter of said adenovirus vector is substituted with a promoter, which is activated in neoplastic cells.

18. The method of claim 17, wherein the promoter, which is activated in neoplastic cells, is the surfactant protein B ("SPB") promoter.

19. The method of claim 1, wherein overexpression relative to dl309 is detectable by western blot, cell lysis, virus release or by a cell spreading assay.

20. The method of claim 19, wherein the overexpression relative to a control virus is detectable by western blot.

21. The method of claim 19, wherein the overexpression relative to a control virus is detectable by cell lysis.

22. The method of claim 19, wherein the overexpression relative to a control virus is detectable by virus release.

23. The method of claim 19, wherein the overexpression relative to a control virus is detectable by a cell spreading assay.

24. The method of claim 1, wherein the adenovirus vector lacks expression of at least one E3 protein selected from the group consisting of gp19K, RIDα, RIDβ and 14.7K.

25. The method of claim 24, wherein the adenovirus vector lacks expression of the gp19K protein.

26. The method of claim 24, wherein the adenovirus vector lacks expression of the RIDα protein.

27. The method of claim 24, wherein the adenovirus vector lacks expression of the RIDβ protein.

28. The method of claim 24, wherein the adenovirus vector lacks expression of the 14.7K protein.

29. The method of claim 24, wherein the adenovirus vector lacks expression of the gp19K, RIDα, RIDβ and 14.7K proteins.

30. The method of claim 15, wherein the adenovirus vector comprises a deletion in the E3 region that removes a splice site for any of the E3 mRNAs.

31. The method of claim 1, wherein the adenovirus vector comprises at least one deletion in the E3 region, wherein the at least one deletion comprises a sequence that encodes at least one E3 protein, wherein the protein is selected from the group consisting of gp19K, RIDα, RIDβ, and 14.7K.

32. The method of claim 31, wherein the at least one deletion comprises a sequence that encodes the gp19K, RIDα, RIDβ and 14.7K proteins.

33. The method of claim 32, wherein the at least one deletion further comprises a sequence that encodes the 6.7K protein.

34. The method of claim 32, wherein the at least one deletion further comprises a sequence that encodes the 12.5K protein.

35. The method of claim 32, wherein the at least one deletion further comprises a sequence that encodes the 6.7K and 12.5K proteins.

36. The method of claim 1, wherein the animal is a human.

37. A method for treating cancer in an animal having a tumor, the method comprising administering to the tumor an adenovirus vector that is replication-competent in neoplastic cells and expresses an adenovirus death protein (ADP), wherein:

a) the ADP is expressed from an ADP coding sequence positioned under the control of a promoter other than the endogenous promoters for ADP;

b) the adenovirus vector comprises a deletion in the E3 region that removes a splice site for an E3 mRNA;

c) the ADP is expressed from an ADP coding sequence flanked by a pre-mRNA splicing and cleavage/polyadenylation signal other than the pre-mRNA splicing and cleavage/polyadenylation signal normally associated with the ADP gene, and/or d) the ADP is expressed from an ADP coding sequence that is positioned downstream of the coding sequence for another adenovirus mRNA, together with a sequence on the 5' side of the ADP coding sequence that allows for internal initiation of translation of ADP.

38. The method of claim 37 wherein the ADP comprises the sequence of SEQ ID NO:5, SEQ ID NO:6, SEQ ID NO:7, SEQ ID NO:8, SEQ ID NO:9, SEQ ID NO:10, SEQ ID NO:11 or SEQ ID NO:12.

39. The method of claim 37, further comprising the step of passively immunizing the animal against the adenovirus vector.

40. The method of claim 37, further comprising treating the tumor with radiation.

41. The method of claim 40 comprising administering more than one distinct type of recombinant adenovirus to the tumor and treating the tumor with radiation, wherein at least one recombinant adenovirus is replication-defective.

42. The method of claim 37, further comprising treating the tumor with chemotherapy.

43. The method of claim 37, further comprising administering to the tumor one or more replication-defective adenoviruses, wherein each replication-defective adenovirus expresses an anti-cancer gene product, and wherein the adenovirus vector facilitates the spread of adenoviruses in the tumor.

44. The method of claim 37, wherein the ADP is expressed from an ADP coding sequence positioned under the control of promoter other than the endogenous promoters for ADP.

45. The method of claim 44, wherein the ADP coding sequence is positioned under the control of a promoter that is exogenous to adenovirus.

46. The method of claim 37, wherein the ADP coding sequence is positioned behind a coding sequence for another adenovirus mRNA together with a sequence on the 5' side of the ADP coding sequence that allows for internal initiation of translation of ADP.

47. The method of claim 46, wherein the sequence on the 5' side of the ADP coding sequence that allows for internal initiation of translation of ADP is an Ad tripartite leader or a viral internal ribosome initiation sequence.

48. The method of claim 37, wherein the adenovirus vector comprises a deletion in the E3 region that removes a splice site for an E3 mRNA.

49. The method of claim 48, wherein the adenovirus vector lacks expression of at least one E3 protein selected from the group consisting of gp19K, RIDα, RIDβ, and 14.7K.

50. The method of claim 49, wherein the adenovirus vector lacks expression of each of gp19K, RIDα, RIDβ, and 14.7K.

51. The method of claim 50, wherein the adenovirus additionally lacks expression of the E3 6.7K and 12.5K proteins.

52. The method of claim 37, wherein the adenovirus vector is replication-restricted to neoplastic cells.

53. The method of claim 37, wherein the adenovirus vector comprises a mutation in its E1 region.

54. The method of claim 53, wherein the adenovirus vector comprises a 1101/1107 mutation in its E1A coding region.

55. The method of claim 37, wherein the adenovirus vector comprises an adenoviral gene essential for replication positioned under the control of a tumor specific promoter.

56. The method of claim 37, wherein the adenovirus vector is an Ad1, Ad2, Ad5 or Ad6 vector.

57. The method of claim 37, wherein the adenovirus vector is administered to the tumor by injection of vector intravenously or intrathecally.

58. The method of claim 37, wherein the adenovirus vector is administered to the tumor by direct injection of the tumor.

59. The method of claim 37, wherein the animal is passively immunized against the recombinant adenovirus.

60. The method of claim 37, wherein the animal is a human.

61. A recombinant adenovirus that comprises SEQ ID NO:1 or SEQ ID NO:2.

* * * * *